US011957689B2

(12) United States Patent
Elzein et al.

(10) Patent No.: US 11,957,689 B2
(45) Date of Patent: *Apr. 16, 2024

(54) CANNABINOID RECEPTOR TYPE 2 (CB2) MODULATORS AND USES THEREOF

(71) Applicant: Teon Therapeutics, Inc., Redwood City, CA (US)

(72) Inventors: Elfatih Elzein, Redwood City, CA (US); Jiwen Liu, Foster City, CA (US)

(73) Assignee: Teon Therapeutics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,625

(22) Filed: Oct. 5, 2022

(65) Prior Publication Data

US 2023/0143502 A1   May 11, 2023

Related U.S. Application Data

(63) Continuation of application No. 17/691,991, filed on Mar. 10, 2022, now Pat. No. 11,564,928, which is a continuation of application No. PCT/US2021/030838, filed on May 5, 2021.

(60) Provisional application No. 63/054,096, filed on Jul. 20, 2020, provisional application No. 63/020,489, filed on May 5, 2020.

(51) Int. Cl.
| *A61K 31/5377* | (2006.01) |
| *A61K 9/00* | (2006.01) |
| *A61K 9/08* | (2006.01) |
| *A61K 9/20* | (2006.01) |
| *A61K 9/48* | (2006.01) |
| *A61K 31/4375* | (2006.01) |
| *A61K 31/444* | (2006.01) |
| *A61K 31/4545* | (2006.01) |
| *A61K 31/5386* | (2006.01) |
| *A61K 39/395* | (2006.01) |
| *A61P 35/00* | (2006.01) |
| *C07D 471/04* | (2006.01) |
| *C07D 519/00* | (2006.01) |

(52) U.S. Cl.
CPC ........ *A61K 31/5377* (2013.01); *A61K 9/0019* (2013.01); *A61K 9/08* (2013.01); *A61K 9/2054* (2013.01); *A61K 9/4825* (2013.01); *A61K 31/4375* (2013.01); *A61K 31/444* (2013.01); *A61K 31/4545* (2013.01); *A61K 31/5386* (2013.01); *A61K 39/3955* (2013.01); *A61P 35/00* (2018.01); *C07D 471/04* (2013.01); *C07D 519/00* (2013.01)

(58) Field of Classification Search
CPC .................................................. A61K 31/5377
USPC .................................................. 514/210.16
See application file for complete search history.

(56) References Cited

U.S. PATENT DOCUMENTS 11,564,928 B1 * 1/2023 Elzein ................ A61K 31/4375

FOREIGN PATENT DOCUMENTS

| DE | 4227747 A1 | 2/1994 |
| EP | 0452873 A1 | 10/1991 |
| EP | 1357111 A1 | 10/2003 |
| WO | WO 2005/047285 | 5/2005 |
| WO | WO 2007/103905 | 9/2007 |
| WO | WO 2008/076425 | 6/2008 |
| WO | WO 2008/130600 | 10/2008 |
| WO | WO 2009/090401 | 7/2009 |
| WO | WO 2011/097553 A1 | 8/2011 |
| WO | WO 2013/165898 | 11/2013 |
| WO | WO 2017/068349 A1 | 4/2017 |
| WO | WO 2019/018583 | 1/2019 |

OTHER PUBLICATIONS

Cichero, Elena et al., "CoMFA and CoMSIA analyses on 4-oxo-1,4-dihydroquinoline and 4-oxo-1,4-dihydro-1,5-,-1,6-and -1,8-naphthyridine derivatives as selective CB2 receptor agonists," Journal of Molecular Modeling, Springer, DE, vol. 16, No. 4, Oct. 1, 2009 , pp. 677-691.
Cooper, Anna G. et al., "Development of selective, fluorescent cannabinoid type 2 receptor ligands based on a 1,8-naphthyridin-2(1 H)-one-3-carboxamide scaffold," MEDCHEMCOMM, vol. 9, No. 12, Dec. 12, 2018 pp. 2055-2067.
Hayashi, Hiroaki et al., "5-HT3 Receptor antagonists. 2. 4-Hydroxy-4-quinolinecarboxylic acid derivatives," Journal of Medicinal Chemistry, vol. 36, No. 5, Mar. 1, 1993, pp. 617-626.
International Search Report and Written Opinion in Intl. App. No. PCT/US2021/030838, dated Nov. 10, 2021.
Lucchesi, Valentina et al., "CB-2 Selective Cannabinoid Receptor Ligands: Synthesis, Pharmacological Evaluation, and Molecular Modeling Investigation of 1,8-Naphthyridin-2(1 H)-one-3-carboxamides," Journal of Medicinal Chemistry, vol. 57, No. 21, Nov. 13, 2014, pp. 8777-8791.
Manera, Clementina et al., "New quinolone and 1,8-naphthyridine-3-carboxamides as selective CB2 receptor agonists with anticancer and immuno-modulatory activity," European Journal of Medicinal Chemistry, Elsevier, Amsterdam, NL, vol. 97, Apr. 24, 2015, pp. 10-18.
Manera, Clementina et al., "Rational design, synthesis and antiproliferative properties of new CB2 selective cannabinoid receptor ligands: An investigation of the 1,8-naphthyridin-2(1 H)-one scaffold," European Journal of Medicinal Chemistry, Elsevier, Amsterdam, NL, vol. 52, Mar. 15, 2012, pp. 284-294.
Manera, Clementina et al., "Rational Design, Synthesis and Pharmacological Properties of New 1, 8-Naphthyridin-2(1 H)-on-3-Carboxamide Derivatives as Highly Selective Cannabinoid-2 Receptor Agonists," Journal of Medicincal Chemistry, vol. 52, No. 12, Jun. 25, 2009, pp. 3644-3651.

(Continued)

*Primary Examiner* — Niloofar Rahmani

(57) ABSTRACT

Disclosed herein are compounds, compositions, and methods for modulating the Cannabinoid receptor 2 (CB2) with the compounds and compositions disclosed herein. Also described are methods of treating diseases or conditions that are mediated by the action of Cannabinoid receptor 2 (CB2) or that we benefit from modulating the Cannabinoid receptor 2 (CB2).

9 Claims, No Drawings

(56) References Cited

OTHER PUBLICATIONS

Mugnaini, Claudia et al., "Investigations on the 4-Quinolone-3-carboxylic Acid Motif. 7. Synthesis and Pharmacological Evaluation of 4-Quinolone-3-carboxamides and 4-Hydroxy-2-quinolone-3-carboxamides as High Affinity Cannabinoid Receptor 2 (CB2R) Ligands with Improved Aqueous Solubility," J. Med. Chem., 2016, 59, 1052-1067.

Pudlo, Marc et al., "Quinolone-benzylpiperidine derivatives as novel acetylcholinesterase inhibitor and antioxidant hybrids for Alzheimer Disease," Bioorg. Med. Chem. 22 (2014), 2496-2507.

* cited by examiner

CANNABINOID RECEPTOR TYPE 2 (CB2) MODULATORS AND USES THEREOF

CROSS REFERENCE TO RELATED APPLICATIONS

This application is a continuation U.S. patent application Ser. No. 17/691,991, filed Mar. 10, 2022, which is a continuation of PCT/US2021/030838 filed on May 5, 2021, which claims the benefit under 35 U.S.C. § 119(e) of U.S. Provisional Application No. 63/020,489 filed May 5, 2020, and U.S. Provisional Application No. 63/054,096 filed Jul. 20, 2020, which are incorporated herein by reference in their entirety.

FIELD

Described herein are compounds, methods of making such compounds, pharmaceutical compositions and medicaments comprising such compounds, and methods of using such compounds for the treatment of conditions, diseases, or disorders that would benefit from reduction or inhibition of cannabinoid receptor CB2 activity.

BACKGROUND

Cannabinoid CB2 receptors ($CB_2R$) modulate immune responses during inflammatory processes, in the tumor microenvironment. Endogenous and exogenous cannabinoids exert immunosuppressive properties in variety of ways, including induction of apoptosis of T cells, NK cells and B cells; inhibition of T, NK and B cells proliferation; inhibition of immunostimulatory cytokine and chemokine production, and induction of immunosuppressive cytokine production and regulatory T cells. Therefore, $CB_2R$ antagonism should restore T, NK and B cells function and relieve innate and adaptive immunosuppression caused by the endocannabinoids. Developing $CB_2$ receptor antagonists constitute a novel approach to treat cancer by enhancing antitumor immune response.

SUMMARY

Compounds described herein, including pharmaceutically acceptable salts, prodrugs, active metabolites and solvates thereof, are CB2 receptor ($CB_2R$) modulators. In some embodiments, the $CB_2R$ modulators are $CB_2R$ antagonists. In some embodiments, the $CB_2R$ modulators are $CB_2R$ inverse agonists.

In one aspect, described herein is a compound of Formula (I), or a pharmaceutically acceptable salt, solvate or stereoisomer thereof:

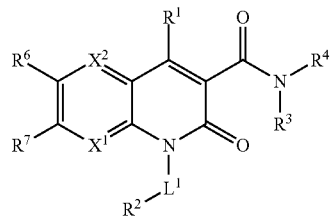

Formula (I)

wherein,
$R^1$ is —OH, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, $C_3$-$C_6$ cycloalkyl, $C_3$-$C_6$ heterocycloalkyl containing 1-2 N atom and 0 or 1 O or S atom, or a $C_3$-$C_6$ heterocycloalkyl containing 0 or 1 N atom and 1 O or S atom;

$L^1$ is absent, $C_1$-$C_4$ alkylene, or $C_3$-$C_5$cycloalkylene;

$R^2$ is a ring A that is unsubstituted or is substituted with 1, 2, 3, or 4 $R^a$;

ring A is $C_3$-$C_6$ heterocycloalkyl containing 1-2 N atom and 0 or 1 O or S atom, $C_3$-$C_6$ heterocycloalkyl containing 0 or 1 N atom and 1 O or S atom, phenyl, $C_3$-$C_{10}$ cycloalkyl, 5-membered heteroaryl, or 6-membered heteroaryl;

each $R^a$ is independently selected from the group consisting of halogen, —CN, —OH, —$OR^{12}$, —$SR^{12}$, —S(=O)$R^{12}$, —S(=O)$_2R^{12}$, —S(=O)$_2N(R^{13})_2$, —$NR^{13}$S(=O)$_2R^{12}$, —N($R^{13}$)$_2$, —OC(=O)($R^{12}$), —$CO_2R^{13}$, —C(=O)N($R^{12}$)$_2$, —$NR^{13}$C(=O)($R^{12}$), —$NR^{13}$C(=O)O($R^{12}$), —OC(=O)N($R^{13}$)$_2$, —$NR^{13}$C(=O)N($R^{13}$)$_2$, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, or substituted or unsubstituted monocyclic $C_3$-$C_6$ heterocycloalkyl;

$R^3$ is H or $C_1$-$C_4$ alkyl;

$R^4$ is -$L^2$-$R^5$;

$L^2$ is absent or —$CR^{10}R^{11}$—;

$R^5$ is a ring B that is unsubstituted or is substituted with 1, 2, 3, or 4 $R^b$;

ring B is $C_3$-$C_{12}$ cycloalkyl, $C_2$-$C_{10}$ heterocycloalkyl, phenyl, naphthyl, or heteroaryl;

each $R^b$ is independently selected from the group consisting of halogen, —CN, —OH, —N($R^{13}$)$_2$, —OC(=O)($R^{12}$), —$CO_2R^{13}$, —C(=O)N($R^{13}$)$_2$, —$NR^{13}$C(=O)($R^{12}$), —$NR^{13}$C(=O)O($R^{12}$), —OC(=O)N($R^{13}$)$_2$, —$NR^{13}$C(=O)N($R^{13}$)$_2$, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, or substituted or unsubstituted monocyclic $C_3$-$C_6$ heterocycloalkyl;

or two $R^b$ that are attached to the same carbon atom are taken together with the carbon atom to form a $C_3$-$C_6$ cycloalkyl or a $C_3$-$C_6$ heterocycloalkyl;

$R^{10}$ and $R^{11}$ are independently selected from H or —$CH_3$;

or $R^{10}$ and $R^{11}$ are taken together with the carbon atom to which they are attached to form a $C_3$-$C_6$ cycloalkyl;

$R^6$ is a ring C that is unsubstituted or is substituted with 1, 2, 3, or 4 $R^c$; ring C is phenyl, naphthyl, heteroaryl, $C_3$-$C_{12}$ cycloalkyl, or $C_2$-$C_{10}$ heterocycloalkyl;

or $R^6$ is hydrogen, halogen, —CN, —OH, —$OR^{12}$, —$SR^{12}$, —S(=O)$R^{12}$, —S(=O)$_2R^{12}$, —S(=O)$_2N$($R^{13}$)$_2$, —$NR^{13}$S(=O)$_2R^{12}$, —N($R^{13}$)$_2$, —OC(=O) ($R^{12}$), —$CO_2R^{13}$, —C(=O)N($R^{13}$)$_2$, —$NR^{13}$C(=O) ($R^{12}$), —$NR^{13}$C(=O)O($R^{12}$), —OC(=O)N($R^{13}$)$_2$, —$NR^{13}$C(=O)N($R^{13}$)$_2$, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, or substituted or unsubstituted monocyclic $C_3$-$C_6$ heterocycloalkyl;

each $R^c$ is independently selected from the group consisting of halogen, —CN, —OH, —$OR^{12}$, —$SR^{12}$, —S(=O)$R^{12}$, —S(=O)$_2R^{12}$, —S(=O)$_2N(R^{13})_2$, —$NR^{13}$S(=O)$_2R^{12}$, —N($R^{13}$)$_2$, —OC(=O)($R^{12}$), —$CO_2R^{13}$, —C(=O)N($R^{13}$)$_2$, —$NR^{13}$C(=O)($R^{12}$), —$NR^{13}$C(=O)O($R^{12}$), —OC(=O)N($R^{13}$)$_2$, —$NR^{13}$C(=O)N($R^{13}$)$_2$, $C_1$-$C_4$ alkyl, $C_2$-$C_4$ alkenyl, C$_2$-C$_4$ alkynyl, C$_1$-C$_4$ deuteroalkyl, C$_1$-C$_4$ fluoroalkyl, C$_1$-C$_4$ heteroalkyl, substituted or unsubstituted C$_3$-C$_6$ cycloalkyl, substituted or unsubstituted C$_3$-C$_7$ heterocycloalkyl, substituted or unsubstituted phenyl, substituted or unsubstituted monocyclic heteroaryl or a 1,4-dioxanyl ring fused to ring C;

R$^7$ is H, halogen, —CN, —OH, —N(R$^{13}$)$_2$, C$_1$-C$_4$ alkyl, C$_3$-C$_6$ cycloalkyl, C$_2$-C$_4$ alkenyl, C$_2$-C$_4$ alkynyl, C$_1$-C$_4$ alkoxy, C$_1$-C$_4$ deuteroalkyl, C$_1$-C$_4$ deuteroalkoxy, C$_1$-C$_4$ fluoroalkyl, C$_1$-C$_4$ fluoroalkoxy, or C$_1$-C$_4$ heteroalkyl or C$_3$-C$_6$ heterocycloalkyl;

X$^1$ is N; and X$^2$ is CR$^8$ or N;

or X$^1$ is CR$^8$ or N; and X$^2$ is N;

R$^8$ is H, halogen, —CN, —OH, —N(R$^{13}$)$_2$, C$_1$-C$_4$ alkyl, C$_2$-C$_4$ alkenyl, C$_2$-C$_4$ alkynyl, C$_1$-C$_4$ alkoxy, C$_1$-C$_4$ deuteroalkyl, C$_1$-C$_4$ deuteroalkoxy, C$_1$-C$_4$ fluoroalkyl, C$_1$-C$_4$ fluoroalkoxy, C$_3$-C$_6$ cycloalkyl, C$_1$-C$_4$ heteroalkyl or C$_3$-C$_6$ heterocycloalkyl;

each R$^{12}$ is independently selected from the group consisting of C$_1$-C$_4$ alkyl, C$_1$-C$_4$ deuteroalkyl, C$_1$-C$_4$ fluoroalkyl, C$_1$-C$_4$ heteroalkyl, substituted or unsubstituted C$_3$-C$_6$ cycloalkyl, substituted or unsubstituted C$_3$-C$_6$ heterocycloalkyl, substituted or unsubstituted phenyl, or substituted or unsubstituted monocyclic heteroaryl;

each R$^{13}$ is independently selected from the group consisting of hydrogen, C$_1$-C$_4$ alkyl, C$_1$-C$_4$ deuteroalkyl, C$_1$-C$_4$ fluoroalkyl, C$_1$-C$_4$ heteroalkyl, substituted or unsubstituted C$_3$-C$_6$ cycloalkyl, substituted or unsubstituted C$_3$-C$_6$ heterocycloalkyl, substituted or unsubstituted phenyl, or substituted or unsubstituted monocyclic heteroaryl;

provided that when R$^6$ is H, R$^4$ is not cyclohexyl, 4-methylcyclohexyl, or cycloheptyl.

In another aspect, described herein is a compound that has the structure of Formula (X), or a pharmaceutically acceptable salt, solvate or stereoisomer thereof:

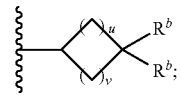

Formula (X)

wherein,

R$^1$ is hydrogen, —OH, C$_1$-C$_4$ alkyl, C$_2$-C$_4$ alkenyl, C$_2$-C$_4$ alkynyl, C$_1$-C$_4$ alkoxy, C$_1$-C$_4$ deuteroalkyl, C$_1$-C$_4$ deuteroalkoxy, C$_1$-C$_4$ fluoroalkyl, C$_1$-C$_4$ fluoroalkoxy, C$_1$-C$_4$ heteroalkyl, C$_3$-C$_6$ cycloalkyl, C$_3$-C$_6$ heterocycloalkyl containing 1 N atom and 0 or 1 O or S atom, or a C$_3$-C$_6$ heterocycloalkyl containing 0 or 1 N atom and 1 O or S atom;

L$^1$ is absent, C$_1$-C$_4$ alkylene, or C$_3$-C$_5$cycloalkylene;

R$^2$ is a ring A that is unsubstituted or is substituted with 1, 2, 3, or 4 R$^a$;

ring A is C$_3$-C$_6$ heterocycloalkyl containing 1-2 N atom and 0 or 1 O or S atom, C$_3$-C$_6$ heterocycloalkyl containing 0 or 1 N atom and 1 O or S atom, phenyl, C$_3$-C$_{10}$ cycloalkyl, 5-membered heteroaryl, or 6-membered heteroaryl;

each R$^a$ is independently selected from the group consisting of halogen, —CN, —OH, —OR$^{12}$, —SR$^{12}$,
—S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, C$_1$-C$_4$ alkyl, C$_2$-C$_4$ alkenyl, C$_2$-C$_4$ alkynyl, C$_1$-C$_4$ deuteroalkyl, C$_1$-C$_4$ fluoroalkyl, C$_1$-C$_4$ heteroalkyl, or substituted or unsubstituted monocyclic C$_3$-C$_6$ heterocycloalkyl;

R$^3$ is H or C$_1$-C$_4$ alkyl;

R$^4$ is

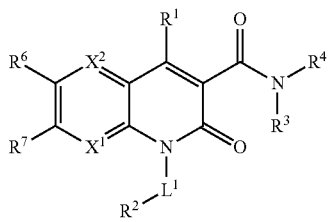

u is 1 or 2; v is 1 or 2;

or R$^4$ is -L$^2$-R$^5$;

L$^2$ is absent or —CR$^{10}$R$^{11}$—;

R$^{10}$ is —CH$_3$;

R$^{11}$ is H or —CH$_3$;

or R$^{10}$ and R$^{11}$ are taken together with the carbon atom to which they are attached to form a cyclopropyl-1,1-diyl;

R$^5$ is a ring B that is unsubstituted or is substituted with 1, 2, 3, or 4 R$^b$;

ring B is bridged C$_5$-C$_{12}$ cycloalkyl, phenyl, naphthyl, or heteroaryl;

each R$^b$ is independently selected from the group consisting of halogen, —CN, —OH, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{15}$C(=O)O(R$^{12}$), —OC(=O)N(R$^{13}$)$_2$, —NR$^{13}$C(=O)N(R$^{13}$)$_2$, C$_1$-C$_4$ alkyl, C$_2$-C$_4$ alkenyl, C$_2$-C$_4$ alkynyl, C$_1$-C$_4$ alkoxy, C$_1$-C$_4$ deuteroalkyl, C$_1$-C$_4$ deuteroalkoxy, C$_1$-C$_4$ fluoroalkyl, C$_1$-C$_4$ fluoroalkoxy, C$_1$-C$_4$ heteroalkyl, or substituted or unsubstituted monocyclic C$_3$-C$_6$ heterocycloalkyl;

or two R$^b$ that are attached to the same carbon atom are taken together with the carbon atom to form a C$_3$-C$_6$ cycloalkyl or a C$_3$-C$_6$ heterocycloalkyl;

R$^6$ is a ring C that is unsubstituted or is substituted with 1, 2, 3, or 4 R$^c$; ring C is phenyl, naphthyl, heteroaryl, C$_3$-C$_{12}$ cycloalkyl, or C$_2$-C$_{10}$ heterocycloalkyl;

or R$^6$ is hydrogen, halogen, —CN, —OH, —OR$^{12}$, —SR$^{12}$, —S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{13}$)$_2$, —NR$^{15}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, C$_1$-C$_4$ alkyl, C$_2$-C$_4$ alkenyl, C$_2$-C$_4$ alkynyl, C$_1$-C$_4$ deuteroalkyl, C$_1$-C$_4$ fluoroalkyl, C$_1$-C$_4$ heteroalkyl, or substituted or unsubstituted monocyclic C$_3$-C$_6$ heterocycloalkyl;

each R$^c$ is independently selected from the group consisting of halogen, —CN, —OH, —OR$^{12}$, —SR$^{12}$, —S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, C$_1$-C$_4$ alkyl, C$_2$-C$_4$ alkenyl, C$_2$-C$_4$ alkynyl, C$_1$-C$_4$ deuteroalkyl, C$_1$-C$_4$ fluoroalkyl, C$_1$-C$_4$ heteroalkyl, substituted or unsubstituted C$_3$-C$_6$ cycloalkyl, substituted or unsubstituted C$_3$-C$_6$ heterocycloalkyl, substituted or unsubstituted phenyl, substituted or unsubstituted monocyclic heteroaryl or a 1,4-dioxanyl ring fused to ring C;

R$^7$ is H, halogen, —CN, —OH, —N(R$^{13}$)$_2$, C$_1$-C$_4$ alkyl, C$_2$-C$_4$ alkenyl, C$_2$-C$_4$ alkynyl, C$_1$-C$_4$ alkoxy, C$_1$-C$_4$ deuteroalkyl, C$_1$-C$_4$ deuteroalkoxy, C$_1$-C$_4$ fluoroalkyl, C$_1$-C$_4$ fluoroalkoxy, or C$_1$-C$_4$ heteroalkyl;

X$^1$ is N; and X$^2$ is CR$^8$ or N;

or X$^1$ is CR$^8$ or N; and X$^2$ is N;

R$^8$ is H, halogen, —CN, —OH, —N(R$^{13}$)$_2$, C$_1$-C$_4$ alkyl, C$_2$-C$_4$ alkenyl, C$_2$-C$_4$ alkynyl, C$_1$-C$_4$ alkoxy, C$_1$-C$_4$ deuteroalkyl, C$_1$-C$_4$ deuteroalkoxy, C$_1$-C$_4$ fluoroalkyl, C$_1$-C$_4$ fluoroalkoxy, or C$_1$-C$_4$ heteroalkyl;

each R$^{12}$ is independently selected from the group consisting of C$_1$-C$_4$ alkyl, C$_1$-C$_4$ deuteroalkyl, C$_1$-C$_4$ fluoroalkyl, C$_1$-C$_4$ heteroalkyl, substituted or unsubstituted C$_3$-C$_6$ cycloalkyl, substituted or unsubstituted C$_3$-C$_6$ heterocycloalkyl, substituted or unsubstituted phenyl, or substituted or unsubstituted monocyclic heteroaryl;

each R$^{13}$ is independently selected from the group consisting of hydrogen, C$_1$-C$_4$ alkyl, C$_1$-C$_4$ deuteroalkyl, C$_1$-C$_4$ fluoroalkyl, C$_1$-C$_4$ heteroalkyl, substituted or unsubstituted C$_3$-C$_6$ cycloalkyl, substituted or unsubstituted C$_3$-C$_6$ heterocycloalkyl, substituted or unsubstituted phenyl, or substituted or unsubstituted monocyclic heteroaryl provided that when R$^1$ is H, R$^4$ is not cyclohexyl substituted by 0, 1, 2, 3 or 4 methyl groups.

In another aspect, described herein is a pharmaceutical composition comprising a compound described herein, or a pharmaceutically acceptable salt, solvate or stereoisomer thereof, and at least one pharmaceutically acceptable excipient.

In some embodiments, the pharmaceutical composition is formulated for administration to a mammal by oral administration, intravenous administration, or subcutaneous administration.

In some embodiments, the pharmaceutical composition is in the form of a tablet, a pill, a capsule, a liquid, a suspension, a dispersion, a solution, or an emulsion.

In another aspect, described herein is a method of modulating the activity of the cannabinoid 2 receptor (CB$_2$R) in a mammal comprising administering to the mammal a compound described herein, or any pharmaceutically acceptable salt, solvate or stereoisomer thereof.

In another aspect, described herein is a method of treating a disease or disorder in a mammal that is mediated by the action of the cannabinoid 2 receptor (CB$_2$R) comprising administering to the mammal a compound described herein, or any pharmaceutically acceptable salt, solvate or stereoisomer thereof.

In another aspect, described herein is a method for treating cancer in a mammal, the method comprising administering to the mammal a selective cannabinoid 2 receptor (CB$_2$R) modulator. In some embodiments, the selective cannabinoid 2 receptor (CB$_2$R) modulator is a selective cannabinoid 2 receptor (CB$_2$R) antagonist. In some embodiments, the selective cannabinoid 2 receptor (CB$_2$R) modulator is a selective cannabinoid 2 receptor (CB$_2$R) inverse agonist. In some embodiments, the selective cannabinoid 2 receptor (CB$_2$R) modulator is a compound of Formula (I) or Formula (X) or any Formula described herein, or any pharmaceutically acceptable salt, solvate or stereoisomer thereof.

In another aspect, described herein is a method for treating cancer in a mammal, the method comprising administering to the mammal a compound of Formula (I) or Formula (X) or any Formula described herein, or any pharmaceutically acceptable salt, solvate or stereoisomer thereof. In some embodiments, the cancer is a solid tumor. In some embodiments, the cancer is bladder cancer, colon cancer, brain cancer, breast cancer, endometrial cancer, heart cancer, kidney cancer, lung cancer, liver cancer, uterine cancer, blood and lymphatic cancer, ovarian cancer, pancreatic cancer, prostate cancer, thyroid cancer, or skin cancer. In some embodiments, the cancer is prostate cancer, breast cancer, colon cancer, or lung cancer. In some embodiments, the cancer is a sarcoma, carcinoma, or lymphoma.

In some embodiments, the method further comprises administering at least one additional therapy to the mammal.

In some embodiments, the mammal is a human.

In any of the aforementioned aspects are further embodiments in which an effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal.

In any of the aforementioned aspects are further embodiments comprising single administrations of an effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

Articles of manufacture, which include packaging material, a formulation within the packaging material (e.g. a formulation suitable for topical administration), and a label that indicates that the compound or composition, or pharmaceutically acceptable salt, or solvate thereof, is used for modulating CB2 activity, or for the treatment, prevention or amelioration of one or more symptoms of a disease or disorder that is associated with CB2 activity or that would benefit from CB2 modulation, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION

Cannabinoids are a group of compounds found in the marijuana plant. Marijuana has been used both for recreational and medicinal purposes for several centuries. Cannabinoids have been shown to be effective in the treatment of nausea and vomiting associated with cancer chemotherapy, anorexia and cachexia seen in HIV/AIDS patients, as well as neuropathic pain, and spasticity in multiple sclerosis. More recently, the anti-inflammatory properties of cannabinoids are drawing significant attention. Studies with marijuana cannabinoids led to the discovery of cannabinoid CB1 and CB2 receptors (CB$_1$R and CB$_2$R) and their endogenous ligands 2-Arachidonoyl-glycerol (2-AG) and anandamide (AEA), which make up what is known as the endocannabinoid system. Both CB1R and CB$_2$R are heterotrimeric G$_{i/o}$-protein coupled receptors. CB$_1$R is mainly expressed in the central nervous system (CNS) while CB$_2$R is mainly expressed in immune cells (B cells>Natural Killer cells>Monocytes>Neutrophils>CD8 leukocytes> CD4 leukocytes).

The mechanism of immunosuppression by endogenous and exogenous cannabinoids has been investigated both in vitro and in vivo studies. $CB_2$ receptors modulate immune responses during inflammatory processes and their immunosuppressive effects have been studied in many disease models such as syngeneic mouse tumors, multiple sclerosis, diabetes, septic shock, rheumatoid arthritis, and allergic asthma. Studies in these disease models along with many in vitro experiments show that endogenous and exogenous cannabinoids exert their immunosuppressive properties in four main ways: (1) induction of T, NK and B cells apoptosis, (2) inhibition of T, NK and B cells proliferation, (3) inhibition of immunostimulatory cytokine and chemokine production (e.g., GM-CSF, IL2, IL8, IL12, IFNγ, TNFα), and (4) induction of immunosuppressive cytokine production (e.g., IL10, TGFβ1) and regulatory T cells. In addition, Cannabis users have decreased NK counts, decreased lymphocyte proliferative response to inflammatory stimulus and low levels of IL2. By contrast, cannabis users also have increased immunosuppressive cytokines IL10 and TGFβ1. Furthermore, a retrospective analysis of clinical data found that cannabis use during cancer immunotherapy significantly reduces anti-PD-1 nivolumab response in patients with advanced melanoma, non-small cell lung cancer and renal clear cell carcinoma. In the tumor microenvironment, $CB_2R$ expression is elevated as both cancer and immune cells produce endocannabinoids AEA and 2-AG. Therefore, $CB_2R$ antagonism should restore T, NK and B cell function and relieve innate and adaptive immunosuppression caused by the endocannabinoids. Developing $CB_2$ receptor antagonists constitute a novel approach to treat cancer by enhancing antitumor immune response.

Cancer

In some embodiments, disclosed herein are methods of treating cancer with a CB2 modulator described herein, or a pharmaceutically acceptable salt or solvate thereof.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

In some embodiments, a mammal treated with a compound described herein has a disease or disorder that is or is associated with a cancer or tumor. Thus, in some embodiments, the mammal is a human that is an oncology patient. Such diseases and disorders and cancers include carcinomas, sarcomas, benign tumors, primary tumors, tumor metastases, solid tumors, non-solid tumors, blood tumors, leukemias and lymphomas, and primary and metastatic tumors.

In some embodiments, the CB2 receptor modulators described herein are used in the treatment of solid tumours. A solid tumor is an abnormal mass of tissue that usually does not contain cysts or liquid areas. Solid tumors may be benign (not cancer), or malignant (cancer). Different types of solid tumors are named for the type of cells that form them. Examples of solid tumors are carcinomas, sarcomas, and lymphomas.

Carcinomas include, but are not limited to, esophageal carcinoma, hepatocellular carcinoma, basal cell carcinoma, squamous cell carcinoma, bladder carcinoma, bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, renal cell carcinoma, Wilm's tumor, cervical carcinoma, uterine carcinoma, testicular carcinoma, osteogenic carcinoma, epithelial carcinoma, and nasopharyngeal carcinoma.

Sarcomas include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Leukemias include, but are not limited to, a) chronic myeloproliferative syndromes (neoplastic disorders of multipotential hematopoietic stem cells); b) acute myelogenous leukemias; c) chronic lymphocytic leukemias (CLL), including B-cell CLL, T-cell CLL prolymphocyte leukemia, and hairy cell leukemia; and d) acute lymphoblastic leukemias (characterized by accumulation of lymphoblasts). Lymphomas include, but are not limited to, B-cell lymphomas (e.g., Burkitt's lymphoma); Hodgkin's lymphoma; and the like.

Benign tumors include, e.g., hemangiomas, hepatocellular adenoma, cavernous hemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

Primary and metastatic tumors include, e.g., lung cancer; breast cancer; colorectal cancer; anal cancer; pancreatic cancer; prostate cancer; ovarian carcinoma; liver and bile duct carcinoma; esophageal carcinoma; bladder carcinoma; carcinoma of the uterus; glioma, glioblastoma, medulloblastoma, and other tumors of the brain; kidney cancers; cancer of the head and neck; cancer of the stomach; multiple myeloma; testicular cancer; germ cell tumor; neuroendocrine tumor; cervical cancer; carcinoids of the gastrointestinal tract, breast, and other organs.

In one aspect, a $CB_2R$ modulator described herein, or a pharmaceutically acceptable salt, solvate or stereoisomer thereof, reduces, ameliorates or inhibits immunosuppression and cell proliferation associated with cancers.

Compounds

Compounds described herein, including pharmaceutically acceptable salts, prodrugs, active metabolites and solvates thereof, are CB2 receptor ($CB_2R$) modulators. In some embodiments, the $CB_2R$ modulators are $CB_2R$ antagonists. In some embodiments, the $CB_2R$ modulators are $CB_2R$ inverse agonists.

In one aspect, described herein is a compound of Formula (I), or a pharmaceutically acceptable salt, solvate or stereoisomer thereof:

Formula (I)

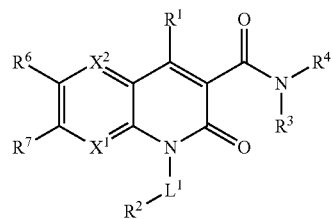

wherein, $R^1$ is —OH, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, $C_3$-$C_6$ cycloalkyl, $C_3$-$C_6$ heterocycloalkyl containing 1-2 N atom and 0 or 1 O or S atom, or a $C_3$-$C_6$ heterocycloalkyl containing 0 or 1 N atom and 1 O or S atom;

$L^1$ is absent, $C_1$-$C_4$ alkylene, or $C_3$-$C_5$cycloalkylene;

$R^2$ is a ring A that is unsubstituted or is substituted with 1, 2, 3, or 4 $R^a$;

ring A is $C_3$-$C_6$ heterocycloalkyl containing 1-2 N atom and 0 or 1 O or S atom, $C_3$-$C_6$ heterocycloalkyl containing 0 or 1 N atom and 1 O or S atom, phenyl, $C_3$-$C_{10}$ cycloalkyl, 5-membered heteroaryl, or 6-membered heteroaryl;

each $R^a$ is independently selected from the group consisting of halogen, —CN, —OH, —OR$^{12}$, —SR$^{12}$, —S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{12}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, or substituted or unsubstituted monocyclic $C_3$-$C_6$ heterocycloalkyl;

$R^3$ is H or $C_1$-$C_4$ alkyl;

$R^4$ is -$L^2$-$R^5$;

$L^2$ is absent or —CR$^{10}$R$^{11}$—;

$R^5$ is a ring B that is unsubstituted or is substituted with 1, 2, 3, or 4 $R^b$;

ring B is $C_3$-$C_{12}$ cycloalkyl, $C_2$-$C_{10}$ heterocycloalkyl, phenyl, naphthyl, or heteroaryl; each $R^b$ is independently selected from the group consisting of halogen, —CN, —OH, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, or substituted or unsubstituted monocyclic $C_3$-$C_6$ heterocycloalkyl;

or two $R^b$ that are attached to the same carbon atom are taken together with the carbon atom to form a $C_3$-$C_6$ cycloalkyl or a $C_3$-$C_6$ heterocycloalkyl;

$R^{10}$ and $R^{11}$ are independently selected from H or —CH$_3$;

or $R^{10}$ and $R^{11}$ are taken together with the carbon atom to which they are attached to form a $C_3$-$C_6$ cycloalkyl;

$R^6$ is a ring C that is unsubstituted or is substituted with 1, 2, 3, or 4 $R^c$; ring C is phenyl, naphthyl, heteroaryl, $C_3$-$C_{12}$ cycloalkyl, or $C_2$-$C_{10}$ heterocycloalkyl;

or $R^6$ is hydrogen, halogen, —CN, —OH, —OR$^{12}$, —SR$^{12}$, —S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, or substituted or unsubstituted monocyclic $C_3$-$C_6$ heterocycloalkyl;

each $R^c$ is independently selected from the group consisting of halogen, —CN, —OH, —OR$^{12}$, —SR$^{12}$, —S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, substituted or unsubstituted $C_3$-$C_6$ cycloalkyl, substituted or unsubstituted $C_3$-$C_7$ heterocycloalkyl, substituted or unsubstituted phenyl, substituted or unsubstituted monocyclic heteroaryl or a 1,4-dioxanyl ring fused to ring C;

$R^7$ is H, halogen, —CN, —OH, —N(R$^{13}$)$_2$, $C_1$-$C_4$ alkyl, $C_3$-$C_6$ cycloalkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, or $C_1$-$C_4$ heteroalkyl or $C_3$-$C_6$ heterocycloalkyl;

$X^1$ is N; and $X^2$ is CR$^8$ or N;

or $X^1$ is CR$^8$ or N; and $X^2$ is N;

$R^8$ is H, halogen, —CN, —OH, —N(R$^{13}$)$_2$, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_3$-$C_6$ cycloalkyl, $C_1$-$C_4$ heteroalkyl or $C_3$-$C_6$ heterocycloalkyl;

each $R^{12}$ is independently selected from the group consisting of $C_1$-$C_4$ alkyl, $C_1$-$C_4$ deuteroalkyl, $C_1$-$C_4$ fluoroalkyl, $C_1$-$C_4$ heteroalkyl, substituted or unsubstituted $C_3$-$C_6$ cycloalkyl, substituted or unsubstituted $C_3$-$C_6$ heterocycloalkyl, substituted or unsubstituted phenyl, or substituted or unsubstituted monocyclic heteroaryl;

each $R^{13}$ is independently selected from the group consisting of hydrogen, $C_1$-$C_4$ alkyl, $C_1$-$C_4$ deuteroalkyl, $C_1$-$C_4$ fluoroalkyl, $C_1$-$C_4$ heteroalkyl, substituted or unsubstituted $C_3$-$C_6$ cycloalkyl, substituted or unsubstituted $C_3$-$C_6$ heterocycloalkyl, substituted or unsubstituted phenyl, or substituted or unsubstituted monocyclic heteroaryl.

In some embodiments of Formula (I), when $R^6$ is H, $R^4$ is not cyclohexyl, 4-methylcyclohexyl, or cycloheptyl. In some embodiments, $R^6$ is H and $R^4$ is cis-4-methylcyclohexyl.

In some embodiments, $R^3$ is H or —CH$_3$; $L^1$ is absent, —CH$_2$—, —CH$_2$CH$_2$—, —CH$_2$CH$_2$CH$_2$—, —CH(CH$_3$)—, —C(CH$_3$)$_2$—, or cyclopropyl-1,1-diyl; $R^{10}$ and $R^{11}$ are independently selected from H or —CH$_3$; or $R^{10}$ and $R^{11}$ are taken together with the carbon atom to which they are attached to form a cyclopropyl-1,1-diyl; $X^1$ is N; and $X^2$ is CR$^8$; or $X^1$ is CR$^8$; and $X^2$ is N.

In some embodiments, $R^1$ is —OH, —CH$_3$, —OCH$_3$, —CD$_3$, —OCD$_3$, —CFH$_2$, —CHF$_2$, —CF$_3$, —OCFH$_2$, —OCHF$_2$, —OCF$_3$, cyclopropyl, aziridinyl, azetidinyl, oxetanyl, thietanyl, pyrrolidinyl, morpholinyl, thiomorpholinyl, piperazinyl, or piperidinyl. In some embodiments, $R^1$ is —OH, —CH$_3$, —OCH$_3$, —OC(CH$_3$)$_2$, —CD$_3$, —OCD$_3$, —CFH$_2$, —CHF$_2$, —CF$_3$, —OCFH$_2$, —OCHF$_2$, —OCF$_3$, cyclopropyl, aziridinyl, azetidinyl, oxetanyl, thietanyl, pyrrolidinyl, morpholinyl, thiomorpholinyl, piperazinyl, or piperidinyl.

In some embodiments, $R^1$ is —OH or —CH$_3$. In some embodiments, $R^1$ is —O—$C_1$-$C_3$alkyl.

In some embodiments, the compound of Formula (I) has the following structure of Formula (II), or a pharmaceutically acceptable salt, solvate or stereoisomer thereof:

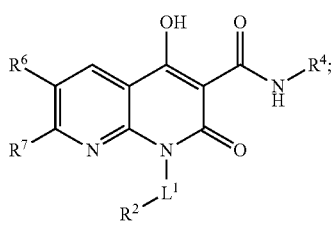

Formula (II)

wherein $L^1$, $R^2$, $R^4$, $R^6$, and $R^7$ are as defined in some or any embodiments of Formula (I).

In some embodiments, $R^5$ is a ring B that is unsubstituted or is substituted with 1, 2, 3, or 4 $R^b$; ring B is a monocyclic $C_3$-$C_8$ cycloalkyl, or bicyclic $C_5$-$C_{12}$ cycloalkyl that is a fused bicyclic $C_5$-$C_{12}$ cycloalkyl, bridged bicyclic $C_5$-$C_{12}$ cycloalkyl, or spiro bicyclic $C_5$-$C_{12}$ cycloalkyl; or ring B is a monocyclic $C_2$-$C_6$ heterocycloalkyl, or bicyclic $C_5$-$C_8$ heterocycloalkyl that is a fused bicyclic $C_5$-$C_8$ heterocycloalkyl, bridged bicyclic $C_5$-$C_8$ heterocycloalkyl, or spiro bicyclic $C_5$-$C_8$ heterocycloalkyl; or ring B is a phenyl; or ring B is a monocyclic heteroaryl selected from furanyl, thienyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl.

In some embodiments, $L^2$ is absent; $R^5$ is a ring B that is unsubstituted or is substituted with 1, 2, 3, or 4 $R^b$; ring B is a monocyclic $C_3$-$C_8$ cycloalkyl, or bicyclic $C_5$-$C_{12}$ cycloalkyl that is a fused bicyclic $C_5$-$C_{12}$ cycloalkyl, bridged bicyclic $C_5$-$C_{12}$ cycloalkyl, or spiro bicyclic $C_5$-$C_{12}$ cycloalkyl; or ring B is a monocyclic $C_3$-$C_6$ heterocycloalkyl, or bicyclic $C_5$-$C_8$ heterocycloalkyl that is a fused bicyclic $C_5$-$C_8$ heterocycloalkyl, bridged bicyclic $C_5$-$C_8$ heterocycloalkyl, or spiro bicyclic $C_5$-$C_8$ heterocycloalkyl.

In some embodiments, $L^2$ is absent; $R^5$ is a ring B that is unsubstituted or is substituted with 1, 2, 3, or 4 $R^b$; ring B is cyclobutyl, cyclopentyl, or cyclohexyl; or ring B is a bicyclic $C_5$-$C_{12}$ cycloalkyl that is a spiro[2.2]pentanyl, spiro[3.3]heptanyl, spiro[4.3]octanyl, spiro[3.4]octanyl, spiro[3.5]nonanyl, spiro[4.4]nonanyl, spiro[4.5]decanyl, spiro[5.4]decanyl, spiro[5.5]undecanyl, bicyclo[1.1.1]pentanyl, bicyclo[2.2.2]octanyl, bicyclo[2.2.1]heptanyl, adamantyl, or decalinyl.

In some embodiments, $L^2$ is absent; $R^5$ is a ring B that is unsubstituted or is substituted with 1, 2, 3, or 4 $R^b$; ring B is cyclobutyl, cyclopentyl, or cyclohexyl; or ring B is spiro[3.3]heptanyl, bicyclo[1.1.1]pentanyl, or bicyclo[2.2.2]octanyl.

In some embodiments, $L^2$ is absent; $R^5$ is a ring B that is unsubstituted or is substituted with 1, 2, 3, or 4 $R^b$; ring B is

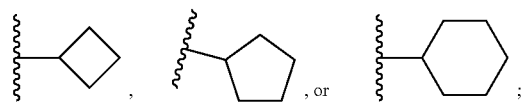 [SMILES: *C1CCC1 ; *C1CCCC1 ; *C1CCCCC1]

or ring B is

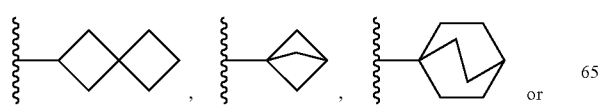

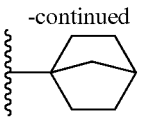

In some embodiments, $R^4$ is

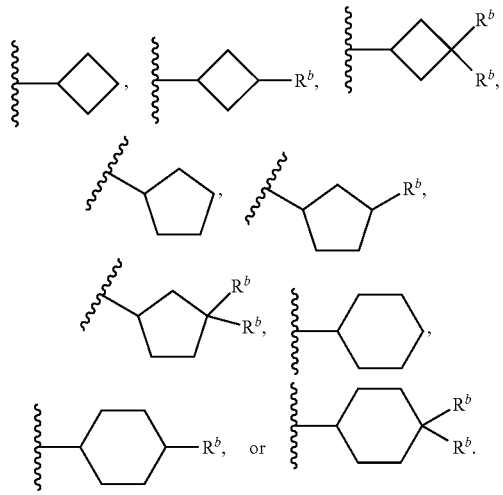

In some embodiments, each $R^b$ is independently selected from the group consisting of F, Cl, Br, —CN, —OH, —NH$_2$, —NH(CH$_3$), —N(CH$_3$)$_2$, —CH$_3$, —OCH$_3$, —CD$_3$, —OCD$_3$, —CFH$_2$, —CHF$_2$, —CF$_3$, —OCFH$_2$, —OCHF$_2$, and —OCF$_3$; or two $R^b$ that are attached to the same carbon atom are taken together with the carbon atom to form a cyclopropyl, cyclobutyl, cyclopentyl, cyclohexyl, azetidinyl, oxetanyl, thietanyl, pyrrolidinyl, thiomorpholinyl, or piperidinyl.

In some embodiments, $R^4$ is

In some embodiments $R^4$ is

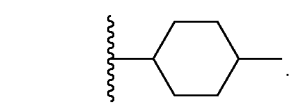

In some embodiments, $R^4$ is
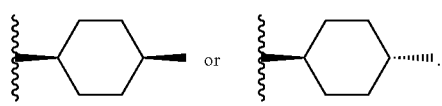
In some embodiments $R^4$ is
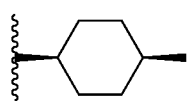
In some embodiments for any Formula described herein, $R^4$ is
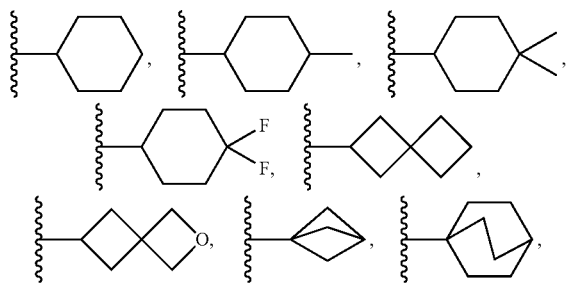
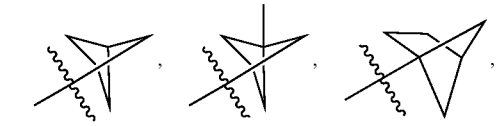
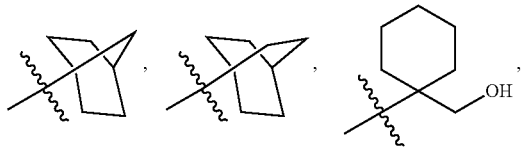
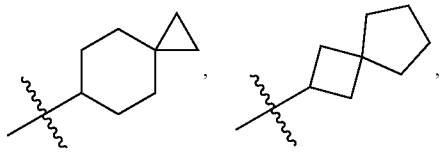
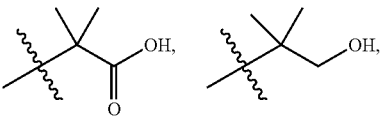
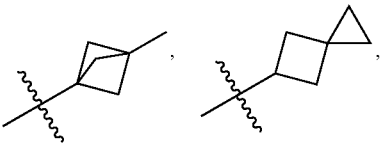
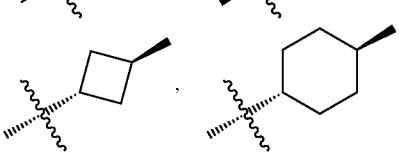
-continued
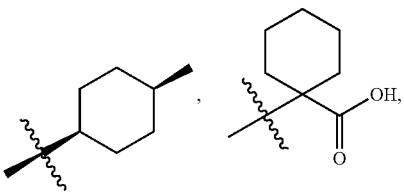
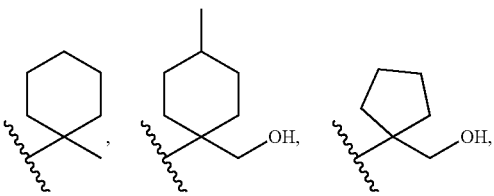
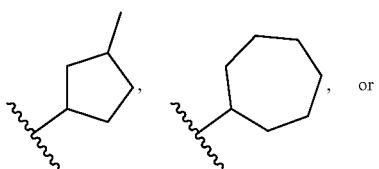
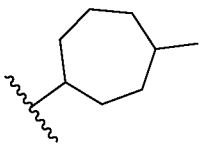
In some embodiments, for any Formula described herein, $R^4$ is
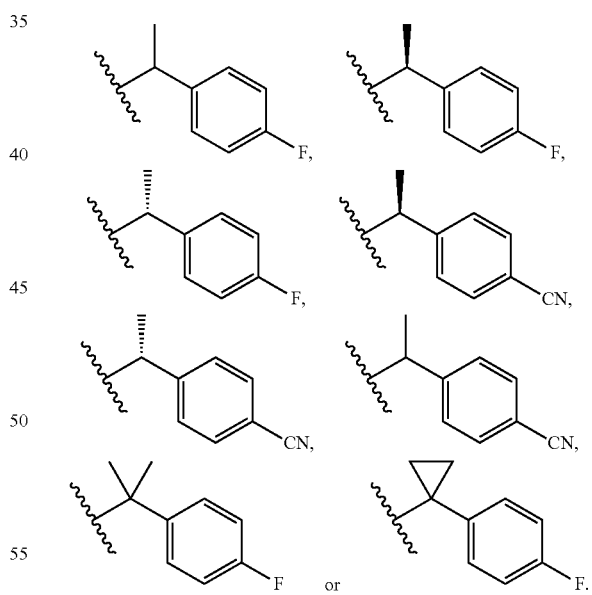
In some embodiments, for any Formula described herein, $R^4$ is a bridged $C_5$-$C_{12}$ cycloalkyl selected from
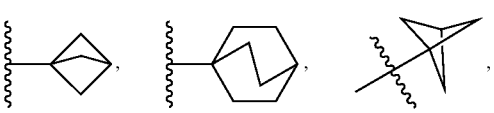

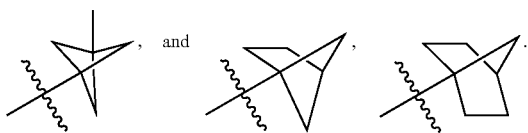

In some embodiments, L² is absent or —CR¹⁰R¹¹—; R¹⁰ and R¹¹ are independently selected from H or —CH₃; or R¹⁰ and R¹¹ are taken together with the carbon atom to which they are attached to form a cyclopropyl-1,1-diyl; R⁵ is a ring B that is unsubstituted or is substituted with 1, 2, 3, or 4 R$^b$; ring B is phenyl or monocyclic heteroaryl.

In some embodiments, ring B is phenyl, pyridinyl, pyrimidinyl, pyrazinyl, or pyridazinyl.

In some embodiments, L² is absent or —CR¹⁰R¹¹—; R¹⁰ and R¹¹ are independently selected from H or —CH₃; or R¹⁰ and R¹¹ are taken together with the carbon atom to which they are attached to form a cyclopropyl-1,1-diyl; R⁵ is

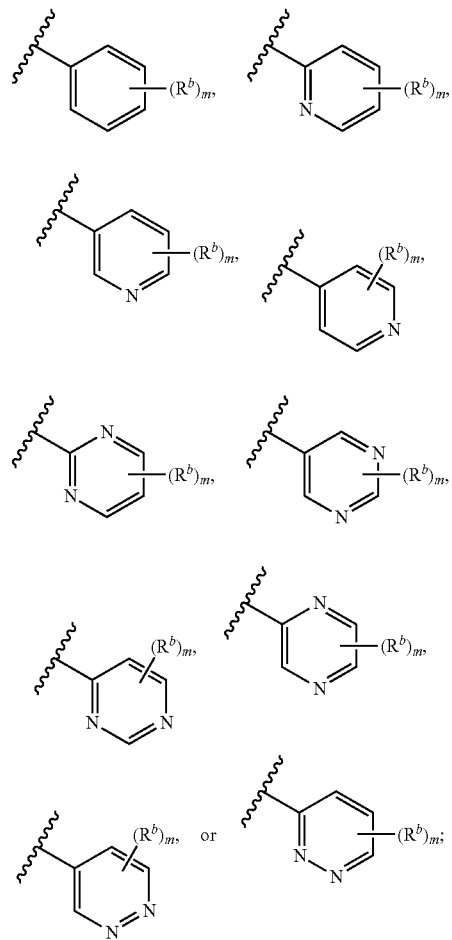

m is 0, 1, or 2.

In some embodiments, each R$^b$ is independently selected from the group consisting of F, Cl, Br, —CN, —OH, —NH₂, —NH(CH₃), —N(CH₃)₂, —CH₃, —OCH₃, —CD₃, —OCD₃, —CFH₂, —CHF₂, —CF₃, —OCFH₂, —OCHF₂, and —OCF₃.

In some embodiments, R⁴ is

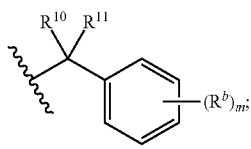

R¹⁰ and R¹¹ are independently selected from H or —CH₃; or R¹⁰ and R¹¹ are taken together with the carbon atom to which they are attached to form a cyclopropyl-1,1-diyl; m is 0, 1, or 2; each R$^b$ is independently selected from the group consisting of F, Cl, Br, —CN, —OH, —NH₂, —NH(CH₃), —N(CH₃)₂, —CH₃, —OCH₃, —CD₃, —OCD₃, —CFH₂, —CHF₂, —CF₃, —OCFH₂, —OCHF₂, and —OCF₃.

In some embodiments, L¹ is —CH₂CH₂—; R² is a ring A that is unsubstituted or is substituted with 1, 2, 3, or 4 R$^a$; ring A is C₃-C₆ heterocycloalkyl containing 1-2 N atoms and 0 or 1 O or S atom, or C₄-C₇ heterocycloalkyl containing 0 or 1 N atom and 1 O or S atom; R⁶ is a ring C that is unsubstituted or is substituted with 1, 2, 3, or 4 R$^c$; ring C is phenyl, naphthyl, heteroaryl, C₃-C₁₂ cycloalkyl, or C₃-C₆ heterocycloalkyl.

In some embodiments, L¹ is —CH₂CH₂—; R² is a ring A that is unsubstituted or is substituted with 1, 2, 3, or 4 R$^a$; ring A is azetidinyl, pyrrolidinyl, morpholinyl, thiomorpholinyl, piperidinyl, or piperazinyl. In some embodiments, for any Formula described herein, -L¹-R² is

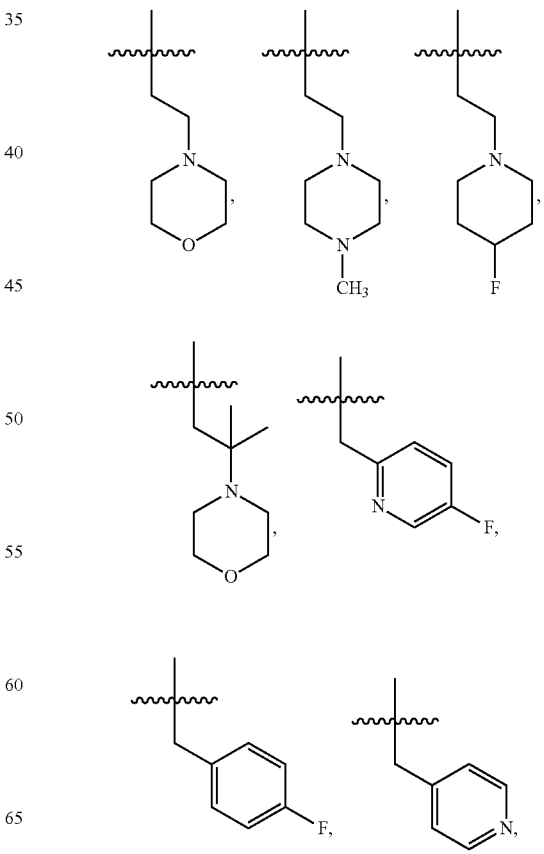

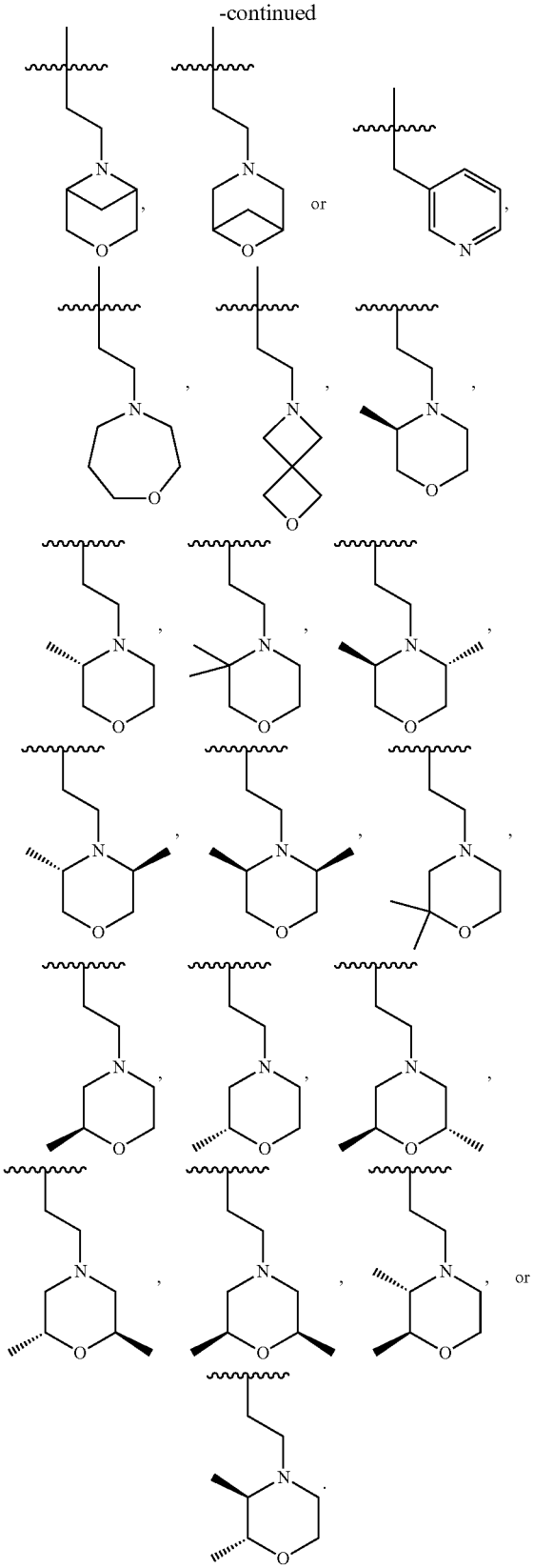

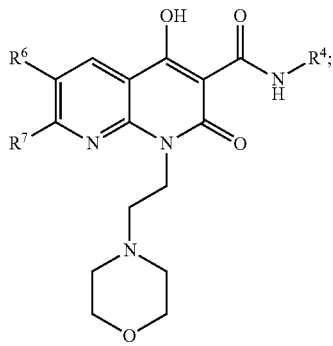

Formula (III)

wherein $R^4$, $R^6$, and $R^7$ are as defined in some or any embodiments of Formula (I).

In some embodiments, $R^6$ is a ring C that is unsubstituted or is substituted with 1, 2, 3, or 4 $R^c$; ring C is phenyl, pyridinyl, pyrimidinyl, pyrazinyl, pyridazinyl, cyclopropyl, cyclobutyl, cyclopentyl, cyclohexyl, azetidinyl, oxetanyl, thietanyl, pyrrolidinyl, thiomorpholinyl, or piperidinyl.

In some embodiments, $R^6$ is

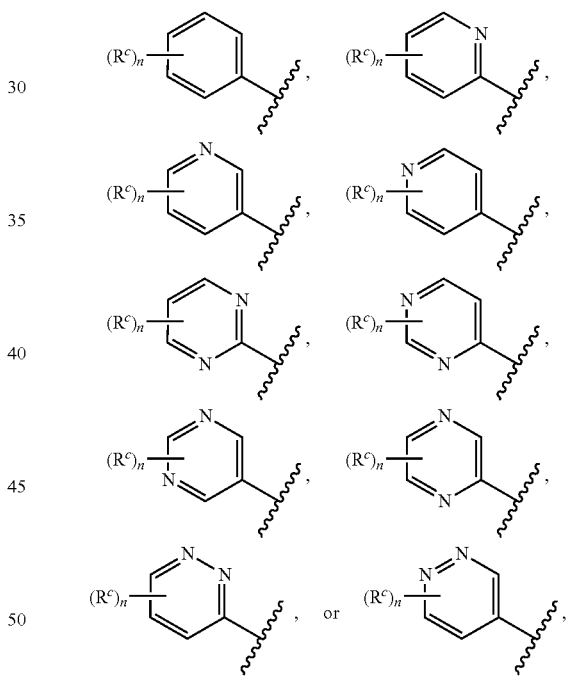

n is 0, 1, or 2.

In some embodiments, each $R^c$ is independently selected from the group consisting of F, Cl, Br, —CN, —OH, —OCH$_3$, —OCD$_3$, —OCFH$_2$, —OCHF$_2$, —OCF$_3$, —O-cyclopropyl, —S(=O)$_2$CH$_3$, —S(=O)$_2$NH$_2$, —S(=O)$_2$NH(CH$_3$), —S(=O)$_2$N(CH$_3$)$_2$, —NHS(=O)$_2$CH$_3$, —NH$_2$, —NH(CH$_3$), —N(CH$_3$)$_2$, —OC(=O)CH$_3$, —CO$_2$H, —CO$_2$CH$_3$, —CO$_2$CH$_2$CH$_3$, —C(=O)N(R$^{15}$)$_2$, —C(=O)—NH$_2$, —C(=O)NH(CH$_3$), —C(=O)N(CH$_3$)$_2$, —NHC(=O)CH$_3$, —CH$_3$, —CH$_2$CH$_3$, —CH(CH$_3$)$_2$, —C(CH$_3$)$_3$, —CD$_3$, —CFH$_2$, —CHF$_2$, —CF$_3$, —CH=CH$_2$, —C(CH$_3$)=CH$_2$, —CH=CH, —CH=CCH$_3$, cyclopropyl, or oxetanyl.

In some embodiments, the compound of Formula (I) has the following structure of Formula (III), or a pharmaceutically acceptable salt, solvate or stereoisomer thereof:

In some embodiments, for any Formula described herein, $R^6$ is

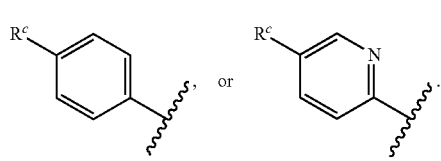

In some of such embodiments, $R^c$ is CN, $CH_3$, F, $O-C_1$-$C_3$alkyl or $O-C_1$-$C_3$haloalkyl. In some embodiments, $R^6$ is

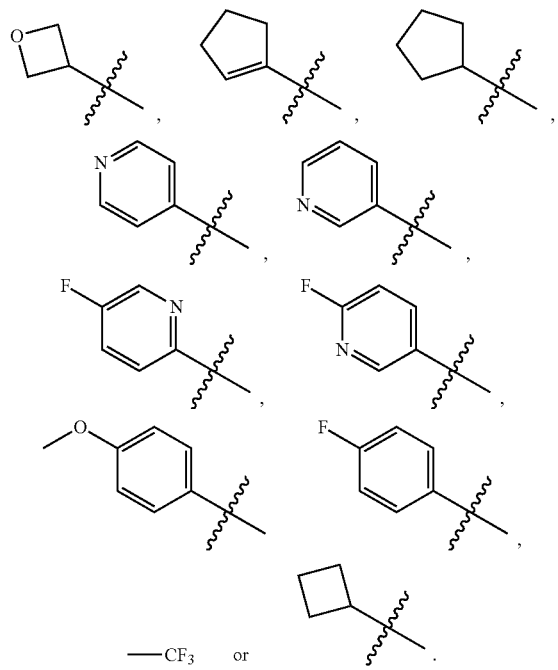

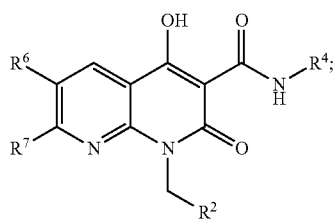

In some embodiments, $R^6$ is not H. In some embodiments, $R^6$ is halo.

In some embodiments, the compound of Formula (I) has the following structure of Formula (IV), or a pharmaceutically acceptable salt, solvate or stereoisomer thereof:

Formula (IV)

[Structure of Formula (IV)]

wherein $R^2$, $R^4$, $R^6$, and $R^7$ are as defined in some or any embodiments of Formula (I).

In some embodiments, $L^1$ is $-CH_2-$, $-CH(CH_3)-$, $-C(CH_3)_2-$, or cyclopropyl-1,1-diyl; $R^2$ is a ring A that is unsubstituted or is substituted with 1, 2, 3, or 4 $R^a$; ring A is phenyl, or 6-membered heteroaryl.

In some embodiments, $R^2$ is

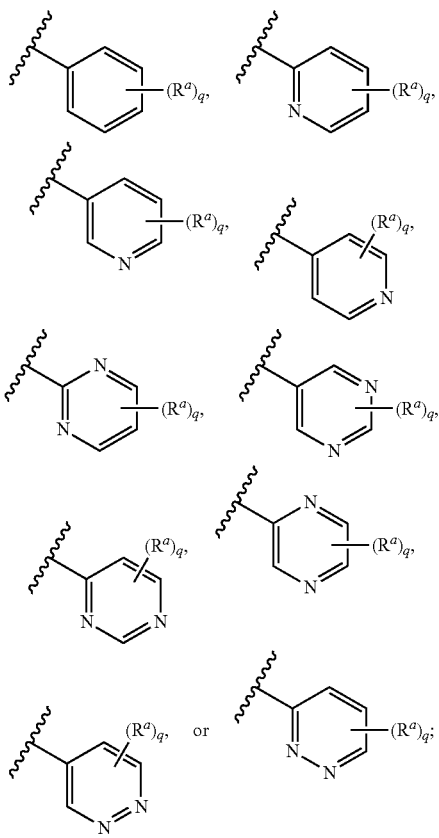

q is 0, 1, or 2.

In some embodiments, $R^2$ is

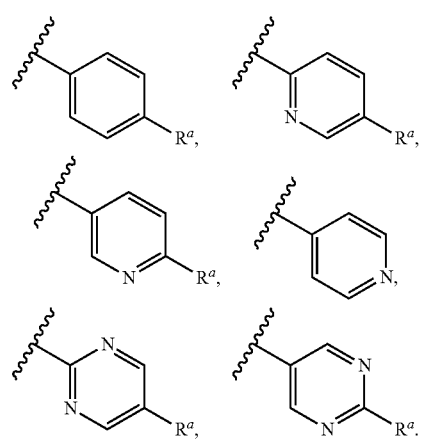

In some embodiments, each $R^a$ is independently selected from the group consisting of F, Cl, Br, $-CN$, $-OH$, $-OCH_3$, $-OCD_3$, $-OCFH_2$, $-OCHF_2$, $-OCF_3$, $-O$-cyclopropyl, $-S(=O)_2CH_3$, $-NH_2$, $-NH(CH_3)$, $-N(CH_3)_2$, $-CH_3$, $-CH_2CH_3$, $-CH(CH_3)_2$, $-C(CH_3)_3$, $-CD_3$, $-CFH_2$, $-CHF_2$, $-CF_3$, cyclopropyl, or oxetanyl.

In some embodiments, for any Formula described herein, $R^6$ is H, F, Cl, Br, $-CN$, $-OH$, $-OCH_3$, $-OCD_3$, $-OCFH_2$, $-OCHF_2$, $-OCF_3$, $-O$-cyclopropyl, $-S(=O)_2CH_3$, $-S(=O)_2NH_2$, $-S(=O)_2NH(CH_3)$, —S(=O)₂N(CH₃)₂, —NHS(=O)₂CH₃, —NH₂, —NH (CH₃), —N(CH₃)₂, —OC(=O)CH₃, —CO₂H, —CO₂CH₃, —CO₂CH₂CH₃, —C(=O)N(R¹⁵)₂, —C(=O)—NH₂, —C(=O)NH(CH₃), —C(=O)N(CH₃)₂, —NHC(=O)CH₃, —CH₃, —CH₂CH₃, —CH(CH₃)₂, —C(CH₃)₃, —CD₃, —CFH₂, —CHF₂, —CF₃, —CH=CH₂, —C(CH₃)=CH₂, —CH=CH, —CH=CCH₃, cyclopropyl, or oxetanyl.

In some embodiments, for any Formula described herein, $R^6$ is H, F, Cl, Br, —CN, —OH, —OCH₃, —OCD₃, —OCFH₂, —OCHF₂, —OCF₃, —O-cyclopropyl, —S(=O)₂CH₃, —CH₃, —CH₂CH₃, —CH(CH₃)₂, —C(CH₃)₃, —CD₃, —CFH₂, —CHF₂, —CF₃, —CH=CH₂, —C(CH₃)=CH₂, cyclopropyl, or oxetanyl.

In another aspect, described herein is a compound that has the structure of Formula (X), or a pharmaceutically acceptable salt, solvate or stereoisomer thereof:

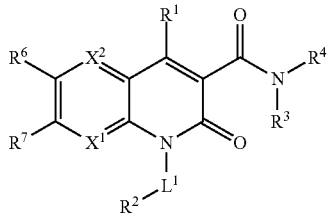

Formula (X)

wherein,
$R^1$ is hydrogen, —OH, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, $C_3$-$C_6$ cycloalkyl, $C_3$-$C_6$ heterocycloalkyl containing 1 N atom and 0 or 1 O or S atom, or a $C_3$-$C_6$ heterocycloalkyl containing 0 or 1 N atom and 1 O or S atom;

$L^1$ is absent, $C_1$-$C_4$ alkylene, or $C_3$-$C_5$ cycloalkylene;

$R^2$ is a ring A that is unsubstituted or is substituted with 1, 2, 3, or 4 $R^a$;
ring A is $C_3$-$C_6$ heterocycloalkyl containing 1-2 N atom and 0 or 1 O or S atom, $C_3$-$C_6$ heterocycloalkyl containing 0 or 1 N atom and 1 O or S atom, phenyl, $C_3$-$C_{10}$ cycloalkyl, 5-membered heteroaryl, or 6-membered heteroaryl;

each $R^a$ is independently selected from the group consisting of halogen, —CN, —OH, —OR¹², —SR¹², —S(=O)R¹², —S(=O)₂R¹², —S(=O)₂N(R¹³)₂, —NR¹³S(=O)₂R¹², —N(R¹³)₂, —OC(=O)(R¹²), —CO₂R¹³, —C(=O)N(R¹³)₂, —NR¹³C(=O)(R¹²), —NR¹³C(=O)O(R¹²), —OC(=O)N(R¹³)₂, —NR¹³C(=O)N(R¹³)₂, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, or substituted or unsubstituted monocyclic $C_3$-$C_6$ heterocycloalkyl;

$R^3$ is H or $C_1$-$C_4$ alkyl;

$R^4$ is

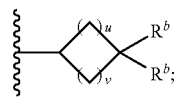

u is 1 or 2; v is 1 or 2;
or $R^4$ is -$L^2$-$R^5$;
$L^2$ is absent or —CR¹⁰R¹¹—;

$R^{10}$ is —CH₃;
$R^{11}$ is H or —CH₃;
or $R^{10}$ and $R^{11}$ are taken together with the carbon atom to which they are attached to form a cyclopropyl-1,1-diyl;

$R^5$ is a ring B that is unsubstituted or is substituted with 1, 2, 3, or 4 $R^b$;
ring B is bridged $C_5$-$C_{12}$ cycloalkyl, phenyl, naphthyl, or heteroaryl;
each $R^b$ is independently selected from the group consisting of halogen, —CN, —OH, —N(R¹³)₂, —OC(=O)(R¹²), —CO₂R¹³, —C(=O)N(R¹³)₂, —NR¹³C(=O)(R¹²), —NR¹⁵C(=O)O(R¹²), —OC(=O)N(R¹³)₂, —NR¹³C(=O)N(R¹³)₂, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, or substituted or unsubstituted monocyclic $C_3$-$C_6$ heterocycloalkyl;
or two $R^b$ that are attached to the same carbon atom are taken together with the carbon atom to form a $C_3$-$C_6$ cycloalkyl or a $C_3$-$C_6$ heterocycloalkyl;

$R^6$ is a ring C that is unsubstituted or is substituted with 1, 2, 3, or 4 $R^c$; ring C is phenyl, naphthyl, heteroaryl, $C_3$-$C_{12}$ cycloalkyl, or $C_2$-$C_{10}$ heterocycloalkyl;
or $R^6$ is hydrogen, halogen, —CN, —OH, —OR¹², —SR¹², —S(=O)R¹², —S(=O)₂R¹², —S(=O)₂N(R¹³)₂, —NR¹³S(=O)₂R¹², —N(R¹³)₂, —OC(=O)(R¹²), —CO₂R¹³, —C(=O)N(R¹³)₂, —NR¹⁵C(=O)(R¹²), —NR¹³C(=O)O(R¹²), —OC(=O)N(R¹³)₂, —NR¹³C(=O)N(R¹³)₂, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, or substituted or unsubstituted monocyclic $C_3$-$C_6$ heterocycloalkyl;

each $R^c$ is independently selected from the group consisting of halogen, —CN, —OH, —OR¹², —SR¹², —S(=O)R¹², —S(=O)₂R¹², —S(=O)₂N(R¹³)₂, —NR¹³S(=O)₂R¹², —N(R¹³)₂, —OC(=O)(R¹²), —CO₂R¹³, —C(=O)N(R¹³)₂, —NR¹³C(=O)(R¹²), —NR¹³C(=O)O(R¹²), —OC(=O)N(R¹³)₂, —NR¹³C(=O)N(R¹³)₂, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, substituted or unsubstituted $C_3$-$C_6$ cycloalkyl, substituted or unsubstituted $C_3$-$C_6$ heterocycloalkyl, substituted or unsubstituted phenyl, substituted or unsubstituted monocyclic heteroaryl or a 1,4-dioxanyl ring fused to ring C;

$R^7$ is H, halogen, —CN, —OH, —N(R¹³)₂, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, or $C_1$-$C_4$ heteroalkyl;

$X^1$ is N; and $X^2$ is $CR^8$ or N;
or $X^1$ is $CR^8$ or N; and $X^2$ is N;
$R^8$ is H, halogen, —CN, —OH, —N(R¹³)₂, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, or $C_1$-$C_4$ heteroalkyl;

each $R^{12}$ is independently selected from the group consisting of $C_1$-$C_4$ alkyl, $C_1$-$C_4$ deuteroalkyl, $C_1$-$C_4$ fluoroalkyl, $C_1$-$C_4$ heteroalkyl, substituted or unsubstituted $C_3$-$C_6$ cycloalkyl, substituted or unsubstituted $C_3$-$C_6$ heterocycloalkyl, substituted or unsubstituted phenyl, or substituted or unsubstituted monocyclic heteroaryl;

each $R^{13}$ is independently selected from the group consisting of hydrogen, $C_1$-$C_4$ alkyl, $C_1$-$C_4$ deuteroalkyl, $C_1$-$C_4$ fluoroalkyl, $C_1$-$C_4$ heteroalkyl, substituted or unsubstituted $C_3$-$C_6$ cycloalkyl, substituted or unsubstituted $C_3$-$C_6$ heterocycloalkyl, substituted or unsubstituted phenyl, or substituted or unsubstituted monocyclic heteroaryl.

In some embodiments of Formula (X), when $R^1$ is H, $R^4$ is not cyclohexyl substituted by 0, 1, 2, 3 or 4 methyl groups. In some embodiments, the bridged cycloalkyl is bridged bicyclic $C_5$-$C_{12}$ cycloalkyl.

In some embodiments, $R^3$ is H or —$CH_3$; $L^1$ is absent, —$CH_2$—, —$CH_2CH_2$—, —$CH_2CH_2CH_2$—, —$CH(CH_3)$—, —$C(CH_3)_2$—, or cyclopropyl-1,1-diyl; $X^1$ is N; and $X^2$ is $CR^8$; or $X^1$ is $CR^8$; and $X^2$ is N.

In some embodiments, $R^1$ is hydrogen, —OH, —$CH_3$, —$OCH_3$, —$CD_3$, —$OCD_3$, —$CFH_2$, —$CHF_2$, —$CF_3$, —$OCFH_2$, —$OCHF_2$, —$OCF_3$, cyclopropyl, aziridinyl, azetidinyl, oxetanyl, thietanyl, pyrrolidinyl, morpholinyl, thiomorpholinyl, piperazinyl or piperidinyl.

In some embodiments, $R^1$ is hydrogen, —OH or —$CH_3$.

In some embodiments, the compound of Formula (X) has the following structure of Formula (XI), or a pharmaceutically acceptable salt, solvate or stereoisomer thereof:

Formula (XI)

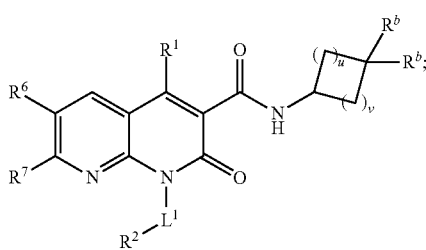

wherein $L^1$, $R^b$, u, v, $R^1$, $R^2$, $R^4$, $R^6$, and $R^7$ are as defined in some or any embodiments of Formula (X).

In some embodiments,

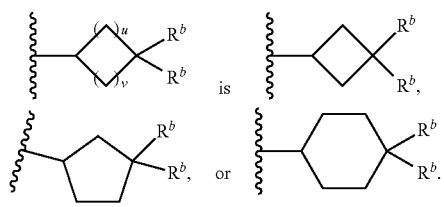

In some embodiments,

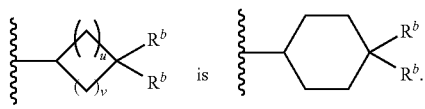

In some embodiments, each $R^b$ is independently selected from the group consisting of F, Cl, Br, —CN, —OH, —$NH_2$, —$NH(CH_3)$, —$N(CH_3)_2$, —$CH_3$, —$OCH_3$, —$CD_3$, —$OCD_3$, —$CFH_2$, —$CHF_2$, —$CF_3$, —$OCFH_2$, —$OCHF_2$, and —$OCF_3$; or two $R^b$ that are attached to the same carbon atom are taken together with the carbon atom to form a cyclopropyl, cyclobutyl, cyclopentyl, cyclohexyl, azetidinyl, oxetanyl, thietanyl, pyrrolidinyl, thiomorpholinyl, or piperidinyl.

In some embodiments,

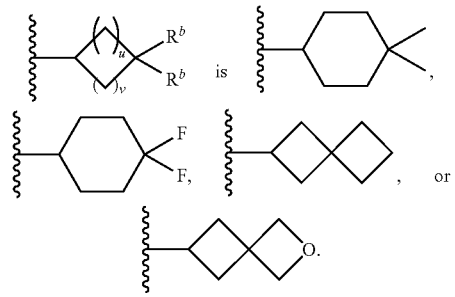

In some embodiments, the compound of Formula (X) has the following structure of Formula (XII), or a pharmaceutically acceptable salt, solvate or stereoisomer thereof:

Formula (XII)

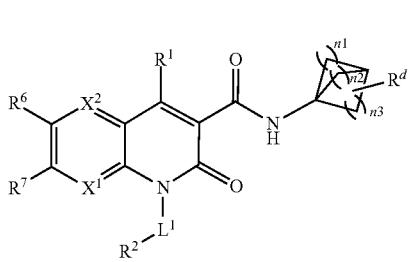

wherein $X^1$, $X^2$, $L^1$, $R^1$, $R^2$, $R^6$, and $R^7$ are as defined in some or any embodiments of Formula (X); n1, n2, and n3 are each independently 1, 2 or 3; and $R^d$ is halogen, —CN, —OH, —$N(R^{13})_2$, —$OC(=O)(R^{12})$, —$CO_2R^{13}$, —$C(=O)N(R^{13})_2$, —$NR^{13}C(=O)(R^{12})$, —$NR^{15}C(=O)O(R^{12})$, —$OC(=O)N(R^{13})_2$, —$NR^{13}C(=O)N(R^{13})_2$, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, or substituted or unsubstituted monocyclic $C_3$-$C_6$ heterocycloalkyl.

In some embodiments, the compound of Formula (X) has the following structure of Formula (XIII), or a pharmaceutically acceptable salt, solvate or stereoisomer thereof:

Formula (XIII)

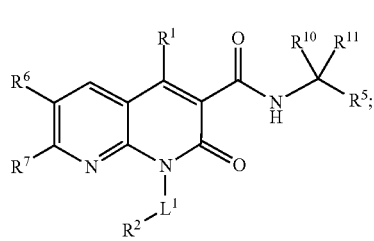

wherein $L^1$, $R^1$, $R^2$, $R^5$, $R^6$, $R^7$, $R^{10}$ and $R^{11}$ are as defined in some or any embodiments of Formula (X).

In some embodiments, $R^5$ is a ring B that is unsubstituted or is substituted with 1, 2, 3, or 4 $R^b$; ring B is phenyl or monocyclic heteroaryl.

In some embodiments, $R^5$ is a ring B that is unsubstituted or is substituted with 1, 2, 3, or 4 $R^b$; or ring B is phenyl, furanyl, thienyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, ring B is phenyl, pyridinyl, pyrimidinyl, pyrazinyl, or pyridazinyl.

In some embodiments, $R^5$ is

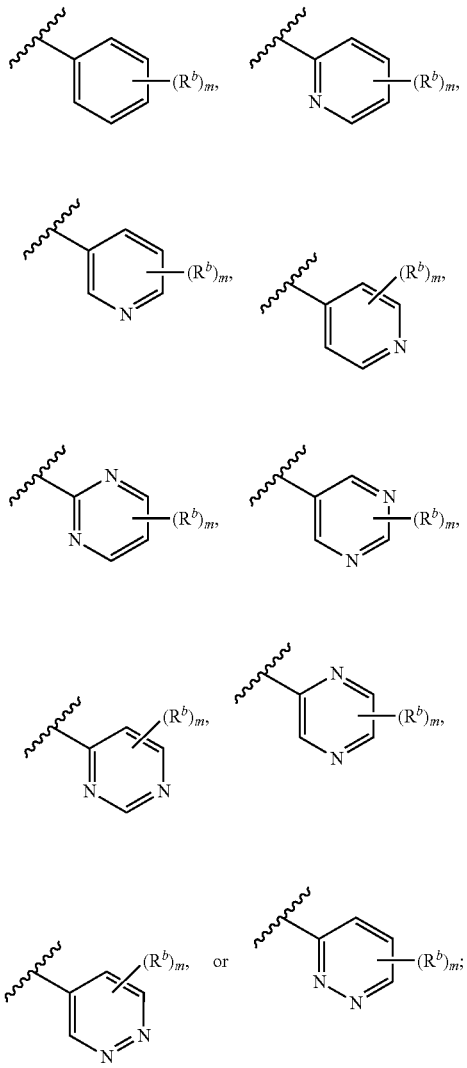

m is 0, 1, or 2.

In some embodiments, each $R^b$ is independently selected from the group consisting of F, Cl, Br, —CN, —OH, —NH$_2$, —NH(CH$_3$), —N(CH$_3$)$_2$, —CH$_3$, —OCH$_3$, —CD$_3$, —OCD$_3$, —CFH$_2$, —CHF$_2$, —CF$_3$, —OCFH$_2$, —OCHF$_2$, and —OCF$_3$.

In some embodiments, $L^1$ is —CH$_2$CH$_2$—; $R^2$ is a ring A that is unsubstituted or is substituted with 1, 2, 3, or 4 $R^a$; ring A is $C_3$-$C_6$ heterocycloalkyl containing 1-2 N atoms and 0 or 1 O or S atom, or $C_3$-$C_6$ heterocycloalkyl containing 0 or 1 N atom and 1 O or S atom; $R^6$ is a ring C that is unsubstituted or is substituted with 1, 2, 3, or 4 $R^c$; ring C is phenyl, naphthyl, heteroaryl, $C_3$-$C_{12}$ cycloalkyl, or $C_2$-$C_{10}$ heterocycloalkyl.

In some embodiments, $L^1$ is —CH$_2$CH$_2$—; $R^2$ is a ring A that is unsubstituted or is substituted with 1, 2, 3, or 4 $R^a$; ring A is azetidinyl, pyrrolidinyl, morpholinyl, thiomorpholinyl, piperidinyl, or piperazinyl.

In some embodiments, the compound of Formula (X) has the following structure of Formula (XIA), or a pharmaceutically acceptable salt, solvate or stereoisomer thereof:

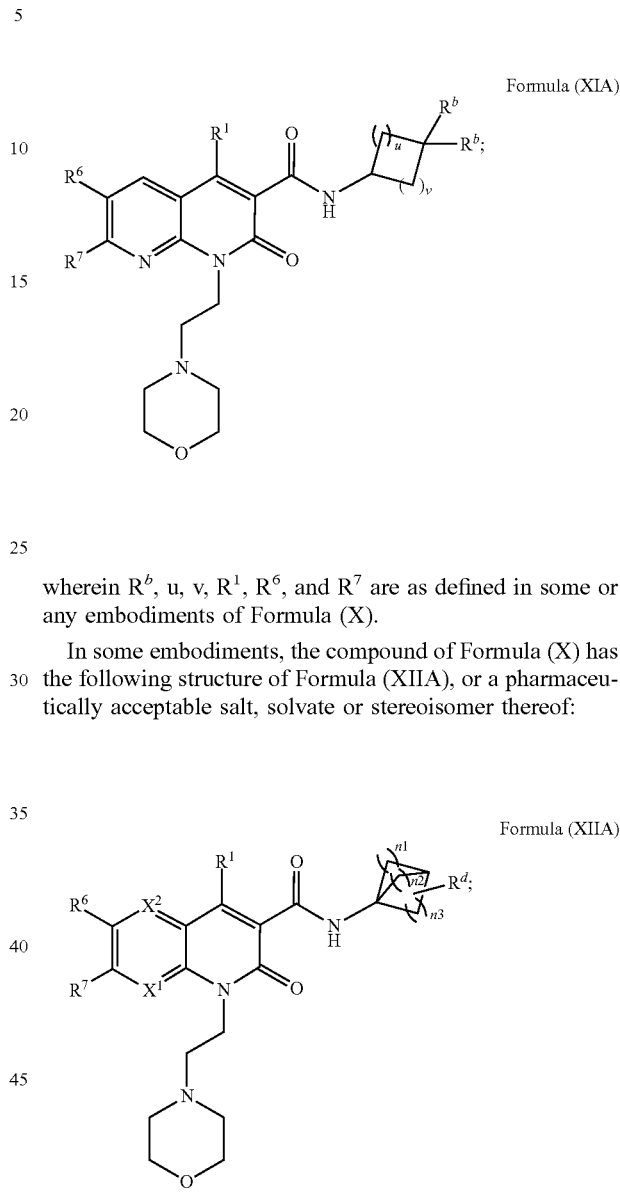

Formula (XIA)

wherein $R^b$, u, v, $R^1$, $R^6$, and $R^7$ are as defined in some or any embodiments of Formula (X).

In some embodiments, the compound of Formula (X) has the following structure of Formula (XIIA), or a pharmaceutically acceptable salt, solvate or stereoisomer thereof:

Formula (XIIA)

wherein $X^1$, $X^2$, $R^1$, $R^6$, and $R^7$ are as defined in some or any embodiments of Formula (X); n1, n2, and n3 are each independently 1, 2 or 3; and $R^d$ is halogen, —CN, —OH, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{15}$C(=O)O(R$^{12}$), —OC(=O)N(R$^{13}$)$_2$, —NR$^{13}$C(=O)N(R$^{13}$)$_2$, $C_1$-$C_4$ alkyl, $C_2$-$C_4$ alkenyl, $C_2$-$C_4$ alkynyl, $C_1$-$C_4$ alkoxy, $C_1$-$C_4$ deuteroalkyl, $C_1$-$C_4$ deuteroalkoxy, $C_1$-$C_4$ fluoroalkyl, $C_1$-$C_4$ fluoroalkoxy, $C_1$-$C_4$ heteroalkyl, or substituted or unsubstituted monocyclic $C_3$-$C_6$ heterocycloalkyl.

In some embodiments, the compound of Formula (X) has the following structure of Formula (XIIIA), or a pharmaceutically acceptable salt, solvate or stereoisomer thereof:

Formula (XIIIA)

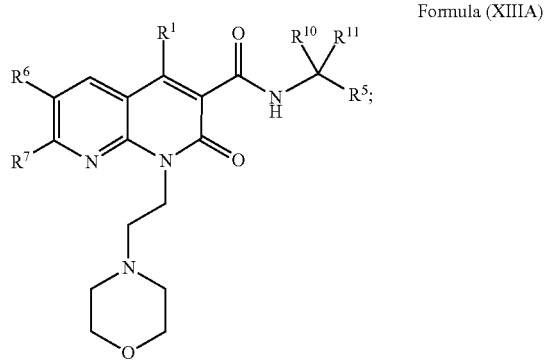

wherein R¹, R⁵, R⁶, R⁷, R¹⁰, and R¹¹, are as defined in some or any embodiments of Formula (X).

In some embodiments, R⁶ is a ring C that is unsubstituted or is substituted with 1, 2, 3, or 4 $R^c$; ring C is phenyl, pyridinyl, pyrimidinyl, pyrazinyl, pyridazinyl, cyclopropyl, cyclobutyl, cyclopentyl, cyclohexyl, azetidinyl, oxetanyl, thietanyl, pyrrolidinyl, thiomorpholinyl, or piperidinyl.

In some embodiments, R⁶ is

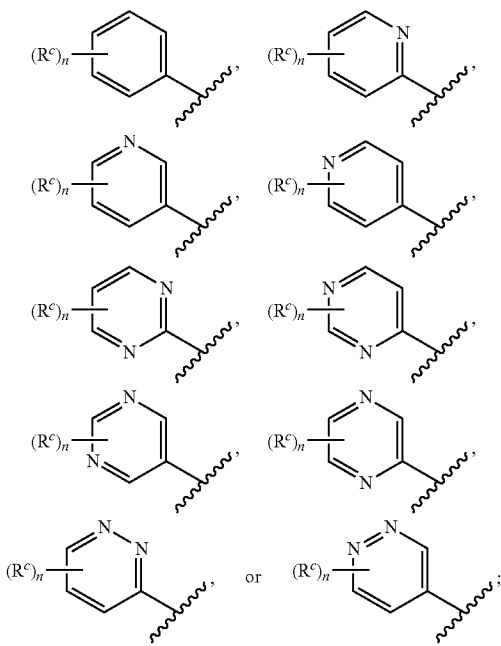

n is 0, 1, or 2.

In some embodiments, each $R^c$ is independently selected from the group consisting of F, Cl, Br, —CN, —OH, —OCH₃, —OCD₃, —OCFH₂, —OCHF₂, —OCF₃, —O-cyclopropyl, —S(=O)₂CH₃, —S(=O)₂NH₂, —S(=O)₂NH(CH₃), —S(=O)₂N(CH₃)₂, —NHS(=O)₂CH₃, —NH₂, —NH(CH₃), —N(CH₃)₂, —OC(=O)CH₃, —CO₂H, —CO₂CH₃, —CO₂CH₂CH₃, —C(=O)N(R¹⁵)₂, —C(=O)—NH₂, —C(=O)NH(CH₃), —C(=O)N(CH₃)₂, —NHC(=O)CH₃, —CH₃, —CH₂CH₃, —CH(CH₃)₂, —C(CH₃)₃, —CD₃, —CFH₂, —CHF₂, —CF₃, —CH=CH₂, —C(CH₃)=CH₂, —CH=CH, —CH=CCH₃, cyclopropyl, or oxetanyl.

In some embodiments, R⁶ is

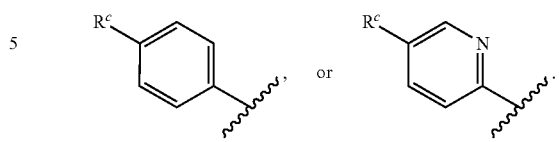

In some embodiments, L¹ is —CH₂—, —CH(CH₃)—, —C(CH₃)₂—, or cyclopropyl-1,1-diyl; R² is a ring A that is unsubstituted or is substituted with 1, 2, 3, or 4 $R^a$; ring A is phenyl, C₃-C₁₀ cycloalkyl, 5-membered heteroaryl, or 6-membered heteroaryl.

In some embodiments, the compound of Formula (X) has the following structure of Formula (XI), or a pharmaceutically acceptable salt, solvate or stereoisomer thereof:

Formula (XIB)

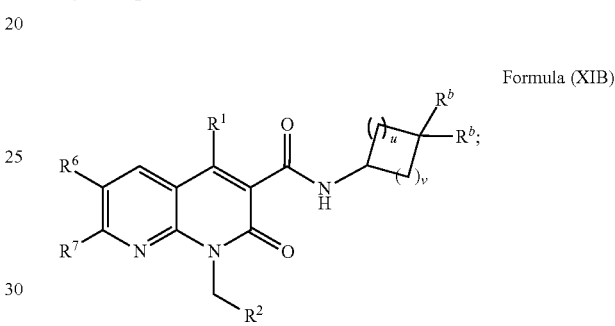

wherein $R^b$, u, v, R¹, R², R⁶, and R⁷ are as defined in some or any embodiments of Formula (X).

In some embodiments, the compound of Formula (X) has the following structure of Formula (XIIB), or a pharmaceutically acceptable salt, solvate or stereoisomer thereof:

Formula (XIIB)

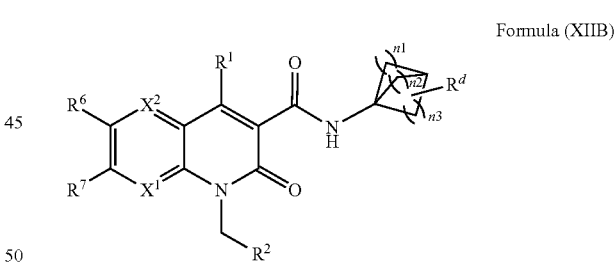

wherein R¹, R², R⁶, and R⁷ are as defined in some or any embodiments of Formula (X); n1, n2, and n3 are each independently 1, 2 or 3; and $R^d$ is halogen, —CN, —OH, —N(R¹³)₂, —OC(=O)(R¹²), —CO₂R¹³, —C(=O)N(R¹³)₂, —NR¹³C(=O)(R¹²), —NR¹⁵C(=O)O(R¹²), —OC(=O)N(R¹³)₂, —NR¹³C(=O)N(R¹³)₂, C₁-C₄ alkyl, C₂-C₄ alkenyl, C₂-C₄ alkynyl, C₁-C₄ alkoxy, C₁-C₄ deuteroalkyl, C₁-C₄ deuteroalkoxy, C₁-C₄ fluoroalkyl, C₁-C₄ fluoroalkoxy, C₁-C₄ heteroalkyl, or substituted or unsubstituted monocyclic C₃-C₆ heterocycloalkyl.

In some embodiments, the compound of Formula (X) has the following structure of Formula (XII), or a pharmaceutically acceptable salt, solvate or stereoisomer thereof:

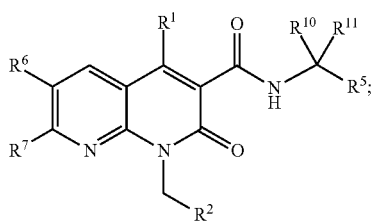

Formula (XIIIB)

wherein $R^1$, $R^5$, $R^6$, $R^7$, $R^{10}$, and $R^{11}$, are as defined in some or any embodiments of Formula (X).

In some embodiments, $R^2$ is

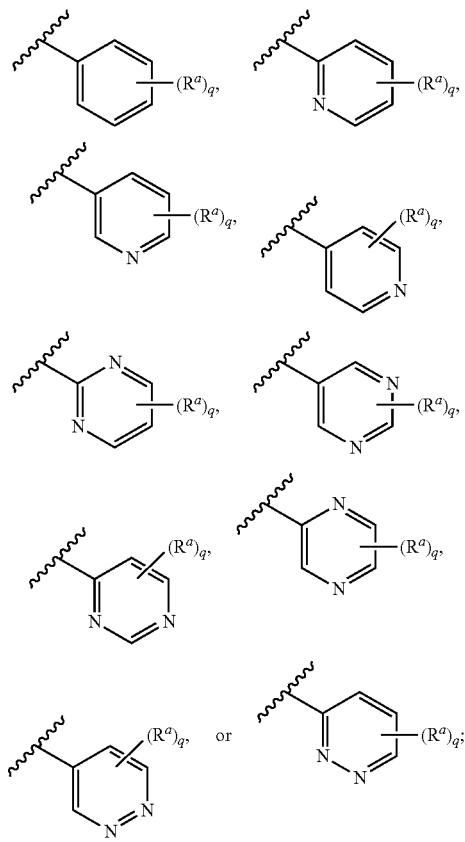

q is 0, 1, or 2.

In some embodiments, $R^2$ is

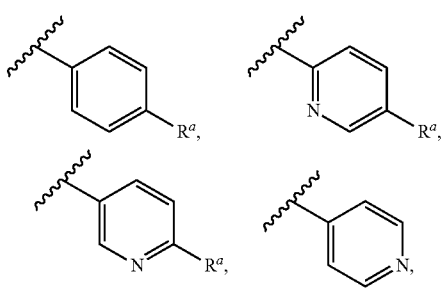

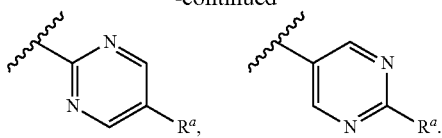

In some embodiments, each $R^a$ is independently selected from the group consisting of F, Cl, Br, —CN, —OH, —OCH$_3$, —OCD$_3$, —OCFH$_2$, —OCHF$_2$, —OCF$_3$, —O-cyclopropyl, —S(=O)$_2$CH$_3$, —NH$_2$, —NH(CH$_3$), —N(CH$_3$)$_2$, —CH$_3$, —CH$_2$CH$_3$, —CH(CH$_3$)$_2$, —C(CH$_3$)$_3$, —CD$_3$, —CFH$_2$, —CHF$_2$, —CF$_3$, cyclopropyl, or oxetanyl.

In some embodiments, for any Formula described herein, $R^6$ is H, F, Cl, Br, —CN, —OH, —OCH$_3$, —OCD$_3$, —OCFH$_2$, —OCHF$_2$, —OCF$_3$, —O-cyclopropyl, —S(=O)$_2$CH$_3$, —S(=O)$_2$NH$_2$, —S(=O)$_2$NH(CH$_3$), —S(=O)$_2$N(CH$_3$)$_2$, —NHS(=O)$_2$CH$_3$, —NH$_2$, —NH(CH$_3$), —N(CH$_3$)$_2$, —OC(=O)CH$_3$, —CO$_2$H, —CO$_2$CH$_3$, —CO$_2$CH$_2$CH$_3$, —C(=O)N(R$^{15}$)$_2$, —C(=O)—NH$_2$, —C(=O)NH(CH$_3$), —C(=O)N(CH$_3$)$_2$, —NHC(=O)CH$_3$, —CH$_3$, —CH$_2$CH$_3$, —CH(CH$_3$)$_2$, —C(CH$_3$)$_3$, —CD$_3$, —CFH$_2$, —CHF$_2$, —CF$_3$, —CH=CH$_2$, —C(CH$_3$)=CH$_2$, —CH=CH, —CH=CCH$_3$, cyclopropyl, or oxetanyl.

In some embodiments, for any Formula described herein, $R^6$ is H, F, Cl, Br, —CN, —OH, —OCH$_3$, —OCD$_3$, —OCFH$_2$, —OCHF$_2$, —OCF$_3$, —O-cyclopropyl, —S(=O)$_2$CH$_3$, —CH$_3$, —CH$_2$CH$_3$, —CH(CH$_3$)$_2$, —C(CH$_3$)$_3$, —CD$_3$, —CFH$_2$, —CHF$_2$, —CF$_3$, —CH=CH$_2$, —C(CH$_3$)=CH$_2$, cyclopropyl, or oxetanyl.

In some embodiments, for any Formula described herein, $R^6$ is a ring C that is unsubstituted or is substituted with 1, 2, 3, or 4 $R^c$; ring C is phenyl, naphthyl, heteroaryl, $C_3$-$C_{12}$ cycloalkyl, or $C_2$-$C_{10}$ heterocycloalkyl;

or $R^6$ is halogen, —CN, —OH, —OR$^{12}$, —SR$^{12}$, —S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, or substituted or unsubstituted monocyclic $C_3$-$C_6$ heterocycloalkyl;

each $R^c$ is independently selected from the group consisting of halogen, —CN, —OH, —OR$^{12}$, —SR$^{12}$, —S(=O)R$^{12}$, —S(=O)$_2$R$^{12}$, —S(=O)$_2$N(R$^{13}$)$_2$, —NR$^{13}$S(=O)$_2$R$^{12}$, —N(R$^{13}$)$_2$, —OC(=O)(R$^{12}$), —CO$_2$R$^{13}$, —C(=O)N(R$^{13}$)$_2$, —NR$^{13}$C(=O)(R$^{12}$), —NR$^{13}$C(=O)O(R$^{12}$), —OC(=O)N(R$^{13}$)$_2$, —NR$^{13}$C(=O)N(R$^{13}$)$_2$, $C_1$-$C_4$ alkyl, $C_2$-$C_4$ alkenyl, $C_2$-$C_4$ alkynyl, $C_1$-$C_4$ deuteroalkyl, $C_1$-$C_4$ fluoroalkyl, $C_1$-$C_4$ heteroalkyl, substituted or unsubstituted $C_3$-$C_6$ cycloalkyl, substituted or unsubstituted $C_3$-$C_7$ heterocycloalkyl, substituted or unsubstituted phenyl, substituted or unsubstituted monocyclic heteroaryl or a 1,4-dioxanyl ring fused to ring C.

In some embodiments, for any Formula described herein, $R^6$ is a ring C that is unsubstituted or is substituted with 1, 2, 3, or 4 $R^c$, where $R^c$ is as defined herein; ring C is phenyl, naphthyl, heteroaryl, $C_3$-$C_6$ cycloalkyl, or $C_2$-$C_6$ heterocycloalkyl; $R^4$ is a bridged cycloalkyl selected from

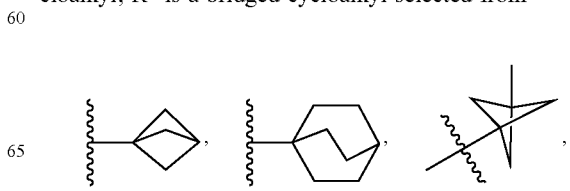

-continued

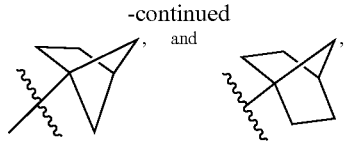

and -L¹-R² is any -L¹-R² selected from Table 2. In some of such embodiments, R¹ is H. In some other such embodiments, R¹ is OH or O—C₁-C₃alkyl.

In some embodiments, for any Formula described herein, R⁶ is halo; R⁴ is a bridged cycloalkyl selected from

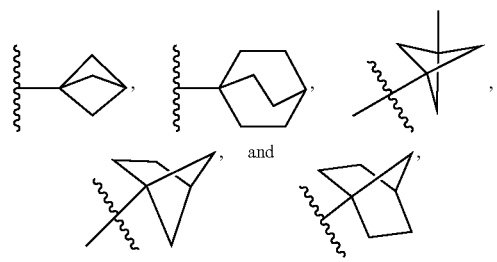

and -L-R² is any -L¹-R² selected from Table 2. In some of such embodiments, R¹ is H. In some other such embodiments, R¹ is OH or O—C₁-C₃alkyl.

In another aspect, provided herein is a compound that has a structure of any one of compounds 1-109 as shown in Table 2, or a pharmaceutically acceptable salt, solvate or stereoisomer thereof. In a further aspect, provided herein is a compound selected from compounds 1-6, 8-11, 13-17, 19-23, 26-63, 65-70, 72-73, 76-112, 114-119, 121-122, 125, 128, 132-135, 137-138, 140-143, 145, 148-150, 152-153, 158-159, and 161 as shown in Table 2, or a pharmaceutically acceptable salt, solvate or stereoisomer thereof. In yet another aspect, provided herein is a compound selected from compounds 1-136, 138-142, and 145-180 as shown in Table 2, or a pharmaceutically acceptable salt, solvate or stereoisomer thereof. In an additional aspect, provided herein is a compound selected from compounds 1-136, 138-142, and 145-257 as shown in Table 2, or a pharmaceutically acceptable salt, solvate or stereoisomer thereof. In a further aspect, provided herein is a compound selected from compounds 1-136, 138-142, 145-220, 223, 225-228, 233a-233b, 237, 242, and 247-248b as shown in Table 2, or a pharmaceutically acceptable salt, solvate or stereoisomer thereof.

In another aspect, described herein is a compound that has one of the following structures of Table 2, or a pharmaceutically acceptable salt, solvate or stereoisomer thereof:

TABLE 2

| Compound | Structure | Name |
|---|---|---|
| 1 | 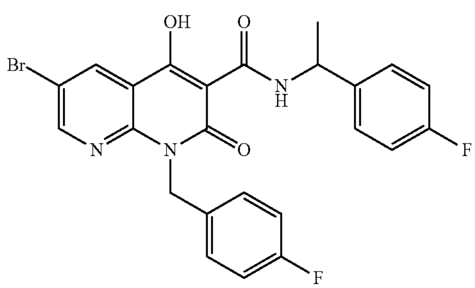 [SMILES: CC(NC(=O)c1c(O)c2cc(Br)cnc2n(Cc2ccc(F)cc2)c1=O)c1ccc(F)cc1] | 6-bromo-1-(4-fluorobenzyl)-N-(1-(4-fluorophenyl)ethyl)-4-hydroxy-2-oxo-1,2-dihydro-1,8-naphthyridine-3-carboxamide |
| 2 | 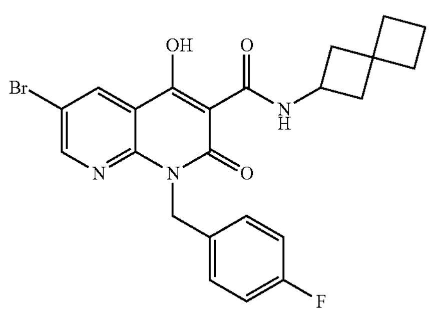 [SMILES: O=C(NC1CC2(CCC2)C1)c1c(O)c2cc(Br)cnc2n(Cc2ccc(F)cc2)c1=O] | 6-bromo-1-(4-fluorobenzyl)-4-hydroxy-2-oxo-N-(spiro[3.3]heptan-2-yl)-1,2-dihydro-1,8-naphthyridine-3-carboxamide |
| 3 | 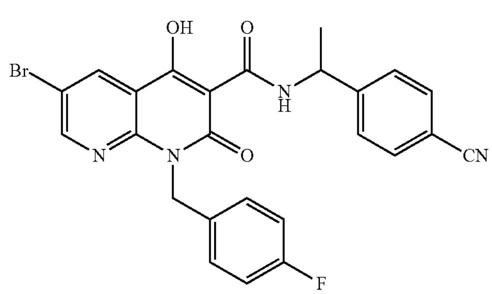 [SMILES: CC(NC(=O)c1c(O)c2cc(Br)cnc2n(Cc2ccc(F)cc2)c1=O)c1ccc(C#N)cc1] | 6-bromo-N-(1-(4-cyanophenyl)ethyl)-1-(4-fluorobenzyl)-4-hydroxy-2-oxo-1,2-dihydro-1,8-naphthyridine-3-carboxamide |

TABLE 2-continued

| Compound | Structure | Name |
|---|---|---|
| 4 | 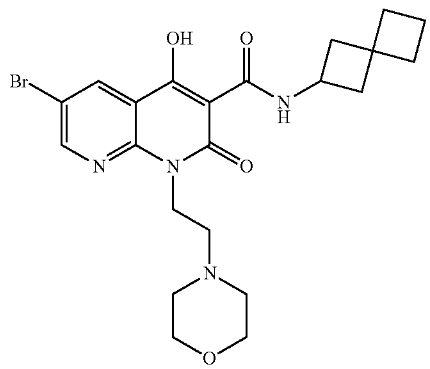 [SMILES: O=C(NC1CC2(CCC2)C1)c1c(O)c2cc(Br)cnc2n(CCN2CCOCC2)c1=O] | 6-bromo-4-hydroxy-1-(2-morpholinoethyl)-2-oxo-N-(spiro[3.3]heptan-2-yl)-1,2-dihydro-1,8-naphthyridine-3-carboxamide |
| 5 | 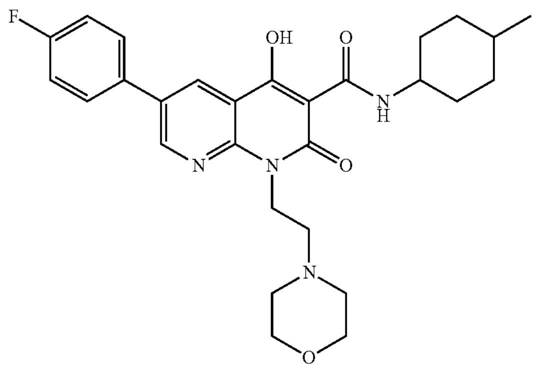 [SMILES: CC1CCC(NC(=O)c2c(O)c3cc(-c4ccc(F)cc4)cnc3n(CCN3CCOCC3)c2=O)CC1] | 6-(4-fluorophenyl)-4-hydroxy-N-(4-methylcyclohexyl)-1-(2-morpholinoethyl)-2-oxo-1,2-dihydro-1,8-naphthyridine-3-carboxamide |
| 6 | 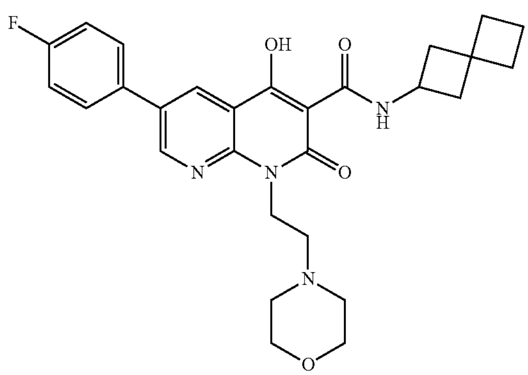 [SMILES: O=C(NC1CC2(CCC2)C1)c1c(O)c2cc(-c3ccc(F)cc3)cnc2n(CCN2CCOCC2)c1=O] | 6-(4-fluorophenyl)-4-hydroxy-1-(2-morpholinoethyl)-2-oxo-N-(spiro[3.3]heptan-2-yl)-1,2-dihydro-1,8-naphthyridine-3-carboxamide |
| 7 | 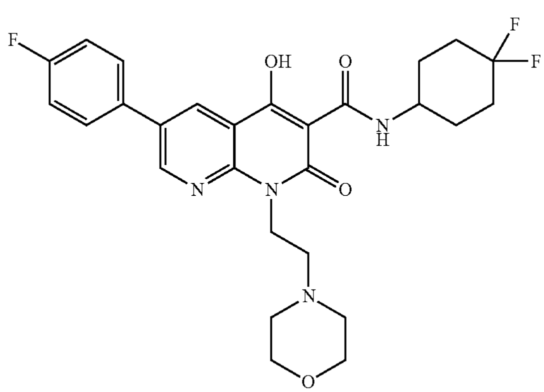 [SMILES: O=C(NC1CCC(F)(F)CC1)c1c(O)c2cc(-c3ccc(F)cc3)cnc2n(CCN2CCOCC2)c1=O] | N-(4,4-difluorocyclohexyl)-6-(4-fluorophenyl)-4-hydroxy-1-(2-morpholinoethyl)-2-oxo-1,2-dihydro-1,8-naphthyridine-3-carboxamide |

TABLE 2-continued

| Compound | Structure | Name |
|---|---|---|
| 8 | 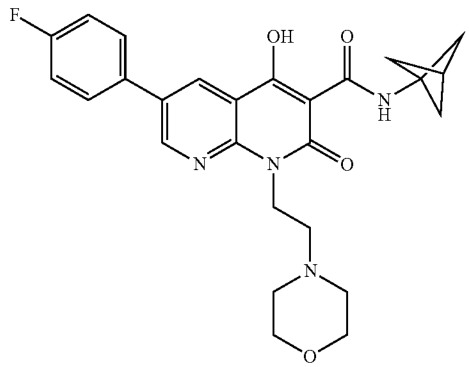 [SMILES: O=C(NC12CC(C1)C2)c1c(O)c2cc(-c3ccc(F)cc3)cnc2n(CCN2CCOCC2)c1=O] | N-(bicyclo[1.1.1]pentan-1-yl)-6-(4-fluorophenyl)-4-hydroxy-1-(2-morpholinoethyl)-2-oxo-1,2-dihydro-1,8-naphthyridine-3-carboxamide |
| 9 | 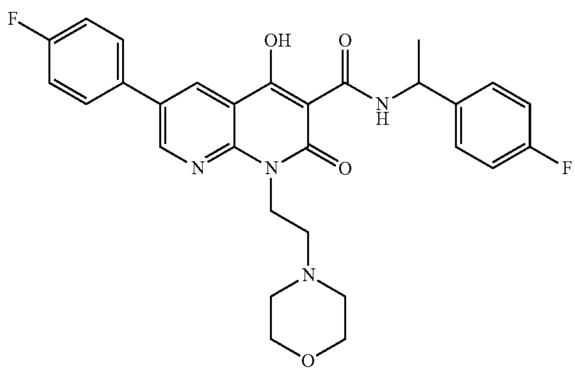 [SMILES: CC(NC(=O)c1c(O)c2cc(-c3ccc(F)cc3)cnc2n(CCN2CCOCC2)c1=O)c1ccc(F)cc1] | 6-(4-fluorophenyl)-N-(1-(4-fluorophenyl)ethyl)-4-hydroxy-1-(2-morpholinoethyl)-2-oxo-1,2-dihydro-1,8-naphthyridine-3-carboxamide |
| 10 | 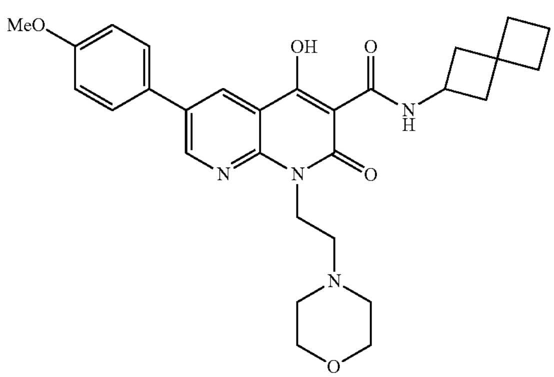 [SMILES: COc1ccc(-c2cnc3c(c2)c(O)c(C(=O)NC2CC4(CCC4)C2)c(=O)n3CCN2CCOCC2)cc1] | 4-hydroxy-6-(4-methoxyphenyl)-1-(2-morpholinoethyl)-2-oxo-N-(spiro[3.3]heptan-2-yl)-1,2-dihydro-1,8-naphthyridine-3-carboxamide |
| 11 | 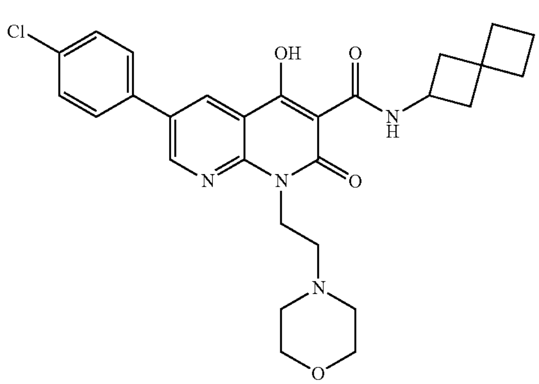 [SMILES: O=C(NC1CC2(CCC2)C1)c1c(O)c2cc(-c3ccc(Cl)cc3)cnc2n(CCN2CCOCC2)c1=O] | 6-(4-chlorophenyl)-4-hydroxy-1-(2-morpholinoethyl)-2-oxo-N-(spiro[3.3]heptan-2-yl)-1,2-dihydro-1,8-naphthyridine-3-carboxamide |

TABLE 2-continued

| Compound | Structure | Name |
|---|---|---|
| 12 | 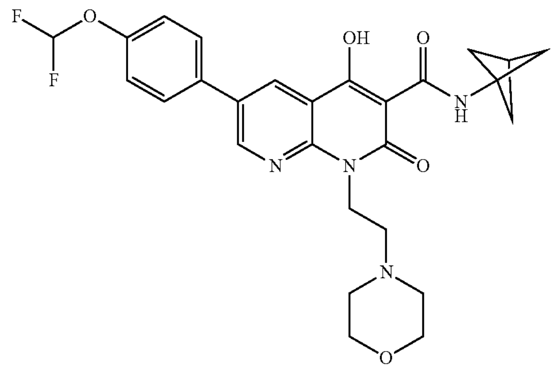 [SMILES: O=C(NC12CC(C1)C2)c1c(O)c2cc(-c3ccc(OC(F)F)cc3)cnc2n(CCN2CCOCC2)c1=O] | N-(bicyclo[1.1.1]pentan-1-yl)-6-(4-(difluoromethoxy)phenyl)-4-hydroxy-1-(2-morpholinoethyl)-2-oxo-1,2-dihydro-1,8-naphthyridine-3-carboxamide |
| 13 | 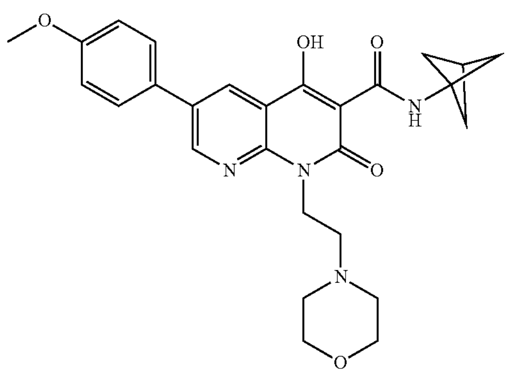 [SMILES: COc1ccc(-c2cnc3c(c2)c(O)c(C(=O)NC24CC(C2)C4)c(=O)n3CCN2CCOCC2)cc1] | N-(bicyclo[1.1.1]pentan-1-yl)-4-hydroxy-6-(4-methoxyphenyl)-1-(2-morpholinoethyl)-2-oxo-1,2-dihydro-1,8-naphthyridine-3-carboxamide |
| 14 | 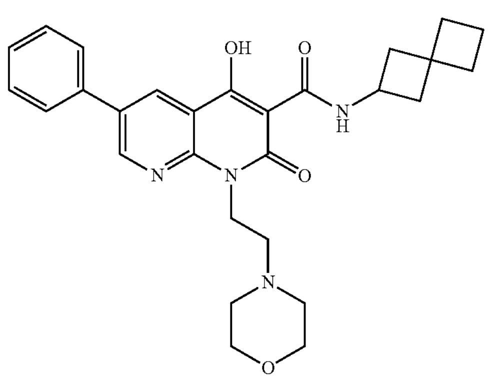 [SMILES: O=C(NC1CC2(CCC2)C1)c1c(O)c2cc(-c3ccccc3)cnc2n(CCN2CCOCC2)c1=O] | 4-hydroxy-1-(2-morpholinoethyl)-2-oxo-6-phenyl-N-(spiro[3.3]heptan-2-yl)-1,2-dihydro-1,8-naphthyridine-3-carboxamide |
| 15 | 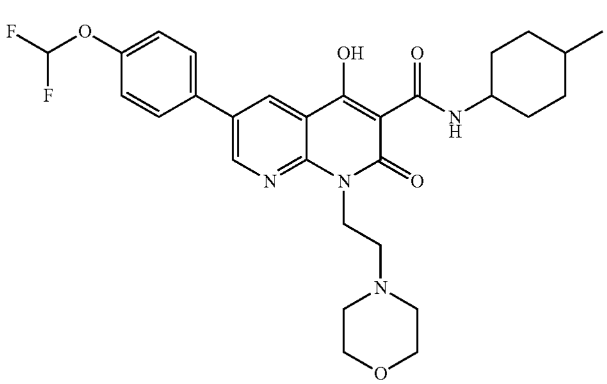 [SMILES: CC1CCC(NC(=O)c2c(O)c3cc(-c4ccc(OC(F)F)cc4)cnc3n(CCN3CCOCC3)c2=O)CC1] | 6-(4-(difluoromethoxy)phenyl)-4-hydroxy-N-(4-methylcyclohexyl)-1-(2-morpholinoethyl)-2-oxo-1,2-dihydro-1,8-naphthyridine-3-carboxamide |

TABLE 2-continued

| Compound | Structure | Name |
| --- | --- | --- |
| 16 | 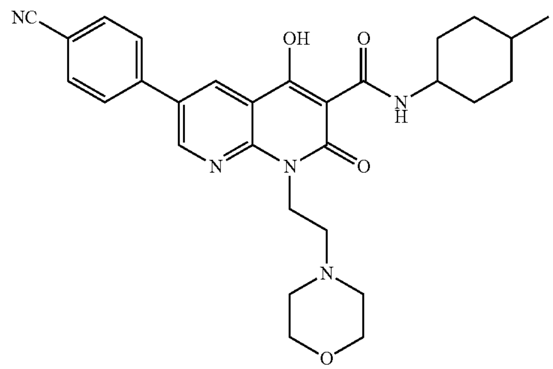 [SMILES: CC1CCC(NC(=O)c2c(O)c3cc(-c4ccc(C#N)cc4)cnc3n(CCN3CCOCC3)c2=O)CC1] | 6-(4-cyanophenyl)-4-hydroxy-N-(4-methylcyclohexyl)-1-(2-morpholinoethyl)-2-oxo-1,2-dihydro-1,8-naphthyridine-3-carboxamide |
| 17 | 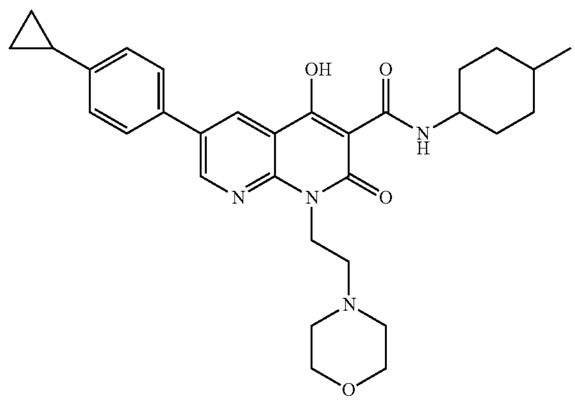 [SMILES: CC1CCC(NC(=O)c2c(O)c3cc(-c4ccc(C5CC5)cc4)cnc3n(CCN3CCOCC3)c2=O)CC1] | 6-(4-cyclopropylphenyl)-4-hydroxy-N-(4-methylcyclohexyl)-1-(2-morpholinoethyl)-2-oxo-1,2-dihydro-1,8-naphthyridine-3-carboxamide |
| 18 | 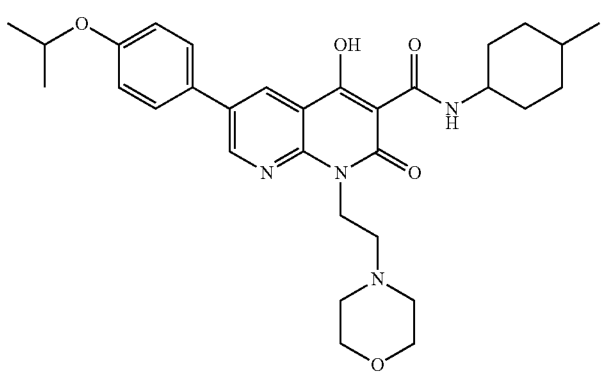 [SMILES: CC1CCC(NC(=O)c2c(O)c3cc(-c4ccc(OC(C)C)cc4)cnc3n(CCN3CCOCC3)c2=O)CC1] | 4-hydroxy-6-(4-isopropoxyphenyl)-N-(4-methylcyclohexyl)-1-(2-morpholinoethyl)-2-oxo-1,2-dihydro-1,8-naphthyridine-3-carboxamide |
| 19 | 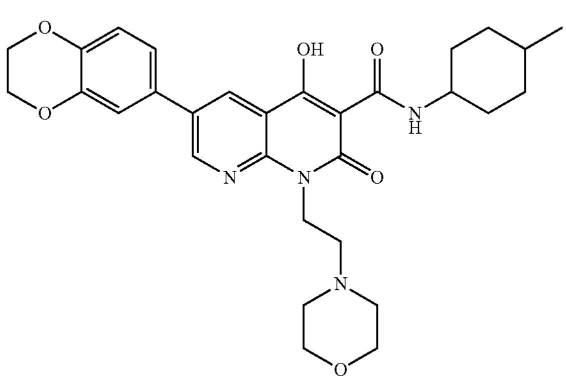 [SMILES: CC1CCC(NC(=O)c2c(O)c3cc(-c4ccc5c(c4)OCCO5)cnc3n(CCN3CCOCC3)c2=O)CC1] | 6-(2,3-dihydrobenzo[b][1,4]dioxin-6-yl)-4-hydroxy-N-(4-methylcyclohexyl)-1-(2-morpholinoethyl)-2-oxo-1,2-dihydro-1,8-naphthyridine-3-carboxamide |

TABLE 2-continued

| Compound | Structure | Name |
|---|---|---|
| 20 | 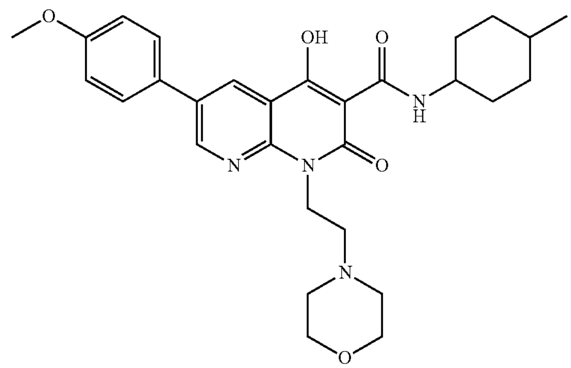 | 4-hydroxy-6-(4-methoxyphenyl)-N-(4-methylcyclohexyl)-1-(2-morpholinoethyl)-2-oxo-1,2-dihydro-1,8-naphthyridine-3-carboxamide |
| 21 | 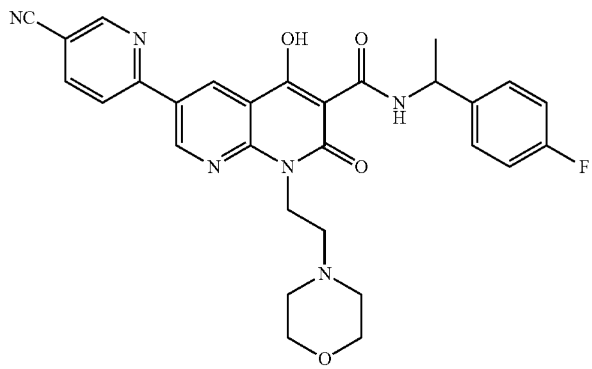 [SMILES: CC(NC(=O)c1c(O)c2cc(-c3ccc(C#N)cn3)cnc2n(CCN2CCOCC2)c1=O)c1ccc(F)cc1] | 6-(5-cyanopyridin-2-yl)-N-(1-(4-fluorophenyl)ethyl)-4-hydroxy-1-(2-morpholinoethyl)-2-oxo-1,2-dihydro-1,8-naphthyridine-3-carboxamide |
| 22 | 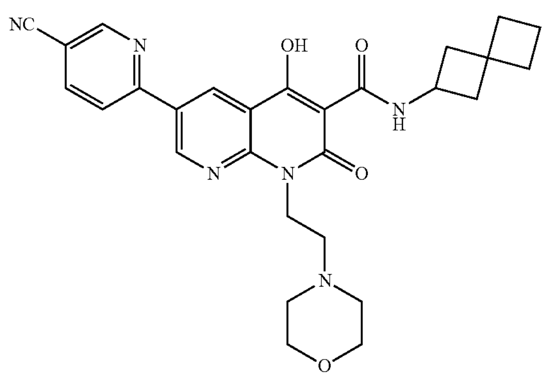 [SMILES: N#Cc1ccc(-c2cnc3c(c2)c(O)c(C(=O)NC2CC4(CCC4)C2)c(=O)n3CCN2CCOCC2)nc1] | 6-(5-cyanopyridin-2-yl)-4-hydroxy-1-(2-morpholinoethyl)-2-oxo-N-(spiro[3.3]heptan-2-yl)-1,2-dihydro-1,8-naphthyridine-3-carboxamide |
| 23 | 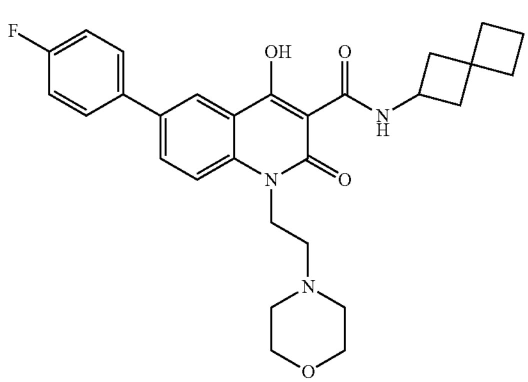 | 6-(4-fluorophenyl)-4-hydroxy-1-(2-morpholinoethyl)-2-oxo-N-(spiro[3.3]heptan-2-yl)-1,2-dihydroquinoline-3-carboxamide |

TABLE 2-continued

| Compound | Structure | Name |
| --- | --- | --- |
| 24 | 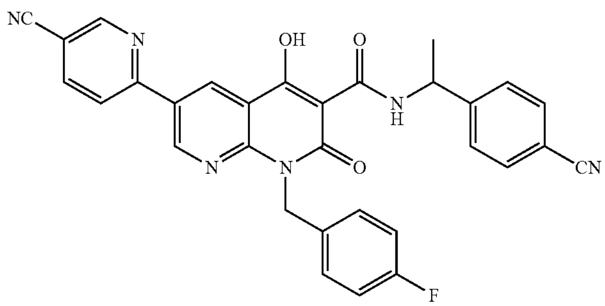 [SMILES: CC(NC(=O)c1c(O)c2cc(-c3ccc(C#N)cn3)cnc2n(Cc2ccc(F)cc2)c1=O)c1ccc(C#N)cc1] | N-(1-(4-cyanophenyl)ethyl)-6-(5-cyanopyridin-2-yl)-1-(4-fluorobenzyl)-4-hydroxy-2-oxo-1,2-dihydro-1,8-naphthyridine-3-carboxamide |
| 25 | 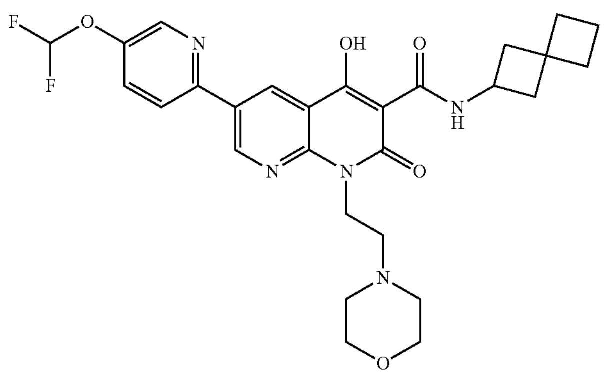 [SMILES: O=C(NC1CC2(CCC2)C1)c1c(O)c2cc(-c3ccc(OC(F)F)cn3)cnc2n(CCN2CCOCC2)c1=O] | 6-(5-(difluoromethoxy)pyridin-2-yl)-4-hydroxy-1-(2-morpholinoethyl)-2-oxo-N-(spiro[3.3]heptan-2-yl)-1,2-dihydro-1,8-naphthyridine-3-carboxamide |
| 26 | 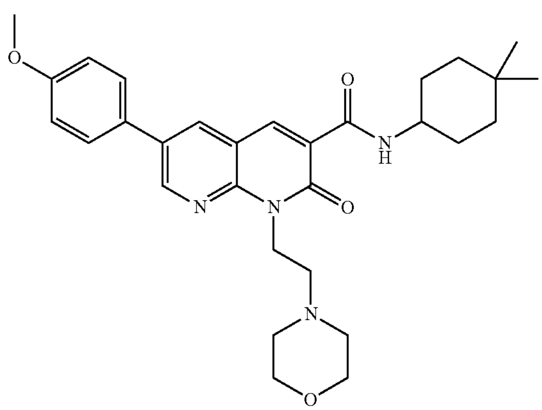 [SMILES: COc1ccc(-c2cnc3c(c2)cc(C(=O)NC2CCC(C)(C)CC2)c(=O)n3CCN2CCOCC2)cc1] | N-(4,4-dimethylcyclohexyl)-6-(4-methoxyphenyl)-1-(2-morpholinoethyl)-2-oxo-1,2-dihydro-1,8-naphthyridine-3-carboxamide |
| 27 | 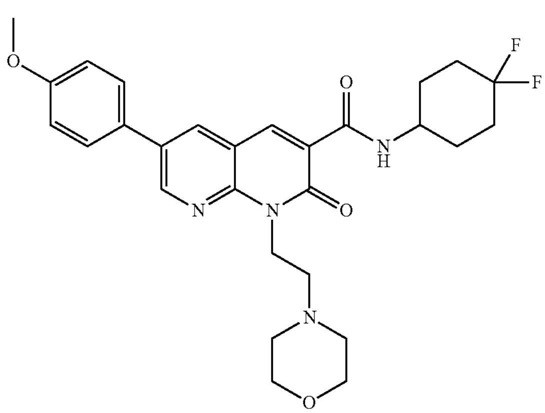 [SMILES: COc1ccc(-c2cnc3c(c2)cc(C(=O)NC2CCC(F)(F)CC2)c(=O)n3CCN2CCOCC2)cc1] | N-(4,4-difluorocyclohexyl)-6-(4-methoxyphenyl)-1-(2-morpholinoethyl)-2-oxo-1,2-dihydro-1,8-naphthyridine-3-carboxamide |

TABLE 2-continued

| Compound | Structure | Name |
|---|---|---|
| 28 | 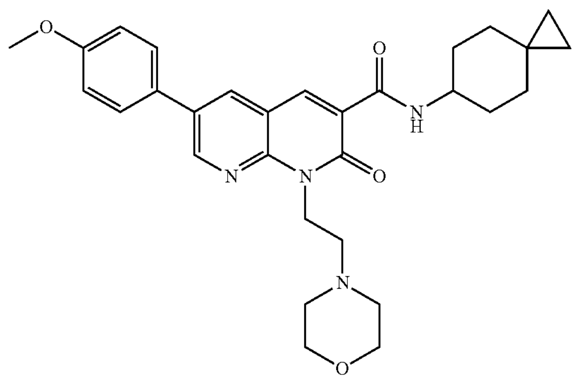 [SMILES: COc1ccc(-c2cnc3c(c2)cc(C(=O)NC2CCC4(CC2)CC4)c(=O)n3CCN2CCOCC2)cc1] | 6-(4-methoxyphenyl)-1-(2-morpholinoethyl)-2-oxo-N-(spiro[2.5]octan-6-yl)-1,2-dihydro-1,8-naphthyridine-3-carboxamide |
| 29 | 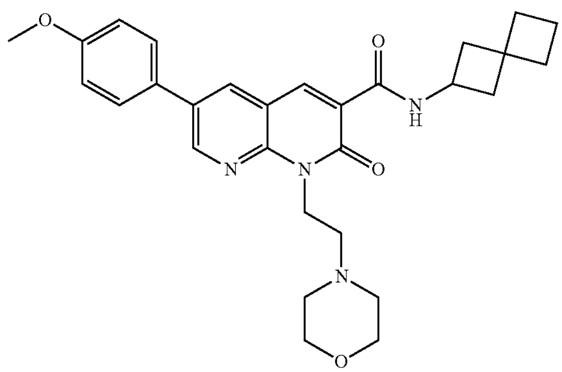 [SMILES: COc1ccc(-c2cnc3c(c2)cc(C(=O)NC2CC4(CCC4)C2)c(=O)n3CCN2CCOCC2)cc1] | 6-(4-methoxyphenyl)-1-(2-morpholinoethyl)-2-oxo-N-(spiro[3.3]heptan-2-yl)-1,2-dihydro-1,8-naphthyridine-3-carboxamide |
| 30 | 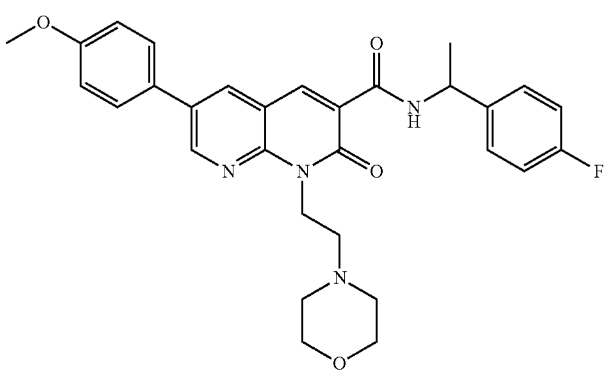 [SMILES: COc1ccc(-c2cnc3c(c2)cc(C(=O)NC(C)c2ccc(F)cc2)c(=O)n3CCN2CCOCC2)cc1] | N-(1-(4-fluorophenyl)ethyl)-6-(4-methoxyphenyl)-1-(2-morpholinoethyl)-2-oxo-1,2-dihydro-1,8-naphthyridine-3-carboxamide |
| 31 | 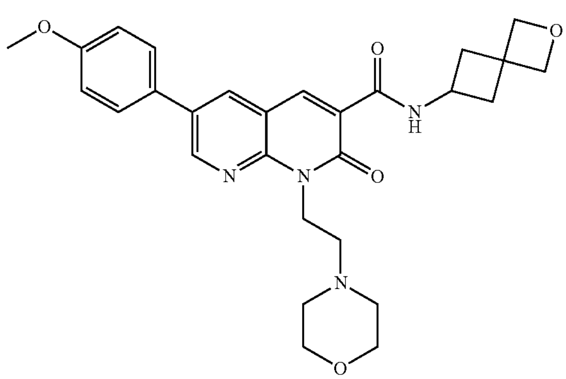 [SMILES: COc1ccc(-c2cnc3c(c2)cc(C(=O)NC2CC4(COC4)C2)c(=O)n3CCN2CCOCC2)cc1] | 6-(4-methoxyphenyl)-1-(2-morpholinoethyl)-2-oxo-N-(2-oxaspiro[3.3]heptan-6-yl)-1,2-dihydro-1,8-naphthyridine-3-carboxamide |

TABLE 2-continued

| Compound | Structure | Name |
|---|---|---|
| 32 | 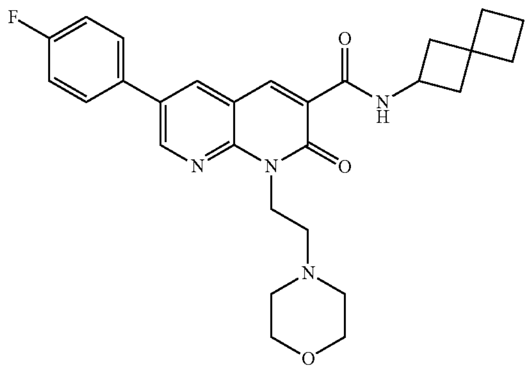 | 6-(4-fluorophenyl)-1-(2-morpholinoethyl)-2-oxo-N-(spiro[3.3]heptan-2-yl)-1,2-dihydro-1,8-naphthyridine-3-carboxamide |
| 33 | 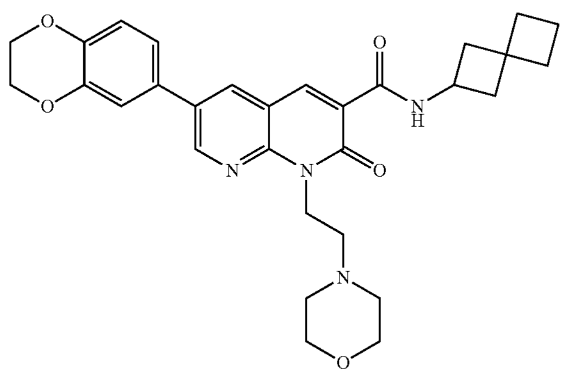 [SMILES: O=C(NC1CC2(CCC2)C1)c1cc2cc(-c3ccc4c(c3)OCCO4)cnc2n(CCN2CCOCC2)c1=O] | 6-(2,3-dihydrobenzo[b][1,4]dioxin-6-yl)-1-(2-morpholinoethyl)-2-oxo-N-(spiro[3.3]heptan-2-yl)-1,2-dihydro-1,8-naphthyridine-3-carboxamide |
| 34 | 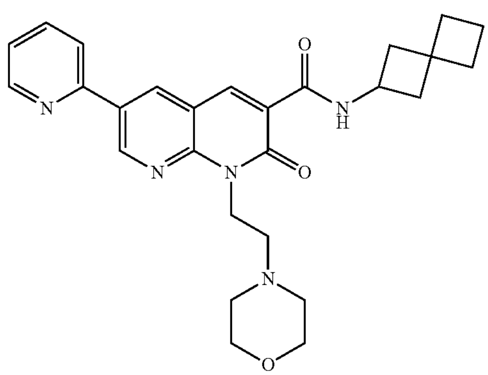 [SMILES: O=C(NC1CC2(CCC2)C1)c1cc2cc(-c3ccccn3)cnc2n(CCN2CCOCC2)c1=O] | 1-(2-morpholinoethyl)-2-oxo-6-(pyridin-2-yl)-N-(spiro[3.3]heptan-2-yl)-1,2-dihydro-1,8-naphthyridine-3-carboxamide |
| 35 | 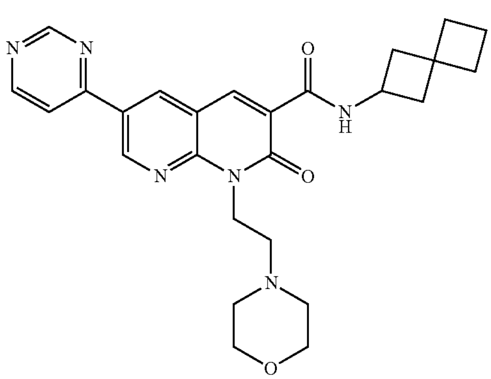 [SMILES: O=C(NC1CC2(CCC2)C1)c1cc2cc(-c3ccncn3)cnc2n(CCN2CCOCC2)c1=O] | 1-(2-morpholinoethyl)-2-oxo-6-(pyrimidin-4-yl)-N-(spiro[3.3]heptan-2-yl)-1,2-dihydro-1,8-naphthyridine-3-carboxamide |

TABLE 2-continued

| Compound | Structure | Name |
| --- | --- | --- |
| 36 | 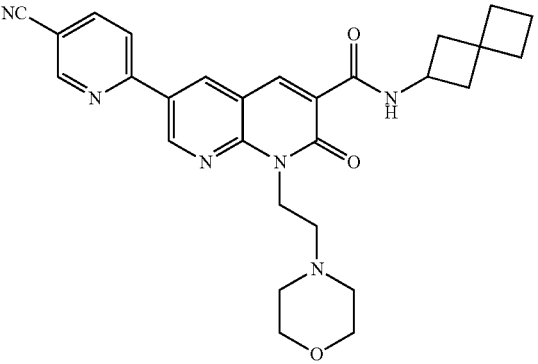 [SMILES: N#Cc1ccc(-c2cnc3c(c2)cc(C(=O)NC2CC4(CCC4)C2)c(=O)n3CCN2CCOCC2)nc1] | 6-(5-cyanopyridin-2-yl)-1-(2-morpholinoethyl)-2-oxo-N-(spiro[3.3]heptan-2-yl)-1,2-dihydro-1,8-naphthyridine-3-carboxamide |
| 37 | 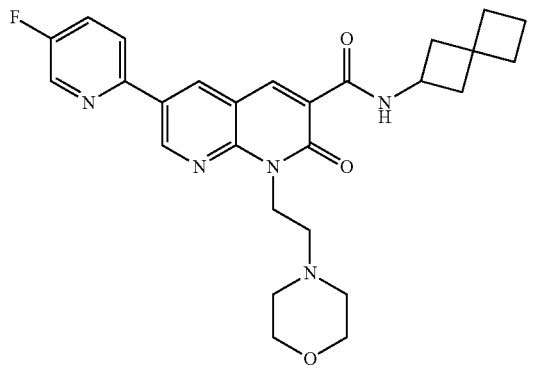 | 6-(5-fluoropyridin-2-yl)-1-(2-morpholinoethyl)-2-oxo-N-(spiro[3.3]heptan-2-yl)-1,2-dihydro-1,8-naphthyridine-3-carboxamide |
| 38 | 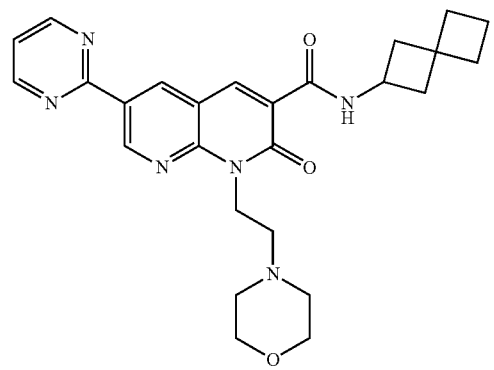 [SMILES: O=C(NC1CC2(CCC2)C1)c1cc2cc(-c3ncccn3)cnc2n(CCN2CCOCC2)c1=O] | 1-(2-morpholinoethyl)-2-oxo-6-(pyrimidin-2-yl)-N-(spiro[3.3]heptan-2-yl)-1,2-dihydro-1,8-naphthyridine-3-carboxamide |
| 39 | 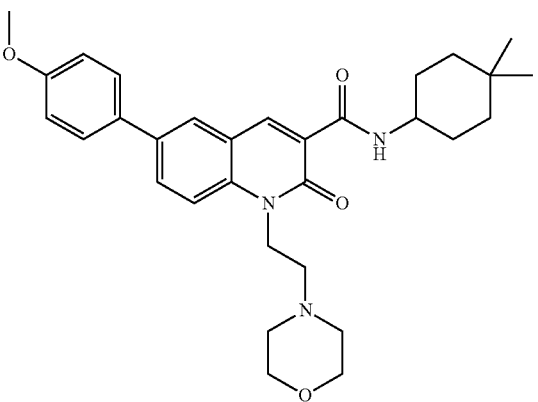 [SMILES: COc1ccc(-c2ccc3c(c2)cc(C(=O)NC2CCC(C)(C)CC2)c(=O)n3CCN2CCOCC2)cc1] | N-(4,4-dimethylcyclohexyl)-6-(4-methoxyphenyl)-1-(2-morpholinoethyl)-2-oxo-1,2-dihydroquinoline-3-carboxamide |

TABLE 2-continued

| Compound | Structure | Name |
| --- | --- | --- |
| 40 | 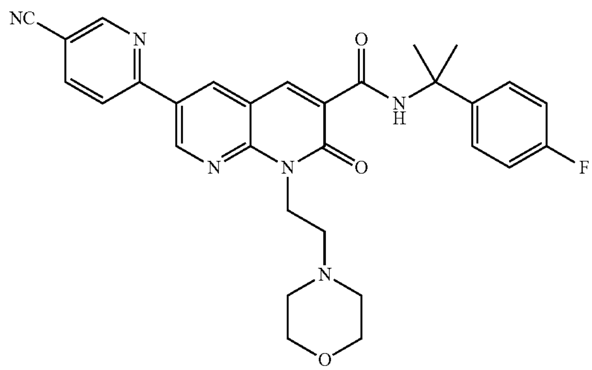 [SMILES: CC(C)(NC(=O)c1cc2cc(-c3ccc(C#N)cn3)cnc2n(CCN2CCOCC2)c1=O)c1ccc(F)cc1] | 6-(5-cyanopyridin-2-yl)-N-(2-(4-fluorophenyl)propan-2-yl)-1-(2-morpholinoethyl)-2-oxo-1,2-dihydro-1,8-naphthyridine-3-carboxamide |
| 41 | 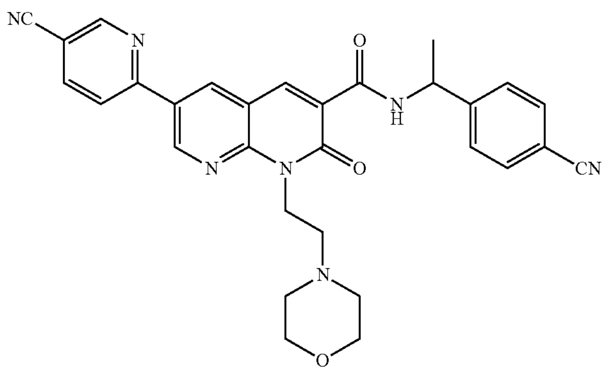 [SMILES: CC(NC(=O)c1cc2cc(-c3ccc(C#N)cn3)cnc2n(CCN2CCOCC2)c1=O)c1ccc(C#N)cc1] | N-(1-(4-cyanophenyl)ethyl)-6-(5-cyanopyridin-2-yl)-1-(2-morpholinoethyl)-2-oxo-1,2-dihydro-1,8-naphthyridine-3-carboxamide |
| 42 | 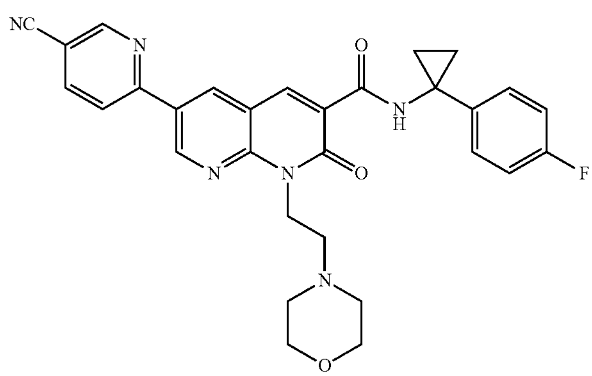 [SMILES: N#Cc1ccc(-c2cnc3c(c2)cc(C(=O)NC2(c4ccc(F)cc4)CC2)c(=O)n3CCN2CCOCC2)nc1] | 6-(5-cyanopyridin-2-yl)-N-(1-(4-fluorophenyl)cyclopropyl)-1-(2-morpholinoethyl)-2-oxo-1,2-dihydro-1,8-naphthyridine-3-carboxamide |
| 43 | 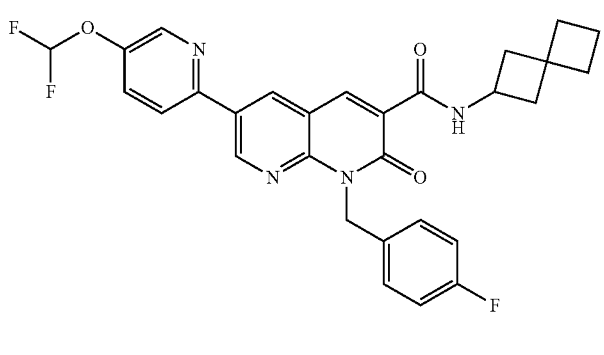 [SMILES: O=C(NC1CC2(CCC2)C1)c1cc2cc(-c3ccc(OC(F)F)cn3)cnc2n(Cc2ccc(F)cc2)c1=O] | 6-(5-(difluoromethoxy)pyridin-2-yl)-1-(4-fluorobenzyl)-2-oxo-N-(spiro[3.3]heptan-2-yl)-1,2-dihydro-1,8-naphthyridine-3-carboxamide |

TABLE 2-continued

| Compound | Structure | Name |
|---|---|---|
| 44 | 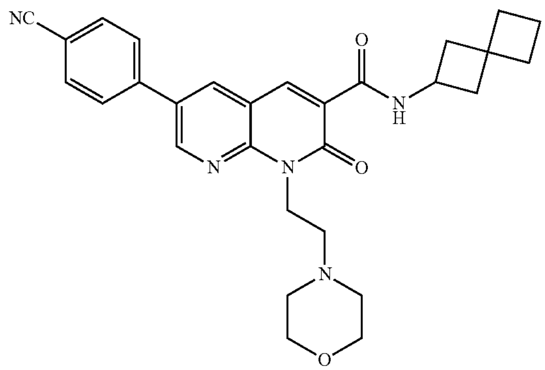 [SMILES: N#Cc1ccc(-c2cnc3c(c2)cc(C(=O)NC2CC4(CCC4)C2)c(=O)n3CCN2CCOCC2)cc1] | 6-(4-cyanophenyl)-1-(2-morpholinoethyl)-2-oxo-N-(spiro[3.3]heptan-2-yl)-1,2-dihydro-1,8-naphthyridine-3-carboxamide |
| 45 | 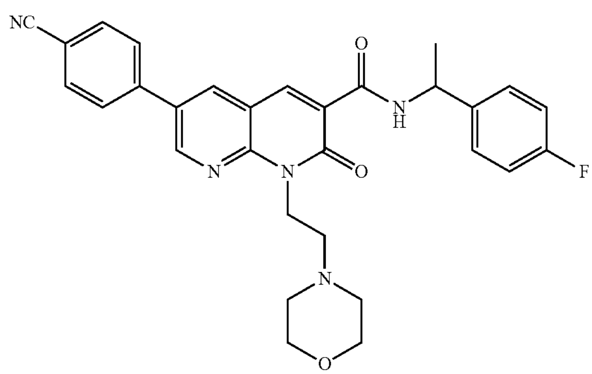 [SMILES: CC(NC(=O)c1cc2cc(-c3ccc(C#N)cc3)cnc2n(CCN2CCOCC2)c1=O)c1ccc(F)cc1] | 6-(4-cyanophenyl)-N-(1-(4-fluorophenyl)ethyl)-1-(2-morpholinoethyl)-2-oxo-1,2-dihydro-1,8-naphthyridine-3-carboxamide |
| 46 | 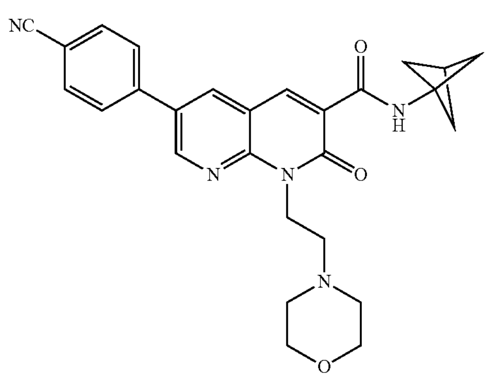 | N-(bicyclo[1.1.1]pentan-1-yl)-6-(4-cyanophenyl)-1-(2-morpholinoethyl)-2-oxo-1,2-dihydro-1,8-naphthyridine-3-carboxamide |
| 47 | 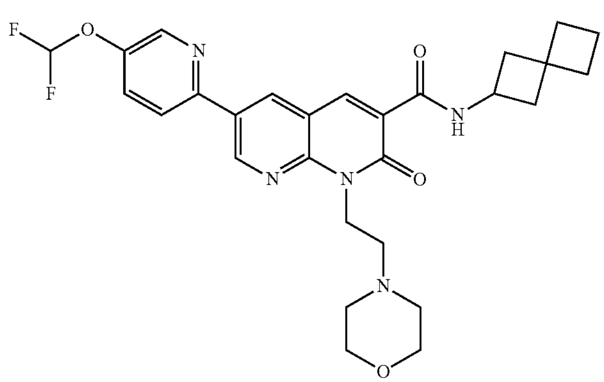 | 6-(5-(difluoromethoxy)pyridin-2-yl)-1-(2-morpholinoethyl)-2-oxo-N-(spiro[3.3]heptan-2-yl)-1,2-dihydro-1,8-naphthyridine-3-carboxamide |

TABLE 2-continued

| Compound | Structure | Name |
|---|---|---|
| 48 | 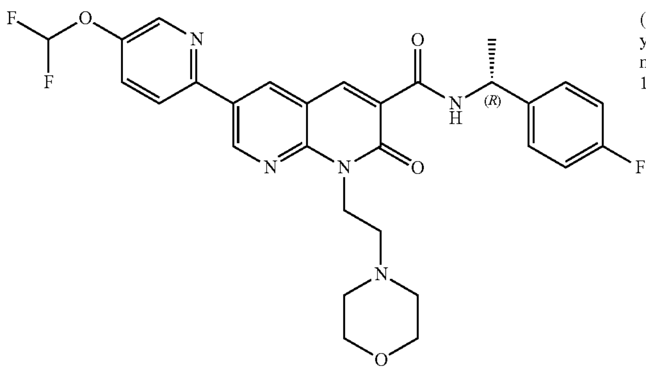 | (R)-6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide |
| 49 | 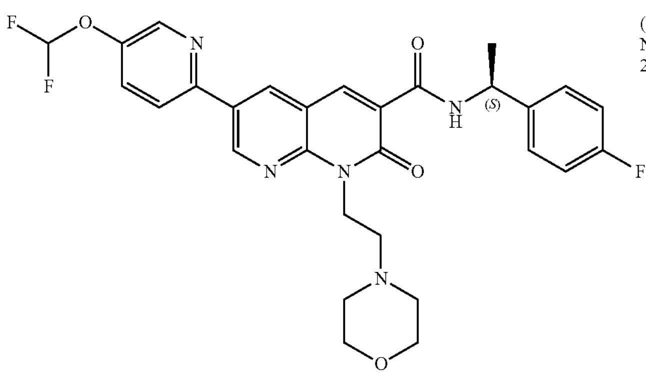 | (S)-6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide |
| 50 | 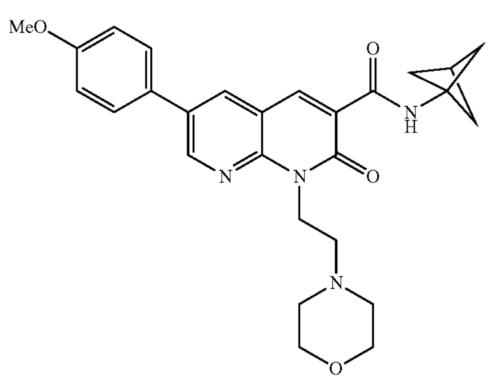 [SMILES: COc1ccc(-c2cnc3c(c2)cc(C(=O)NC24CC(C2)C4)c(=O)n3CCN2CCOCC2)cc1] | N-(bicyclo[1.1.1]pentan-1-yl)-6-(4-methoxyphenyl)-1-(2-morpholinoethyl)-2-oxo-1,2-dihydro-1,8-naphthyridine-3-carboxamide |
| 51 | 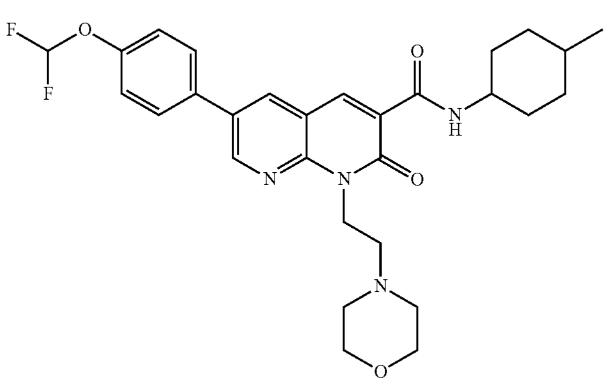 [SMILES: CC1CCC(NC(=O)c2cc3cc(-c4ccc(OC(F)F)cc4)cnc3n(CCN3CCOCC3)c2=O)CC1] | 6-(4-(difluoromethoxy)phenyl)-N-(4-methylcyclohexyl)-1-(2-morpholinoethyl)-2-oxo-1,2-dihydro-1,8-naphthyridine-3-carboxamide |

TABLE 2-continued

| Compound | Structure | Name |
|---|---|---|
| 52 | 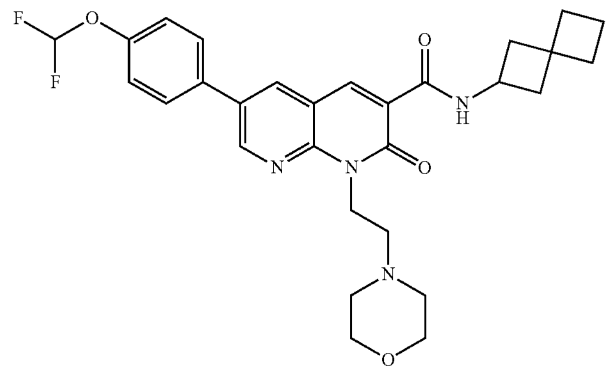 [SMILES: O=C(NC1CC2(CCC2)C1)c1cc2cc(-c3ccc(OC(F)F)cc3)cnc2n(CCN2CCOCC2)c1=O] | 6-(4-(difluoromethoxy)phenyl)-1-(2-morpholinoethyl)-2-oxo-N-(spiro[3.3]heptan-2-yl)-1,2-dihydro-1,8-naphthyridine-3-carboxamide |
| 53 | 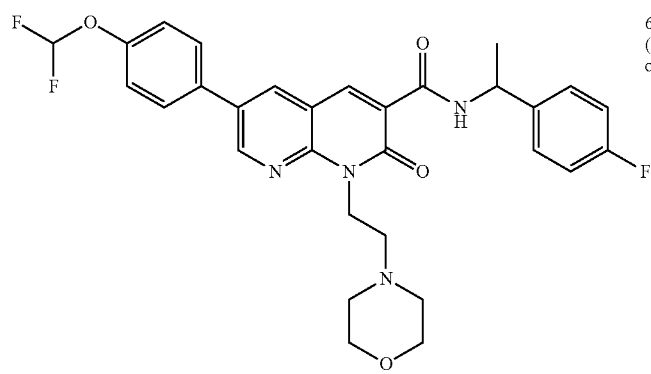 [SMILES: CC(NC(=O)c1cc2cc(-c3ccc(OC(F)F)cc3)cnc2n(CCN2CCOCC2)c1=O)c1ccc(F)cc1] | 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide |
| 54 | 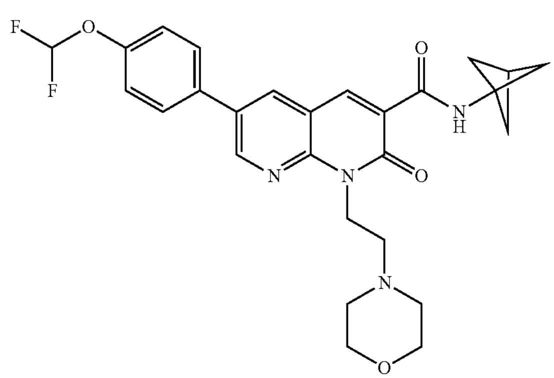 [SMILES: O=C(NC12CC(C1)C2)c1cc2cc(-c3ccc(OC(F)F)cc3)cnc2n(CCN2CCOCC2)c1=O] | N-(bicyclo[1.1.1]pentan-1-yl)-6-(4-(difluoromethoxy)phenyl)-1-(2-morpholinoethyl)-2-oxo-1,2-dihydro-1,8-naphthyridine-3-carboxamide |
| 55 | 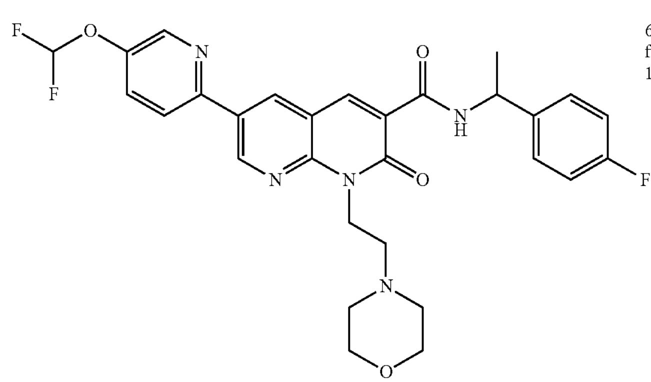 | 6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide |

TABLE 2-continued

| Compound | Structure | Name |
|---|---|---|
| 56 | 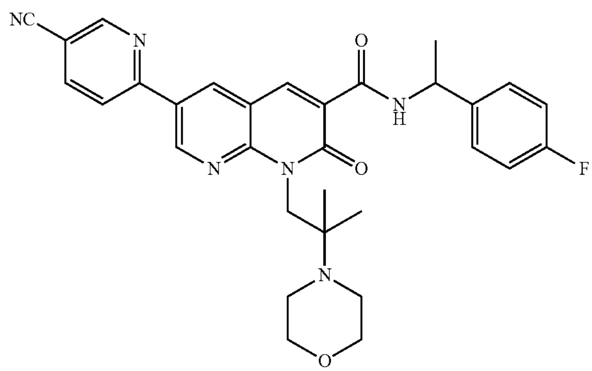 [SMILES: CC(NC(=O)c1cc2cc(-c3ccc(C#N)cn3)cnc2n(CC(C)(C)N2CCOCC2)c1=O)c1ccc(F)cc1] | 6-(5-cyanopyridin-2-yl)-N-(1-(4-fluorophenyl)ethyl)-1-(2-methyl-2-morpholinopropyl)-2-oxo-1,2-dihydro-1,8-naphthyridine-3-carboxamide |
| 57 | 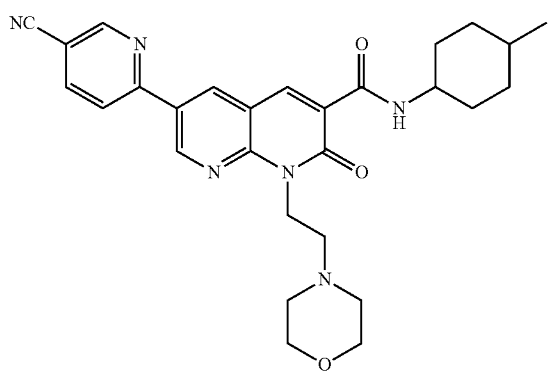 [SMILES: CC1CCC(NC(=O)c2cc3cc(-c4ccc(C#N)cn4)cnc3n(CCN3CCOCC3)c2=O)CC1] | 6-(5-cyanopyridin-2-yl)-N-(4-methylcyclohexyl)-1-(2-morpholinoethyl)-2-oxo-1,2-dihydro-1,8-naphthyridine-3-carboxamide |
| 58 | 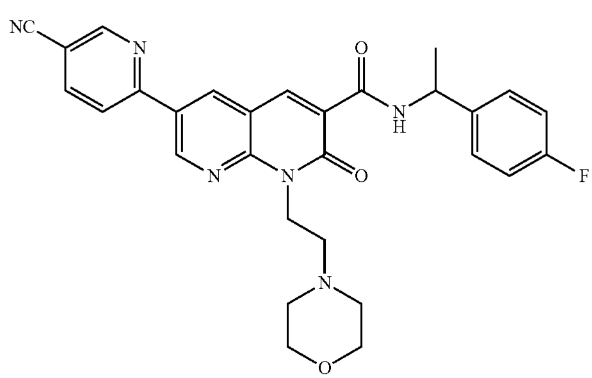 [SMILES: CC(NC(=O)c1cc2cc(-c3ccc(C#N)cn3)cnc2n(CCN2CCOCC2)c1=O)c1ccc(F)cc1] | 6-(5-cyanopyridin-2-yl)-N-(1-(4-fluorophenyl)ethyl)-1-(2-morpholinoethyl)-2-oxo-1,2-dihydro-1,8-naphthyridine-3-carboxamide |
| 59 | 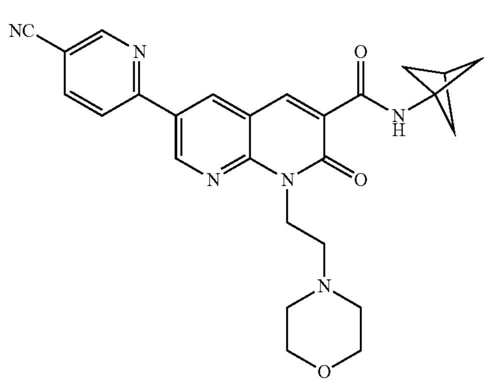 | N-(bicyclo[1.1.1]pentan-1-yl)-6-(5-cyanopyridin-2-yl)-1-(2-morpholinoethyl)-2-oxo-1,2-dihydro-1,8-naphthyridine-3-carboxamide |

TABLE 2-continued

| Compound | Structure | Name |
|---|---|---|
| 60 | 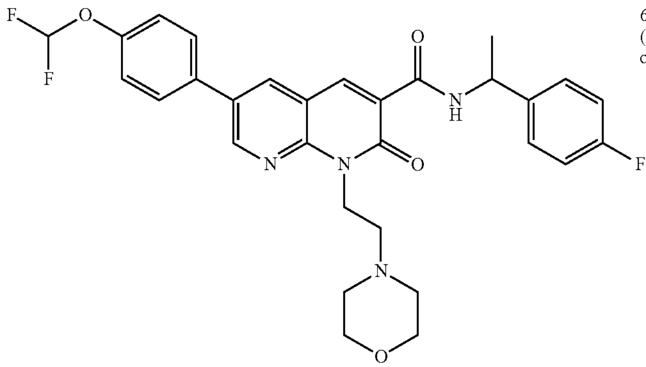 [SMILES: CC(NC(=O)c1cc2cc(-c3ccc(OC(F)F)cc3)cnc2n(CCN2CCOCC2)c1=O)c1ccc(F)cc1] | 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide |
| 61 | 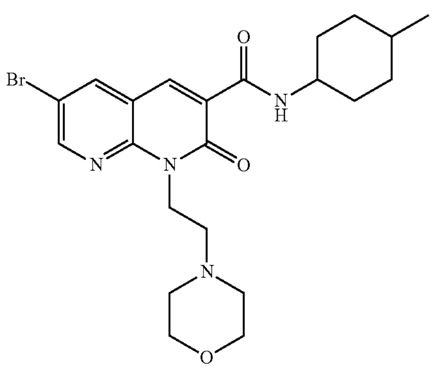 [SMILES: CC1CCC(NC(=O)c2cc3cc(Br)cnc3n(CCN3CCOCC3)c2=O)CC1] | 6-bromo-N-(4-methylcyclohexyl)-1-(2-morpholinoethyl)-2-oxo-1,2-dihydro-1,8-naphthyridine-3-carboxamide |
| 62 | 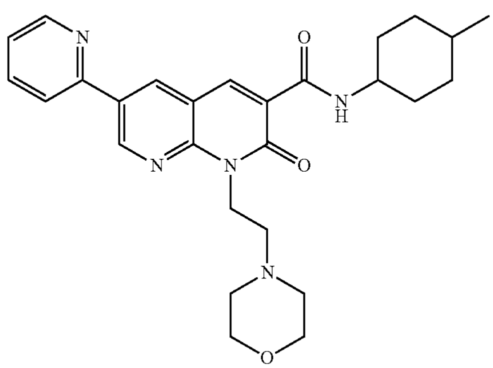 [SMILES: CC1CCC(NC(=O)c2cc3cc(-c4ccccn4)cnc3n(CCN3CCOCC3)c2=O)CC1] | N-(4-methylcyclohexyl)-1-(2-morpholinoethyl)-2-oxo-6-(pyridin-2-yl)-1,2-dihydro-1,8-naphthyridine-3-carboxamide |
| 63 | 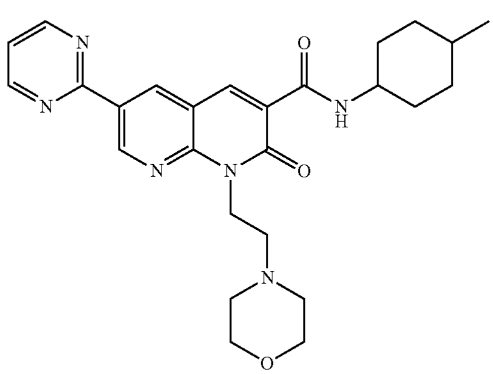 [SMILES: CC1CCC(NC(=O)c2cc3cc(-c4ncccn4)cnc3n(CCN3CCOCC3)c2=O)CC1] | N-(4-methylcyclohexyl)-1-(2-morpholinoethyl)-2-oxo-6-(pyrimidin-2-yl)-1,2-dihydro-1,8-naphthyridine-3-carboxamide |

TABLE 2-continued

| Compound | Structure | Name |
|---|---|---|
| 64 | 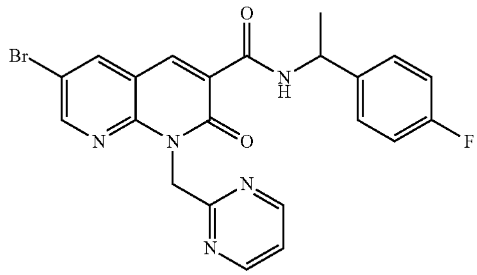 [SMILES: CC(NC(=O)c1cc2cc(Br)cnc2n(Cc2ncccn2)c1=O)c1ccc(F)cc1] | 6-bromo-N-(1-(4-fluorophenyl)ethyl)-2-oxo-1-(pyrimidin-2-ylmethyl)-1,2-dihydro-1,8-naphthyridine-3-carboxamide |
| 65 | 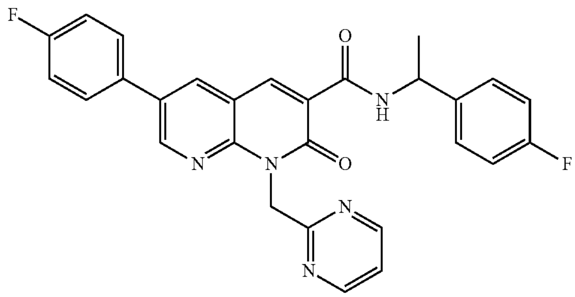 [SMILES: CC(NC(=O)c1cc2cc(-c3ccc(F)cc3)cnc2n(Cc2ncccn2)c1=O)c1ccc(F)cc1] | 6-(4-fluorophenyl)-N-(1-(4-fluorophenyl)ethyl)-2-oxo-1-(pyrimidin-2-ylmethyl)-1,2-dihydro-1,8-naphthyridine-3-carboxamide |
| 66 | 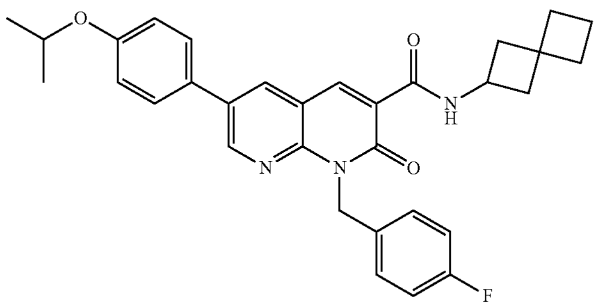 [SMILES: CC(C)Oc1ccc(-c2cnc3c(c2)cc(C(=O)NC2CC4(CCC4)C2)c(=O)n3Cc2ccc(F)cc2)cc1] | 6-(4-isopropoxyphenyl)-1-(4-fluorobenzyl)-2-oxo-N-(spiro[3.3]heptan-2-yl)-1,2-dihydro-1,8-naphthyridine-3-carboxamide |
| 67 | 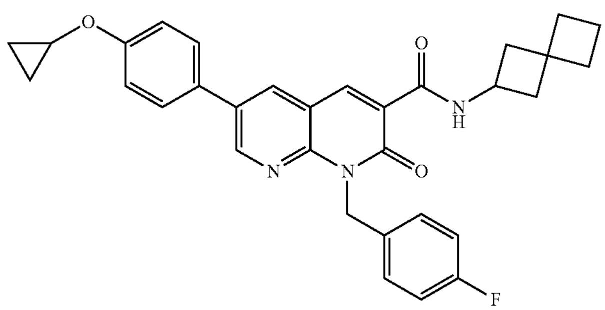 [SMILES: O=C(NC1CC2(CCC2)C1)c1cc2cc(-c3ccc(OC4CC4)cc3)cnc2n(Cc2ccc(F)cc2)c1=O] | 6-(4-cyclopropoxyphenyl)-1-(4-fluorobenzyl)-2-oxo-N-(spiro[3.3]heptan-2-yl)-1,2-dihydro-1,8-naphthyridine-3-carboxamide |
| 68 | 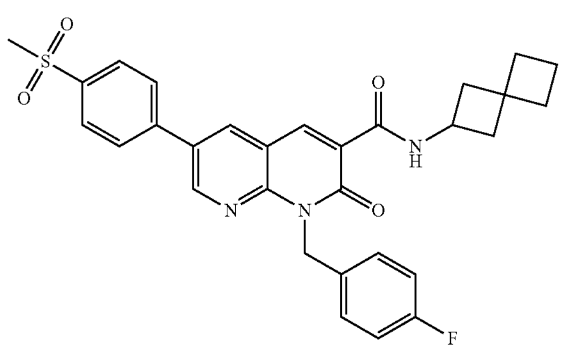 [SMILES: CS(=O)(=O)c1ccc(-c2cnc3c(c2)cc(C(=O)NC2CC4(CCC4)C2)c(=O)n3Cc2ccc(F)cc2)cc1] | 1-(4-fluorobenzyl)-6-(4-(methylsulfonyl)phenyl)-2-oxo-N-(spiro[3.3]heptan-2-yl)-1,2-dihydro-1,8-naphthyridine-3-carboxamide |

TABLE 2-continued

| Compound | Structure | Name |
|---|---|---|
| 69 | 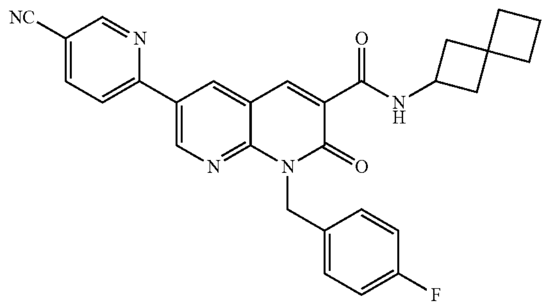 [SMILES: N#Cc1ccc(-c2cnc3c(c2)cc(C(=O)NC2CC4(CCC4)C2)c(=O)n3Cc2ccc(F)cc2)nc1] | 6-(5-cyanopyridin-2-yl)-1-(4-fluorobenzyl)-2-oxo-N-(spiro[3.3]heptan-2-yl)-1,2-dihydro-1,8-naphthyridine-3-carboxamide |
| 70 | 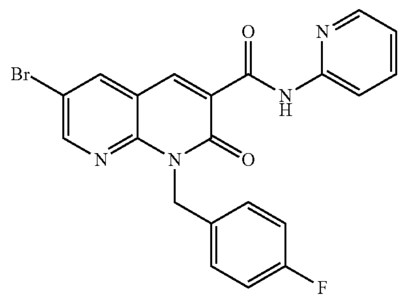 [SMILES: O=C(Nc1ccccn1)c1cc2cc(Br)cnc2n(Cc2ccc(F)cc2)c1=O] | 6-bromo-1-(4-fluorobenzyl)-2-oxo-N-(pyridin-2-yl)-1,2-dihydro-1,8-naphthyridine-3-carboxamide |
| 71 | 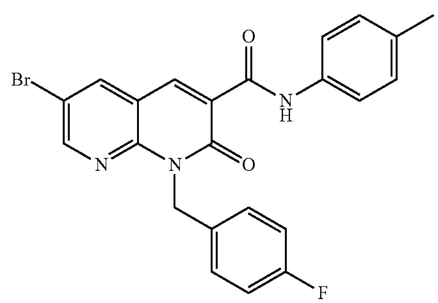 [SMILES: Cc1ccc(NC(=O)c2cc3cc(Br)cnc3n(Cc3ccc(F)cc3)c2=O)cc1] | 6-bromo-1-(4-fluorobenzyl)-2-oxo-N-(p-tolyl)-1,2-dihydro-1,8-naphthyridine-3-carboxamide |
| 72 | 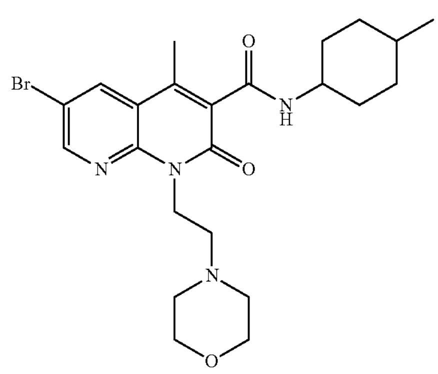 [SMILES: Cc1c(C(=O)NC2CCC(C)CC2)c(=O)n(CCN2CCOCC2)c2ncc(Br)cc12] | 6-bromo-4-methyl-N-(4-methylcyclohexyl)-1-(2-morpholinoethyl)-2-oxo-1,2-dihydro-1,8-naphthyridine-3-carboxamide |

TABLE 2-continued

| Compound | Structure | Name |
|---|---|---|
| 73 | 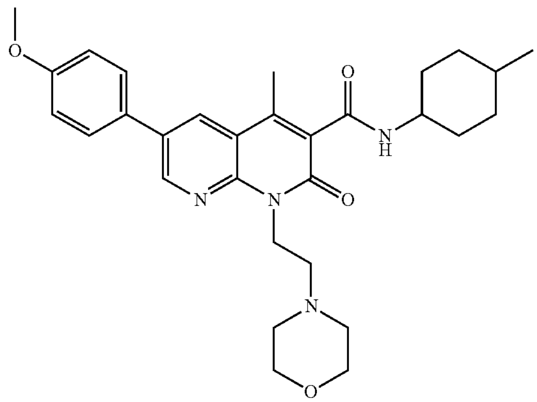 [SMILES: COc1ccc(-c2cnc3c(c2)c(C)c(C(=O)NC2CCC(C)CC2)c(=O)n3CCN2CCOCC2)cc1] | 6-(4-methoxyphenyl)-4-methyl-N-(4-methylcyclohexyl)-1-(2-morpholinoethyl)-2-oxo-1,2-dihydro-1,8-naphthyridine-3-carboxamide |
| 74 | 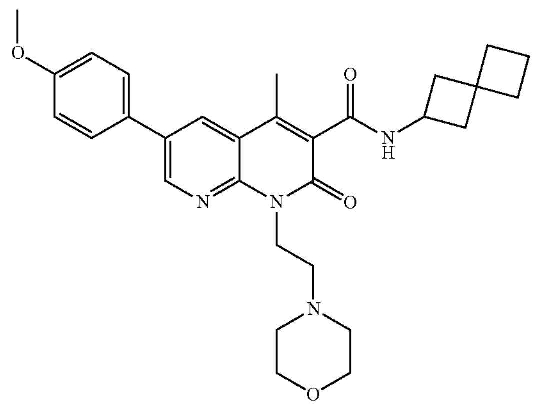 [SMILES: COc1ccc(-c2cnc3c(c2)c(C)c(C(=O)NC2CC4(CCC4)C2)c(=O)n3CCN2CCOCC2)cc1] | 6-(4-methoxyphenyl)-4-methyl-1-(2-morpholinoethyl)-2-oxo-N-(spiro[3.3]heptan-2-yl)-1,2-dihydro-1,8-naphthyridine-3-carboxamide |
| 75 | 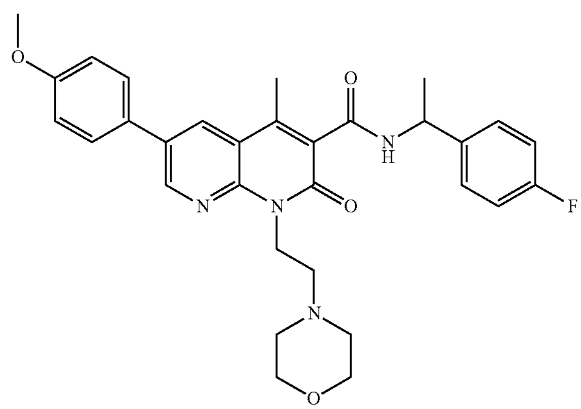 [SMILES: COc1ccc(-c2cnc3c(c2)c(C)c(C(=O)NC(C)c2ccc(F)cc2)c(=O)n3CCN2CCOCC2)cc1] | N-(1-(4-fluorophenyl)ethyl)-6-(4-methoxyphenyl)-4-methyl-1-(2-morpholinoethyl)-2-oxo-1,2-dihydro-1,8-naphthyridine-3-carboxamide |
| 76 | 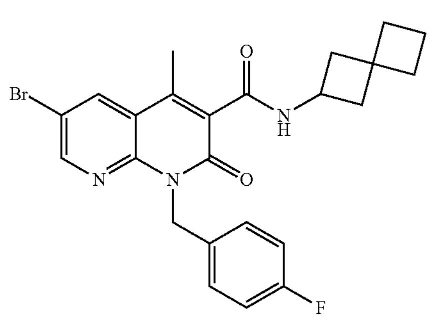 [SMILES: Cc1c(C(=O)NC2CC3(CCC3)C2)c(=O)n(Cc2ccc(F)cc2)c2ncc(Br)cc12] | 6-bromo-1-(4-fluorobenzyl)-4-methyl-2-oxo-N-(spiro[3.3]heptan-2-yl)-1,2-dihydro-1,8-naphthyridine-3-carboxamide |

TABLE 2-continued

| Compound | Structure | Name |
|---|---|---|
| 77 | 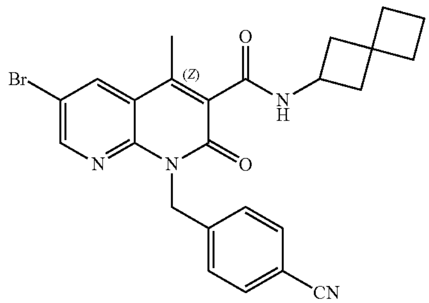 [SMILES: Cc1c(C(=O)NC2CC3(CCC3)C2)c(=O)n(Cc2ccc(C#N)cc2)c2ncc(Br)cc12] | 6-bromo-1-(4-cyanobenzyl)-4-methyl-2-oxo-N-(spiro[3.3]heptan-2-yl)-1,2-dihydro-1,8-naphthyridine-3-carboxamide |
| 78 | 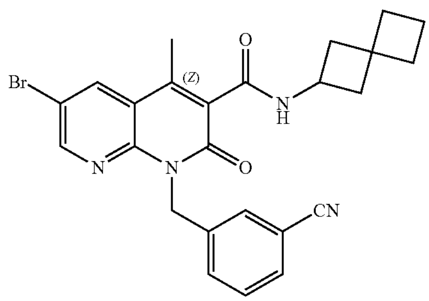 [SMILES: Cc1c(C(=O)NC2CC3(CCC3)C2)c(=O)n(Cc2cccc(C#N)c2)c2ncc(Br)cc12] | 6-bromo-1-(3-cyanobenzyl)-4-methyl-2-oxo-N-(spiro[3.3]heptan-2-yl)-1,2-dihydro-1,8-naphthyridine-3-carboxamide |
| 79 | 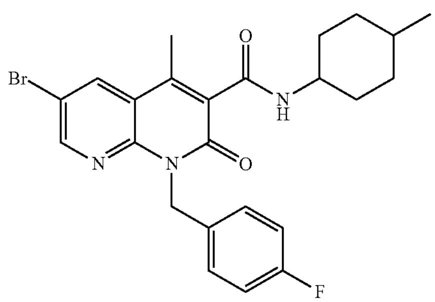 [SMILES: Cc1c(C(=O)NC2CCC(C)CC2)c(=O)n(Cc2ccc(F)cc2)c2ncc(Br)cc12] | 6-bromo-1-(4-fluorobenzyl)-4-methyl-N-(4-methylcyclohexyl)-2-oxo-1,2-dihydro-1,8-naphthyridine-3-carboxamide |
| 80 | 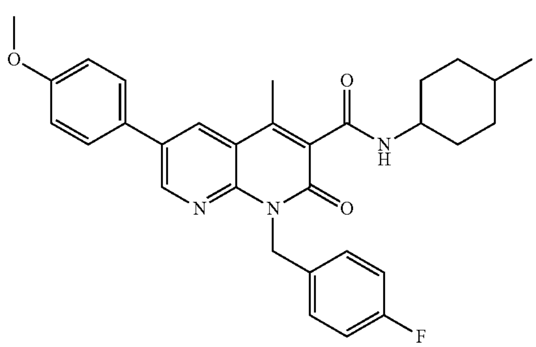 [SMILES: COc1ccc(-c2cnc3c(c2)c(C)c(C(=O)NC2CCC(C)CC2)c(=O)n3Cc2ccc(F)cc2)cc1] | 1-(4-fluorobenzyl)-6-(4-methoxyphenyl)-4-methyl-N-(4-methylcyclohexyl)-2-oxo-1,2-dihydro-1,8-naphthyridine-3-carboxamide |
| 81 | 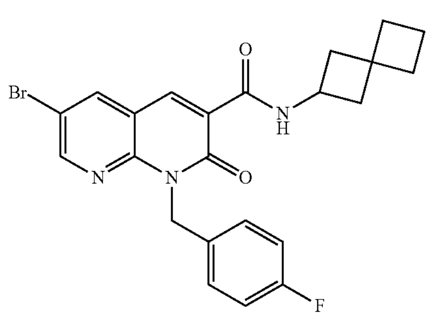 | 6-bromo-1-(4-fluorobenzyl)-2-oxo-N-(spiro[3.3]heptan-2-yl)-1,2-dihydro-1,8-naphthyridine-3-carboxamide |

TABLE 2-continued

| Compound | Structure | Name |
|---|---|---|
| 82 | 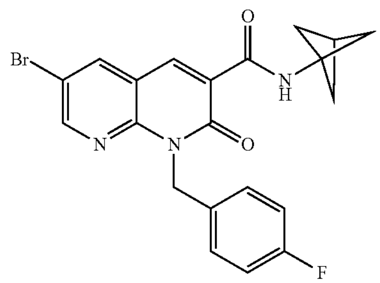 [SMILES: O=C(NC12CC(C1)C2)c1cc2cc(Br)cnc2n(Cc2ccc(F)cc2)c1=O] | N-(bicyclo[1.1.1]pentan-1-yl)-6-bromo-1-(4-fluorobenzyl)-2-oxo-1,2-dihydro-1,8-naphthyridine-3-carboxamide |
| 83 | 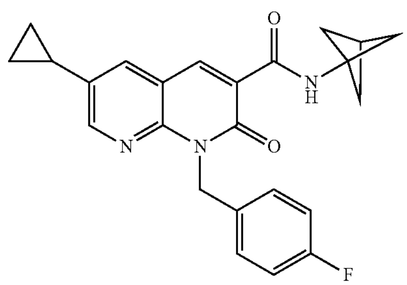 [SMILES: O=C(NC12CC(C1)C2)c1cc2cc(C3CC3)cnc2n(Cc2ccc(F)cc2)c1=O] | N-(bicyclo[1.1.1]pentan-1-yl)-6-cyclopropyl-1-(4-fluorobenzyl)-2-oxo-1,2-dihydro-1,8-naphthyridine-3-carboxamide |
| 84 | 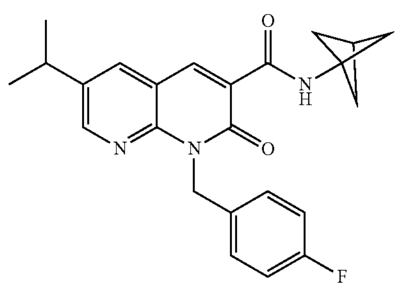 [SMILES: CC(C)c1cnc2c(c1)cc(C(=O)NC13CC(C1)C3)c(=O)n2Cc1ccc(F)cc1] | N-(bicyclo[1.1.1]pentan-1-yl)-1-(4-fluorobenzyl)-6-isopropyl-2-oxo-1,2-dihydro-1,8-naphthyridine-3-carboxamide |
| 85 | 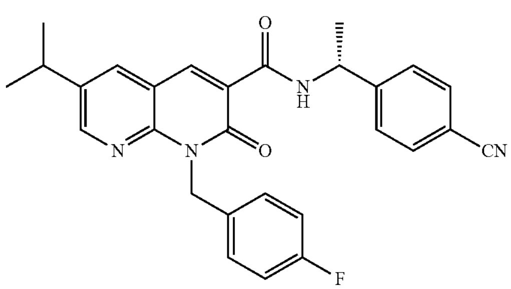 [SMILES: CC(C)c1cnc2c(c1)cc(C(=O)N[C@H](C)c1ccc(C#N)cc1)c(=O)n2Cc1ccc(F)cc1] | (R)-N-(1-(4-cyanophenyl)ethyl)-1-(4-fluorobenzyl)-6-isopropyl-2-oxo-1,2-dihydro-1,8-naphthyridine-3-carboxamide |
| 86 | 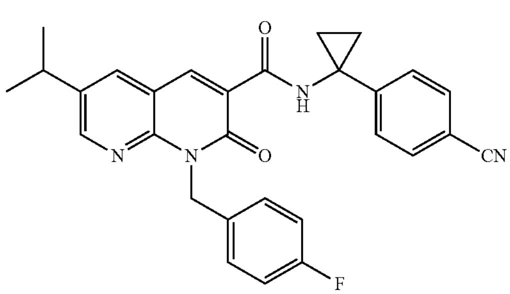 [SMILES: CC(C)c1cnc2c(c1)cc(C(=O)NC1(c3ccc(C#N)cc3)CC1)c(=O)n2Cc1ccc(F)cc1] | N-(1-(4-cyanophenyl)cyclopropyl)-1-(4-fluorobenzyl)-6-isopropyl-2-oxo-1,2-dihydro-1,8-naphthyridine-3-carboxamide |

TABLE 2-continued

| Compound | Structure | Name |
|---|---|---|
| 87 | 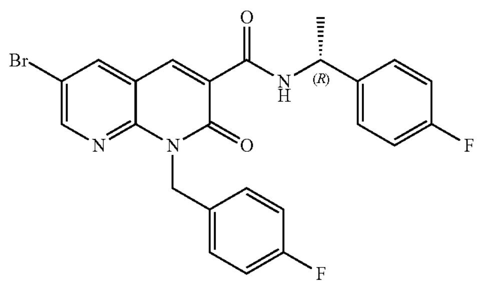 | (R)-6-bromo-1-(4-fluorobenzyl)-N-(1-(4-fluorophenyl)ethyl)-2-oxo-1,2-dihydro-1,8-naphthyridine-3-carboxamide |
| 88 | 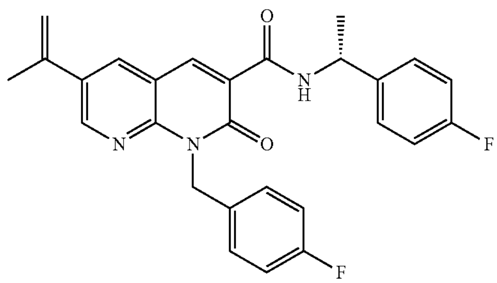 [SMILES: C=C(C)c1cnc2c(c1)cc(C(=O)N[C@H](C)c1ccc(F)cc1)c(=O)n2Cc1ccc(F)cc1] | (R)-1-(4-fluorobenzyl)-N-(1-(4-fluorophenyl)ethyl)-2-oxo-6-(prop-1-en-2-yl)-1,2-dihydro-1,8-naphthyridine-3-carboxamide |
| 89 | 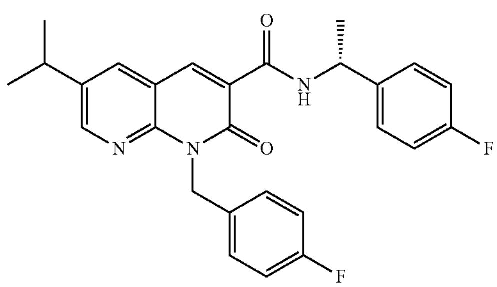 [SMILES: CC(C)c1cnc2c(c1)cc(C(=O)N[C@H](C)c1ccc(F)cc1)c(=O)n2Cc1ccc(F)cc1] | (R)-1-(4-fluorobenzyl)-N-(1-(4-fluorophenyl)ethyl)-6-isopropyl-2-oxo-1,2-dihydro-1,8-naphthyridine-3-carboxamide |
| 90 | 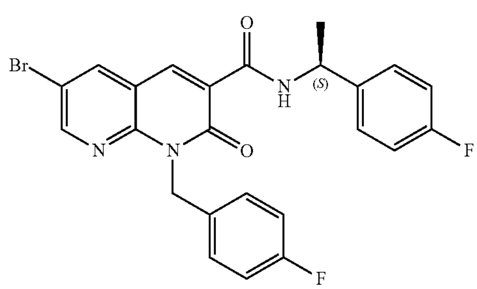 | (S)-6-bromo-1-(4-fluorobenzyl)-N-(1-(4-fluorophenyl)ethyl)-2-oxo-1,2-dihydro-1,8-naphthyridine-3-carboxamide |
| 91 | 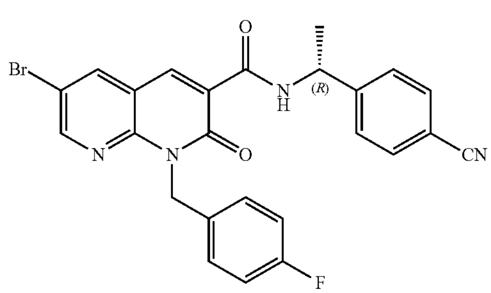 | (R)-6-bromo-N-(1-(4-cyanophenyl)ethyl)-1-(4-fluorobenzyl)-2-oxo-1,2-dihydro-1,8-naphthyridine-3-carboxamide |

TABLE 2-continued

| Compound | Structure | Name |
|---|---|---|
| 92 | 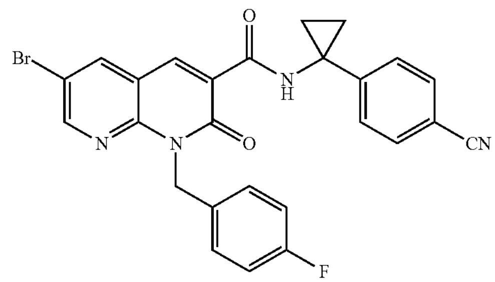 [SMILES: N#Cc1ccc(C2(NC(=O)c3cc4cc(Br)cnc4n(Cc4ccc(F)cc4)c3=O)CC2)cc1] | 6-bromo-N-(1-(4-cyanophenyl)cyclopropyl)-1-(4-fluorobenzyl)-2-oxo-1,2-dihydro-1,8-naphthyridine-3-carboxamide |
| 93 | 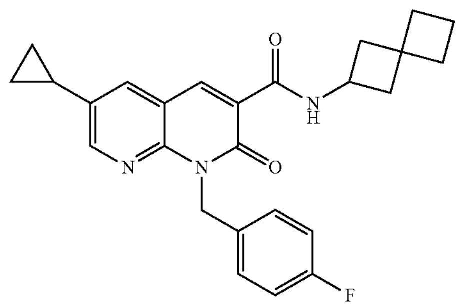 [SMILES: O=C(NC1CC2(CCC2)C1)c1cc2cc(C3CC3)cnc2n(Cc2ccc(F)cc2)c1=O] | 6-cyclopropyl-1-(4-fluorobenzyl)-2-oxo-N-(spiro[3.3]heptan-2-yl)-1,2-dihydro-1,8-naphthyridine-3-carboxamide |
| 94 | 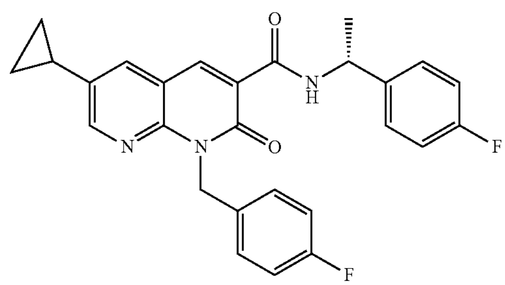 [SMILES: C[C@@H](NC(=O)c1cc2cc(C3CC3)cnc2n(Cc2ccc(F)cc2)c1=O)c1ccc(F)cc1] | (R)-6-cyclopropyl-1-(4-fluorobenzyl)-N-(1-(4-fluorophenyl)ethyl)-2-oxo-1,2-dihydro-1,8-naphthyridine-3-carboxamide |
| 95 | 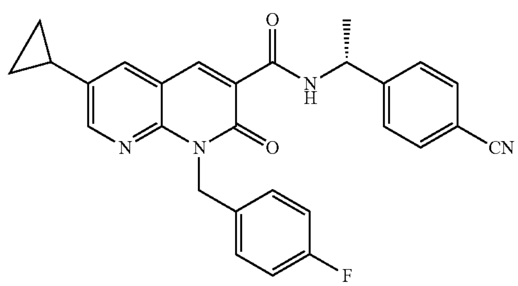 [SMILES: C[C@@H](NC(=O)c1cc2cc(C3CC3)cnc2n(Cc2ccc(F)cc2)c1=O)c1ccc(C#N)cc1] | (R)-N-(1-(4-cyanophenyl)ethyl)-6-cyclopropyl-1-(4-fluorobenzyl)-2-oxo-1,2-dihydro-1,8-naphthyridine-3-carboxamide |
| 96 | 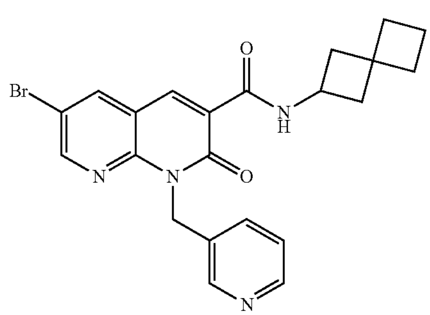 [SMILES: O=C(NC1CC2(CCC2)C1)c1cc2cc(Br)cnc2n(Cc2cccnc2)c1=O] | 6-bromo-2-oxo-1-(pyridin-3-ylmethyl)-N-(spiro[3.3]heptan-2-yl)-1,2-dihydro-1,8-naphthyridine-3-carboxamide |

TABLE 2-continued

| Compound | Structure | Name |
|---|---|---|
| 97 | 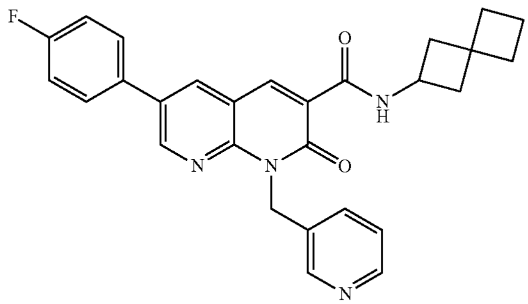 [SMILES: O=C(NC1CC2(CCC2)C1)c1cc2cc(-c3ccc(F)cc3)cnc2n(Cc2cccnc2)c1=O] | 6-(4-fluorophenyl)-2-oxo-1-(pyridin-3-ylmethyl)-N-(spiro[3.3]heptan-2-yl)-1,2-dihydro-1,8-naphthyridine-3-carboxamide |
| 98 | 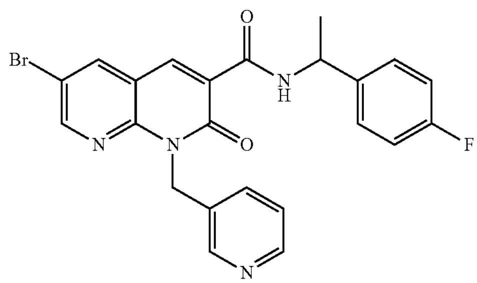 [SMILES: CC(NC(=O)c1cc2cc(Br)cnc2n(Cc2cccnc2)c1=O)c1ccc(F)cc1] | 6-bromo-N-(1-(4-fluorophenyl)ethyl)-2-oxo-1-(pyridin-3-ylmethyl)-1,2-dihydro-1,8-naphthyridine-3-carboxamide |
| 99 | 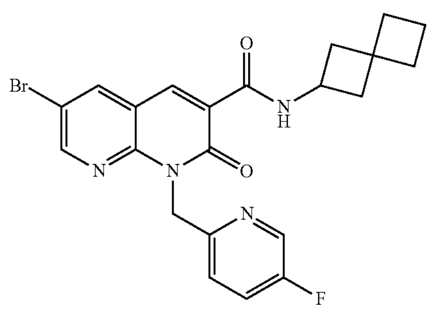 [SMILES: O=C(NC1CC2(CCC2)C1)c1cc2cc(Br)cnc2n(Cc2ccc(F)cn2)c1=O] | 6-bromo-1-((5-fluoropyridin-2-yl)methyl)-2-oxo-N-(spiro[3.3]heptan-2-yl)-1,2-dihydro-1,8-naphthyridine-3-carboxamide |
| 100 | 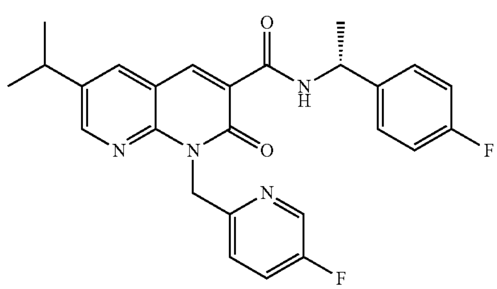 [SMILES: CC(C)c1cnc2c(c1)cc(C(=O)N[C@H](C)c1ccc(F)cc1)c(=O)n2Cc1ccc(F)cn1] | (R)-N-(1-(4-fluorophenyl)ethyl)-1-((5-fluoropyridin-2-yl)methyl)-6-isopropyl-2-oxo-1,2-dihydro-1,8-naphthyridine-3-carboxamide |
| 101 | 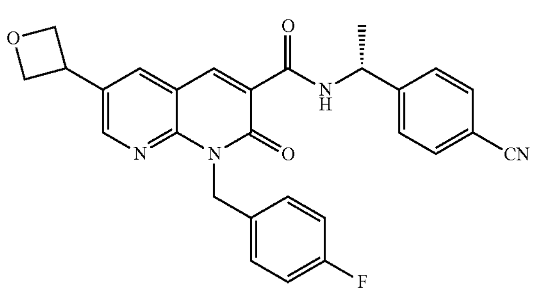 [SMILES: C[C@@H](NC(=O)c1cc2cc(C3COC3)cnc2n(Cc2ccc(F)cc2)c1=O)c1ccc(C#N)cc1] | (R)-N-(1-(4-cyanophenyl)ethyl)-1-(4-fluorobenzyl)-6-(oxetan-3-yl)-2-oxo-1,2-dihydro-1,8-naphthyridine-3-carboxamide |

TABLE 2-continued

| Compound | Structure | Name |
|---|---|---|
| 102 | 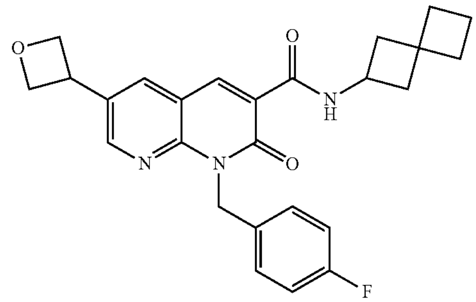 [SMILES: O=C(NC1CC2(CCC2)C1)c1cc2cc(C3COC3)cnc2n(Cc2ccc(F)cc2)c1=O] | 1-(4-fluorobenzyl)-6-(oxetan-3-yl)-2-oxo-N-(spiro[3.3]heptan-2-yl)-1,2-dihydro-1,8-naphthyridine-3-carboxamide |
| 103 | 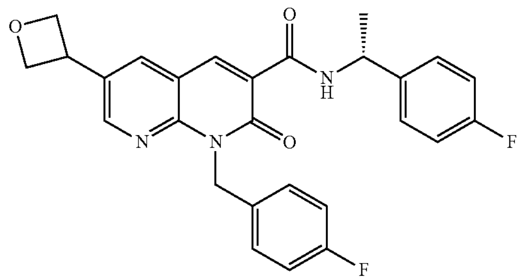 [SMILES: C[C@@H](NC(=O)c1cc2cc(C3COC3)cnc2n(Cc2ccc(F)cc2)c1=O)c1ccc(F)cc1] | (R)-1-(4-fluorobenzyl)-N-(1-(4-fluorophenyl)ethyl)-6-(oxetan-3-yl)-2-oxo-1,2-dihydro-1,8-naphthyridine-3-carboxamide |
| 104 | 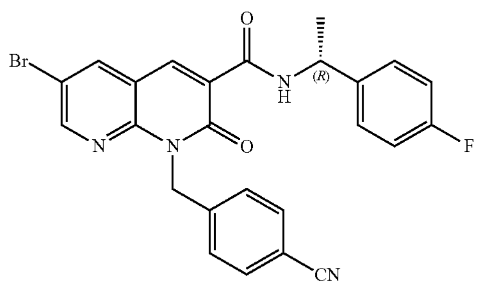 | (R)-6-bromo-1-(4-cyanobenzyl)-N-(1-(4-fluorophenyl)ethyl)-2-oxo-1,2-dihydro-1,8-naphthyridine-3-carboxamide |
| 105 | 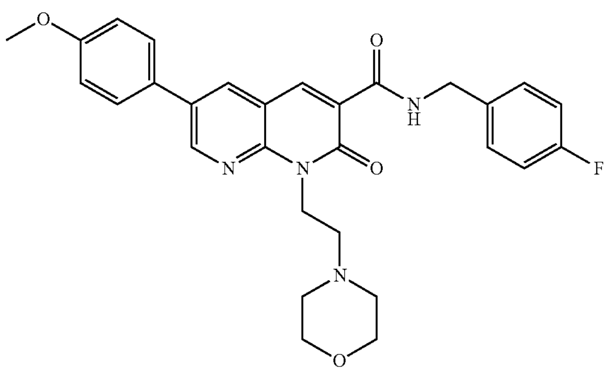 [SMILES: COc1ccc(-c2cnc3c(c2)cc(C(=O)NCc2ccc(F)cc2)c(=O)n3CCN2CCOCC2)cc1] | N-(4-fluorobenzyl)-6-(4-methoxyphenyl)-1-(2-morpholinoethyl)-2-oxo-1,2-dihydro-1,8-naphthyridine-3-carboxamide |
| 106 | 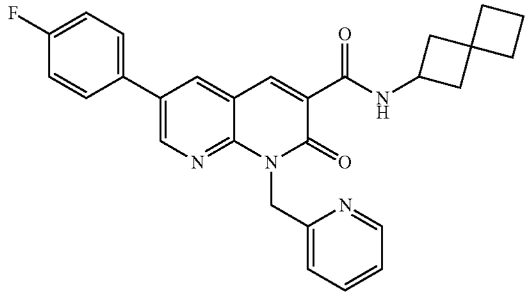 [SMILES: O=C(NC1CC2(CCC2)C1)c1cc2cc(-c3ccc(F)cc3)cnc2n(Cc2ccccn2)c1=O] | 6-(4-fluorophenyl)-2-oxo-1-(pyridin-2-ylmethyl)-N-(spiro[3.3]heptan-2-yl)-1,2-dihydro-1,8-naphthyridine-3-carboxamide |

TABLE 2-continued

| Compound | Structure | Name |
|---|---|---|
| 107 | 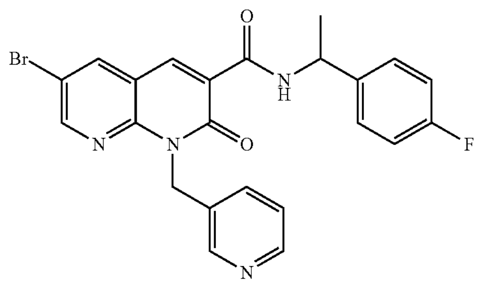 [SMILES: CC(NC(=O)c1cc2cc(Br)cnc2n(Cc2cccnc2)c1=O)c1ccc(F)cc1] | 6-bromo-N-(1-(4-fluorophenyl)ethyl)-2-oxo-1-(pyridin-3-ylmethyl)-1,2-dihydro-1,8-naphthyridine-3-carboxamide |
| 108 | 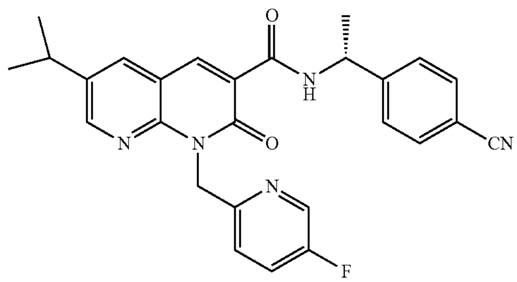 [SMILES: CC(C)c1cnc2c(c1)cc(C(=O)N[C@H](C)c1ccc(C#N)cc1)c(=O)n2Cc1ccc(F)cn1] | (R)-N-(1-(4-cyanophenyl)ethyl)-1-((5-fluoropyridin-2-yl)methyl)-6-isopropyl-2-oxo-1,2-dihydro-1,8-naphthyridine-3-carboxamide |
| 109 | 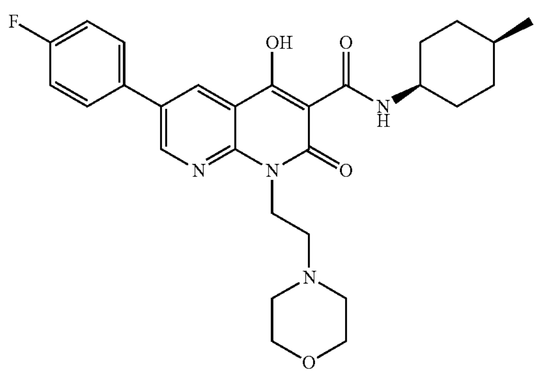 [SMILES: C[C@H]1CC[C@@H](NC(=O)c2c(O)c3cc(-c4ccc(F)cc4)cnc3n(CCN3CCOCC3)c2=O)CC1] | 6-(4-fluorophenyl)-4-hydroxy-N-((1s,4s)-4-methylcyclohexyl)-1-(2-morpholinoethyl)-2-oxo-1,2-dihydro-1,8-naphthyridine-3-carboxamide |
| 110 | 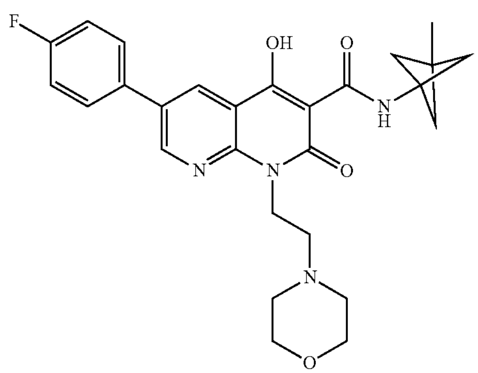 | 6-(4-fluorophenyl)-4-hydroxy-N-(3-methylbicyclo[1.1.1]pentan-1-yl)-1-(2-morpholinoethyl)-2-oxo-1,2-dihydro-1,8-naphthyridine-3-carboxamide |

TABLE 2-continued

| Compound | Structure | Name |
| --- | --- | --- |
| 111 | 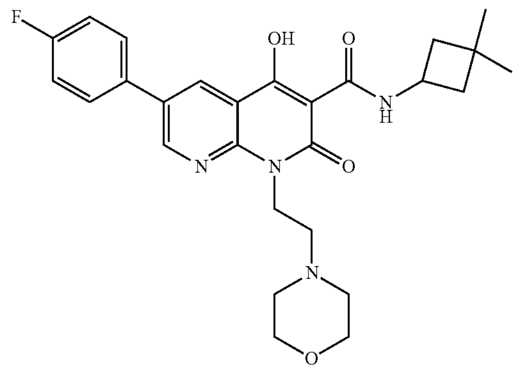 [SMILES: CC1(C)CC(NC(=O)c2c(O)c3cc(-c4ccc(F)cc4)cnc3n(CCN3CCOCC3)c2=O)C1] | N-(3,3-dimethylcyclobutyl)-6-(4-fluorophenyl)-4-hydroxy-1-(2-morpholinoethyl)-2-oxo-1,2-dihydro-1,8-naphthyridine-3-carboxamide |
| 112 | 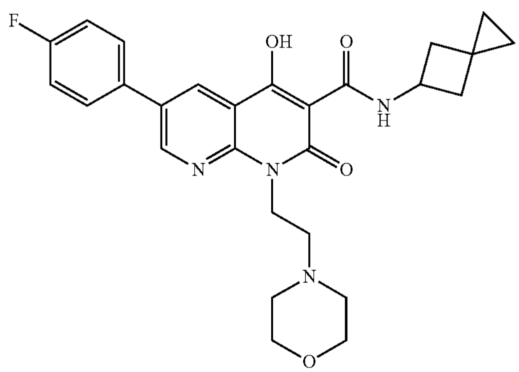 [SMILES: O=C(NC1CC2(CC2)C1)c1c(O)c2cc(-c3ccc(F)cc3)cnc2n(CCN2CCOCC2)c1=O] | 6-(4-fluorophenyl)-4-hydroxy-1-(2-morpholinoethyl)-2-oxo-N-(spiro[2.3]hexan-5-yl)-1,2-dihydro-1,8-naphthyridine-3-carboxamide |
| 113 | 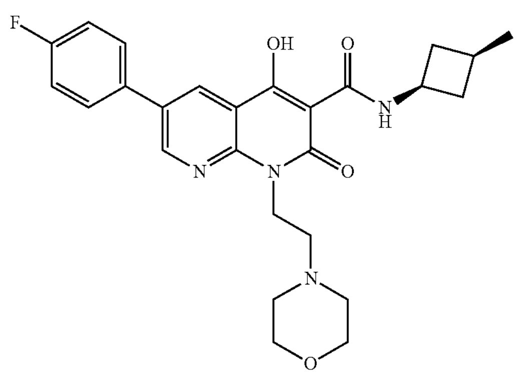 [SMILES: C[C@H]1C[C@@H](NC(=O)c2c(O)c3cc(-c4ccc(F)cc4)cnc3n(CCN3CCOCC3)c2=O)C1] | 6-(4-fluorophenyl)-4-hydroxy-N-((1s,3s)-3-methylcyclobutyl)-1-(2-morpholinoethyl)-2-oxo-1,2-dihydro-1,8-naphthyridine-3-carboxamide |
| 114 | 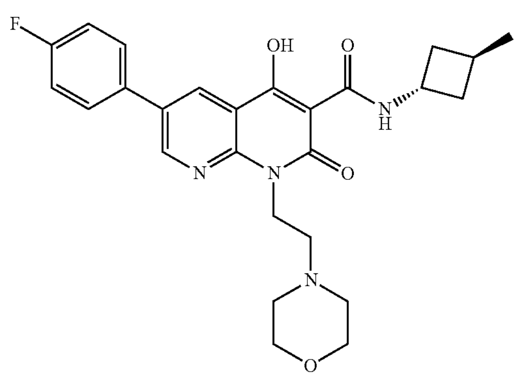 [SMILES: C[C@H]1C[C@H](NC(=O)c2c(O)c3cc(-c4ccc(F)cc4)cnc3n(CCN3CCOCC3)c2=O)C1] | 6-(4-fluorophenyl)-4-hydroxy-N-((1r,3r)-3-methylcyclobutyl)-1-(2-morpholinoethyl)-2-oxo-1,2-dihydro-1,8-naphthyridine-3-carboxamide |

TABLE 2-continued

| Compound | Structure | Name |
| --- | --- | --- |
| 115 | 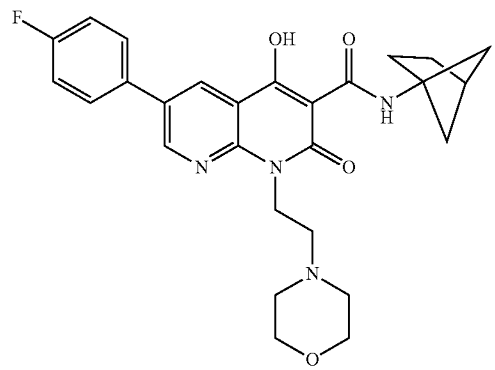 [SMILES: O=C(NC12CCC(C1)C2)c1c(O)c2cc(-c3ccc(F)cc3)cnc2n(CCN2CCOCC2)c1=O] | N-(bicyclo[2.1.1]hexan-1-yl)-6-(4-fluorophenyl)-4-hydroxy-1-(2-morpholinoethyl)-2-oxo-1,2-dihydro-1,8-naphthyridine-3-carboxamide |
| 116 | 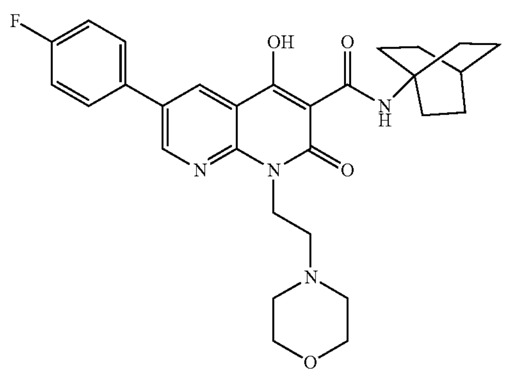 [SMILES: O=C(NC12CCC(CC1)CC2)c1c(O)c2cc(-c3ccc(F)cc3)cnc2n(CCN2CCOCC2)c1=O] | N-(bicyclo[2.2.2]octan-1-yl)-6-(4-fluorophenyl)-4-hydroxy-1-(2-morpholinoethyl)-2-oxo-1,2-dihydro-1,8-naphthyridine-3-carboxamide |
| 117 | 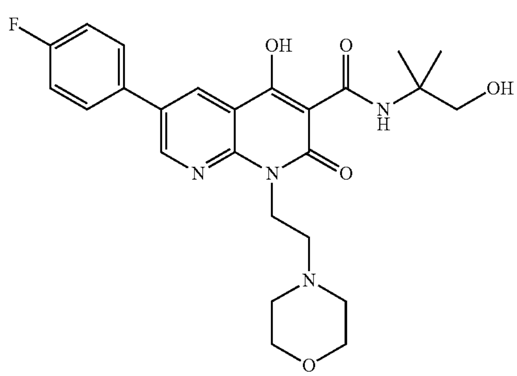 [SMILES: CC(C)(CO)NC(=O)c1c(O)c2cc(-c3ccc(F)cc3)cnc2n(CCN2CCOCC2)c1=O] | 6-(4-fluorophenyl)-4-hydroxy-N-(1-hydroxy-2-methylpropan-2-yl)-1-(2-morpholinoethyl)-2-oxo-1,2-dihydro-1,8-naphthyridine-3-carboxamide |
| 118 | 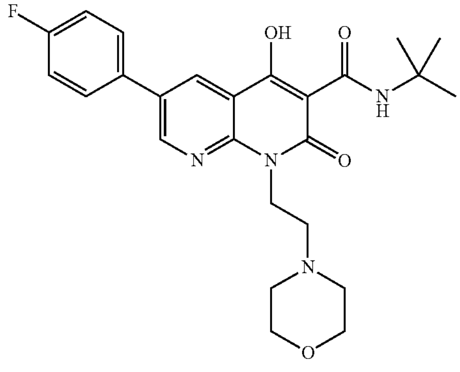 [SMILES: CC(C)(C)NC(=O)c1c(O)c2cc(-c3ccc(F)cc3)cnc2n(CCN2CCOCC2)c1=O] | N-(tert-butyl)-6-(4-fluorophenyl)-4-hydroxy-1-(2-morpholinoethyl)-2-oxo-1,2-dihydro-1,8-naphthyridine-3-carboxamide |

TABLE 2-continued

| Compound | Structure | Name |
|---|---|---|
| 119 | 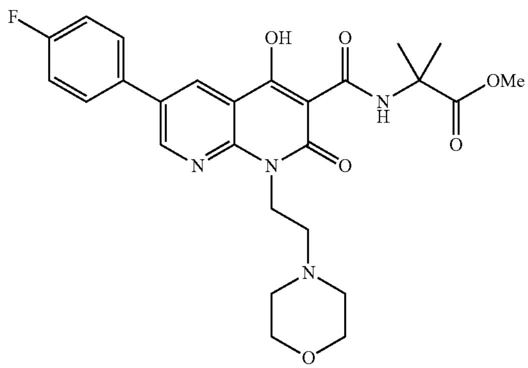 [SMILES: COC(=O)C(C)(C)NC(=O)c1c(O)c2cc(-c3ccc(F)cc3)cnc2n(CCN2CCOCC2)c1=O] | methyl 2-(6-(4-fluorophenyl)-4-hydroxy-1-(2-morpholinoethyl)-2-oxo-1,2-dihydro-1,8-naphthyridine-3-carboxamido)-2-methylpropanoate |
| 120 | 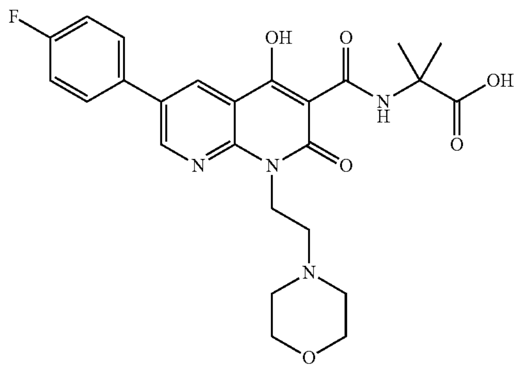 [SMILES: CC(C)(NC(=O)c1c(O)c2cc(-c3ccc(F)cc3)cnc2n(CCN2CCOCC2)c1=O)C(=O)O] | 2-(6-(4-fluorophenyl)-4-hydroxy-1-(2-morpholinoethyl)-2-oxo-1,2-dihydro-1,8-naphthyridine-3-carboxamido)-2-methylpropanoic acid |
| 121 | 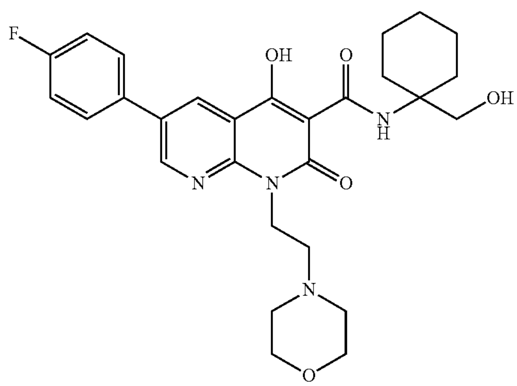 [SMILES: O=C(NC1(CO)CCCCC1)c1c(O)c2cc(-c3ccc(F)cc3)cnc2n(CCN2CCOCC2)c1=O] | 6-(4-fluorophenyl)-4-hydroxy-N-(1-(hydroxymethyl)cyclohexyl)-1-(2-morpholinoethyl)-2-oxo-1,2-dihydro-1,8-naphthyridine-3-carboxamide |
| 122 | 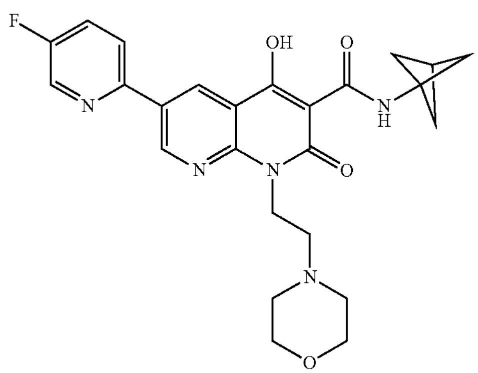 | N-(bicyclo[1.1.1]pentan-1-yl)-6-(5-fluoropyridin-2-yl)-4-hydroxy-1-(2-morpholinoethyl)-2-oxo-1,2-dihydro-1,8-naphthyridine-3-carboxamide |

TABLE 2-continued

| Compound | Structure | Name |
| --- | --- | --- |
| 123 | 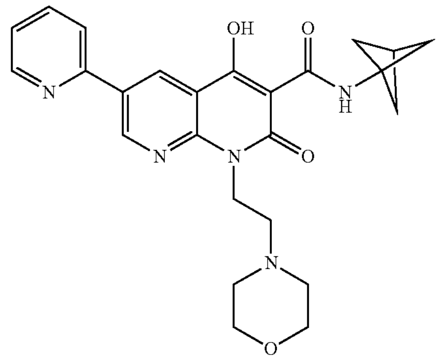 [SMILES: O=C(NC12CC(C1)C2)c1c(O)c2cc(-c3ccccn3)cnc2n(CCN2CCOCC2)c1=O] | N-(bicyclo[1.1.1]pentan-1-yl)-4-hydroxy-1-(2-morpholinoethyl)-2-oxo-6-(pyridin-3-yl)-1,2-dihydro-1,8-naphthyridine-3-carboxamide |
| 124 | 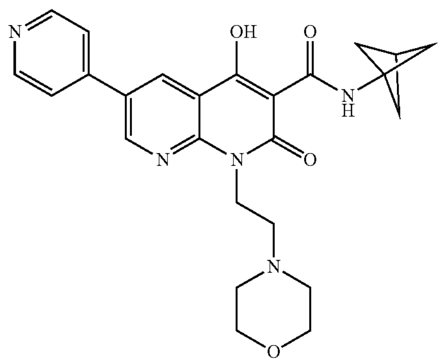 [SMILES: O=C(NC12CC(C1)C2)c1c(O)c2cc(-c3ccncc3)cnc2n(CCN2CCOCC2)c1=O] | N-(bicyclo[1.1.1]pentan-1-yl)-4-hydroxy-1-(2-morpholinoethyl)-2-oxo-6-(pyridin-4-yl)-1,2-dihydro-1,8-naphthyridine-3-carboxamide |
| 125 | 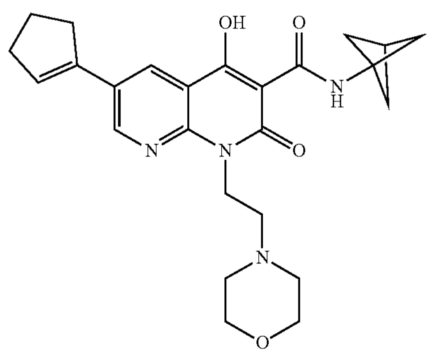 | N-(bicyclo[1.1.1]pentan-1-yl)-6-(cyclopent-1-en-1-yl)-4-hydroxy-1-(2-morpholinoethyl)-2-oxo-1,2-dihydro-1,8-naphthyridine-3-carboxamide |
| 126 | 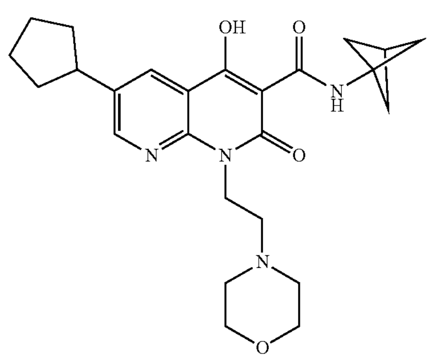 [SMILES: O=C(NC12CC(C1)C2)c1c(O)c2cc(C3CCCC3)cnc2n(CCN2CCOCC2)c1=O] | N-(bicyclo[1.1.1]pentan-1-yl)-6-cyclopentyl-4-hydroxy-1-(2-morpholinoethyl)-2-oxo-1,2-dihydro-1,8-naphthyridine-3-carboxamide |

TABLE 2-continued

| Compound | Structure | Name |
|---|---|---|
| 127 | 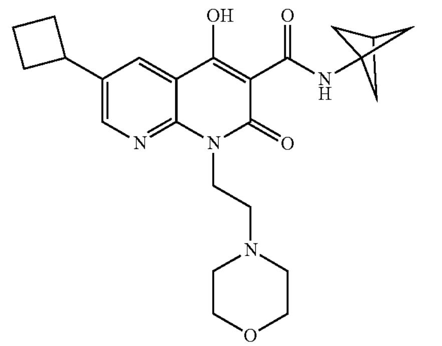 [SMILES: O=C(NC12CC(C1)C2)c1c(O)c2cc(C3CCC3)cnc2n(CCN2CCOCC2)c1=O] | N-(bicyclo[1.1.1]pentan-1-yl)-6-cyclobutyl-4-hydroxy-1-(2-morpholinoethyl)-2-oxo-1,2-dihydro-1,8-naphthyridine-3-carboxamide |
| 128 | 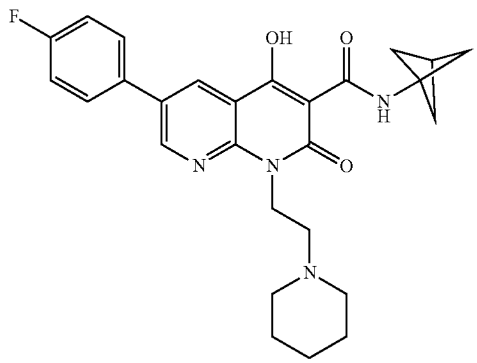 [SMILES: O=C(NC12CC(C1)C2)c1c(O)c2cc(-c3ccc(F)cc3)cnc2n(CCN2CCCCC2)c1=O] | N-(bicyclo[1.1.1]pentan-1-yl)-6-(4-fluorophenyl)-4-hydroxy-2-oxo-1-(2-(piperidin-1-yl)ethyl)-1,2-dihydro-1,8-naphthyridine-3-carboxamide |
| 129 | 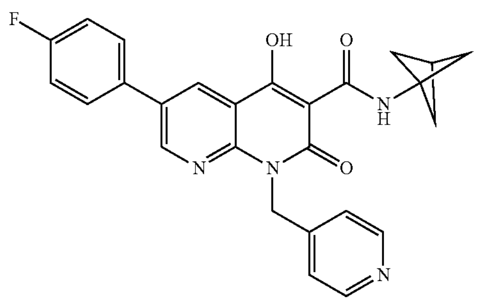 [SMILES: O=C(NC12CC(C1)C2)c1c(O)c2cc(-c3ccc(F)cc3)cnc2n(Cc2ccncc2)c1=O] | N-(bicyclo[1.1.1]pentan-1-yl)-6-(4-fluorophenyl)-4-hydroxy-2-oxo-1-(pyridin-4-ylmethyl)-1,2-dihydro-1,8-naphthyridine-3-carboxamide |
| 130 | 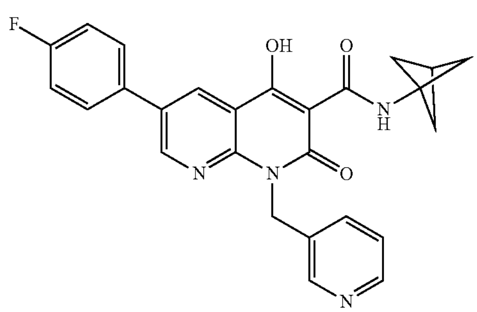 [SMILES: O=C(NC12CC(C1)C2)c1c(O)c2cc(-c3ccc(F)cc3)cnc2n(Cc2cccnc2)c1=O] | N-(bicyclo[1.1.1]pentan-1-yl)-6-(4-fluorophenyl)-4-hydroxy-2-oxo-1-(pyridin-3-ylmethyl)-1,2-dihydro-1,8-naphthyridine-3-carboxamide |

TABLE 2-continued

| Compound | Structure | Name |
| --- | --- | --- |
| 131 | 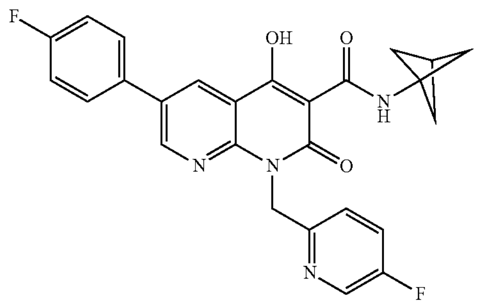 [SMILES: O=C(NC12CC(C1)C2)c1c(O)c2cc(-c3ccc(F)cc3)cnc2n(Cc2ccc(F)cn2)c1=O] | N-(bicyclo[1.1.1]pentan-1-yl)-6-(4-fluorophenyl)-1-((5-fluoropyridin-2-yl)methyl)-4-hydroxy-2-oxo-1,2-dihydro-1,8-naphthyridine-3-carboxamide |
| 132 | 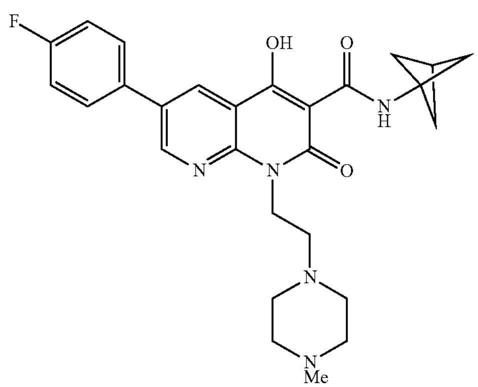 [SMILES: CN1CCN(CCn2c(=O)c(C(=O)NC34CC(C3)C4)c(O)c3cc(-c4ccc(F)cc4)cnc32)CC1] | N-(bicyclo[1.1.1]pentan-1-yl)-6-(4-fluorophenyl)-4-hydroxy-1-(2-(4-methylpiperazin-1-yl)ethyl)-2-oxo-1,2-dihydro-1,8-naphthyridine-3-carboxamide |
| 133 | 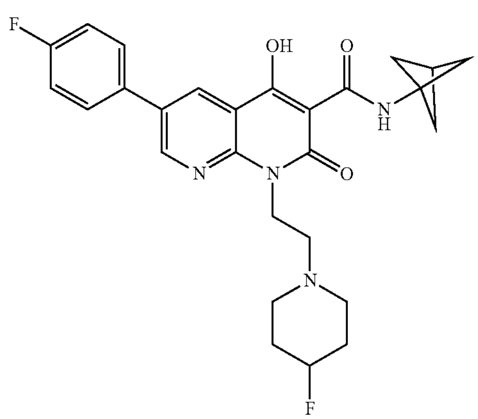 [SMILES: O=C(NC12CC(C1)C2)c1c(O)c2cc(-c3ccc(F)cc3)cnc2n(CCN2CCC(F)CC2)c1=O] | N-(bicyclo[1.1.1]pentan-1-yl)-6-(4-fluorophenyl)-4-hydroxy-2-oxo-1-(2-(4-fluoropiperidin-1-yl)ethyl)-1,2-dihydro-1,8-naphthyridine-3-carboxamide |
| 134 | 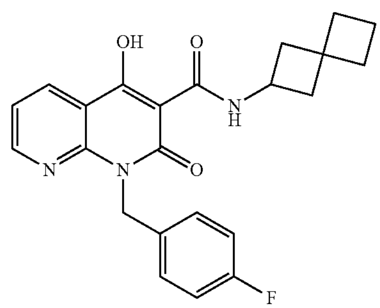 [SMILES: O=C(NC1CC2(CCC2)C1)c1c(O)c2cccnc2n(Cc2ccc(F)cc2)c1=O] | 1-(4-fluorobenzyl)-4-hydroxy-2-oxo-N-(spiro[3.3]heptan-2-yl)-1,2-dihydro-1,8-naphthyridine-3-carboxamide |

TABLE 2-continued

| Compound | Structure | Name |
| --- | --- | --- |
| 135 | 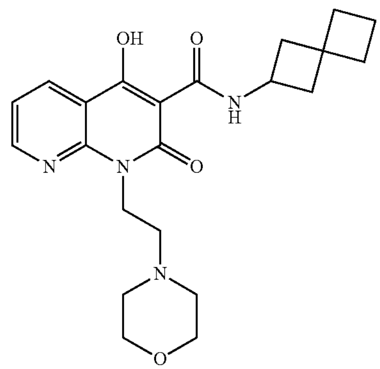 [SMILES: O=C(NC1CC2(CCC2)C1)c1c(O)c2cccnc2n(CCN2CCOCC2)c1=O] | 4-hydroxy-2-oxo-1-(2-morpholinoethyl)-N-(spiro[3.3]heptan-2-yl)-1,2-dihydro-1,8-naphthyridine-3-carboxamide |
| 136 | 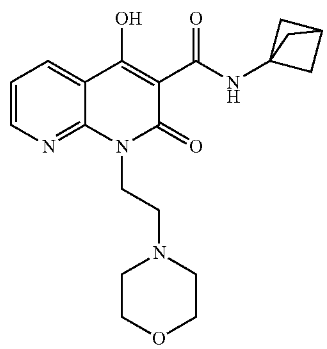 [SMILES: O=C(NC12CC(C1)C2)c1c(O)c2cccnc2n(CCN2CCOCC2)c1=O] | N-(bicyclo[1.1.1]pentan-1-yl)-4-hydroxy-1-(2-morpholinoethyl)-2-oxo-1,2-dihydro-1,8-naphthyridine-3-carboxamide |
| 137 | 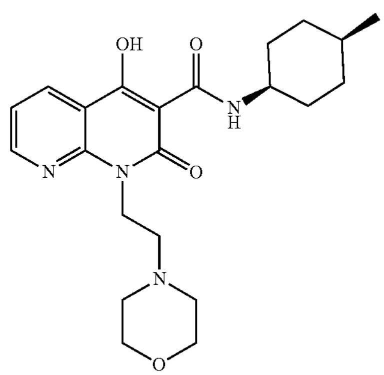 [SMILES: C[C@H]1CC[C@@H](NC(=O)c2c(O)c3cccnc3n(CCN3CCOCC3)c2=O)CC1] | 4-hydroxy-N-((1s,4s)-4-methylcyclohexyl)-1-(2-morpholinoethyl)-2-oxo-1,2-dihydro-1,8-naphthyridine-3-carboxamide |
| 138 | 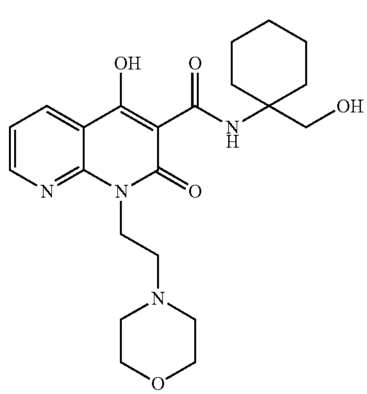 [SMILES: O=C(NC1(CO)CCCCC1)c1c(O)c2cccnc2n(CCN2CCOCC2)c1=O] | 4-hydroxy-N-[1-(hydroxymethyl)cyclohexyl]-1-(2-morpholinoethyl)-2-oxo-1,8-naphthyridine-3-carboxamide |

TABLE 2-continued

| Compound | Structure | Name |
|---|---|---|
| 139 | 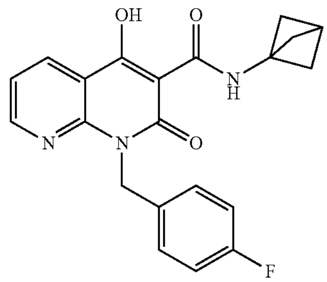 [SMILES: O=C(NC12CC(C1)C2)c1c(O)c2cccnc2n(Cc2ccc(F)cc2)c1=O] | N-(1-bicyclo[1.1.1]pentanyl)-1-[(4-fluorophenyl)methyl]-4-hydroxy-2-oxo-1,8-naphthyridine-3-carboxamide |
| 140 | 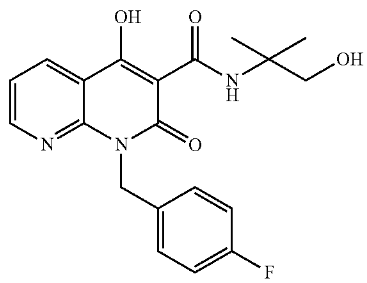 [SMILES: CC(C)(CO)NC(=O)c1c(O)c2cccnc2n(Cc2ccc(F)cc2)c1=O] | 1-[(4-fluorophenyl)methyl]-4-hydroxy-N-(2-hydroxy-1,1-dimethyl-ethyl)-2-oxo-1,8-naphthyridine-3-carboxamide |
| 141 | 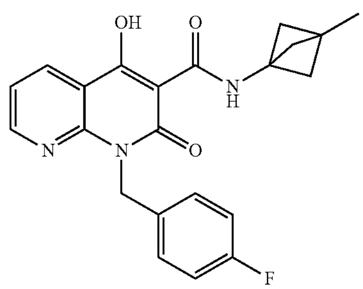 [SMILES: CC12CC(NC(=O)c3c(O)c4cccnc4n(Cc4ccc(F)cc4)c3=O)(C1)C2] | 1-[(4-fluorophenyl)methyl]-4-hydroxy-N-(3-methyl-1-bicyclo[1.1.1]pentanyl)-2-oxo-1,8-naphthyridine-3-carboxamide |
| 142 | 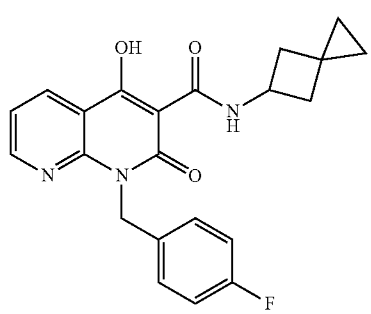 [SMILES: O=C(NC1CC2(CC2)C1)c1c(O)c2cccnc2n(Cc2ccc(F)cc2)c1=O] | 1-[(4-fluorophenyl)methyl]-4-hydroxy-2-oxo-N-spiro[2.3]hexan-5-yl-1,8-naphthyridine-3-carboxamide |
| 143 | 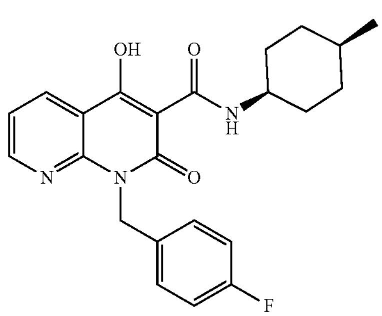 [SMILES: C[C@H]1CC[C@@H](NC(=O)c2c(O)c3cccnc3n(Cc3ccc(F)cc3)c2=O)CC1] | 1-(4-fluorobenzyl)-4-hydroxy-N-((1s,4s)-4-methylcyclohexyl)-2-oxo-1,2-dihydro-1,8-naphthyridine-3-carboxamide |

TABLE 2-continued

| Compound | Structure | Name |
|---|---|---|
| 144 | 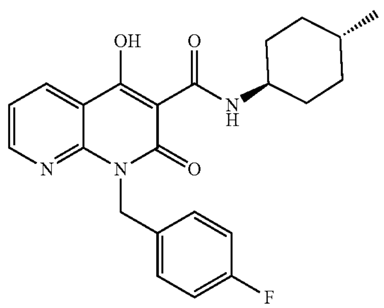 [SMILES: C[C@H]1CC[C@H](NC(=O)c2c(O)c3cccnc3n(Cc3ccc(F)cc3)c2=O)CC1] | 1-(4-fluorobenzyl)-4-hydroxy-N-((1r,4r)-4-methylcyclohexyl)-2-oxo-1,2-dihydro-1,8-naphthyridine-3-carboxamide |
| 145 | 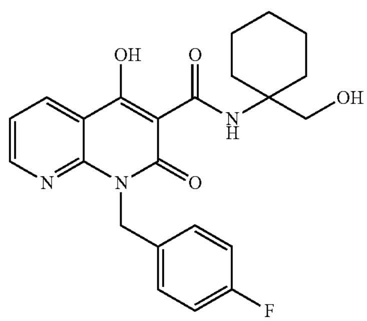 [SMILES: O=C(NC1(CO)CCCCC1)c1c(O)c2cccnc2n(Cc2ccc(F)cc2)c1=O] | 1-[(4-fluorophenyl)methyl]-4-hydroxy-N-[1-(hydroxymethyl)cyclohexyl]-2-oxo-1,8-naphthyridine-3-carboxamide |
| 146 | 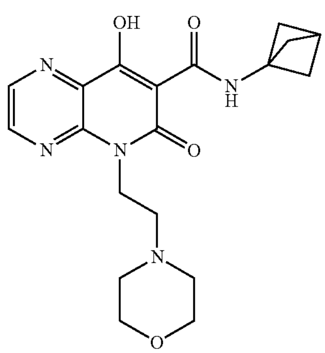 [SMILES: O=C(NC12CC(C1)C2)c1c(O)c2nccnc2n(CCN2CCOCC2)c1=O] | N-(bicyclo[1.1.1]pentan-1-yl)-8-hydroxy-5-(2-morpholinoethyl)-6-oxo-5,6-dihydropyrido[2,3-b]pyrazine-7-carboxamide |
| 147 | 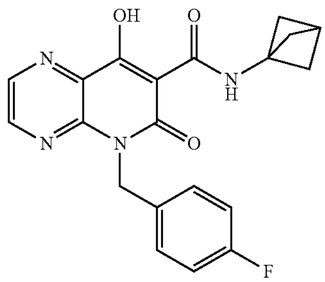 [SMILES: O=C(NC12CC(C1)C2)c1c(O)c2nccnc2n(Cc2ccc(F)cc2)c1=O] | N-(bicyclo[1.1.1]pentan-1-yl)-5-(4-fluorobenzyl)-8-hydroxy-6-oxo-5,6-dihydropyrido[2,3-b]pyrazine-7-carboxamide |

TABLE 2-continued

| Compound | Structure | Name |
|---|---|---|
| 148 | 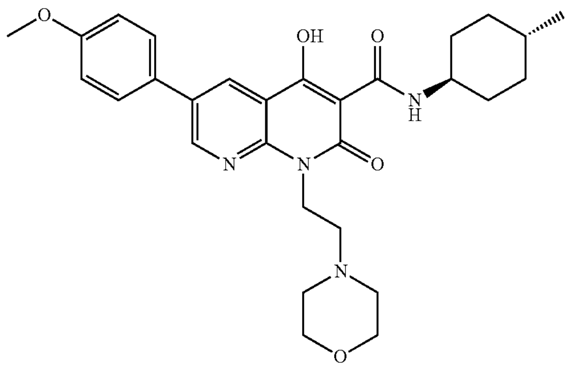 | 4-hydroxy-6-(4-methoxyphenyl)-N-((1R,4R)-4-methylcyclohexyl)-1-(2-morpholinoethyl)-2-oxo-1,2-dihydro-1,8-naphthyridine-3-carboxamide |
| 149 | 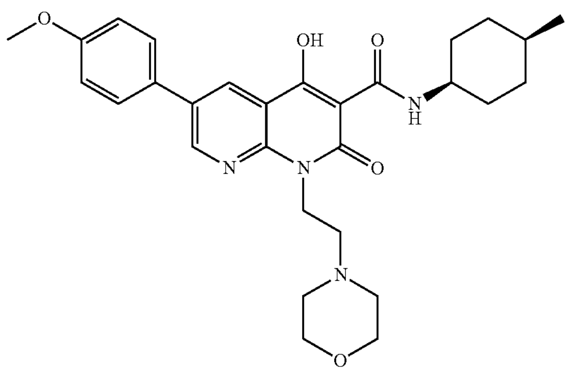 | 4-hydroxy-6-(4-methoxyphenyl)-N-((1s,4S)-4-methylcyclohexyl)-1-(2-morpholinoethyl)-2-oxo-1,2-dihydro-1,8-naphthyridine-3-carboxamide |
| 150 | 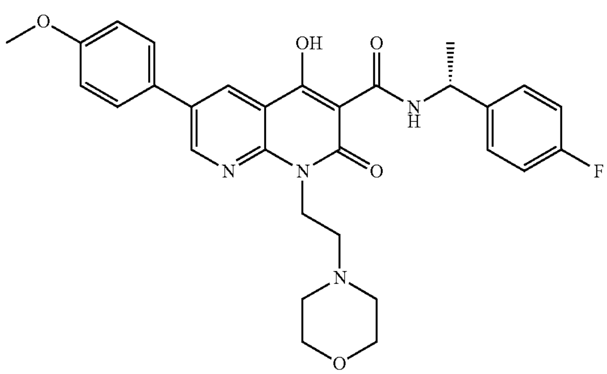 | (R)-N-(1-(4-fluorophenyl)ethyl)-4-hydroxy-6-(4-methoxyphenyl)-1-(2-morpholinoethyl)-2-oxo-1,2-dihydro-1,8-naphthyridine-3-carboxamide |
| 151 | 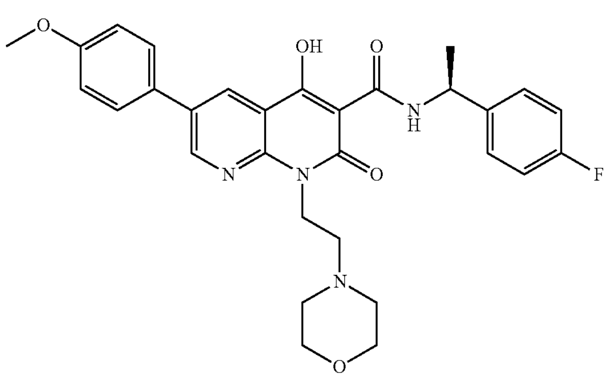 [SMILES: COc1ccc(-c2cnc3c(c2)c(O)c(C(=O)N[C@@H](C)c2ccc(F)cc2)c(=O)n3CCN2CCOCC2)cc1] | (R)-N-(1-(4-fluorophenyl)ethyl)-4-hydroxy-6-(4-methoxyphenyl)-1-(2-morpholinoethyl)-2-oxo-1,2-dihydro-1,8-naphthyridine-3-carboxamide |

TABLE 2-continued

| Compound | Structure | Name |
|---|---|---|
| 152 | 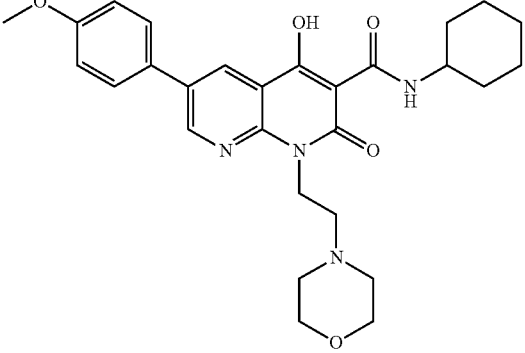 | N-cyclohexyl-4-hydroxy-6-(4-methoxyphenyl)-1-(2-morpholinoethyl)-2-oxo-1,2-dihydro-1,8-naphthyridine-3-carboxamide |
| 153 | 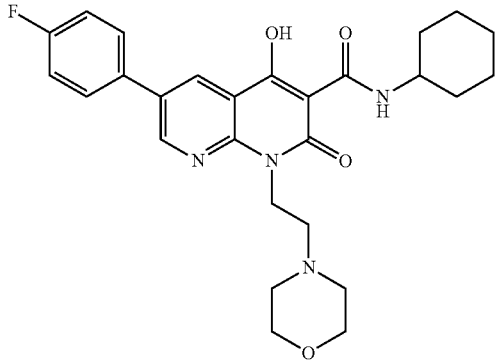 [SMILES: O=C(NC1CCCCC1)c1c(O)c2cc(-c3ccc(F)cc3)cnc2n(CCN2CCOCC2)c1=O] | N-cyclohexyl-6-(4-fluorophenyl)-4-hydroxy-1-(2-morpholinoethyl)-2-oxo-1,2-dihydro-1,8-naphthyridine-3-carboxamide |
| 154 | 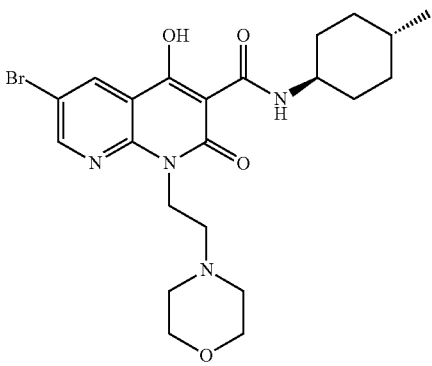 [SMILES: C[C@H]1CC[C@H](NC(=O)c2c(O)c3cc(Br)cnc3n(CCN3CCOCC3)c2=O)CC1] | 6-bromo-4-hydroxy-N-((1R,4R)-4-methylcyclohexyl)-1-(2-morpholinoethyl)-2-oxo-1,2-dihydro-1,8-naphthyridine-3-carboxamide |
| 155 | 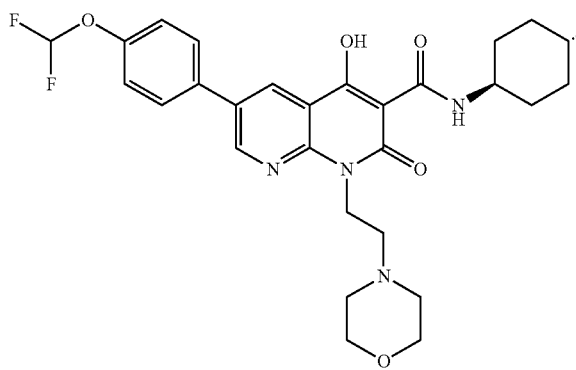 | 6-(4-(difluoromethoxy)phenyl)-4-hydroxy-N-((1R,4R)-4-methylcyclohexyl)-1-(2-morpholinoethyl)-2-oxo-1,2-dihydro-1,8-naphthyridine-3-carboxamide |

TABLE 2-continued

| Compound | Structure | Name |
|---|---|---|
| 158 | 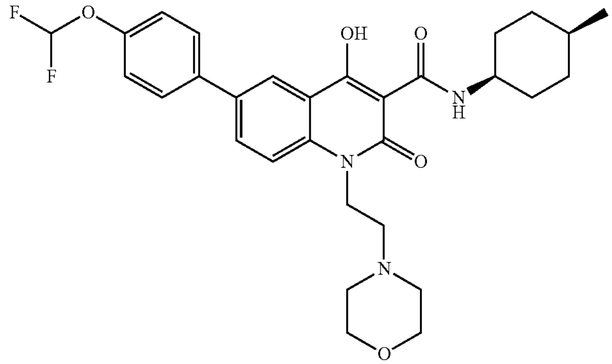 [SMILES: C[C@H]1CC[C@@H](NC(=O)c2c(O)c3cc(-c4ccc(OC(F)F)cc4)ccc3n(CCN3CCOCC3)c2=O)CC1] | 6-(4-(difluoromethoxy)phenyl)-4-hydroxy-N-((1s,4S)-4-methylcyclohexyl)-1-(2-morpholinoethyl)-2-oxo-1,2-dihydroquinoline-3-carboxamide |
| 159 | 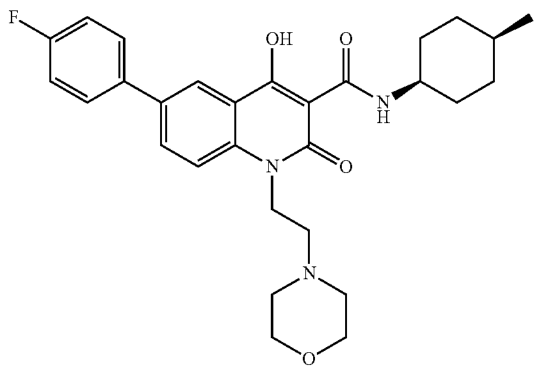 [SMILES: C[C@H]1CC[C@@H](NC(=O)c2c(O)c3cc(-c4ccc(F)cc4)ccc3n(CCN3CCOCC3)c2=O)CC1] | 6-(4-fluorophenyl)-4-hydroxy-N-((1s,4S)-4-methylcyclohexyl)-1-(2-morpholinoethyl)-2-oxo-1,2-dihydroquinoline-3-carboxamide |
| 161 | 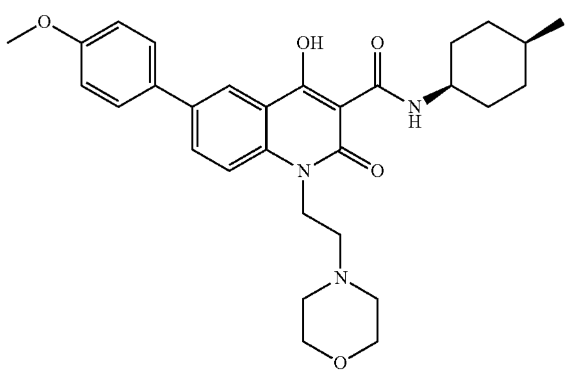 | 4-hydroxy-6-(4-methoxyphenyl)-N-((1s,4S)-4-methylcyclohexyl)-1-(2-morpholinoethyl)-2-oxo-1,2-dihydroquinoline-3-carboxamide |
| 165 | 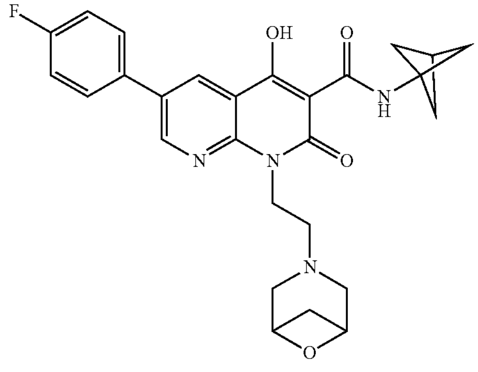 [SMILES: O=C(NC12CC(C1)C2)c1c(O)c2cc(-c3ccc(F)cc3)cnc2n(CCN2CC3CC(C2)O3)c1=O] | 1-(2-(6-oxa-3-azabicyclo[3.1.1]heptan-3-yl)ethyl)-N-(bicyclo[1.1.1]pentan-1-yl)-6-(4-fluorophenyl)-4-hydroxy-2-oxo-1,2-dihydro-1,8-naphthyridine-3-carboxamide |

TABLE 2-continued

| Compound | Structure | Name |
|---|---|---|
| 166 | 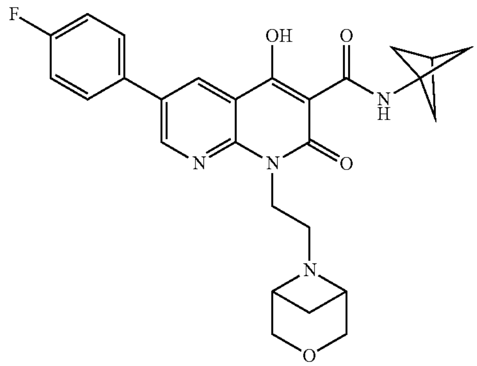 [SMILES: O=C(NC12CC(C1)C2)c1c(O)c2cc(-c3ccc(F)cc3)cnc2n(CCN2C3COCC2C3)c1=O] | 1-(2-(3-oxa-6-azabicyclo[3.1.1]heptan-6-yl)ethyl)-N-(bicyclo[1.1.1]pentan-1-yl)-6-(4-fluorophenyl)-4-hydroxy-2-oxo-1,2-dihydro-1,8-naphthyridine-3-carboxamide |
| 173 | 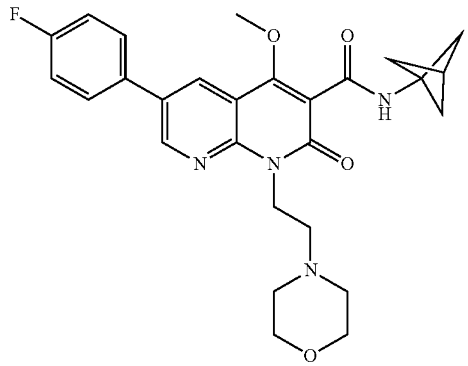 [SMILES: COc1c(C(=O)NC23CC(C2)C3)c(=O)n(CCN2CCOCC2)c2ncc(-c3ccc(F)cc3)cc12] | N-(bicyclo[1.1.1]pentan-1-yl)-6-(4-fluorophenyl)-4-methoxy-1-(2-morpholinoethyl)-2-oxo-1,2-dihydro-1,8-naphthyridine-3-carboxamide |
| 177 | 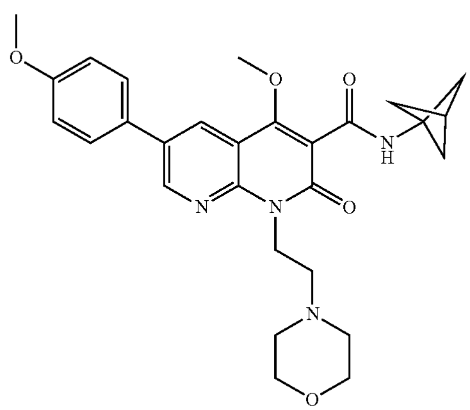 [SMILES: COc1ccc(-c2cnc3c(c2)c(OC)c(C(=O)NC24CC(C2)C4)c(=O)n3CCN2CCOCC2)cc1] | N-(bicyclo[1.1.1]pentan-1-yl)-4-methoxy-6-(4-methoxyphenyl)-1-(2-morpholinoethyl)-2-oxo-1,2-dihydro-1,8-naphthyridine-3-carboxamide |
| 180 | 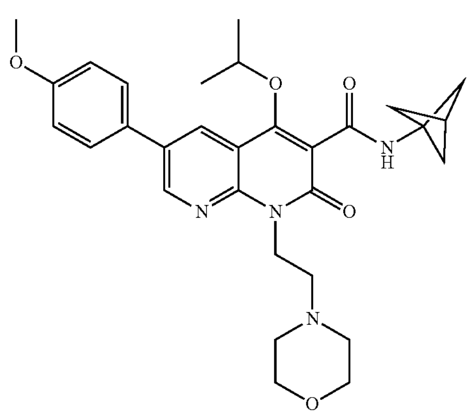 [SMILES: COc1ccc(-c2cnc3c(c2)c(OC(C)C)c(C(=O)NC24CC(C2)C4)c(=O)n3CCN2CCOCC2)cc1] | N-(bicyclo[1.1.1]pentan-1-yl)-4-isopropoxy-6-(4-methoxyphenyl)-1-(2-morpholinoethyl)-2-oxo-1,2-dihydro-1,8-naphthyridine-3-carboxamide |

TABLE 2-continued

| Compound | Structure | Name |
|---|---|---|
| 181 | 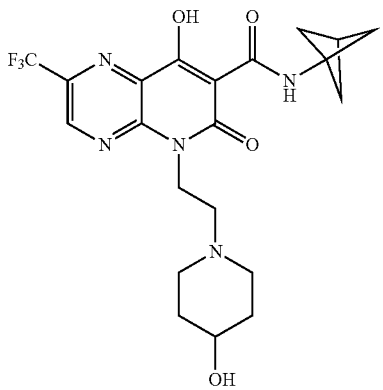 [SMILES: O=C(NC12CC(C1)C2)c1c(O)c2nc(C(F)(F)F)cnc2n(CCN2CCC(O)CC2)c1=O] | N-(bicyclo[1.1.1]pentan-1-yl)-8-hydroxy-5-(2-(4-hydroxypiperidin-1-yl)ethyl)-6-oxo-2-(trifluoromethyl)-5,6-dihydropyrido[2,3-b]pyrazine-7-carboxamide |
| 182 | 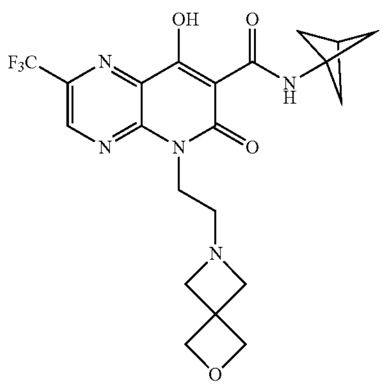 | 5-(2-(2-oxa-6-azaspiro[3.3]heptan-6-yl)ethyl)-N-(bicyclo[1.1.1]pentan-1-yl)-8-hydroxy-6-oxo-2-(trifluoromethyl)-5,6-dihydropyrido[2,3-b]pyrazine-7-carboxamide |
| 183 | 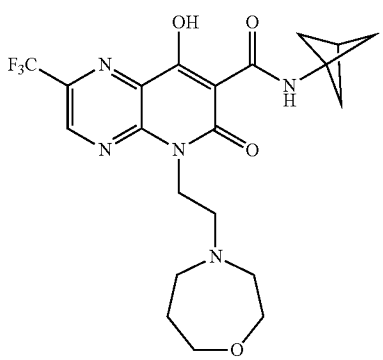 [SMILES: O=C(NC12CC(C1)C2)c1c(O)c2nc(C(F)(F)F)cnc2n(CCN2CCCOCC2)c1=O] | 5-(2-(1,4-oxazepan-4-yl)ethyl)-N-(bicyclo[1.1.1]pentan-1-yl)-8-hydroxy-6-oxo-2-dihydropyrido[2,3-b]pyrazine-7-carboxamide |
| 184 | 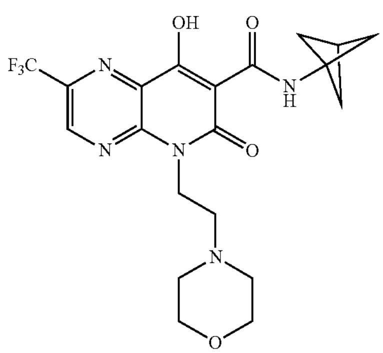 [SMILES: O=C(NC12CC(C1)C2)c1c(O)c2nc(C(F)(F)F)cnc2n(CCN2CCOCC2)c1=O] | N-(bicyclo[1.1.1]pentan-1-yl)-8-hydroxy-5-(2-morpholinoethyl)-6-oxo-2-(trifluoromethyl)-5,6-dihydropyrido[2,3-b]pyrazine-7-carboxamide |

TABLE 2-continued

| Compound | Structure | Name |
|---|---|---|
| 185 | 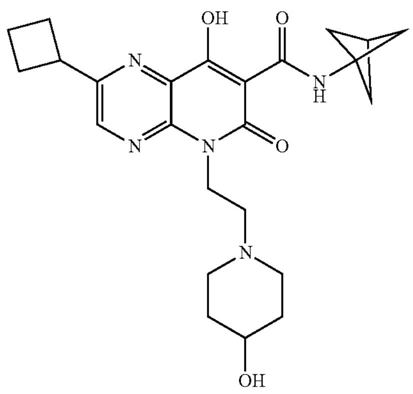 [SMILES: O=C(NC12CC(C1)C2)c1c(O)c2nc(C3CCC3)cnc2n(CCN2CCC(O)CC2)c1=O] | N-(bicyclo[1.1.1]pentan-1-yl)-2-cyclobutyl-8-hydroxy-5-(2-(4-hydroxypiperidin-1-yl)ethyl)-6-oxo-5,6-dihydropyrido[2,3-b]pyrazine-7-carboxamide |
| 186 | 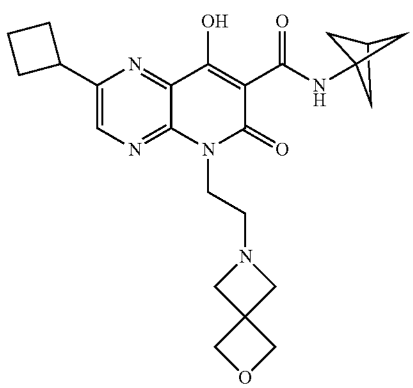 [SMILES: O=C(NC12CC(C1)C2)c1c(O)c2nc(C3CCC3)cnc2n(CCN2CC3(COC3)C2)c1=O] | 5-(2-(2-oxa-6-azaspiro[3.3]heptan-6-yl)ethyl)-N-(bicyclo[1.1.1]pentan-1-yl)-2-cyclobutyl-8-hydroxy-6-oxo-5,6-dihydropyrido[2,3-b]pyrazine-7-carboxamide |
| 187 | 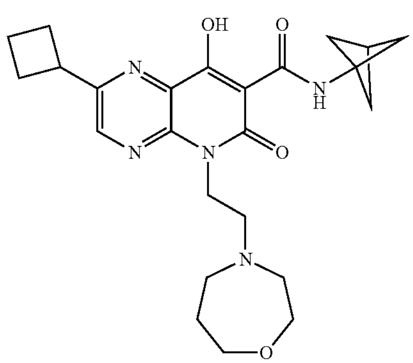 [SMILES: O=C(NC12CC(C1)C2)c1c(O)c2nc(C3CCC3)cnc2n(CCN2CCCOCC2)c1=O] | 5-(2-(1,4-oxazepan-4-yl)ethyl)-N-(bicyclo[1.1.1]pentan-1-yl)-2-cyclobutyl-8-hydroxy-6-oxo-5,6-dihydropyrido[2,3-b]pyrazine-7-carboxamide |
| 188 | 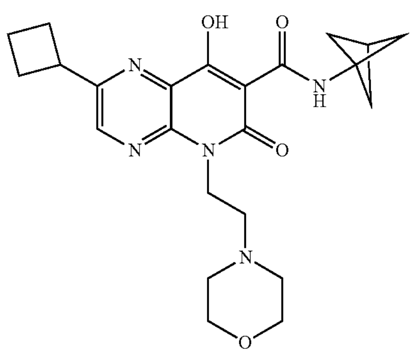 | N-(bicyclo[1.1.1]pentan-1-yl)-2-cyclobutyl-8-hydroxy-5-(2-morpholinoethyl)-6-oxo-5,6-dihydropyrido[2,3-b]pyrazine-7-carboxamide |

TABLE 2-continued

| Compound | Structure | Name |
|---|---|---|
| 189 | 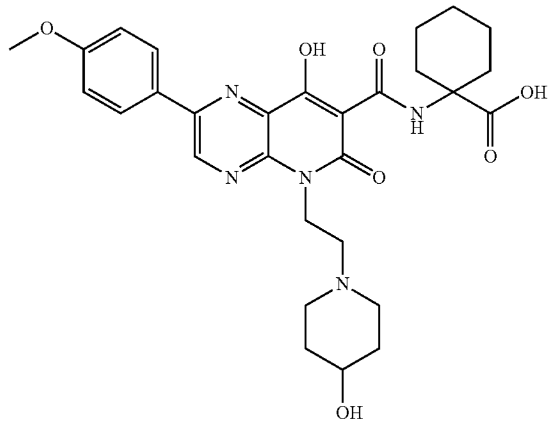 [SMILES: COc1ccc(-c2cnc3c(n2)c(O)c(C(=O)NC2(C(=O)O)CCCCC2)c(=O)n3CCN2CCC(O)CC2)cc1] | 1-(8-hydroxy-5-(2-(4-hydroxypiperidin-1-yl)ethyl)-2-(4-methoxyphenyl)-6-oxo-5,6-dihydropyrido[2,3-b]pyrazine-7-carboxamido)cyclohexane-1-carboxylic acid |
| 190 | 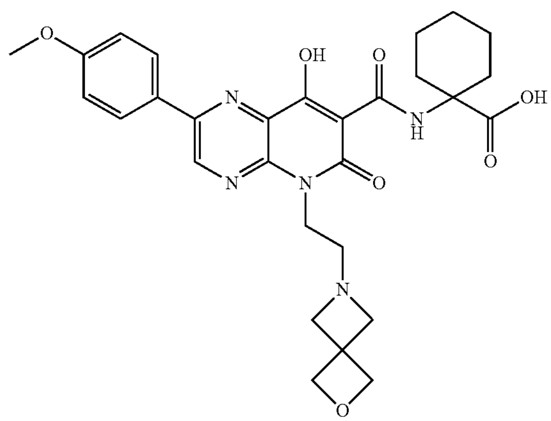 [SMILES: COc1ccc(-c2cnc3c(n2)c(O)c(C(=O)NC2(C(=O)O)CCCCC2)c(=O)n3CCN2CC3(COC3)C2)cc1] | 1-(5-(2-(2-oxa-6-azaspiro[3.3]heptan-6-yl)ethyl)-8-hydroxy-2-(4-methoxyphenyl)-6-oxo-5,6-dihydropyrido[2,3-b]pyrazine-7-carboxamido)cyclohexane-1-carboxylic acid |
| 191 | 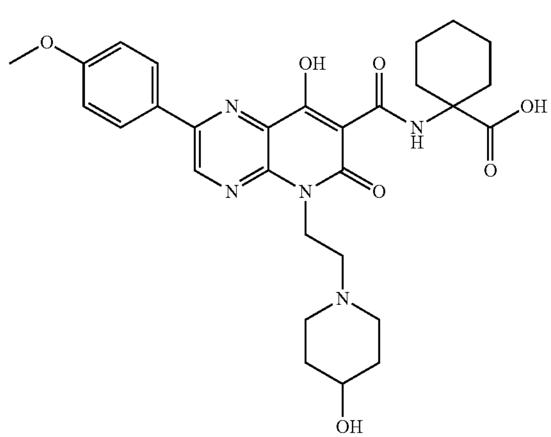 [SMILES: COc1ccc(-c2cnc3c(n2)c(O)c(C(=O)NC2(C(=O)O)CCCCC2)c(=O)n3CCN2CCC(O)CC2)cc1] | 1-(5-(2-(1,4-oxazepan-4-yl)ethyl)-8-hydroxy-2-(4-methoxyphenyl)-6-oxo-5,6-dihydropyrido[2,3-b]pyrazine-7-carboxamido)cyclohexane-1-carboxylic acid |

TABLE 2-continued

| Compound | Structure | Name |
|---|---|---|
| 192 | 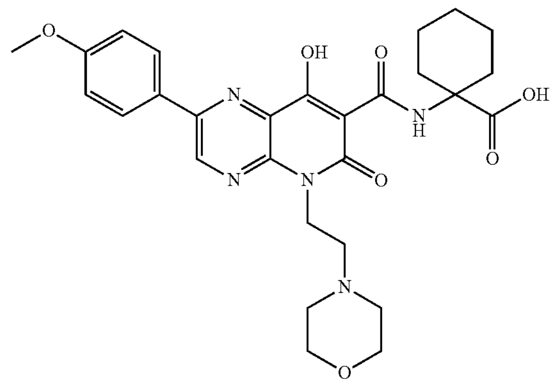 [SMILES: COc1ccc(-c2cnc3c(n2)c(O)c(C(=O)NC2(C(=O)O)CCCCC2)c(=O)n3CCN2CCOCC2)cc1] | 1-(8-hydroxy-2-(4-methoxyphenyl)-5-(2-morpholinoethyl)-6-oxo-5,6-dihydropyrido[2,3-b]pyrazine-7-carboxamido)cyclohexane-1-carboxylic acid |
| 193 | 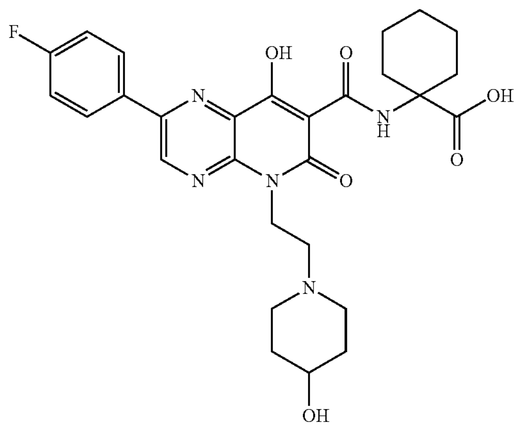 [SMILES: O=C(NC1(C(=O)O)CCCCC1)c1c(O)c2nc(-c3ccc(F)cc3)cnc2n(CCN2CCC(O)CC2)c1=O] | 1-(2-(4-fluorophenyl)-8-hydroxy-5-(2-(4-hydroxypiperidin-1-yl)ethyl)-6-oxo-5,6-dihydropyrido[2,3-b]pyrazine-7-carboxamido)cyclohexane-1-carboxylic acid |
| 194 | 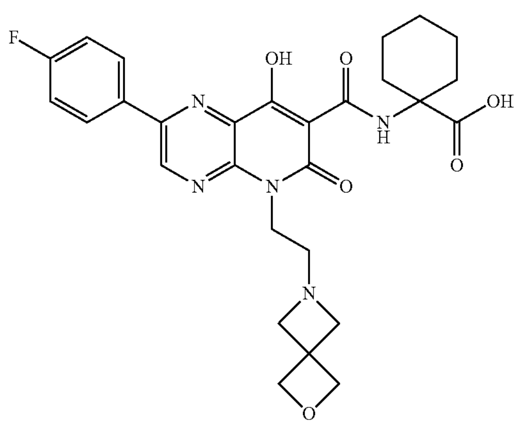 [SMILES: O=C(NC1(C(=O)O)CCCCC1)c1c(O)c2nc(-c3ccc(F)cc3)cnc2n(CCN2CC3(COC3)C2)c1=O] | 1-(5-(2-(2-oxa-6-azaspiro[3.3]heptan-6-yl)ethyl)-2-(4-fluorophenyl)-8-hydroxy-6-oxo-5,6-dihydropyrido[2,3-b]pyrazine-7-carboxamido)cyclohexane-1-carboxylic acid |
| 195 | 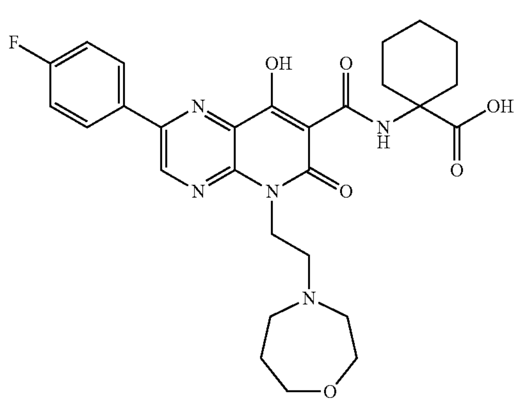 [SMILES: O=C(NC1(C(=O)O)CCCCC1)c1c(O)c2nc(-c3ccc(F)cc3)cnc2n(CCN2CCCOCC2)c1=O] | 1-(5-(2-(1,4-oxazepan-4-yl)ethyl)-2-(4-fluorophenyl)-8-hydroxy-6-oxo-5,6-dihydropyrido[2,3-b]pyrazine-7-carboxamido)cyclohexane-1-carboxylic acid |

TABLE 2-continued

| Compound | Structure | Name |
|---|---|---|
| 196 | 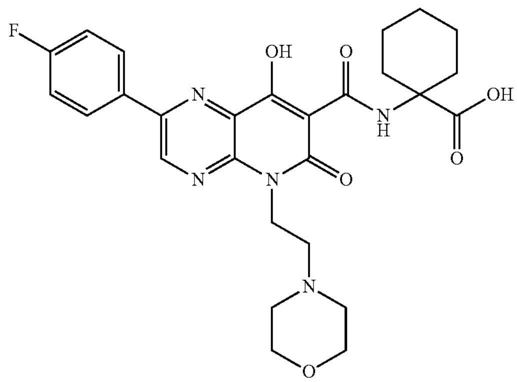 [SMILES: O=C(NC1(C(=O)O)CCCCC1)c1c(O)c2nc(-c3ccc(F)cc3)cnc2n(CCN2CCOCC2)c1=O] | 1-(2-(4-fluorophenyl)-8-hydroxy-5-(2-morpholinoethyl)-6-oxo-5,6-dihydropyrido[2,3-b]pyrazine-7-carboxamido)cyclohexane-1-carboxylic acid |
| 197 | 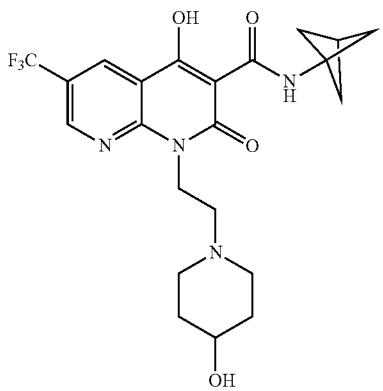 | N-(bicyclo[1.1.1]pentan-1-yl)-4-hydroxy-1-(2-(4-hydroxypiperidin-1-yl)ethyl)-2-oxo-6-(trifluoromethyl)-1,2-dihydro-1,8-naphthyridine-3-carboxamide |
| 198 | 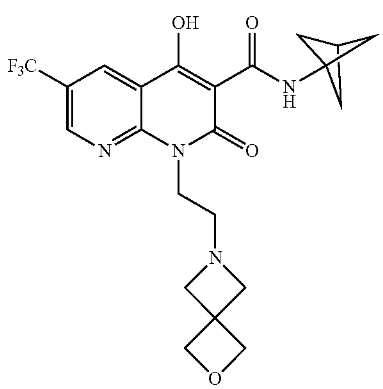 [SMILES: O=C(NC12CC(C1)C2)c1c(O)c2cc(C(F)(F)F)cnc2n(CCN2CC3(COC3)C2)c1=O] | 1-(2-(2-oxa-6-azaspiro[3.3]heptan-6-yl)ethyl)-N-(bicyclo[1.1.1]pentan-1-yl)-4-hydroxy-2-oxo-6-(trifluoromethyl)-1,2-dihydro-1,8-naphthyridine-3-carboxamide |
| 199 | 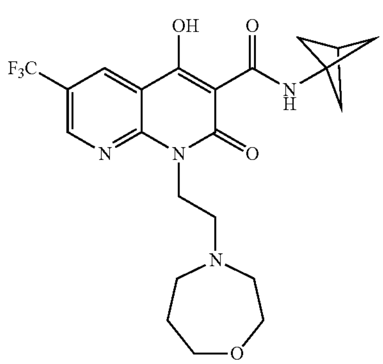 [SMILES: O=C(NC12CC(C1)C2)c1c(O)c2cc(C(F)(F)F)cnc2n(CCN2CCCOCC2)c1=O] | 1-(2-(1,4-oxazepan-4-yl)ethyl)-N-(bicyclo[1.1.1]pentan-1-yl)-4-hydroxy-2-oxo-6-(trifluoromethyl)-1,2-dihydro-1,8-naphthyridine-3-carboxamide |

TABLE 2-continued

| Compound | Structure | Name |
|---|---|---|
| 200 | 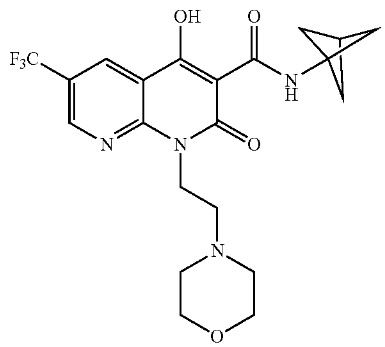 [SMILES: O=C(NC12CC(C1)C2)c1c(O)c2cc(C(F)(F)F)cnc2n(CCN2CCOCC2)c1=O] | N-(bicyclo[1.1.1]pentan-1-yl)-4-hydroxy-1-(2-morpholinoethyl)-2-oxo-6-(trifluoromethyl)-1,2-dihydro-1,8-naphthyridine-3-carboxamide |
| 201 | 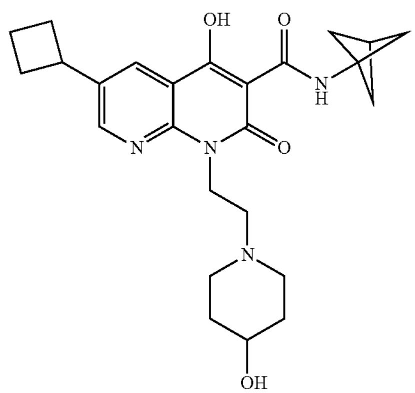 [SMILES: O=C(NC12CC(C1)C2)c1c(O)c2cc(C3CCC3)cnc2n(CCN2CCC(O)CC2)c1=O] | N-(bicyclo[1.1.1]pentan-1-yl)-6-cyclobutyl-4-hydroxy-1-(2-(4-hydroxypiperidin-1-yl)ethyl)-2-oxo-1,2-dihydro-1,8-naphthyridine-3-carboxamide |
| 202 | 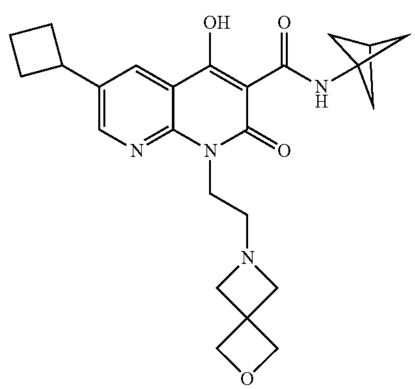 [SMILES: O=C(NC12CC(C1)C2)c1c(O)c2cc(C3CCC3)cnc2n(CCN2CC3(COC3)C2)c1=O] | 1-(2-(2-oxa-6-azaspiro[3.3]heptan-6-yl)ethyl)-N-(bicyclo[1.1.1]pentan-1-yl)-6-cyclobutyl-4-hydroxy-2-oxo-1,2-dihydro-1,8-naphthyridine-3-carboxamide |
| 203 | 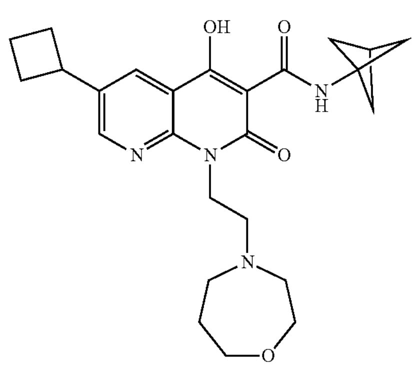 [SMILES: O=C(NC12CC(C1)C2)c1c(O)c2cc(C3CCC3)cnc2n(CCN2CCCOCC2)c1=O] | 1-(2-(1,4-oxazepan-4-yl)ethyl)-N-(bicyclo[1.1.1]pentan-1-yl)-6-cyclobutyl-4-hydroxy-2-oxo-1,2-dihydro-1,8-naphthyridine-3-carboxamide |

TABLE 2-continued

| Compound | Structure | Name |
|---|---|---|
| 204 | 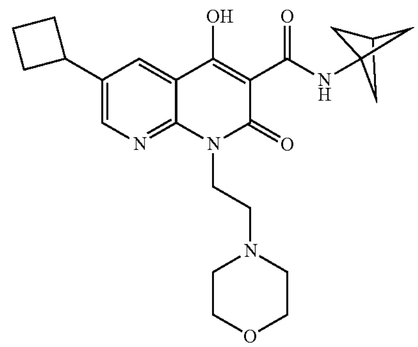 [SMILES: O=C(NC12CC(C1)C2)c1c(O)c2cc(C3CCC3)cnc2n(CCN2CCOCC2)c1=O] | N-(bicyclo[1.1.1]pentan-1-yl)-6-cyclobutyl-4-hydroxy-1-(2-morpholinoethyl)-2-oxo-1,2-dihydro-1,8-naphthyridine-3-carboxamide |
| 205 | 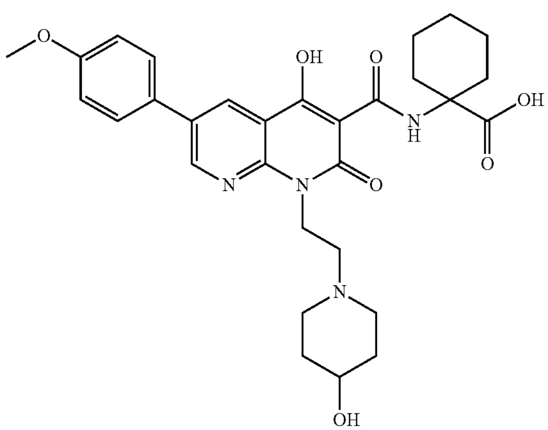 [SMILES: COc1ccc(-c2cnc3c(c2)c(O)c(C(=O)NC2(C(=O)O)CCCCC2)c(=O)n3CCN2CCC(O)CC2)cc1] | 1-(4-hydroxy-1-(2-(4-hydroxypiperidin-1-yl)ethyl)-6-(4-methoxyphenyl)-2-oxo-1,2-dihydro-1,8-naphthyridine-3-carboxamido)cyclohexane-1-carboxylic acid |
| 206 | 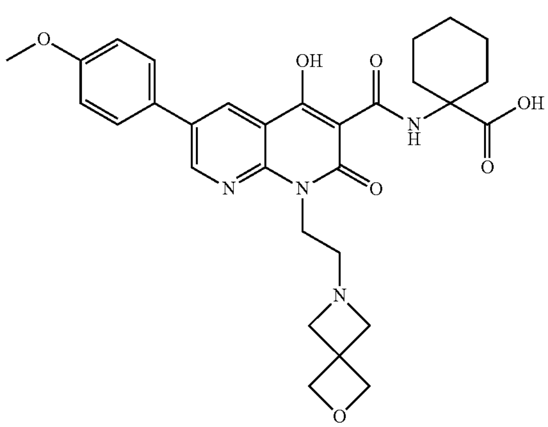 [SMILES: COc1ccc(-c2cnc3c(c2)c(O)c(C(=O)NC2(C(=O)O)CCCCC2)c(=O)n3CCN2CC3(COC3)C2)cc1] | 1-(1-(2-(2-oxa-6-azaspiro[3.3]heptan-6-yl)ethyl)-4-hydroxy-6-(4-methoxyphenyl)-2-oxo-1,2-dihydro-1,8-naphthyridine-3-carboxamido)cyclohexane-1-carboxylic acid |
| 207 | 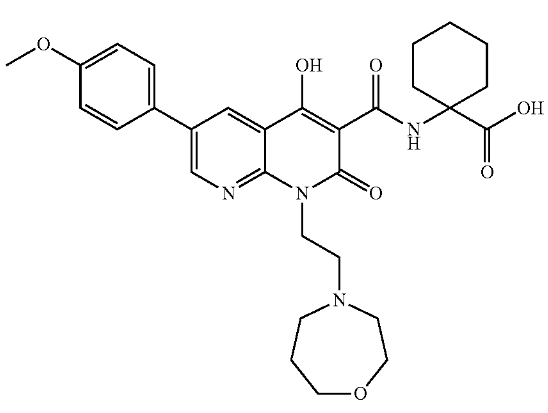 [SMILES: COc1ccc(-c2cnc3c(c2)c(O)c(C(=O)NC2(C(=O)O)CCCCC2)c(=O)n3CCN2CCCOCC2)cc1] | 1-(1-(2-(1,4-oxazepan-4-yl)ethyl)-4-hydroxy-6-(4-methoxyphenyl)-2-oxo-1,2-dihydro-1,8-naphthyridine-3-carboxamido)cyclohexane-1-carboxylic acid |

TABLE 2-continued

| Compound | Structure | Name |
| --- | --- | --- |
| 208 | 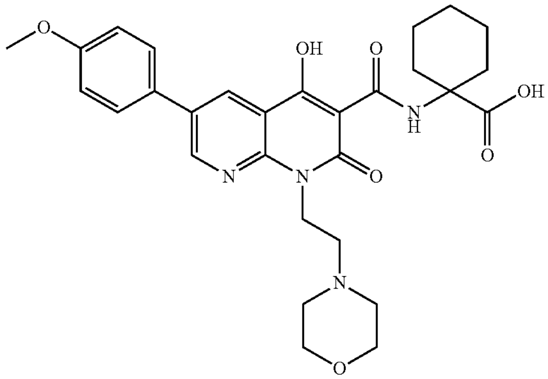 [SMILES: COc1ccc(-c2cnc3c(c2)c(O)c(C(=O)NC2(C(=O)O)CCCCC2)c(=O)n3CCN2CCOCC2)cc1] | 1-(4-hydroxy-6-(4-methoxyphenyl)-1-(2-morpholinoethyl)-2-oxo-1,2-dihydro-1,8-naphthyridine-3-carboxamido)cyclohexane-1-carboxylic acid |
| 209 | 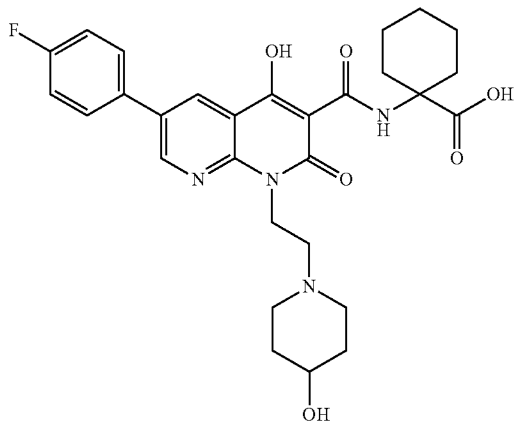 [SMILES: O=C(NC1(C(=O)O)CCCCC1)c1c(O)c2cc(-c3ccc(F)cc3)cnc2n(CCN2CCC(O)CC2)c1=O] | 1-(6-(4-fluorophenyl)-4-hydroxy-1-(2-(4-hydroxypiperidin-1-yl)ethyl)-2-oxo-1,2-dihydro-1,8-naphthyridine-3-carboxamido)cyclohexane-1-carboxylic acid |
| 210 | 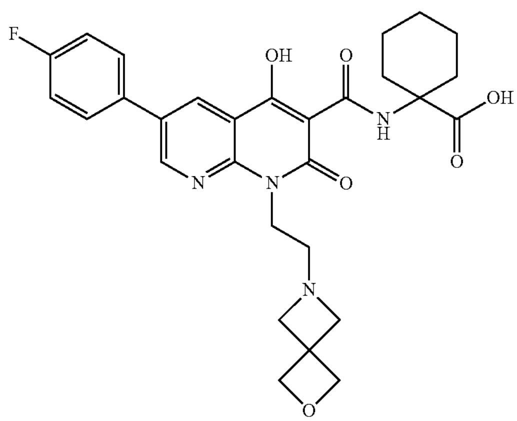 [SMILES: O=C(NC1(C(=O)O)CCCCC1)c1c(O)c2cc(-c3ccc(F)cc3)cnc2n(CCN2CC3(COC3)C2)c1=O] | 1-(1-(2-(2-oxa-6-azaspiro[3.3]heptan-6-yl)ethyl)-6-(4-fluorophenyl)-4-hydroxy-2-oxo-1,2-dihydro-1,8-naphthyridine-3-carboxamido)cyclohexane-1-carboxylic acid |
| 211 | 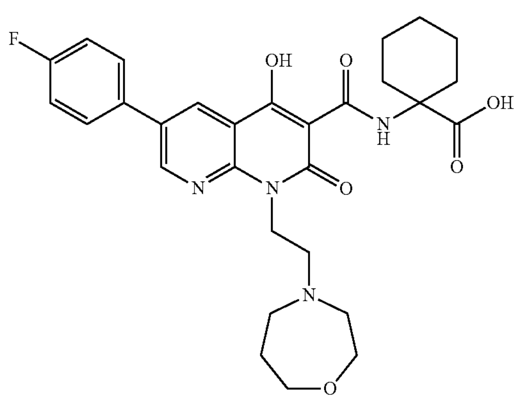 [SMILES: O=C(NC1(C(=O)O)CCCCC1)c1c(O)c2cc(-c3ccc(F)cc3)cnc2n(CCN2CCCOCC2)c1=O] | 1-(1-(2-(1,4-oxazepan-4-yl)ethyl)-6-(4-fluorophenyl)-4-hydroxy-2-oxo-1,2-dihydro-1,8-naphthyridine-3-carboxamido)cyclohexane-1-carboxylic acid |

TABLE 2-continued

| Compound | Structure | Name |
|---|---|---|
| 212 | 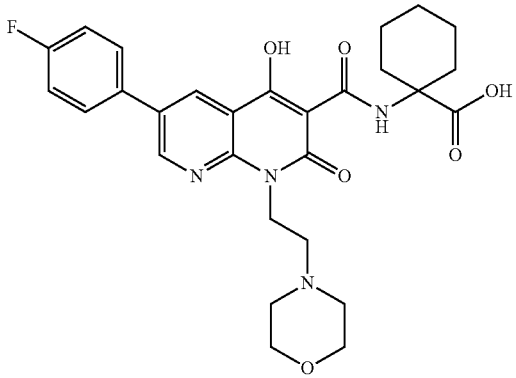 [SMILES: O=C(NC1(C(=O)O)CCCCC1)c1c(O)c2cc(-c3ccc(F)cc3)cnc2n(CCN2CCOCC2)c1=O] | 1-(6-(4-fluorophenyl)-4-hydroxy-1-(2-morpholinoethyl)-2-oxo-1,2-dihydro-1,8-naphthyridine-3-carboxamido)cyclohexane-1-carboxylic acid |
| 213 | 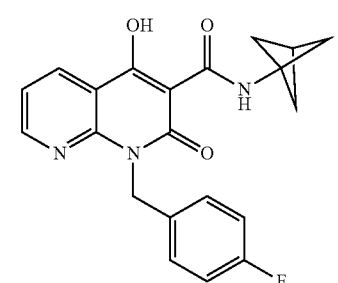 | N-(bicyclo[1.1.1]pentan-1-yl)-1-(4-fluorobenzyl)-4-hydroxy-2-oxo-1,2-dihydro-1,8-naphthyridine-3-carboxamide |
| 214 | 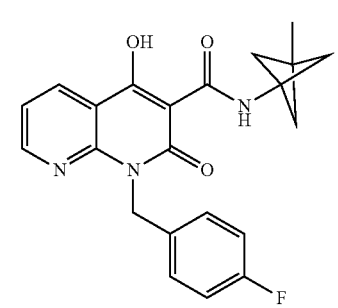 [SMILES: CC12CC(NC(=O)c3c(O)c4cccnc4n(Cc4ccc(F)cc4)c3=O)(C1)C2] | 1-(4-fluorobenzyl)-4-hydroxy-N-(3-methylbicyclo[1.1.1]pentan-1-yl)-2-oxo-1,2-dihydro-1,8-naphthyridine-3-carboxamide |
| 215 | 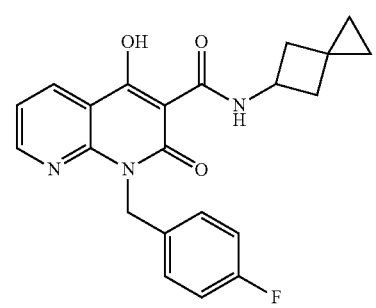 [SMILES: O=C(NC1CC2(CC2)C1)c1c(O)c2cccnc2n(Cc2ccc(F)cc2)c1=O] | 1-(4-fluorobenzyl)-4-hydroxy-2-oxo-N-(spiro[2.3]hexan-5-yl)-1,2-dihydro-1,8-naphthyridine-3-carboxamide |
| 216 | 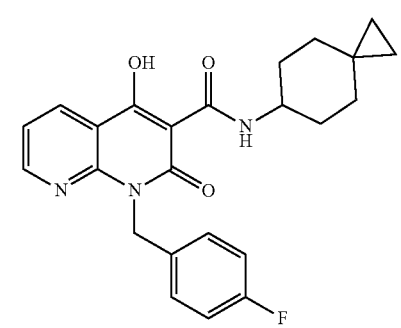 [SMILES: O=C(NC1CCC2(CC1)CC2)c1c(O)c2cccnc2n(Cc2ccc(F)cc2)c1=O] | 1-(4-fluorobenzyl)-4-hydroxy-2-oxo-N-(spiro[2.5]octan-6-yl)-1,2-dihydro-1,8-naphthyridine-3-carboxamide |

| Compound | Structure | Name |
|---|---|---|
| 217 | 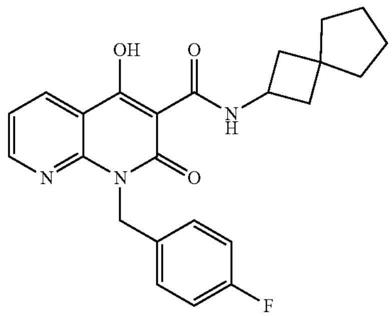 [SMILES: O=C(NC1CC2(CCCC2)C1)c1c(O)c2cccnc2n(Cc2ccc(F)cc2)c1=O] | 1-(4-fluorobenzyl)-4-hydroxy-2-oxo-N-(spiro[3.4]octan-2-yl)-1,2-dihydro-1,8-naphthyridine-3-carboxamide |
| 218 | 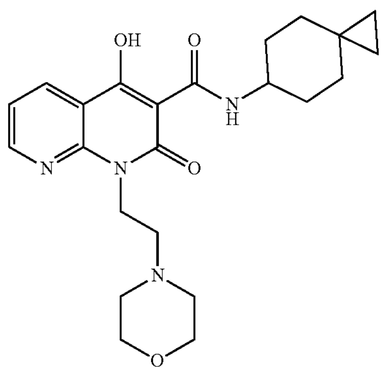 [SMILES: O=C(NC1CCC2(CC1)CC2)c1c(O)c2cccnc2n(CCN2CCOCC2)c1=O] | 4-hydroxy-1-(2-morpholinoethyl)-2-oxo-N-(spiro[2.5]octan-6-yl)-1,2-dihydro-1,8-naphthyridine-3-carboxamide |
| 219 | 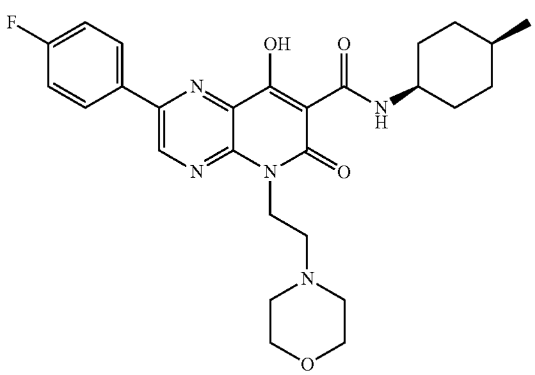 | 2-(4-fluorophenyl)-8-hydroxy-N-((1s,4s)-4-methylcyclohexyl)-5-(2-morpholinoethyl)-6-oxo-5,6-dihydropyrido[2,3-b]pyrazine-7-carboxamide |
| 220 | 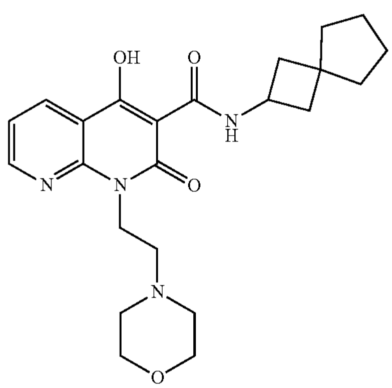 [SMILES: O=C(NC1CC2(CCCC2)C1)c1c(O)c2cccnc2n(CCN2CCOCC2)c1=O] | 4-hydroxy-1-(2-morpholinoethyl)-2-oxo-N-(spiro[3.4]octan-2-yl)-1,2-dihydro-1,8-naphthyridine-3-carboxamide |

TABLE 2-continued

| Compound | Structure | Name |
| --- | --- | --- |
| 221 | 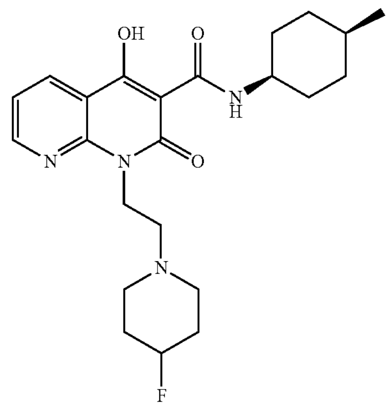 [SMILES: C[C@H]1CC[C@@H](NC(=O)c2c(O)c3cccnc3n(CCN3CCC(F)CC3)c2=O)CC1] | 1-(2-(4-fluoropiperidin-1-yl)ethyl)-4-hydroxy-N-((1s,4s)-4-methylcyclohexyl)-2-oxo-1,2-dihydro-1,8-naphthyridine-3-carboxamide |
| 222 | 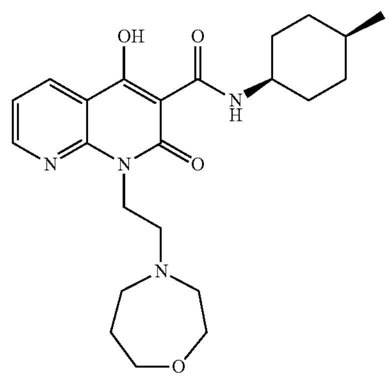 [SMILES: C[C@H]1CC[C@@H](NC(=O)c2c(O)c3cccnc3n(CCN3CCCOCC3)c2=O)CC1] | 1-(2-(1,4-oxazepan-4-yl)ethyl)-4-hydroxy-N-((1s,4s)-4-methylcyclohexyl)-2-oxo-1,2-dihydro-1,8-naphthyridine-3-carboxamide |
| 223 | 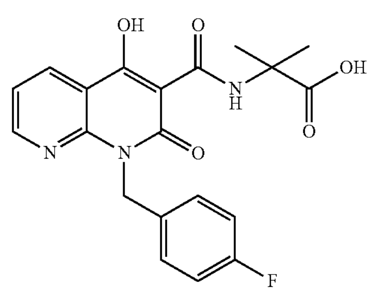 [SMILES: CC(C)(NC(=O)c1c(O)c2cccnc2n(Cc2ccc(F)cc2)c1=O)C(=O)O] | 2-(1-(4-fluorobenzyl)-4-hydroxy-2-oxo-1,2-dihydro-1,8-naphthyridine-3-carboxamido)-2-methylpropanoic acid |
| 224 | 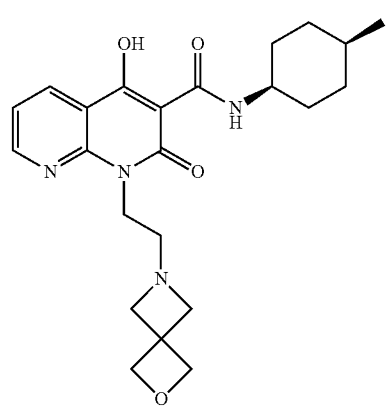 [SMILES: C[C@H]1CC[C@@H](NC(=O)c2c(O)c3cccnc3n(CCN3CC4(COC4)C3)c2=O)CC1] | 1-(2-(2-oxa-6-azaspiro[3.3]heptan-6-yl)ethyl)-4-hydroxy-N-((1s,4s)-4-methylcyclohexyl)-2-oxo-1,2-dihydro-1,8-naphthyridine-3-carboxamide |

TABLE 2-continued

| Compound | Structure | Name |
|---|---|---|
| 225 | 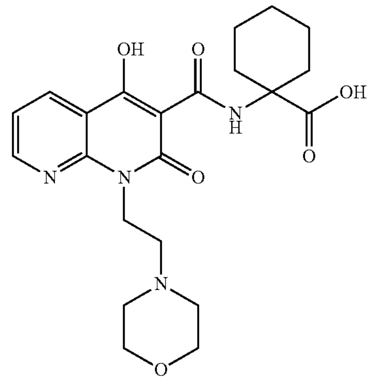 [SMILES: O=C(NC1(C(=O)O)CCCCC1)c1c(O)c2cccnc2n(CCN2CCOCC2)c1=O] | 1-(4-hydroxy-1-(2-morpholinoethyl)-2-oxo-1,2-dihydro-1,8-naphthyridine-3-carboxamido)cyclohexane-1-carboxylic acid |
| 226 | 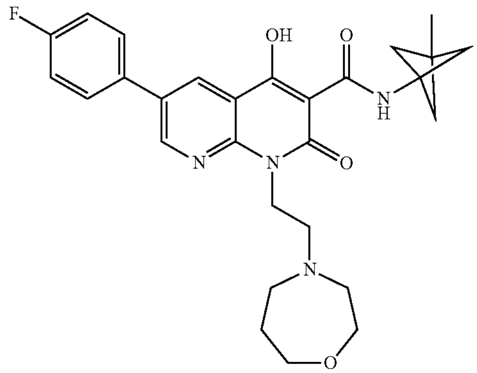 [SMILES: CC12CC(NC(=O)c3c(O)c4cc(-c5ccc(F)cc5)cnc4n(CCN4CCCOCC4)c3=O)(C1)C2] | 1-(2-(1,4-oxazepan-4-yl)ethyl)-6-(4-fluorophenyl)-4-hydroxy-N-(3-methylbicyclo[1.1.1]pentan-1-yl)-2-oxo-1,2-dihydro-1,8-naphthyridine-3-carboxamide |
| 227 | 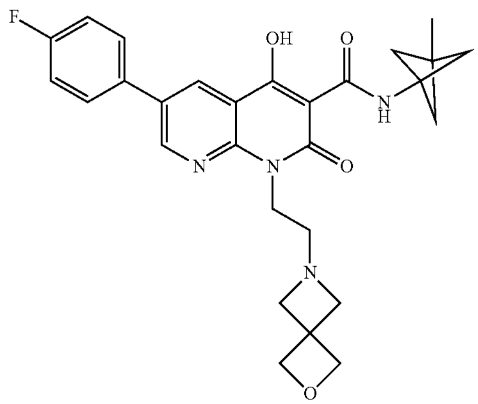 [SMILES: CC12CC(NC(=O)c3c(O)c4cc(-c5ccc(F)cc5)cnc4n(CCN4CC5(COC5)C4)c3=O)(C1)C2] | 1-(2-(2-oxa-6-azaspiro[3.3]heptan-6-yl)ethyl)-6-(4-fluorophenyl)-4-hydroxy-N-(3-methylbicyclo[1.1.1]pentan-1-yl)-2-oxo-1,2-dihydro-1,8-naphthyridine-3-carboxamide |
| 228 | 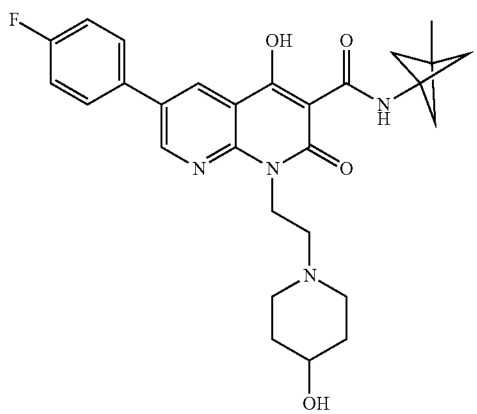 [SMILES: CC12CC(NC(=O)c3c(O)c4cc(-c5ccc(F)cc5)cnc4n(CCN4CCC(O)CC4)c3=O)(C1)C2] | 6-(4-fluorophenyl)-4-hydroxy-1-(2-(4-hydroxypiperidin-1-yl)ethyl)-N-(3-methylbicyclo[1.1.1]pentan-1-yl)-2-oxo-1,2-dihydro-1,8-naphthyridine-3-carboxamide |

TABLE 2-continued

| Compound | Structure | Name |
|---|---|---|
| 229 | 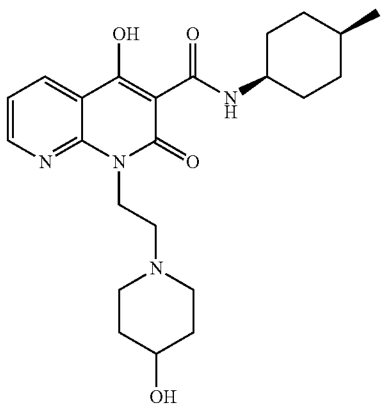 [SMILES: C[C@H]1CC[C@@H](NC(=O)c2c(O)c3cccnc3n(CCN3CCC(O)CC3)c2=O)CC1] | 4-hydroxy-1-(2-(4-hydroxypiperidin-1-yl)ethyl)-N-((1s,4s)-4-methylcyclohexyl)-2-oxo-1,2-dihydro-1,8-naphthyridine-3-carboxamide |
| 230 | 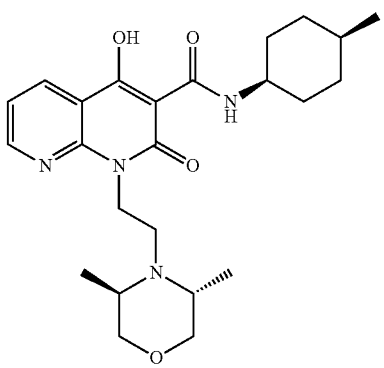 [SMILES: C[C@@H]1COC[C@@H](C)N1CCn1c(=O)c(C(=O)N[C@H]2CC[C@@H](C)CC2)c(O)c2cccnc21] | 1-(2-((3R,5R)-3,5-dimethylmorpholino)ethyl)-4-hydroxy-N-((1s,4S)-4-methylcyclohexyl)-2-oxo-1,2-dihydro-1,8-naphthyridine-3-carboxamide |
| 231 | 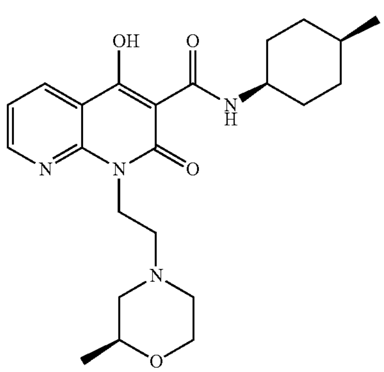 [SMILES: C[C@H]1CN(CCn2c(=O)c(C(=O)N[C@H]3CC[C@@H](C)CC3)c(O)c3cccnc32)CCO1] | 4-hydroxy-N-((1s,4R)-4-methylcyclohexyl)-1-(2-((S)-2-methylmorpholino)ethyl)-2-oxo-1,2-dihydro-1,8-naphthyridine-3-carboxamide |
| 232a | 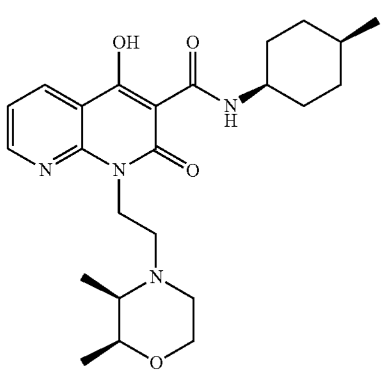 [SMILES: C[C@@H]1OCCN(CCn2c(=O)c(C(=O)N[C@H]3CC[C@@H](C)CC3)c(O)c3cccnc32)[C@@H]1C] | 1-(2-((2S,3R)-2,3-dimethylmorpholino)ethyl)-4-hydroxy-N-((1s,4S)-4-methylcyclohexyl)-2-oxo-1,2-dihydro-1,8-naphthyridine-3-carboxamide |

TABLE 2-continued

| Compound | Structure | Name |
|---|---|---|
| 232b | 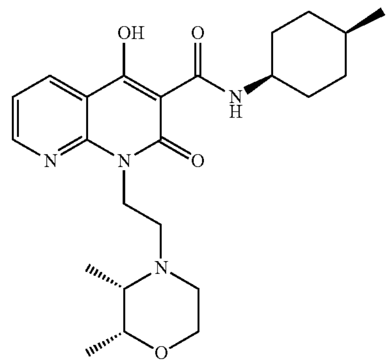 [SMILES: C[C@H]1OCCN(CCn2c(=O)c(C(=O)N[C@H]3CC[C@@H](C)CC3)c(O)c3cccnc32)[C@H]1C] | 1-(2-((2R,3S)-2,3-dimethylmorpholino)ethyl)-4-hydroxy-N-((1s,4R)-4-methylcyclohexyl)-2-oxo-1,2-dihydro-1,8-naphthyridine-3-carboxamide |
| 232c | 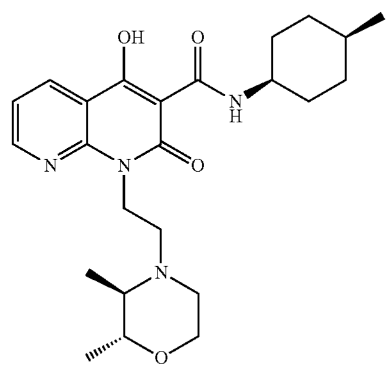 [SMILES: C[C@@H]1[C@@H](C)OCCN1CCn1c(=O)c(C(=O)N[C@H]2CC[C@@H](C)CC2)c(O)c2cccnc21] | 1-(2-((2R,3R)-2,3-dimethylmorpholino)ethyl)-4-hydroxy-N-((1s,4S)-4-methylcyclohexyl)-2-oxo-1,2-dihydro-1,8-naphthyridine-3-carboxamide |
| 232d | 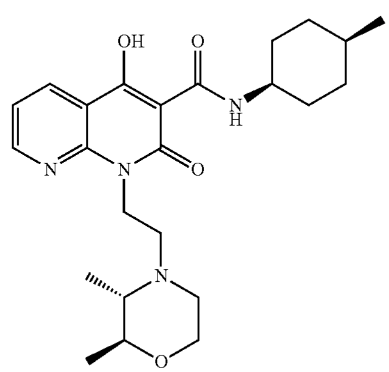 [SMILES: C[C@@H]1OCCN(CCn2c(=O)c(C(=O)N[C@H]3CC[C@@H](C)CC3)c(O)c3cccnc32)[C@H]1C] | 1-(2-((2S,3S)-2,3-dimethylmorpholino)ethyl)-4-hydroxy-N-((1s,4R)-4-methylcyclohexyl)-2-oxo-1,2-dihydro-1,8-naphthyridine-3-carboxamide |
| 233a | 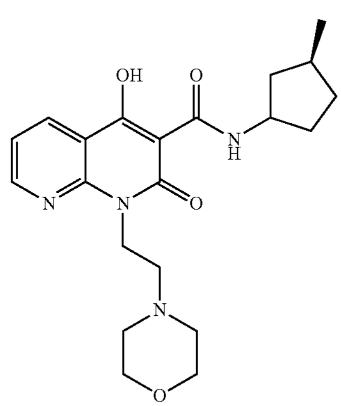 [SMILES: C[C@H]1CCC(NC(=O)c2c(O)c3cccnc3n(CCN3CCOCC3)c2=O)C1] | 4-hydroxy-N-((3S)-3-methylcyclopentyl)-1-(2-morpholinoethyl)-2-oxo-1,2-dihydro-1,8-naphthyridine-3-carboxamide |

TABLE 2-continued

| Compound | Structure | Name |
| --- | --- | --- |
| 233b | 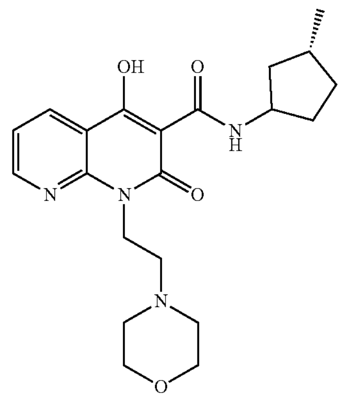 [SMILES: C[C@@H]1CCC(NC(=O)c2c(O)c3cccnc3n(CCN3CCOCC3)c2=O)C1] | 4-hydroxy-N-((3R)-3-methylcyclopentyl)-1-(2-morpholinoethyl)-2-oxo-1,2-dihydro-1,8-naphthyridine-3-carboxamide |
| 234 | 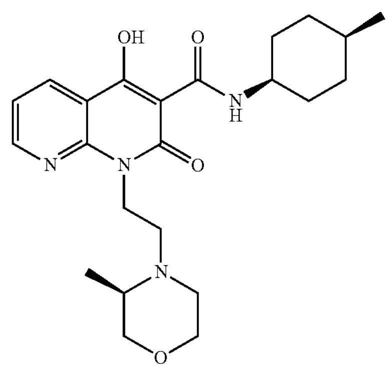 [SMILES: C[C@@H]1COCCN1CCn1c(=O)c(C(=O)N[C@H]2CC[C@@H](C)CC2)c(O)c2cccnc21] | 4-hydroxy-N-((1s,4S)-4-methylcyclohexyl)-1-(2-((R)-3-methylmorpholino)ethyl)-2-oxo-1,2-dihydro-1,8-naphthyridine-3-carboxamide |
| 235 | 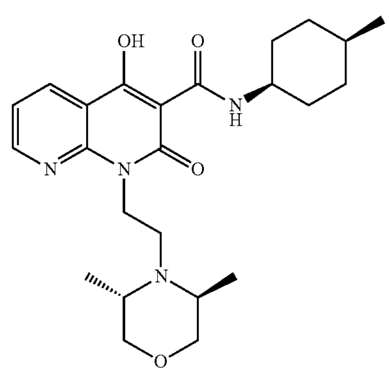 [SMILES: C[C@H]1COC[C@H](C)N1CCn1c(=O)c(C(=O)N[C@H]2CC[C@@H](C)CC2)c(O)c2cccnc21] | 1-(2-((3S,5S)-3,5-dimethylmorpholino)ethyl)-4-hydroxy-N-((1s,4R)-4-methylcyclohexyl)-2-oxo-1,2-dihydro-1,8-naphthyridine-3-carboxamide |
| 236 | 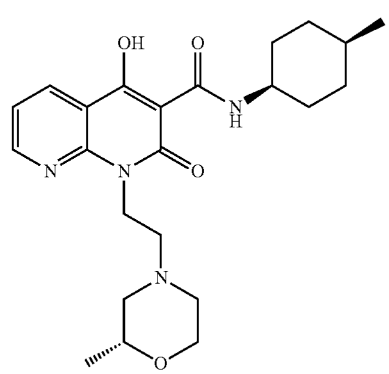 [SMILES: C[C@@H]1CN(CCn2c(=O)c(C(=O)N[C@H]3CC[C@@H](C)CC3)c(O)c3cccnc32)CCO1] | 4-hydroxy-N-((1s,4S)-4-methylcyclohexyl)-1-(2-((R)-2-methylmorpholino)ethyl)-2-oxo-1,2-dihydro-1,8-naphthyridine-3-carboxamide |

TABLE 2-continued

| Compound | Structure | Name |
|---|---|---|
| 237 | 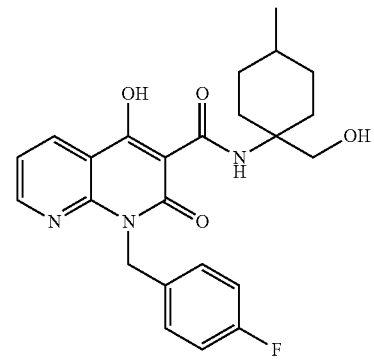 [SMILES: CC1CCC(CO)(NC(=O)c2c(O)c3cccnc3n(Cc3ccc(F)cc3)c2=O)CC1] | 1-(4-fluorobenzyl)-4-hydroxy-N-(1-(hydroxymethyl)-4-methylcyclohexyl)-2-oxo-1,2-dihydro-1,8-naphthyridine-3-carboxamide |
| 238 | 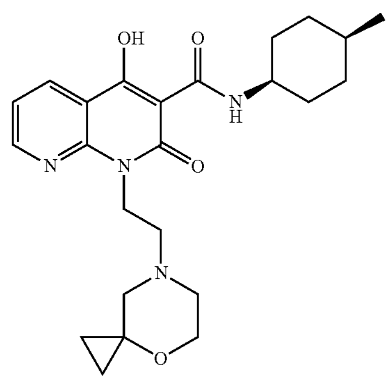 [SMILES: C[C@H]1CC[C@@H](NC(=O)c2c(O)c3cccnc3n(CCN3CCOC4(CC4)C3)c2=O)CC1] | 1-(2-(4-oxa-7-azaspiro[2.5]octan-7-yl)ethyl)-4-hydroxy-N-((1s,4s)-4-methylcyclohexyl)-2-oxo-1,2-dihydro-1,8-naphthyridine-3-carboxamide |
| 239 | 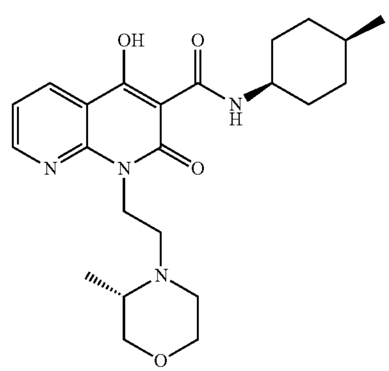 [SMILES: C[C@H]1COCCN1CCn1c(=O)c(C(=O)N[C@H]2CC[C@@H](C)CC2)c(O)c2cccnc21] | 4-hydroxy-N-((1s,4R)-4-methylcyclohexyl)-1-(2-((S)-3-methylmorpholino)ethyl)-2-oxo-1,2-dihydro-1,8-naphthyridine-3-carboxamide |
| 240 | 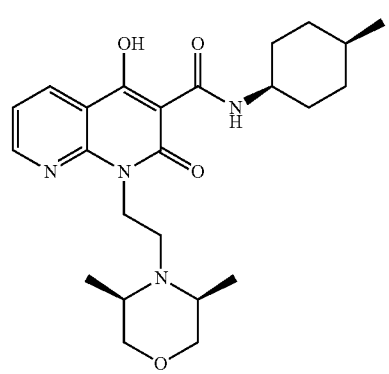 [SMILES: C[C@@H]1COC[C@H](C)N1CCn1c(=O)c(C(=O)N[C@H]2CC[C@@H](C)CC2)c(O)c2cccnc21] | 1-(2-((3R,5S)-3,5-dimethylmorpholino)ethyl)-4-hydroxy-N-((1s,4S)-4-methylcyclohexyl)-2-oxo-1,2-dihydro-1,8-naphthyridine-3-carboxamide |

TABLE 2-continued

| Compound | Structure | Name |
|---|---|---|
| 241a | 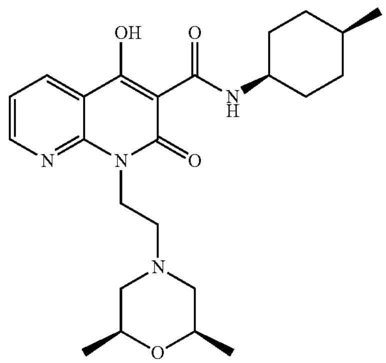 [SMILES: C[C@@H]1CN(CCn2c(=O)c(C(=O)N[C@H]3CC[C@@H](C)CC3)c(O)c3cccnc32)C[C@H](C)O1] | 1-(2-((2S,6R)-2,6-dimethylmorpholino)ethyl)-4-hydroxy-N-((1s,4S)-4-methylcyclohexyl)-2-oxo-1,2-dihydro-1,8-naphthyridine-3-carboxamide |
| 241b | 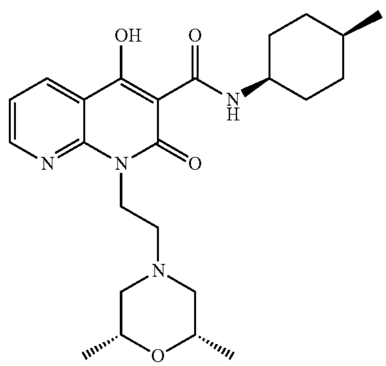 [SMILES: C[C@@H]1CN(CCn2c(=O)c(C(=O)N[C@H]3CC[C@@H](C)CC3)c(O)c3cccnc32)C[C@H](C)O1] | 1-(2-((2R,6S)-2,6-dimethylmorpholino)ethyl)-4-hydroxy-N-((1s,4S)-4-methylcyclohexyl)-2-oxo-1,2-dihydro-1,8-naphthyridine-3-carboxamide |
| 241c | 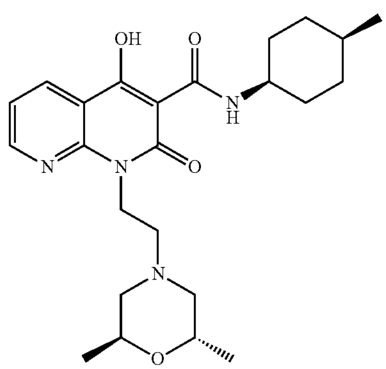 [SMILES: C[C@H]1CN(CCn2c(=O)c(C(=O)N[C@H]3CC[C@@H](C)CC3)c(O)c3cccnc32)C[C@H](C)O1] | 1-(2-((2S,6S)-2,6-dimethylmorpholino)ethyl)-4-hydroxy-N-((1s,4R)-4-methylcyclohexyl)-2-oxo-1,2-dihydro-1,8-naphthyridine-3-carboxamide |
| 241d | 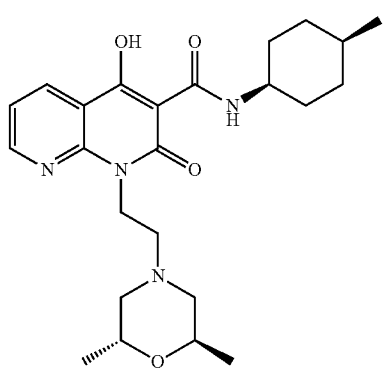 [SMILES: C[C@@H]1CN(CCn2c(=O)c(C(=O)N[C@H]3CC[C@@H](C)CC3)c(O)c3cccnc32)C[C@@H](C)O1] | 1-(2-((2R,6R)-2,6-dimethylmorpholino)ethyl)-4-hydroxy-N-((1s,4S)-4-methylcyclohexyl)-2-oxo-1,2-dihydro-1,8-naphthyridine-3-carboxamide |

TABLE 2-continued

| Compound | Structure | Name |
| --- | --- | --- |
| 242 | 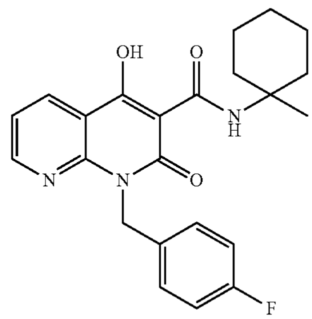 [SMILES: CC1(NC(=O)c2c(O)c3cccnc3n(Cc3ccc(F)cc3)c2=O)CCCCC1] | 1-(4-fluorobenzyl)-4-hydroxy-N-(1-methylcyclohexyl)-2-oxo-1,2-dihydro-1,8-naphthyridine-3-carboxamide |
| 243 | 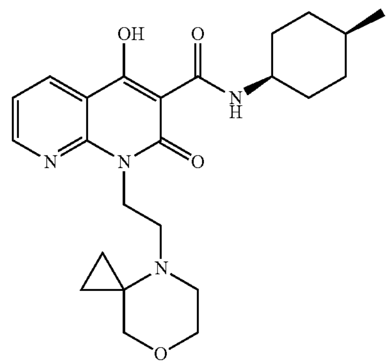 [SMILES: C[C@H]1CC[C@@H](NC(=O)c2c(O)c3cccnc3n(CCN3CCOCC34CC4)c2=O)CC1] | 1-(2-(7-oxa-4-azaspiro[2.5]octan-4-yl)ethyl)-4-hydroxy-N-((1s,4s)-4-methylcyclohexyl)-2-oxo-1,2-dihydro-1,8-naphthyridine-3-carboxamide |
| 244 | 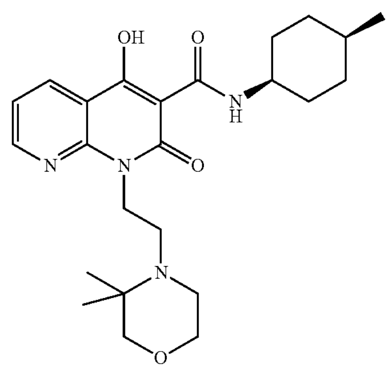 [SMILES: CC1(C)COCCN1CCn1c(=O)c(C(=O)N[C@H]2CC[C@@H](C)CC2)c(O)c2cccnc21] | 1-(2-(3,3-dimethylmorpholino)ethyl)-4-hydroxy-N-((1s,4s)-4-methylcyclohexyl)-2-oxo-1,2-dihydro-1,8-naphthyridine-3-carboxamide |
| 245 | 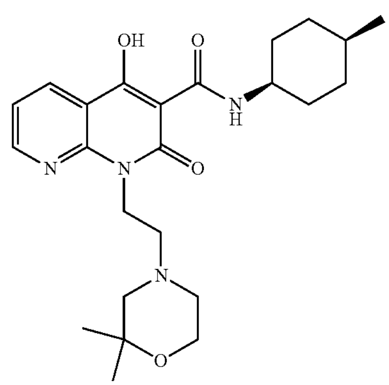 [SMILES: CC1(C)CN(CCn2c(=O)c(C(=O)N[C@H]3CC[C@@H](C)CC3)c(O)c3cccnc32)CCO1] | 1-(2-(2,2-dimethylmorpholino)ethyl)-4-hydroxy-N-((1s,4s)-4-methylcyclohexyl)-2-oxo-1,2-dihydro-1,8-naphthyridine-3-carboxamide |

TABLE 2-continued

| Compound | Structure | Name |
|---|---|---|
| 246 | 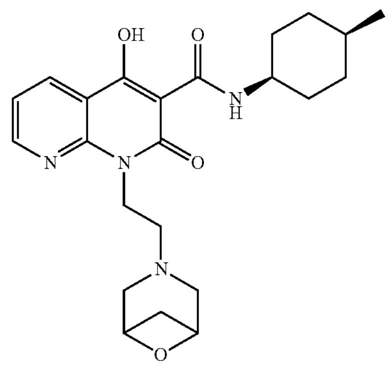 [SMILES: C[C@H]1CC[C@@H](NC(=O)c2c(O)c3cccnc3n(CCN3CC4CC(C3)O4)c2=O)CC1] | 1-(2-(6-oxa-3-azabicyclo[3.1.1]heptan-3-yl)ethyl)-4-hydroxy-N-((1s,4s)-4-methylcyclohexyl)-2-oxo-1,2-dihydro-1,8-naphthyridine-3-carboxamide |
| 247 | 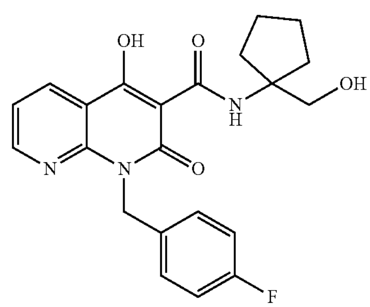 [SMILES: O=C(NC1(CO)CCCC1)c1c(O)c2cccnc2n(Cc2ccc(F)cc2)c1=O] | 1-(4-fluorobenzyl)-4-hydroxy-N-(1-(hydroxymethyl)cyclopentyl)-2-oxo-1,2-dihydro-1,8-naphthyridine-3-carboxamide |
| 248a | 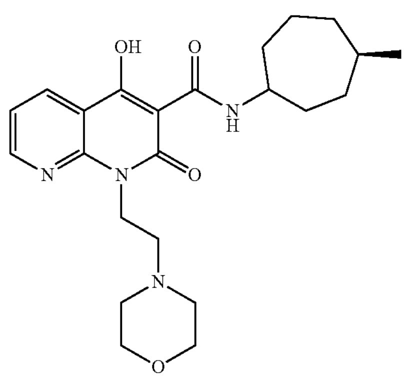 [SMILES: C[C@@H]1CCCC(NC(=O)c2c(O)c3cccnc3n(CCN3CCOCC3)c2=O)CC1] | 4-hydroxy-N-((4R)-4-methylcycloheptyl)-1-(2-morpholinoethyl)-2-oxo-1,2-dihydro-1,8-naphthyridine-3-carboxamide |
| 248b | 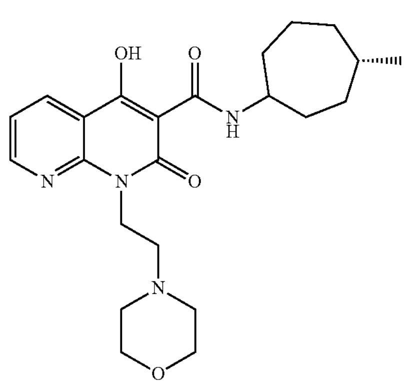 [SMILES: C[C@H]1CCCC(NC(=O)c2c(O)c3cccnc3n(CCN3CCOCC3)c2=O)CC1] | 4-hydroxy-N-((4S)-4-methylcycloheptyl)-1-(2-morpholinoethyl)-2-oxo-1,2-dihydro-1,8-naphthyridine-3-carboxamide |

TABLE 2-continued

| Compound | Structure | Name |
|---|---|---|
| 249 | 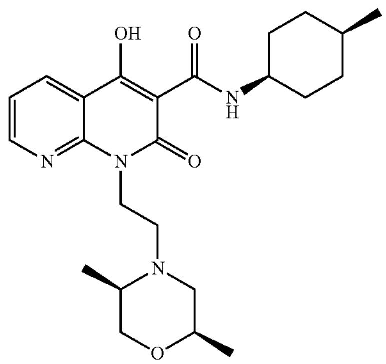 [SMILES: C[C@@H]1CN(CCn2c(=O)c(C(=O)N[C@H]3CC[C@@H](C)CC3)c(O)c3cccnc32)[C@H](C)CO1] | 1-(2-((2R,5R)-2,5-dimethylmorpholino)ethyl)-4-hydroxy-N-((1s,4S)-4-methylcyclohexyl)-2-oxo-1,2-dihydro-1,8-naphthyridine-3-carboxamide |
| 250 | 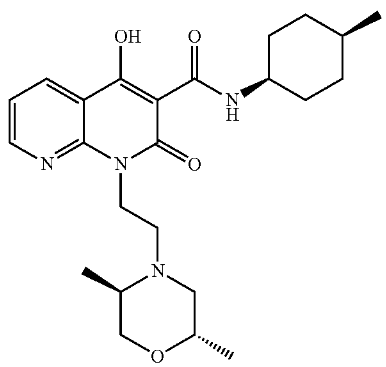 [SMILES: C[C@@H]1CO[C@@H](C)CN1CCn1c(=O)c(C(=O)N[C@H]2CC[C@@H](C)CC2)c(O)c2cccnc21] | 1-(2-((2S,5R)-2,5-dimethylmorpholino)ethyl)-4-hydroxy-N-((1s,4S)-4-methylcyclohexyl)-2-oxo-1,2-dihydro-1,8-naphthyridine-3-carboxamide |
| 251 | 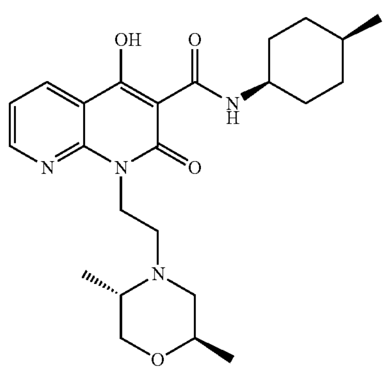 [SMILES: C[C@@H]1CN(CCn2c(=O)c(C(=O)N[C@H]3CC[C@@H](C)CC3)c(O)c3cccnc32)[C@@H](C)CO1] | 1-(2-((2R,5S)-2,5-dimethylmorpholino)ethyl)-4-hydroxy-N-((1s,4R)-4-methylcyclohexyl)-2-oxo-1,2-dihydro-1,8-naphthyridine-3-carboxamide |
| 252 | 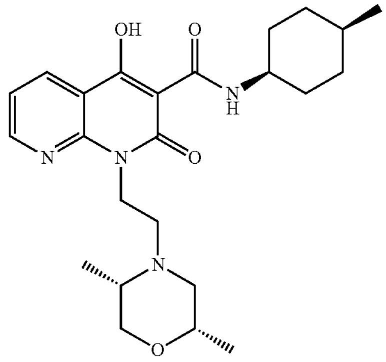 [SMILES: C[C@H]1CN(CCn2c(=O)c(C(=O)N[C@H]3CC[C@@H](C)CC3)c(O)c3cccnc32)[C@@H](C)CO1] | 1-(2-((2S,5S)-2,5-dimethylmorpholino)ethyl)-4-hydroxy-N-((1s,4R)-4-methylcyclohexyl)-2-oxo-1,2-dihydro-1,8-naphthyridine-3-carboxamide |

TABLE 2-continued

| Compound | Structure | Name |
| --- | --- | --- |
| 253 | 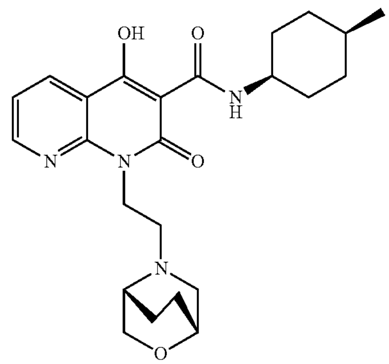 [SMILES: C[C@H]1CC[C@@H](NC(=O)c2c(O)c3cccnc3n(CCN3C[C@H]4CC[C@@H]3CO4)c2=O)CC1] | 1-(2-((1R,4R)-2-oxa-5-azabicyclo[2.2.2]octan-5-yl)ethyl)-4-hydroxy-N-((1s,4S)-4-methylcyclohexyl)-2-oxo-1,2-dihydro-1,8-naphthyridine-3-carboxamide |
| 254 | 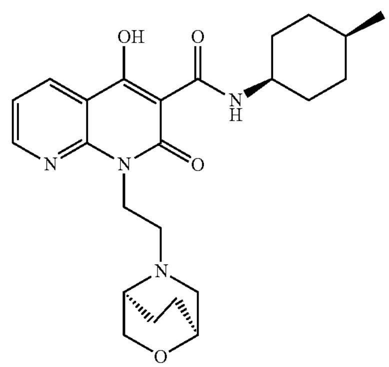 [SMILES: C[C@H]1CC[C@@H](NC(=O)c2c(O)c3cccnc3n(CCN3C[C@@H]4CC[C@H]3CO4)c2=O)CC1] | 1-(2-((1S,4S)-2-oxa-5-azabicyclo[2.2.2]octan-5-yl)ethyl)-4-hydroxy-N-((1s,4R)-4-methylcyclohexyl)-2-oxo-1,2-dihydro-1,8-naphthyridine-3-carboxamide |
| 255 | 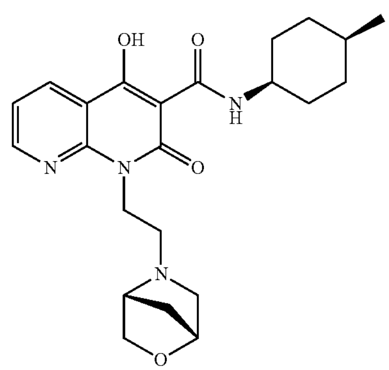 [SMILES: C[C@H]1CC[C@@H](NC(=O)c2c(O)c3cccnc3n(CCN3C[C@H]4C[C@@H]3CO4)c2=O)CC1] | 1-(2-((1R,4R)-2-oxa-5-azabicyclo[2.2.1]heptan-5-yl)ethyl)-4-hydroxy-N-((1s,4S)-4-methylcyclohexyl)-2-oxo-1,2-dihydro-1,8-naphthyridine-3-carboxamide |
| 256 | 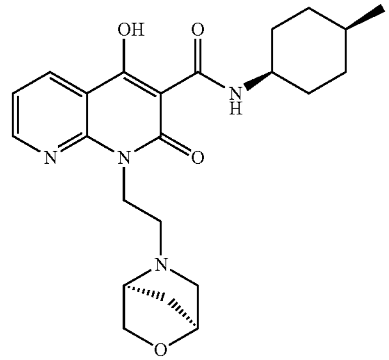 [SMILES: C[C@H]1CC[C@@H](NC(=O)c2c(O)c3cccnc3n(CCN3C[C@@H]4C[C@H]3CO4)c2=O)CC1] | 1-(2-((1S,4S)-2-oxa-5-azabicyclo[2.2.1]heptan-5-yl)ethyl)-4-hydroxy-N-((1s,4R)-4-methylcyclohexyl)-2-oxo-1,2-dihydro-1,8-naphthyridine-3-carboxamide |

TABLE 2-continued

| Compound | Structure | Name |
|---|---|---|
| 257 | 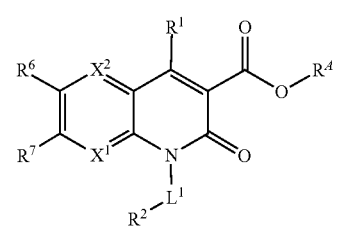 | 1-(2-(3-oxa-6-azabicyclo[3.1.1]heptan-6-yl)ethyl)-4-hydroxy-N-((1s,4s)-4-methylcyclohexyl)-2-oxo-1,2-dihydro-1,8-naphthyridine-3-carboxamide |

In a further aspect, provided herein are compounds of Formula (A)

(A)

wherein $R^1$, $R^2$, $L^1$, $X^1$, $X^2$, $R^6$ and $R^7$ are as defined herein for any of the preceding formulas and $R^A$ is H, $C_1$-$C_6$alkyl or $C_1$-$C_6$alkyl-aryl where aryl is substituted with $C_1$-$C_3$alkyl, $C_1$-$C_3$alkoxy, halo or $NO_2$.

Further Forms of Compounds

In one aspect, compounds described herein (compounds of Formula (I), (II), (III), (IV), (X), (XI), (XIA), (XIB), (XII), (XIIA), (XIIB), (XIII), (XIIIA), and/or (XIIIB)), are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, Handbook of Pharmaceutical Salts: Properties, Selection and Use, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I), (II), (III), (IV), (X), (XI), (XIA), (XIB), (XII), (XIIA), (XIIB), (XIII), (XIIIA), and/or (XIIIB) with an acid. In some embodiments, the compound of Formula (I), (II), (III), (IV), (X), (XI), (XIA), (XIB), (XII), (XIIA), (XIIB), (XIII), (XIIIA), and/or (XIIIB), (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, pharmaceutically acceptable salts are obtained by reacting a compound of Formula (I), (II), (III), (IV), (X), (XI), (XIA), (XIB), (XII), (XIIA), (XIIB), (XIII), (XIIIA), and/or (XIIIB), with a base. In some embodiments, the compound of Formula (I), (II), (III), (IV), (X), (XI), (XIA), (XIB), (XII), (XIIA), (XIIB), (XIII), (XIIIA), and/or (XIIIB), is acidic and is reacted with a base. In such situations, an acidic proton of the compound of Formula (I), (II), (III), (IV), (X), (XI), (XIA), (XIB), (XII), (XIIA), (XIIB), (XIII), (XIIIA), and/or (XIIIB), is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), (II), (III), (IV), (X), (XI), (XIA), (XIB), (XII), (XIIA), (XIIB), (XIII), (XIIIA), and/or (XIIIB) as well as active metabolites of these compounds having the same type of activity.

In some embodiments, sites on the organic radicals (e.g. alkyl groups, aromatic rings) of compounds of Formula (I), (II), (III), (IV), (X), ((XIA), (XIB), (XII), (XIIA), (XIIB), (XIII), (XIIIA), and/or (XIIIB), are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^2$H, $^3$H, $^{13}$C, $^{14}$C, $^{15}$N, $^{18}$O, $^{17}$O, $^{35}$S, $^{18}$F, $^{36}$Cl, $^{123}$I, $^{124}$I, $^{125}$I, $^{131}$I, $^{32}$P and $^{33}$P. In one aspect, isotopically-labeled compounds described herein, for example those into which radioactive isotopes such as $^3$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogens of the compounds of Formula (I) are replaced with deuterium.

In some embodiments, the compounds of Formula (I), (II), (III), (IV), (X), (XI), (XIA), (XIB), (XII), (XIIA), (XIIB), (XIII), (XIIIA), and/or (XIIIB), possess one or more stereocenters and each stereocenter exists independently in either the R or S configuration. In some embodiments, the compound of Formula (I), (II), (III), (IV), (X), (XI), (XIA), (XIB), (XII), (XIIA), (XIIB), (XIII), (XIIIA), and/or (XIIIB), exists in the R configuration. In some embodiments, the compound of Formula (I), (II), (III), (IV), (X), (XI), (XIA), (XIB), (XII), (XIIA), (XIIB), (XIII), (XIIIA), and/or (XIIIB), exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I), (II), (III), (IV), (X), (XI), (XIA), (XIB), (XII), (XIIA), (XIIB), (XIII), (XIIIA), and/or (XIIIB), are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I), (II), (III), (IV), (X), (XIA), (XIB), (XII), (XIIA), (XIIB), (XIII), (XIIIA), and/or (XIIIB), as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I), (II), (III), (IV), (X), (XI), (XIA), (XIB), (XII), (XIIA), (XIIB), (XIII), (XIIIA), and/or (XIIIB), described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are synthesized as outlined in the Schemes and the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$ alkylene. Typical alkylene groups include, but are not limited to, —$CH_2$—, —$CH(CH_3)$—, —$C(CH_3)_2$—, —$CH_2CH_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

The term "alkenyl" refers to a type of alkyl group in which at least one carbon-carbon double bond is present. In one embodiment, an alkenyl group has the formula —C(R)═CR$_2$, wherein R refers to the remaining portions of the alkenyl group, which may be the same or different. In some embodiments, R is H or an alkyl. Non-limiting examples of an alkenyl group include —CH═CH$_2$, —C(CH$_3$)═CH$_2$, —CH═CHCH$_3$, —C(CH$_3$)═CHCH$_3$, and —CH$_2$CH═CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to —NH(alkyl), or —N(alkyl)$_2$.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a C$_6$-C$_{10}$ aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. A cycloalkyl may be saturated or partially saturated. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, adamantyl, norbornyl, and decalinyl. In some embodiments, a cycloalkyl is a C$_3$-C$_6$ cycloalkyl.

"Cycloalkylene" refers to -cycloalkyl-, i.e., a cycloalkyl ring as defined herein which is bonded to two groups.

"1,4-dioxanyl ring fused to ring C" refers to

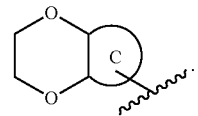

"Deuteroalkyl" refers to an alkyl group as defined herein, in which at least one H is replaced by an isotope of hydrogen, i.e., by deuterium ($^2$H) or tritium ($^3$H).

"Deuteroalkoxy" refers to an alkoxy group as defined herein, in which at least one H is replaced by an isotope of hydrogen, i.e., by deuterium ($^2$H) or tritium ($^3$H).

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a C$_1$-C$_6$ fluoroalkyl.

"Fluoroalkoxy" refers to an alkoxy group as defined herein, in which at least one H is replaced by a fluorine atom.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a C$_1$-C$_6$ heteroalkyl.

Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, and —CH$_2$SCH$_3$.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1 (2H)-onyl, 3,4-dihydroquinolin-2 (1H)-onyl, isoindoline-1,3-dithionyl, benzo[d]oxazol-2 (3H)-onyl, 1H-benzo[d]imidazol-2 (3H)-onyl, benzo[d]thiazol-2 (3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic. The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, bicyclic heteroaryl is a $C_6$-$C_9$ heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In some embodiments, the sulfur atom in a heterocycloalkyl is not oxidized. The term heteroalicyclic also includes all ring forms of the carbohydrates, including but not limited to the monosaccharides, the disaccharides and the oligosaccharides. In one aspect, a heterocycloalkyl is a $C_2$-$C_{10}$ heterocycloalkyl. In another aspect, a heterocycloalkyl is a $C_4$-$C_{10}$ heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$ alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH (CH$_3$), —N(CH$_3$)$_2$, —OH, —CO$_2$H, —CO$_2$(C$_1$-C$_4$ alkyl), —C(=O)NH$_2$, —C(=O)NH(C$_1$-C$_4$ alkyl), —C(=O)N (C$_1$-C$_4$ alkyl)$_2$, —S(=O)$_2$NH$_2$, —S(=O)$_2$NH(C$_1$-C$_4$ alkyl), —S(=O)$_2$N(C$_1$-C$_4$ alkyl)$_2$, C$_1$-C$_4$ alkyl, C$_3$-C$_6$ cycloalkyl, C$_1$-C$_4$ fluoroalkyl, C$_1$-C$_4$ heteroalkyl, C$_1$-C$_4$ alkoxy, C$_1$-C$_4$ fluoroalkoxy, —SC$_1$-C$_4$ alkyl, —S(=O)C$_1$-C$_4$ alkyl, and —S(=O)$_2$C$_1$-C$_4$ alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target. In some embodiments, "modulate" means to interact with a target either directly or indirectly so as to decrease or inhibit receptor activity, The term "modulator" as used herein, refers to a molecule that interacts with a target either directly or indirectly. The interactions include, but are not limited to, the interactions of an agonist, partial agonist, an inverse agonist, antagonist, or combinations thereof. In some embodiments, a modulator is an antagonist. Receptor antagonists are inhibitors of receptor activity. Antagonists mimic ligands that bind to a receptor and prevent receptor activation by a natural ligand. Preventing activation may have many effects. If a natural agonist binding to a receptor leads to an increase in cellular function, an antagonist that binds and blocks this receptor decreases the function.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

It should be understood that in addition to the ingredients particularly mentioned above, the compounds and compositions described herein may include other agents conventional in the art having regard to the type of formulation in question, for example those suitable for oral administration may include flavoring agents.

Methods of Treatment

The compounds disclosed herein, or pharmaceutically acceptable salts, solvates, or stereoisomers thereof, are useful for the modulation of cannabinoid receptors. In some embodiments, the cannabinoid receptor modulated by the compounds and methods is the cannabinoid 2 receptor ($CB_2R$).

Provided herein are $CB_2R$ modulators that are useful for treating one or more diseases or disorders associated with or that would benefit from modulation of $CB_2R$ activity.

In some embodiments, described herein are methods for treating a disease or disorder, wherein the disease or disorder is cancer, a hyperproliferative disorder, an autoimmune disorder, or inflammatory disorder.

In some embodiments, provided herein is a method of modulating the activity of the cannabinoid 2 receptor ($CB_2R$) in a mammal comprising administering to the mammal a compound described herein, or any pharmaceutically acceptable salt, solvate or stereoisomer thereof.

In some embodiments, provided herein is a method of treating a disease or disorder in a mammal that is mediated by the action of the cannabinoid 2 receptor ($CB_2R$) comprising administering to the mammal a compound described herein, or any pharmaceutically acceptable salt, solvate or stereoisomer thereof.

In some embodiments, provided herein is a method for treating cancer in a mammal, the method comprising administering to the mammal a selective cannabinoid 2 receptor ($CB_2R$) modulator. In some embodiments, the selective cannabinoid 2 receptor ($CB_2R$) modulator is a selective cannabinoid 2 receptor ($CB_2R$) antagonist. In some embodiments, the selective cannabinoid 2 receptor ($CB_2R$) modulator is a selective cannabinoid 2 receptor ($CB_2R$) inverse agonist.

In some embodiments, the selective cannabinoid 2 receptor ($CB_2R$) modulator is a compound described herein, or a pharmaceutically acceptable salt, solvate or stereoisomer thereof.

In some embodiments, provided herein is a method for treating cancer in a mammal, the method comprising administering to the mammal a $CB_2R$ antagonist or $CB_2R$ inverse agonist. In some embodiments, the $CB_2R$ antagonist or $CB_2R$ inverse agonist is a compound described herein, or a pharmaceutically acceptable salt, solvate or stereoisomer thereof.

In some embodiments, the $CB_2R$ antagonist or $CB_2R$ inverse agonist is 5-(4-chloro-3-methylphenyl)-1-[(4-methylphenyl)methyl]-N-[(1S,2S,4R)-1,3,3-trimethylbicyclo[2.2.1]hept-2-yl]-1H-pyrazole-3-carboxamide (SR144528), [6-iodo-2-methyl-1-[2-(4-morpholinyl)ethyl]-1H-indol-3-yl](4-methoxyphenyl)-methanone (AM630), or N-(1,3-benzodioxol-5-ylmethyl)-1,2-dihydro-7-methoxy-2-oxo-8-(pentyloxy)-3-quinolinecarboxamide (JTE 907), or a pharmaceutically acceptable salt, solvate or stereoisomer thereof.

In some or any of the preceding embodiments, the cancer is a solid tumor.

In some or any of the preceding embodiments, the cancer is bladder cancer, colon cancer, brain cancer, breast cancer, endometrial cancer, heart cancer, kidney cancer, lung cancer, liver cancer, uterine cancer, blood and lymphatic cancer, ovarian cancer, pancreatic cancer, prostate cancer, thyroid cancer, or skin cancer.

In some or any of the preceding embodiments, the cancer is prostate cancer, breast cancer, colon cancer, or lung cancer.

In some or any of the preceding embodiments, the cancer is a sarcoma, carcinoma, or lymphoma.

In some or any of the preceding embodiments, the methods comprise administering at least one additional therapy to the mammal.

In some or any of the preceding embodiments, the methods comprise administering at least one immune checkpoint inhibitor to the mammal. In some or any of the preceding embodiments, the immune checkpoint inhibitor is an anti-PD-1 agent or an anti-PD-L1 agent. In some or any of the preceding embodiments, the anti-PD-1 agent or anti-PD-L1 agent is nivolumab, pembrolizumab, cemiplimab, labrolizumab, avelumab, durvalumab or atezolizumab.

In some embodiments, the mammal is a human.

Anti-PD-1/Anti-PD-L1 Agents

In some embodiments, a compound described herein (i.e. a $CB_2R$ antagonist or inverse agonist), or a pharmaceutically acceptable salt thereof, is administered in combination with an immune checkpoint inhibitor. Immune checkpoint inhibitors include, but are not limited to, anti-PD-1, anti-PD-L1, or anti-ligand 2 of programmed cell death protein 1 (PD-L2) agents/inhibitors. In some embodiments, immune checkpoint inhibitors include, but are not limited to anti-PD-1, anti-PD-L1, or anti-ligand 2 of programmed cell death protein 1 (PD-L2) antibodies.

As used herein, "PD-1" or "PD1" refers to the Programmed Death 1 (PD-1) receptor. Other names include programmed cell death protein 1 and CD279 (cluster of differentiation 279). PD-1 has two ligands, PD-L1 and PD-L2. In some embodiments, targeting PD-1 restores immune function in the tumor microenvironment.

As used herein, "PD-L1" or "PDL1" refers to the programmed death ligand 1 (PD-L1).

As used herein, "PD-L2" or "PDL2" refers to the programmed death ligand 2 (PD-L2).

In some embodiments, the anti-PD-1 or anti-PDL-1 agent is an antibody, a peptide, a small molecule or a nucleic acid.

In some embodiments, a compound described herein (i.e. a $CB_2R$ antagonist or inverse agonist), or a pharmaceutically acceptable salt thereof, is administered in combination with an anti-PD-1 or anti-PD-L1 agent. In some embodiments, the anti-PD-1 agent is an anti-PD-1 antibody. In some embodiments, the anti-PD-L1 agent is an anti-PD-L1 antibody.

In some embodiments, the anti PD-1 agent for use in combination with compound described herein (i.e. a $CB_2R$ antagonist or inverse agonist), or a pharmaceutically acceptable salt thereof, is nivolumab, pembrolizumab, atezolizumab, durvalumab, pidilizumab, avelumab, TSR-042, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, BGB-A333, AMP-514 (MEDI-0680), AGEN-2034, CSIOOI, Sym-021, SHR-1316, PF-06801591, LZM009, KN-035, AB122, genolimzumab (CBT-501), FAZ-053, CK-301, AK 104, or GLS-010, BGB-108, SHR-1210, PDR-001, PF-06801591, STI-1110, mDX-400, Spartalizumab (PDR001), Camrelizumab (SHR1210), Sintilimab (IBI308), Tislelizumab (BGB-A317), Toripalimab (JS 001), Dostarlimab (TSR-042, WBP-285), INCMGA00012 (MGA012), AMP-224, or AMP-514 (MEDI0680).

In some embodiments, the anti PD-1 agent is an anti PD-1 antibody.

"Anti-PD-1 antibody" refers to an antibody directed towards programmed death protein 1 (PD1). In some embodiments, an anti-PD-1 antibody binds an epitope of PD-1 which blocks the binding of PD-1 to any one or more of its putative ligands. In some embodiments, an anti-PD1 antibody binds an epitope of a PD-1 protein which blocks the binding of PD-1 to PD-L1 and/or PD-L2.

Exemplary anti-PD-1 antibodies include but are not limited to: nivolumab/MDX-1106/BMS-9300/ONO1152, a fully human IgG4 anti-PD-1 monoclonal antibody; pidilizumab (MDV9300/CT-011), a humanized IgG1 monoclonal antibody; pembrolizumab (MK-3475/pembrolizumab/lambrolizumab), a humanized monoclonal IgG4 antibody; durvalumab (MEDI-4736) and atezolizumab.

In some embodiments, the anti-PD-1 antibody is nivolumab (OPDIVO®, Bristol-Myers Squibb), pembrolizumab (KEYTRUDA®, Merck), cemiplimab (Libtayo), labrolizumab (Merck), or BGB-A317.

In some embodiments, the anti-PD1 antibody is an antibody set forth in U.S. Pat. Nos. 7,029,674, 7,488,802, 7,521,051, 8,008,449, 8,354,509, 8,617,546, 8,709,417, or WO2014/179664.

The terms "antibody" and "antibodies" as used herein is inclusive of all types of immunoglobulins, including IgG, IgM, IgA, IgD, and IgE, or fragments thereof, that may be appropriate for the medical uses disclosed herein. The antibodies may be monoclonal or polyclonal and may be of any species of origin, including, for example, mouse, rat, rabbit, horse, or human. Antibody fragments that retain specific binding to the protein or epitope, for example, PD-L1 or PD-1, bound by the antibody used in the present disclosure are included within the scope of the term "antibody." The antibodies may be chimeric or humanized, particularly when they are used for therapeutic purposes. Antibodies and antibody fragments may be obtained or prepared using various methods.

In some embodiments, the anti PD-1 agent for use in combination with a compound described herein (i.e. a $CB_2R$ antagonist or inverse agonist), or a pharmaceutically acceptable salt thereof, is atezolizumab, avelumab, AMP-224, MEDI-0680, RG-7446, GX-P2, durvalumab, KY-1003, KD-033, MSB-0010718C, TSR-042, ALN-PDL, STI-A1014, CX-072, BMS-936559, KN035, CK-301 (Checkpoint Therapeutics), AUNP12, CA-170 (Aurigene/Curis), MEDI4736, MSB0010718C, MDX 1105-01, and BMS-986189.

In some embodiments, the anti PD-L1 agent is an anti PD-L1 antibody.

"Anti-PD-L1 antibody" refers to an antibody directed towards programmed death ligand 1 (PD-L1).

Anti-PD-L1 antibodies for use in combination with a compound described herein (i.e. a $CB_2R$ antagonist or inverse agonist), or a pharmaceutically acceptable salt thereof, include: avelumab; BMS-936559, a fully human IgG4 antibody; atezolizumab (MPDL3280A/RG-7446), a human monoclonal antibody; MEDI4736; MSB0010718C, and MDX 1105-01.

In some embodiments, the anti-PD-L1 antibody is avelumab (Bavencio®, Merck KGA/Pfizer), durvalumab (AstraZeneca) and atezolizumab (TECENTRIQ®, Roche).

Additional exemplary antibodies include, but are not limited to, the antibodies set forth in U.S. Pat. Nos. 8,217,149, 8,383,796, 8,552,154 and 8,617,546.

Peptide anti-PD-1/PD-L1 agents include AUNP12 (a 29-mer peptide by Aurigene and Laboratoires Pierre Fabre), CA-170 (Aurigene/Curis), BMS-986189 (a macrocyclic peptide by BMS).

Small molecule anti-PD-1/PD-L1 agents include those described in WO/2020/086556, WO/2020/014643, WO/2019/204609, WO/2019/160882, WO/2018/195321, WO2018026971, US20180044329, US20180044305, US20180044304, US20180044303, US20180044350, US20180057455, US20180057486, US20180045142, WO20180044963, WO2018044783, WO2018009505, WO20180044329, WO2017066227, WO2017087777, US20170145025, WO2017079669, WO2017070089, US2017107216, WO2017222976, US20170262253, WO2017205464, US20170320875, WO2017192961, WO2017112730, US20170174679, WO2017106634, WO2017202744, WO2017202275, WO2017202273, WO2017202274, WO2017202276, WO2017180769, WO2017118762, WO2016041511, WO2016039749, WO2016142835, WO2016142852, WO2016142886, WO2016142894, and WO2016142833. In some embodiments, the small molecule anti-PD-1/PD-L1 agent is GS-4224. In some embodiments, GS-4224 is administered at about 400 mg to about 1000 mg.

Dosing and Treatment Regimens

In one embodiment, the compounds described herein, or a pharmaceutically acceptable salt thereof, are used in the preparation of medicaments for the treatment of diseases or conditions in a mammal that would benefit from inhibition or reduction of $CB_2R$ activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a mammal already suffering from a disease or condition, in an amount sufficient to cure or at least partially arrest at least one of the symptoms of the disease or condition. Amounts effective for this use depend on the severity and course of the disease or condition, previous therapy, the mammal's health status, weight, and response to the drugs, and the judgment of a healthcare practitioner. Therapeutically effective amounts are optionally determined by methods including, but not limited to, a dose escalation and/or dose ranging clinical trial.

In prophylactic applications, compositions containing the compounds described herein are administered to a mammal susceptible to or otherwise at risk of a particular disease, disorder or condition. Such an amount is defined to be a "prophylactically effective amount or dose." In this use, the precise amounts also depend on the mammal's state of health, weight, and the like. When used in mammals, effective amounts for this use will depend on the severity and course of the disease, disorder or condition, previous therapy, the mammal's health status and response to the drugs, and the judgment of a healthcare professional. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the mammal's condition does not improve, upon the discretion of a healthcare professional the administration of the compounds are administered chronically, that is, for an extended period of time, including throughout the duration of the mammal's life in order to ameliorate or otherwise control or limit the symptoms of the mammal's disease or condition.

In certain embodiments wherein a mammal's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the mammal requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the disease(s) for which relief is sought, is modified in accordance with a variety of factors (e.g. the disease or disorder from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a compound described herein, or a pharmaceutically acceptable salt thereof, is administered in combination with chemotherapy, radiation therapy, monoclonal antibodies, or combinations thereof.

Chemotherapy includes the use of anti-cancer agents.

In addition to the $CB_2R$ antagonists or inverse agonists described above, the following $CB_2R$ antagonists or inverse agonists are contemplated in the combination therapies described herein for use in the treatment of cancer: 5-(4-chloro-3-methylphenyl)-1-[(4-methylphenyl)methyl]-N-[(1S,2S,4R)-1,3,3-trimethylbicyclo[2.2.1]hept-2-yl]-1H-pyrazole-3-carboxamide (SR144528), [6-iodo-2-methyl-1-[2-(4-morpholinyl)ethyl]-1H-indol-3-yl](4-methoxyphenyl)-methanone (AM630), or N-(1,3-benzodioxol-5-ylmethyl)-1,2-dihydro-7-methoxy-2-oxo-8-(pentyloxy)-3-quinolinecarboxamide (JTE 907), or any one of the $CB_2R$ antagonists or inverse agonists described in V. Lucchesi et al., J. Med. Chem. 2014, 57, 8777-8791.

ABBREVIATIONS

CAN Acetonitrile
$CDCl_3$ Chloroform, deuterated
DCM Dichloromethane
DMSO Dimethyl sulfoxide
DMF Dimethyl formamide
DMA Dimethylacetamide DIEA Diisopropyl ethyl amine
EA or EtOAc Ethyl Acetate
EtOH Ethanol
h Hours
HATU 1-[Bis(dimethylamino)methylene]-1H-1,2,3-triazolo[4,5-b]pyridinium 3-oxid hexafluorophosphate
MeOH Methanol
NaOMe Sodium methoxide
PE Petroleum ether
Pd(dppf)Cl$_2$·CH$_2$Cl$_2$ [1,1'- Bis(diphenylphosphino)ferrocene]dichloropalladium(II), complex with dichloromethane*
Pd(PPh$_3$)$_2$Cl$_2$ Bis(triphenylphosphine)palladium dichloride
Pd(PPh$_3$)$_4$ Tetrakis(triphenylphosphine)-palladium(0)
Rt Retention time
TFA Trifluoro acetic acid
THF Tetrahydrofuran
TLC Thin Layer Chromatography
T3P Propanephosphonic acid anhydride, General Synthetic Methods The compounds of Formula (I) and/or (X) are prepared as described in the schemes below.

Scheme 1 shows an embodiment for preparing compounds of Formula (I) and/or Formula (X).

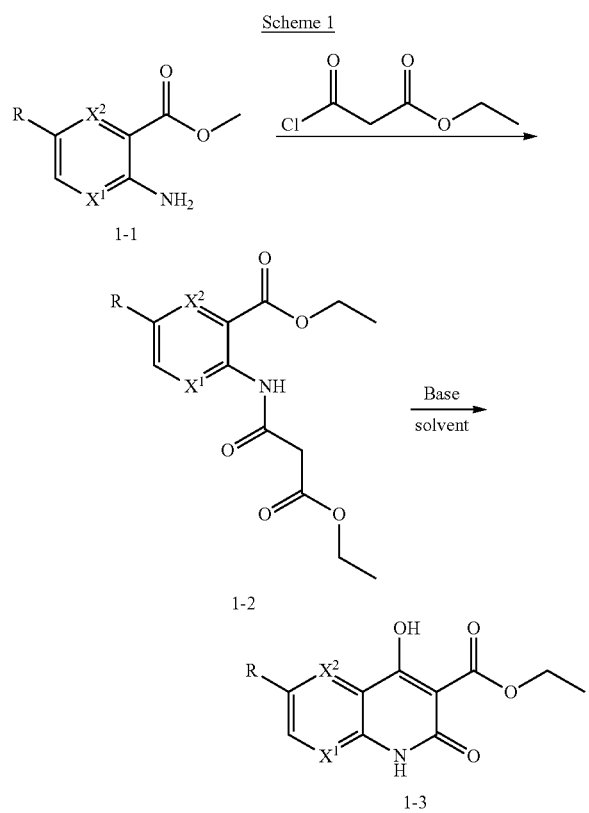

Starting with compound 1-1, wherein X$^1$ and X$^2$ is as defined herein, and R may be H, halo or a triflate group, or any other suitable leaving group, reaction with ethyl 3-chloro-3-oxopropanoate provides compound 1-2 which can be cyclized in the presence of a base and a protic solvent to provide compound 1-3 which can be converted to compounds of Formula (I) and/or Formula (X). Examples of suitable bases for the cyclization include sodium methoxide, sodium ethoxide and the like. Suitable solvents include methanol, ethanol and the like.

Scheme 2 shows a further embodiment for the preparation of compounds of Formula (I) and/or Formula (X).

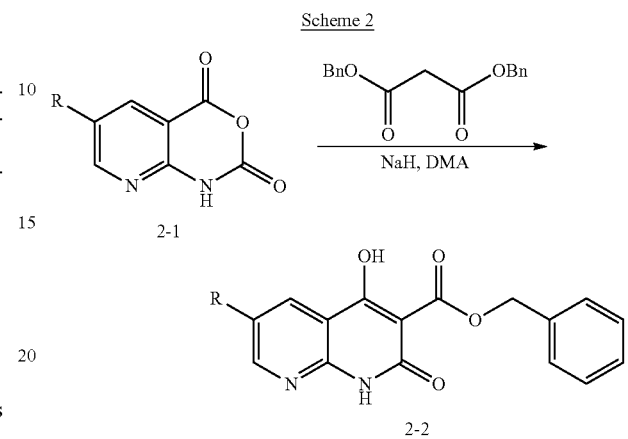

Starting with compound 2-1, wherein R may be H, halo or a triflate group, or any other suitable leaving group, reaction with dibenzyl malonate provides compound 2-2 which can be converted to compounds of Formula (I) and/or Formula (X).

Scheme 3 shows an embodiment for the preparation of compounds of Formula (X).

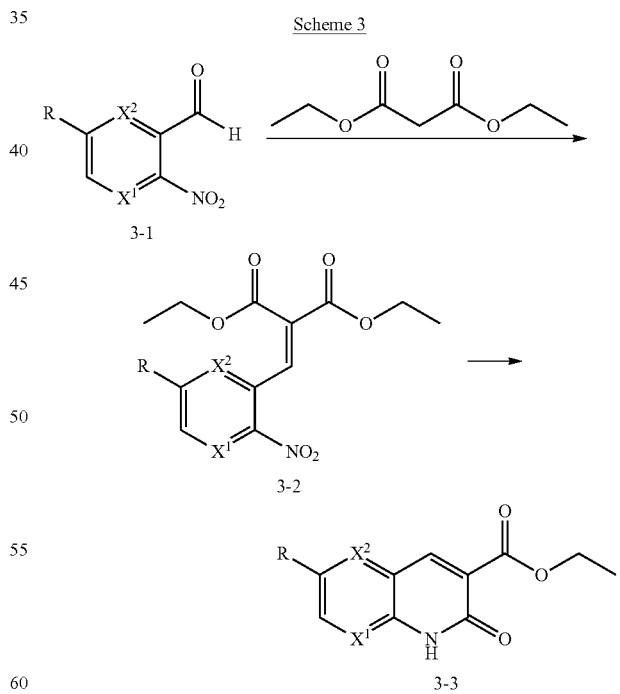

Starting with compound 3-1, wherein X$^1$ and X$^2$ are as defined herein, and R may be H, halo or a triflate group, or any other suitable leaving group, reaction with diethyl malonate in the presence of a base (e.g., piperidine) provides compound 3-2 which can be cyclized in the presence of a metal (e.g., Fe) and an acid (e.g., acetic acid) to provide compound 3-3 which can be converted to compounds of Formula (X).

Scheme 4 shows an embodiment wherein $R^1$ is H or OH, and compounds 1-3 and/or 2-3 and/or 3-3 shown above (collectively summarized as compound 4-1) can be converted to compounds of Formula (I) and/or Formula (X).

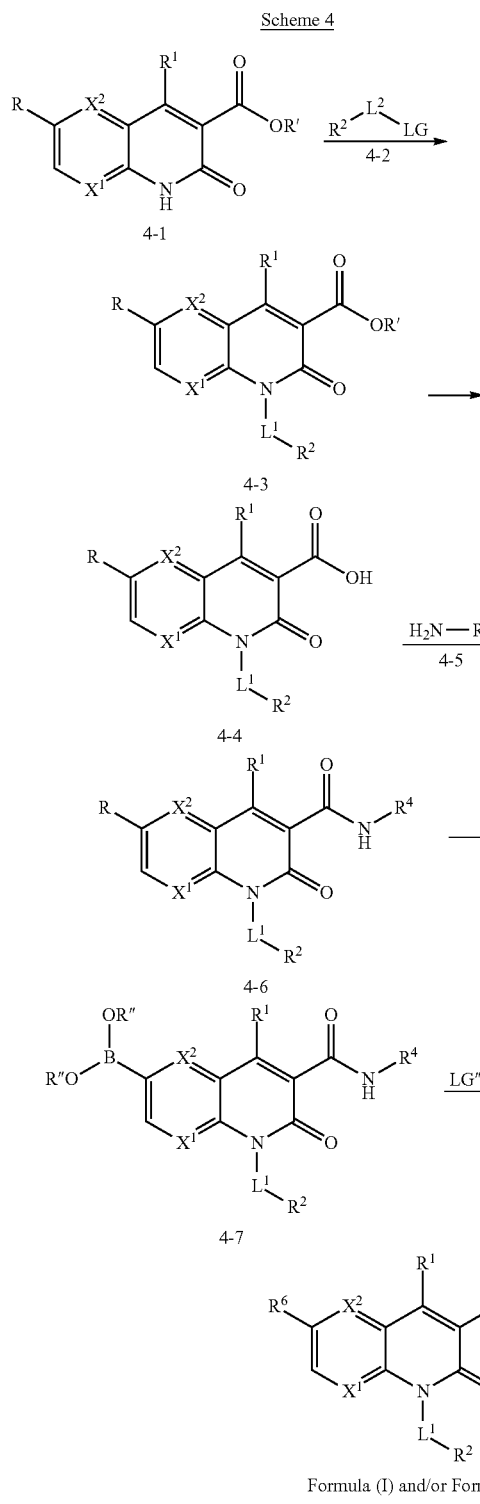

4-1

4-3

4-4

4-6

4-7

Formula (I) and/or Formula (X)

Starting with compound 1-3, or 2-3, or 3-3, collectively summarized as compound 4-1, wherein $X^1$ and $X^2$ are as defined herein and R may be H, halo or a triflate group, or any other suitable leaving group, and R' is a $C_1$-$C_3$ alkyl or benzyl, a reaction of compound 4-1 with compound 4-2 provides compound 4-3. Any suitable base may be used for this reaction (e.g., $K_2CO_3$, $Cs_2CO_3$). $R^2$ in compound 4-2 is as defined herein and LG may be any suitable leaving group (e.g., halo). The ester in compound 4-3 is hydrolyzed to provide compound 4-4. Coupling of compound 4-4 with compound 4-5 under any suitable amide coupling conditions (e.g., HATU, EDCI) provides compound 4-6. $R^4$ in compound 4-5 is as defined herein. Compound 4-6 is converted to compound 4-7 using any suitable borylating agent. Each R" in compound 4-7 is independently H, $C_1$-$C_3$ alkyl, or phenyl, or, the two R" together with the atoms to which they are attached, form a dioxaborolane ring. Compound 4-7 is coupled with a suitable compound 4-8 to provide compounds of Formula (I) or Formula (X). In compound 4-8, $R^6$ is as defined herein and LG" is any suitable leaving group (e.g., halo). The coupling reaction between compounds 4-7 and 4-8 may be mediated by any suitable palladium catalyst or any other similar organometallic coupling method known to one of skill in the art.

Scheme 5 shows an embodiment wherein $R^1$ is H or OH, and compounds 1-3 and/or 2-3 and/or 3-3 shown above (collectively summarized as compound 4-1) can be converted to compounds of Formula (I) and/or Formula (X).

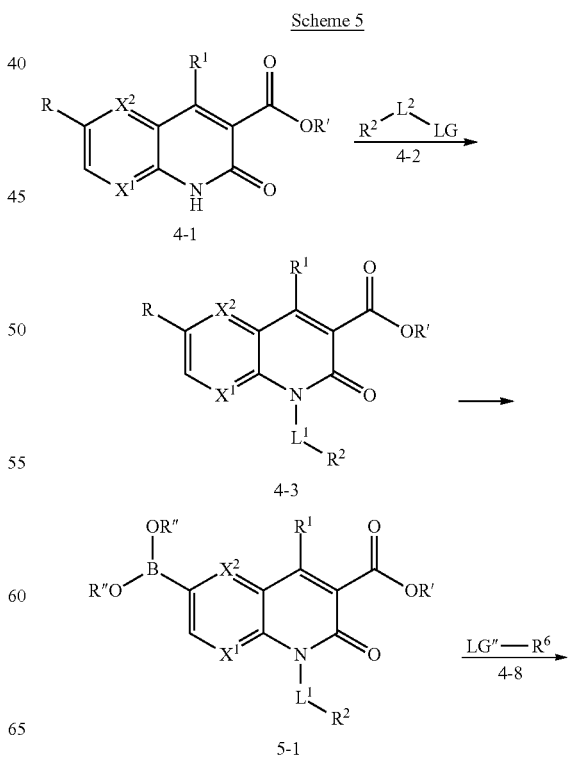

4-1

4-3

5-1

-continued

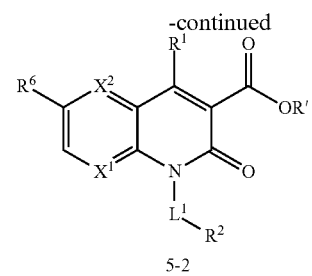
5-2

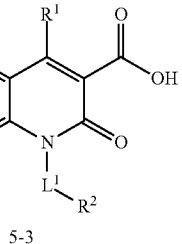
5-3

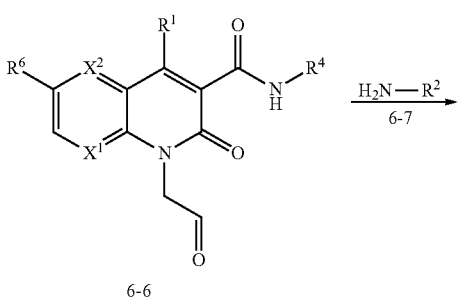
Formula (I) and/or Formula (X)

Starting with compound 1-3, or 2-3, or 3-3, collectively summarized as compound 4-1, wherein $X^1$ and $X^2$ are as defined herein and R may be H, halo or a triflate group, or any other suitable leaving group, and R' is a $C_1$-$C_3$ alkyl or benzyl, a reaction of compound 4-1 with compound 4-2 provides compound 4-3. Any suitable base may be used for this reaction (e.g., $K_2CO_3$, $Cs_2CO_3$). $R^2$ in compound 4-2 is as defined herein and LG may be any suitable leaving group (e.g., halo). Compound 4-3 is converted to compound 5-1 using any suitable borylating agent. Each R" in compound 5-1 is independently H, $C_1$-$C_3$ alkyl, or phenyl, or, the two R" together with the atoms to which they are attached, form a dioxaborolane ring. Compound 5-1 is coupled with a suitable compound 4-8 to provide a compound 5-2. The coupling reaction between compounds 5-1 and 4-8 may be mediated by any suitable palladium catalyst or any other similar organometallic coupling method known to one of skill in the art. In compound 4-8, $R^6$ is as defined herein and LG" is any suitable leaving group (e.g., halo). The ester in compound 5-2 is hydrolyzed to provide compound 5-3. Compound 5-3 is coupled with compound 4-5 under any suitable amide coupling conditions (e.g., HATU, EDCI) to provide compounds of Formula (I) and/or Formula (X).

Scheme 6 shows an embodiment wherein $R^1$ is H or OH, and compounds 1-3 and/or 2-3 and/or 3-3 shown above (collectively summarized as compound 4-1) can be converted to compounds of Formula (I) and/or Formula (X).

Scheme 6

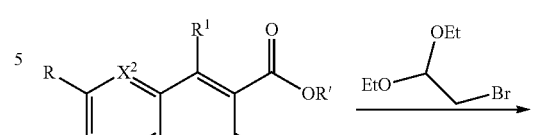
4-1

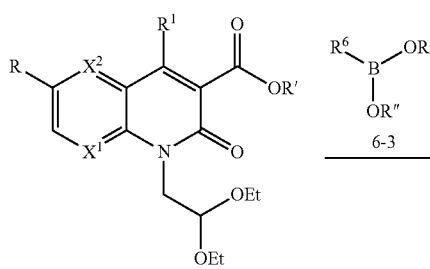
6-2

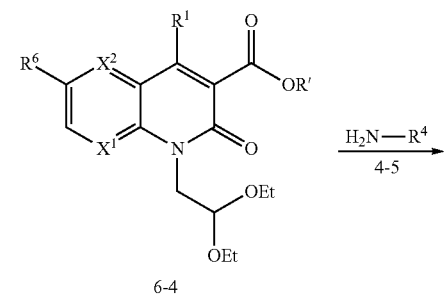
6-4

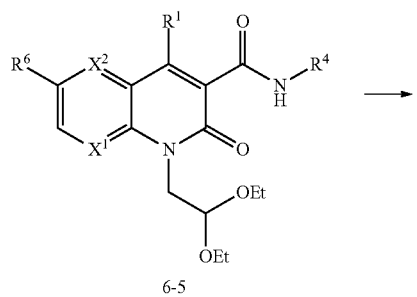
6-5

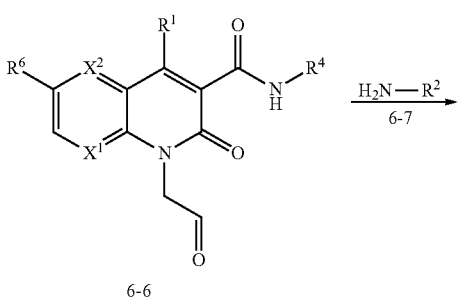
6-6

-continued

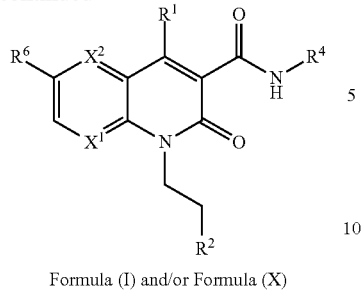

Formula (I) and/or Formula (X)

Starting with compound 1-3, or 2-3, or 3-3, collectively summarized as compound 4-1, wherein $X^1$ and $X^2$ is as defined herein and R may be H, halo or a triflate group, or any other suitable leaving group, and R' is a $C_1$-$C_3$ alkyl or benzyl, reaction with 2-bromo-1,1-diethoxyethane provides compound 6-2. Compound 6-2 is coupled with a boronate 6-3 to provide compound 6-4. In compound 6-3, $R^6$ is as defined herein. In compound 6-3, each R" is independently H, $C_1$-$C_3$ alkyl, or phenyl, or, the two R" together with the atoms to which they are attached, form a dioxaborolane ring. The coupling reaction between compounds 6-2 and 6-3 may be mediated by any suitable palladium catalyst or any other similar organometallic coupling method known to one of skill in the art. Compound 6-4 is converted to an amide 6-5 via a reaction with compound 4-5, wherein $R^4$ is as defined herein. The ketal in compound 6-5 is hydrolyzed under acidic conditions (e.g., HCl) to provide the aldehyde 6-6 which is aminated with compound 6-7 to provide compounds of Formula (I) and/or (X). $R^2$ in compound 6-7 is as defined herein.

Scheme 7 shows an embodiment for preparation of compounds of Formula (I) and/or (X) wherein $R^1$ is alkyl.

-continued

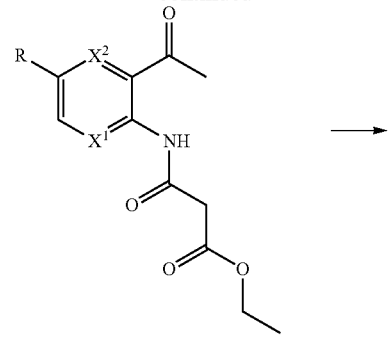

7-4

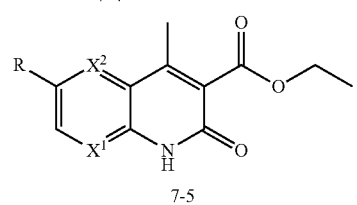

7-5

Formula (I) and/or Formula (X)

Starting with compound 7-1, wherein $X^1$ and $X^2$ is a defined herein and R may be H, halo or a triflate group, or any other suitable leaving group, conversion to a Weinreb amide provides compound 7-2. Reaction with a suitable Grignard reagent provides compound 7-3 which is converted to compound 7-4 by reaction with ethyl 3-chloro-3-oxopropanoate. Compound 7-4 is cyclized in the presence of a base to provide compound 7-5 which can be converted to compounds of Formula (I) and/or (X) using the methods described in Schemes 4-6.

Scheme 8 shows an embodiment for preparation of compounds of Formula (I) and/or (X) wherein $R^1$ is alkoxy.

Scheme 7

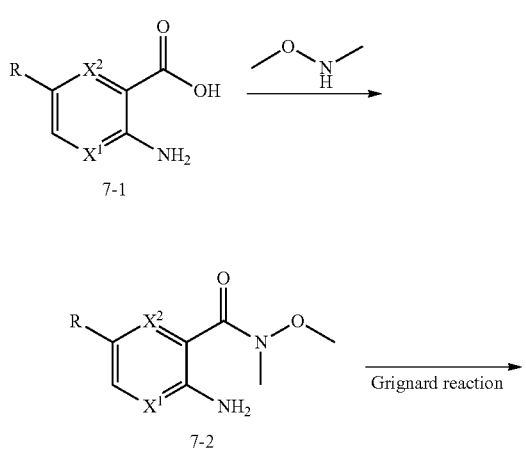

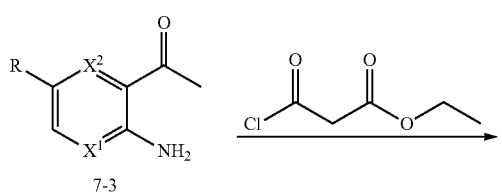

Scheme 8

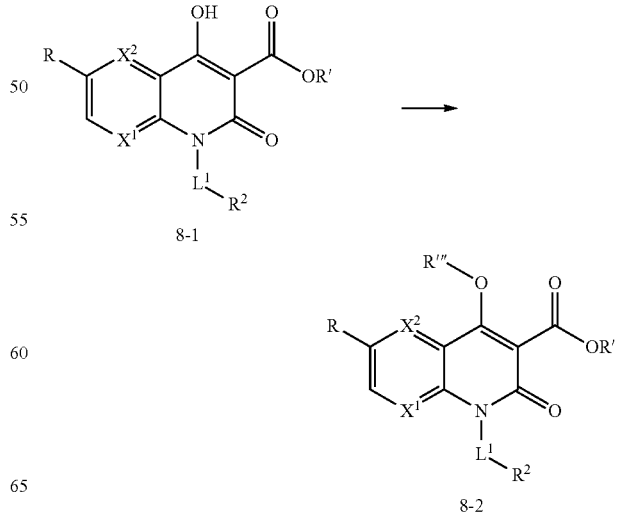

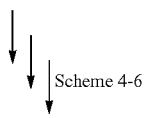

Formula (I) and/or Formula (X)

Compound 8-1, wherein $X^1$ and $X^2$ is as defined herein and R may be H, halo or a triflate group, or any other suitable leaving group, and R' is a $C_1$-$C_3$ alkyl or benzyl is reacted with an alkylating agent to provide compound 8-2 wherein R''' is $C_1$-$C_6$ alkyl, which can be converted to compounds of Formula (I) and/or (X) using the using the methods described in Schemes 4-6. By way of example, reaction of compound 8-1 with DMSO gives R''' methyl, reaction of compound 8-1 with propyl iodide gives R''' isopropyl.

Any combination of steps described above may be used in the preparation of compounds described herein, including any procedures described in the Examples section.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemie or Sigma (St. Louis, Missouri, USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

EXAMPLES

The following examples are provided for illustrative purposes only and not to limit the scope of the claims provided herein. All starting materials are commercially available unless stated otherwise.

Example 1—Synthesis of 6-bromo-1-(4-fluorobenzyl)-N-(1-(4-fluorophenyl)ethyl)-4-hydroxy-2-oxo-1,2-dihydro-1,8-naphthyridine-3-carboxamide (Compound 1)

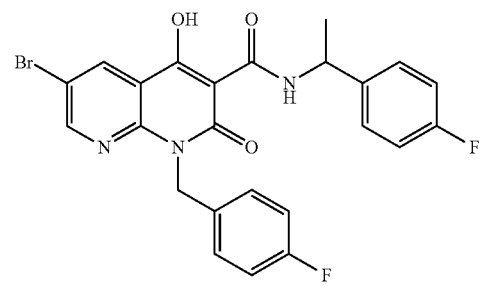 [SMILES: CC(NC(=O)c1c(O)c2cc(Br)cnc2n(Cc2ccc(F)cc2)c1=O)c1ccc(F)cc1]

Step 1: Preparation of ethyl 5-bromo-2-(3-ethoxy-3-oxopropanamido)nicotinate

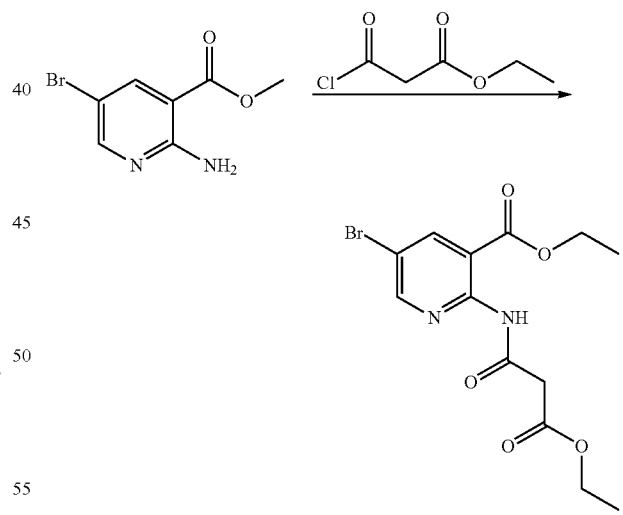

To a solution of methyl 2-amino-5-bromo-pyridine-3-carboxylate (0.5 g, 2.16 mmol, 1 eq) in DCM (10 mL) was added a solution of ethyl 3-chloro-3-oxo-propanoate (390.99 mg, 2.60 mmol, 325.82 μL, 1.2 eq) in DCM (10 mL) at 0° C. The mixture was stirred at 20° C. for 2 h. TLC showed complete consumption of the starting material and formation of a new spot. The mixture was poured into water (100 mL). The aqueous phase was extracted with ethyl acetate (3×50 mL). The combined organic phase was dried with anhydrous $Na_2SO_4$, filtered and concentrated.

The residue was purified by flash silica gel chromatography (PE/EA=50:1 to 5:1) to produce ethyl 5-bromo-2-(3-ethoxy-3-oxopropanamido)nicotinate (1 g, 2.90 mmol) as a white solid.

¹H NMR (400 MHz, CDCl₃) δ=11.01 (br s, 1H), 8.56 (d, J=2.5 Hz, 1H), 8.43 (d, J=2.5 Hz, 1H), 4.31-4.20 (m, 4H), 3.79 (s, 2H), 1.32 (t, J=7.3 Hz, 3H), 1.29-1.26 (m, 3H).

Step 2: Preparation of ethyl 6-bromo-4-hydroxy-2-oxo-1,2-dihydro-1,8-naphthyridine-3-carboxylate

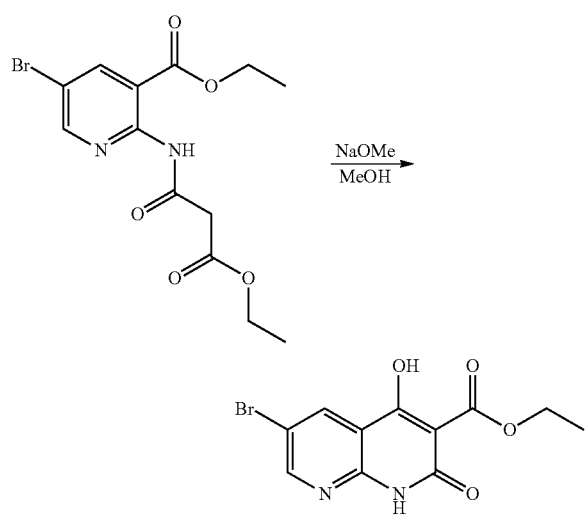

To a solution of methyl 5-bromo-2-[(3-ethoxy-3-oxopropanoyl) amino]pyridine-3-carboxylate (0.5 g, 1.45 mmol, 1 eq) in MeOH (10 mL) was added NaOMe (469.57 mg, 8.69 mmol, 6 eq) at 20° C. The mixture was stirred at 70° C. for 1 h. TLC showed complete consumption of the starting material and formation of a new spot.

The reaction mixture was acidified to pH=5 by adding 2 N hydrochloric acid dropwise at 0° C. The mixture was filtered, and the resulting solid was washed with water (5 mL) to produce 6-bromo-4-hydroxy-2-oxo-1,2-dihydro-1,8-naphthyridine-3-carboxylate (730 mg, 2.33 mmol) as a white solid (used without further purification).

¹H NMR (400 MHz, DMSO-d₆) δ=10.25 (s, 1H), 8.34 (d, J=2.5 Hz, 1H), 8.15 (d, J=2.0 Hz, 1H), 4.05 (q, J=7.2 Hz, 2H), 1.19 (t, J=7.3 Hz, 3H).

Step 3: Preparation of ethyl 6-bromo-1-(4-fluorobenzyl)-4-hydroxy-2-oxo-1,2-dihydro-1,8-naphthyridine-3-carboxylate

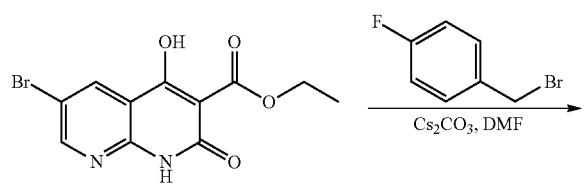

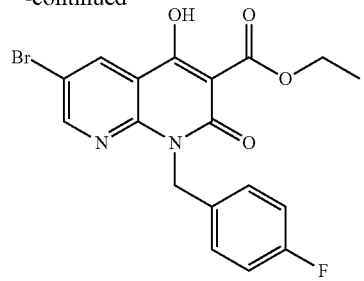

To a mixture of ethyl 6-bromo-4-hydroxy-2-oxo-1H-1,8-naphthyridine-3-carboxylate (480 mg, 1.53 mmol, 1 eq) and 1-(bromomethyl)-4-fluoro-benzene (318.76 mg, 1.69 mmol, 208.34 μL, 1.1 eq) in DMF (5 mL) was added Cs₂CO₃ (1.50 g, 4.60 mmol, 3 eq). The mixture was stirred at 90° C. for 12 h. LCMS showed TLC showed complete consumption of the starting material and formation of a new peak.

The mixture was poured into water (50 mL). The aqueous phase was extracted with ethyl acetate (3×10 mL). The combined organic phase was dried over Na₂SO₄, filtered and concentrated in vacuum. The residue was purified by flash silica gel chromatography (petroleum ether/ethyl acetate=50:1 to 10:1) to produce ethyl 6-bromo-1-(4-fluorobenzyl)-4-hydroxy-2-oxo-1,2-dihydro-1,8-naphthyridine-3-carboxylate (600 mg) as a yellow solid (used without further purification).

¹H NMR (400 MHz, CDCl₃) δ=14.55-14.00 (m, 1H), 8.72 (d, J=2.5 Hz, 1H), 8.53 (d, J=2.5 Hz, 1H), 7.35 (s, 2H), 7.08-7.07 (m, 2H), 4.52 (d, J=3.0 Hz, 2H), 1.48 (t, J=7.3 Hz, 3H). LCMS (ESI+): m/z 421.1, 423.1 [M+H]⁺, Rt: 2.315 min.

LCMS Method 5-95 AB-HPLC: LCMS (positive electrospray ionization) (The gradient was 5-95% B in 2.20 min 0.5% B in 0.01 min, 5-95% B (0.01-1.00 min), 95-100% B (1.00-1.80 min), 5% B in 1.81 min, held at 5% B for 0.40 min. Mobile phase A was 0.037% TFA in water, and mobile phase B was 0.018% TFA in HPLC grade acetonitrile. The column used for chromatography was a HALO AQ-C18 2.1*30 mm, (2.7 μm particles). Detection methods is diode array (DAD).

Step 4: Preparation of 6-bromo-1-(4-fluorobenzyl)-N-(1-(4-fluorophenyl)ethyl)-4-hydroxy-2-oxo-1,2-dihydro-1,8-naphthyridine-3-carboxamide -continued

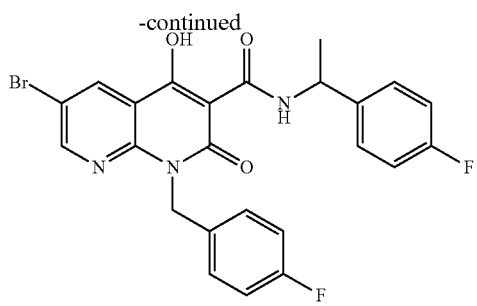

To a mixture of ethyl 6-bromo-1-[(4-fluorophenyl)methyl]-4-hydroxy-2-oxo-1,8-naphthyridine-3-carboxylate (100 mg, 237.41 μmol, 1 eq) and 1-(4-fluorophenyl)ethanamine (39.65 mg, 284.89 μmol, 37.40 μL, 1.2 eq) in toluene (1 mL) was added DIEA (92.05 mg, 712.22 μmol, 124.06 μL, 3 eq). The mixture was stirred at 120° C. for 1 h. LCMS showed complete consumption of the starting material and formation of a new peak.

The mixture was concentrated. The residue was purified by prep-HPLC (column: Welch Xtimate C18 150*25 mm*5 μm; mobile phase: [water (0.04% HCl)-ACN]; B %: 60%-85%, 10 min) to produce 6-bromo-1-(4-fluorobenzyl)-N-(1-(4-fluorophenyl)ethyl)-4-hydroxy-2-oxo-1,2-dihydro-1,8-naphthyridine-3-carboxamide (2.2 mg, 4.28 μmol) as a white solid.

$^1$H NMR (400 MHz, CDCl$_3$) δ=10.51 (br d, J=7.3 Hz, 1H), 8.72 (d, J=2.4 Hz, 1H), 8.57 (d, J=2.4 Hz, 1H), 7.39 (ddd, J=5.4, 8.4, 17.0 Hz, 4H), 7.06 (t, J=8.7 Hz, 2H), 6.97 (t, J=8.6 Hz, 2H), 5.63 (s, 2H), 5.30-5.19 (m, 1H), 1.62 (d, J=7.0 Hz, 3H). LCMS for product (ESI+): m/z 514.0, 516.0 [M+H]$^+$, Rt: 3.419 min.

LCMS Method 5-95 AB-HPLC: LCMS (positive electrospray ionization) (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD), evaporative light scattering (ELSD) detection, and positive electrospray ionization.

Example 2—Synthesis of 6-bromo-1-(4-fluorobenzyl)-4-hydroxy-2-oxo-N-(spiro[3.3]heptan-2-yl)-1,2-dihydro-1,8-naphthyridine-3-carboxamide (Compound 2)

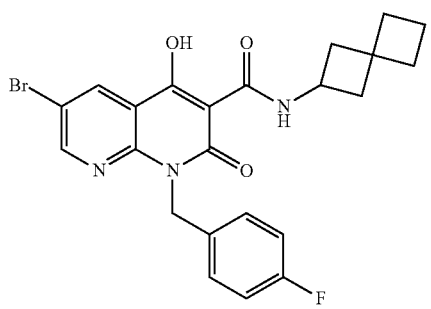

Preparation of 6-bromo-1-(4-fluorobenzyl)-4-hydroxy-2-oxo-N-(spiro[3.3]heptan-2-yl)-1,2-dihydro-1,8-naphthyridine-3-carboxamide

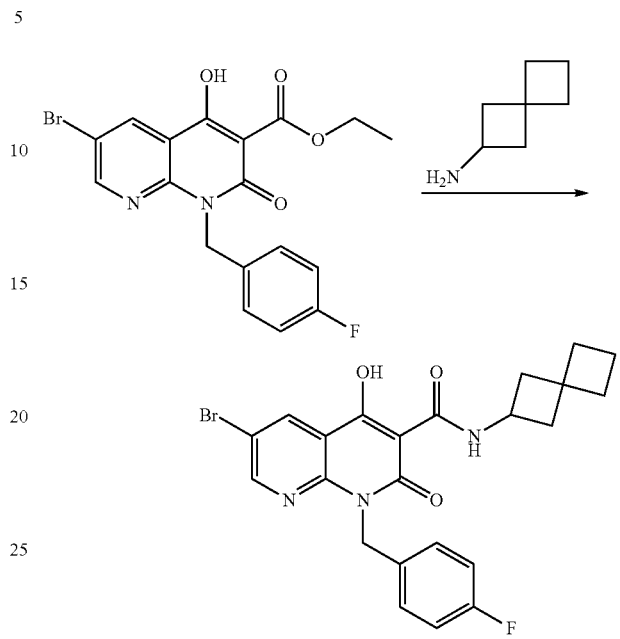

To a mixture of ethyl 6-bromo-1-[(4-fluorophenyl)methyl]-4-hydroxy-2-oxo-1,8-naphthyridine-3-carboxylate (100 mg, 237.41 μmol, 1 eq) and spiro[3.3]heptan-2-amine (42.06 mg, 284.89 μmol, 1.2 eq, HCl) in toluene (1 mL) was added DIEA (92.05 mg, 712.22 μmol, 124.06 μL, 3 eq). The mixture was stirred at 120° C. for 1 h. LCMS showed complete consumption of the starting material and formation of a new peak.

The solid formed was collected by filtration and air-dried to produce 6-bromo-1-(4-fluorobenzyl)-4-hydroxy-2-oxo-N-(spiro[3.3]heptan-2-yl)-1,2-dihydro-1,8-naphthyridine-3-carboxamide (21.9 mg, 45.03 μmol) as a white solid.

$^1$H NMR (400 MHz, DMSO-d$_6$) δ=10.31-10.14 (m, 1H), 8.90 (d, J=2.5 Hz, 1H), 8.58 (d, J=2.5 Hz, 1H), 7.34-7.27 (m, 2H), 7.09 (t, J=9.0 Hz, 2H), 5.55 (s, 2H), 4.27 (q, J=8.0 Hz, 1H), 2.68-2.66 (m, 1H), 2.45-2.39 (m, 2H), 2.33 (td, J=1.6, 3.8 Hz, 1H), 2.08-1.99 (m, 4H), 1.97-1.91 (m, 2H), 1.84-1.76 (m, 2H). LCMS for product (ESI+): m/z 486.0, 488.0 [M+H]$^+$, Rt: 2.989 min.

LCMS Method 50-50 AB-HPLC: LCMS (positive electrospray ionization) (The gradient was 50% B in 0.40 min and 50-100% B at 0.40-3.00 min, hold on 100% B for 1.00 min, and then 100-50% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD), evaporative light scattering (ELSD) detection, and positive electrospray ionization.

Example 3—Synthesis of 6-bromo-N-(1-(4-cyano-phenyl)ethyl)-1-(4-fluorobenzyl)-4-hydroxy-2-oxo-1,2-dihydro-1,8-naphthyridine-3-carboxamide (Compound 3)

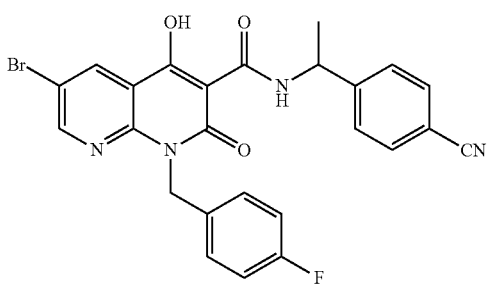 [SMILES: CC(NC(=O)c1c(O)c2cc(Br)cnc2n(Cc2ccc(F)cc2)c1=O)c1ccc(C#N)cc1]

Preparation of 6-bromo-N-(1-(4-cyanophenyl)ethyl)-1-(4-fluorobenzyl)-4-hydroxy-2-oxo-1,2-dihydro-1,8-naphthyridine-3-carboxamide

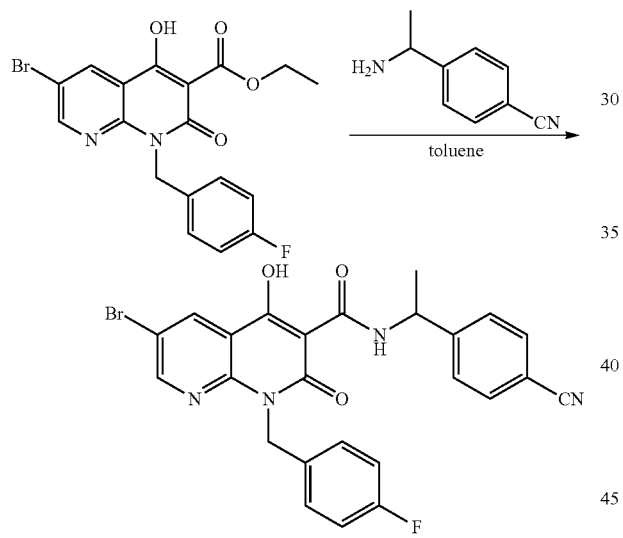

To a mixture of ethyl 6-bromo-1-[(4-fluorophenyl)methyl]-4-hydroxy-2-oxo-1,8-naphthyridine-3-carboxylate (100 mg, 237.41 μmol, 1 eq) and 4-(1-aminoethyl)benzonitrile (38.18 mg, 261.15 μmol, 1.1 eq) in toluene (1 mL) was added DIEA (92.05 mg, 712.22 μmol, 124.05 μL, 3 eq). The mixture was stirred at 120° C. for 1 h. LCMS showed complete consumption of the starting material and formation of a new peak.

The mixture was filtered. The filtrate was purified by prep-HPLC (column: Luna Omega 5u Polar C18 100A; mobile phase: [water (0.04% HCl)-ACN]; B %: 70%-98%, 7 min) to yield 6-bromo-N-(1-(4-cyanophenyl)ethyl)-1-(4-fluorobenzyl)-4-hydroxy-2-oxo-1,2-dihydro-1,8-naphthyridine-3-carboxamide (8.5 mg, 14.69 μmol, HCl) as a white solid.

$^1$H NMR (400 MHz, CDCl$_3$) δ=10.61 (br d, J=7.1 Hz, 1H), 8.73 (d, J=2.5 Hz, 1H), 8.56 (d, J=2.4 Hz, 1H), 7.67 (d, J=8.4 Hz, 2H), 7.53-7.47 (m, 2H), 7.42 (dd, J=5.4, 8.6 Hz, 2H), 7.02-6.94 (m, 2H), 5.64 (s, 2H), 5.26 (quin, J=7.2 Hz, 1H), 1.63 (d, J=7.0 Hz, 3H). LCMS for product (ESI+): m/z 521.1, 523.1 [M+H]$^+$, Rt: 3.259 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD).

Example 4—Synthesis of 6-bromo-4-hydroxy-1-(2-morpholinoethyl)-2-oxo-N-(spiro[3.3]heptan-2-yl)-1,2-dihydro-1,8-naphthyridine-3-carboxamide (Compound 4)

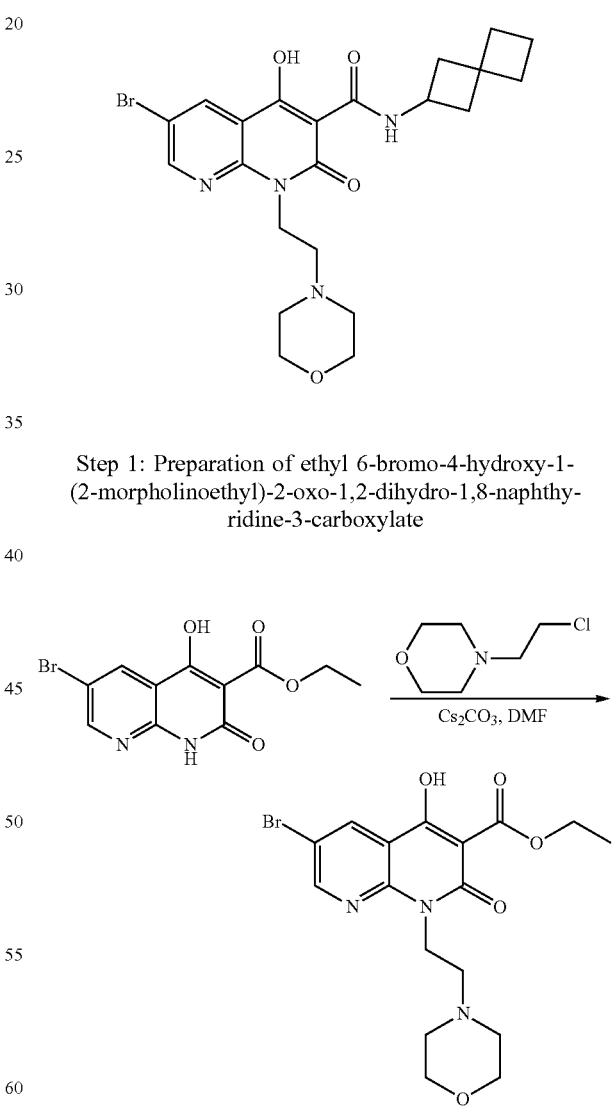

Step 1: Preparation of ethyl 6-bromo-4-hydroxy-1-(2-morpholinoethyl)-2-oxo-1,2-dihydro-1,8-naphthyridine-3-carboxylate Method A: To a solution of ethyl 6-bromo-4-hydroxy-2-oxo-1H-1,8-naphthyridine-3-carboxylate (900 mg, 2.87 mmol, 1 eq) and 4-(2-chloroethyl) morpholine (516.08 mg, 3.45 mmol, 1.2 eq) in DMF (1 mL) was added Cs$_2$CO$_3$ (7.49 g, 23.00 mmol, 8 eq). The mixture was stirred at 50° C. for 12 h. LCMS showed complete consumption of the starting material and formation of a new peak.

The mixture was filtered and concentrated under reduced pressure. The residue was purified by reversed phase HPLC (0.1% HCl condition) to produce ethyl 6-bromo-4-hydroxy-1-(2-morpholinoethyl)-2-oxo-1,2-dihydro-1,8-naphthyridine-3-carboxylate (400 mg) as a yellow solid.

LCMS for product (ESI+): m/z 426.1 [M+H]$^+$, Rt: 0.740 min.

5-95AB-2 min: The column used for chromatography was a Luna-C 18 2.0*30 mm, (3 μm particles). Detection methods are diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-95% B in 2.00 min. 5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min).

Method B: To a mixture of ethyl 6-bromo-4-hydroxy-2-oxo-1H-1,8-naphthyridine-3-carboxylate (1 g, 3.19 mmol, 1 eq) and 4-(2-chloroethyl)morpholine (653.74 mg, 3.51 mmol, 1.1 eq, HCl) in DMF (20 mL) was added Cs$_2$CO$_3$ (8.32 g, 25.55 mmol, 8 eq) under N2. The mixture was stirred at 50° C. for 5 h. LCMS showed complete consumption of the starting material and formation of a new peak. The mixture was purified by prep-HPLC (neutral condition) to produce the desired product (0.85 g) as a yellow solid (used without further purification).

LCMS for product (ESI+): m/z 426.1, 428.1 [M+H]$^+$, Rt: 1.726 min.

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 mL/min.

Step 2: Preparation of 6-bromo-4-hydroxy-1-(2-morpholinoethyl)-2-oxo-N-(spiro[3.3]heptan-2-yl)-1,2-dihydro-1,8-naphthyridine-3-carboxamide

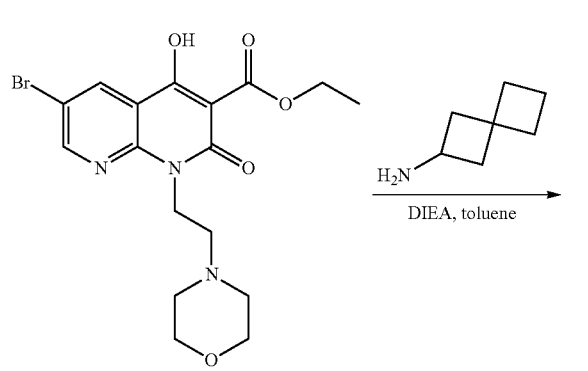

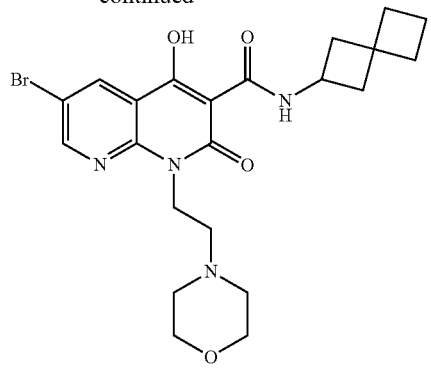

To a solution of ethyl 6-bromo-4-hydroxy-1-(2-morpholinoethyl)-2-oxo-1,8-naphthyridine-3-carboxylate (30 mg, 70.38 μmol, 1 eq) and spiro[3.3]heptan-2-amine (7.83 mg, 70.38 μmol, 1 eq) in toluene (1 mL) was added DIEA (9.10 mg, 70.38 μmol, 12.26 μL, 1 eq). The mixture was stirred at 120° C. for 2 h. LCMS showed complete consumption of the starting material and formation of a new peak.

The mixture was filtered and concentrated under reduced pressure. The residue was purified by prep-HPLC (HCl condition) to produce 6-bromo-4-hydroxy-1-(2-morpholinoethyl)-2-oxo-N-(spiro[3.3]heptan-2-yl)-1,2-dihydro-1,8-naphthyridine-3-carboxamide (6 mg, 12.21 μmol) as a white solid.

$^1$H NMR (400 MHz, CDCl$_3$) δ=13.54-13.39 (m, 1H), 9.88 (br d, J=6.4 Hz, 1H), 8.62 (br s, 1H), 8.51 (s, 1H), 4.89 (br s, 2H), 4.36-4.20 (m, 3H), 3.94 (br d, J=11.5 Hz, 2H), 3.64 (br s, 2H), 3.27 (br s, 2H), 2.93 (br d, J=1.4 Hz, 2H), 2.49-2.40 (m, 2H), 2.05-1.99 (m, 2H), 1.98-1.88 (m, 4H), 1.84-1.74 (m, 2H). LCMS for product (ESI+): m/z 491.1, 493.1 [M+H]$^+$, Rt: 2.440 min.

LCMS Method 5-95AB-6 min-220-254-ELSD: The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 5—Synthesis of 6-(4-fluorophenyl)-4-hydroxy-N-(4-methylcyclohexyl)-1-(2-morpholinoethyl)-2-oxo-1,2-dihydro-1,8-naphthyridine-3-carboxamide (Compound 5)

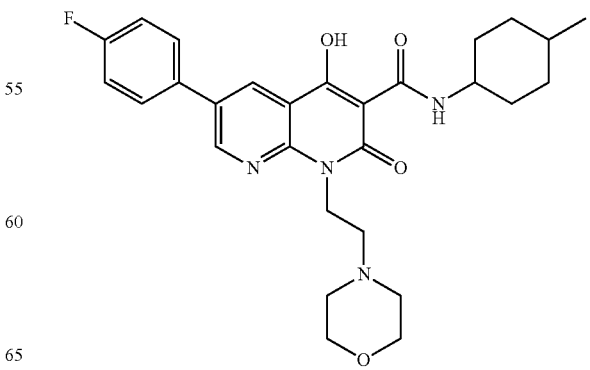

Step 1: Preparation of ethyl 6-(4-fluorophenyl)-4-hydroxy-1-(2-morpholinoethyl)-2-oxo-1,2-dihydro-1,8-naphthyridine-3-carboxylate

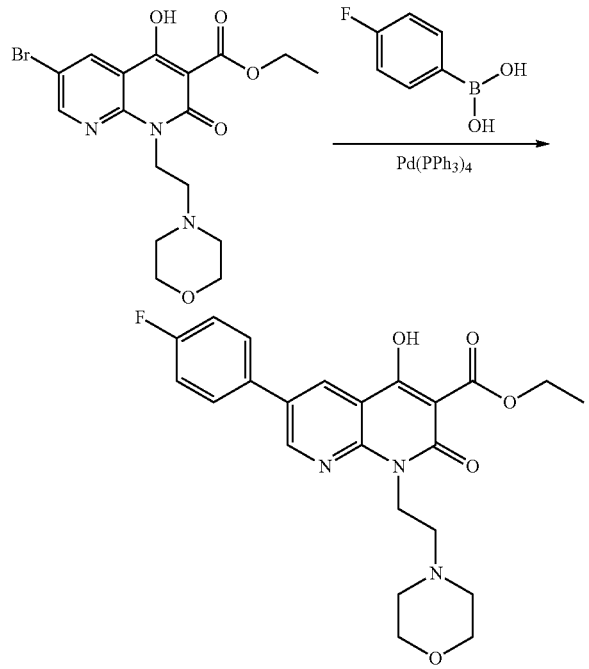

To a mixture of ethyl 6-bromo-4-hydroxy-1-(2-morpholinoethyl)-2-oxo-1,2-dihydro-1,8-naphthyridine-3-carboxylate (200 mg, 469.20 μmol, 1 eq), K$_2$CO$_3$ (194.54 mg, 1.41 mmol, 3 eq) and (4-fluorophenyl)boronic acid (78.78 mg, 563.04 μmol, 1.2 eq) in dioxane (0.2 mL) and H$_2$O (0.02 mL) was added Pd(PPh$_3$)$_4$ (54.22 mg, 46.92 μmol, 0.1 eq) under N2. The mixture was stirred at 100° C. for 1 h. LCMS showed complete consumption of the starting material and formation of a new peak.

The mixture was filtered was the filtrate was purified by prep-HPLC (column: Luna Omega 5u Polar C18 100A; mobile phase: [water (0.04% HCl)-ACN]; B %: 25%-55%, 7 min) to produce ethyl 6-(4-fluorophenyl)-4-hydroxy-1-(2-morpholinoethyl)-2-oxo-1,2-dihydro-1,8-naphthyridine-3-carboxylate (110 mg, 249.18 μmol) as a white solid.

$^1$H NMR (400 MHz, CDCl$_3$) δ=13.37-13.13 (m, 1H), 8.89 (d, J=2.1 Hz, 1H), 8.59 (d, J=2.1 Hz, 1H), 7.60 (dd, J=5.2, 8.6 Hz, 2H), 7.23-7.19 (m, 2H), 5.07-4.98 (m, 2H), 4.61-4.49 (m, 2H), 4.36 (br t, J=12.0 Hz, 2H), 4.07-3.94 (m, 2H), 3.76 (br d, J=11.6 Hz, 2H), 3.43 (br s, 2H), 3.11-2.95 (m, 2H), 1.50 (t, J=7.1 Hz, 3H). LCMS for product (ESI+): m/z 442.3 [M+H]$^+$, Rt: 1.877 min.

5-95AB: The column used for chromatography was a HALO AQ-C18 2.1*30 mm, (2.7 m particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 mL/min.

Step 2: Preparation of 6-(4-fluorophenyl)-4-hydroxy-N-(4-methylcyclohexyl)-1-(2-morpholinoethyl-2-oxo-1,2-dihydro-1,8-naphthyridine-3-carboxamide

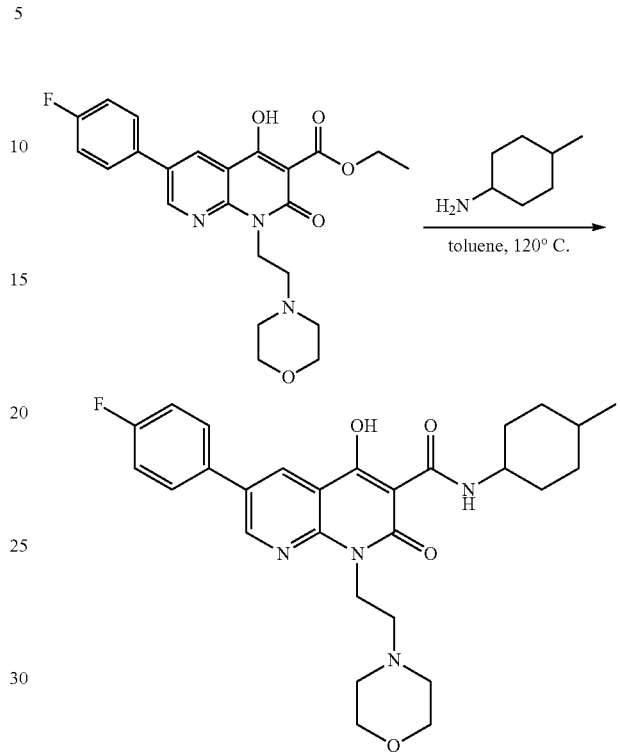

To a mixture of ethyl 6-(4-fluorophenyl)-4-hydroxy-1-(2-morpholinoethyl)-2-oxo-1,2-dihydro-1,8-naphthyridine-3-carboxylate (20 mg, 45.31 μmol, 1 eq) and 4-methylcyclohexanamine (6.15 mg, 54.37 μmol, 7.20 μL, 1.2 eq) in toluene (0.5 mL) was added DIEA (5.86 mg, 45.31 μmol, 7.89 μL, 1 eq). The mixture stirred at 120° C. for 1 h. LCMS showed complete consumption of the starting material and formation of a new peak.

The mixture was filtered and concentrated under reduced pressure. The residue was triturated in MeOH (0.3 mL) and filtered to produce 6-(4-fluorophenyl)-4-hydroxy-N-(4-methylcyclohexyl)-1-(2-morpholinoethyl)-2-oxo-1,2-dihydro-1,8-naphthyridine-3-carboxamide (11.1 mg, 21.83 μmol) as a white solid.

$^1$H NMR (400 MHz, CDCl$_3$) δ=10.57-10.10 (m, 1H), 8.88 (d, J=2.5 Hz, 1H), 8.60 (d, J=2.5 Hz, 1H), 7.68-7.58 (m, 2H), 7.21 (t, J=8.5 Hz, 2H), 4.72-4.65 (m, 2H), 4.28-3.81 (m, 1H), 3.71 (br d, J=4.0 Hz, 4H), 2.77-2.55 (m, 6H), 2.12-1.58 (m, 5H), 1.46-1.04 (m, 4H), 1.01-0.92 (m, 3H). LCMS for product (ESI-): m/z 509.3 [M+H]$^+$, Rt: 2.818 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization. MS range was 100-1000.

Example 6—Synthesis of 6-(4-fluorophenyl)-4-hydroxy-1-(2-morpholinoethyl)-2-oxo-N-(spiro[3.3]heptan-2-yl)-1,2-dihydro-1,8-naphthyridine-3-carboxamide (Compound 6)

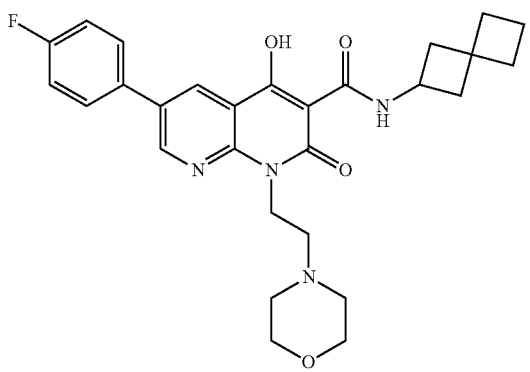 [SMILES: O=C(NC1CC2(CCC2)C1)c1c(O)c2cc(-c3ccc(F)cc3)cnc2n(CCN2CCOCC2)c1=O]

Preparation of 6-(4-fluorophenyl)-4-hydroxy-1-(2-morpholinoethyl)-2-oxo-N-(spiro[3.3]heptan-2-yl)-1,2-dihydro-1,8-naphthyridine-3-carboxamide

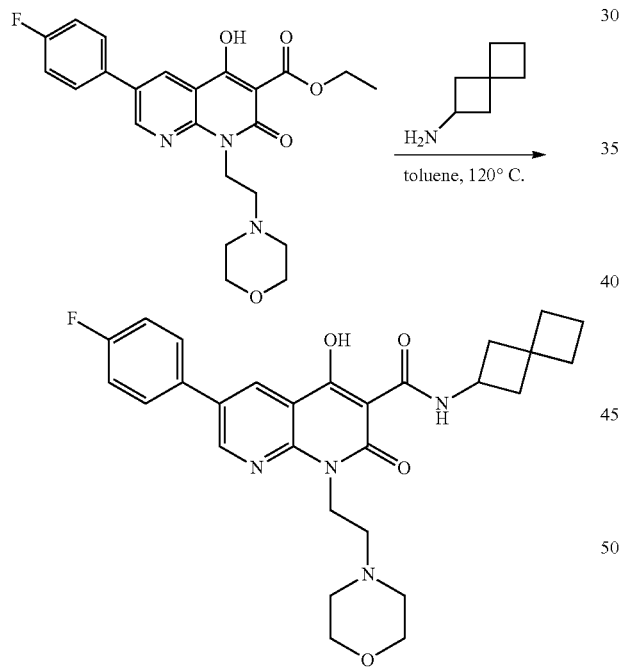

To a mixture of ethyl 6-(4-fluorophenyl)-4-hydroxy-1-(2-morpholinoethyl)-2-oxo-1,8-naphthyridine-3-carboxylate (50 mg, 113.26 μmol, 1 eq) and spiro[3.3]heptan-2-amine (20.07 mg, 135.92 μmol, 1.2 eq, HCl) in toluene (0.5 mL) was added DIEA (14.64 mg, 113.26 μmol, 19.73 μL, 1 eq) at 20° C. The mixture was stirred at 120° C. for 1 h. LCMS showed complete consumption of the starting material and formation of a new peak.

The mixture was filtered, concentrated and the residue was triturated in MeOH (0.5 mL) and filtered to yield 6-(4-fluorophenyl)-4-hydroxy-1-(2-morpholinoethyl)-2-oxo-N-(spiro[3.3]heptan-2-yl)-1,2-dihydro-1,8-naphthyridine-3-carboxamide (27.3 mg, 53.30 μmol) as a white solid.

$^1$H NMR (400 MHz, CDCl$_3$) δ=10.31 (br d, J=8.5 Hz, 1H), 8.88 (d, J=2.0 Hz, 1H), 8.59 (d, J=2.0 Hz, 1H), 7.62 (dd, J=5.3, 8.8 Hz, 2H), 7.23-7.17 (m, 2H), 4.69 (br t, J=7.0 Hz, 2H), 4.46-4.34 (m, 1H), 3.71 (br s, 4H), 2.78-2.56 (m, 6H), 2.55-2.48 (m, 2H), 2.14-1.95 (m, 6H), 1.92-1.82 (m, 2H). LCMS for product (ESI+): m/z 507.3 [M+H]$^+$, Rt: 2.603 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 7—Synthesis of N-(4,4-difluorocyclohexyl)-6-(4-fluorophenyl)-4-hydroxy-1-(2-morpholinoethyl)-2-oxo-1,2-dihydro-1,8-naphthyridine-3-carboxamide (Compound 7)

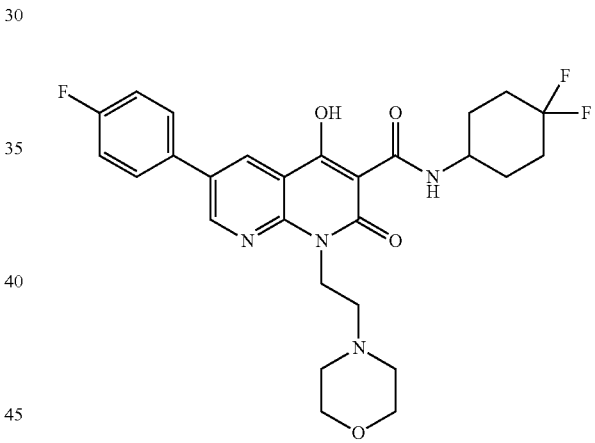

Preparation of N-(4,4-difluorocyclohexyl)-6-(4-fluorophenyl)-4-hydroxy-1-(2-morpholinoethyl)-2-oxo-1,2-dihydro-1,8-naphthyridine-3-carboxamide

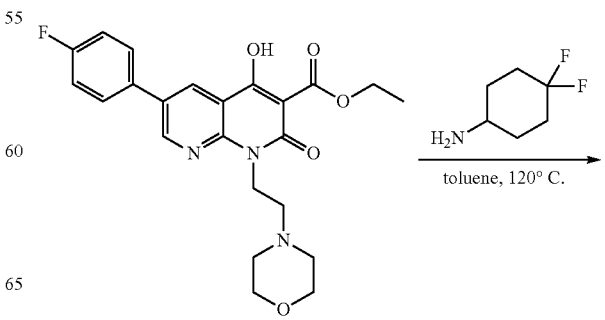

193
-continued

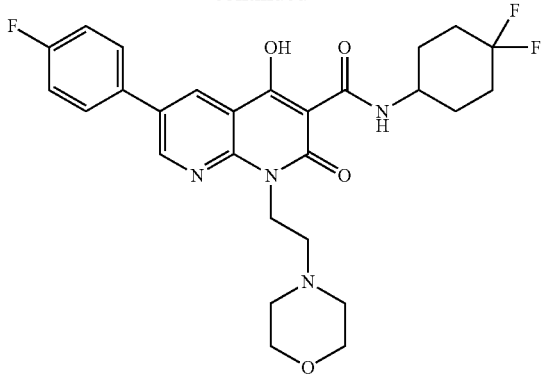 [SMILES: O=C(NC1CCC(F)(F)CC1)c1c(O)c2cc(-c3ccc(F)cc3)cnc2n(CCN2CCOCC2)c1=O]

To a mixture of ethyl 6-(4-fluorophenyl)-4-hydroxy-1-(2-morpholinoethyl)-2-oxo-1,8-naphthyridine-3-carboxylate (5 mg, 11.33 μmol, 1 eq) and 4,4-Difluorocyclohexanamine (2.33 mg, 13.59 μmol, 1.2 eq, HCl) in toluene (0.2 mL) was added DIEA (1.46 mg, 11.33 μmol, 1.97 μL, 1 eq) at 20° C. The mixture was stirred at 120° C. for 1 h. LCMS showed complete consumption of the starting material and formation of a new peak.

The mixture was filtered, concentrated and the residue was purified by prep-HPLC (column: Kromasil C18 (250*50 mm*10 μm); mobile phase: [water (10 mM NH$_4$HCO$_3$)-ACN]; B %: 60%-85%, 10 min) to produce N-(4,4-difluorocyclohexyl)-6-(4-fluorophenyl)-4-hydroxy-1-(2-morpholinoethyl)-2-oxo-1,2-dihydro-1,8-naphthyridine-3-carboxamide (6.1 mg, 11.47 μmol) as a white solid.

$^1$H NMR (400 MHz, CDCl$_3$) δ=10.38 (br d, J=8.0 Hz, 1H), 8.90 (d, J=2.0 Hz, 1H), 8.60 (d, J=2.0 Hz, 1H), 7.63 (dd, J=5.0, 8.5 Hz, 2H), 7.22 (br t, J=8.5 Hz, 2H), 4.68 (br t, J=7.3 Hz, 2H), 4.17-4.05 (m, 1H), 3.71 (br t, J=4.3 Hz, 4H), 2.71 (br t, J=7.3 Hz, 2H), 2.63 (br s, 4H), 2.23-2.06 (m, 4H), 2.03-1.76 (m, 4H). LCMS for product (ESI+): m/z 531.3 [M+H]$^+$, Rt: 2.429 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 8—Synthesis of N-(bicyclo[1.1.1]pentan-1-yl)-6-(4-fluorophenyl)-4-hydroxy-1-(2-morpholinoethyl)-2-oxo-1,2-dihydro-1,8-naphthyridine-3-carboxamide (Compound 8)

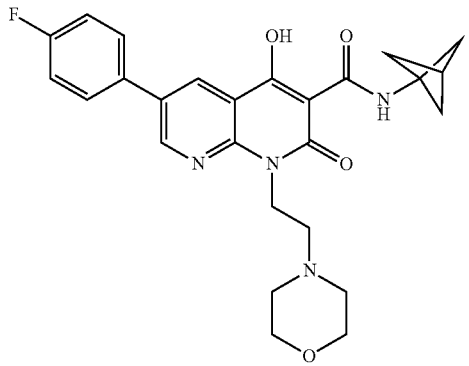 [SMILES: O=C(NC12CC(C1)C2)c1c(O)c2cc(-c3ccc(F)cc3)cnc2n(CCN2CCOCC2)c1=O]

194

Preparation of N-(bicyclo[1.1.1]pentan-1-yl)-6-(4-fluorophenyl)-4-hydroxy-1-(2-morpholinoethyl)-2-oxo-1,2-dihydro-1,8-naphthyridine-3-carboxamide

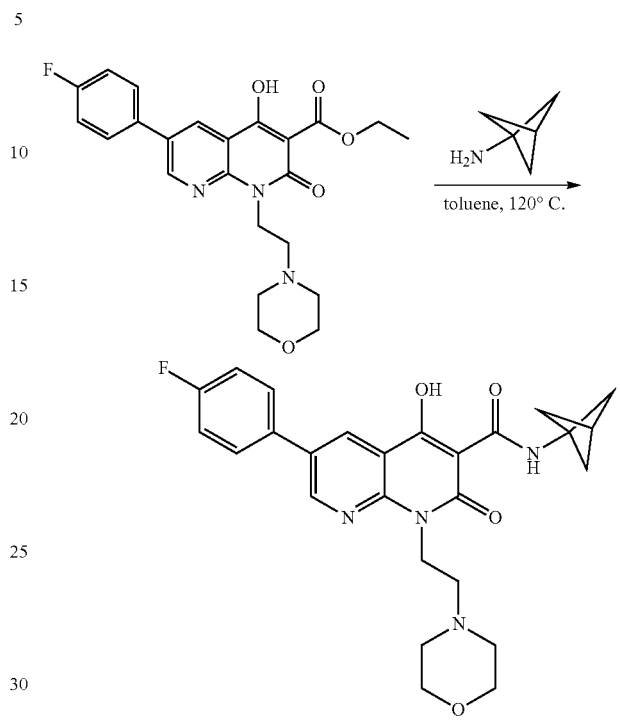

To a mixture of ethyl 6-(4-fluorophenyl)-4-hydroxy-1-(2-morpholinoethyl)-2-oxo-1,8-naphthyridine-3-carboxylate (5 mg, 11.33 μmol, 1 eq) and [1.1.1]pentan-1-amine HCl (1.63 mg, 13.59 μmol, 1.2 eq, HCl) in toluene (0.3 mL) was added DIEA (1.46 mg, 11.33 μmol, 1.97 μL, 1 eq) at 20° C. The mixture was stirred at 120° C. for 1 h. LCMS showed complete consumption of the starting material and formation of a new peak.

The mixture was filtered, concentrated and the residue was triturated in MeOH (0.5 mL) and filtered to produce N-(bicyclo[1.1.1]pentan-1-yl)-6-(4-fluorophenyl)-4-hydroxy-1-(2-morpholinoethyl)-2-oxo-1,2-dihydro-1,8-naphthyridine-3-carboxamide (7.2 mg, 14.99 μmol) was obtained as a white solid.

$^1$H NMR (400 MHz, CDCl$_3$) δ=10.51 (br s, 1H), 8.89 (d, J=2.0 Hz, 1H), 8.60 (d, J=2.5 Hz, 1H), 7.63 (dd, J=5.0, 8.5 Hz, 2H), 7.21 (t, J=8.8 Hz, 2H), 4.68 (br t, J=7.0 Hz, 2H), 3.71 (br t, J=4.3 Hz, 4H), 2.70 (br t, J=7.0 Hz, 2H), 2.63 (br s, 4H), 2.54 (s, 1H), 2.23 (s, 6H). LCMS for product (ESI+): m/z 479.2 [M+H]$^+$, Rt: 2.444 min.

LCMS Method:

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 9—Synthesis of 6-(4-fluorophenyl)-N-(1-(4-fluorophenyl)ethyl)-4-hydroxy-1-(2-morpholinoethyl)-2-oxo-1,2-dihydro-1,8-naphthyridine-3-carboxamide (Compound 9)

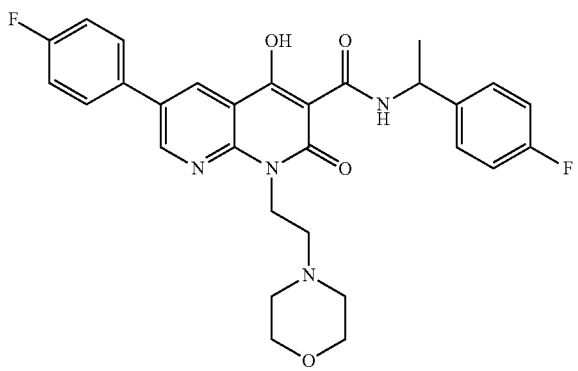 [SMILES: CC(NC(=O)c1c(O)c2cc(-c3ccc(F)cc3)cnc2n(CCN2CCOCC2)c1=O)c1ccc(F)cc1]

Preparation of 6-(4-fluorophenyl)-N-(1-(4-fluorophenyl)ethyl)-4-hydroxy-1-(2-morpholinoethyl)-2-oxo-1,2-dihydro-1,8-naphthyridine-3-carboxamide

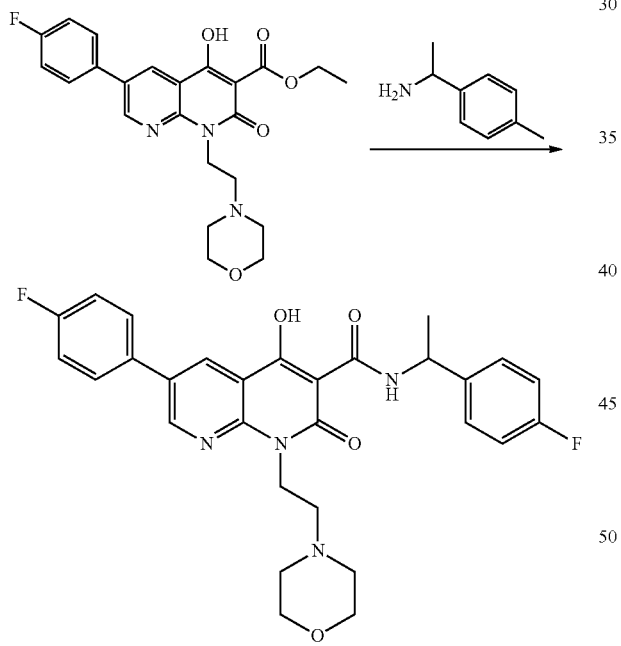

To a mixture of ethyl 6-(4-fluorophenyl)-4-hydroxy-1-(2-morpholinoethyl)-2-oxo-1,8-naphthyridine-3-carboxylate (39 mg, 88.34 μmol, 1 eq) and 1-(4-fluorophenyl)ethanamine (14.75 mg, 106.01 μmol, 13.92 μL, 1.2 eq) in toluene (1 mL) was added DIEA (11.42 mg, 88.34 μmol, 15.39 μL, 1 eq). The mixture was stirred at 120° C. for 1 h. LCMS showed complete consumption of the starting material and formation of a new peak.

The mixture was filtered and concentrated under reduced pressure and the residue was purified using HPLC (neutral condition) to produce 6-(4-fluorophenyl)-N-(1-(4-fluorophenyl)ethyl)-4-hydroxy-1-(2-morpholinoethyl)-2-oxo-1,2-dihydro-1,8-naphthyridine-3-carboxamide (15.8 mg, 28.97 μmol) as a white solid.

$^1$H NMR (400 MHz, CDCl$_3$) δ=10.69-10.62 (m, 1H), 8.89 (d, J=2.4 Hz, 1H), 8.59 (d, J=2.1 Hz, 1H), 7.67-7.58 (m, 2H), 7.39 (dd, J=5.4, 8.6 Hz, 2H), 7.23-7.19 (m, 2H), 7.06 (br t, J=8.6 Hz, 2H), 5.26 (quin, J=7.1 Hz, 1H), 4.72-4.65 (m, 2H), 3.70 (br t, J=4.4 Hz, 4H), 2.76-2.68 (m, 2H), 2.63 (br s, 4H), 1.63 (d, J=6.9 Hz, 3H). LCMS for product (ESI+): m/z 535.2 [M+H]$^+$, Rt: 2.510 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 10—Synthesis of 4-hydroxy-6-(4-methoxyphenyl)-1-(2-morpholinoethyl)-2-oxo-N-(spiro[3.3]heptan-2-yl)-1,2-dihydro-1,8-naphthyridine-3-carboxamide (Compound 10)

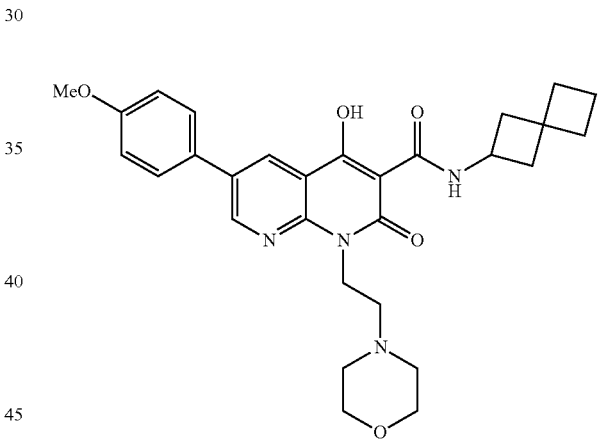

Step 1: Preparation of ethyl 4-hydroxy-6-(4-methoxyphenyl)-1-(2-morpholinoethyl)-2-oxo-1,2-dihydro-1,8-naphthyridine-3-carboxylate

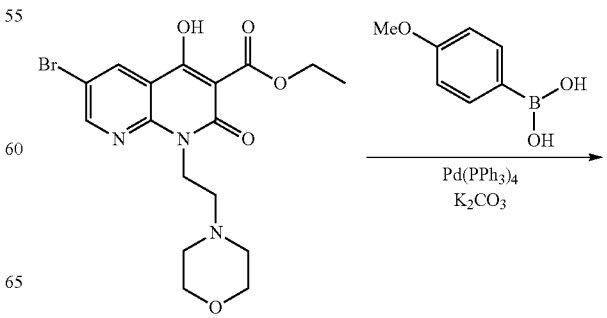

197

-continued

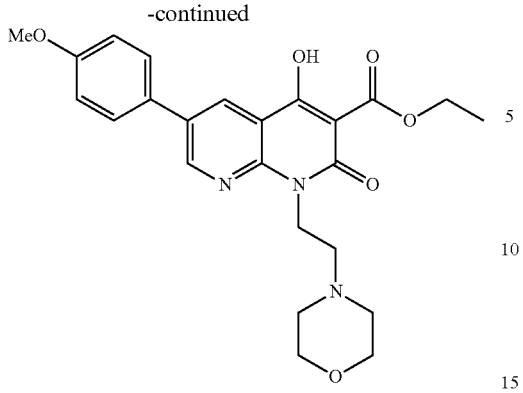

To a mixture of ethyl 6-bromo-4-hydroxy-1-(2-morpholinoethyl)-2-oxo-1,8-naphthyridine-3-carboxylate (100 mg, 234.60 µmol, 1 eq), K₂CO₃ (97.27 mg, 703.79 µmol, 3 eq) and (4-methoxyphenyl)boronic acid (53.47 mg, 351.90 µmol, 1.5 eq) in dioxane (10 mL) and H₂O (1 mL) was added Pd(PPh₃)₄ (27.11 mg, 23.46 µmol, 0.1 eq) under N2. The mixture was stirred at 100° C. for 1 h. LCMS showed complete consumption of the starting material and formation of a new peak.

The mixture was filtered, concentrated and the residue was purified by prep-HPLC (column: Welch Xtimate C18 150*25 mm*5 µm; mobile phase: [water (0.04% HCl)-ACN]; B %: 15%-35%, 10 min) to produce ethyl 4-hydroxy-6-(4-methoxyphenyl)-1-(2-morpholinoethyl)-2-oxo-1,2-dihydro-1,8-naphthyridine-3-carboxylate (15 mg, 33.08 µmol) as a yellow solid.

$^1$H NMR (400 MHz, CDCl₃) δ=14.45 (s, 1H), 8.91 (d, J=1.9 Hz, 1H), 8.58 (d, J=1.9 Hz, 1H), 7.57 (d, J=8.6 Hz, 2H), 7.05 (d, J=8.6 Hz, 2H), 5.02 (br t, J=6.3 Hz, 2H), 4.55 (q, J=7.0 Hz, 2H), 4.37 (br t, J=12.1 Hz, 2H), 4.00 (br d, J=11.9 Hz, 2H), 3.89 (s, 3H), 3.74 (br d, J=11.3 Hz, 2H), 3.41 (br s, 2H), 3.05 (br d, J=9.6 Hz, 2H), 1.54-1.43 (m, 3H).

Step 2: Preparation of 4-hydroxy-6-(4-methoxyphenyl)-1-(2-morpholinoethyl)-2-oxo-N-(spiro[3.3]heptan-2-yl)-1,2-dihydro-1,8-naphthyridine-3-carboxamide

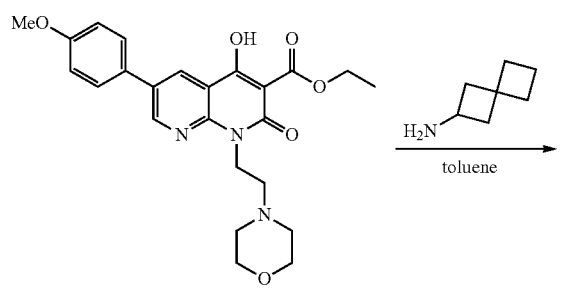

198

-continued

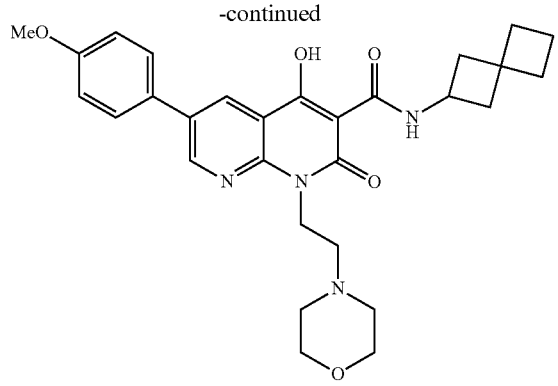

To a mixture of ethyl 4-hydroxy-6-(4-methoxyphenyl)-1-(2-morpholinoethyl)-2-oxo-1,8-naphthyridine-3-carboxylate (15 mg, 33.08 µmol, 1 eq) and spiro[3.3]heptan-2-amine (5.86 mg, 39.69 µmol, 1.2 eq, HCl) in toluene (1 mL) was added DIEA (4.27 mg, 33.08 µmol, 5.76 µL, 1 eq) at 20° C. The mixture was stirred at 120° C. for 1 h. LCMS showed complete consumption of the starting material and formation of a new peak.

The mixture was filtered, concentrated and the residue was triturated in MeOH and filtered (0.5 mL) and filtered to produce-hydroxy-6-(4-methoxyphenyl)-1-(2-morpholinoethyl)-2-oxo-N-(spiro[3.3]heptan-2-yl)-1,2-dihydro-1,8-naphthyridine-3-carboxamide (10.4 mg, 20.05 µmol) as a white solid.

$^1$H NMR (400 MHz, CDCl₃) δ=10.34 (br d, J=7.6 Hz, 1H), 8.90 (d, J=2.5 Hz, 1H), 8.59 (d, J=2.5 Hz, 1H), 7.59 (d, J=8.6 Hz, 2H), 7.05 (d, J=8.6 Hz, 2H), 4.73-4.62 (m, 2H), 4.40 (sxt, J=8.0 Hz, 1H), 3.89 (s, 3H), 3.76-3.66 (m, 4H), 2.75-2.68 (m, 2H), 2.64 (br s, 4H), 2.56-2.48 (m, 2H), 2.14-1.95 (m, 6H), 1.91-1.82 (m, 2H). LCMS for product (ESI+): m/z 519.3 [M+H]⁺, Rt: 2.570 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH₄HCO₃, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 11—Synthesis of 6-(4-chlorophenyl)-4-hydroxy-1-(2-morpholinoethyl)-2-oxo-N-(spiro[3.3]heptan-2-yl)-1,2-dihydro-1,8-naphthyridine-3-carboxamide (Compound 11)

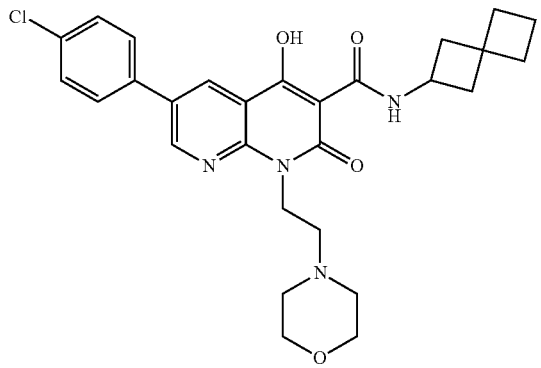 [SMILES: O=C(NC1CC2(CCC2)C1)c1c(O)c2cc(-c3ccc(Cl)cc3)cnc2n(CCN2CCOCC2)c1=O]

Step 1: Preparation of ethyl 6-(4-chlorophenyl)-4-hydroxy-1-(2-morpholinoethyl)-2-oxo-1,2-dihydro-1,8-naphthyridine-3-carboxylate

Step 2: Preparation of 6-(4-chlorophenyl)-4-hydroxy-1-(2-morpholinoethyl)-2-oxo-N-(spiro[3.3]heptan-2-yl)-1,2-dihydro-1,8-naphthyridine-3-carboxamide

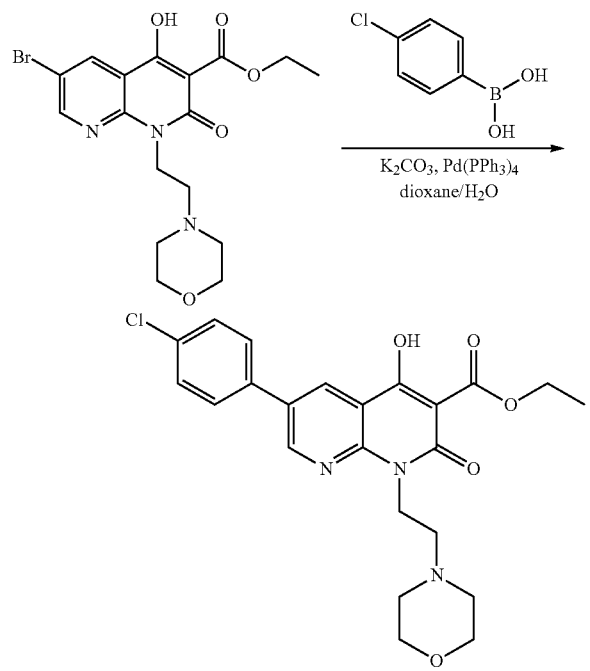

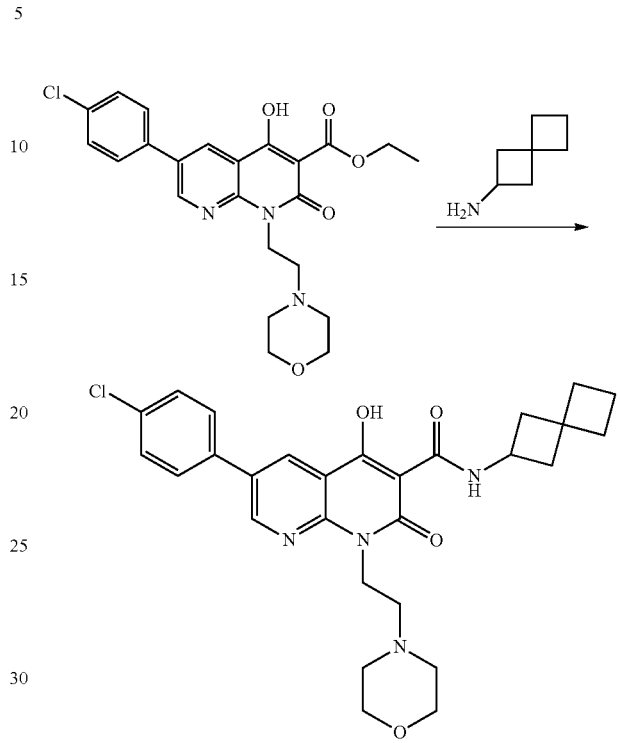

To a mixture of ethyl 6-bromo-4-hydroxy-1-(2-morpholinoethyl)-2-oxo-1,8-naphthyridine-3-carboxylate (100 mg, 234.60 μmol, 1 eq), $K_2CO_3$ (97.27 mg, 703.79 μmol, 3 eq) and (4-chlorophenyl)boronic acid (44.02 mg, 281.52 μmol, 1.2 eq) in dioxane (1 mL) and $H_2O$ (0.1 mL) was added $Pd(PPh_3)_4$ (27.11 mg, 23.46 μmol, 0.1 eq) under $N_2$. The mixture was stirred at 100° C. for 1 h. LCMS showed complete consumption of the starting material and formation of a new peak.

The mixture was filtered, concentrated under reduced pressure and the residue was purified by prep-HPLC (column: Welch Xtimate C18 150*25 mm*5 μm; mobile phase: [water (0.04% HCl)-ACN]; B %: 25%-45%, 10 min) to produce the desired product (33 mg) as a white solid (used without further purification).

LCMS for product (ESI+): m/z 458.2 $[M+H]^+$, Rt: 1.583 min.

LCMS Method

The column used for chromatography was a HALO AQ-C18 2.1*30 mm, (2.7 m particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

To a mixture of ethyl 6-(4-chlorophenyl)-4-hydroxy-1-(2-morpholinoethyl)-2-oxo-1,8-naphthyridine-3-carboxylate (32 mg, 69.88 μmol, 1 eq) and spiro[3.3]heptan-2-amine (12.38 mg, 83.86 μmol, 1.2 eq, HCl) in toluene (1 mL) was added DIEA (9.03 mg, 69.88 μmol, 12.17 μL, 1 eq). The mixture was stirred at 120° C. for 1 h. TLC showed completion of the reaction and formation of a new spot.

The mixture was filtered, concentrated under reduced and the residue was triturated in MeOH (0.5 mL) and filtered to produce the desired product (10.4 mg, 19.49 μmol) as a white solid.

$^1$H NMR (400 MHz, $CDCl_3$) δ=10.34-10.27 (m, 1H), 8.90 (d, J=2.3 Hz, 1H), 8.61 (d, J=2.4 Hz, 1H), 7.59 (d, J=8.6 Hz, 2H), 7.49 (br d, J=8.3 Hz, 2H), 4.70-4.65 (m, 2H), 4.45-4.36 (m, 1H), 3.75-3.67 (m, 4H), 2.75-2.68 (m, 2H), 2.63 (br s, 4H), 2.56-2.49 (m, 2H), 2.12-1.96 (m, 6H), 1.92-1.82 (m, 2H). LCMS for product (ESI+): m/z 523.2 $[M+H]^+$, Rt: 2.711 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 12—Synthesis of N-(bicyclo[1.1.1]pentan-1-yl)-6-(4-(difluoromethoxy)phenyl)-4-hydroxy-1-(2-morpholinoethyl)-2-oxo-1,2-dihydro-1,8-naphthyridine-3-carboxamide (Compound 12)

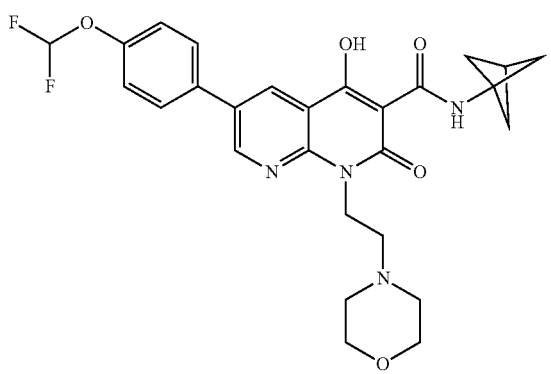 [SMILES: O=C(NC12CC(C1)C2)c1c(O)c2cc(-c3ccc(OC(F)F)cc3)cnc2n(CCN2CCOCC2)c1=O]

Step 1: Preparation of N-(bicyclo[1.1.1]pentan-1-yl)-6-bromo-4-hydroxy-1-(2-morpholinoethyl)-2-oxo-1,2-dihydro-1,8-naphthyridine-3-carboxamide

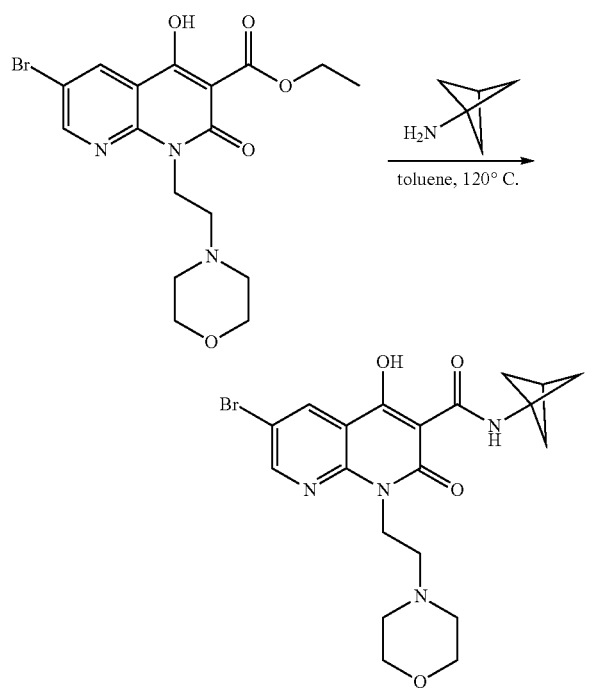

To a solution of ethyl 6-bromo-4-hydroxy-1-(2-morpholinoethyl)-2-oxo-1,8-naphthyridine-3-carboxylate (200 mg, 469.20 μmol, 1 eq) and bicyclo[1.1.1]pentan-3-amine (61.72 mg, 516.12 μmol, 1.1 eq, HCl) in toluene (1 mL) was added DIEA (60.64 mg, 469.20 μmol, 81.73 μL, 1 eq). The mixture was stirred at 120° C. for 12 h. LCMS showed complete consumption of the starting material and formation of a new peak.

The mixture was concentrated to produce N-(bicyclo[1.1.1]pentan-1-yl)-6-bromo-4-hydroxy-1-(2-morpholinoethyl)-2-oxo-1,2-dihydro-1,8-naphthyridine-3-carboxamide (240 mg) as a brownness solid (used without further purification).

LCMS for product (ESI+): m/z 465.3, 463.3 [M+H]$^+$, Rt: 0.687 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 2: Preparation of N-(bicyclo[1.1.1]pentan-1-yl)-6-(4-(difluoromethoxy)phenyl)-4-hydroxy-1-(2-morpholinoethyl)-2-oxo-1,2-dihydro-1,8-naphthyridine-3-carboxamide

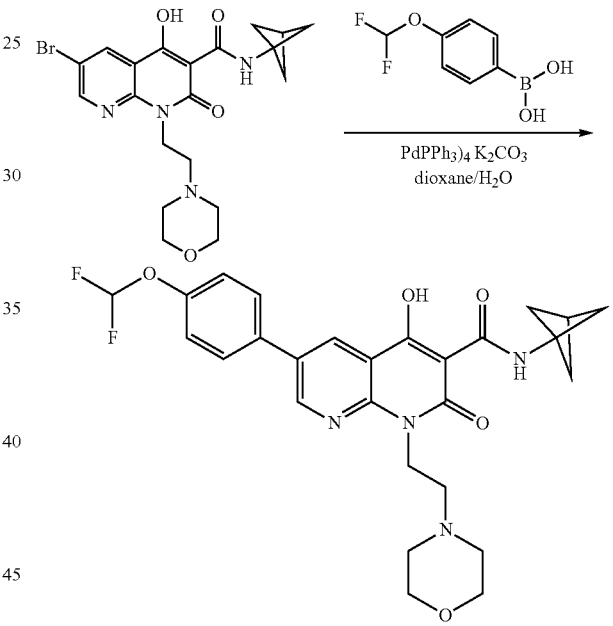

To a solution of N-(3-bicyclo[1.1.1]pentanyl)-6-bromo-4-hydroxy-1-(2-morpholinoethyl)-2-oxo-1,8-naphthyridine-3-carboxamide (120 mg, 259.00 μmol, 1 eq) and [4-(difluoromethoxy)phenyl]boronic acid (58.41 mg, 310.80 μmol, 1.2 eq) in dioxane (1 mL) and H$_2$O (0.25 mL) was added K$_2$CO$_3$ (107.39 mg, 776.99 μmol, 3 eq) and Pd(PPh$_3$)$_4$ (29.93 mg, 25.90 μmol, 0.1 eq). The mixture was stirred at 80° C. for 2 h under N2. LCMS showed complete consumption of the starting material and formation of a new peak.

The mixture was concentrated, and the residue was purified by prep-HPLC (neutral condition; column: mobile phase: [water (10 mM NH$_4$HCO$_3$)-ACN]; B %: 75%-95%, 10 min) to produce N-(bicyclo[1.1.1]pentan-1-yl)-6-(4-(difluoromethoxy)phenyl)-4-hydroxy-1-(2-morpholinoethyl)-2-oxo-1,2-dihydro-1,8-naphthyridine-3-carboxamide (21.2 mg, 40.26 μmol) as a white solid.

$^1$H NMR (400 MHz, CDCl$_3$) δ=10.51 (br s, 1H), 8.90 (d, J=2.1 Hz, 1H), 8.61 (d, J=2.1 Hz, 1H), 7.66 (br d, J=8.6 Hz, 2H), 7.31-7.28 (m, 2H), 6.83-6.34 (m, 1H), 4.68 (br t, J=6.9

Hz, 2H), 3.72 (br d, J=3.5 Hz, 4H), 2.73-2.52 (m, 7H), 2.23 (s, 6H). LCMS for product (ESI+): m/z 527.2 [M+H]$^+$, Rt: 3.692 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was Acetonitrile. The column used for chromatography was a Xbridge Shield RP18 2.1*50 mm column (5 um particles). Detection methods are diode array (DAD) as well as positive electrospray ionization.

Example 13—Synthesis of N-(bicyclo[1.1.1]pentan-1-yl)-4-hydroxy-6-(4-methoxyphenyl)-1-(2-morpholinoethyl)-2-oxo-1,2-dihydro-1,8-naphthyridine-3-carboxamide (Compound 13)

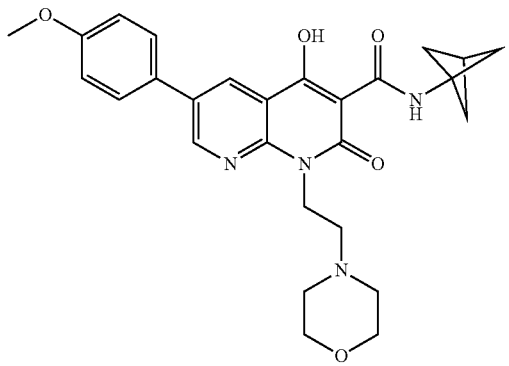 [SMILES: COc1ccc(-c2cnc3c(c2)c(O)c(C(=O)NC24CC(C2)C4)c(=O)n3CCN2CCOCC2)cc1]

Preparation of N-(bicyclo[1.1.1]pentan-1-yl)-4-hydroxy-6-(4-methoxyphenyl)-1-(2-morpholinoethyl)-2-oxo-1,2-dihydro-1,8-naphthyridine-3-carboxamide

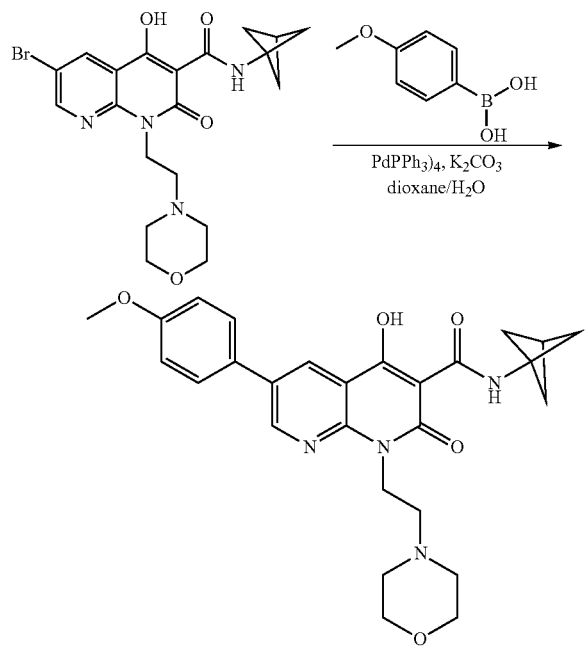

To a solution of N-(3-bicyclo[1.1.1]pentanyl)-6-bromo-4-hydroxy-1-(2-morpholinoethyl)-2-oxo-1,8-naphthyridine-3-carboxamide (60 mg, 129.50 μmol, 1 eq) and (4-methoxyphenyl)boronic acid (23.61 mg, 155.40 μmol, 1.2 eq) in dioxane (1 mL) and H$_2$O (0.25 mL) was added K$_2$CO$_3$ (53.69 mg, 388.50 μmol, 3 eq) and Pd(PPh$_3$)$_4$ (14.96 mg, 12.95 μmol, 0.1 eq). The mixture was stirred at 80° C. for 2 h under N$_2$. LCMS showed complete consumption of the starting material and formation of a new peak.

The mixture was concentrated, and the residue was purified by prep-HPLC (neutral condition) to produce the desired product (7 mg, 14.27 μmol) as a white solid.

$^1$H NMR (400 MHz, CDCl$_3$) δ=10.53 (br s, 1H), 8.89 (br s, 1H), 8.59 (br s, 1H), 7.59 (br d, J=8.3 Hz, 2H), 7.04 (br d, J=8.3 Hz, 2H), 4.68 (br t, J=6.7 Hz, 2H), 3.88 (s, 3H), 3.71 (br s, 4H), 2.86-2.48 (m, 7H), 2.23 (s, 6H). LCMS for product (ESI+): m/z 491.2 [M+H]$^+$, Rt: 3.746 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 um particles). Detection methods are diode array (DAD) as well as positive electrospray ionization.

Example 14—Synthesis of 4-hydroxy-1-(2-morpholinoethyl)-2-oxo-6-phenyl-N-(spiro[3.3]heptan-2-yl)-1,2-dihydro-1,8-naphthyridine-3-carboxamide (Compound 14)

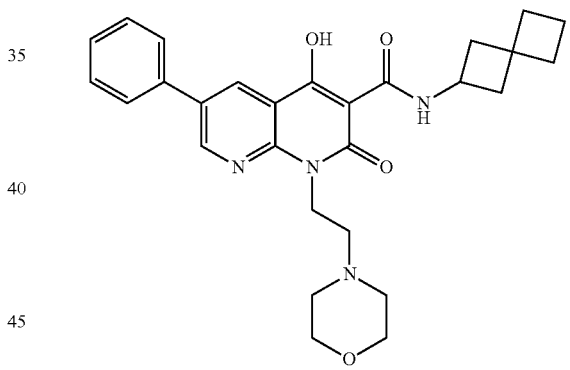

Step 1: Preparation of ethyl 4-hydroxy-1-(2-morpholinoethyl)-2-oxo-6-phenyl-1,2-dihydro-1,8-naphthyridine-3-carboxylate

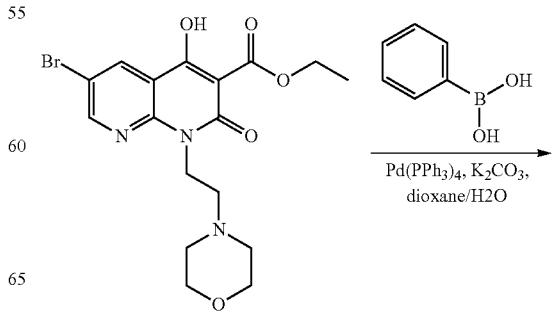

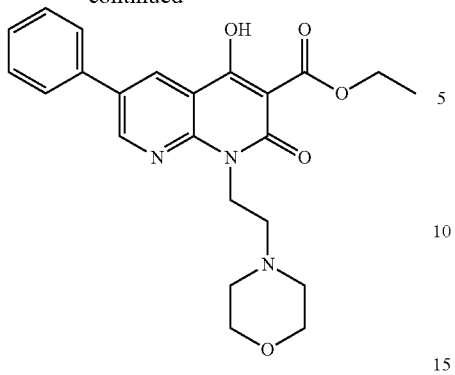

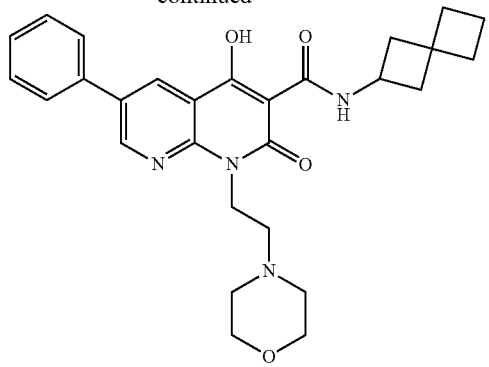

A mixture of ethyl 6-bromo-4-hydroxy-1-(2-morpholino-ethyl)-2-oxo-1,8-naphthyridine-3-carboxylate (200 mg, 469.20 μmol, 1 eq), phenylboronic acid (57.21 mg, 469.20 μmol, 1 eq), K$_2$CO$_3$ (194.54 mg, 1.41 mmol, 3 eq), Pd(PPh$_3$)$_4$ (54.22 mg, 46.92 μmol, 0.1 eq) in water (0.5 mL) and dioxane (2 mL) was degassed and purged with N$_2$ for 3 times, and then the mixture was stirred at 120° C. for 2 h under N$_2$ atmosphere. LCMS showed complete consumption of the starting material and formation of a new peak.

The mixture was filtered, concentrated under reduced pressure and the residue was purified by prep-HPLC (neutral condition) to produce ethyl 4-hydroxy-1-(2-morpholino-ethyl)-2-oxo-6-phenyl-1,2-dihydro-1,8-naphthyridine-3-carboxylate (100 mg, 236.15 μmol) as a white solid.

$^1$H NMR (400 MHz, DMSO-d$_6$) δ=8.89-8.82 (m, 1H), 8.54-8.48 (m, 1H), 8.02 (s, 3H), 7.53 (s, 2H), 4.54-4.44 (m, 2H), 4.21-4.12 (m, 2H), 3.64 (br s, 4H), 2.67 (br d, J=1.8 Hz, 2H), 2.54 (br s, 4H), 1.25 (s, 3H). LCMS for product (ESI+): m/z 426.1 [M+H]$^+$, Rt: 0.740 min.

LCMS Method 5-95AB_2 min: The column used for chromatography was a Luna-C 18 2.0*30 mm, (3 μm particles). Detection methods are diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-95% B in 2.00 min. 5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min).

Step 2: Preparation of 4-hydroxy-1-(2-morpholino-ethyl)-2-oxo-6-phenyl-N-(spiro[3.3]heptan-2-yl)-1,2-dihydro-1,8-naphthyridine-3-carboxamide

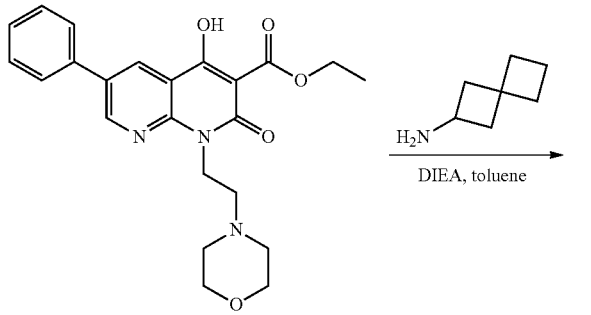

To a solution of spiro[3.3]heptan-2-amine (23.63 mg, 212.53 μmol, 1 eq) and ethyl 4-hydroxy-1-(2-morpholino-ethyl)-2-oxo-6-phenyl-1,8-naphthyridine-3-carboxylate (90 mg, 212.53 μmol, 1 eq) in toluene (1 mL) was added DIEA (54.94 mg, 425.07 μmol, 74.04 μL, 2 eq). The mixture was stirred at 120° C. for 2 h. LCMS showed complete consumption of the starting material and formation of a new peak.

The mixture was filtered, concentrated under reduced pressure and the residue was purified by prep-HPLC (HCl condition) to produce the desired product (21 mg, 42.98 μmol) as a white solid.

$^1$H NMR (400 MHz, CDCl$_3$) δ=13.68-13.57 (m, 1H), 10.08-10.01 (m, 1H), 8.93 (d, J=2.2 Hz, 1H), 8.67 (d, J=2.2 Hz, 1H), 7.65 (d, J=7.5 Hz, 2H), 7.53 (t, J=7.5 Hz, 2H), 7.49-7.42 (m, 1H), 5.10-5.02 (m, 2H), 4.45-4.35 (m, 3H), 4.08-3.98 (m, 2H), 3.77-3.67 (m, 2H), 3.48-3.36 (m, 2H), 3.13-3.00 (m, 2H), 2.57-2.50 (m, 2H), 2.11 (t, J=7.5 Hz, 2H), 2.07-1.99 (m, 4H), 1.91-1.85 (m, 2H). LCMS for product (ESI+): m/z 489.3 [M+H]$^+$, Rt: 2.587 min.

LCMS Method

5_95AB_6 min-220-254-ELSD: The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a kinetex C18 50*2.1 mm column (5 um particles). Detection methods are diode array (DAD) and evaporative light scattering (ELSD) detection as well as positive electrospray ionization.

Example 15—Synthesis of 6-(4-(difluoromethoxy)phenyl)-4-hydroxy-N-(4-methylcyclohexyl)-1-(2-morpholinoethyl)-2-oxo-1,2-dihydro-1,8-naphthyridine-3-carboxamide (Compound 15)

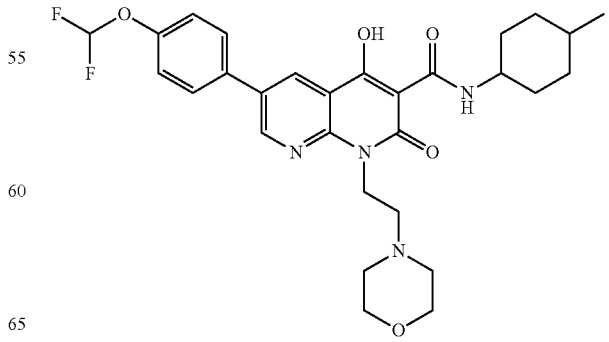

207

Preparation of 1-phenylethyl 2-[[4-(3-isoquinolylmethyl) pyrazolo[1,5-a]pyridine-3-carbonyl]amino]spiro[3.3]heptane-6-carboxylate

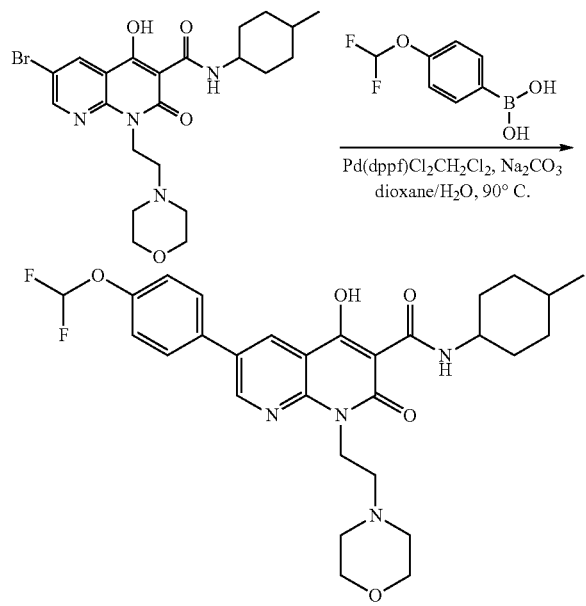

A mixture of 6-bromo-4-hydroxy-N-(4-methylcyclohexyl)-1-(2-morpholinoethyl)-2-oxo-1,8-naphthyridine-3-carboxamide (90 mg, 182.41 μmol, 1 eq), [4-(difluoromethoxy)phenyl]boronic acid (41.14 mg, 218.89 μmol, 1.2 eq), Pd(dppf)Cl$_2$·CH$_2$Cl$_2$ (14.90 mg, 18.24 μmol, 0.1 eq), Na$_2$CO$_3$ (29.00 mg, 273.62 μmol, 1.5 eq) in dioxane (2 mL) and water (0.2 mL) was stirred at 90° C. for 2 h under N$_2$. LCMS showed complete consumption of the starting material and formation of a new peak.

The mixture was concentrated and the residue was purified by prep-HPLC (column: Phenomenex Gemini-NX C18 75*30 mm*3 μm; mobile phase: [water (10 mM NH$_4$HCO$_3$)-ACN]; B %: 70%-90%, 6 min) to produce 1-phenylethyl 2-[[4-(3-isoquinolylmethyl) pyrazolo[1,5-a]pyridine-3-carbonyl]amino]spiro[3.3]heptane-6-carboxylate (31.2 mg, 55.21 μmol) as a yellow solid.

$^1$H NMR (400 MHz, CDCl$_3$) δ=10.61-10.07 (m, 1H), 8.89 (d, J=2.5 Hz, 1H), 8.62 (d, J=2.5 Hz, 1H), 7.66 (d, J=8.6 Hz, 2H), 7.29 (s, 2H), 6.83-6.30 (m, 1H), 4.80-4.59 (m, 2H), 4.30-3.81 (m, 1H), 3.71 (br d, J=3.9 Hz, 4H), 2.72 (q, J=7.2 Hz, 2H), 2.63 (br s, 4H), 2.12-2.00 (m, 1H), 1.92-1.76 (m, 2H), 1.73-1.63 (m, 2H), 1.46-1.22 (m, 3H), 1.21-1.05 (m, 1H), 1.04-0.90 (m, 3H). LCMS for product (ESI+): m/z 557.3 [M+H]$^+$, Rt: 3.903 min.

LCMS Method

The gradient was 0-80% B in 3.4 min, 80-100% B in 0.45 min, 100-0% B in 0.01 min, and then held at 0% B for 0.65 min (0.6 m/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

208

Example 16—Synthesis of 6-(4-cyanophenyl)-4-hydroxy-N-(4-methylcyclohexyl)-1-(2-morpholinoethyl)-2-oxo-1,2-dihydro-1,8-naphthyridine-3-carboxamide (Compound 16)

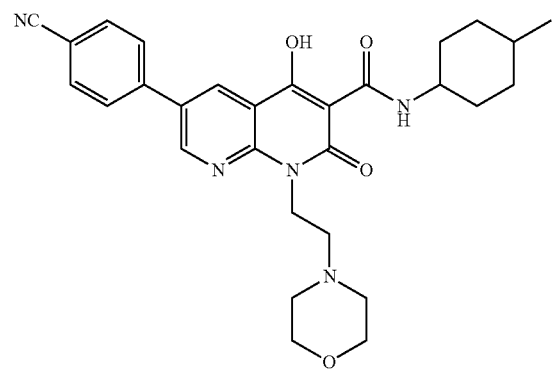 [SMILES: CC1CCC(NC(=O)c2c(O)c3cc(-c4ccc(C#N)cc4)cnc3n(CCN3CCOCC3)c2=O)CC1]

Preparation of 6-(4-cyanophenyl)-4-hydroxy-N-(4-methylcyclohexyl (2-morpholinoethyl)-2-oxo-1,2-dihydro-1,8-naphthyridine-3-carboxamide

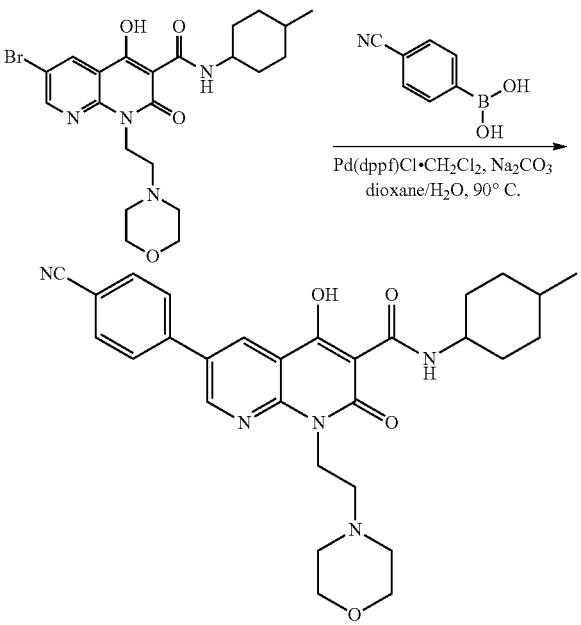

A mixture of 6-bromo-4-hydroxy-N-(4-methylcyclohexyl)-1-(2-morpholinoethyl)-2-oxo-1,8-naphthyridine-3-carboxamide (90 mg, 182.41 μmol, 1 eq), (4-cyanophenyl)boronic acid (32.16 mg, 218.89 μmol, 1.2 eq), Pd(dppf)Cl$_2$·CH$_2$Cl$_2$ (14.90 mg, 18.24 μmol, 0.1 eq), Na$_2$CO$_3$ (29.00 mg, 273.62 μmol, 1.5 eq) in dioxane (2 mL) and water (0.2 mL) was stirred at 90° C. under N$_2$ for 2 h. LCMS showed complete consumption of the starting material and formation of a new peak.

The mixture was concentrated and the residue was purified by prep-HPLC (column: Phenomenex Gemini-NX C18 75*30 mm*3 μm; mobile phase: [water (10 mM NH$_4$HCO$_3$)-ACN]; B %: 70%-98%, 8 min) to produce 6-(4-cyanophenyl)-4-hydroxy-N-(4-methylcyclohexyl)-1-(2-morpholinoethyl)-2-oxo-1,2-dihydro-1,8-naphthyridine-3-carboxamide (26.6 mg, 51.02 μmol) as a yellow solid.

$^1$H NMR (400 MHz, CDCl$_3$) δ=10.61-9.94 (m, 1H), 8.92 (d, J=2.5 Hz, 1H), 8.66 (d, J=2.5 Hz, 1H), 7.94-7.69 (m, 4H), 4.77-4.59 (m, 2H), 4.34-3.79 (m, 1H), 3.69 (br s, 4H), 2.71 (q, J=6.9 Hz, 2H), 2.62 (br s, 4H), 2.15-2.00 (m, 1H), 1.93-1.74 (m, 2H), 1.72-1.64 (m, 2H), 1.43-1.25 (m, 3H), 1.19-1.04 (m, 1H), 1.01-0.91 (m, 3H). LCMS for product (ESI+): m/z 516.3 [M+H]$^+$, Rt: 3.753 min.

LCMS Method

The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 17—Synthesis of 6-(4-cyclopropylphenyl)-4-hydroxy-N-(4-methylcyclohexyl)-1-(2-morpholinoethyl)-2-oxo-1,2-dihydro-1,8-naphthyridine-3-carboxamide (Compound 17)

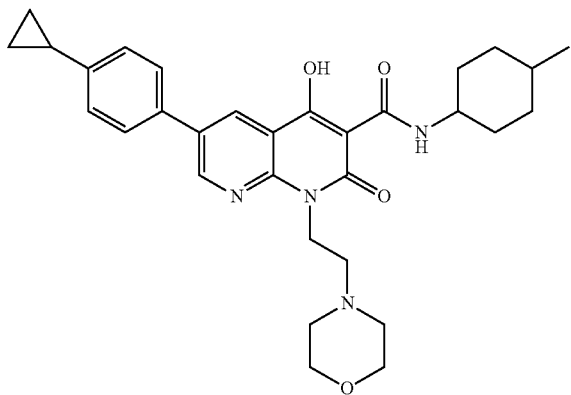 [SMILES: CC1CCC(NC(=O)c2c(O)c3cc(-c4ccc(C5CC5)cc4)cnc3n(CCN3CCOCC3)c2=O)CC1]

Preparation of 6-(4-cyclopropylphenyl)-4-hydroxy-N-(4-methylcyclohexyl)-1-(2-morpholinoethyl)-2-oxo-1,2-dihydro-1,8-naphthyridine-3-carboxamide

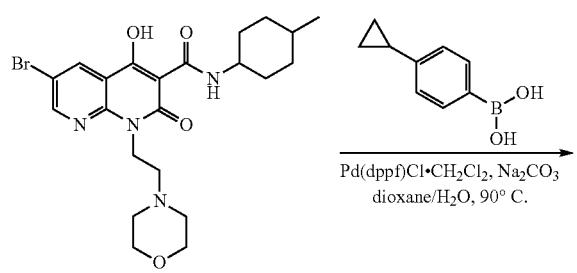

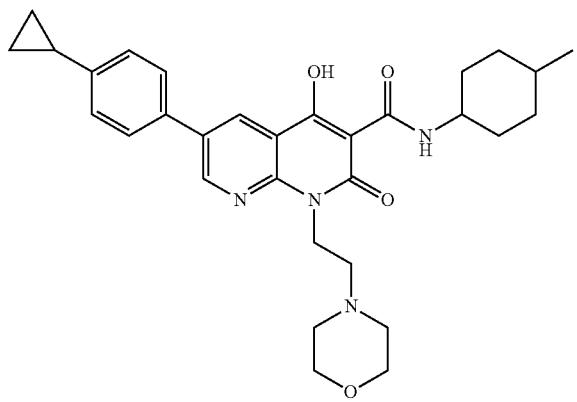

A mixture of 6-bromo-4-hydroxy-N-(4-methylcyclohexyl)-1-(2-morpholinoethyl)-2-oxo-1,8-naphthyridine-3-carboxamide (90 mg, 182.41 μmol, 1 eq), (4-cyclopropylphenyl)boronic acid (35.46 mg, 218.89 μmol, 1.2 eq), Pd(dppf)Cl$_2$·CH$_2$Cl$_2$ (14.90 mg, 18.24 μmol, 0.1 eq), Na$_2$CO$_3$ (29.00 mg, 273.62 μmol, 1.5 eq) in dioxane (2 mL) and water (0.2 mL) was stirred at 90° C. under N$_2$ for 2 h. LCMS showed complete consumption of the starting material and formation of a new peak.

The mixture was concentrated, and the residue was purified by prep-HPLC (column: Waters Xbridge BEH C18 100*25 mm*5 μm; mobile phase: [water (10 mM NH$_4$HCO$_3$)-ACN]; B %: 85%-98%, 10 min) to produce 6-(4-cyclopropylphenyl)-4-hydroxy-N-(4-methylcyclohexyl)-1-(2-morpholinoethyl)-2-oxo-1,2-dihydro-1,8-naphthyridine-3-carboxamide (11.3 mg, 21.29 μmol) as a yellow solid.

$^1$H NMR (400 MHz, CDCl$_3$) δ=10.78-9.87 (m, 1H), 8.90 (br s, 1H), 8.61 (br s, 1H), 7.55 (br d, J=6.4 Hz, 2H), 7.21 (br d, J=6.8 Hz, 2H), 4.68 (br d, J=6.0 Hz, 2H), 4.38-3.81 (m, 1H), 3.70 (br s, 4H), 2.94-2.45 (m, 6H), 2.16-1.94 (m, 2H), 1.91-1.76 (m, 2H), 1.69 (br s, 1H), 1.50-1.22 (m, 4H), 1.13 (br s, 1H), 1.02 (br dd, J=5.9, 17.3 Hz, 3H), 0.94 (br d, J=5.1 Hz, 2H), 0.77 (br s, 2H). LCMS for product (ESI+): m/z 531.3 [M+H]$^+$, Rt: 4.174 min.

LCMS Method

The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 18—Synthesis of 4-hydroxy-6-(4-isopropoxyphenyl)-N-(4-methylcyclohexyl)-1-(2-morpholinoethyl)-2-oxo-1,2-dihydro-1,8-naphthyridine-3-carboxamide (Compound 18)

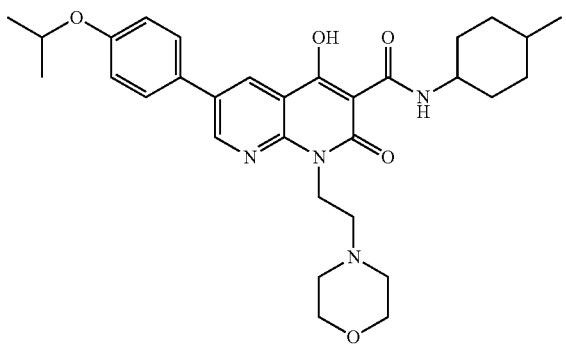 [SMILES: CC1CCC(NC(=O)c2c(O)c3cc(-c4ccc(OC(C)C)cc4)cnc3n(CCN3CCOCC3)c2=O)CC1]

Preparation of 4-hydroxy-6-(4-isopropoxyphenyl)-N-(4-methylcyclohexyl)-1-(2-morpholinoethyl)-2-oxo-1,2-dihydro-1,8-naphthyridine-3-carboxamide

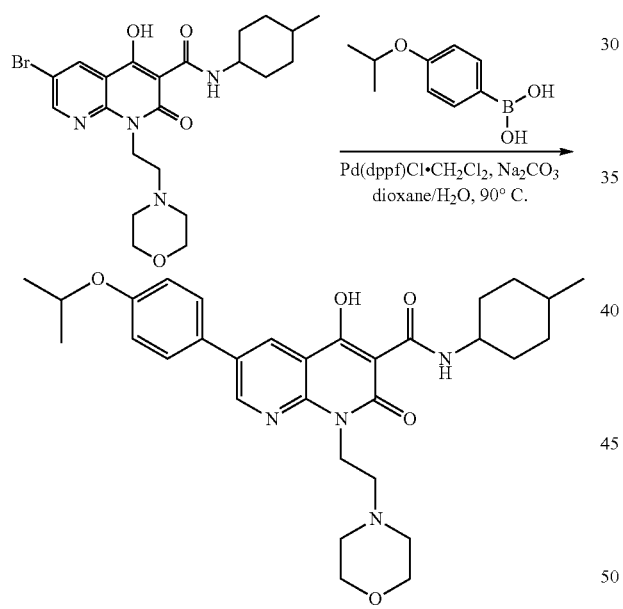

A mixture of 6-bromo-4-hydroxy-N-(4-methylcyclohexyl)-1-(2-morpholinoethyl)-2-oxo-1,8-naphthyridine-3-carboxamide (150 mg, 304.02 μmol, 1 eq), (4-isopropoxyphenyl)boronic acid (65.67 mg, 364.82 μmol, 1.2 eq), Pd(dppf)Cl$_2$·CH$_2$Cl$_2$ (24.83 mg, 30.40 μmol, 0.1 eq), Na$_2$CO$_3$ (48.33 mg, 456.03 μmol, 1.5 eq) in dioxane (1 mL) and water (0.2 mL) was stirred at 90° C. for 2 h under N$_2$. LCMS showed complete consumption of the starting material and formation of a new peak.

The mixture was concentrated and residue was purified by prep-HPLC (column: Waters Xbridge BEH C18 100*25 mm*5 μm; mobile phase: [water (10 mM NH$_4$HCO$_3$)-ACN]; B %: 70%-95%, 10 min) to yield 4-hydroxy-6-(4-isopropoxyphenyl)-N-(4-methylcyclohexyl)-1-(2-morpholinoethyl)-2-oxo-1,2-dihydro-1,8-naphthyridine-3-carboxamide (51.2 mg, 93.32 μmol) as a yellow solid.

$^1$H NMR (400 MHz, CDCl$_3$) δ=10.63-10.10 (m, 1H), 8.89 (d, J=2.5 Hz, 1H), 8.59 (d, J=2.5 Hz, 1H), 7.58 (d, J=7.8 Hz, 2H), 7.02 (d, J=8.8 Hz, 2H), 4.80-4.57 (m, 3H), 4.30-3.83 (m, 1H), 3.70 (br s, 4H), 2.80-2.52 (m, 6H), 2.08 (br dd, J=1.9, 13.3 Hz, 1H), 1.92-1.76 (m, 2H), 1.73-1.63 (m, 2H), 1.39 (d, J=6.0 Hz, 9H), 1.19-1.05 (m, 1H), 1.04-0.91 (m, 3H). LCMS for product (ESI+): m/z 549.3 [M+H]$^+$, Rt: 4.085 min.

LCMS Method

The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 19—Synthesis of 6-(2,3-dihydrobenzo[b][1,4]dioxin-6-yl)-4-hydroxy-N-(4-methylcyclohexyl)-1-(2-morpholinoethyl)-2-oxo-1,2-dihydro-1,8-naphthyridine-3-carboxamide (Compound 19)

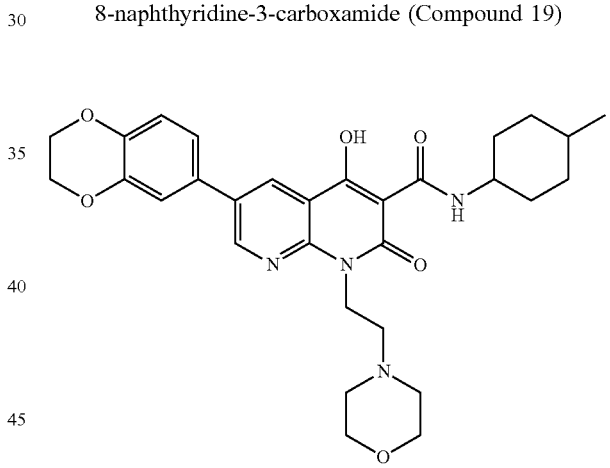

Preparation of 6-(2,3-dihydrobenzo[b][1,4]dioxin-6-yl)-4-hydroxy-N-(4-methylcyclohexyl)-1-(2-morpholinoethyl)-2-oxo-1,2-dihydro-1,8-naphthyridine-3-carboxamide

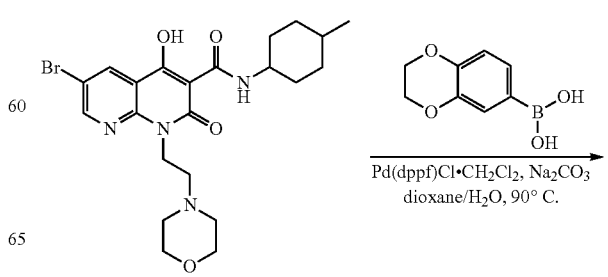

-continued

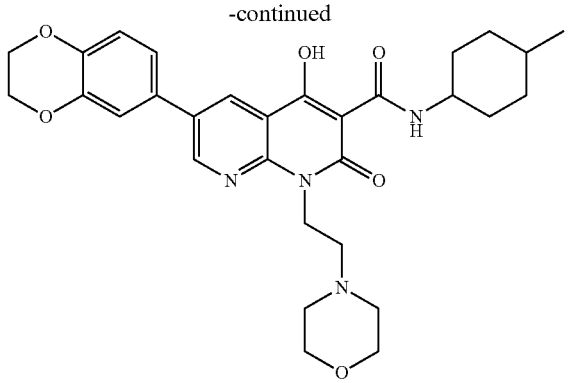

A mixture of 6-bromo-4-hydroxy-N-(4-methylcyclohexyl)-1-(2-morpholinoethyl)-2-oxo-1,8-naphthyridine-3-carboxamide (90 mg, 182.41 μmol, 1 eq), 2,3-dihydro-1,4-benzodioxin-6-ylboronic acid (39.39 mg, 218.89 μmol, 1.2 eq), Pd(dppf)Cl$_2$·CH$_2$Cl$_2$ (14.90 mg, 18.24 μmol, 0.1 eq), Na$_2$CO$_3$ (29.00 mg, 273.62 μmol, 1.5 eq) in dioxane (1 mL) and water (0.1 mL) was stirred at 90° C. under N$_2$ for 2 h. LCMS showed complete consumption of the starting material and formation of a new peak.

The mixture was concentrated and the residue was purified by prep-HPLC (column: Phenomenex Gemini-NX C18 75*30 mm*3 μm; mobile phase: [water (10 mM NH$_4$HCO$_3$)-ACN]; B %: 75%-99%, 6 min) to produce 6-(2,3-dihydrobenzo[b][1,4]dioxin-6-yl)-4-hydroxy-N-(4-methylcyclohexyl)-1-(2-morpholinoethyl)-2-oxo-1,2-dihydro-1,8-naphthyridine-3-carboxamide (8.3 mg, 14.64 μmol) as a white solid.

$^1$H NMR (400 MHz, CDCl$_3$) δ=10.64-10.05 (m, 1H), 8.86 (d, J=2.4 Hz, 1H), 8.57 (d, J=2.4 Hz, 1H), 7.19-7.12 (m, 2H), 7.00 (d, J=8.1 Hz, 1H), 4.77-4.54 (m, 2H), 4.33 (s, 4H), 4.27-3.84 (m, 1H), 3.70 (br s, 4H), 2.80-2.55 (m, 6H), 2.11-2.04 (m, 1H), 1.90-1.75 (m, 2H), 1.73-1.58 (m, 2H), 1.45-1.29 (m, 3H), 1.15-1.08 (m, 1H), 1.02-0.90 (m, 3H). LCMS for product (ESI+): m/z 549.3 [M+H]$^+$, Rt: 3.898 min.

LCMS Method

The gradient was 0-80% B in 3.4 min, 80-100% B in 0.45 min, 100-0% B in 0.01 min, and then held at 0% B for 0.65 min (0.6 m/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 20—Synthesis of 4-hydroxy-6-(4-methoxyphenyl)-N-(4-methylcyclohexyl)-1-(2-morpholinoethyl)-2-oxo-1,2-dihydro-1,8-naphthyridine-3-carboxamide (Compound 20)

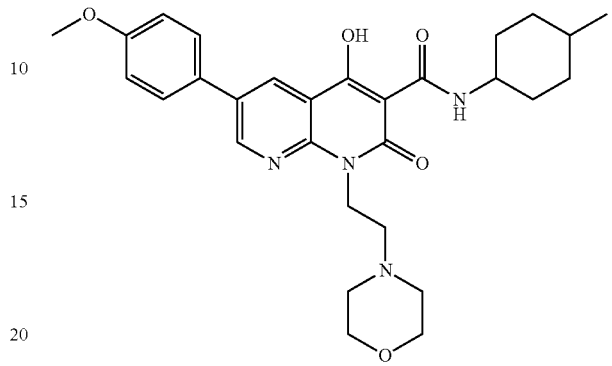

Preparation of 4-hydroxy-6-(4-methoxyphenyl)-N-(4-methylcyclohexyl)-1-(2-morpholinoethyl)-2-oxo-1,2-dihydro-1,8-naphthyridine-3-carboxamide

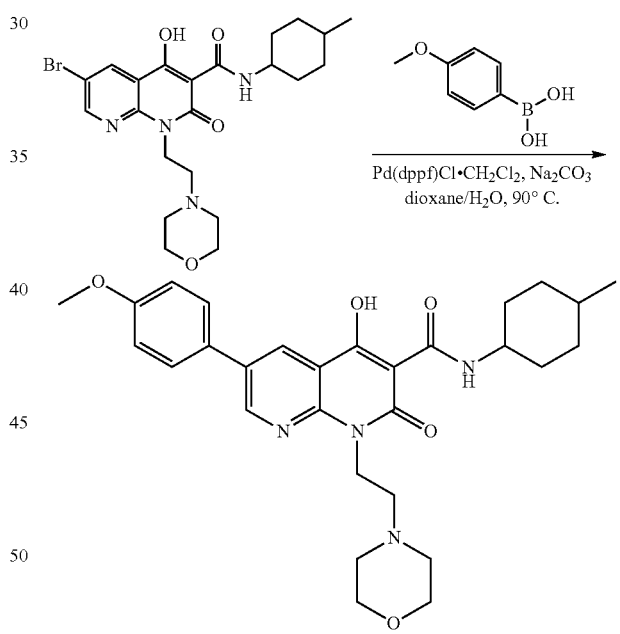

A mixture of 6-bromo-4-hydroxy-N-(4-methylcyclohexyl)-1-(2-morpholinoethyl)-2-oxo-1,8-naphthyridine-3-carboxamide (56 mg, 113.50 μmol, 1 eq), (4-methoxyphenyl)boronic acid (20.70 mg, 136.20 μmol, 1.2 eq), Pd(dppf)Cl$_2$·CH$_2$Cl$_2$ (9.27 mg, 11.35 μmol, 0.1 eq), Na$_2$CO$_3$ (18.04 mg, 170.25 μmol, 1.5 eq) in dioxane (2 mL) and water (0.2 mL) was stirred at 90° C. under N$_2$ for 2 h. LCMS showed starting material was consumed, and the desired product was detected.

The mixture was concentrated and the residue was purified by prep-HPLC (column: Waters Xbridge BEH C18 100*25 mm*5 μm; mobile phase: [water (10 mM NH$_4$HCO$_3$)-ACN]; B %: 70%-95%, 10 min) to produce 4-hydroxy-6-(4-methoxyphenyl)-N-(4-methylcyclohexyl)-1-(2-morpholinoethyl)-2-oxo-1,2-dihydro-1,8-naphthyridine-3-carboxamide (11.1 mg, 21.24 μmol) as a white solid.

$^1$H NMR (400 MHz, CDCl$_3$) δ=10.71-9.86 (m, 1H), 8.89 (br s, 1H), 8.59 (br s, 1H), 7.59 (br d, J=7.8 Hz, 2H), 7.04 (br d, J=7.9 Hz, 2H), 4.68 (br d, J=6.6 Hz, 2H), 3.88 (s, 4H), 3.70 (br s, 4H), 2.98-2.42 (m, 6H), 2.08 (br d, J=10.8 Hz, 1H), 1.95-1.77 (m, 2H), 1.73-1.62 (m, 2H), 1.45-1.24 (m, 3H), 1.18-1.04 (m, 1H), 1.02-0.86 (m, 3H). LCMS for product (ESI+): m/z 521.3 [M+H]$^+$, Rt: 3.948 min.

LCMS Method

The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 21—Synthesis of 6-(5-cyanopyridin-2-yl)-N-(1-(4-fluorophenyl)ethyl)-4-hydroxy-1-(2-morpholinoethyl)-2-oxo-1,2-dihydro-1,8-naphthyridine-3-carboxamide (Compound 21)

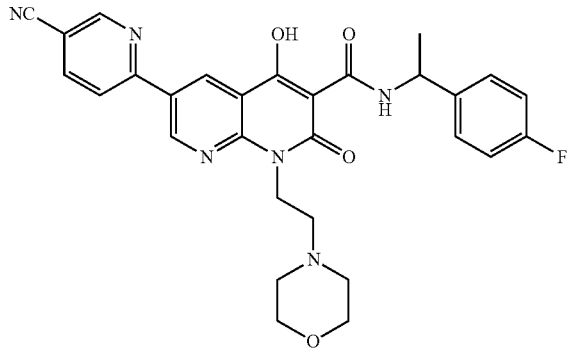 [SMILES: CC(NC(=O)c1c(O)c2cc(-c3ccc(C#N)cn3)cnc2n(CCN2CCOCC2)c1=O)c1ccc(F)cc1]

Step 1: ethyl 4-hydroxy-1-(2-morpholinoethyl)-2-oxo-6-(4,4,5,5-tetramethyl-1,3,2-dioxaborolan-2-yl)-1,2-dihydro-1,8-naphthyridine-3-carboxylate

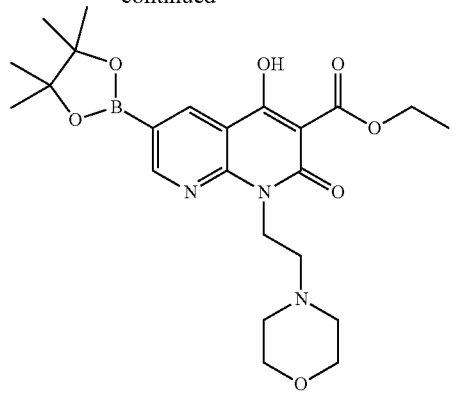

To a mixture of ethyl 6-bromo-4-hydroxy-1-(2-morpholinoethyl)-2-oxo-1,8-naphthyridine-3-carboxylate (800 mg, 1.88 mmol, 1 eq), KOAc (552.58 mg, 5.63 mmol, 3 eq) and 4,4,5,5-tetramethyl-2-(4,4,5,5-tetramethyl-1,3,2-dioxaborolan-2-yl)-1,3,2-dioxaborolane (4.77 g, 18.77 mmol, 10 eq) in DMSO (20 mL) was added Pd(PPh$_3$)$_2$Cl$_2$ (131.73 mg, 187.68 μmol, 0.1 eq) under N$_2$. The mixture was stirred at 80° C. for 1 h. LCMS showed complete consumption of the starting material and formation of a new peak.

The mixture was filtered and the residue was purified by prep-HPLC (column: Phenomenex luna C18 250*50 mm*10 mobile μm; phase: [water (0.05% HCl)-ACN]; B %: 0%-30%, 20 min) to yield ethyl 4-hydroxy-1-(2-morpholinoethyl)-2-oxo-6-(4,4,5,5-tetramethyl-1,3,2-dioxaborolan-2-yl)-1,2-dihydro-1,8-naphthyridine-3-carboxylate (400 mg) as a yellow oil (used into the next step without further purification).

LCMS for product (ESI+): m/z 474.3 [M+H]$^+$, Rt: 1.453 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 2: ethyl 6-(5-cyanopyridin-2-yl)-4-hydroxy-1-(2-morpholinoethyl)-2-oxo-1,2-dihydro-1,8-naphthyridine-3-carboxylate

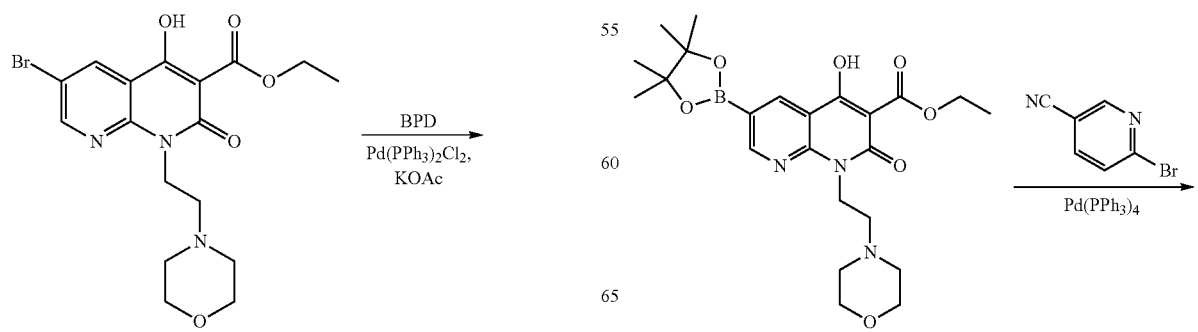

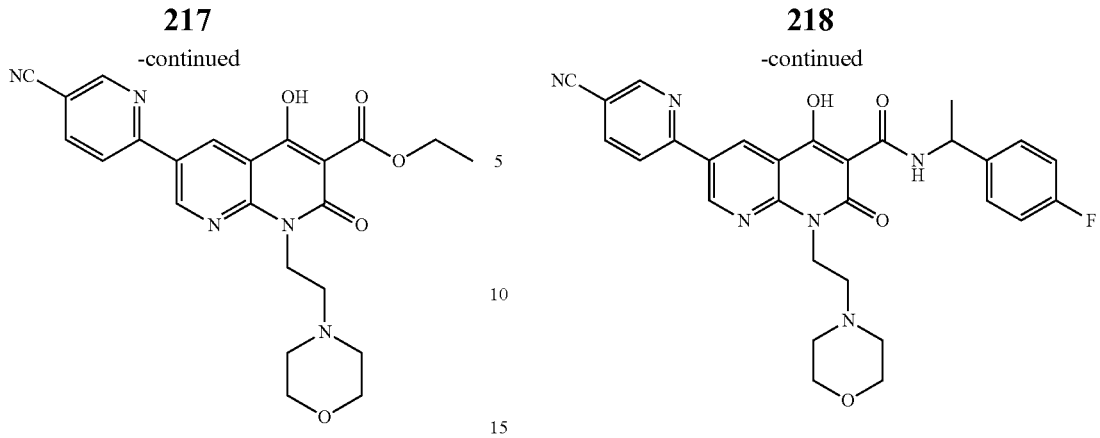

To a mixture of ethyl 4-hydroxy-1-(2-morpholinoethyl)-2-oxo-6-(4,4,5,5-tetramethyl-1,3,2-dioxaborolan-2-yl)-1,8-naphthyridine-3-carboxylate (270 mg, 570.43 µmol, 1 eq), K₂CO₃ (473.02 mg, 3.42 mmol, 6 eq) and 6-bromopyridine-3-carbonitrile (125.27 mg, 684.52 µmol, 1.2 eq) in dioxane (4 mL) and H₂O (0.4 mL) was added Pd(PPh₃)₄ (65.92 mg, 57.04 µmol, 0.1 eq) under N₂. The mixture was stirred at 100° C. for 1 h. LCMS showed complete consumption of the starting material and formation of a new peak.

The mixture was filtered and concentrated under reduced pressure. The residue was purified by prep-HPLC (column: Phenomenex luna C18 250*50 mm*10 µm; mobile phase: [water (0.05% HCl)-ACN]; B %: 5%-35%, 10 min) to produce ethyl 6-(5-cyanopyridin-2-yl)-4-hydroxy-1-(2-morpholinoethyl)-2-oxo-1,2-dihydro-1,8-naphthyridine-3-carboxylate (120 mg, 266.99 µmol) as a white solid.

¹H NMR (ET26059-546-P1C, 400 MHz, DMSO-d₆) δ=9.48 (d, J=2.5 Hz, 1H), 8.51 (s, 1H), 8.44 (s, 1H), 8.39-8.35 (m, 1H), 4.77-4.69 (m, 4H), 4.34 (q, J=7.0 Hz, 4H), 4.04-4.00 (m, 2H), 3.52 (br s, 4H), 1.31 (s, 3H). LCMS for product (ESI+): m/z 450.2 [M+H]⁺, Rt: 1.213 min.
LCMS Method The column used for chromatography was a HALO AQ-C18 2.1*30 mm, (2.7 µm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 3: Preparation of 6-(5-cyanopyridin-2-yl)-N-(1-(4-fluorophenyl)ethyl)-4-hydroxy-1-(2-morpholinoethyl)-2-oxo-1,2-dihydro-1,8-naphthyridine-3-carboxamide

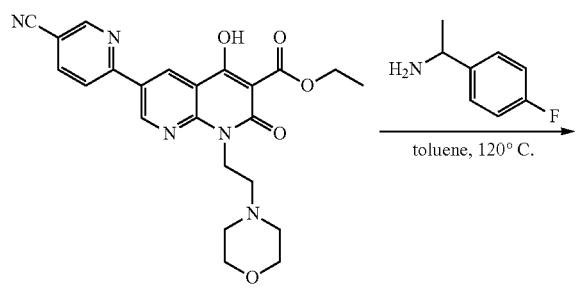

To a mixture of ethyl 6-(5-cyano-2-pyridyl)-4-hydroxy-1-(2-morpholinoethyl)-2-oxo-1,8-naphthyridine-3-carboxylate (30 mg, 66.75 µmol, 1 eq) and 1-(4-fluorophenyl)ethanamine (11.15 mg, 80.10 µmol, 10.52 µL, 1.2 eq) in toluene (0.5 mL) was added DIEA (8.63 mg, 66.75 µmol, 11.63 µL, 1 eq). The mixture was stirred at 120° C. for 1 h. LCMS showed complete consumption of the starting material and formation of a new peak.

The mixture was filtered and concentrated under reduced pressure. The residue was purified by prep-HPLC (column: Phenomenex Gemini-NX C18 75*30 mm*3 µm; mobile phase: [water (10 mM NH₄HCO₃)-ACN]; B %: 50%-80%, 10 min) to yield 6-(5-cyanopyridin-2-yl)-N-(1-(4-fluorophenyl)ethyl)-4-hydroxy-1-(2-morpholinoethyl)-2-oxo-1,2-dihydro-1,8-naphthyridine-3-carboxamide (11.5 mg, 20.77 µmol) as a white solid.

¹H NMR (400 MHz, CDCl₃) δ=10.23 (br d, J=7.6 Hz, 1H), 9.44 (d, J=2.4 Hz, 1H), 9.05 (d, J=2.4 Hz, 1H), 8.99 (d, J=1.6 Hz, 1H), 8.09 (dd, J=2.1, 8.4 Hz, 1H), 7.97 (d, J=8.3 Hz, 1H), 4.70 (t, J=7.1 Hz, 2H), 4.40 (sxt, J=8.0 Hz, 1H), 3.74-3.67 (m, 4H), 2.71 (t, J=7.1 Hz, 2H), 2.63 (br s, 4H), 2.56-2.49 (m, 2H), 2.02 (br s, 6H), 1.91-1.83 (m, 2H). LCMS for product (ESI+): m/z 543.2 [M+H]⁺, Rt: 2.366 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 22—Synthesis of 6-(5-cyanopyridin-2-yl)-4-hydroxy-1-(2-morpholinoethyl)-2-oxo-N-(spiro[3.3]heptan-2-yl)-1,2-dihydro-1,8-naphthyridine-3-carboxamide (Compound 22)

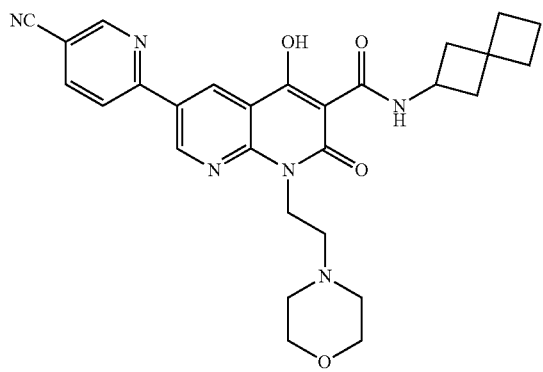 [SMILES: N#Cc1ccc(-c2cnc3c(c2)c(O)c(C(=O)NC2CC4(CCC4)C2)c(=O)n3CCN2CCOCC2)nc1]

Preparation of 6-(5-cyanopyridin-2-yl)-4-hydroxy-1-(2-morpholinoethyl)-2-oxo-N-(spiro[3.3]heptan-2-yl)-1,2-dihydro-1,8-naphthyridine-3-carboxamide

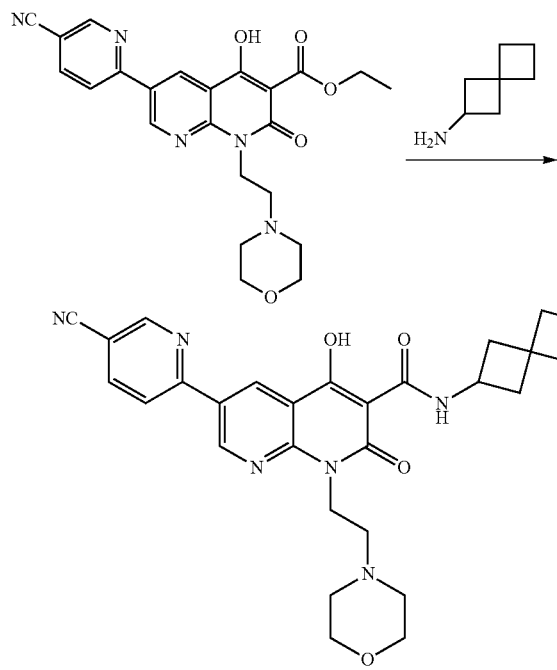

To a mixture of ethyl 6-(5-cyano-2-pyridyl)-4-hydroxy-1-(2-morpholinoethyl)-2-oxo-1,8-naphthyridine-3-carboxylate (30 mg, 66.75 μmol, 1 eq) and spiro[3.3]heptan-2-amine (8.91 mg, 80.10 μmol, 1.2 eq) in toluene (0.5 mL) was added DIEA (8.63 mg, 66.75 μmol, 11.63 μL, 1 eq). The mixture was stirred at 120° C. for 1 h. LCMS showed complete consumption of the starting material and formation of a new peak.

The mixture was filtered and concentrated under reduced pressure. The residue was purified by prep-HPLC (column: Phenomenex Gemini-NX C18 75*30 mm*3 μm; mobile phase: [water (10 mM NH$_4$HCO$_3$)-ACN]; B %: 55%-85%, 10 min) to yield 6-(5-cyanopyridin-2-yl)-4-hydroxy-1-(2-morpholinoethyl)-2-oxo-N-(spiro[3.3]heptan-2-yl)-1,2-dihydro-1,8-naphthyridine-3-carboxamide (8.1 mg, 15.43 μmol) as a white solid.

$^1$H NMR (400 MHz, CDCl$_3$) δ=10.23 (br d, J=7.6 Hz, 1H), 9.44 (d, J=2.4 Hz, 1H), 9.05 (d, J=2.4 Hz, 1H), 8.99 (d, J=1.6 Hz, 1H), 8.09 (dd, J=2.1, 8.4 Hz, 1H), 7.97 (d, J=8.3 Hz, 1H), 4.70 (t, J=7.1 Hz, 2H), 4.40 (sxt, J=8.0 Hz, 1H), 3.74-3.67 (m, 4H), 2.71 (t, J=7.1 Hz, 2H), 2.63 (br s, 4H), 2.56-2.49 (m, 2H), 2.02 (br s, 6H), 1.91-1.83 (m, 2H). LCMS for product (ESI+): m/z 515.3 [M+H]$^+$, Rt: 2.436 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 23—Synthesis of 6-(4-fluorophenyl)-4-hydroxy-1-(2-morpholinoethyl)-2-oxo-N-(spiro[3.3]heptan-2-yl)-1,2-dihydroquinoline-3-carboxamide (Compound 23)

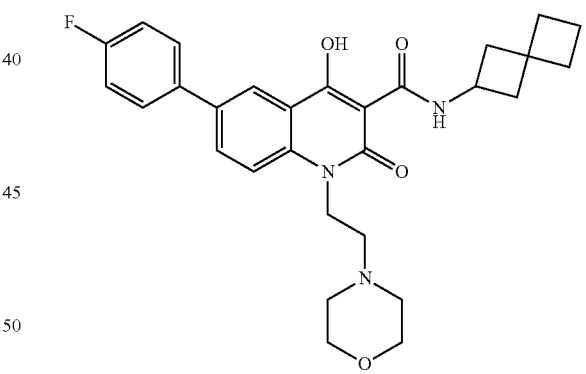

Step 1: 6-bromo-1-(2-morpholinoethyl)-2H-benzo[d][1,3]oxazine-2,4(1H)-dione

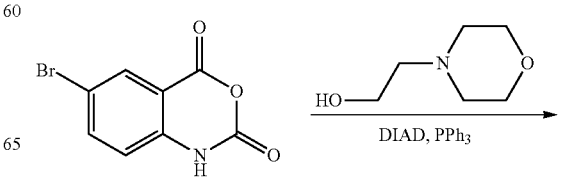

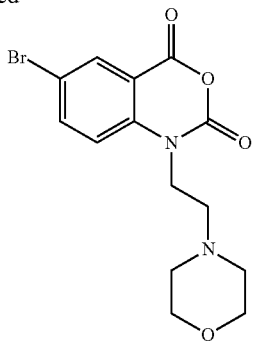

To a solution of 6-bromo-1H-3,1-benzoxazine-2,4-dione (300 mg, 1.24 mmol, 1 eq) in DCM (3 mL) was added 2-morpholinoethanol (195.11 mg, 1.49 mmol, 182.35 μL, 1.2 eq), PPh₃ (487.67 mg, 1.86 mmol, 1.5 eq) and DIAD (375.97 mg, 1.86 mmol, 361.51 μL, 1.5 eq). The mixture was stirred at 25° C. for 2 h. LCMS showed complete consumption of the starting material and formation of a new peak.

The mixture was washed with water (2×5 mL) and the organic layer was washed with brine (5 mL) and dried over Na₂SO₄. The mixture was concentrated to produce 6-bromo-1-(2-morpholinoethyl)-2H-benzo[d][1,3]oxazine-2,4(1H)-dione (350 mg, 985.41 μmol) as a brown solid (used without further purification).

Step 2: ethyl 6-bromo-4-hydroxy-1-(2-morpholino-ethyl)-2-oxo-1,2-dihydroquinoline-3-carboxylate

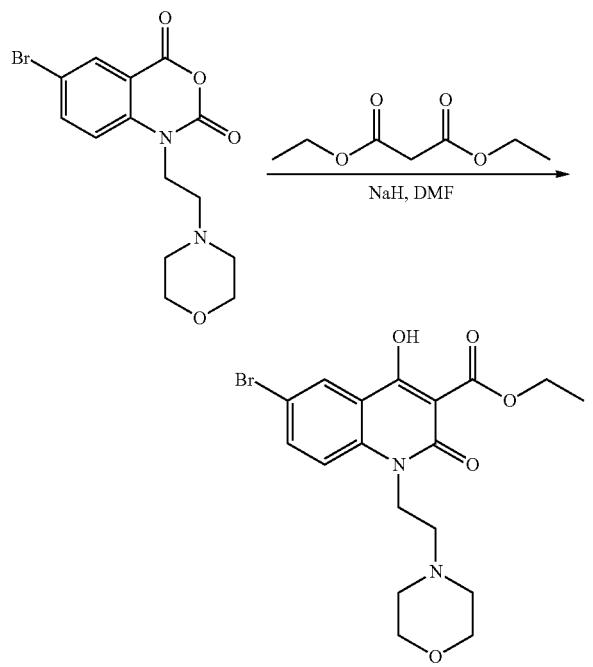

To a mixture of NaH (78.82 mg, 1.97 mmol, 60% purity, 2 eq) in DMF (3 mL) was added diethyl propanedioate (789.15 mg, 4.93 mmol, 744.48 μL, 5 eq) and a solution of 6-bromo-1-(2-morpholinoethyl)-3,1-benzoxazine-2,4-dione (350 mg, 985.41 μmol, 1 eq) in DMF (2 mL) at 0° C. The mixture was stirred at 90° C. for 2 h. LCMS showed complete consumption of the starting material and formation of a new peak. The mixture was poured into water (20 mL) and aqueous layer was extracted with EtOAc (2×20 mL).

The aqueous phase was acidified to pH 3 by adding 2 N hydrochloric acid dropwise. The resulting solid was collected by filtration to produce ethyl 6-bromo-4-hydroxy-1-(2-morpholinoethyl)-2-oxo-1,2-dihydroquinoline-3-carboxylate (280 mg, 658.40 μmol) as a white solid.

¹H NMR (400 MHz, DMSO-d₆) δ=8.19 (d, J=2.1 Hz, 1H), 7.90 (dd, J=2.3, 9.0 Hz, 1H), 7.70 (d, J=9.1 Hz, 1H), 4.56 (br t, J=7.1 Hz, 2H), 4.32 (q, J=7.2 Hz, 2H), 3.97-3.74 (m, 4H), 1.29 (t, J=7.1 Hz, 3H). LCMS for product (ESI+): m/z 425.0, 427.0 [M+H]⁺, Rt: 0.902 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 3: ethyl 6-(4-fluorophenyl)-4-hydroxy-1-(2-morpholinoethyl)-2-oxo-1,2-dihydroquinoline-3-carboxylate

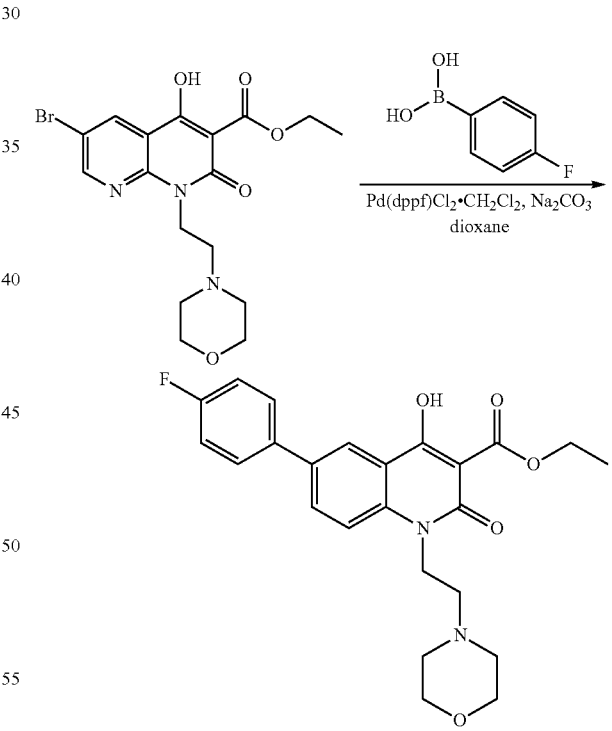

A mixture of (4-fluorophenyl)boronic acid (151.35 mg, 1.08 mmol, 2 eq), ethyl 6-bromo-4-hydroxy-1-(2-morpholinoethyl)-2-oxo-quinoline-3-carboxylate (230 mg, 540.83 μmol, 1 eq), Na₂CO₃ (114.64 mg, 1.08 mmol, 2 eq), Pd(dppf)Cl₂·CH₂Cl₂ (44.17 mg, 54.08 μmol, 0.1 eq) in dioxane (2.5 mL) and H₂O (0.5 mL) was degassed and purged with N2 for 3 times, and then the mixture was stirred at 100° C. for 2 h under N2. LCMS showed complete consumption of the starting material and formation of a new peak. The mixture was poured into water (10 mL) and the aqueous layer was extracted with EtOAc (3×20 mL). The combined organic layers were washed with brine (10 mL) and dried over Na$_2$SO$_4$.

The mixture was concentrated and the residue was purified by column chromatography (SiO2, Petroleum ether/Ethyl acetate=1:2 to 0:1) to produce ethyl 6-(4-fluorophenyl)-4-hydroxy-1-(2-morpholinoethyl)-2-oxo-1,2-dihydroquinoline-3-carboxylate (130 mg, 295.14 µmol) as a yellow solid.

LCMS for product (ESI+): m/z 441.1 [M+H]$^+$, Rt: 1.00 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 4: Preparation of 6-(4-fluorophenyl)-4-hydroxy-1-(2-morpholinoethyl)-2-oxo-N-(spiro[3.3]heptan-2-yl)-1,2-dihydroquinoline-3-carboxamide

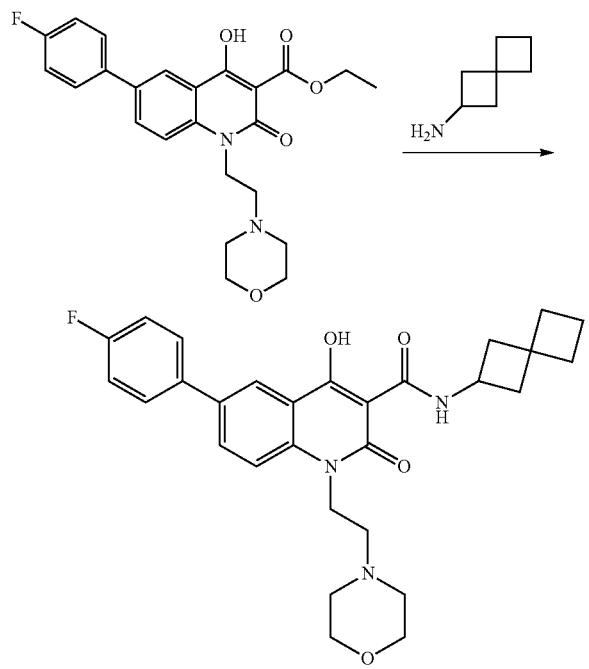

To a solution of ethyl 6-(4-fluorophenyl)-4-hydroxy-1-(2-morpholinoethyl)-2-oxo-quinoline-3-carboxylate (99.78 mg, 226.53 µmol, 1 eq) in toluene (2 mL) was added spiro[3.3]heptan-2-amine (40.13 mg, 271.83 µmol, 1.2 eq, HCl). The mixture was stirred at 110° C. for 6 h. LCMS showed complete consumption of the starting material and formation of a new peak.

The mixture was concentrated, and the residue was purified by prep-HPLC (neutral condition) to yield the 6-(4-fluorophenyl)-4-hydroxy-1-(2-morpholinoethyl)-2-oxo-N-(spiro[3.3]heptan-2-yl)-1,2-dihydroquinoline-3-carboxamide (22 mg, 42.82 µmol) as a white solid.

$^1$H NMR (400 MHz, CDCl$_3$) δ=10.35 (br d, J=7.8 Hz, 1H), 8.40 (d, J=2.1 Hz, 1H), 7.88 (dd, J=2.1, 8.9 Hz, 1H), 7.66-7.58 (m, 2H), 7.48 (d, J=8.9 Hz, 1H), 7.17 (t, J=8.6 Hz, 2H), 4.47-4.36 (m, 3H), 3.78-3.72 (m, 4H), 2.72-2.59 (m, 6H), 2.55-2.46 (m, 2H), 2.13-1.93 (m, 6H), 1.91-1.81 (m, 2H). LCMS for product (ESI+): m/z 506.3 [M+H]$^+$, Rt: 3.906 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was Acetonitrile. The column used for chromatography was a Xbridge Shield RP18 2.1*50 mm column (5 um particles). Detection methods are diode array (DAD) as well as positive electrospray ionization.

Example 24—Synthesis of N-(1-(4-cyanophenyl)ethyl)-6-(5-cyanopyridin-2-yl)-1-(4-fluorobenzyl)-4-hydroxy-2-oxo-1,2-dihydro-1,8-naphthyridine-3-carboxamide (Compound 24)

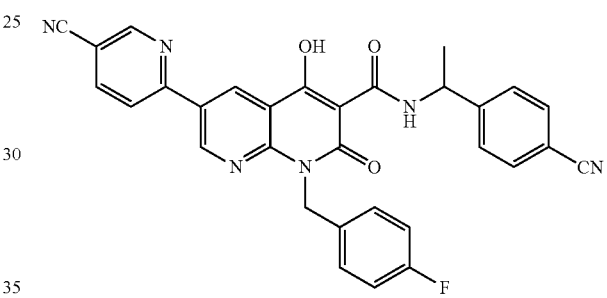

Preparation of N-(1-(4-cyanophenyl)ethyl)-6-(5-cyanopyridin-2-yl)-1-(4-fluorobenzyl)-4-hydroxy-2-oxo-1,2-dihydro-1,8-naphthyridine-3-carboxamide

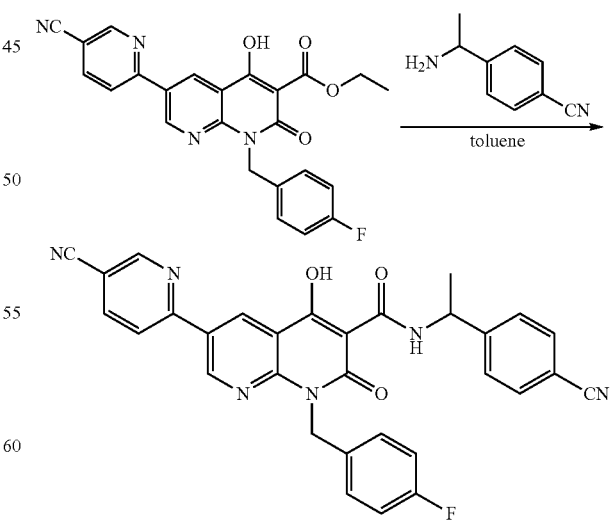

To a mixture of ethyl 1-[(4-fluorophenyl)methyl]-4-hydroxy-6-(5-isocyano-2-pyridyl)-2-oxo-1,8-naphthyridine-3-carboxylate (100 mg, 225.02 µmol, 1 eq) and 4-(1-aminoethyl)benzonitrile (36.18 mg, 247.52 μmol, 1.1 eq) in toluene (1 mL) was added DIEA (87.24 mg, 675.05 μmol, 117.58 μL, 3 eq). The mixture was stirred at 120° C. for 1 h. LCMS showed complete consumption of the starting material and formation of a new peak.

The mixture was filtered and the filtrate was purified by prep-HPLC (column: Luna Omega 5u Polar C18 100A; mobile phase: [water (0.04% HCl)-ACN]; B %: 70%-90%, 7 min) to produce N-(1-(4-cyanophenyl)ethyl)-6-(5-cyano-pyridin-2-yl)-1-(4-fluorobenzyl)-4-hydroxy-2-oxo-1,2-dihydro-1,8-naphthyridine-3-carboxamide (4.2 mg, 7.09 μmol, HCl) as a white solid.

$^1$H NMR (400 MHz, CDCl$_3$) δ=10.62 (br d, J=7.5 Hz, 1H), 9.48 (d, J=2.5 Hz, 1H), 9.08 (d, J=2.5 Hz, 1H), 9.01 (d, J=1.5 Hz, 1H), 8.10 (dd, J=2.0, 8.5 Hz, 1H), 7.97 (d, J=8.5 Hz, 1H), 7.69 (d, J=8.0 Hz, 2H), 7.56-7.47 (m, 4H), 7.01 (t, J=8.8 Hz, 2H), 5.80-5.70 (m, 2H), 5.30 (quin, J=7.0 Hz, 1H), 1.66 (d, J=7.0 Hz, 3H). LCMS for product (ESI+): m/z 545.2 [M+H]$^+$, Rt: 3.138 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/mn. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 25—Synthesis of 6-(5-(difluoromethoxy) pyridin-2-yl)-4-hydroxy-1-(2-morpholinoethyl)-2-oxo-N-(spiro[3.3]heptan-2-yl)-1,2-dihydro-1,8-naphthyridine-3-carboxamide (Compound 25)

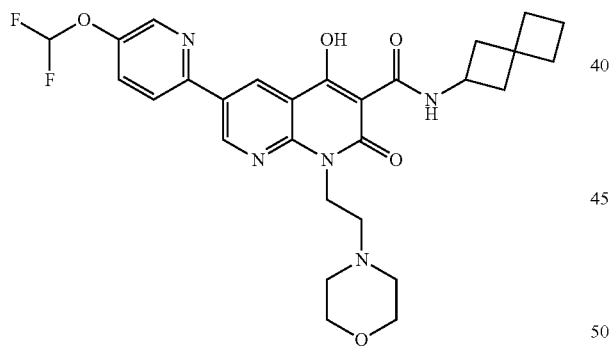

Step 1: 2-bromo-5-(difluoromethoxy)pyridine

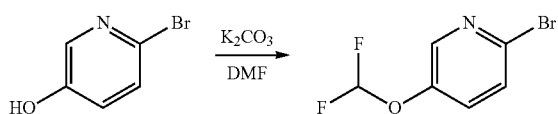

To a mixture of 6-bromopyridin-3-ol (400 mg, 2.30 mmol, 1 eq) and (2-chloro-2,2-difluoro-acetyl)oxysodium (700.98 mg, 4.60 mmol, 2 eq) in DMF (4 mL) was added potassium carbonate (476.59 mg, 3.45 mmol, 1.5 eq) under N2. The mixture was stirred at 80° C. for 12 h. LCMS showed complete consumption of the starting material and formation of a new peak. The mixture was poured into water (40 mL) and stirred for 5 min. The aqueous phase was extracted with ethyl acetate (3×10 mL). The combined organic phase was dried over anhydrous Na$_2$SO$_4$, filtered and concentrated.

The residue was purified by flash silica gel chromatography (petroleum ether/ethyl acetate=20:1 to 1:1) to produce 2-bromo-5-(difluoromethoxy)pyridine (300 mg, 1.34 mmol) as a colorless oil.

$^1$H NMR (400 MHz, CDCl$_3$) δ=8.28 (d, J=3.0 Hz, 1H), 7.50 (d, J=8.5 Hz, 1H), 7.38 (dd, J=3.0, 9.0 Hz, 1H), 6.80-6.25 (m, 1H).

Step 2: ethyl 6-(5-(difluoromethoxy)pyridin-2-yl)-4-hydroxy-1-(2-morpholinoethyl)-2-oxo-1,2-dihydro-1,8-naphthyridine-3-carboxylate

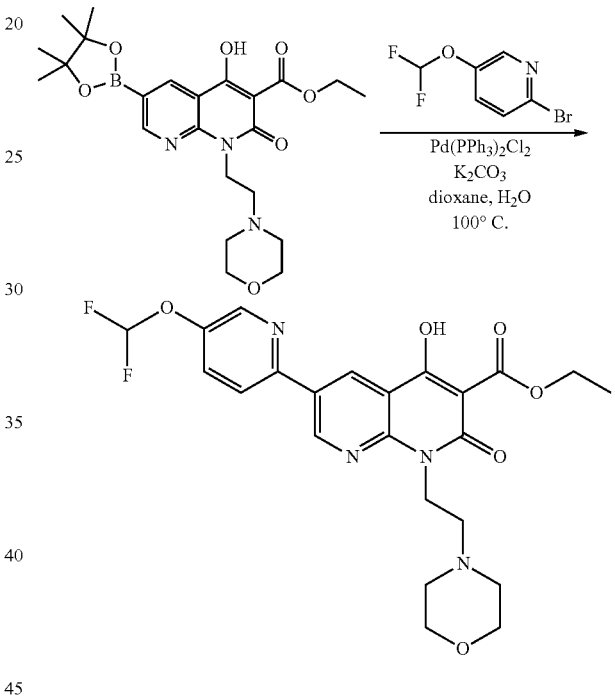

To a mixture of ethyl 4-hydroxy-1-(2-morpholinoethyl)-2-oxo-6-(4,4,5,5-tetramethyl-1,3,2-dioxaborolan-2-yl)-1,8-naphthyridine-3-carboxylate (100 mg, 211.27 μmol, 1 eq), K$_2$CO$_3$ (175.20 mg, 1.27 mmol, 6 eq) and 2-bromo-5-(difluoromethoxy)pyridine (70.99 mg, 316.91 μmol, 1.5 eq) in dioxane (1 mL) and H$_2$O (0.1 mL) was added Pd(PPh$_3$)$_4$ (24.41 mg, 21.13 μmol, 0.1 eq) under N$_2$. The mixture was stirred at 100° C. for 1 h. LCMS showed complete consumption of the starting material and formation of a new peak.

The mixture was filtered and concentrated under reduced pressure. The residue was purified by prep-HPLC (column: Phenomenex luna C18 250*50 mm*10 μm; mobile phase: [water (0.05% HCl)-ACN]; B %: 10%-40%, 10 min) to yield ethyl 6-(5-(difluoromethoxy)pyridin-2-yl)-4-hydroxy-1-(2-morpholinoethyl)-2-oxo-1,2-dihydro-1,8-naphthyridine-3-carboxylate (68 mg, 138.65 μmol) as a white solid.

$^1$H NMR (ET26059-548-P1C, 400 MHz, DMSO-d$_6$) δ=9.39 (d, J=2.5 Hz, 1H), 9.08 (d, J=2.0 Hz, 1H), 8.65 (d, J=2.5 Hz, 1H), 8.26 (d, J=8.5 Hz, 1H), 7.86 (dd, J=3.0, 8.5 Hz, 1H), 7.59 (s, 1H), 7.41 (s, 1H), 7.23 (s, 1H), 4.71 (br t, J=6.0 Hz, 2H), 4.34 (q, J=7.3 Hz, 2H), 3.54-3.41 (m, 4H), 3.17 (s, 2H), 2.53-2.52 (m, 4H), 1.31 (t, J=7.0 Hz, 3H). LCMS for product (ESI+): m/z 491.3 [M+H]$^+$, Rt: 1.370 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 3: Preparation of 6-(5-(difluoromethoxy)pyridin-2-yl)-4-hydroxy-1-(2-morpholinoethyl)-2-oxo-N-(spiro[3.3]heptan-2-yl)-1,2-dihydro-1,8-naphthyridine-3-carboxamide To a mixture of ethyl 6-[5-(difluoromethoxy)-2-pyridyl]-4-hydroxy-1-(2-morpholinoethyl)-2-oxo-1,8-naphthy-ridine-3-carboxylate (39 mg, 79.52 μmol, 1 eq) and spiro[3.3]heptan-2-amine (10.61 mg, 95.42 μmol, 1.2 eq) in toluene (1 mL) was added DIEA (10.28 mg, 79.52 μmol, 13.85 μL, 1 eq). The mixture was stirred at 120° C. for 1 h. LCMS showed complete consumption of the starting material and formation of a new peak.

The reaction mixture was concentrated, and the residue was triturated in MeOH (0.5 mL) to yield 6-(5-(difluoromethoxy)pyridin-2-yl)-4-hydroxy-1-(2-morpholinoethyl)-2-oxo-N-(spiro[3.3]heptan-2-yl)-1,2-dihydro-1,8-naphthyridine-3-carboxamide (20.1 mg, 35.46 μmol) as a white solid.

$^1$H NMR (400 MHz, DMSO-d$_6$) δ=10.31 (td, J=1.6, 3.8 Hz, 1H), 9.48 (d, J=2.3 Hz, 1H), 9.02 (d, J=2.4 Hz, 1H), 8.64 (d, J=2.8 Hz, 1H), 8.29 (d, J=8.9 Hz, 1H), 7.83 (dd, J=2.9, 8.6 Hz, 1H), 7.62-7.21 (m, 1H), 4.57 (br t, J=7.1 Hz, 2H), 4.34-4.25 (m, 1H), 3.54 (br d, J=4.4 Hz, 4H), 2.59 (br t, J=6.0 Hz, 2H), 2.55-2.51 (m, 4H), 2.42 (br d, J=2.8 Hz, 2H), 2.09-2.01 (m, 4H), 1.99-1.93 (m, 2H), 1.85-1.77 (m, 2H). LCMS for product (ESI+): m/z 556.3 [M+H]$^+$, Rt: 2.535 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000.

Example 26—Synthesis of N-(4,4-dimethylcyclohexyl)-6-(4-methoxyphenyl)-1-(2-morpholinoethyl)-2-oxo-1,2-dihydro-1,8-naphthyridine-3-carboxamide (Compound 26)

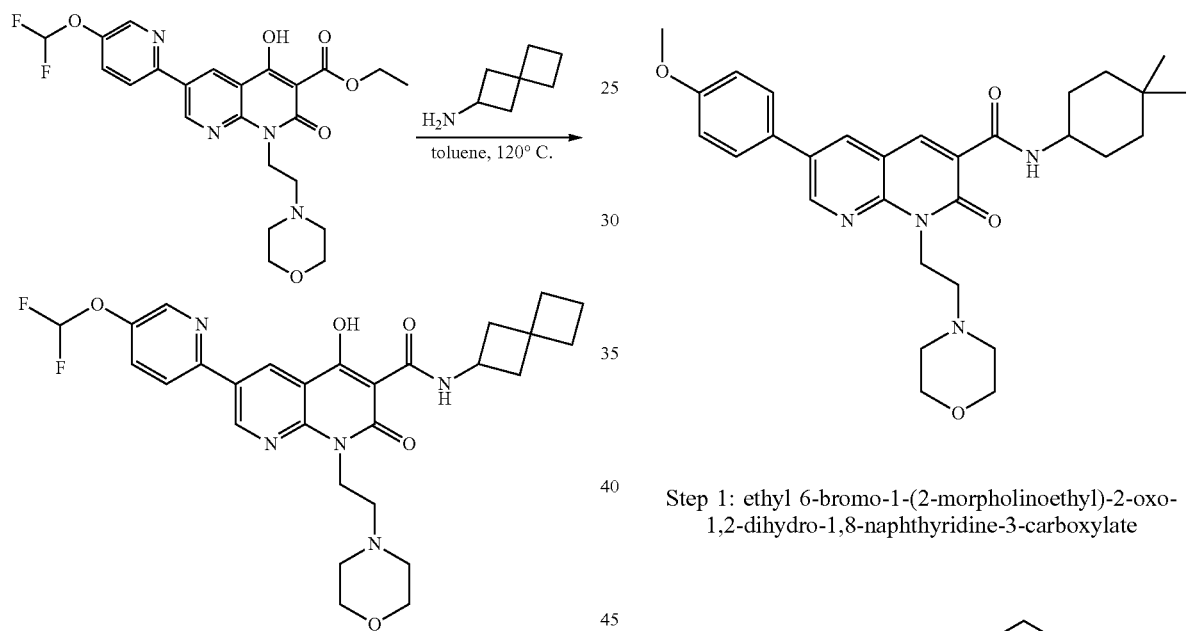

Step 1: ethyl 6-bromo-1-(2-morpholinoethyl)-2-oxo-1,2-dihydro-1,8-naphthyridine-3-carboxylate To a solution of ethyl 6-bromo-2-oxo-1H-1,8-naphthyridine-3-carboxylate (2 g, 6.73 mmol, 1 eq) in DMF (15 mL)

was added Cs₂CO₃ (6.14 g, 18.85 mmol, 2.8 eq) at 20° C. The mixture was stirred at 20° C. for 1 h, 4-(2-chloroethyl)morpholine (2.51 g, 13.46 mmol, 2 eq, HCl) was added into the mixture at 20° C., the mixture was stirred at 50° C. for 14 h. TLC showed all the starting material was consumed and formation of a major spot. The residue was poured into water (200 mL), the aqueous phase was extracted with ethyl acetate (3×100 mL).

The combined organic phase was washed with brine (100 mL), dried with anhydrous Na₂SO₄, filtered and concentrated. The residue was purified by column chromatography (SiO₂, petroleum ether:ethyl acetate=0:1) ethyl 6-bromo-1-(2-morpholinoethyl)-2-oxo-1,8-naphthyridine-3-carboxylate to produce ethyl 6-bromo-1-(2-morpholinoethyl)-2-oxo-1,2-dihydro-1,8-naphthyridine-3-carboxylate (2 g, 4.87 mmol) as a yellow solid.

Step 2: 6-(4-methoxyphenyl)-1-(2-morpholinoethyl)-2-oxo-1,2-dihydro-1,8-naphthyridine-3-carboxylic acid

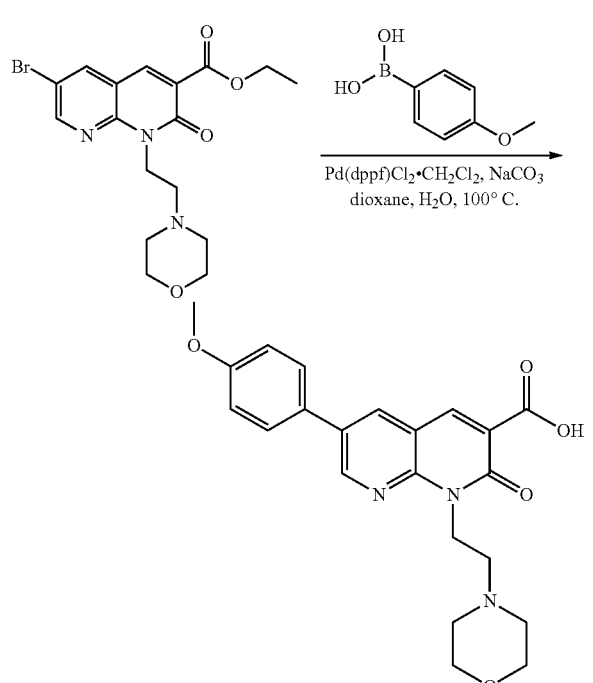

To a solution of (4-methoxyphenyl) boronic acid (1.26 g, 8.29 mmol, 2 eq), ethyl 6-bromo-1-(2-morpholinoethyl)-2-oxo-1,8-naphthyridine-3-carboxylate (1.7 g, 4.14 mmol, 1 eq) in H₂O (5 mL) and dioxane (20 mL) was added Na₂CO₃ (878.38 mg, 8.29 mmol, 2 eq), Pd (dppf) Cl₂·CH₂Cl₂ (338.39 mg, 414.37 μmol, 0.1 eq) at 20° C. under N2. The mixture was stirred at 100° C. for 15 h. LCMS showed all the starting material was consumed and the formation of a major peak.

The mixture was filtered. The filtrate was purified by prep-HPLC (column: Phenomenex Luna C18 150*30 mm*5 μm; mobile phase: [water (0.04% HCl)-ACN]; B %: 20%-32%, 10 min) to produce 6-(4-methoxyphenyl)-1-(2-morpholinoethyl)-2-oxo-1,2-dihydro-1,8-naphthyridine-3-carboxylic acid (1.3 g, 2.98 mmol) as a light yellow solid.

¹H NMR (400 MHz, DMSO-d₆) δ=9.15 (s, 1H), 8.96 (s, 1H), 8.81 (s, 1H), 7.77 (br d, J=8.4 Hz, 2H), 7.12 (br d, J=8.6 Hz, 2H), 4.80 (br s, 2H), 3.86-3.57 (m, 7H). LCMS for product (ESI+): m/z 410.3 [M+H]⁺, Rt: 0.739 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% CF₃CO₂H in water, mobile phase B was 0.018% CF₃CO₂H in CH₃CN. The column used for the chromatography is a Chromolith Flash RP-18e 25-2 mm column. Detection methods are diode array (DAD) and evaporative light scattering (ELSD) detection as well as positive electrospray ionization (MS)).

Step 3: Preparation of N-(4,4-dimethylcyclohexyl)-6-(4-methoxyphenyl)-1-(2-morpholinoethyl)-2-oxo-1,2-dihydro-1,8-naphthyridine-3-carboxamide

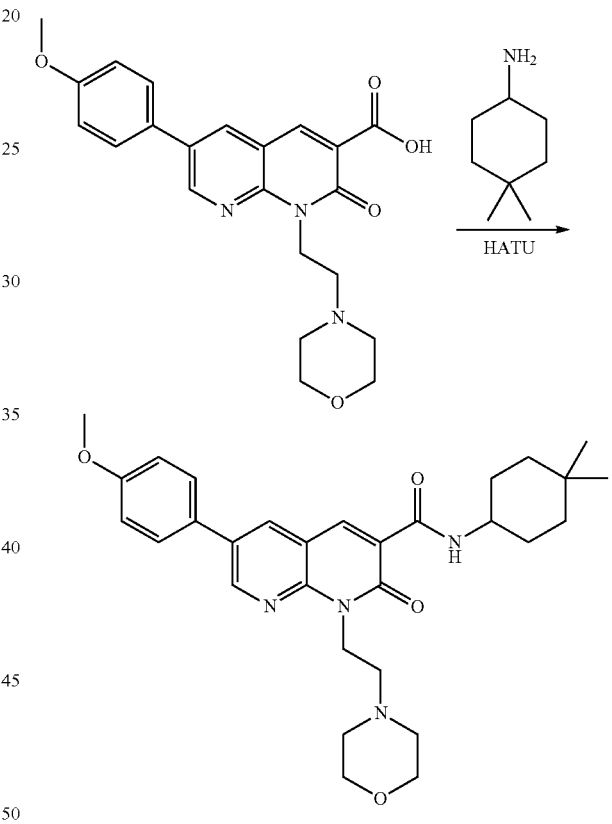

To a solution of 6-(4-methoxyphenyl)-1-(2-morpholinoethyl)-2-oxo-1,8-naphthyridine-3-carboxylic acid (70 mg, 170.97 μmol, 1 eq) in DMF (1 mL) was added HATU (130.01 mg, 341.94 μmol, 2 eq), DIEA (66.29 mg, 512.90 μmol, 89.34 μL, 3 eq) at 20° C. 4,4-dimethylcyclohexanamine (26.10 mg, 205.16 μmol, 1.2 eq) was added into the mixture at 20° C., the mixture was stirred at 20° C. for 1 h. LCMS showed complete consumption of the starting material and formation of a new peak.

The mixture was filtered ad the filtrate was purified by prep-HPLC (column: Waters Xbridge BEH C18 100*25 mm*5 μm; mobile phase: [water (10 mM NH₄HCO₃)-ACN]; B %: 50%-85%, 8 min) to produce N-(4,4-dimethylcyclohexyl)-6-(4-methoxyphenyl)-1-(2-morpholinoethyl)-2-oxo-1,2-dihydro-1,8-naphthyridine-3-carboxamide (38.7 mg, 72.60 μmol) as a light yellow solid.

$^1$H NMR (400 MHz, CDCl$_3$) δ=9.95-9.60 (m, 1H), 8.93 (s, 1H), 8.90 (d, J=1.5 Hz, 1H), 8.18 (d, J=1.8 Hz, 1H), 7.57 (d, J=8.8 Hz, 2H), 7.06 (d, J=8.6 Hz, 2H), 4.85-4.77 (m, 2H), 4.01-3.94 (m, 1H), 3.89 (s, 3H), 3.77-3.62 (m, 4H), 2.84-2.57 (m, 6H), 1.98-1.82 (m, 2H), 1.57-1.26 (m, 6H), 0.97 (d, J=7.1 Hz, 6H). LCMS for product (ESI+): m/z 519.2 [M+H]$^+$, Rt: 2.341 min.

LCMS Method

The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization.

Example 27—Synthesis of N-(4,4-difluorocyclohexyl)-6-(4-methoxyphenyl)-1-(2-morpholinoethyl)-2-oxo-1,2-dihydro-1,8-naphthyridine-3-carboxamide (Compound 27)

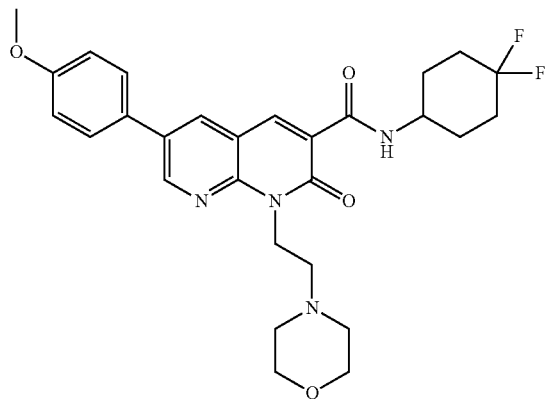 [SMILES: COc1ccc(-c2cnc3c(c2)cc(C(=O)NC2CCC(F)(F)CC2)c(=O)n3CCN2CCOCC2)cc1]

Preparation of N-(4,4-difluorocyclohexyl)-6-(4-methoxyphenyl)-1-(2-morpholinoethyl)-2-oxo-1,2-dihydro-1,8-naphthyridine-3-carboxamide

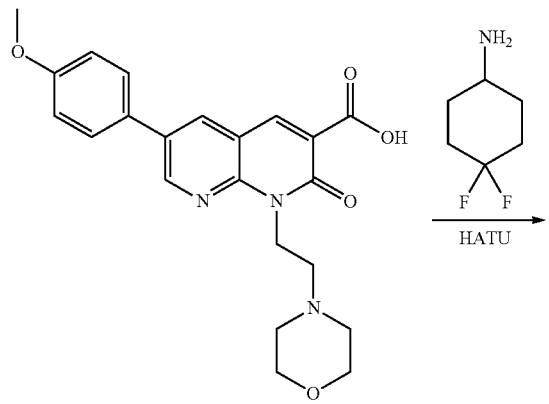

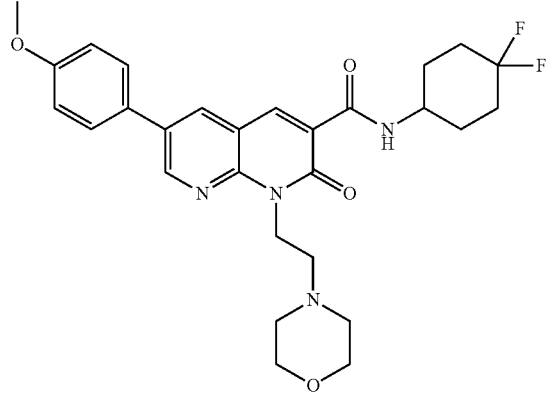

To a solution of 6-(4-methoxyphenyl)-1-(2-morpholinoethyl)-2-oxo-1,8-naphthyridine-3-carboxylic acid (70 mg, 170.97 μmol, 1 eq) in DMF (1 mL) was added HATU (130.01 mg, 341.94 μmol, 2 eq), DIEA (66.29 mg, 512.90 μmol, 89.34 μL, 3 eq) at 20° C. 4,4-difluorocyclohexanamine (35.21 mg, 205.16 μmol, 1.2 eq, HCl) was added into the mixture at 20° C., the mixture was stirred at 20° C. for 1 h. LCMS showed complete consumption of the starting material and formation of a new peak.

The mixture was filtered and the filtrate was purified by prep-HPLC (column: Waters Xbridge BEH C18 100*25 mm*5 μm; mobile phase: [water (10 mM NH$_4$HCO$_3$)-ACN]; B %: 50%-85%, 8 min) to produce N-(4,4-difluorocyclohexyl)-6-(4-methoxyphenyl)-1-(2-morpholinoethyl)-2-oxo-1,2-dihydro-1,8-naphthyridine-3-carboxamide (26.5 mg, 49.67 μmol) was obtained as a light yellow solid.

$^1$H NMR (400 MHz, CDCl$_3$) δ=9.91 (br d, J=7.7 Hz, 1H), 8.93-8.87 (m, 2H), 8.17 (d, J=2.4 Hz, 1H), 7.56 (d, J=8.6 Hz, 2H), 7.05 (d, J=8.6 Hz, 2H), 4.78 (br t, J=7.1 Hz, 2H), 4.14 (br s, 1H), 3.88 (s, 3H), 3.68 (br d, J=4.0 Hz, 4H), 2.74 (br t, J=6.9 Hz, 2H), 2.63 (br s, 4H), 2.12 (br s, 4H), 1.93 (br s, 2H), 1.84-1.70 (m, 2H). LCMS for product (ESI+): m/z 527.1 [M+H]$^+$, Rt: 2.141 min.

LCMS Method

The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization.

Example 28—Synthesis of 6-(4-methoxyphenyl)-1-(2-morpholinoethyl)-2-oxo-N-(spiro[2.5]octan-6-yl)-1,2-dihydro-1,8-naphthyridine-3-carboxamide (Compound 28)

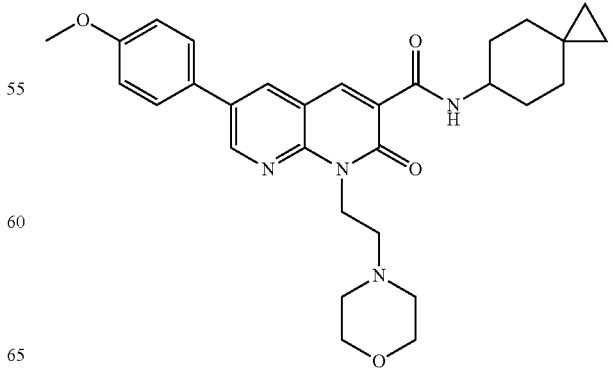

Step 1: tert-butyl (4-methylenecyclohexyl)carbamate (F2)

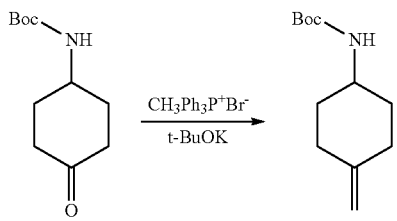

To a solution of methyltriphenylphosphonium bromide (16.75 g, 46.89 mmol, 2 eq) in THF (40 mL) was added potassium; 2-methylpropan-2-olate (1 M, 47.0 mL, 2 eq) at −20° C. under $N_2$. The mixture was stirred at −20° C. for 0.5 h, tert-butyl N-(4-oxocyclohexyl)carbamate (5 g, 23.44 mmol, 5.00 mL, 1 eq) was added into the mixture at 0° C. The mixture was stirred at 20° C. for 14.5 h. LCMS showed complete consumption of the starting material and formation of a new peak. TLC showed all the starting material was consumed and the new major spot was the desired product. The reaction mixture was poured into water (500 mL), the aqueous phase was extracted with ethyl acetate (3×100 mL).

The combined organic phase was washed with brine (100 mL), dried with anhydrous $Na_2SO_4$, filtered and concentrated. The residue was purified by silica gel chromatography (column height: 250 mm, diameter: 100 mm, 100-200 mesh silica gel, Petroleum ether:Ethyl acetate=10:1 to 0:1) to produce tert-butyl (4-methylenecyclohexyl)carbamate (4 g, 18.93 mmol) as a white solid.

Step 2: tert-butyl spiro[2.5]octan-6-ylcarbamate (F3)

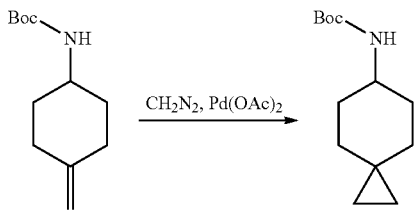 [SMILES: C=C1CCC(NC(=O)OC(C)(C)C)CC1 ; CC(C)(C)OC(=O)NC1CCC2(CC1)CC2]

To a solution of tert-butyl N-(4-methylenecyclohexyl) carbamate (200 mg, 946.52 μmol, 1 eq) in DCM (30 mL) was added diazomethane (39.79 mg, 946.52 μmol, 1 eq), $Pd(OAc)_2$ (21.25 mg, 94.65 μmol, 0.1 eq) at −78° C., the mixture was stirred at −78° C. for 30 min, warm to 20° C., the mixture was stirred at 20° C. for 15 h.

LCMS formation of the desired product the desires mass. The mixture was concentrated, dissolved in DMF (1 mL) and purified by prep-HPLC (column: Phenomenex Luna C18 100*30 mm*5 μm; mobile phase: [water (0.1% TFA)-ACN]; B %: 45%-75%, 12 min) to yield tert-butyl spiro [2.5]octan-6-ylcarbamate (6 mg, 26.63 μmol, 2.81% yield) as a white solid.

$^1$H NMR (400 MHz, $CDCl_3$) δ=4.54-4.36 (m, 1H), 3.57-3.43 (m, 1H), 1.95-1.86 (m, 2H), 1.76-1.66 (m, 2H), 1.46 (s, 9H), 1.37-1.26 (m, 2H), 1.03-0.94 (m, 2H), 0.34-0.26 (m, 2H), 0.23-0.17 (m, 2H).

Step 3: spiro[2,5]octan-6-amine (F)

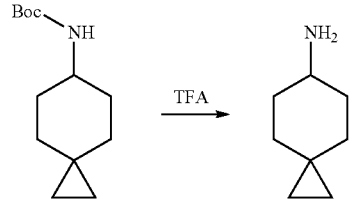 [SMILES: CC(C)(C)OC(=O)NC1CCC2(CC1)CC2 ; NC1CCC2(CC1)CC2]

To a solution of tert-butyl N-spiro[2.5]octan-6-ylcarbamate (5 mg, 22.19 μmol, 1 eq) in DCM (0.2 mL) was added TFA (77.00 mg, 675.30 μmol, 0.05 mL, 30.43 eq) at 20° C., the mixture was stirred at 20° C. for 1 h.

LCMS showed complete consumption of the starting material and formation of a new peak. The mixture was concentrated to produce spiro[2.5]octan-6-amine (2.5 mg) as yellow oil (used without further purification).

LCMS for product (ESI+): m/z 126.4 $[M+1]^+$, Rt: 0.161 min.

LCMS Method

The gradient was 10-90% B in 1.15 min, with a hold at 90% B for 0.4 min, 90-10% B in 0.01 min, and then hold at 10% B for 0.54 min (1.0 mL/min flow rate). Mobile phase A was 0.0375% $CF_3CO_2H$ in water, mobile phase B was 0.018% $CF_3CO_2H$ in $CH_3CN$. The column used for the chromatography was a 2.1×30 mm phenomenex Luna-C18 column (5 μm particles). Detection methods are diode array (DAD) and evaporative light scattering (ELSD) detection as well as positive electrospray ionization (MS).

Step 4: Preparation of 6-(4-methoxyphenyl)-1-(2-morpholinoethyl)-2-oxo-N-(spiro[2.5]octan-6-yl)-1, 2-dihydro-1,8-naphthyridine-3-carboxamide

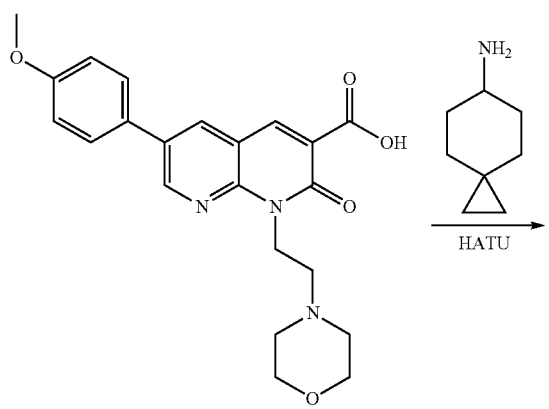

-continued

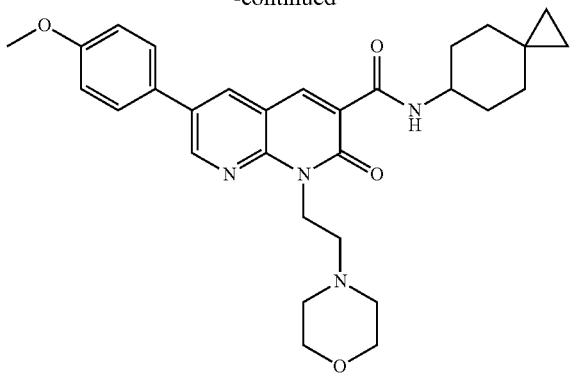

To a solution of 6-(4-methoxyphenyl)-1-(2-morpholinoethyl)-2-oxo-1,8-naphthyridine-3-carboxylic acid (8 mg, 19.54 μmol, 1 eq) in DMF (0.5 mL) was added HATU (14.86 mg, 39.08 μmol, 2 eq), DIEA (7.58 mg, 58.62 μmol, 89.34 μL, 3 eq) at 20° C. (4-fluorophenyl) methanamine (25.67 mg, 205.16 μmol, 10.21 μL, 3 eq) was added into the mixture at 20° C., the mixture was stirred at 20° C. for 1 h. LCMS showed complete consumption of the starting material and formation of a new peak.

The mixture was filtered and the filtrate was purified by prep-HPLC (column: Waters Xbridge BEH C18 100*25 mm*5 μm; mobile phase: [water (10 mM $NH_4HCO_3$)-ACN]; B %: 50%-85%, 8 min) to produce 6-(4-methoxyphenyl)-1-(2-morpholinoethyl)-2-oxo-N-(spiro[2.5]octan-6-yl)-1,2-dihydro-1,8-naphthyridine-3-carboxamide (2.3 mg, 4.43 μmol) as a light yellow solid.

$^1$H NMR (400 MHz, $CDCl_3$) δ=9.82 (br d, J=8.4 Hz, 1H), 8.94 (s, 1H), 8.90 (d, J=2.4 Hz, 1H), 8.19 (d, J=2.4 Hz, 1H), 7.57 (d, J=8.6 Hz, 2H), 7.06 (d, J=8.6 Hz, 2H), 4.83-4.77 (m, 2H), 4.12 (br s, 1H), 3.89 (s, 3H), 3.71 (t, J=4.5 Hz, 4H), 2.76 (t, J=7.4 Hz, 2H), 2.65 (br s, 4H), 2.02 (br d, J=8.6 Hz, 2H), 1.80-1.71 (m, 2H), 1.65-1.62 (m, 2H), 1.13 (br d, J=13.5 Hz, 2H), 0.36-0.31 (m, 2H), 0.30-0.24 (m, 2H). LCMS for product (ESI+): m/z 517.3 [M+H]$^+$, Rt: 2.282 min.

LCMS Method

The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization.

Example 29—Synthesis of 6-(4-methoxyphenyl)-1-(2-morpholinoethyl)-2-oxo-N-(spiro[3.3]heptan-2-yl)-1,2-dihydro-1,8-naphthyridine-3-carboxamide (Compound 29)

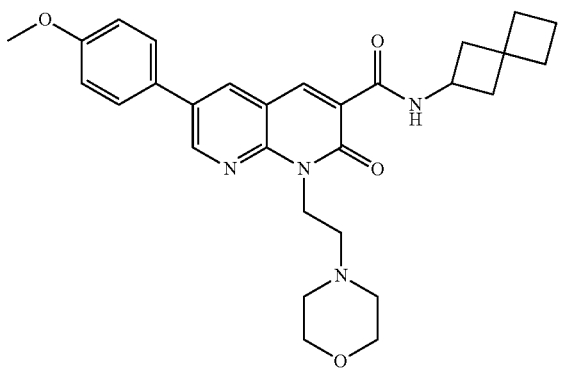 [SMILES: COc1ccc(-c2cnc3c(c2)cc(C(=O)NC2CC4(CCC4)C2)c(=O)n3CCN2CCOCC2)cc1]

Preparation of 6-(4-methoxyphenyl)-1-(2-morpholinoethyl)-2-oxo-N-(spiro[3.3]heptan-2-yl)-1,2-dihydro-1,8-naphthyridine-3-carboxamide

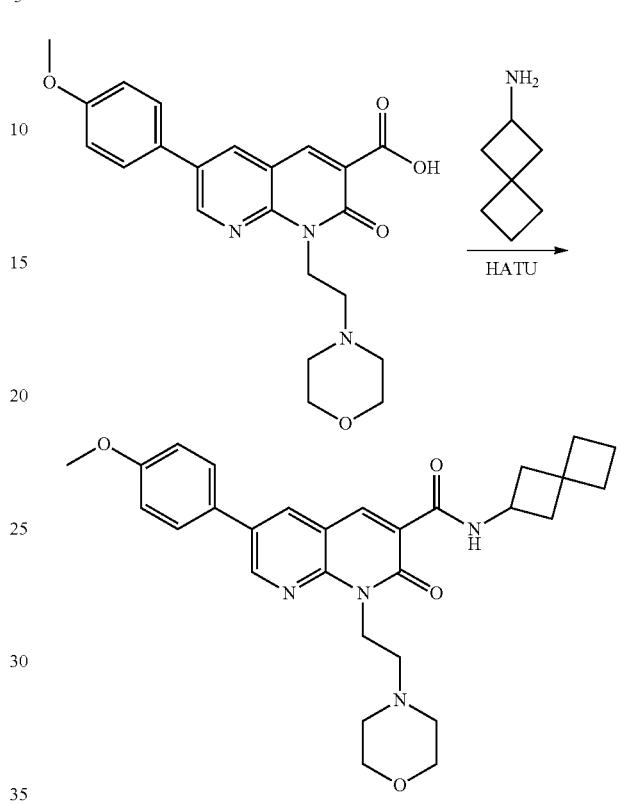

To a solution of 6-(4-methoxyphenyl)-1-(2-morpholinoethyl)-2-oxo-1,8-naphthyridine-3-carboxylic acid (75 mg, 183.18 μmol, 1 eq) in DMF (1 mL) was added HATU (139.30 mg, 366.36 μmol, 2 eq), DIEA (71.02 mg, 549.54 μmol, 95.72 μL, 3 eq) at 20° C. spiro[3.3]heptan-2-amine (24.44 mg, 219.82 μmol, 1.2 eq) was added into the mixture at 20° C., the mixture was stirred at 20° C. for 1 h. LCMS showed complete consumption of the starting material and formation of a new peak.

The mixture was filtered and the filtrate was purified by prep-HPLC (column: Waters Xbridge BEH C18 100*25 mm*5 μm; mobile phase: [water (10 mM $NH_4HCO_3$)-ACN]; B %: 50%-85%, 8 min) to produce 6-(4-methoxyphenyl)-1-(2-morpholinoethyl)-2-oxo-N-(spiro[3.3]heptan-2-yl)-1,2-dihydro-1,8-naphthyridine-3-carboxamide (37.3 mg, 73.69 μmol) as light yellow solid.

$^1$H NMR (400 MHz, $CDCl_3$) δ=9.87 (br d, J=7.5 Hz, 1H), 8.95-8.86 (m, 2H), 8.17 (d, J=2.4 Hz, 1H), 7.65-7.47 (m, 2H), 7.06 (d, J=8.8 Hz, 2H), 4.87-4.69 (m, 2H), 4.57-4.40 (m, 1H), 3.89 (s, 3H), 3.71 (t, J=4.5 Hz, 4H), 2.83-2.71 (m, 2H), 2.65 (br s, 4H), 2.58-2.46 (m, 2H), 2.10 (t, J=7.3 Hz, 2H), 2.05-1.95 (m, 4H), 1.90-1.81 (m, 2H). LCMS for product (ESI+): m/z 503.3 [M+H]$^+$, Rt: 2.236 min.

LCMS Method

The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1

Example 30—Synthesis of N-(1-(4-fluorophenyl)ethyl)-6-(4-methoxyphenyl)-1-(2-morpholinoethyl)-2-oxo-1,2-dihydro-1,8-naphthyridine-3-carboxamide (Compound 30)

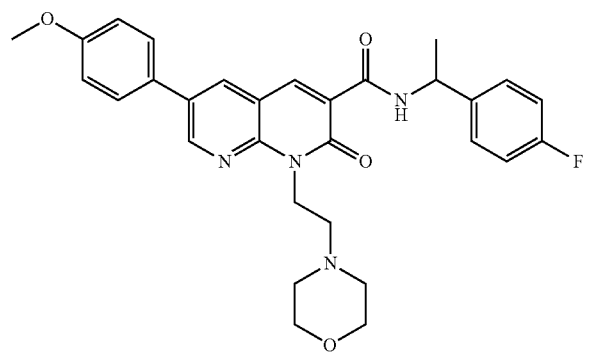 [SMILES: COc1ccc(-c2cnc3c(c2)cc(C(=O)NC(C)c2ccc(F)cc2)c(=O)n3CCN2CCOCC2)cc1]

Preparation of N-(1-(4-fluorophenyl)ethyl)-6-(4-methoxyphenyl)-1-(2-morpholinoethyl)-2-oxo-1,2-dihydro-1,8-naphthyridine-3-carboxamide

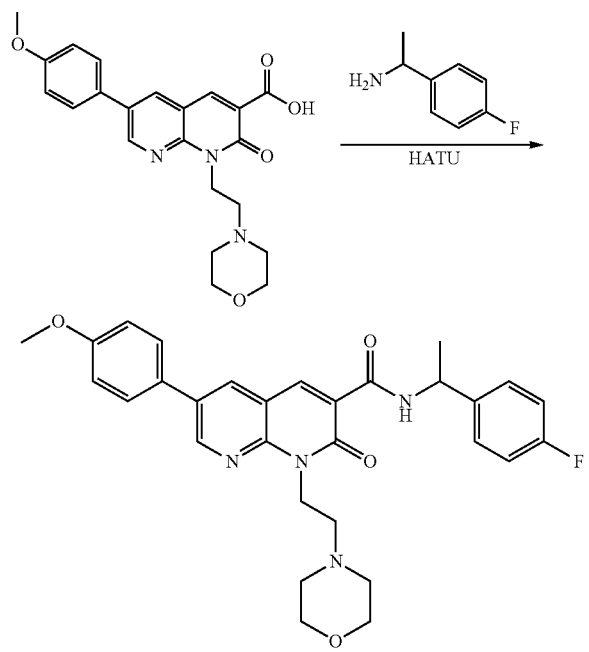

To a solution of 6-(4-methoxyphenyl)-1-(2-morpholinoethyl)-2-oxo-1,8-naphthyridine-3-carboxylic acid (70 mg, 170.97 µmol, 1 eq) in DMF (1 mL) was added HATU (130.01 mg, 341.94 µmol, 2 eq), DIEA (66.29 mg, 512.90 µmol, 89.34 µL, 3 eq) at 20° C. 1-(4-fluorophenyl)ethanamine (26.17 mg, 188.06 µmol, 24.69 µL, 1.1 eq) was added into the mixture at 20° C., the mixture was stirred at 20° C. for 1 h. LCMS showed complete consumption of the starting material and formation of a new peak.

The mixture was filtered and the filtrate was purified by prep-HPLC (column: Waters Xbridge BEH C18 100*25 mm*5 µm; mobile phase: [water (10 mM NH$_4$HCO$_3$)-ACN]; B %: 50%-85%, 8 min) to produce N-(1-(4-fluorophenyl)ethyl)-6-(4-methoxyphenyl)-1-(2-morpholinoethyl)-2-oxo-1,2-dihydro-1,8-naphthyridine-3-carboxamide (12.1 mg, 22.35 µmol) as a light yellow solid.

$^1$H NMR (400 MHz, CDCl$_3$) δ=10.20 (br d, J=7.7 Hz, 1H), 9.07-8.72 (m, 2H), 8.16 (d, J=2.0 Hz, 1H), 7.56 (br d, J=8.6 Hz, 2H), 7.48-7.36 (m, 2H), 7.15-6.94 (m, 4H), 5.42-5.23 (m, 1H), 4.92-4.66 (m, 2H), 3.89 (s, 3H), 3.70 (br t, J=4.0 Hz, 4H), 2.76 (br t, J=7.2 Hz, 2H), 2.65 (br s, 4H), 1.61 (br s, 3H). LCMS for product (ESI+): m/z 531.3 [M+H]$^+$, Rt: 2.226 min.

LCMS Method

The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization.

Example 31—Synthesis of 6-(4-methoxyphenyl)-1-(2-morpholinoethyl)-2-oxo-N-(2-oxaspiro[3.3]heptan-6-yl)-1,2-dihydro-1,8-naphthyridine-3-carboxamide (Compound 31)

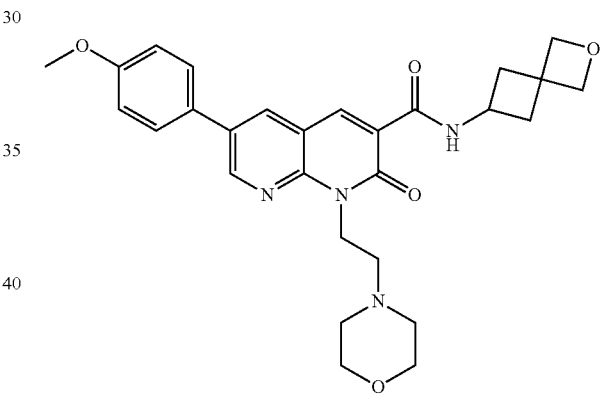

Preparation of 6-(4-methoxyphenyl)-1-(2-morpholinoethyl)-2-oxo-N-(2-oxaspiro[3.3]heptan-6-yl)-1,2-dihydro-1,8-napthyridine-3-carboxamide

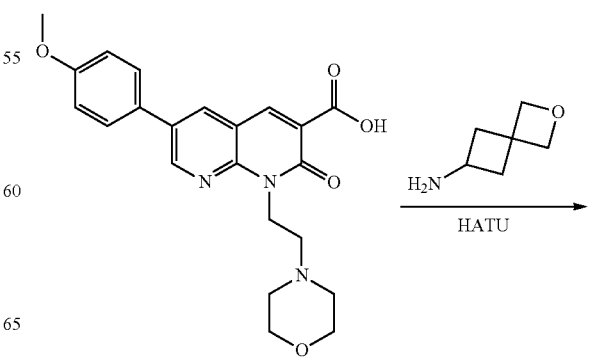

-continued

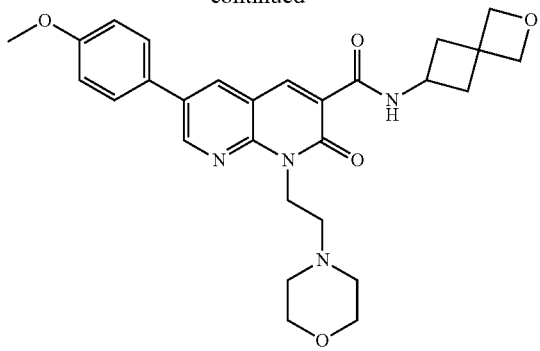

To a solution of 6-(4-methoxyphenyl)-1-(2-morpholinoethyl)-2-oxo-1,8-naphthyridine-3-carboxylic acid (70 mg, 170.97 μmol, 1 eq) in DMF (1 mL) was added HATU (130.01 mg, 341.94 μmol, 2 eq), DIEA (66.29 mg, 512.90 μmol, 89.34 μL, 3 eq) at 20° C. 2-oxaspiro[3.3]heptan-6-amine (28.14 mg, 188.06 μmol, 1.1 eq, HCl) was added into the mixture at 20° C., the mixture was stirred at 20° C. for 1 h. LCMS showed complete consumption of the starting material and formation of a new peak.

The mixture was filtered and the filtrate was purified by prep-HPLC (column: Waters Xbridge BEH C18 100*25 mm*5 μm; mobile phase: [water (10 mM NH$_4$HCO$_3$)-ACN]; B %: 50%-85%, 8 min) to produce 6-(4-methoxyphenyl)-1-(2-morpholinoethyl)-2-oxo-N-(2-oxaspiro[3.3]heptan-6-yl)-1,2-dihydro-1,8-naphthyridine-3-carboxamide (21.2 mg, 41.76 μmol) as light yellow solid.

$^1$H NMR (400 MHz, CDCl$_3$) δ=10.03-9.90 (m, 1H), 8.91 (s, 2H), 8.17 (d, J=2.2 Hz, 1H), 7.56 (d, J=8.6 Hz, 2H), 7.06 (d, J=8.4 Hz, 2H), 4.86-4.74 (m, 4H), 4.67 (s, 2H), 4.47-4.31 (m, 1H), 3.89 (s, 3H), 3.70 (t, J=4.5 Hz, 4H), 2.87-2.71 (m, 4H), 2.64 (br s, 4H), 2.37-2.21 (m, 2H). LCMS for product (ESI+): m/z 505.2 [M+H]$^+$, Rt: 1.912 min.

LCMS Method

5_95AB_6 min-220: The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization.

Example 32—Synthesis of 6-(4-fluorophenyl)-1-(2-morpholinoethyl)-2-oxo-N-(spiro[3.3]heptan-2-yl)-1,2-dihydro-1,8-naphthyridine-3-carboxamide (Compound 32)

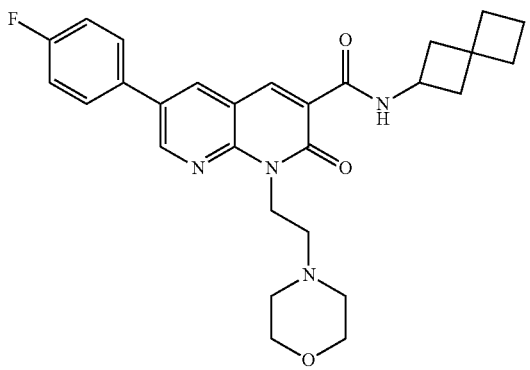 [SMILES: O=C(NC1CC2(CCC2)C1)c1cc2cc(-c3ccc(F)cc3)cnc2n(CCN2CCOCC2)c1=O]

Step 1: tert-butyl (4-methylenecyclohexyl)carbamate

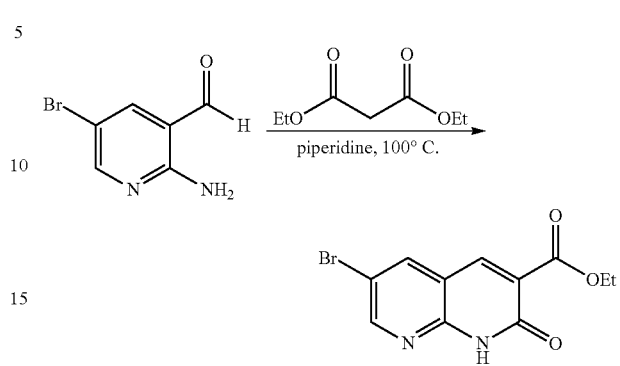

A solution of 2-amino-5-bromo-pyridine-3-carbaldehyde (6 g, 29.9 mmol, 1 eq), diethyl propanedioate (47.8 g, 298 mmol, 45 mL, 10 eq) and piperidine (12.7 g, 149 mmol, 14.7 mL, 5.0 eq) was heated to 100° C. for 12 h.

TLC (petroleum ether/ethyl acetate=1/1) showed the starting material was consumed and a new spot was detected. The reaction mixture was cooled to 0° C. The mixture was filtrated, and the resulting solid was collected by filtration and washed with methyl tertiary-butyl ether (30 mL) to produce tert-butyl (4-methylenecyclohexyl)carbamate (6 g, 20.2 mmol) as a white solid (used into next step without purification).

$^1$H NMR (400 MHz, DMSO-d$_6$) δ=12.61 (s, 1H), 8.69 (s, 1H), 8.55 (s, 1H), 8.44 (s, 1H), 4.28 (q, J=6.8 Hz, 2H), 1.29 (t, J=7.6 Hz, 3H).

Step 2: ethyl 6-bromo-1-(2-morpholinoethyl)-2-oxo-1,2-dihydro-1,8-naphthyridine-3-carboxylate

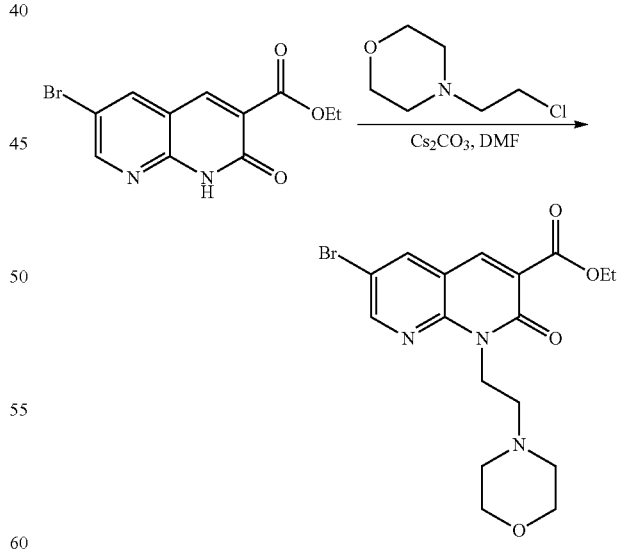

Ethyl 6-bromo-2-oxo-1H-1,8-naphthyridine-3-carboxylate (3 g, 10.1 mmol, 1 eq) and 4-(2-chloroethyl)morpholine (3.76 g, 20.2 mmol, 2.0 eq) were dissolved in DMF (50 mL). Cs$_2$CO$_3$ (9.87 g, 30.3 mmol, 3.0 eq) was added into the reaction solution. The solution was stirred at 50° C. for 12 h. LCMS showed complete consumption of the starting material and formation of a new peak. Water (100 mL) and ethyl acetate (50 mL) was added and the mixture was stirred for 5 min. The two phases were separated, and the water phase was extracted with ethyl acetate (3×50 mL).

The combined organic phases were washed with brine (50 mL), dried over anhydrous Na$_2$SO$_4$, filtered and concentrated. The residue was washed with methyl tertiary-butyl ether (30 mL) to yield ethyl 6-bromo-1-(2-morpholinoethyl)-2-oxo-1,2-dihydro-1,8-naphthyridine-3-carboxylate t (3 g, 7.31 mmol) as white solid.

$^1$H NMR (400 MHz, CHLOROFORM-d) δ=8.68 (d, J=2.0 Hz, 1H), 8.25 (s, 1H), 8.08 (d, J=2.4 Hz, 1H), 4.72-4.62 (m, 2H), 4.43 (q, J=7.3 Hz, 2H), 3.67 (t, J=4.6 Hz, 4H), 2.70 (t, J=7.1 Hz, 2H), 2.61 (br d, J=3.9 Hz, 4H), 1.42 (t, J=7.1 Hz, 3H).

Step 3: 6-bromo-1-(2-morpholinoethyl)-2-oxo-1,2-dihydro-1,8-naphthyridine-3-carboxylic acid

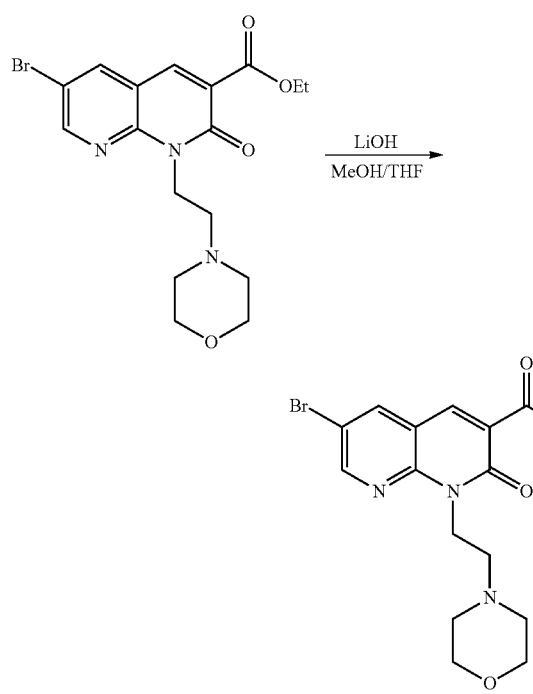

Ethyl 6-bromo-1-(2-morpholinoethyl)-2-oxo-1,8-naphthyridine-3-carboxylate (1 g, 2.44 mmol, 1 eq) was dissolved in THF (5 mL), MeOH (5 mL) and H$_2$O (5 mL). LiOH·H$_2$O (409 mg, 9.75 mmol, 4.0 eq) was added into the reaction solution. The solution was stirred at 30° C. for 12 h. LCMS showed complete consumption of the starting material and formation of a new peak. To the reaction mixture was added dropwise 6 N HCl to adjust the pH to 4-5. The reaction solution was stirred at 30° C. for 5 min.

The resulting solid was collected by filtration and dried under reduced pressure to produce 6-bromo-1-(2-morpholinoethyl)-2-oxo-1,2-dihydro-1,8-naphthyridine-3-carboxylic acid (0.8 g, 2.09 mmol) as a white solid.

$^1$H NMR (400 MHz, DMSO-d$_6$) δ=8.92 (s, 1H), 8.91-8.80 (m, 2H), 4.80 (t, J=6.0 Hz, 2H), 3.94 (br s, 2H), 3.76 (br s, 2H), 3.64 (br s, 2H), 3.50 (br s, 2H), 3.16 (br s, 2H).

Step 4: 6-bromo-1-(2-morpholinoethyl)-2-oxo-N-(spiro[3.3]heptan-2-yl)-1,2-dihydro-1,8-naphthyridine-3-carboxamide

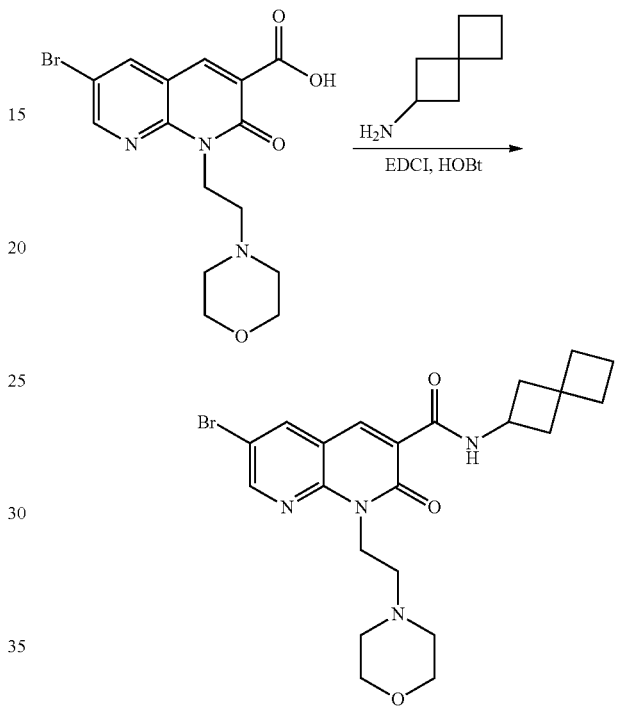

6-bromo-1-(2-morpholinoethyl)-2-oxo-1,8-naphthyridine-3-carboxylic acid (700 mg, 1.83 mmol, 1 eq), spiro[3.3]heptan-2-amine (270 mg, 1.83 mmol, 1.0 eq, HCl), EDCI (702 mg, 3.66 mmol, 2.0 eq) and HOBt (495 mg, 3.66 mmol, 2.0 eq) were dissolved in DMF (10 mL). The solution was stirred at 30° C. for 5 min. Then TEA (927 mg, 9.16 mmol, 1.27 mL, 5.0 eq) was added into the reaction solution. The solution was stirred at 30° C. for 12 h. LCMS showed complete consumption of the starting material and formation of a new peak. To the reaction solution was added methyl tertiary-butyl ether (20 mL).

The suspension was stirred at 30° C. for 5 min and the resulting solid was collected by filtration, washed with H$_2$O (10 mL) and dried under reduced pressure to produce 6-bromo-1-(2-morpholinoethyl)-2-oxo-N-(spiro[3.3]heptan-2-yl)-1,2-dihydro-1,8-naphthyridine-3-carboxamide (500 mg, 1.05 mmol) as a white solid (used in next step without purification).

$^1$H NMR (400 MHz, DMSO-d$_6$) δ=9.67 (d, J=7.8 Hz, 1H), 8.88 (d, J=2.4 Hz, 1H), 8.82 (s, 1H), 8.79 (d, J=2.4 Hz, 1H), 4.59 (br t, J=7.1 Hz, 2H), 4.29 (d, J=7.8 Hz, 1H), 3.53 (br t, J=4.2 Hz, 4H), 2.59 (br s, 2H), 2.42 (ddd, J=2.4, 7.2, 9.4 Hz, 2H), 2.09-2.01 (m, 2H), 1.99-1.90 (m, 4H), 1.85-1.76 (m, 2H).

Step 5: Preparation of 6-(4-fluorophenyl)-1-(2-morpholinoethyl)-2-oxo-N-(spiro[3.3]heptan-2-yl)-1,2-dihydro-1,8-naphthyridine-3-carboxamide

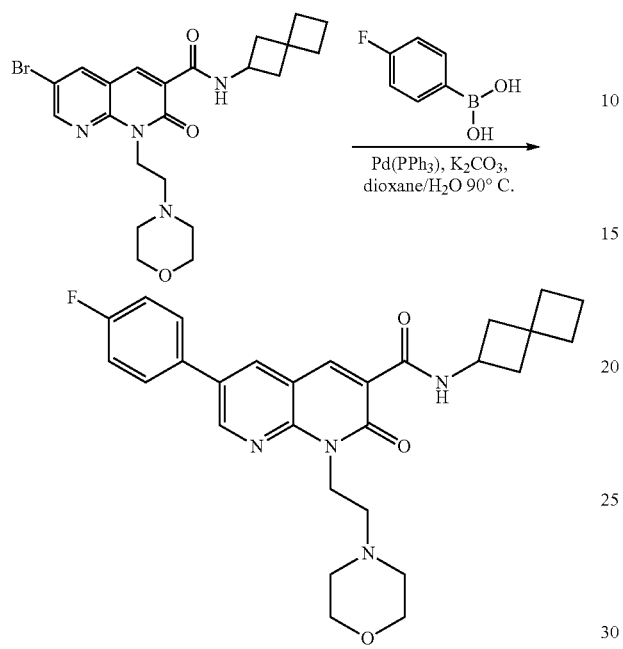

6-bromo-1-(2-morpholinoethyl)-2-oxo-N-spiro[3.3]heptan-2-yl-1,8-naphthyridine-3-carboxamide (10 mg, 21.0 µmol, 1 eq), (4-fluorophenyl)boronic acid (4.42 mg, 31.6 µmol, 1.5 eq), Pd(PPh$_3$)$_4$ (2.43 mg, 2.10 µmol, 0.1 eq) and K$_2$CO$_3$ (7.27 mg, 52.6 µmol, 2.5 eq) were dissolved in dioxane (0.5 mL) and H$_2$O (0.1 mL). The suspension was stirred at 90° C. for 12 h. LCMS showed complete consumption of the starting material and formation of a new peak. One additional vial was set up as described above and the reaction mixtures were combined.

The solvent was removed under reduced pressure and the residue was purified by prep-HPLC. Column: Phenomenex Luna C18 150*30 mm*5 µm; mobile phase: [water (0.04% HCl)—CH$_3$CN]; B %: 35%-63%, 10 min) to produce 6-(4-fluorophenyl)-1-(2-morpholinoethyl)-2-oxo-N-(spiro[3.3]heptan-2-yl)-1,2-dihydro-1,8-naphthyridine-3-carboxamide (10 mg, 17.8 µmol, HCl) as a white solid.

$^1$H NMR (400 MHz, METHANOL-d$_4$) δ=9.05 (d, J=2.4 Hz, 1H), 8.97 (s, 1H), 8.63 (s, 1H), 7.84-7.74 (m, 2H), 7.34-7.20 (m, 2H), 5.01 (br t, J=5.9 Hz, 2H), 4.37 (t, J=8.1 Hz, 1H), 4.06-3.47 (m, 10H), 2.59-2.46 (m, 2H), 2.17-2.09 (m, 2H), 2.05-1.96 (m, 4H), 1.92-1.83 (m, 2H). LCMS (ESI+): m/z 491.2 (M+H)$^+$, Rt: 2.28 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 33—Synthesis of 6-(2,3-dihydrobenzo[b][1,4]dioxin-6-yl)-1-(2-morpholinoethyl)-2-oxo-N-(spiro[3.3]heptan-2-yl)-1,2-dihydro-1,8-naphthyridine-3-carboxamide (Compound 33)

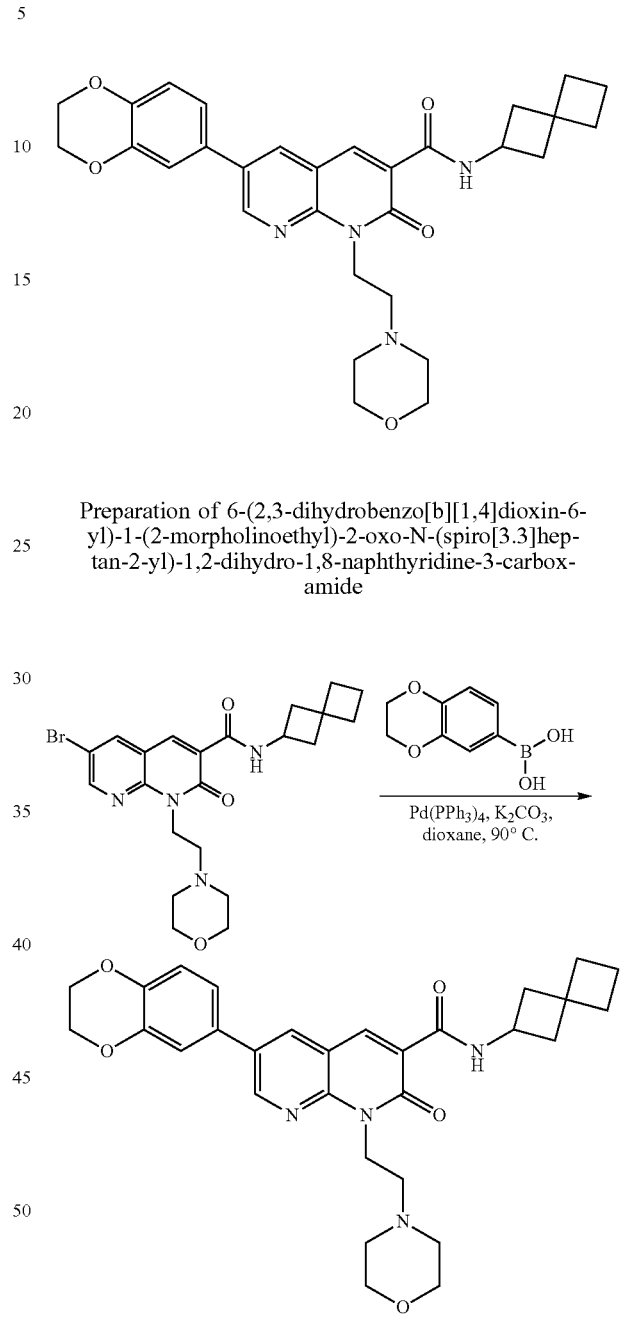

Preparation of 6-(2,3-dihydrobenzo[b][1,4]dioxin-6-yl)-1-(2-morpholinoethyl)-2-oxo-N-(spiro[3.3]heptan-2-yl)-1,2-dihydro-1,8-naphthyridine-3-carboxamide 6-bromo-1-(2-morpholinoethyl)-2-oxo-N-spiro[3.3]heptan-2-yl-1,8-naphthyridine-3-carboxamide (30 mg, 63.1 µmol, 1 eq), 2,3-dihydro-1,4-benzodioxin-6-ylboronic acid (11.4 mg, 63.1 µmol, 1 eq), Pd(PPh$_3$)$_4$ (7.29 mg, 6.31 µmol, 0.1 eq) and K$_2$CO$_3$ (21.8 mg, 158 µmol, 2.5 eq) were dissolved in dioxane (1 mL) and H$_2$O (0.5 mL). The suspension was stirred at 90° C. for 2 h. LCMS showed complete consumption of the starting material and formation of a new peak. One additional vial was set up as described above and the reaction mixtures were combined.

The solvent was removed under reduced pressure and the residue was purified by prep-HPLC (Column: Phenomenex Luna C18 150*30 mm*5 μm; mobile phase: [water (0.04% HCl)—CH₃CN]; B %: 35%-65%, 10 min) to produce 6-(2,3-dihydrobenzo[b][1,4]dioxin-6-yl)-1-(2-morpholinoethyl)-2-oxo-N-(spiro[3.3]heptan-2-yl)-1,2-dihydro-1,8-naphthyridine-3-carboxamide (14 mg, 24.5 μmol, HCl) as a yellow solid.

¹H NMR (400 MHz, METHANOL-d₄) δ=9.93 (br d, J=7.3 Hz, 1H), 9.00 (d, J=2.0 Hz, 1H), 8.95 (s, 1H), 8.55 (d, J=2.4 Hz, 1H), 7.29-7.19 (m, 2H), 6.99 (d, J=8.3 Hz, 1H), 5.02 (t, J=6.1 Hz, 2H), 4.40-4.33 (m, 1H), 4.11-3.37 (m, 10H), 2.55-2.47 (m, 2H), 2.15-2.10 (m, 2H), 2.05-1.96 (m, 4H), 1.93-1.84 (m, 2H). LCMS (ESI+): m/z 531.3 (M+H)+, Rt: 2.264 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 34—Synthesis of 1-(2-morpholinoethyl)-2-oxo-6-(pyridin-2-yl)-N-(spiro[3.3]heptan-2-yl)-1,2-dihydro-1,8-naphthyridine-3-carboxamide (Compound 34)

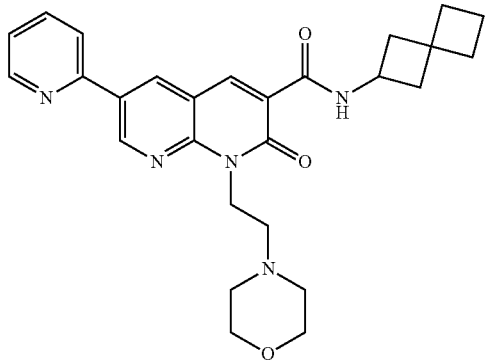 [SMILES: O=C(NC1CC2(CCC2)C1)c1cc2cc(-c3ccccn3)cnc2n(CCN2CCOCC2)c1=O]

Preparation of 1-(2-morpholinoethyl)-2-oxo-6-(pyridin-2-yl)-N-(spiro[3.3]heptan-2-yl)-1,2-dihydro-1,8-naphthyridine-3-carboxamide

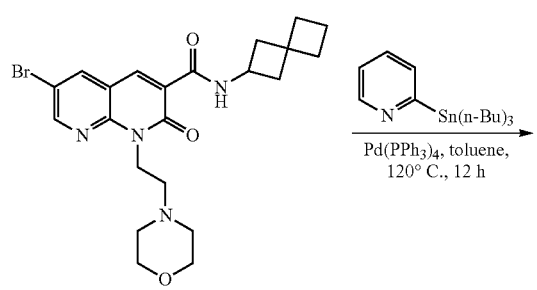

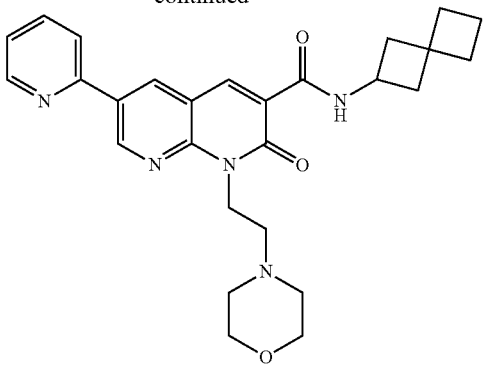

6-bromo-1-(2-morpholinoethyl)-2-oxo-N-spiro[3.3]heptan-2-yl-1,8-naphthyridine-3-carboxamide (10 mg, 21.0 μmol, 1 eq), tributyl(2-pyridyl)stannane (11.6 mg, 31.6 μmol, 1.5 eq) and Pd(PPh₃)₄ (2.43 mg, 2.10 μmol, 0.1 eq) were dissolved in toluene (0.5 mL). The suspension was stirred at 120° C. for 2 h. LCMS showed complete consumption of the starting material and formation of a new peak. One additional vial was set up as described above and all two reaction mixtures were combined. One additional vial was set up as described above and all two reaction mixtures were combined.

The solvent was removed under reduced pressure and the residue was purified by prep-HPLC (Column: Phenomenex Luna C18 150*30 mm*5 μm; mobile phase: [water (0.04% HCl)—CH₃CN]; B %: 25%-55%, 10 min) to produce 1-(2-morpholinoethyl)-2-oxo-6-(pyridin-2-yl)-N-(spiro[3.3]heptan-2-yl)-1,2-dihydro-1,8-naphthyridine-3-carboxamide (4.5 mg, 8.82 μmol, HCl) as a white solid.

¹H NMR (400 MHz, METHANOL-d₄) δ=9.37 (d, J=2.0 Hz, 1H), 9.00 (s, 1H), 8.96 (d, J=2.0 Hz, 1H), 8.85 (br d, J=5.4 Hz, 1H), 8.39-8.34 (m, 1H), 8.31-8.27 (m, 1H), 7.79 (br t, J=6.4 Hz, 1H), 5.06 (br t, J=5.9 Hz, 2H), 4.38 (t, J=7.8 Hz, 1H), 4.13 (br d, J=11.7 Hz, 2H), 3.91-3.77 (m, 4H), 3.73 (br t, J=5.9 Hz, 2H), 3.38-3.32 (m, 2H), 2.57-2.45 (m, 2H), 2.17-2.11 (m, 2H), 2.05-1.97 (m, 4H), 1.90 (q, J=7.8 Hz, 2H). LCMS for product (ESI+): m/z 474.2 (M+H)+, Rt: 2.003 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 35—Synthesis of 1-(2-morpholinoethyl)-2-oxo-6-(pyrimidin-4-yl)-N-(spiro[3.3]heptan-2-yl)-1,2-dihydro-1,8-naphthyridine-3-carboxamide (Compound 35)

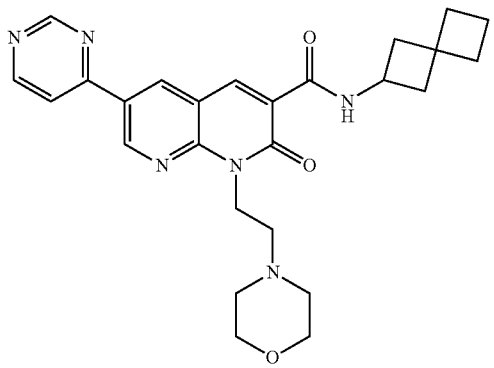 [SMILES: O=C(NC1CC2(CCC2)C1)c1cc2cc(-c3ccncn3)cnc2n(CCN2CCOCC2)c1=O]

Preparation of 1-(2-morpholinoethyl)-2-oxo-6-(pyrimidin-4-yl)-N-(spiro[3.3]heptan-2-yl)-1,2-dihydro-1,8-naphthyridine-3-carboxamide

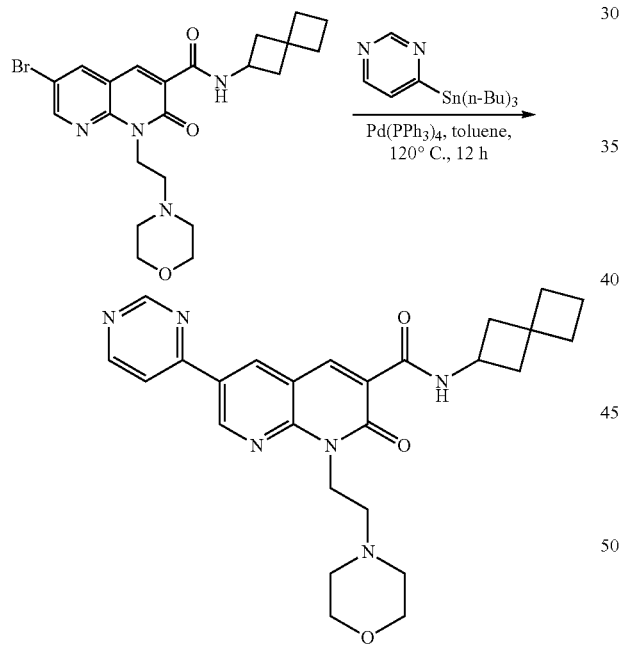

6-bromo-1-(2-morpholinoethyl)-2-oxo-N-spiro[3.3]heptan-2-yl-1,8-naphthyridine-3-carboxamide (10 mg, 21.04 μmol, 1 eq), tributyl(pyrimidin-4-yl)stannane (11.7 mg, 31.6 μmol, 1.5 eq) and Pd(PPh$_3$)$_4$ (2.43 mg, 2.10 μmol, 0.1 eq) were dissolved in toluene (0.5 mL). The suspension was stirred at 120° C. for 12 h. LCMS showed complete consumption of the starting material and formation of a new peak. One additional vial was set up as described above and reaction mixtures were combined.

The solvent was removed under reduced pressure the residue was purified by prep-HPLC (Column: Welch Xtimate C18 150*25 mm*5 μm; mobile phase: [water (0.04% HCl)—CH$_3$CN]; B %: 15%-40%, 10 min) to produce 1-(2-morpholinoethyl)-2-oxo-6-(pyrimidin-4-yl)-N-(spiro[3.3]heptan-2-yl)-1,2-dihydro-1,8-naphthyridine-3-carboxamide (6.5 mg, 12.7 μmol, HCl) as a white solid.

$^1$H NMR (400 MHz, METHANOL-d$_4$) δ=9.60 (d, J=2.4 Hz, 1H), 9.29 (d, J=1.0 Hz, 1H), 9.17 (d, J=2.4 Hz, 1H), 9.02 (s, 1H), 8.91 (d, J=5.4 Hz, 1H), 8.19 (dd, J=1.5, 5.4 Hz, 1H), 5.07 (t, J=5.9 Hz, 2H), 4.38 (t, J=7.8 Hz, 1H), 4.19-4.09 (m, 2H), 3.91-3.70 (m, 6H), 3.40-3.33 (m, 2H), 2.57-2.50 (m, 2H), 2.17-2.11 (m, 2H), 2.05-1.98 (m, 4H), 1.94-1.86 (m, 2H). LCMS for product (ESI+): m/z 475.3 (M+H)$^+$, Rt: 1.915 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 36—Synthesis of 6-(5-cyanopyridin-2-yl)-1-(2-morpholinoethyl)-2-oxo-N-(spiro[3.3]heptan-2-yl)-1,2-dihydro-1,8-naphthyridine-3-carboxamide (Compound 36)

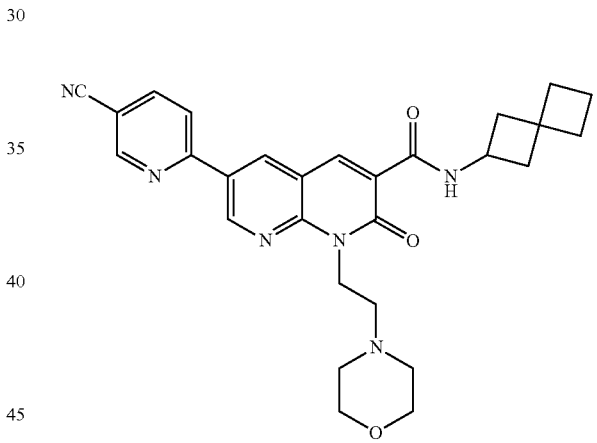

Step 1: 1-(2-morpholinoethyl)-2-oxo-N-(spiro[3.3]heptan-2-yl)-6-(4,4,5,5-tetramethyl-1,3,2-dioxaborolan-2-yl)-1,2-dihydro-1,8-naphthyridine-3-carboxamide

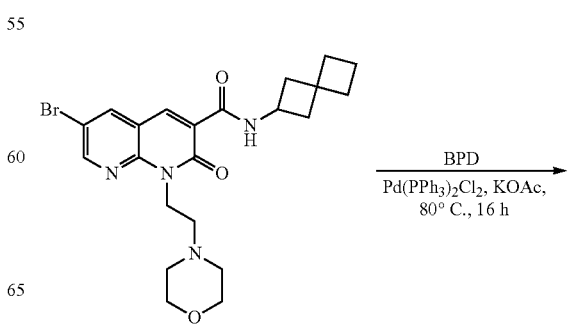

249
-continued

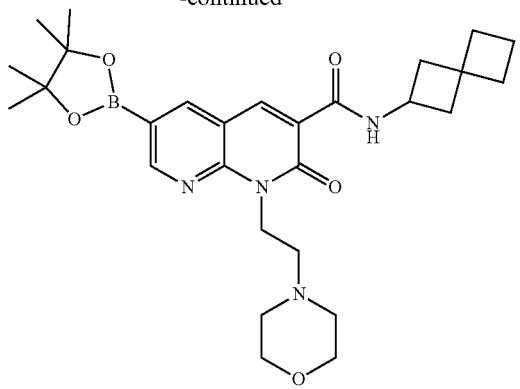

6-bromo-1-(2-morpholinoethyl)-2-oxo-N-spiro[3.3]heptan-2-yl-1,8-naphthyridine-3-carboxamide (250 mg, 526 μmol, 1 eq), 4,4,5,5-tetramethyl-2-(4,4,5,5-tetramethyl-1,3,2-dioxaborolan-2-yl)-1,3,2-dioxaborolane (200 mg, 789 μmol, 1.5 eq), KOAc (155 mg, 1.58 mmol, 3 eq) and Pd(PPh$_3$)$_2$Cl$_2$ (36.9 mg, 52.6 μmol, 0.1 eq) were dissolved in dioxane (10 mL). The suspension was heated to 80° C. for 12 h. LCMS showed complete consumption of the starting material and formation of a new peak. Water (20 mL) and ethyl acetate (30 mL) were added and the mixture was stirred for 5 min. The two phases were separated, and the aqueous phase was extracted with ethyl acetate (3×10 mL). The combined organic phases were washed with brine (30 mL), dried over anhydrous Na$_2$SO$_4$, filtered and concentrated to produce 1-(2-morpholinoethyl)-2-oxo-N-(spiro[3.3]heptan-2-yl)-6-(4,4,5,5-tetramethyl-1,3,2-dioxaborolan-2-yl)-1,2-dihydro-1,8-naphthyridine-3-carboxamide (300 mg) as a black solid (used in next step without further purification).

LCMS for product (ESI+): m/z 441.2 (M-82)$^+$, Rt: 1.024 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% CF$_3$CO$_2$H in water, mobile phase B was 0.018% CF$_3$CO$_2$H in CH$_3$CN. The column used for the chromatography is a Chromolith Flash RP-18e 25-2 mm column. Detection methods are diode array (DAD) and evaporative light scattering (ELSD) detection as well as positive electrospray ionization (MS).

Step 2: Preparation of 6-(5-isocyanopyridin-2-yl)-1-(2-morpholinoethyl)-2-oxo-N-(spiro[3.3]heptan-2-yl)-1,2-dihydro-1,8-naphthyridine-3-carboxamide

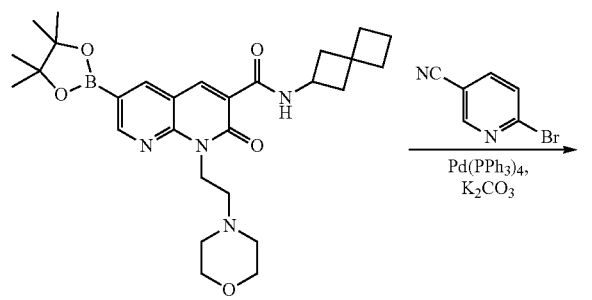

250
-continued

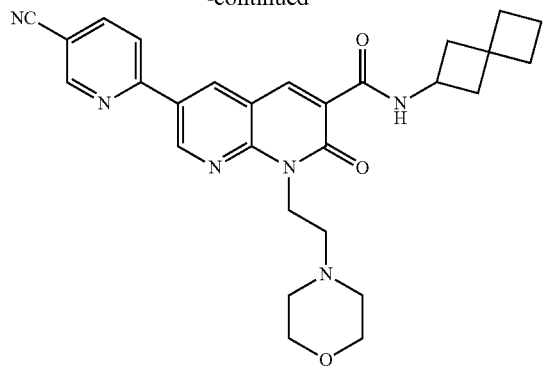

1-(2-morpholinoethyl)-2-oxo-N-spiro[3.3]heptan-2-yl-6-(4,4,5,5-tetramethyl-1,3,2-dioxaborolan-2-yl)-1,8-naphthyridine-3-carboxamide (50 mg, 95.7 μmol, 1 eq), 6-bromopyridine-3-carbonitrile (26.3 mg, 144 μmol, 1.5 eq), Pd(PPh$_3$)$_4$ (11.1 mg, 9.57 μmol, 0.1 eq) and K$_2$CO$_3$ (26.5 mg, 191 μmol, 2.0 eq) were dissolved in dioxane (2 mL) and H$_2$O (0.5 mL). The suspension was heated to 80° C. for 3 h. LCMS showed complete consumption of the starting material and formation of a new peak.

The solvent was removed under reduced pressure and the residue was purified by prep-HPLC (Gilson Auto-Purification System) to produce 6-(5-isocyanopyridin-2-yl)-1-(2-morpholinoethyl)-2-oxo-N-(spiro[3.3]heptan-2-yl)-1,2-dihydro-1,8-naphthyridine-3-carboxamide (2.0 mg, 3.74 μmol, HCl) as a white solid.

$^1$H NMR (400 MHz, METHANOL-d$_4$) δ=9.56 (d, J=2.4 Hz, 1H), 9.12 (d, J=2.0 Hz, 1H), 9.06 (s, 1H), 9.01 (s, 1H), 8.35-8.23 (m, 2H), 5.05 (br t, J=5.9 Hz, 2H), 4.38 (br t, J=8.1 Hz, 1H), 4.20-3.62 (m, 8H), 3.31 (s, 2H), 2.53 (br s, 2H), 2.16-2.10 (m, 2H), 2.05-1.96 (m, 4H), 1.93-1.84 (m, 2H). LCMS for product (ESI+): m/z 499.3 (M+H)$^+$, Rt: 2.095 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 37—Synthesis of 6-(5-fluoropyridin-2-yl)-1-(2-morpholinoethyl)-2-oxo-N-(spiro[3.3]heptan-2-yl)-1,2-dihydro-1,8-naphthyridine-3-carboxamide (Compound 37)

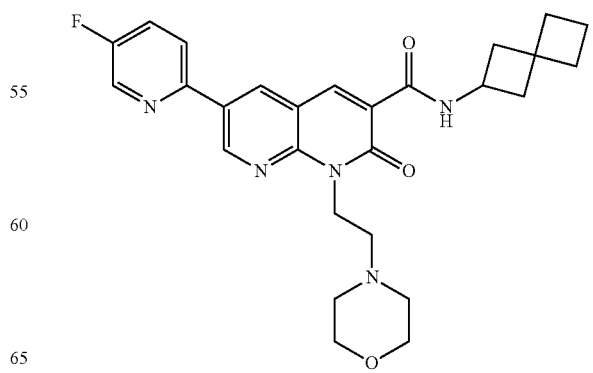

Preparation of 6-(5-fluoropyridin-2-yl)-1-(2-morpholinoethyl)-2-oxo-N-(spiro[3.3]heptan-2-yl)-1,2-dihydro-1,8-naphthyridine-3-carboxamide

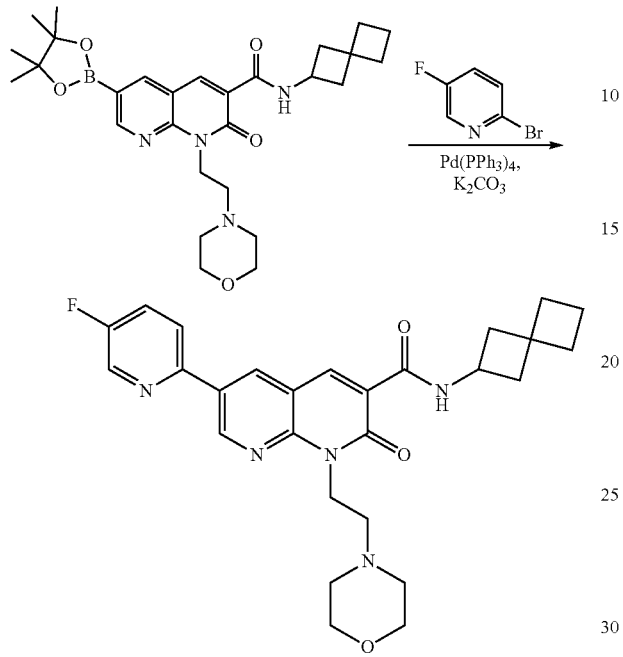

1-(2-morpholinoethyl)-2-oxo-N-spiro[3.3]heptan-2-yl-6-(4,4,5,5-tetramethyl-1,3,2-dioxaborolan-2-yl)-1,8-naphthyridine-3-carboxamide (50 mg, 95.7 μmol, 1 eq), 2-bromo-5-fluoro-pyridine (25.3 mg, 143 μmol, 1.5 eq), Pd(PPh$_3$)$_4$ (11.1 mg, 9.57 μmol, 0.1 eq) and K$_2$CO$_3$ (26.5 mg, 191 μmol, 2.0 eq) were dissolved in dioxane (2 mL) and H$_2$O (0.5 mL). The suspension was heated to 80° C. for 12 h. LCMS showed complete consumption of the starting material and formation of a new peak.

The solvents were removed under reduced and the residue was purified by prep-HPLC (Gilson Auto-Purification System) to yield 6-(5-fluoropyridin-2-yl)-1-(2-morpholinoethyl)-2-oxo-N-(spiro[3.3]heptan-2-yl)-1,2-dihydro-1,8-naphthyridine-3-carboxamide (2.0 mg, 3.74 μmol, HCl) as a white solid.

$^1$H NMR (400 MHz, METHANOL-d$_4$) δ=9.43 (d, J=2.0 Hz, 1H), 8.98 (s, 1H), 8.95 (d, J=2.4 Hz, 1H), 8.62 (d, J=2.9 Hz, 1H), 8.11 (dd, J=3.9, 8.8 Hz, 1H), 7.80-7.75 (m, 1H), 5.05 (t, J=5.9 Hz, 2H), 4.41-4.32 (m, 1H), 4.13 (br d, J=13.2 Hz, 2H), 3.89-3.70 (m, 6H), 3.35 (br d, J=3.4 Hz, 2H), 2.56-2.47 (m, 2H), 2.16-2.11 (m, 2H), 2.05-1.97 (m, 4H), 1.90-1.88 (m, 2H). LCMS for product (ESI+): m/z 492.2 (M+H)$^+$, Rt: 2.100 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 38—Synthesis of 1-(2-morpholinoethyl)-2-oxo-6-(pyrimidin-2-yl)-N-(spiro[3.3]heptan-2-yl)-1,2-dihydro-1,8-naphthyridine-3-carboxamide (Compound 38)

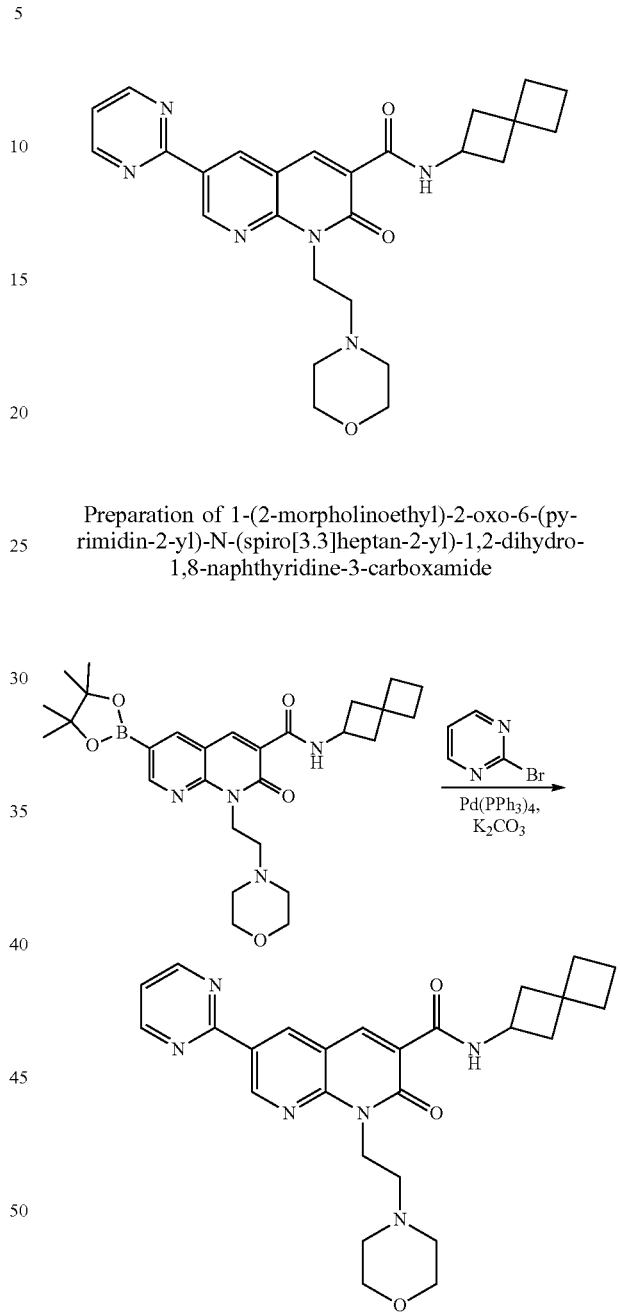

Preparation of 1-(2-morpholinoethyl)-2-oxo-6-(pyrimidin-2-yl)-N-(spiro[3.3]heptan-2-yl)-1,2-dihydro-1,8-naphthyridine-3-carboxamide 1-(2-morpholinoethyl)-2-oxo-N-spiro[3.3]heptan-2-yl-6-(4,4,5,5-tetramethyl-1,3,2-dioxaborolan-2-yl)-1,8-naphthyridine-3-carboxamide (70 mg, 134 μmol, 1 eq), 2-bromopyrimidine (32.0 mg, 201 μmol, 1.5 eq), Pd(PPh$_3$)$_4$ (15.5 mg, 13.4 μmol, 0.1 eq) and K$_2$CO$_3$ (37.0 mg, 268 μmol, 2.0 eq) were dissolved in dioxane (5 mL) and H$_2$O (1 mL). The suspension was heated to 80° C. for 12 h. LCMS showed complete consumption of the starting material and formation of a new peak.

The solvent was removed under reduced pressure and the residue was purified by prep-HPLC (Column: Welch Xtimate C18 150*25 mm*5 μm; mobile phase: [water (0.04%

HCl)—CH₃CN]; B %: 20%-45%, 10 min) to produce 1-(2-morpholinoethyl)-2-oxo-6-(pyrimidin-2-yl)-N-(spiro[3.3]heptan-2-yl)-1,2-dihydro-1,8-naphthyridine-3-carboxamide (9 mg, 19.0 µmol) as a white solid.

¹H NMR (400 MHz, METHANOL-d₄) δ=9.77 (d, J=2.0 Hz, 1H), 9.32 (d, J=2.0 Hz, 1H), 9.03 (s, 1H), 8.94 (d, J=4.9 Hz, 2H), 7.48 (t, J=4.9 Hz, 1H), 5.07 (br t, J=6.1 Hz, 2H), 4.37 (t, J=7.8 Hz, 1H), 4.23-3.43 (m, 8H), 2.55-2.52 (m, 2H), 2.15-2.13 (m, 2H), 1.99-1.92 (m, 4H), 1.90-1.88 (m, 2H). LCMS for product (ESI+): m/z 475.3 (M+H)⁺, Rt: 1.954 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 39—Synthesis of N-(4,4-dimethylcyclohexyl)-6-(4-methoxyphenyl)-1-(2-morpholinoethyl)-2-oxo-1,2-dihydroquinoline-3-carboxamide (Compound 39)

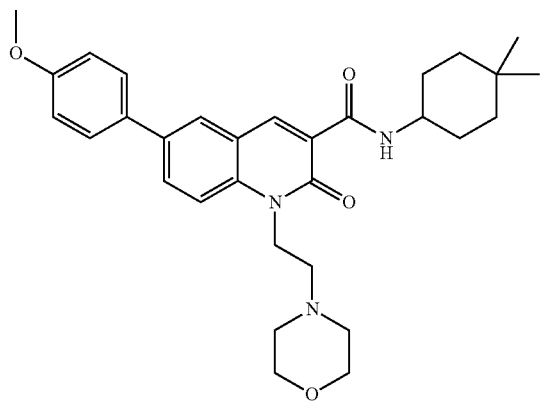 [SMILES: COc1ccc(-c2ccc3c(c2)cc(C(=O)NC2CCC(C)(C)CC2)c(=O)n3CCN2CCOCC2)cc1]

Step 1: diethyl 2-(5-bromo-2-nitrobenzylidene)malonate

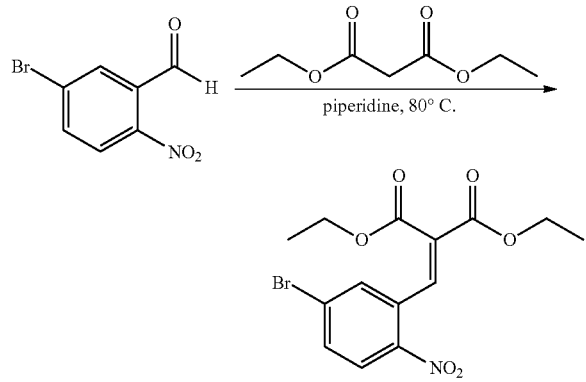

To a solution of 5-bromo-2-nitro-benzaldehyde (2 g, 8.70 mmol, 1 eq) in diethyl propanedioate (8.36 g, 52.17 mmol, 7.9 mL, 6 eq) was added AcOH (2.09 g, 34.78 mmol, 2.0 mL, 4 eq) and piperidine (888.44 mg, 10.43 mmol, 1.0 mL, 1.2 eq) at 25° C. The mixture was stirred at 80 C for 2 h. LCMS showed complete consumption of the starting material and formation of a new peak. The mixture was poured into NaHCO₃ (100 mL), extracted with ethyl acetate (3×50 mL), the organic layer was washed with brine (30 mL), dried over Na₂SO₄ (50 g) and concentrated.

The residue was purified by silica gel column chromatography (Petroleum ether/Ethyl acetate=50:1 to 1:1) to yield diethyl 2-(5-bromo-2-nitrobenzylidene)malonate (4 g, 7.52 mmol) as a yellow oil.

¹H NMR (400 MHz, DMSO-d₆) δ=8.19 (d, J=8.9 Hz, 1H), 8.14 (s, 1H), 7.96 (dd, J=1.6, 8.8 Hz, 1H), 7.64 (d, J=1.6 Hz, 1H), 4.30 (q, J=7.0 Hz, 2H), 4.06-4.00 (m, 2H), 1.29 (t, J=7.1 Hz, 3H), 1.01 (t, J=7.1 Hz, 3H). LCMS for product (ESI+): m/z 372.0, 374.0 [M+H]⁺, Rt: 2.359 min.

LCMS Method 5-95AB_4.5 min: The column used for chromatography was a HALO AQ-C18 2.1*30 mm, (2.7 µm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 4.30 min 0.5% B in 0.01 min, 5-95% B (0.01-3.00 min), with a hold at 95% B for 0.50 min. 95-5% B (3.50-3.51 min), 5% B in 3.51 min, with a hold at 5% B for 0.79 min. The flow rate was 1.0 m/min.

Step 2: ethyl 6-bromo-2-oxo-1,2-dihydroquinoline-3-carboxylate

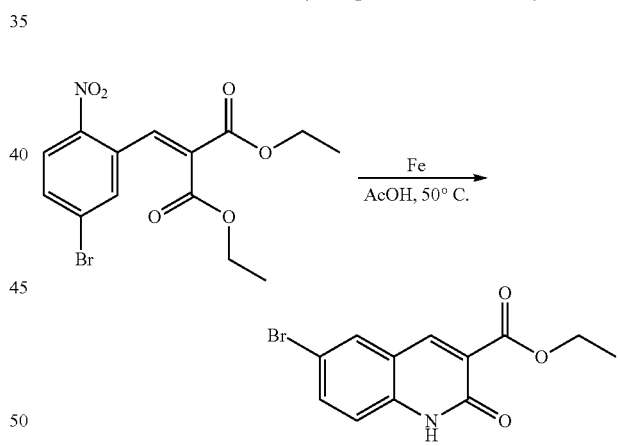

To a solution of diethyl 2-[(5-bromo-2-nitro-phenyl)methylene]propanedioate (3.3 g, 8.87 mmol, 1 eq) in AcOH (20 mL) was added Fe (1.24 g, 22.17 mmol, 2.5 eq) at 25° C. The mixture was stirred at 85° C. for 2 h. LCMS showed complete consumption of the starting material and formation of a new peak.

The mixture was filtered, and the resulting red solid was collected by filtration (ethyl 6-bromo-2-oxo-1,2-dihydroquinoline-3-carboxylate, 2 g, 6.75 mmol, used without further purification).

¹H NMR (400 MHz, DMSO-d₆) δ=12.34-11.88 (m, 1H), 8.66-8.36 (m, 1H), 8.32-7.99 (m, 1H), 7.98-7.66 (m, 1H), 7.47-7.01 (m, 1H), 4.29 (br d, J=3.1 Hz, 2H), 1.51-1.22 (m, 3H). LCMS for product (ESI+): m/z 295.9, 297.9 [M+H]⁺, Rt: 1.383 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 4.30 min 0.5% B in 0.01 min, 5-95% B (0.01-3.00 min), with a hold at 95% B for 0.50 min. 95-5% B (3.50-3.51 min), 5% B in 3.51 min, with a hold at 5% B for 0.79 min. The flow rate was 1.0 m/min.

Step 3: ethyl 6-bromo-1-(2-morpholinoethyl)-2-oxo-1,2-dihydroquinoline-3-carboxylate

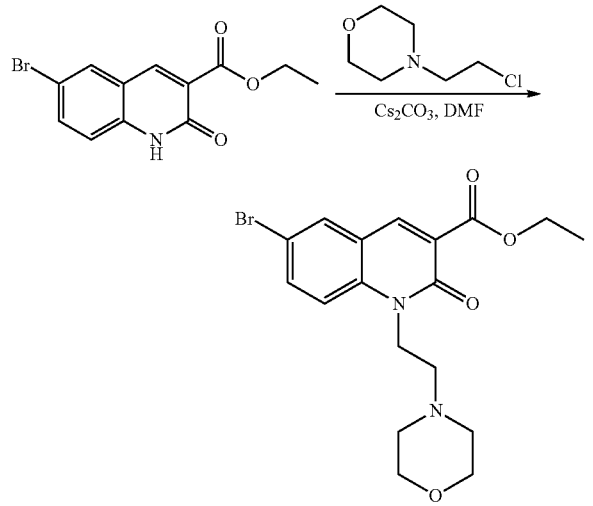

To a solution of ethyl 6-bromo-2-oxo-1H-quinoline-3-carboxylate (1 g, 3.38 mmol, 1 eq) in DMF (20 mL) was added Cs$_2$CO$_3$ (4.95 g, 15.20 mmol, 4.5 eq) at 25° C. The mixture was stirred at 50° C. for 1 h. 4-(2-chloroethyl)morpholine (2.51 g, 13.51 mmol, 4 eq, HCl) was added into the mixture at 50° C., the mixture was stirred at 50° C. for 11 h. LCMS showed complete consumption of the starting material and formation of a new peak. The mixture was poured into HCl (200 mL 0.1 M), extracted with ethyl acetate (3×50 mL), the organic layer was washed with brine (30 mL), dried over Na$_2$SO$_4$ (50 g) and concentrated.

The residue product was purified by silica gel column chromatography (Ethyl acetate/Methanol=100:1 to 1:1) to produce ethyl 6-bromo-1-(2-morpholinoethyl)-2-oxo-1,2-dihydroquinoline-3-carboxylate (180 mg, 439.80 μmol) as a yellow solid.

$^1$H NMR (400 MHz, CDCl$_3$) δ=8.30 (s, 1H), 7.80 (d, J=2.3 Hz, 1H), 7.73 (dd, J=2.3, 9.1 Hz, 1H), 7.33 (d, J=9.1 Hz, 1H), 4.43 (q, J=7.2 Hz, 4H), 3.78-3.66 (m, 4H), 2.74-2.48 (m, 6H), 1.42 (t, J=7.1 Hz, 3H). LCMS for product (ESI+): m/z 409.0, 411.0 [M+H]$^+$, Rt: 1.921 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 4: ethyl 6-(4-methoxyphenyl)-1-(2-morpholinoethyl)-2-oxo-1,2-dihydroquinoline-3-carboxylate

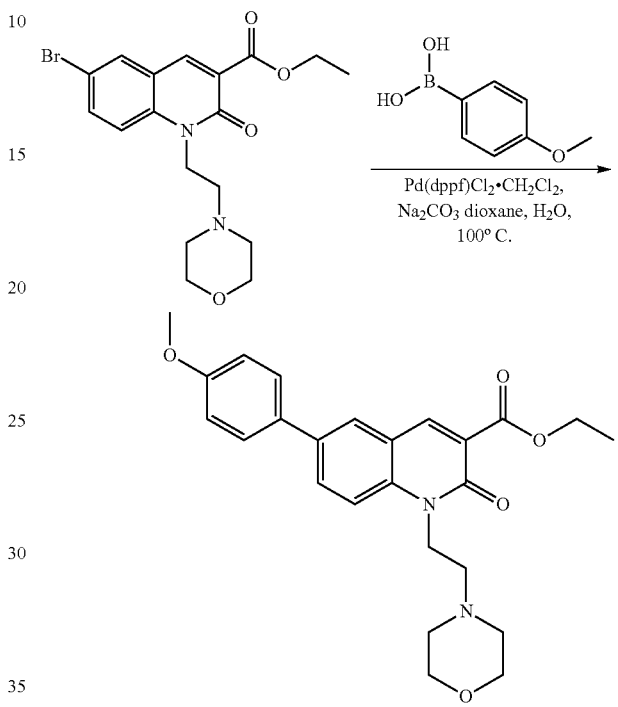

To a solution of ethyl 6-bromo-1-(2-morpholinoethyl)-2-oxo-quinoline-3-carboxylate (160 mg, 390.94 μmol, 1 eq) in dioxane (1.6 mL) and water (0.4 mL) was added Na$_2$CO$_3$ (82.87 mg, 781.87 μmol, 2 eq) and (4-methoxyphenyl)boronic acid (118.81 mg, 781.87 μmol, 2 eq) and Pd(dppf)Cl$_2$·CH$_2$Cl$_2$ (31.93 mg, 39.09 μmol, 0.1 eq) under nitrogen at 25° C. The mixture was stirred at 100° C. for 12 h. LCMS showed complete consumption of the starting material and formation of a new peak.

The mixtures was poured into NH$_4$Cl (15 mL), extracted with ethyl acetate (3×5 mL), the organic layer was washed with brine (3 mL), dried over Na$_2$SO$_4$ (5 g) and concentrated to produce ethyl 6-(4-methoxyphenyl)-1-(2-morpholinoethyl)-2-oxo-1,2-dihydroquinoline-3-carboxylate (110 mg, 252.01 μmol) as a yellow oil (used without further purification).

LCMS for product (ESI+): m/z 437.1 [M+H]$^+$, Rt: 2.118 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 5: 6-(4-methoxyphenyl)-1-(2-morpholino-ethyl)-2-oxo-1,2-dihydroquinoline-3-carboxylic acid

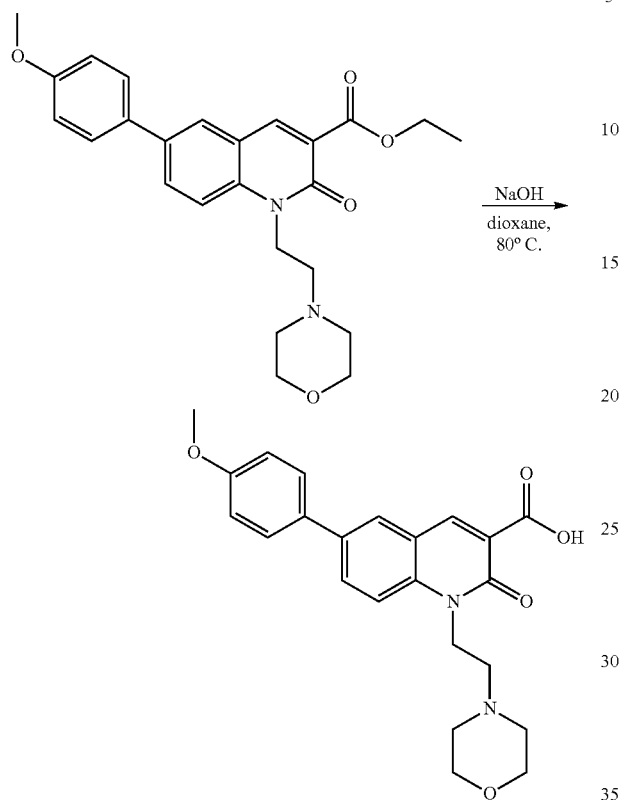

To a solution of ethyl 6-(4-methoxyphenyl)-1-(2-morpholinoethyl)-2-oxo-quinoline-3-carboxylate (99.77 mg, 228.58 μmol, 1 eq) in dioxane (2 mL) was added NaOH (2 M, 0.8 mL, 7.00 eq) at 25° C. The mixture was stirred at 80° C. for 2 h. LCMS showed complete consumption of the starting material and formation of a new peak. The mixture was poured into HCl (20 mL, 0.5 N), extracted with ethyl acetate (3×50 mL), the organic layer was washed with brine (30 mL), dried over $Na_2SO_4$ (20 g) and concentrated to produce the desired product (93 mg, 227.69 μmol) as a brown oil.

The mixtures was poured into $NH_4Cl$ (15 mL), extracted with ethyl acetate (3×5 mL), the organic layer was washed with brine (3 mL), dried over $Na_2SO_4$ (5 g) and concentrated to produce ethyl 6-(4-methoxyphenyl)-1-(2-morpholinoethyl)-2-oxo-1,2-dihydroquinoline-3-carboxylate (110 mg, 252.01 μmol) as a yellow oil (used without further purification).

$^1$H NMR (400 MHz, $CDCl_3$) δ=8.98 (s, 1H), 8.03-7.94 (m, 2H), 7.57 (s, 2H), 7.05 (d, J=8.8 Hz, 2H), 6.79 (s, 1H), 4.60 (br t, J=7.3 Hz, 2H), 3.89 (s, 3H), 3.75-3.72 (m, 4H), 2.77 (t, J=7.3 Hz, 2H), 2.64 (br d, J=4.2 Hz, 4H). LCMS for product (ESI+): m/z 409.2 [M+H]$^+$, Rt: 1.427 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 6: Preparation of N-(4,4-dimethylcyclohexyl)-6-(4-methoxyphenyl)-1-(2-morpholinoethyl)-2-oxo-1,2-dihydroquinoline-3-carboxamide

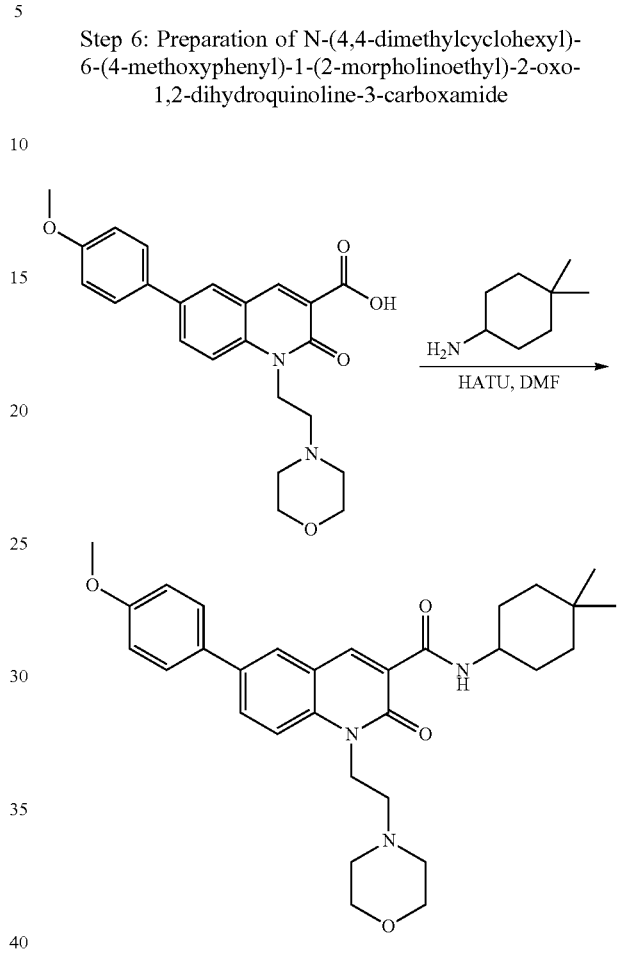

To a solution of 6-(4-methoxyphenyl)-1-(2-morpholinoethyl)-2-oxo-quinoline-3-carboxylic acid (90 mg, 220.35 μmol, 1 eq) in DMF (1 mL) was added HATU (125.67 mg, 330.52 μmol, 1.5 eq) and DIEA (56.96 mg, 440.69 μmol, 76 μL, 2 eq) and 4,4-dimethylcyclohexanamine (33.64 mg, 264.42 μmol, 1.2 eq) at 25° C. The mixture was stirred at 25° C. for 2 h. LCMS showed complete consumption of the starting material and formation of a new peak.

The mixture was filtered and the filtrate was purified by prep-HPLC (column: Waters Xbridge BEH C18 100*30 mm*10 μm; mobile phase: [water (10 mM $NH_4HCO_3$)-ACN]; B %: 45%-75%, 10 min) to produce N-(4,4-dimethylcyclohexyl)-6-(4-methoxyphenyl)-1-(2-morpholinoethyl)-2-oxo-1,2-dihydroquinoline-3-carboxamide (20 mg, 38.17 μmol, 17.32% yield, 98.8% purity) as a light yellow solid.

$^1$H NMR (400 MHz, $CDCl_3$) δ=9.80 (br d, J=7.8 Hz, 1H), 8.96 (s, 1H), 7.95-7.85 (m, 2H), 7.60-7.51 (m, 3H), 7.03 (d, J=8.8 Hz, 2H), 4.60-4.46 (m, 2H), 3.97 (br dd, J=3.2, 7.3 Hz, 1H), 3.88 (s, 3H), 3.80-3.64 (m, 4H), 2.79-2.70 (m, 2H), 2.64 (br d, J=4.1 Hz, 4H), 1.95-1.85 (m, 2H), 1.54-1.30 (m, 6H), 0.97 (d, J=6.4 Hz, 6H). LCMS for product (ESI+): m/z 518.4 [M+H]$^+$, Rt: 1.128 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Example 40—Synthesis of 6-(5-cyanopyridin-2-yl)-N-(2-(4-fluorophenyl)propan-2-yl)-1-(2-morpholinoethyl)-2-oxo-1,2-dihydro-1,8-naphthyridine-3-carboxamide (Compound 40)

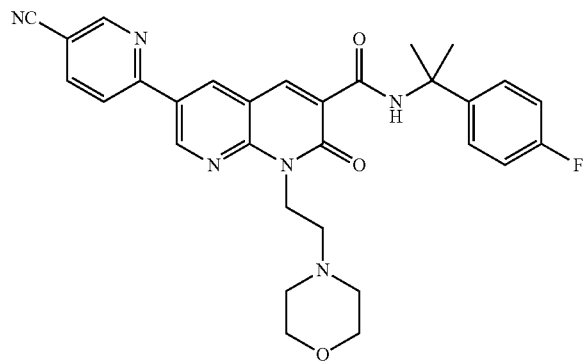 [SMILES: CC(C)(NC(=O)c1cc2cc(-c3ccc(C#N)cn3)cnc2n(CCN2CCOCC2)c1=O)c1ccc(F)cc1]

Step 1: 1-(2-morpholinoethyl)-2-oxo-6-(4,4,5,5-tetramethyl-1,3,2-dioxaborolan-2-yl)-1,2-dihydro-1,8-naphthyridine-3-carboxylic acid

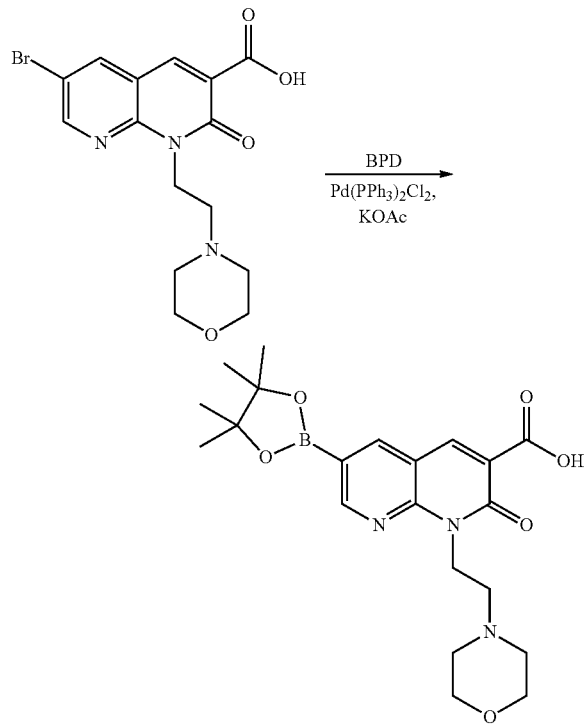

Method 1:

A mixture of 6-bromo-1-(2-morpholinoethyl)-2-oxo-1,8-naphthyridine-3-carboxylic acid (350 mg, 915.73 μmol, 1 eq), BPD (1.86 g, 7.33 mmol, 8 eq), Pd(PPh$_3$)$_2$Cl$_2$ (64.27 mg, 91.57 μmol, 0.1 eq), KOAc (269.62 mg, 2.75 mmol, 3 eq) in dioxane (3 mL) was stirred at 80° C. for 2 h.

LCMS showed complete consumption of the starting material and formation of a new peak with desired mass. The mixture was diluted with water 5 mL and extracted with ethyl acetate (3×3 mL).

The combined aqueous layers were washed with 2M HCl (3 mL), and the resulting solid was filtered and concentrated under reduced pressure to produce 1-(2-morpholinoethyl)-2-oxo-6-(4,4,5,5-tetramethyl-1,3,2-dioxaborolan-2-yl)-1,2-dihydro-1,8-naphthyridine-3-carboxylic acid (200 mg, 465.90 μmol) as a white solid.

LCMS for product (ESI+): m/z 348.2 [M+H]$^+$, Rt: 0.454 min.

LCMS Method

The column used for chromatography was a Luna-C 18 2.0*30 mm, (3 μm particles). Detection methods are diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-95% B in 4.50 min. 5% B in 0.25 min, 5-95% B (0.25-2.25 min), 95-100% B (2.25-4.05 min), 5% B in 1.81 min with a hold at 5% B for 0.43 min. The flow rate was 1.0 mL/min (0.00-4.05 min) and 1.2 m/min (4.05-4.5 min).

Method 2:

A mixture of 6-bromo-1-(2-morpholinoethyl)-2-oxo-1,8-naphthyridine-3-carboxylic acid (120 mg, 313.96 μmol, 1 eq), BPD (637.82 mg, 2.51 mmol, 8 eq), KOAc (92.44 mg, 941.89 mol, 3 eq) and Pd(PPh$_3$)$_2$Cl$_2$ (22.04 mg, 31.40 μmol, 0.1 eq) in dioxane (7 mL) was degassed and purged with N$_2$ for 3 times, and then the mixture was stirred at 80° C. for 2 h under N$_2$ atmosphere. LCMS showed complete consumption of the starting material and formation of a new peak with desired mass.

The mixture was diluted with water (3 mL), extracted with ethyl acetate (3×3 mL) and concentrated under reduced pressure to produce 1-(2-morpholinoethyl)-2-oxo-6-(4,4,5,5-tetramethyl-1,3,2-dioxaborolan-2-yl)-1,2-dihydro-1,8-naphthyridine-3-carboxylic acid (80 mg, 186.36 μmol) as a white solid (used without further purification).

LCMS for product (ESI+): m/z 348.2 [M+H]$^+$, Rt: 0.532 min.

LCMS Method

The column used for chromatography was a Luna-C 18 2.0×30 mm, (3 m particles). Detection methods are diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-95% B in 2.00 min. 5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 m/min (1.81-2.00 min).

Step 2: 6-(5-cyanopyridin-2-yl)-1-(2-morpholino-ethyl)-2-oxo-1,2-dihydro-1,8-naphthyridine-3-carboxylic acid

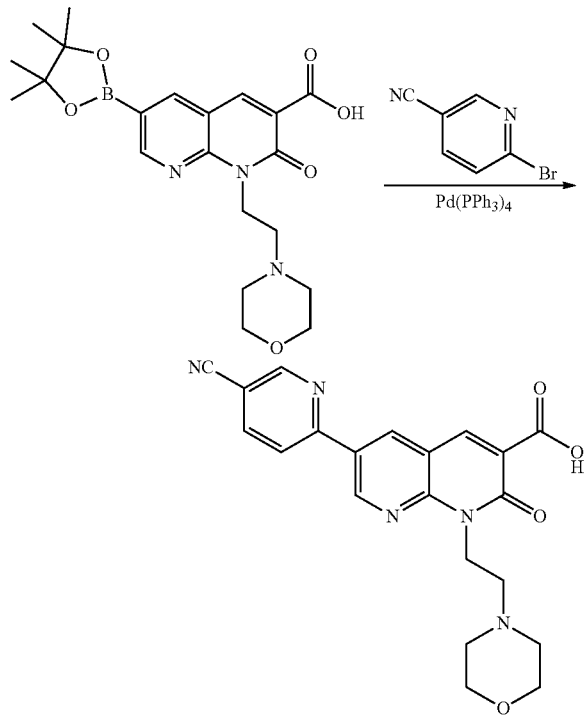

Method 1:

A mixture of 6-bromopyridine-3-carbonitrile (63.95 mg, 349.43 µmol, 1 eq), 1-(2-morpholinoethyl)-2-oxo-6-(4,4,5,5-tetramethyl-1,3,2-dioxaborolan-2-yl)-1,8-naphthyridine-3-carboxylic acid (150 mg, 349.43 µmol, 1 eq), K₂CO₃ (144.88 mg, 1.05 mmol, 3 eq), Pd(PPh₃)₄ (40.38 mg, 34.94 µmol, 0.1 eq) in dioxane (1 mL) and water (0.25 mL) was degassed and purged with N2 for 3 times, and then the mixture was stirred at 80° C. for 2 h under N2 atmosphere. LCMS showed complete consumption of the starting material and formation of a new peak with desired mass.

The mixture was filtered, and the filtrate was concentrated under reduced pressure and the residue was purified by prep-HPLC (HCl condition) to produce 6-(5-cyanopyridin-2-yl)-1-(2-morpholinoethyl)-2-oxo-1,2-dihydro-1,8-naphthyridine-3-carboxylic acid (30 mg, 74.00 µmol, 21.1) as a yellow solid.

LCMS for product (ESI+): m/z 406.2 [M+H]⁺, Rt: 0.878 min.

LCMS Method

The column used for chromatography was a Luna-C 18 2.0*30 mm, (3 µm particles). Detection methods are diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-95% B in 4.50 min. 5% B in 0.25 min, 5-95% B (0.25-2.25 min), 95-100% B (2.25-4.05 min), 5% B in 1.81 min with a hold at 5% B for 0.43 min. The flow rate was 1.0 mL/min (0.00-4.05 min) and 1.2 m/min (4.05-4.5 min).

Method 2:

A mixture of 6-bromopyridine-3-carbonitrile (42.63 mg, 232.95 µmol, 1 eq), 1-(2-morpholinoethyl)-2-oxo-6-(4,4,5,5-tetramethyl-1,3,2-dioxaborolan-2-yl)-1,8-naphthyridine-3-carboxylic acid (100 mg, 232.95 µmol, 1 eq), K₂CO₃ (96.59 mg, 698.86 µmol, 3 eq), Pd(PPh₃)₄ (26.92 mg, 23.30 µmol, 0.1 eq) in dioxane (1 mL) and water (0.25 mL) was degassed and purged with N2 for 3 times, and then the mixture was stirred at 80° C. for 2 h under N2 atmosphere. LCMS showed complete consumption of the starting material and formation of a new peak with desired mass.

The mixture was filtered, concentrated under reduced pressure and the residue was purified by prep-HPLC (HCl condition) to produce the 6-(5-cyanopyridin-2-yl)-1-(2-morpholinoethyl)-2-oxo-1,2-dihydro-1,8-naphthyridine-3-carboxylic acid (60 mg, 148.00 µmol) as a white solid.

LCMS for product (ESI+): m/z 406.2 [M+H]⁺, Rt: 1.038 min.

LCMS Method

The column used for chromatography was a Luna-C 18 2.0*30 mm, (3 µm particles). Detection methods are diode array (DAD). MS mode was positive electrospray ionization. MS range was 100-1000. Mobile phase A was 0.037% trifluoroacetic acid in water, and mobile phase B was 0.018% trifluoroacetic acid in HPLC grade acetonitrile. The gradient was 5-95% B in 2.00 min. 5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 m/min (1.81-2.00 min).

Step 3: Preparation of 6-(5-cyanopyridin-2-yl)-N-(2-(4-fluorophenyl)propan-2-yl)-1-(2-morpholinoethyl)-2-oxo-1,2-dihydro-1,8-naphthyridine-3-carboxamide

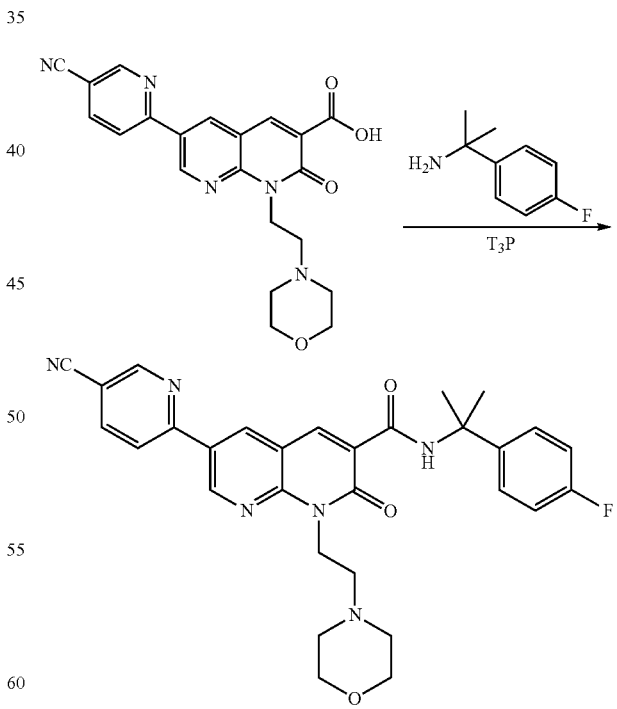

A mixture of 2-(4-fluorophenyl)propan-2-amine (30.23 mg, 197.33 µmol, 2 eq), 6-(5-cyano-2-pyridyl)-1-(2-morpholinoethyl)-2-oxo-1,8-naphthyridine-3-carboxylic acid (40 mg, 98.67 µmol, 1 eq), DIEA (76.51 mg, 592.00 µmol, 103.12 µL, 6 eq), T3P (251.15 mg, 394.67 µmol, 234.72 µL, 50% purity, 4 eq) in DMF (0.5 mL) was stirred at 20° C. for 2 h. LCMS showed complete consumption of the starting material and formation of a new peak with desired mass.

The reaction mixture was filtered, concentrated under reduced pressure and the filtrate was purified by prep-HPLC (neutral condition) to produce the 6-(5-cyanopyridin-2-yl)-N-(2-(4-fluorophenyl)propan-2-yl)-1-(2-morpholinoethyl)-2-oxo-1,2-dihydro-1,8-naphthyridine-3-carboxamide (20 mg, 37.00 μmol) as a white solid.

$^1$H NMR (400 MHz, DMSO-$d_6$) δ=10.05 (s, 1H), 9.52 (d, J=2.0 Hz, 1H), 9.20-9.15 (m, 2H), 8.88 (s, 1H), 8.49 (dd, J=1.4, 8.5 Hz, 1H), 8.37-8.32 (m, 1H), 7.45 (dd, J=5.5, 8.4 Hz, 2H), 7.13 (t, J=8.7 Hz, 2H), 4.75-4.64 (m, 2H), 3.54 (br t, J=3.7 Hz, 4H), 2.69-2.62 (m, 2H), 2.54-2.51 (m, 4H), 1.72 (s, 6H). LCMS for product (ESI+): m/z 541.3 [M+H]$^+$, Rt: 3.137 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was acetonitrile. The column used for chromatography was a xbridge shield RP18 2.1*50 mm column (5 um particles). Detection methods are diode array (DAD) and evaporative light scattering (ELSD) detection as well as positive electrospray ionization. MS range was 100-1000.

Example 41—Synthesis of N-(1-(4-cyanophenyl)ethyl)-6-(5-cyanopyridin-2-yl)-1-(2-morpholinoethyl)-2-oxo-1,2-dihydro-1,8-naphthyridine-3-carboxamide (Compound 41)

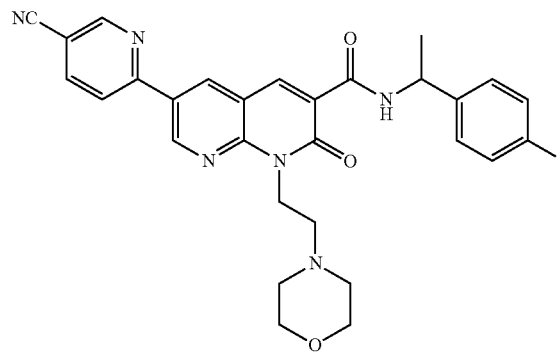

Preparation of N-(1-(4-cyanophenyl)ethyl)-6-(5-cyanopyridin-2-yl)-1-(2-morpholinoethyl)-2-oxo-1,2-dihydro-1,8-naphthyridine-3-carboxamide

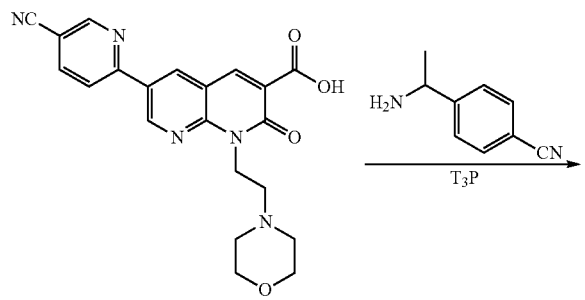

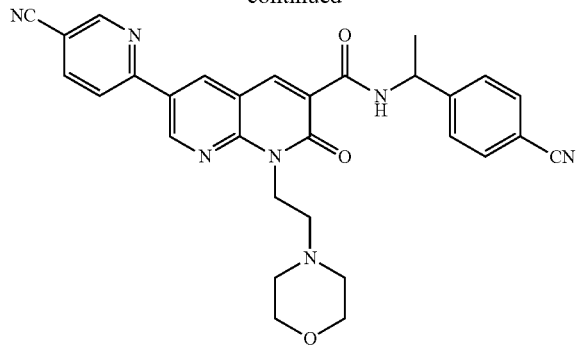

To a solution of 6-(5-cyano-2-pyridyl)-1-(2-morpholinoethyl)-2-oxo-1,8-naphthyridine-3-carboxylic acid (40 mg, 98.67 μmol, 1 eq) and 4-(1-aminoethyl) benzonitrile (21.64 mg, 148.00 μmol, 1.5 eq) in DMF (1 mL) was added DIEA (76.51 mg, 592.00 μmol, 103.12 μL, 6 eq) and T3P (125.58 mg, 197.33 μmol, 117.36 μL, 50% purity, 2 eq). The mixture was stirred at 25° C. for 1 h. LCMS showed complete consumption of the starting material and formation of a new peak.

The mixture was filtered, and the filtrate was purified by prep-HPLC (neutral condition) to produce N-(1-(4-cyanophenyl)ethyl)-6-(5-cyanopyridin-2-yl)-1-(2-morpholinoethyl)-2-oxo-1,2-dihydro-1,8-naphthyridine-3-carboxamide (27.9 mg, 52.29 μmol) as a white solid.

$^1$H NMR (400 MHz, DMSO-$d_6$) δ=10.01-9.94 (m, 1H), 9.52 (d, J=2.0 Hz, 1H), 9.19 (d, J=2.2 Hz, 1H), 9.15 (d, J=0.7 Hz, 1H), 8.95-8.88 (m, 1H), 8.49 (dd, J=1.7, 8.3 Hz, 1H), 8.36-8.29 (m, 1H), 7.83 (d, J=8.2 Hz, 2H), 7.61 (d, J=8.2 Hz, 2H), 5.18 (s, 1H), 4.73-4.63 (m, 2H), 3.58-3.49 (m, 4H), 2.69-2.61 (m, 2H), 2.57-2.51 (m, 4H), 1.54 (br d, J=7.1 Hz, 3H). LCMS for product (ESI+): m/z 534.3 [M+H]$^+$, Rt: 2.919 min.

LCMS Method

The gradient was 5% B in 0.40 min and 5-95% B at 0.40-3.40 min, hold on 95% B for 0.45 min, and then 95-5% B in 0.01 min, the flow rate was 0.8 mL/min. Mobile phase A was H$_2$O+10 mM NH$_4$HCO$_3$, mobile phase B was acetonitrile. The column used for chromatography was a xbridgeShield RP18 2.1*50 mm column (5 um particles). Detection methods are diode array (DAD) and evaporative light scattering (ELSD) detection as well as positive electrospray ionization.

Example 42—Synthesis of 6-(5-cyanopyridin-2-yl)-N-(1-(4-fluorophenyl)cyclopropyl)-1-(2-morpholinoethyl)-2-oxo-1,2-dihydro-1,8-naphthyridine-3-carboxamide (Compound 42)

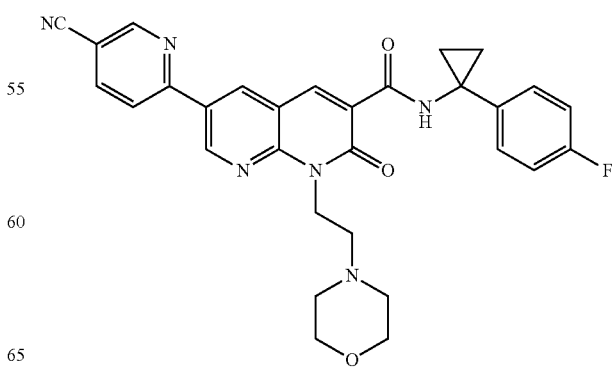

Preparation of 6-(5-cyanopyridin-2-yl)-N-(1-(4-fluorophenyl)cyclopropyl)-1-(2-morpholinoethyl)-2-oxo-1,2-dihydro-1,8-naphthyridine-3-carboxamide

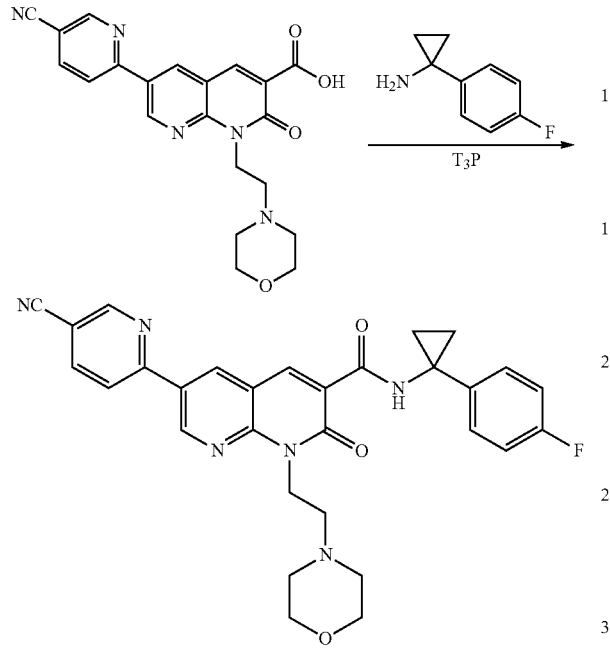

A mixture of 1-(4-fluorophenyl) cyclopropanamine (29.83 mg, 197.34 μmol, 2 eq), 6-(5-cyano-2-pyridyl)-1-(2-morpholinoethyl)-2-oxo-1,8-naphthyridine-3-carboxylic acid (40 mg, 98.67 μmol, 1 eq), DIEA (76.51 mg, 592.02 μmol, 103.12 μL, 6 eq), T3P (125.58 mg, 197.34 μmol, 117.36 μL, 50% purity, 2 eq) in DMF (1 mL) was stirred at 20° C. for 2 h. LCMS showed complete consumption of the starting material and formation of a new peak with desired mass.

The mixture was filtered, and the filtrate was purified by prep-HPLC (neutral condition) to produce 6-(5-cyanopyridin-2-yl)-N-(1-(4-fluorophenyl)cyclopropyl)-1-(2-morpholinoethyl)-2-oxo-1,2-dihydro-1,8-naphthyridine-3-carboxamide (7.9 mg, 14.67 μmol) as a white solid.

$^1$H NMR (400 MHz, DMSO-$d_6$) δ=10.10-10.04 (m, 1H), 9.53 (d, J=2.0 Hz, 1H), 9.21 (d, J=1.3 Hz, 1H), 9.18-9.15 (m, 1H), 8.93 (s, 1H), 8.54-8.45 (m, 1H), 8.37-8.33 (m, 1H), 7.34-7.28 (m, 2H), 7.15-7.08 (m, 2H), 4.72-4.63 (m, 2H), 3.58-3.51 (m, 4H), 2.64 (br d, J=7.1 Hz, 2H), 2.55-2.52 (m, 4H), 1.30 (s, 4H). LCMS for product (ESI+): m/z 539.3 [M+H]$^+$, Rt: 3.042 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was acetonitrile. The column used for chromatography was a xbridge Shield RP18 2.1*50 mm column (5 um particles). Detection methods are diode array (DAD) and evaporative light scattering (ELSD) detection as well as positive electrospray ionization.

Example 43—Synthesis of 6-(5-(difluoromethoxy)pyridin-2-yl)-1-(4-fluorobenzyl)-2-oxo-N-(spiro[3.3]heptan-2-yl)-1,2-dihydro-1,8-naphthyridine-3-carboxamide (Compound 43)

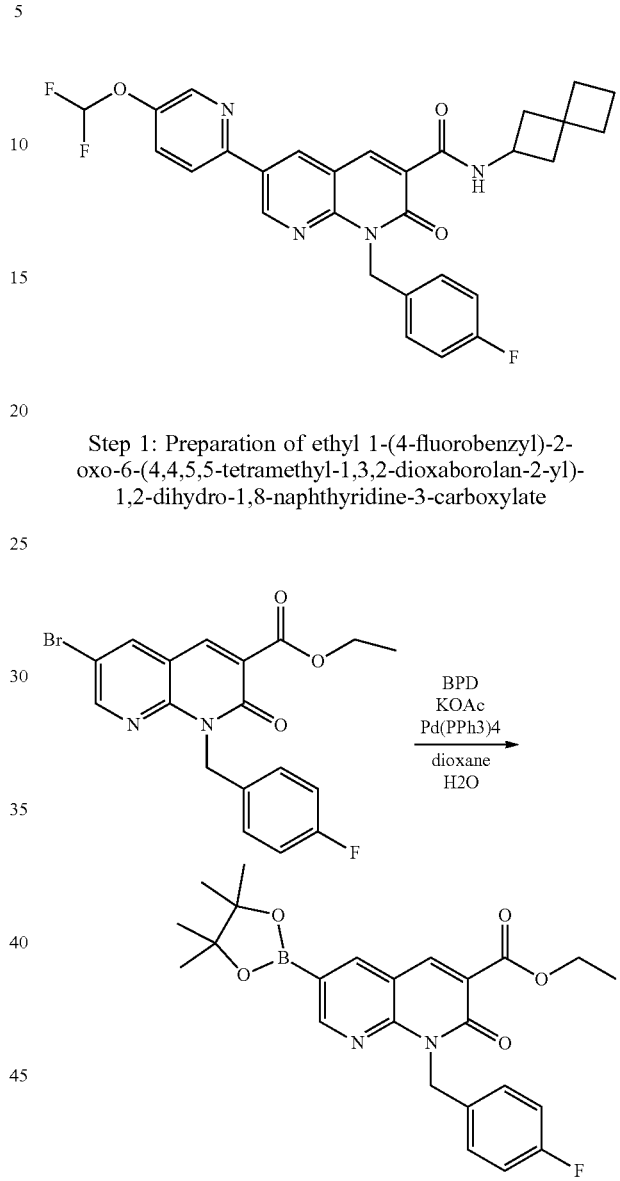

Step 1: Preparation of ethyl 1-(4-fluorobenzyl)-2-oxo-6-(4,4,5,5-tetramethyl-1,3,2-dioxaborolan-2-yl)-1,2-dihydro-1,8-naphthyridine-3-carboxylate To a mixture of ethyl 6-bromo-1-[(4-fluorophenyl)methyl]-2-oxo-1,8-naphthyridine-3-carboxylate (150 mg, 370.17 μmol, 1 eq), KOAc (363.29 mg, 3.70 mmol, 10 eq) and 4,4,5,5-tetramethyl-2-(4,4,5,5-tetramethyl-1,3,2-dioxaborolan-2-yl)-1,3,2-dioxaborolane (940.01 mg, 3.70 mmol, 10 eq) in DMSO (2 mL) was added Pd(PPh$_3$)$_4$ (42.78 mg, 37.02 μmol, 0.1 eq) under N$_2$. The mixture was stirred at 80° C. for 1 h. LCMS showed complete consumption of the starting material and formation of a new peak with desired mass.

The reaction mixture was poured into water (20 mL) and extracted with ethyl acetate (3×5 mL). The combined organic phase was dried with anhydrous Na$_2$SO$_4$, filtered and concentrated in vacuum to produce ethyl 1-(4-fluorobenzyl)-2-oxo-6-(4,4,5,5-tetramethyl-1,3,2-dioxaborolan-2-yl)-1,2-dihydro-1,8-naphthyridine-3-carboxylate (120 mg, 265.32 μmol) that was used without further purification.

LCMS for product (ESI+): m/z 453.3 [M+H]⁺, Rt: 1.240 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 2: Preparation of ethyl 6-(5-(difluoromethoxy)pyridin-2-yl)-1-(4-fluorobenzyl)-2-oxo-1,2-dihydro-1,8-naphthyridine-3-carboxylate

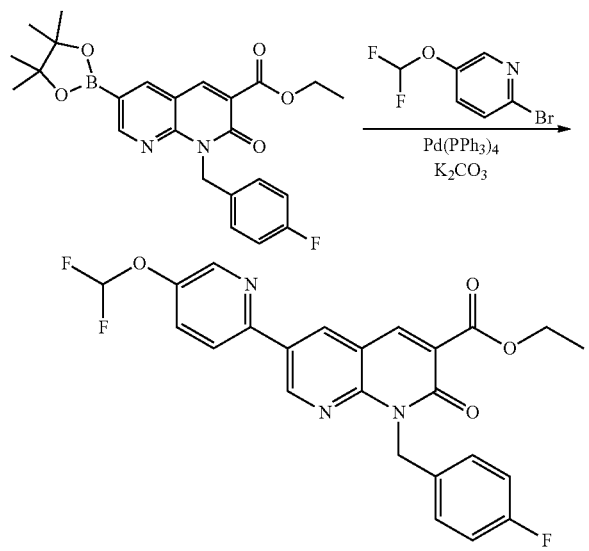

To a mixture of ethyl 1-[(4-fluorophenyl)methyl]-2-oxo-6-(4,4,5,5-tetramethyl-1,3,2-dioxaborolan-2-yl)-1,8-naphthyridine-3-carboxylate (120 mg, 265.32 μmol, 1 eq), K₂CO₃ (110.01 mg, 795.96 μmol, 3 eq) and 2-bromo-5-(difluoromethoxy)pyridine (71.32 mg, 318.39 mol, 1.2 eq) in dioxane (1 mL) and H₂O (0.1 mL) was added Pd(PPh₃)₄ (30.66 mg, 26.53 μmol, 0.1 eq) under N₂. The mixture was stirred at 100° C. for 1 h. LCMS showed complete consumption of the starting material and formation of a new peak with desired mass. The reaction mixture was poured into water (5 mL). The aqueous phase was extracted with ethyl acetate (3×5 mL).

The combined organic phase was dried with anhydrous Na₂SO₄, filtered and concentrated in vacuum to produce ethyl 6-(5-(difluoromethoxy)pyridin-2-yl)-1-(4-fluorobenzyl)-2-oxo-1,2-dihydro-1,8-naphthyridine-3-carboxylate (90 mg) that was used without further purification.

LCMS for product (ESI+): m/z 470.2 [M+H]⁺, Rt: 1.150 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 3: Preparation of 6-(5-(difluoromethoxy)pyridin-2-yl)-1-(4-fluorobenzyl)-2-oxo-1,2-dihydro-1,8-naphthyridine-3-carboxylic acid

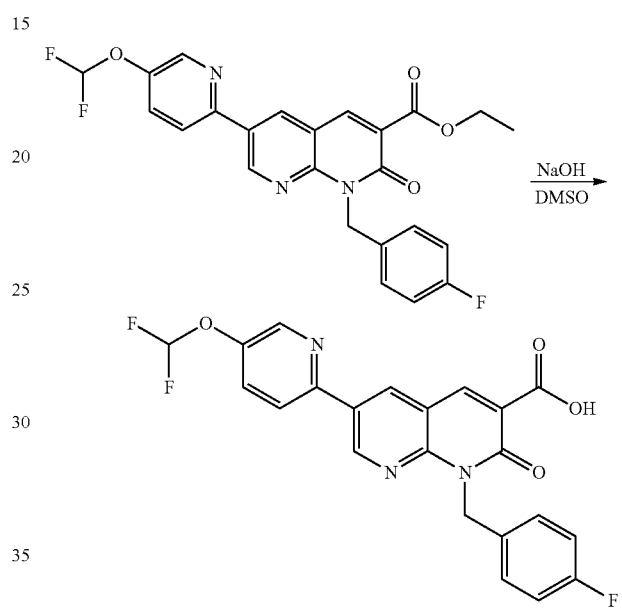

To a mixture of ethyl 6-[5-(difluoromethoxy)-2-pyridyl]-1-[(4-fluorophenyl)methyl]-2-oxo-1,8-naphthyridine-3-carboxylate (90 mg, 191.73 μmol, 1 eq) in DMSO (5 mL) was added NaOH (2 M, 958.65 μL, 10 eq). The mixture was stirred at 50° C. for 2 h. LCMS showed complete consumption of the starting material and formation of a new peak with desired mass. The reaction mixture was poured into water (10 mL) and extracted with ethyl acetate (3×5 mL).

The combined organic phase was dried with anhydrous Na₂SO₄, filtered and concentrated in vacuum to produce 6-(5-(difluoromethoxy)pyridin-2-yl)-1-(4-fluorobenzyl)-2-oxo-1,2-dihydro-1,8-naphthyridine-3-carboxylic acid (65 mg) as a yellow solid (used without further purification).

LCMS for product (ESI+): m/z 442.2 [M+H]⁺, Rt: 1.149 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 4: Preparation of 6-(5-(difluoromethoxy)pyridin-2-yl)-1-(4-fluorobenzyl)-2-oxo-N-(spiro[3.3]heptan-2-yl)-1,2-dihydro-1,8-naphthyridine-3-carboxamide

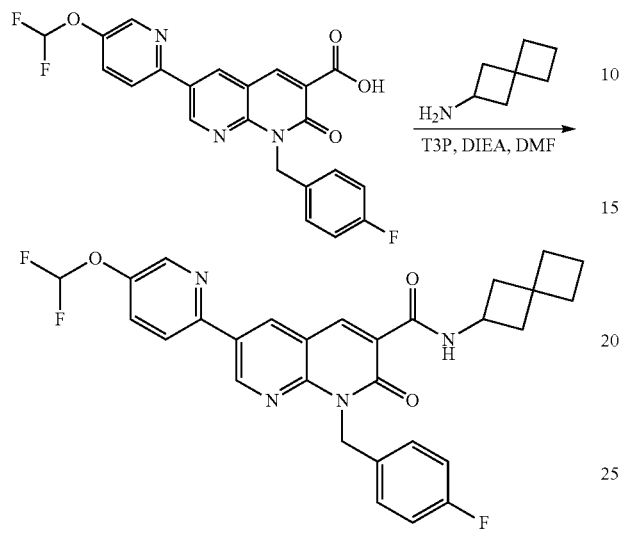

To a mixture of 6-[5-(difluoromethoxy)-2-pyridyl]-1-[(4-fluorophenyl)methyl]-2-oxo-1,8-naphthyridine-3-carboxylic acid (32 mg, 72.50 μmol, 1 eq) and spiro[3.3]heptan-2-amine (12.85 mg, 87.00 μmol, 1.2 eq, HCl) in DMF (1 mL) was added DIEA (56.22 mg, 435.02 μmol, 75.77 μL, 6 eq) and T3P (92.28 mg, 145.01 μmol, 86.24 μL, 50% purity, 2 eq). The mixture was stirred at 20° C. for 1 h. LCMS showed complete consumption of the starting material and formation of a new peak with desired mass.

The mixture was filtered and the filtrate was purified by prep-HPLC (column: Phenomenex Gemini-NX 150*30 mm*5 μm; mobile phase: [water (10 mM NH$_4$HCO$_3$)-ACN]; B %: 55%-85%, 8 min) to produce 6-(5-(difluoromethoxy)pyridin-2-yl)-1-(4-fluorobenzyl)-2-oxo-N-(spiro[3.3]heptan-2-yl)-1,2-dihydro-1,8-naphthyridine-3-carboxamide (4.6 mg, 8.26 μmol) as a white solid.

$^1$H NMR (400 MHz, CDCl$_3$) δ=9.76 (br d, J=7.1 Hz, 1H), 9.33 (d, J=2.3 Hz, 1H), 8.98 (s, 1H), 8.65 (d, J=2.3 Hz, 1H), 8.62 (d, J=2.5 Hz, 1H), 7.82 (d, J=8.6 Hz, 1H), 7.64 (dd, J=2.7, 8.7 Hz, 1H), 7.51 (dd, J=5.5, 8.6 Hz, 2H), 6.99 (t, J=8.7 Hz, 2H), 6.84-6.42 (m, 1H), 5.83 (s, 2H), 4.56-4.39 (m, 1H), 2.59-2.47 (m, 2H), 2.10 (t, J=7.4 Hz, 2H), 2.05-1.96 (m, 4H), 1.92-1.82 (m, 2H). LCMS for product (ESI-): m/z 535.2 [M+H]$^+$, Rt: 3.680 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 44—Synthesis of 6-(4-cyanophenyl)-1-(2-morpholinoethyl)-2-oxo-N-(spiro[3.3]heptan-2-yl)-1,2-dihydro-1,8-naphthyridine-3-carboxamide (Compound 44)

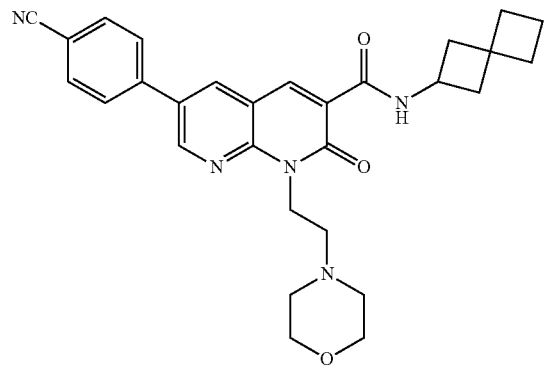

Step 1: Preparation of 6-(4-cyanophenyl)-1-(2-morpholinoethyl)-2-oxo-1,2-dihydro-1,8-naphthyridine-3-carboxylic acid

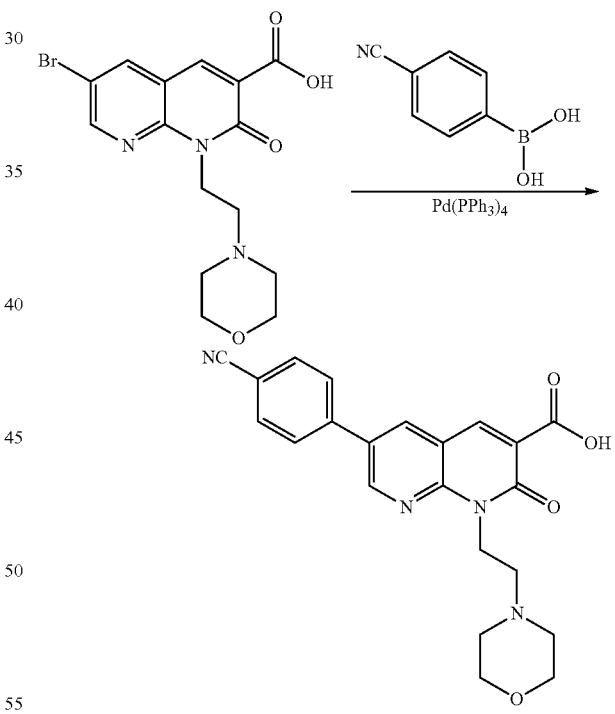

To a mixture of 6-bromo-1-(2-morpholinoethyl)-2-oxo-1,8-naphthyridine-3-carboxylic acid (190 mg, 497.11 μmol, 1 eq) in dioxane (2 mL) and Water (0.2 mL) was added (4-cyanophenyl) boronic acid (87.65 mg, 596.53 μmol, 1.2 eq), K$_2$CO$_3$ (206.11 mg, 1.49 mmol, 3 eq) and Pd(PPh$_3$)$_4$ (57.44 mg, 49.71 μmol, 0.1 eq). The mixture was stirred at 80° C. for 2 h under N2. LCMS showed complete consumption of the starting material and formation of a new peak with desired mass.

The mixture was concentrated, and the residue was purified by prep-HPLC (neutral condition) to produce 6-(4- cyanophenyl)-1-(2-morpholinoethyl)-2-oxo-1,2-dihydro-1,8-naphthyridine-3-carboxylic acid (90 mg, 222.54 µmol) as a white solid.

LCMS for product (ESI+): m/z 405.2 [M+H]$^+$, Rt: 1.058 min.

LCMS Method

The column used for chromatography was a ZORBAX Eclipse XDB-C18 2.1*30 mm, (3.5 µm particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min with a hold at 5% B for 0.39 min. The flow rate was 1.0 mL/min.

Step 2: Preparation of 6-(4-cyanophenyl)-1-(2-morpholinoethyl)-2-oxo-N-(spiro[3.3]heptan-2-yl)-1,2-dihydro-1,8-naphthyridine-3-carboxamide

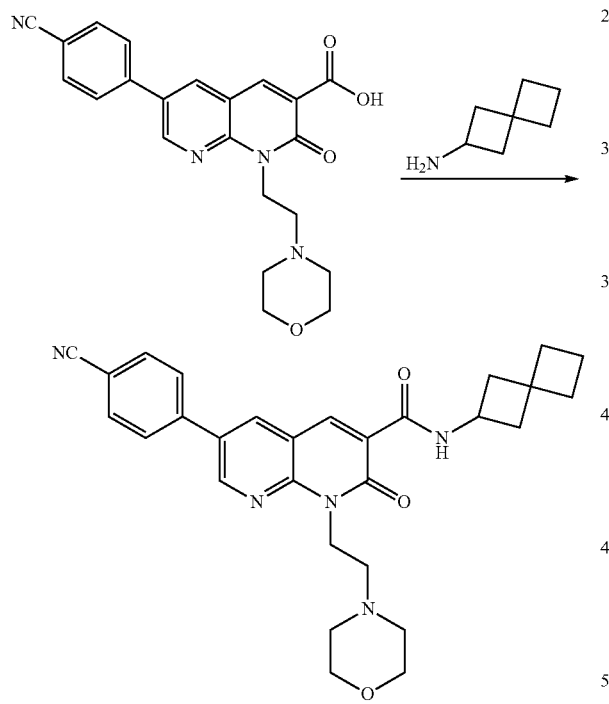

To a mixture of 6-(4-cyanophenyl)-1-(2-morpholinoethyl)-2-oxo-1,8-naphthyridine-3-carboxylic acid (25 mg, 61.82 µmol, 1 eq) in DMF (0.5 mL) was added spiro[3.3]heptan-2-amine (10.95 mg, 74.18 µmol, 1.2 eq, HCl), T3P (39.34 mg, 123.63 µmol, 36.76 µL, 2 eq) and DIEA (47.94 mg, 370.90 µmol, 64.60 µL, 6 eq).

The mixture was stirred at 25° C. for 1 h. LCMS showed complete consumption of the starting material and formation of a new peak with desired mass. The mixture was purified by prep-HPLC (neutral condition) to produce 6-(4-cyanophenyl)-1-(2-morpholinoethyl)-2-oxo-N-(spiro[3.3]heptan-2-yl)-1,2-dihydro-1,8-naphthyridine-3-carboxamide (9 mg, 18.09 µmol) as a white solid.

$^1$H NMR (400 MHz, DMSO-d$_6$) δ=9.71 (br d, J=7.6 Hz, 1H), 9.21 (d, J=2.3 Hz, 1H), 8.96-8.86 (m, 2H), 8.09-7.98 (m, 4H), 4.66 (br t, J=6.9 Hz, 2H), 4.30 (sxt, J=7.9 Hz, 1H), 3.54 (br s, 4H), 2.62 (br t, J=7.1 Hz, 2H), 2.56-2.51 (m, 4H), 2.45-2.40 (m, 2H), 2.06 (br t, J=7.2 Hz, 2H), 1.99-1.92 (m, 4H), 1.86-1.77 (m, 2H). LCMS for product (ESI+): m/z 498.3 [M+H]$^+$, Rt: 3.283 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 45—Synthesis of 6-(4-cyanophenyl)-N-(1-(4-fluorophenyl)ethyl)-1-(2-morpholinoethyl)-2-oxo-1,2-dihydro-1,8-naphthyridine-3-carboxamide (Compound 45)

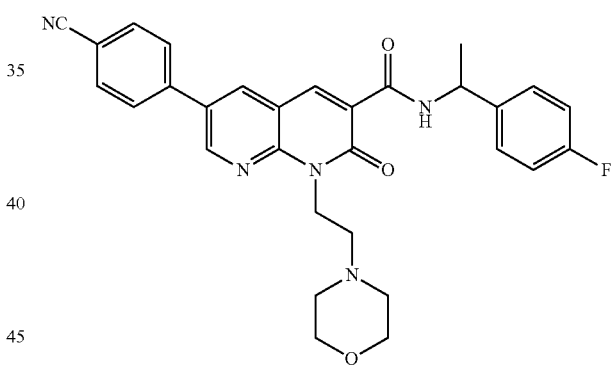

Preparation of 6-(4-cyanophenyl)-N-(1-(4-fluorophenyl)ethyl)-1-(2-morpholinoethyl)-2-oxo-1,2-dihydro-1,8-naphthyridine-3-carboxamide

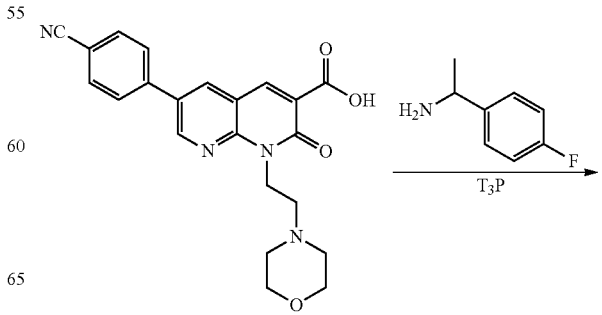

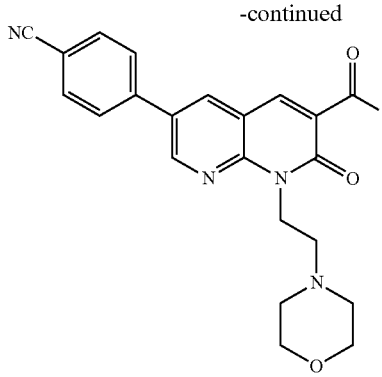

To a mixture of 6-(4-cyanophenyl)-1-(2-morpholinoethyl)-2-oxo-1,8-naphthyridine-3-carboxylic acid (20 mg, 49.45 μmol, 1 eq) in DMF (0.5 mL) was added 1-(4-fluorophenyl)ethanamine (10.42 mg, 59.34 μmol, 9.83 μL, 1.2 eq, HCl), T3P (31.47 mg, 98.91 mol, 29.41 μL, 2 eq) and DIEA (38.35 mg, 296.72 μmol, 51.68 μL, 6 eq). The mixture was stirred at 25° C. for 1 h. LCMS showed complete consumption of the starting material and formation of a new peak with desired mass.

The mixture was purified by prep-HPLC (neutral condition) to produce 6-(4-cyanophenyl)-N-(1-(4-fluorophenyl)ethyl)-1-(2-morpholinoethyl)-2-oxo-1,2-dihydro-1,8-naphthyridine-3-carboxamide (4.8 mg, 9.13 μmol) as a white solid.

$^1$H NMR (400 MHz, DMSO-d$_6$) δ=9.98 (br d, J=7.9 Hz, 1H), 9.23 (d, J=2.0 Hz, 1H), 8.93 (s, 2H), 8.11-7.99 (m, 4H), 7.46 (br dd, J=5.6, 8.2 Hz, 2H), 7.19 (br t, J=8.8 Hz, 2H), 5.19 (quin, J=6.9 Hz, 1H), 4.68 (br t, J=6.2 Hz, 2H), 3.54 (br s, 4H), 2.63 (br t, J=6.9 Hz, 2H), 2.57-2.52 (m, 4H), 1.52 (br d, J=6.9 Hz, 3H). LCMS for product (ESI+): m/z 526.3 [M+H]$^+$, Rt: 3.184 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 46—Synthesis of N-(bicyclo[1.1.1]pentan-1-yl)-6-(4-cyanophenyl)-1-(2-morpholinoethyl)-2-oxo-1,2-dihydro-1,8-naphthyridine-3-carboxamide (Compound 46)

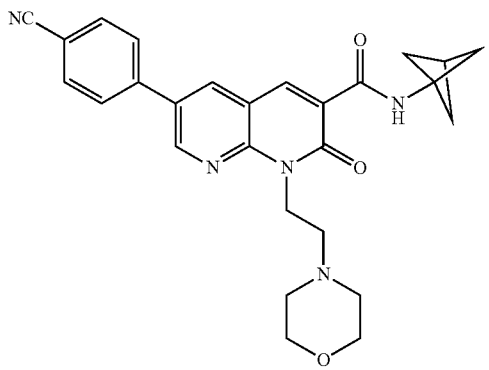 [SMILES: N#Cc1ccc(-c2cnc3c(c2)cc(C(=O)NC24CC(C2)C4)c(=O)n3CCN2CCOCC2)cc1]

Preparation of 1-(2-morpholinoethyl)-2-oxo-6-(pyridin-2-yl)-N-(spiro[3.3]heptan-2-yl)-1,2-dihydro-1,8-naphthyridine-3-carboxamide

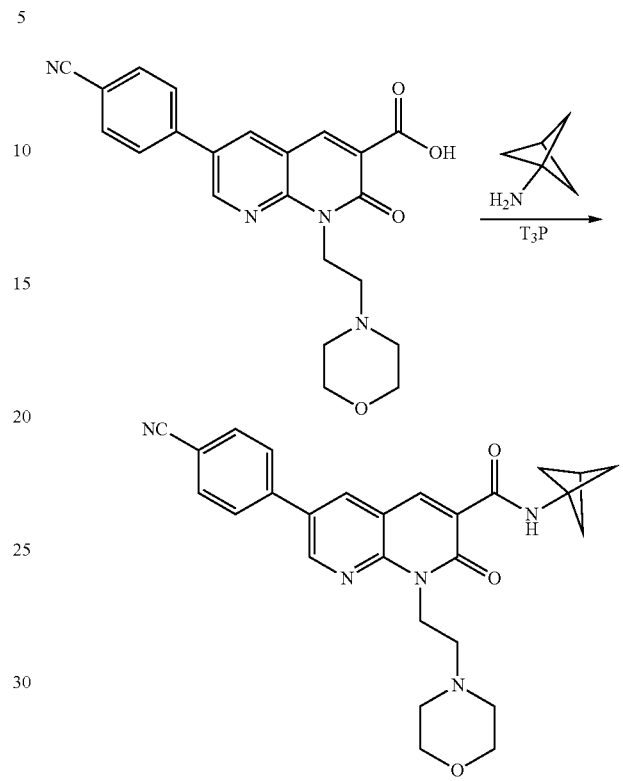

To a mixture of 6-(4-cyanophenyl)-1-(2-morpholinoethyl)-2-oxo-1,8-naphthyridine-3-carboxylic acid (25 mg, 61.82 μmol, 1 eq) in DMF (0.5 mL) was added bicyclo[1.1.1]pentan-3-amine (8.87 mg, 74.18 μmol, 2.46 μL, 1.2 eq, HCl), T3P (39.34 mg, 123.63 μmol, 36.76 μL, 2 eq) and DIEA (47.94 mg, 370.90 μmol, 64.60 μL, 6 eq). The mixture was stirred at 25° C. for 1 h. LCMS showed complete consumption of the starting material and formation of a new peak with desired mass.

The mixture was purified by prep-HPLC (neutral condition) to produce 1-(2-morpholinoethyl)-2-oxo-6-(pyridin-2-yl)-N-(spiro[3.3]heptan-2-yl)-1,2-dihydro-1,8-naphthyridine-3-carboxamide (9 mg, 19.09 μmol) as a white solid.

$^1$H NMR (400 MHz, DMSO-d$_6$) δ=9.82 (s, 1H), 9.56 (br s, 1H), 9.20 (d, J=2.1 Hz, 1H), 9.03-8.93 (m, 2H), 8.11-8.02 (m, 4H), 4.86 (br s, 2H), 4.01 (br s, 2H), 3.76-3.56 (m, 6H), 3.24-3.14 (m, 2H), 2.52 (br s, 1H), 2.14 (s, 6H). LCMS for product (ESI+): m/z 470.3 [M+H]$^+$, Rt: 3.092 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 47—Synthesis of 6-(5-(difluoromethoxy)pyridin-2-yl)-1-(2-morpholinoethyl)-2-oxo-N-(spiro[3.3]heptan-2-yl)-1,2-dihydro-1,8-naphthyridine-3-carboxamide (Compound 47)

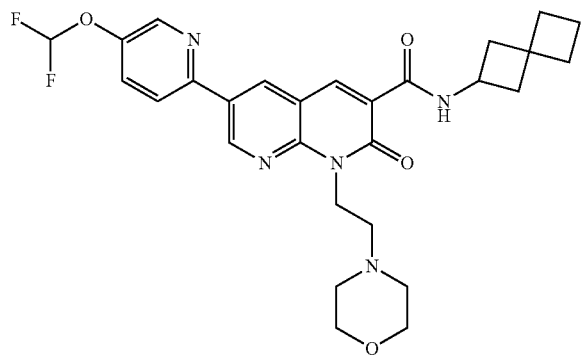

Step 1: Preparation of 6-(5-(difluoromethoxy)pyridin-2-yl)-1-(2-morpholinoethyl)-2-oxo-1,2-dihydro-1,8-naphthyridine-3-carboxylic acid

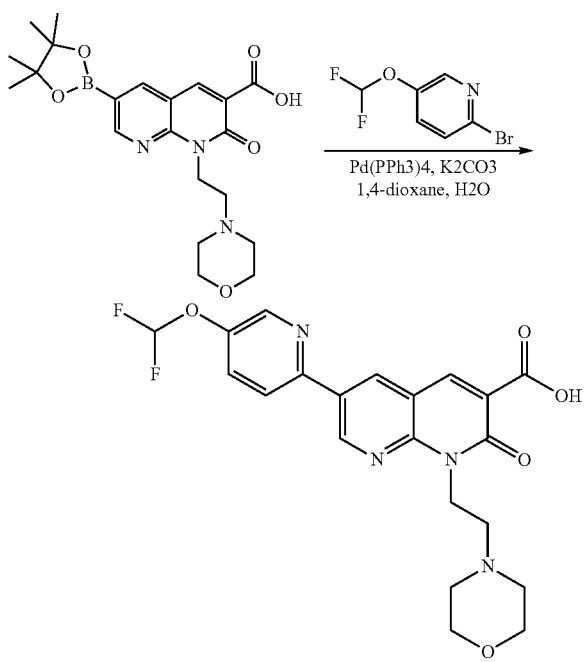

To a mixture of 1-(2-morpholinoethyl)-2-oxo-6-(4,4,5,5-tetramethyl-1,3,2-dioxaborolan-2-yl)-1,8-naphthyridine-3-carboxylic acid (10 mg, 23.30 μmol, 1 eq) in dioxane (2 mL) and H₂O (0.2 mL) was added 2-bromo-5-(difluoromethoxy)pyridine (5.22 mg, 23.30 μmol, 1 eq), Pd(PPh₃)₄ (2.69 mg, 2.33 μmol, 0.1 eq) and K₂CO₃ (9.66 mg, 69.89 μmol, 3 eq) under N2. The mixture was stirred at 80° C. for 2 h under N2. Sixteen additional vials were set up as described above. LCMS showed complete consumption of the starting material and formation of a new peak with desired mass. All seventeen reaction mixtures were combined.

The mixture was poured into water (100 mL) and mixture was extracted with EtOAc (200 mL). The aqueous phase was adjusted pH=3 by HCl (1 M) and the resulting solid was collected by filtration to produce the desired product (100 mg, 224.01 μmol) as a yellow solid.

LCMS for product (ESI+): m/z 447.1 [M+H]⁺, Rt: 1.078 min.

LCMS Method

The column used for chromatography was a ZORBAX Eclipse XDB-C18 2.1*30 mm, (3.5 μm particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min with a hold at 5% B for 0.39 min. The flow rate was 1.0 mL/min.

Step 2: Preparation of 6-(5-(difluoromethoxy)pyridin-2-yl)-1-(2-morpholinoethyl)-2-oxo-N-(spiro[3.3]heptan-2-yl)-1,2-dihydro-1,8-naphthyridine-3-carboxamide

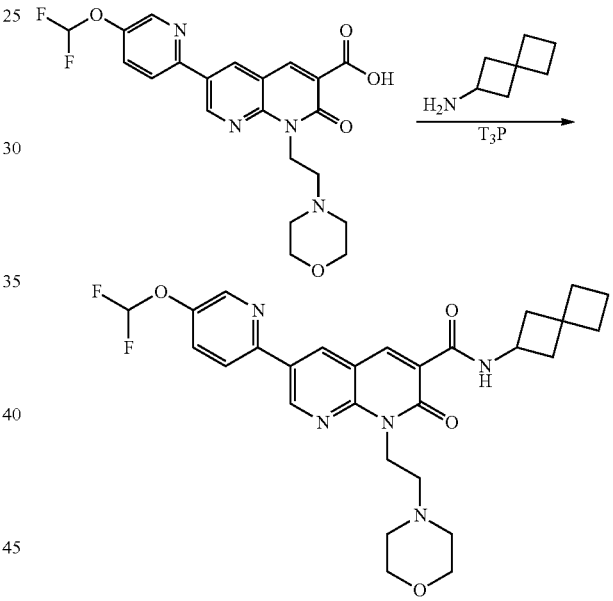

To a mixture of 6-[5-(difluoromethoxy)-2-pyridyl]-1-(2-morpholinoethyl)-2-oxo-1,8-naphthyridine-3-carboxylic acid (30 mg, 67.20 μmol, 1 eq) in DMF (0.5 mL) was added spiro[3.3]heptan-2-amine (11.91 mg, 80.64 μmol, 1.2 eq, HCl), DIEA (52.11 mg, 403.22 μmol, 70.23 μL, 6 eq) and T3P (42.77 mg, 134.41 μmol, 39.97 μL, 2 eq) under N₂. The mixture was stirred at 25° C. for 1 h under N₂. LCMS showed complete consumption of the starting material and formation of a new peak with desired mass.

The mixture was filtered, and the filtrate was purified by prep-HPLC (neutral condition) to produce 6-(5-(difluoromethoxy)pyridin-2-yl)-1-(2-morpholinoethyl)-2-oxo-N-(spiro[3.3]heptan-2-yl)-1,2-dihydro-1,8-naphthyridine-3-carboxamide (25 mg, 46.33 μmol) as a white solid.

¹H NMR (400 MHz, DMSO-d₆) δ=9.70 (d, J=7.6 Hz, 1H), 9.44 (d, J=2.3 Hz, 1H), 9.10 (d, J=2.3 Hz, 1H), 8.94 (s, 1H), 8.64 (d, J=2.8 Hz, 1H), 8.21 (d, J=8.7 Hz, 1H), 7.87 (dd, J=2.8, 8.7 Hz, 1H), 7.60-7.21 (m, 1H), 4.67 (br t, J=7.1 Hz, 2H), 4.36-4.25 (m, 1H), 3.53 (t, J=4.4 Hz, 4H), 2.65-

2.61 (m, 2H), 2.44 (br d, J=2.7 Hz, 4H), 2.41 (br dd, J=2.3, 9.4 Hz, 2H), 2.09-2.03 (m, 2H), 2.00-1.93 (m, 4H), 1.85-1.77 (m, 2H). LCMS for product (ESI+): m/z 540.3 [M+H]$^+$, Rt: 3.284 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 48—Synthesis of (R)-6-(5-(difluoromethoxy)pyridin-2-yl)-N-(1-(4-fluorophenyl) ethyl)-1-(2-morpholinoethyl)-2-oxo-1,2-dihydro-1,8-naphthyridine-3-carboxamide (Compound 48)

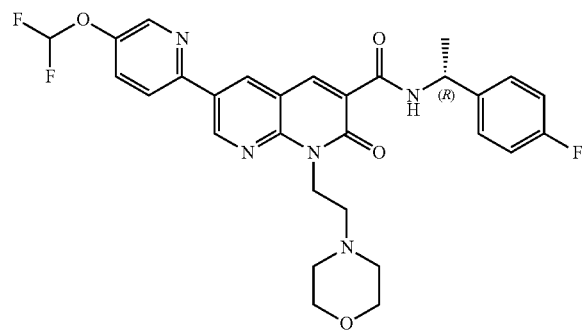

Preparation of (R)-6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide

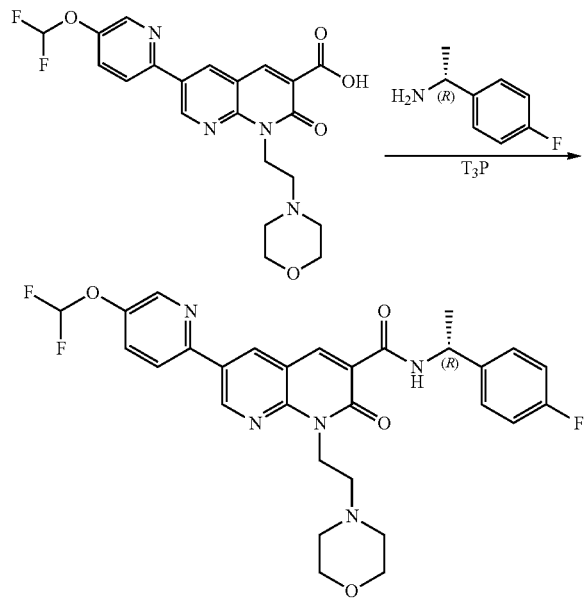

To a mixture of 6-[5-(difluoromethoxy)-2-pyridyl]-1-(2-morpholinoethyl)-2-oxo-1,8-naphthyridine-3-carboxylic acid (35 mg, 78.40 μmol, 1 eq) in DMF (0.5 mL) was added (1R)-1-(4-fluorophenyl)ethanamine (16.52 mg, 94.09 μmol, 1.2 eq, HCl), DIEA (60.80 mg, 470.43 μmol, 81.94 μL, 6 eq) and T3P (49.89 mg, 156.81 μmol, 46.63 μL, 2 eq) under N$_2$. The mixture was stirred at 25° C. for 1 h under N$_2$. LCMS showed complete consumption of the starting material and formation of a new peak with desired mass.

The mixture was filtered, and the filtrate was purified by prep-HPLC (neutral condition) to produce (R)-6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide (29 mg, 51.10 μmol) as a white solid.

$^1$H NMR (400 MHz, DMSO-d$_6$) δ=9.98 (d, J=7.6 Hz, 1H), 9.45 (d, J=2.4 Hz, 1H), 9.11 (d, J=2.4 Hz, 1H), 8.96 (s, 1H), 8.64 (d, J=2.9 Hz, 1H), 8.21 (d, J=8.8 Hz, 1H), 7.87 (dd, J=2.8, 8.8 Hz, 1H), 7.61-7.16 (m, 5H), 5.19 (quin, J=7.0 Hz, 1H), 4.72-4.64 (m, 2H), 3.53 (br t, J=4.3 Hz, 4H), 2.63 (br t, J=7.2 Hz, 2H), 2.52 (br s, 4H), 1.52 (d, J=6.9 Hz, 3H). LCMS for product (ESI+): m/z 568.3 [M+H]$^+$, Rt: 3.181 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 49—Synthesis of (S)-6-(5-(difluoromethoxy)pyridin-2-yl)-N-(1-(4-fluorophenyl) ethyl)-1-(2-morpholinoethyl)-2-oxo-1,2-dihydro-1,8-naphthyridine-3-carboxamide (Compound 49)

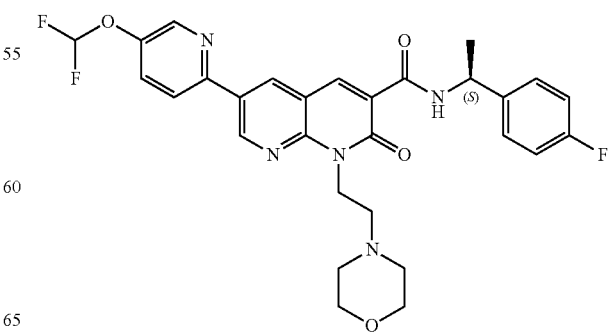

Preparation of (S)-6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide

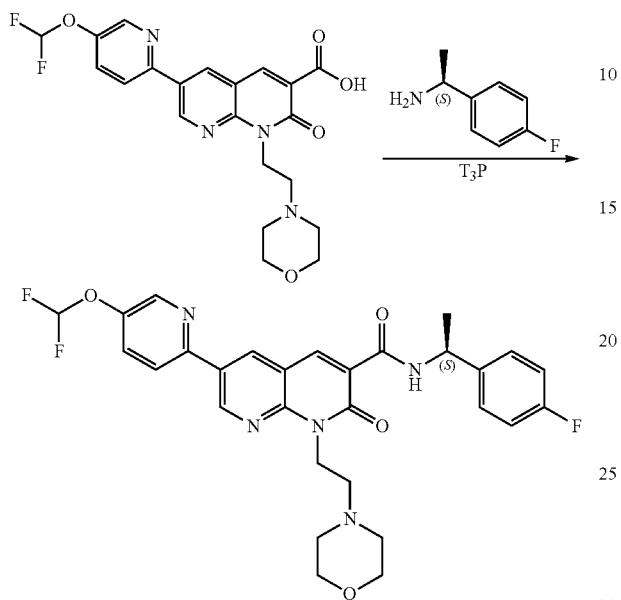

To a mixture of 6-[5-(difluoromethoxy)-2-pyridyl]-1-(2-morpholinoethyl)-2-oxo-1,8-naphthyridine-3-carboxylic acid (30 mg, 67.20 μmol, 1 eq) in DMF (0.5 mL) was added (1S)-1-(4-fluorophenyl)ethanamine (14.16 mg, 80.64 μmol, 1.2 eq, HCl), DIEA (52.11 mg, 403.22 μmol, 70.23 μL, 6 eq) and T3P (42.77 mg, 134.41 μmol, 39.97 μL, 2 eq) under $N_2$. The mixture was stirred at 25° C. for 1 h under $N_2$. LCMS showed complete consumption of the starting material and formation of a new peak with desired mass.

The mixture was filtered and the filtrate was purified by prep-HPLC (neutral condition) to produce (S)-6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide (25 mg, 44.05 μmol) as a white solid.

$^1$H NMR (400 MHz, DMSO-$d_6$) δ=9.97 (d, J=7.6 Hz, 1H), 9.45 (d, J=2.3 Hz, 1H), 9.10 (d, J=2.4 Hz, 1H), 8.95 (s, 1H), 8.64 (d, J=2.8 Hz, 1H), 8.21 (d, J=8.8 Hz, 1H), 7.86 (dd, J=2.8, 8.7 Hz, 1H), 7.60-7.16 (m, 5H), 5.19 (quin, J=7.0 Hz, 1H), 4.72-4.64 (m, 2H), 3.53 (br t, J=4.3 Hz, 4H), 2.64 (br t, J=7.1 Hz, 2H), 2.53-2.51 (m, 4H), 1.52 (d, J=7.0 Hz, 3H). LCMS for product (ESI+): m/z 568.3 [M+H]$^+$, Rt: 3.136 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 50—Synthesis of N-(bicyclo[1.1.1]pentan-1-yl)-6-(4-methoxyphenyl)-1-(2-morpholinoethyl)-2-oxo-1,2-dihydro-1,8-naphthyridine-3-carboxamide (Compound 50)

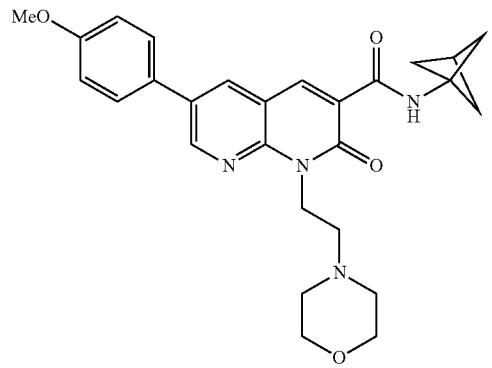 [SMILES: COc1ccc(-c2cnc3c(c2)cc(C(=O)NC24CC(C2)C4)c(=O)n3CCN2CCOCC2)cc1]

Step 1: Preparation of 6-(4-methoxyphenyl)-1-(2-morpholinoethyl)-2-oxo-1,2-dihydro-1,8-naphthyridine-3-carboxylic acid

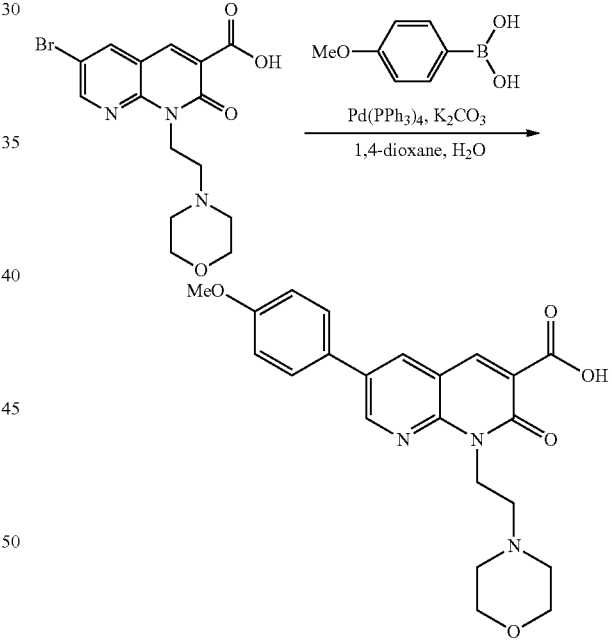

To a mixture of 6-bromo-1-(2-morpholinoethyl)-2-oxo-1,8-naphthyridine-3-carboxylic acid (50 mg, 130.82 μmol, 1 eq) in dioxane (0.5 mL) and $H_2O$ (0.05 mL) was added (4-methoxyphenyl)boronic acid (23.85 mg, 156.98 μmol, 1.2 eq), $K_2CO_3$ (54.24 mg, 392.46 μmol, 3 eq) and Pd(PPh$_3$)$_4$ (15.12 mg, 13.08 μmol, 0.1 eq) under $N_2$. The mixture was stirred at 80° C. for 2 h under $N_2$. LCMS showed complete consumption of the starting material and formation of a new peak with desired mass.

The mixture was concentrated the residue was triturated in petroleum ether\ethyl acetate (4:1), filtered and the solid was air-dried to produce 6-(4-methoxyphenyl)-1-(2-morpholinoethyl)-2-oxo-1,2-dihydro-1,8-naphthyridine-3-carboxylic acid (50 mg, 122.12 µmol) as a yellow solid.

LCMS for product (ESI+): m/z 410.2 [M+H]⁺, Rt: 1.082 min.

LCMS Method

The column used for chromatography was a ZORBAX Eclipse XDB-C18 2.1*30 mm, (3.5 µm particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min with a hold at 5% B for 0.39 min. The flow rate was 1.0 m/min.

Step 2: Preparation of N-(bicyclo[1.1.1]pentan-1-yl)-6-(4-methoxyphenyl)-1-(2-morpholinoethyl)-2-oxo-1,2-dihydro-1,8-naphthyridine-3-carboxamide

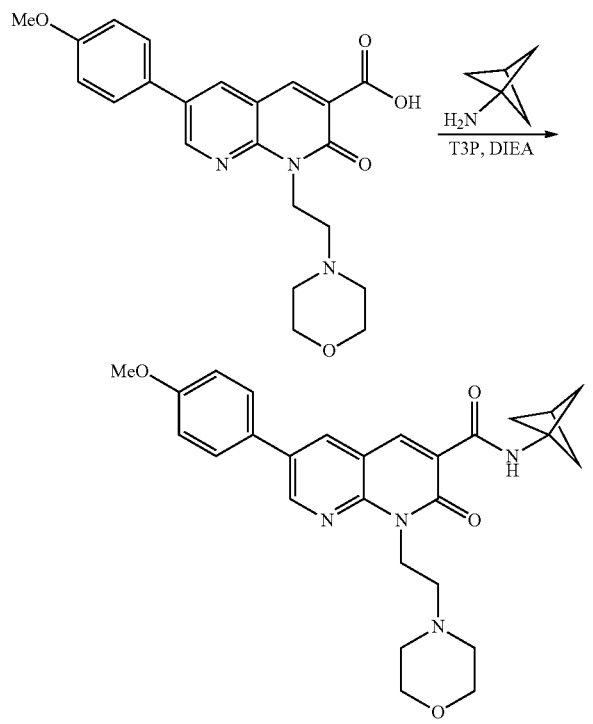

To a mixture of 6-(4-methoxyphenyl)-1-(2-morpholinoethyl)-2-oxo-1,8-naphthyridine-3-carboxylic acid (5 mg, 12.21 µmol, 1 eq) in DMF (0.5 mL) was added bicyclo[1.1.1]pentan-3-amine (1.75 mg, 14.65 µmol, 1.2 eq, HCl), DIEA (9.56 mg, 74.00 µmol, 12.89 µL, 6 eq) and T3P (15.54 mg, 24.42 µmol, 14.53 µL, 50% purity, 2 eq). The mixture was stirred at 25° C. for 1 h. LCMS showed complete consumption of the starting material and formation of a new peak with desired mass.

The mixture was filtered, and the filtrate was purified by prep-HPLC (neutral condition) to produce N-(bicyclo[1.1.1]pentan-1-yl)-6-(4-methoxyphenyl)-1-(2-morpholinoethyl)-2-oxo-1,2-dihydro-1,8-naphthyridine-3-carboxamide (6.3 mg, 13.21 µmol) as a pale-yellow solid.

¹H NMR (400 MHz, DMSO-d₆) δ=10.01 (s, 1H), 9.11 (d, J=2.4 Hz, 1H), 8.90 (s, 1H), 8.75 (d, J=2.4 Hz, 1H), 7.78 (d, J=8.8 Hz, 2H), 7.10 (d, J=8.8 Hz, 2H), 4.65 (br t, J=7.1 Hz, 2H), 3.83 (s, 3H), 3.54 (br t, J=4.4 Hz, 4H), 2.62 (br t, J=7.1 Hz, 2H), 2.53-2.52 (m, 4H), 2.47-2.46 (m, 2H), 2.13 (s, 6H).

LCMS for product (ESI+): m/z 475.3 [M+H]⁺, Rt: 3.239 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH₄HCO₃, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 51—Synthesis of 6-(4-(difluoromethoxy)phenyl)-N-(4-methylcyclohexyl)-1-(2-morpholinoethyl)-2-oxo-1,2-dihydro-1,8-naphthyridine-3-carboxamide (Compound 51)

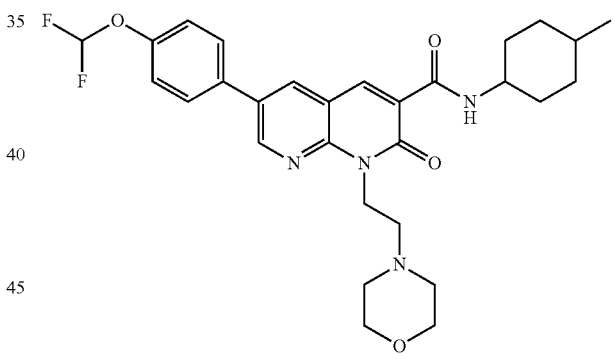

Step 1: Preparation of 6-(4-methoxyphenyl)-1-(2-morpholinoethyl)-2-oxo-1,2-dihydro-1,8-naphthyridine-3-carboxylic acid

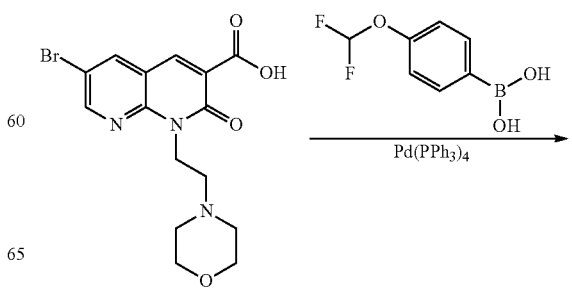

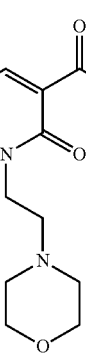

To a mixture of 6-bromo-1-(2-morpholinoethyl)-2-oxo-1,8-naphthyridine-3-carboxylic acid (50 mg, 130.82 μmol, 1 eq) in 1,4-dioxane (2 mL) and H₂O (0.5 mL) was added [4-(difluoromethoxy)phenyl]boronic acid (29.50 mg, 156.98 μmol, 1.2 eq), K₂CO₃ (54.24 mg, 392.46 μmol, 3 eq) and Pd(PPh₃)₄ (15.12 mg, 13.08 μmol, 0.1 eq) under N₂. The mixture was stirred at 80° C. for 2 h. LCMS showed complete consumption of the starting material and formation of a new peak with desired mass. The mixture was poured into water (20 mL), washed with ethyl acetate (4×10 mL). The aqueous layer was acidified to pH=5 by adding 1 N hydrochloric acid dropwise at 0° C. The mixture was extracted with ethyl acetate (3×10 mL). The organic layer was washed with brine, dried and concentrated.

The residue was triturated in petroleum ether/ethyl acetate (10:1, 10 mL) at 25° C. for 1 h. The mixture was filtered, and filtered cake was air-dried to yield 6-(4-methoxyphenyl)-1-(2-morpholinoethyl)-2-oxo-1,2-dihydro-1,8-naphthyridine-3-carboxylic acid (60 mg, 134.71 μmol) as a yellow solid.

¹H NMR (400 MHz, DMSO-d₆) δ=15.10-13.22 (m, 1H), 9.21 (d, J=2.4 Hz, 1H), 8.97 (s, 1H), 8.87 (d, J=2.4 Hz, 1H), 7.90 (d, J=8.8 Hz, 2H), 7.54-7.16 (m, 3H), 4.71 (br s, 2H), 3.65-3.40 (m, 6H), 2.67 (br s, 4H). LCMS for product (ESI+): m/z 446.2 [M+H]⁺, Rt: 0.683 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% CF₃CO₂H in water, mobile phase B was 0.018% CF₃CO₂H in CH₃CN. The column used for the chromatography is a Chromolith Flash RP-18e 25-2 mm column. Detection methods are diode array (DAD) and evaporative light scattering (ELSD) detection as well as positive electrospray ionization (MS).

Step 2: Preparation of 6-(4-(difluoromethoxy)phenyl)-N-(4-methylcyclohexyl)-1-(2-morpholinoethyl)-2-oxo-1,2-dihydro-1,8-naphthyridine-3-carboxamide

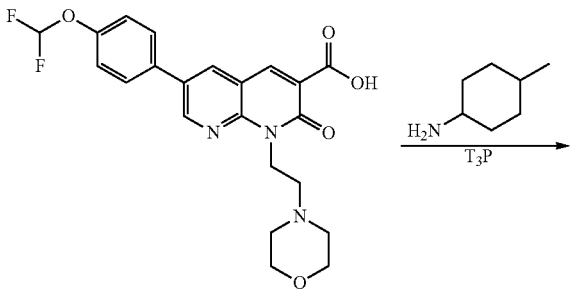

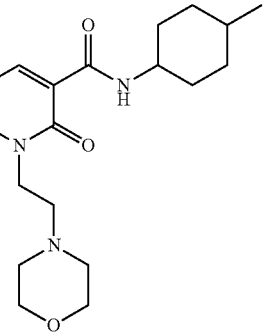

To a solution of 6-[4-(difluoromethoxy)phenyl]-1-(2-morpholinoethyl)-2-oxo-1,8-naphthyridine-3-carboxylic acid (30 mg, 67.35 μmol, 1 eq) in DMF (1 mL) was added 4-methylcyclohexanamine (9.15 mg, 80.82 μmol, 10.70 μL, 1.2 eq) and DIEA (52.23 mg, 404.12 μmol, 70.39 μL, 6 eq) and T3P (85.72 mg, 134.71 μmol, 80.11 μL, 50% purity, 2 eq). The mixture was stirred at 20° C. for 1 h. LCMS showed complete consumption of the starting material and formation of a new peak with desired mass.

The mixture was filtered and the filtrate was purified by prep-HPLC (column: Phenomenex Luna 80*30 mm*3 μm; mobile phase: [water (10 mM NH₄HCO₃)-ACN]; B %: 50%-80%, 7 min) to produce 6-(4-(difluoromethoxy)phenyl)-N-(4-methylcyclohexyl)-1-(2-morpholinoethyl)-2-oxo-1,2-dihydro-1,8-naphthyridine-3-carboxamide (15.5 mg, 28.41 μmol) as a white solid.

¹H NMR (400 MHz, DMSO-d₆) δ=10.04-9.49 (m, 1H), 9.13 (t, J=2.3 Hz, 1H), 8.94 (d, J=7.5 Hz, 1H), 8.82 (d, J=2.1 Hz, 1H), 7.89 (br d, J=7.6 Hz, 2H), 7.61-7.07 (m, 3H), 4.80-4.54 (m, 2H), 4.21-3.69 (m, 1H), 3.54 (br d, J=4.1 Hz, 4H), 2.78-2.53 (m, 6H), 2.00-1.88 (m, 1H), 1.78-1.56 (m, 4H), 1.46-1.02 (m, 4H), 0.91 (br dd, J=6.4, 15.2 Hz, 3H). LCMS for product (ESI+): m/z 541.3 [M+H]⁺, Rt: 3.489 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Example 52—Synthesis of 6-(4-(difluoromethoxy)phenyl)-1-(2-morpholinoethyl)-2-oxo-N-(spiro[3.3]heptan-2-yl)-1,2-dihydro-1,8-naphthyridine-3-carboxamide (Compound 52)

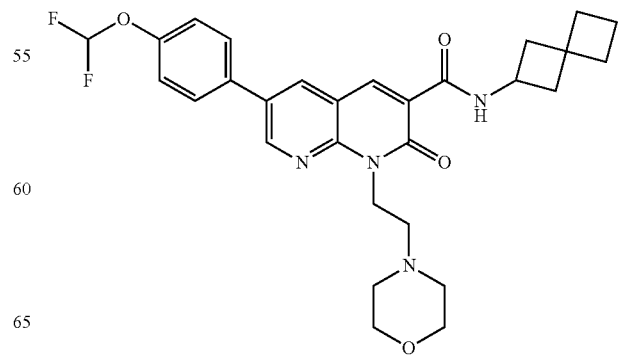

Preparation of 6-(4-(difluoromethoxy)phenyl)-1-(2-morpholinoethyl)-2-oxo-N-(spiro[3.3]heptan-2-yl)-1,2-dihydro-1,8-naphthyridine-3-carboxamide

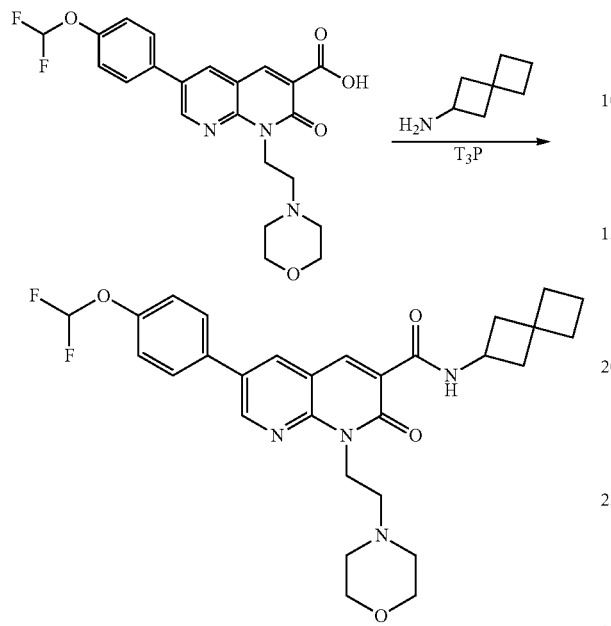

To a mixture of 6-[4-(difluoromethoxy)phenyl]-1-(2-morpholinoethyl)-2-oxo-1,8-naphthyridine-3-carboxylic acid (30 mg, 67.35 μmol, 1 eq) in DMF (1 mL) was added spiro[3.3]heptan-2-amine (11.93 mg, 80.82 μmol, 1.2 eq, HCl), T3P (85.72 mg, 134.71 μmol, 80.11 μL, 50% purity, 2 eq) and DIEA (52.23 mg, 404.12 μmol, 70.39 μL, 6 eq). The mixture was stirred at 20° C. for 1 h. LCMS showed complete consumption of the starting material and formation of a new peak with desired mass.

The pH of the reaction mixture was adjusted to 5 by dropwise addition of TFA and purified by prep-HPLC (neutral condition) to produce 6-(4-(difluoromethoxy)phenyl)-1-(2-morpholinoethyl)-2-oxo-N-(spiro[3.3]heptan-2-yl)-1,2-dihydro-1,8-naphthyridine-3-carboxamide (24 mg, 44.56 μmol) as a light-yellow solid.

$^1$H NMR (400 MHz, DMSO-$d_6$) δ=9.76 (br d, J=7.6 Hz, 1H), 9.13 (d, J=2.3 Hz, 1H), 8.91 (s, 1H), 8.81 (d, J=2.4 Hz, 1H), 7.89 (d, J=8.8 Hz, 2H), 7.53-7.14 (m, 3H), 4.65 (br t, J=6.9 Hz, 2H), 4.30 (sxt, J=7.9 Hz, 1H), 3.54 (br s, 4H), 2.62 (br t, J=7.1 Hz, 2H), 2.54-2.51 (m, 4H), 2.44-2.39 (m, 2H), 2.09-2.02 (m, 2H), 1.99-1.91 (m, 4H), 1.86-1.75 (m, 2H). LCMS for product (ESI+): m/z 539.3 [M+H]$^+$, Rt: 3.443 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 53—Synthesis of 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide (Compound 53)

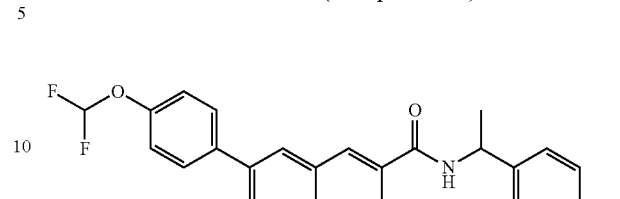

Preparation of 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide

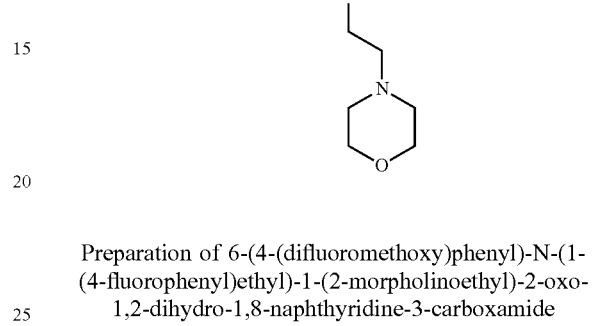

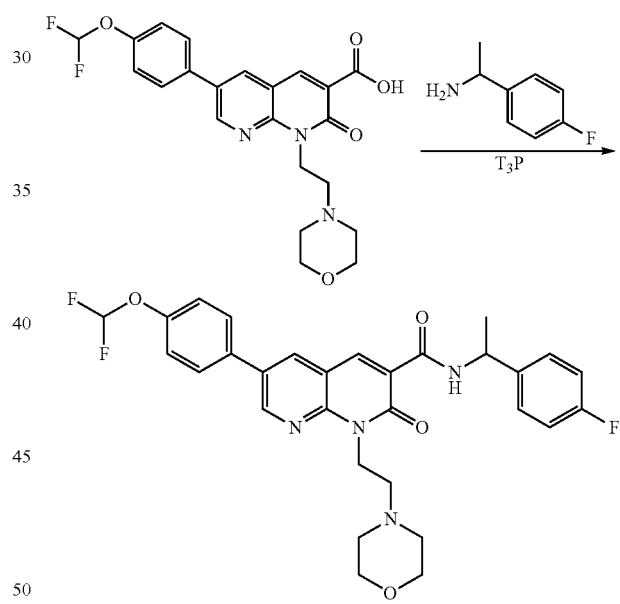

To a mixture of 6-[4-(difluoromethoxy)phenyl]-1-(2-morpholinoethyl)-2-oxo-1,8-naphthyridine-3-carboxylic acid (30 mg, 67.35 μmol, 1 eq) in DMF (1 mL) was added 1-(4-fluorophenyl)ethanamine (11.25 mg, 80.82 μmol, 10.61 μL, 1.2 eq), T3P (85.72 mg, 134.71 μmol, 80.11 μL, 50% purity, 2 eq) and DIEA (52.23 mg, 404.12 μmol, 70.39 μL, 6 eq). The mixture was stirred at 20° C. for 1 h. LCMS showed complete consumption of the starting material and formation of a new peak with desired mass.

The pH of the reaction mixture was adjusted to 5 by dropwise addition of TFA and purified by prep-HPLC (neutral condition) to produce 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide (24.5 mg, 43.24 μmol) as a light-yellow solid.

$^1$H NMR (400 MHz, DMSO-d$_6$) δ=10.01 (d, J=7.6 Hz, 1H), 9.14 (d, J=2.1 Hz, 1H), 8.93 (s, 1H), 8.81 (d, J=2.3 Hz, 1H), 7.89 (d, J=8.6 Hz, 2H), 7.53-7.13 (m, 7H), 5.20 (t, J=7.2 Hz, 1H), 4.68 (br t, J=6.6 Hz, 2H), 3.54 (br t, J=4.3 Hz, 4H), 2.64 (br t, J=7.0 Hz, 2H), 2.58-2.53 (m, 4H), 1.52 (d, J=6.9 Hz, 3H). LCMS for product (ESI+): m/z 567.3 [M+H]$^+$, Rt: 3.274 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 54—Synthesis of N-(bicyclo[1.1.1]pentan-1-yl)-6-(4-(difluoromethoxy)phenyl)-1-(2-morpholinoethyl)-2-oxo-1,2-dihydro-1,8-naphthyridine-3-carboxamide (Compound 54)

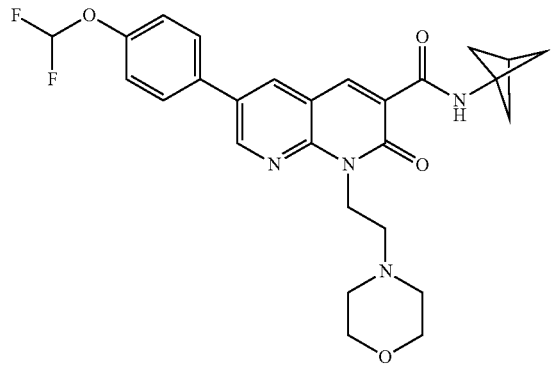 [SMILES: O=C(NC12CC(C1)C2)c1cc2cc(-c3ccc(OC(F)F)cc3)cnc2n(CCN2CCOCC2)c1=O]

Preparation of N-(bicyclo[1.1.1]pentan-1-yl)-6-(4-(difluoromethoxy)phenyl)-1-(2-morpholinoethyl)-2-oxo-1,2-dihydro-1,8-naphthyridine-3-carboxamide

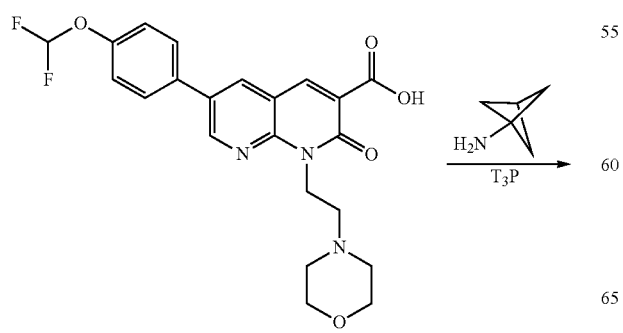

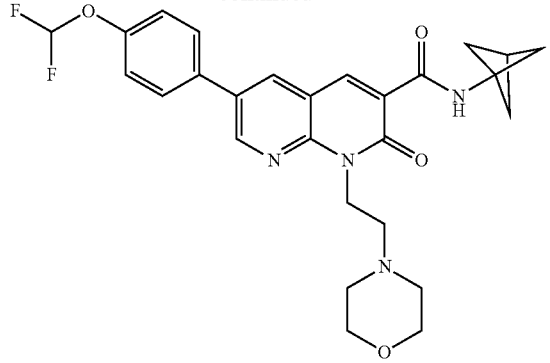

To a solution of 6-[4-(difluoromethoxy)phenyl]-1-(2-morpholinoethyl)-2-oxo-1,8-naphthyridine-3-carboxylic acid (28 mg, 62.86 μmol, 1 eq) in DMF (1 mL) was added bicyclo[1.1.1]pentan-3-amine (9.02 mg, 75.44 μmol, 1.2 eq, HCl), DIEA (48.75 mg, 377.18 mol, 65.70 μL, 6 eq) and T3P (80.01 mg, 125.73 μmol, 74.77 μL, 50% purity, 2 eq). The mixture was stirred at 20° C. for 1 h. LCMS showed complete consumption of the starting material and formation of a new peak with desired mass.

The mixture was filtered and the filtrate was purified by prep-HPLC (column: Phenomenex Luna 80*30 mm*3 μm; mobile phase: [water (10 NH$_4$HCO$_3$)-ACN]; B %: 50%-80%, 7 min) to produce N-(bicyclo[1.1.1]pentan-1-yl)-6-(4-(difluoromethoxy)phenyl)-1-(2-morpholinoethyl)-2-oxo-1,2-dihydro-1,8-naphthyridine-3-carboxamide (15 mg, 29.38 μmol) as a white solid.

$^1$H NMR (400 MHz, DMSO-d$_6$) δ=9.99 (s, 1H), 9.14 (d, J=2.4 Hz, 1H), 8.90 (s, 1H), 8.82 (d, J=2.4 Hz, 1H), 7.90 (d, J=8.8 Hz, 2H), 7.59-7.10 (m, 3H), 4.66 (br t, J=7.1 Hz, 2H), 3.54 (br t, J=4.4 Hz, 4H), 2.64-2.60 (m, 2H), 2.58-2.53 (m, 5H), 2.13 (s, 6H). LCMS for product (ESI+): m/z 511.3 [M+H]$^+$, Rt: 3.249 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Example 55—Synthesis of 6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide (Compound 55)

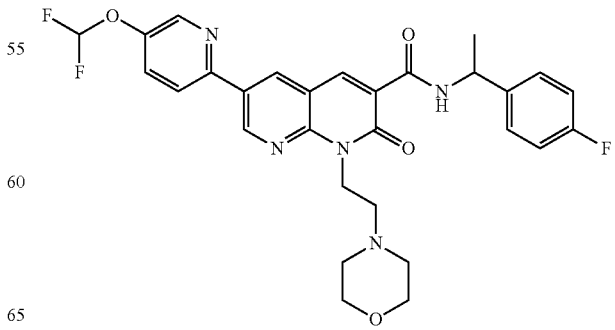

Step 1: 6-bromo-2-oxo-1,2-dihydro-1,8-naphthyridine-3-carboxylic acid

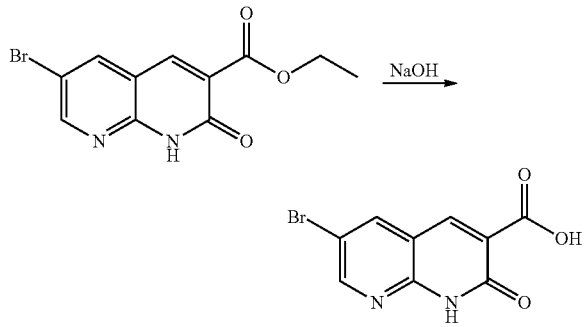

To a solution of ethyl 6-bromo-2-oxo-1H-1,8-naphthyridine-3-carboxylate (1 g, 3.37 mmol, 1 eq) in DMSO (10 mL) was added NaOH (2 M, 3.8 mL, 2 eq) at 20° C., the mixture was stirred at 20° C. for 1 h. LCMS showed complete consumption of the starting material and formation of a new peak with desired mass.

The mixture was acidified by adding 0.5 N hydrochloric acid dropwise to pH=2, and the resulting solid was collected by filtration to produce 6-bromo-2-oxo-1,2-dihydro-1,8-naphthyridine-3-carboxylic acid (800 mg) as a white solid (used without further purification).

$^1$H NMR (400 MHz, DMSO-$d_6$) $\delta$=14.24 (br s, 1H), 13.61 (br s, 1H), 8.92-8.83 (m, 2H), 8.77 (d, J=2.5 Hz, 1H). LCMS for product (ESI+): m/z 268.9, 270.9 [M+H]$^+$, Rt: 0.909 min.

LCMS Method

The gradient was 5-95% B in 0.7 min, 95-95% B in 0.45 min, 95-5% B in 0.01 min, and then held at 0% B for 0.44 min (1.5 mL/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 2: 6-bromo-N-(1-(4-fluorophenyl)ethyl)-2-oxo-1,2-dihydro-1,8-naphthyridine-3-carboxamide

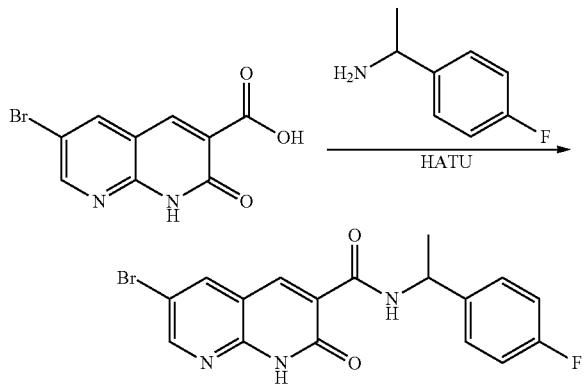

To a solution of 6-bromo-2-oxo-1H-1,8-naphthyridine-3-carboxylic acid (400 mg, 1.31 mmol, 1 eq) in DMF (5 mL) was added HATU (995.65 mg, 2.62 mmol, 2 eq), DIEA (507.64 mg, 3.93 mmol, 0.7 mL, 3 eq) at 20° C. The mixture was stirred at 20° C. for 0.5 h. 1-(4-fluorophenyl)ethanamine (182.21 mg, 1.31 mmol, 171.90 µL, 1 eq) was added into the mixture at 20° C., the mixture was stirred at 20° C. for 0.5 h. LCMS showed complete consumption of the starting material and formation of a new peak with desired mass. One additional vial was set up as described above, and the mixture was poured into ice-water (10 mL).

The resulting solid was collected by filtration to produce 6-bromo-N-(1-(4-fluorophenyl)ethyl)-2-oxo-1,2-dihydro-1,8-naphthyridine-3-carboxamide (900 mg) as a brown solid (used without further purification).

$^1$H NMR (400 MHz, DMSO-$d_6$) $\delta$=13.16-12.87 (m, 1H), 9.99 (d, J=7.6 Hz, 1H), 8.80 (s, 1H), 8.76 (d, J=2.4 Hz, 1H), 8.71 (d, J=2.4 Hz, 1H), 7.43 (dd, J=5.5, 8.6 Hz, 2H), 7.17 (t, J=8.9 Hz, 2H), 5.16 (t, J=7.1 Hz, 1H), 1.49 (d, J=6.9 Hz, 3H). LCMS for product (ESI+): m/z 496.1, 498.1 [M+H]$^+$, Rt: 1.222 min.

LCMS Method

The gradient was 5-95% B in 1.0 min, 95-100% B in 0.8 min, 100-5% B in 0.01 min, and then held at 5% B for 0.24 min (1.0 m/min flow rate). Mobile phase A was 10 mM NH$_4$HCO$_3$ in water, mobile phase B was CH$_3$CN. The column used for the chromatography was Xbridge Shield RP18 2.1*50 mm, 5 µm column. Detection methods are diode array (DAD) and positive electrospray ionization (MS).

Step 3: N-(1-(4-fluorophenyl)ethyl)-2-oxo-6-(4,4,5,5-tetramethyl-1,3,2-dioxaborolan-2-yl)-1,2-dihydro-1,8-naphthyridine-3-carboxamide

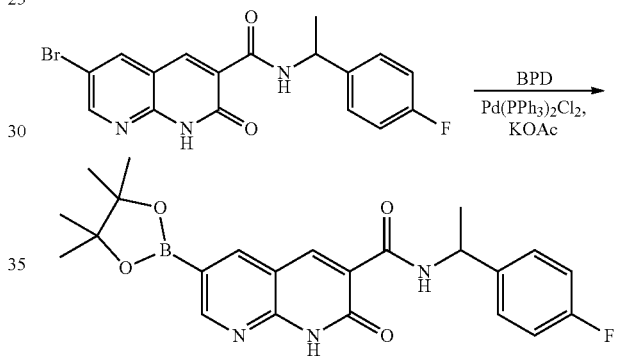

To a solution of 6-bromo-N-[1-(4-fluorophenyl)ethyl]-2-oxo-1H-1,8-naphthyridine-3-carboxamide (700 mg, 1.79 mmol, 1 eq) in dioxane (5 mL) was added 4,4,5,5-tetramethyl-2-(4,4,5,5-tetramethyl-1,3,2-dioxaborolan-2-yl)-1,3,2-dioxaborolane (3.64 g, 14.35 mmol, 8 eq), potassium; acetate (528.17 mg, 5.38 mmol, 3 eq) at 20° C. Pd(dppf)Cl$_2$ (131.26 mg, 179.39 µmol, 0.1 eq) was added into the mixture under N$_2$, the mixture was stirred at 100° C. for 1 h. LCMS showed complete consumption of the starting material and formation of a new peak with desired mass.

Water (2 mL) was added to the reaction mixture and the resulting solid was collected by filtration and triturated in ethyl acetate (3 mL) to produce N-(1-(4-fluorophenyl)ethyl)-2-oxo-6-(4,4,5,5-tetramethyl-1,3,2-dioxaborolan-2-yl)-1,2-dihydro-1,8-naphthyridine-3-carboxamide (550 mg, 1.26 mmol) as a brown solid.

$^1$H NMR (400 MHz, DMSO-$d_6$) $\delta$=13.04 (s, 1H), 10.00 (d, J=7.6 Hz, 1H), 8.89 (s, 1H), 8.82 (d, J=1.6 Hz, 1H), 8.65 (s, 1H), 7.45 (dd, J=5.6, 8.5 Hz, 2H), 7.19 (t, J=8.8 Hz, 2H), 5.17 (quin, J=7.1 Hz, 1H), 1.51 (d, J=6.9 Hz, 3H), 1.35 (s, 12H). LCMS for product (ESI+): m/z 438.1 [M+H]$^+$, Rt: 1.270 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 4: 6-(5-(difluoromethoxy)pyridin-2-yl)-N-(1-(4-fluorophenyl)ethyl)-2-oxo-1,2-dihydro-1,8-naphthyridine-3-carboxamide

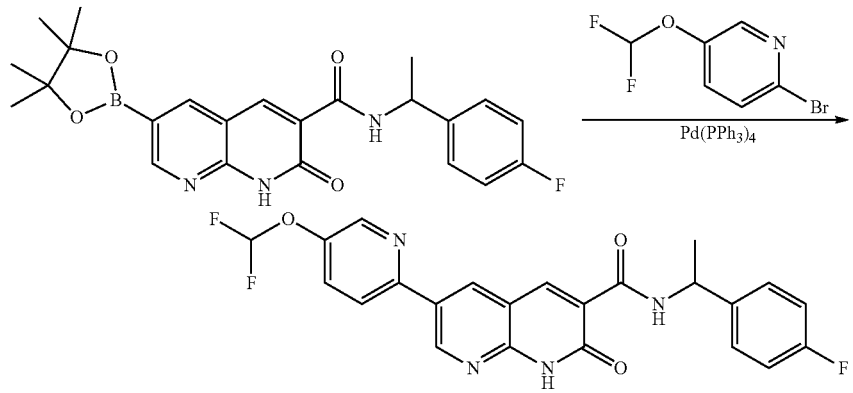

To a solution of N-[1-(4-fluorophenyl)ethyl]-2-oxo-6-(4,4,5,5-tetramethyl-1,3,2-dioxaborolan-2-yl)-1H-1,8-naphthyridine-3-carboxamide (100 mg, 228.69 μmol, 1 eq), 2-bromo-5-(difluoromethoxy) pyridine (76.84 mg, 343.04 μmol, 1.5 eq) in dioxane (2 mL) and H$_2$O (0.5 mL) was added K$_2$CO$_3$ (63.21 mg, 457.38 μmol, 2 eq) at 20° C. Pd(PPh$_3$)$_4$ (26.43 mg, 22.87 μmol, 0.1 eq) was added into the mixture under N$_2$, the mixture was stirred at 110° C. for 3 h. LCMS showed complete consumption of the starting material and formation of a new peak with desired mass.

The mixture was concentrated and the residue was triturated in ethyl acetate (2 mL) and the solid was collected by filtration and air-dried to produce 6-(5-(difluoromethoxy)pyridin-2-yl)-N-(1-(4-fluorophenyl)ethyl)-2-oxo-1,2-dihydro-1,8-naphthyridine-3-carboxamide (90 mg, 198.06 μmol) as a brown solid.

$^1$H NMR (400 MHz, DMSO-d$_6$) δ=13.21-12.90 (m, 1H), 10.30-9.94 (m, 1H), 9.35 (d, J=1.8 Hz, 1H), 9.02 (s, 1H), 8.90 (s, 1H), 8.62 (d, J=2.4 Hz, 1H), 8.17 (d, J=8.8 Hz, 1H), 7.89-7.81 (m, 1H), 7.47-7.41 (m, 2H), 7.22-7.14 (m, 3H), 5.18 (br t, J=7.2 Hz, 1H), 1.50 (br d, J=6.9 Hz, 3H). LCMS for product (ESI+): m/z 455.1 [M+H]$^+$, Rt: 1.241 min.

LCMS Method

The gradient was 5-95% B in 1.0 min, 95-100% B in 0.8 min, 100-5% B in 0.01 min, and then held at 5% B for 0.24 min (1.0 mL/min flow rate). Mobile phase A was 10 mM NH$_4$HCO$_3$ in water, mobile phase B was CH$_3$CN. The column used for the chromatography was Xbridge Shield RP18 2.1*50 mm, 5 μm column. Detection methods are diode array (DAD) and positive electrospray ionization (MS).

Step 5: Preparation of 6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide

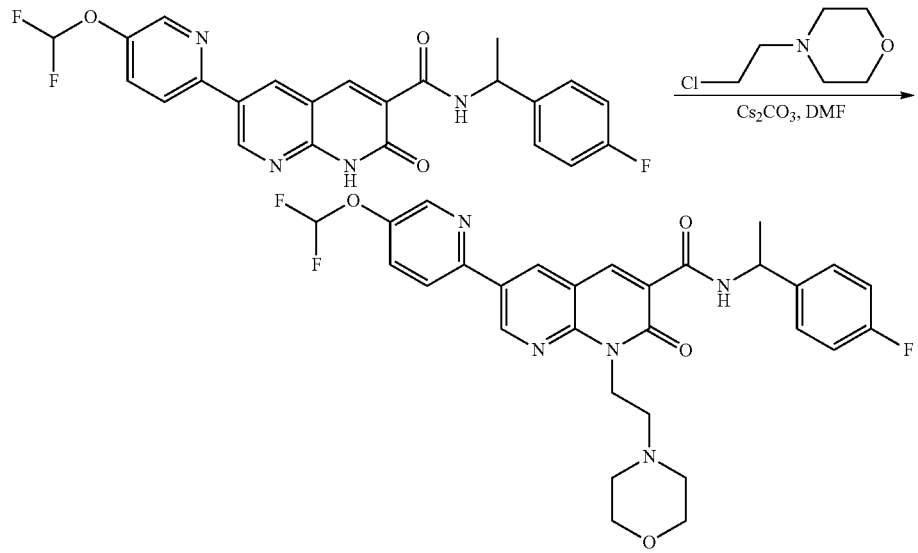

To a solution of 6-[5-(difluoromethoxy)-2-pyridyl]-N-[1-(4-fluorophenyl)ethyl]-2-oxo-1H-1,8-naphthyridine-3-carboxamide (75 mg, 165.05 μmol, 1 eq) in DMF (2 mL) was added Cs₂CO₃ (150.58 mg, 462.15 μmol, 2.8 eq) at 20° C., the mixture was stirred at 20° C. for 1 h. 4-(2-chloroethyl) morpholine (61.43 mg, 330.11 μmol, 2 eq, HCl) was added into the mixture at 20° C., the mixture was stirred at 50° C. for 1 h. LCMS showed complete consumption of the starting material and formation of a new peak with desired mass. The mixture was filtered and the filtrate was purified by prep-HPLC (column: Waters Xbridge BEH C18 100*25 mm*5 μm; mobile phase: [water (10 mM NH₄HCO₃)-ACN]; B %: 45%-75%, 10 min) to produce 6-(5-(difluoromethoxy)pyridin-2-yl)-N-(1-(4-fluorophenyl)ethyl)-1-(2-morpholinoethyl)-2-oxo-1,2-dihydro-1,8-naphthyridine-3-carboxamide (38.0 mg, 65.48 μmol) as a light yellow solid.

¹H NMR (400 MHz, CDCl₃) δ=10.14 (br d, J=7.7 Hz, 1H), 9.31 (d, J=2.4 Hz, 1H), 8.96 (s, 1H), 8.70-8.52 (m, 2H), 7.83 (d, J=8.6 Hz, 1H), 7.64 (dd, J=2.6, 8.6 Hz, 1H), 7.40 (dd, J=5.4, 8.5 Hz, 2H), 7.05 (t, J=8.7 Hz, 2H), 6.86-6.41 (m, 1H), 5.33 (t, J=7.2 Hz, 1H), 4.89-4.69 (m, 2H), 3.69 (t, J=4.5 Hz, 4H), 2.76 (br t, J=7.1 Hz, 2H), 2.64 (br s, 4H), 1.62 (d, J=6.8 Hz, 3H). LCMS for product (ESI+): m/z 568.3 [M+H]⁺, Rt: 2.207 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 56—Synthesis of 6-(5-cyanopyridin-2-yl)-N-(1-(4-fluorophenyl)ethyl)-1-(2-methyl-2-morpholinopropyl)-2-oxo-1,2-dihydro-1,8-naphthyridine-3-carboxamide (Compound 56)

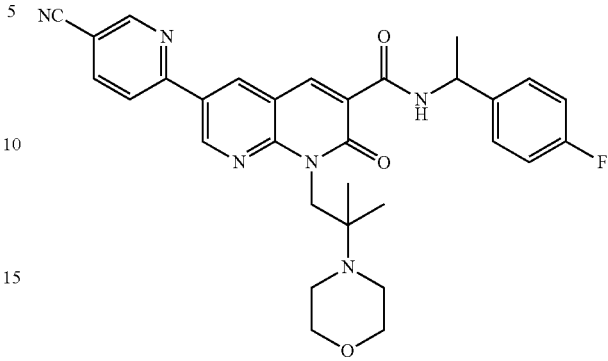

Step 1: 6-(5-cyanopyridin-2-yl)-N-(1-(4-fluorophenyl)ethyl)-2-oxo-1,2-dihydro-1,8-naphthyridine-3-carboxamide

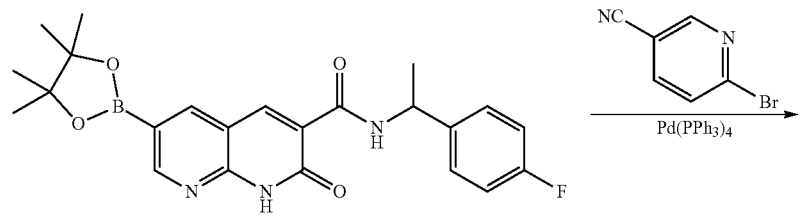

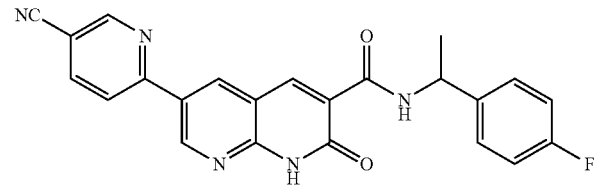

To a solution of N-[1-(4-fluorophenyl)ethyl]-2-oxo-6-(4,4,5,5-tetramethyl-1,3,2-dioxaborolan-2-yl)-1H-1,8-naphthyridine-3-carboxamide (150 mg, 343.04 μmol, 1 eq), 6-bromopyridine-3-carbonitrile (94.17 mg, 514.56 μmol, 1.5 eq) in dioxane (0.8 mL) and H₂O (0.2 mL) was added Na₂CO₃ (72.72 mg, 686.07 μmol, 2 eq), Pd(PPh₃)₄ (39.64 mg, 34.30 μmol, 0.1 eq) under N₂, the mixture was stirred at 90° C. for 1 h. LCMS showed complete consumption of the starting material and formation of a new peak with desired mass.

The mixture was poured into water (1 mL) the resulting solid was collected by filtration to produce 6-(5-cyanopyridin-2-yl)-N-(1-(4-fluorophenyl)ethyl)-2-oxo-1,2-dihydro-1,8-naphthyridine-3-carboxamide (100 mg) as a brown solid (used without further purification).

¹H NMR (400 MHz, DMSO-d₆) δ=10.25-9.91 (m, 1H), 9.57-9.40 (m, 1H), 9.22-9.12 (m, 1H), 8.98-8.89 (m, 1H), 8.55-8.44 (m, 1H), 8.44-8.36 (m, 1H), 8.35-8.28 (m, 1H), 8.21-8.13 (m, 1H), 7.62 (br dd, J=7.5, 12.0 Hz, 2H), 7.18-7.14 (m, 2H), 5.26-5.12 (m, 1H), 1.50 (br d, J=6.8 Hz, 3H).

Step 2: Preparation of 6-(5-cyanopyridin-2-yl)-N-(1-(4-fluorophenyl)ethyl)-1-(2-methyl-2-morpholinopropyl)-2-oxo-1,2-dihydro-1,8-naphthyridine-3-carboxamide

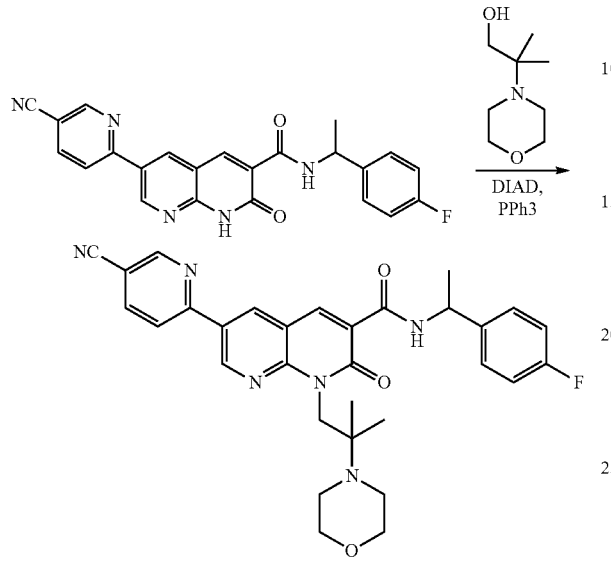

To a solution of 6-(5-cyano-2-pyridyl)-N-[1-(4-fluorophenyl)ethyl]-2-oxo-1H-1,8-naphthyridine-3-carboxamide (50 mg, 120.95 µmol, 1 eq) in DCM (1 mL) was added 2-methyl-2-morpholino-propan-1-ol (23.11 mg, 145.14 µmol, 1.2 eq), PPh$_3$ (47.58 mg, 181.42 µmol, 1.5 eq) at 20° C. DIAD (36.69 mg, 181.42 µmol, 35.27 µL, 1.5 eq) was added into the mixture at 0° C., the mixture was stirred at 20° C. for 2 h. LCMS showed complete consumption of the starting material and formation of a new peak with desired mass.

The mixture was filtered and the filtrate was purified by prep-HPLC (column: Waters Xbridge BEH C18 100*25 mm*5 µm; mobile phase: [water (10 mM NH$_4$HCO$_3$)-ACN]; B %: 45%-75%, 10 min to produce 6-(5-cyanopyridin-2-yl)-N-(1-(4-fluorophenyl)ethyl)-1-(2-methyl-2-morpholinopropyl)-2-oxo-1,2-dihydro-1,8-naphthyridine-3-carboxamide (7.4 mg, 12.68 µmol) as a light yellow solid.

$^1$H NMR (400 MHz, CDCl$_3$) δ=10.09 (br d, J=7.8 Hz, 1H), 9.35 (d, J=2.3 Hz, 1H), 9.00 (d, J=1.3 Hz, 1H), 8.93 (s, 1H), 8.69 (d, J=2.3 Hz, 1H), 8.10 (dd, J=2.2, 8.3 Hz, 1H), 7.94 (d, J=8.4 Hz, 1H), 7.39 (dd, J=5.4, 8.6 Hz, 2H), 7.05 (t, J=8.7 Hz, 2H), 5.32 (t, J=7.1 Hz, 1H), 4.61 (s, 2H), 3.67 (br s, 4H), 2.77 (br s, 4H), 1.62 (d, J=7.0 Hz, 3H), 1.05 (s, 6H). LCMS for product (ESI+): m/z 555.3 [M+H]$^+$, Rt: 2.141 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 57—Synthesis of 6-(5-cyanopyridin-2-yl)-N-(4-methylcyclohexyl)-1-(2-morpholinoethyl)-2-oxo-1,2-dihydro-1,8-naphthyridine-3-carboxamide (Compound 57)

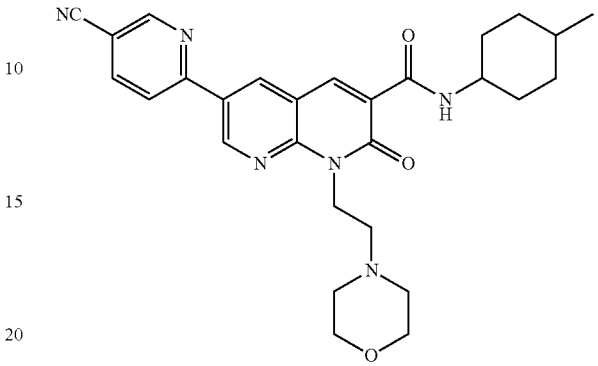

Preparation of 6-(5-cyanopyridin-2-yl)-N-(4-methylcyclohexyl)-1-(2-morpholinoethyl)-2-oxo-1,2-dihydro-1,8-naphthyridine-3-carboxamide

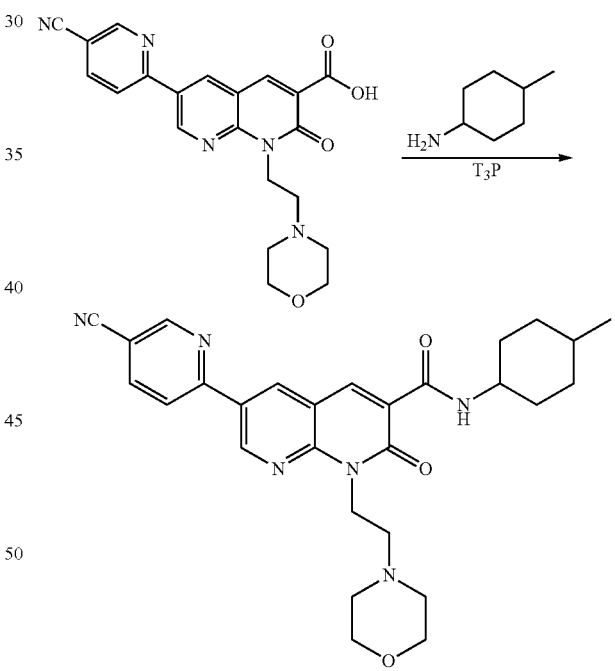

To a solution of 6-(5-cyano-2-pyridyl)-1-(2-morpholinoethyl)-2-oxo-1,8-naphthyridine-3-carboxylic acid (30 mg, 74.00 µmol, 1 eq) and 4-methylcyclohexanamine (10.05 mg, 88.80 µmol, 11.76 µL, 1.2 eq) in dimethyl formamide was added diisopropylethylamine (57.38 mg, 444.00 µmol, 77.34 µL, 6 eq) and T3P (188.36 mg, 296.00 µmol, 176.04 µL, 50% purity, 4 eq). The mixture was stirred at 25° C. for 2 h. LCMS showed complete consumption of the starting material and formation of a new peak with desired mass.

The mixture was filtered, and the filtrate was purified by prep-HPLC (neutral condition) to produce 6-(5-cyanopyridin-2-yl)-N-(4-methylcyclohexyl)-1-(2-morpholinoethyl)-2-oxo-1,2-dihydro-1,8-naphthyridine-3-carboxamide (6 mg, 11.99 μmol) was obtained as a white solid.

$^1$H NMR (400 MHz, DMSO-d$_6$) δ=9.89-9.44 (m, 2H), 9.30-9.11 (m, 2H), 9.05-8.92 (m, 1H), 8.60-8.26 (m, 2H), 4.72-4.66 (m, 2H), 4.12 (br s, 1H), 3.52 (br d, J=3.5 Hz, 4H), 2.66 (br d, J=7.3 Hz, 2H), 2.60 (br s, 4H), 1.98-1.91 (m, 1H), 1.73-1.58 (m, 4H), 1.35-1.00 (m, 4H), 0.97-0.87 (m, 3H). LCMS for product (ESI+): m/z 501.3 [M+H]$^+$, Rt: 3.190 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was acetonitrile. The column used for chromatography was a xbridge shield RP18 2.1*50 mm column (5 um particles). Detection methods are diode array (DAD) and evaporative light scattering (ELSD) detection as well as positive electrospray ionization.

Example 58—Synthesis of 6-(5-cyanopyridin-2-yl)-N-(1-(4-fluorophenyl)ethyl)-1-(2-morpholinoethyl)-2-oxo-1,2-dihydro-1,8-naphthyridine-3-carboxamide (Compound 58)

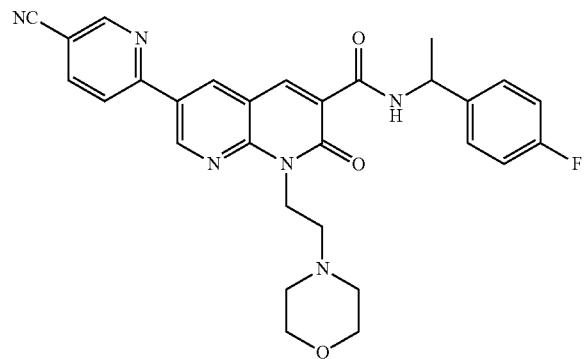 [SMILES: CC(NC(=O)c1cc2cc(-c3ccc(C#N)cn3)cnc2n(CCN2CCOCC2)c1=O)c1ccc(F)cc1]

Preparation of 6-(5-cyanopyridin-2-yl)-N-(1-(4-fluorophenyl)ethyl)-1-(2-morpholinoethyl)-2-oxo-1,2-dihydro-1,8-naphthyridine-3-carboxamide

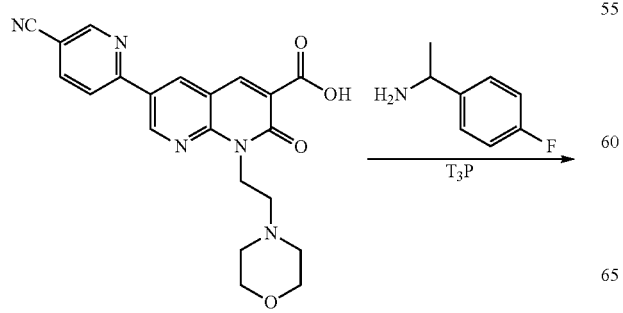

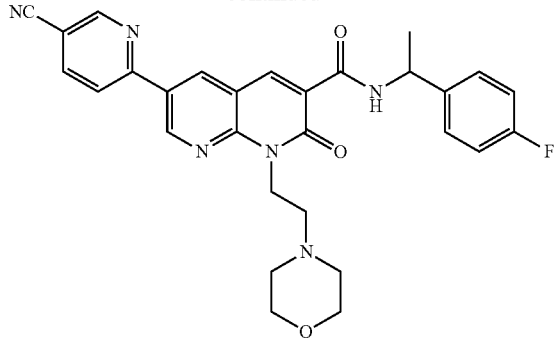

To a solution of 6-(5-cyano-2-pyridyl)-1-(2-morpholinoethyl)-2-oxo-1,8-naphthyridine-3-carboxylic acid (22 mg, 54.27 μmol, 1 eq) in DMF (1 mL) was added 1-(4-fluorophenyl)ethanamine (9.06 mg, 65.12 μmol, 8.55 μL, 1.2 eq), DIEA (42.08 mg, 325.60 μmol, 56.71 μL, 6 eq) and T3P (69.07 mg, 108.53 μmol, 64.55 μL, 50% purity, 2 eq). The mixture was stirred at 25° C. for 2 h. LCMS showed complete consumption of the starting material and formation of a new peak with desired mass.

The mixture was filtered, and the filtrate was purified by prep-HPLC (neutral condition) to produce 6-(5-cyanopyridin-2-yl)-N-(1-(4-fluorophenyl)ethyl)-1-(2-morpholinoethyl)-2-oxo-1,2-dihydro-1,8-naphthyridine-3-carboxamide (13 mg, 24.69 μmol) as a white solid.

$^1$H NMR (400 MHz, DMSO-d$_6$) δ=9.93 (d, J=7.3 Hz, 1H), 9.55-9.50 (m, 1H), 9.22 (d, J=1.8 Hz, 1H), 9.17 (d, J=1.1 Hz, 1H), 8.96 (s, 1H), 8.52-8.47 (m, 1H), 8.36-8.31 (m, 1H), 7.48-7.40 (m, 2H), 7.22 (br d, J=1.3 Hz, 2H), 5.24-5.13 (m, 1H), 4.72-4.63 (m, 2H), 3.53 (br s, 4H), 2.66-2.61 (m, 2H), 2.57-2.52 (m, 4H), 1.52 (d, J=7.1 Hz, 3H). LCMS for product (ESI+): m/z 527.3 [M+H]$^+$, Rt: 3.071 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was acetonitrile. The column used for chromatography was a xbridge Shield RP18 2.1*50 mm column (5 um particles). Detection methods are diode array (DAD) and evaporative light scattering (ELSD) detection as well as positive electrospray ionization.

Example 59—Synthesis of N-(bicyclo[1.1.1]pentan-1-yl)-6-(5-cyanopyridin-2-yl)-1-(2-morpholinoethyl)-2-oxo-1,2-dihydro-1,8-naphthyridine-3-carboxamide (Compound 59)

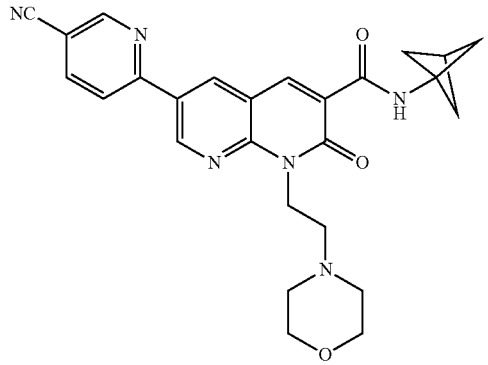 [SMILES: N#Cc1ccc(-c2cnc3c(c2)cc(C(=O)NC24CC(C2)C4)c(=O)n3CCN2CCOCC2)nc1]

Preparation of N-(bicyclo[1.1.1]pentan-1-yl)-6-(5-cyanopyridin-2-yl)-1-(2-morpholinoethyl)-2-oxo-1,2-dihydro-1,8-naphthyridine-3-carboxamide Example 60—Synthesis of 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide (Compound 60)

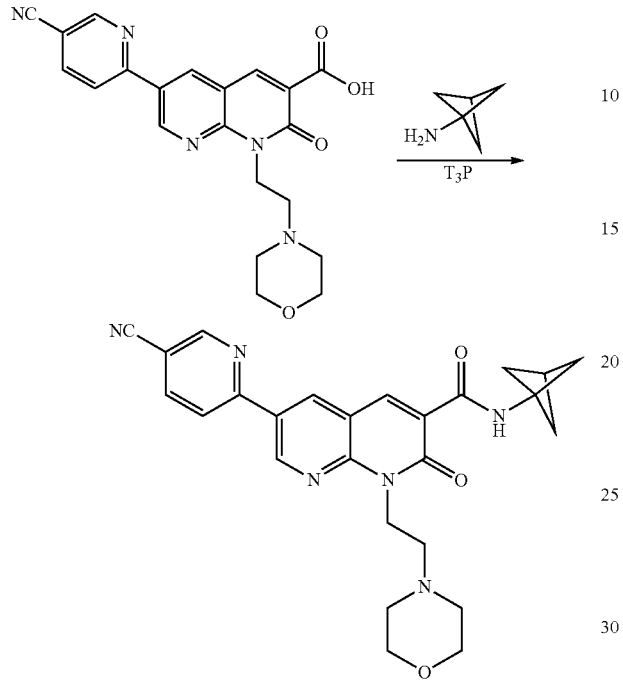

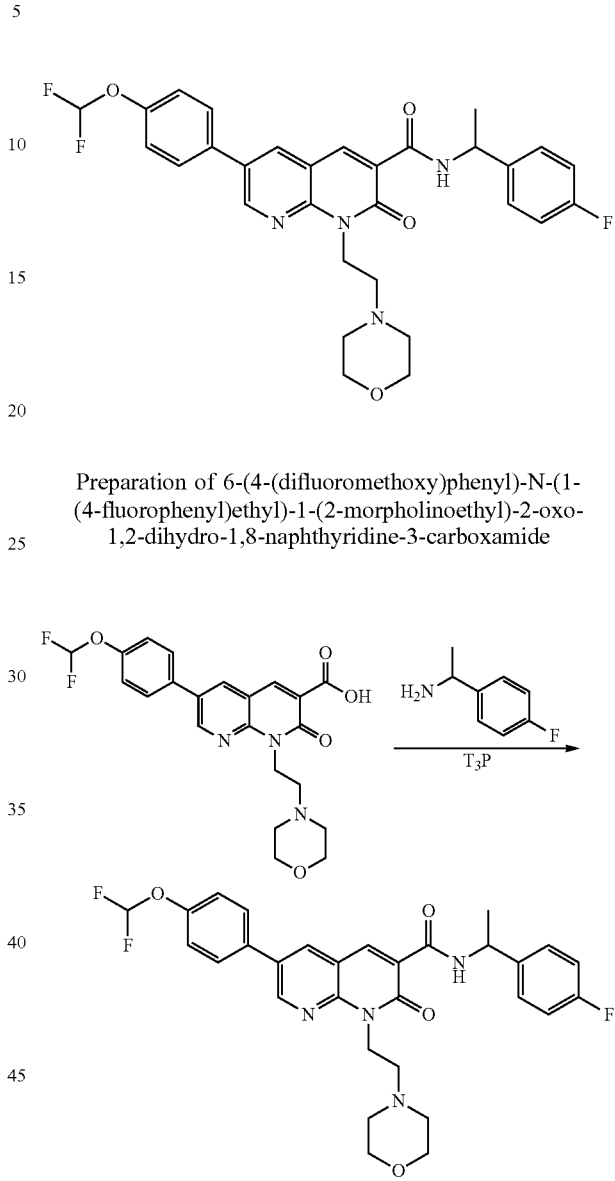

Preparation of 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide To a mixture of 6-(5-cyano-2-pyridyl)-1-(2-morpholinoethyl)-2-oxo-1,8-naphthyridine-3-carboxylic acid (20 mg, 49.33 μmol, 1 eq) in DMF (0.5 mL) was added bicyclo[1.1.1]pentan-3-amine (7.08 mg, 59.20 μmol, 1.2 eq, HCl), T3P (62.79 mg, 98.67 μmol, 58.68 μL, 50% purity, 2 eq) and DIEA (38.26 mg, 296.00 μmol, 51.56 μL, 6 eq). The mixture was stirred at 25° C. for 1 h. LCMS showed complete consumption of the starting material and formation of a new peak with desired mass.

The mixture was purified by prep-HPLC (neutral condition) to produce N-(bicyclo[1.1.1]pentan-1-yl)-6-(5-cyano-pyridin-2-yl)-1-(2-morpholinoethyl)-2-oxo-1,2-dihydro-1,8-naphthyridine-3-carboxamide (5.7 mg, 11.69 μmol, 4.74% yield) as a white solid.

$^1$H NMR (400 MHz, DMSO-d$_6$) δ=9.78 (s, 1H), 9.53 (d, J=2.3 Hz, 1H), 9.31 (d, J=2.1 Hz, 1H), 9.20 (d, J=1.6 Hz, 1H), 9.01 (s, 1H), 8.55 (dd, J=2.1, 8.3 Hz, 1H), 8.38 (d, J=8.3 Hz, 1H), 4.92-4.81 (m, 2H), 4.03 (br d, J=13.1 Hz, 2H), 3.73 (br d, J=9.7 Hz, 2H), 3.59 (br s, 4H), 3.25-3.18 (m, 2H), 2.53 (br s, 1H), 2.13 (s, 6H). LCMS for product (ESI+): m/z 471.3 [M+H]$^+$, Rt: 2.974 min.

LCMS Method

The gradient was 5% B in 0.40 min and 5-95% B at 0.40-3.40 min, hold on 95% B for 0.45 min, and then 95-5% B in 0.01 min, the flow rate was 0.8 m/min. Mobile phase A was H$_2$O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

To a mixture of 6-[4-(difluoromethoxy)phenyl]-1-(2-morpholinoethyl)-2-oxo-1,8-naphthyridine-3-carboxylic acid (30 mg, 67.35 μmol, 1 eq) in DMF (1 mL) was added 1-(4-fluorophenyl)ethanamine (11.25 mg, 80.82 μmol, 10.61 μL, 1.2 eq), T3P (85.72 mg, 134.71 μmol, 80.11 μL, 50% purity, 2 eq) and DIEA (52.23 mg, 404.12 μmol, 70.39 μL, 6 eq). The mixture was stirred at 20° C. for 1 h. LCMS showed complete consumption of the starting material and formation of a new peak with desired mass.

The pH of the reaction mixture was adjusted to 5 by dropwise addition of TFA and purified by prep-HPLC (neutral condition) to produce 6-(4-(difluoromethoxy)phenyl)-N-(1-(4-fluorophenyl)ethyl)-1-(2-morpholinoethyl)-2-oxo-1,2-dihydro-1,8-naphthyridine-3-carboxamide (24.5 mg, 43.24 μmol) as a light-yellow solid.

$^1$H NMR (400 MHz, DMSO-d$_6$) δ=10.01 (d, J=7.6 Hz, 1H), 9.14 (d, J=2.1 Hz, 1H), 8.93 (s, 1H), 8.81 (d, J=2.3 Hz,

1H), 7.89 (d, J=8.6 Hz, 2H), 7.53-7.13 (m, 7H), 5.20 (t, J=7.2 Hz, 1H), 4.68 (br t, J=6.6 Hz, 2H), 3.54 (br t, J=4.3 Hz, 4H), 2.64 (br t, J=7.0 Hz, 2H), 2.58-2.53 (m, 4H), 1.52 (d, J=6.9 Hz, 3H). LCMS for product (ESI+): m/z 567.3 [M+H]$^+$, Rt: 3.274 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 61—Synthesis of 6-bromo-N-(4-methylcyclohexyl)-1-(2-morpholinoethyl)-2-oxo-1,2-dihydro-1,8-naphthyridine-3-carboxamide (Compound 61)

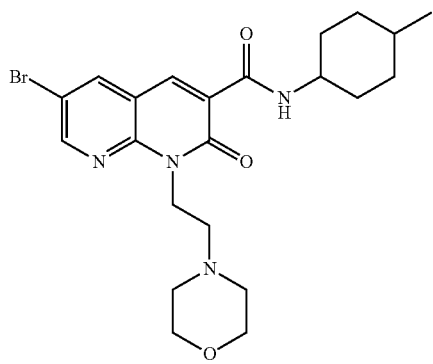

Step 1: 6-bromo-N-(4-methylcyclohexyl)-2-oxo-1,2-dihydro-1,8-naphthyridine-3-carboxamide

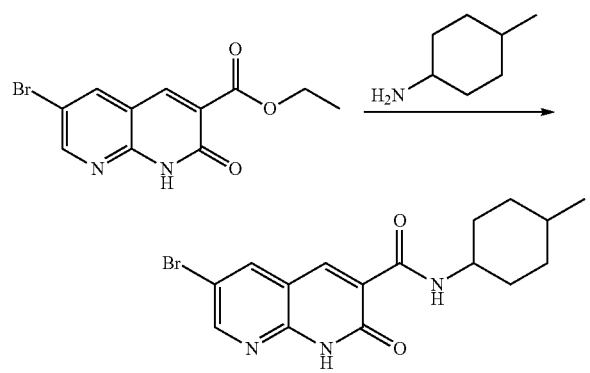

A mixture of ethyl 6-bromo-2-oxo-1H-1,8-naphthyridine-3-carboxylate (100 mg, 336.58 µmol, 1 eq) and 4-methylcyclohexanamine (190.51 mg, 1.68 mmol, 222.82 µL, 5 eq) was stirred at 150° C. for 12 h. LCMS showed complete consumption of the starting material and formation of a new peak with desired mass.

The residue was triturated in EtOAc (3 mL) and the resulting solid was collected by filtration to produce 6-bromo-N-(4-methylcyclohexyl)-2-oxo-1,2-dihydro-1,8-naphthyridine-3-carboxamide (80 mg, 219.64 µmol) as a white solid.

$^1$H NMR (400 MHz, DMSO-d$_6$) δ=13.35-12.58 (m, 1H), 9.97 (br d, J=7.6 Hz, 1H), 9.61-9.44 (m, 1H), 8.93-8.59 (m, 3H), 4.17-4.07 (m, 1H), 3.79-3.65 (m, 1H), 1.98-1.86 (m, 1H), 1.74-1.36 (m, 6H), 1.34-0.98 (m, 3H), 0.97-0.83 (m, 3H). LCMS for product (ESI+): m/z 364.0, 366.0 [M+H]$^+$ LCMS Method The column used for chromatography was a HALO AQ-C18 2.1*30 mm, (2.7 µm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 4.30 min 0.5% B in 0.01 min, 5-95% B (0.01-3.00 min), with a hold at 95% B for 0.50 min. 95-5% B (3.50-3.51 min), 5% B in 3.51 min, with a hold at 5% B for 0.79 min. The flow rate was 1.0 m/min.

Step 2: Preparation of 6-bromo-N-(4-methylcyclohexyl)-1-(2-morpholinoethyl)-2-oxo-1,2-dihydro-1,8-naphthyridine-3-carboxamide

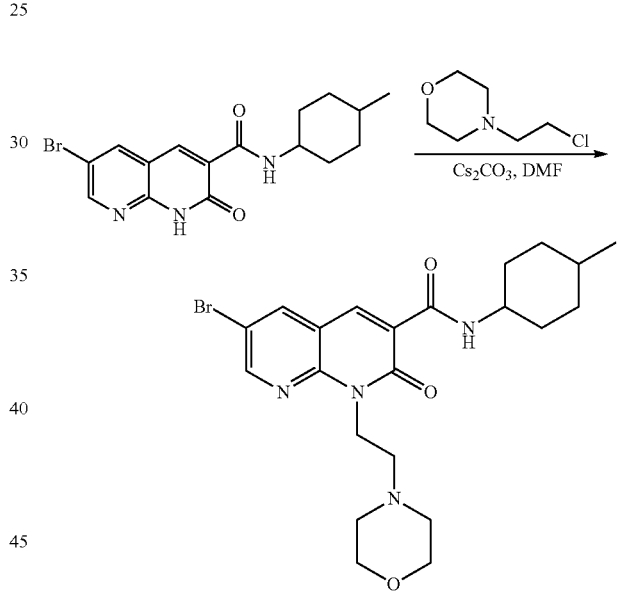

A solution of 6-bromo-N-(4-methylcyclohexyl)-2-oxo-1H-1,8-naphthyridine-3-carboxamide (100 mg, 274.55 µmol, 1 eq) in DMF (1 mL) was treated with $Cs_2CO_3$ (250.47 mg, 768.74 µmol, 2.8 eq) at 25° C. for 1 h. Then 4-(2-chloroethyl)morpholine (102.17 mg, 549.10 mol, 2 eq, HCl) and 4-(2-chloroethyl)morpholine (102.17 mg, 549.10 µmol, 2 eq, HCl) was added, and the mixture was stirred for 12 h at 50° C. LCMS showed complete consumption of the starting material and formation of a new peak with desired mass. The mixture was poured into water (5 mL). The aqueous layer was extracted with EtOAc (3×10 mL).

The combined organic phase was washed with brine (10 mL) and dried over $Na_2SO_4$. The mixture was concentrated, and the residue was purified by prep-HPLC (neutral condition) to produce 6-bromo-N-(4-methylcyclohexyl)-1-(2-morpholinoethyl)-2-oxo-1,2-dihydro-1,8-naphthyridine-3-carboxamide (10 mg, 20.95 µmol) as a white solid.

$^1$H NMR (400 MHz, CDCl$_3$) δ=10.02-9.48 (m, 1H), 8.80 (s, 1H), 8.70 (d, J=2.4 Hz, 1H), 8.19 (t, J=2.6 Hz, 1H), 4.78-4.66 (m, 2H), 4.32-3.85 (m, 1H), 3.68 (br d, J=3.8 Hz, 4H), 2.71 (q, J=7.4 Hz, 2H), 2.61 (br s, 4H), 2.13-2.04 (m, 1H), 1.90-1.73 (m, 2H), 1.72-1.63 (m, 2H), 1.54-1.21 (m, 3H), 1.19-1.05 (m, 1H), 1.00-0.90 (m, 3H). (ESI+): m/z 477.2, 479.2 [M+H]$^+$.

LCMS Method

The gradient was 5-95% B in 1.0 min, 95-100% B in 0.8 min, 100-5% B in 0.01 min, and then held at 5% B for 0.24 min (1.0 mL/min flow rate). Mobile phase A was 10 mM NH$_4$HCO$_3$ in water, mobile phase B was CH$_3$CN. The column used for the chromatography was Xbridge Shield RP18 2.1*50 mm, 5 μm column. Detection methods are diode array (DAD) and positive electrospray ionization (MS).

Example 62—Synthesis of N-(4-methylcyclohexyl)-1-(2-morpholinoethyl)-2-oxo-6-(pyridin-2-yl)-1,2-dihydro-1,8-naphthyridine-3-carboxamide (Compound 62)

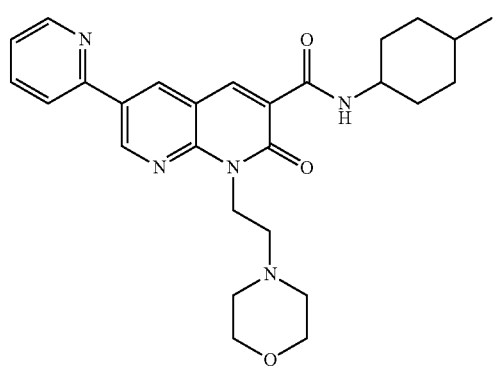 [SMILES: CC1CCC(NC(=O)c2cc3cc(-c4ccccn4)cnc3n(CCN3CCOCC3)c2=O)CC1]

Preparation of N-(4-methylcyclohexyl)-1-(2-morpholinoethyl)-2-oxo-6-(pyridin-2-yl)-1,2-dihydro-1,8-naphthyridine-3-carboxamide

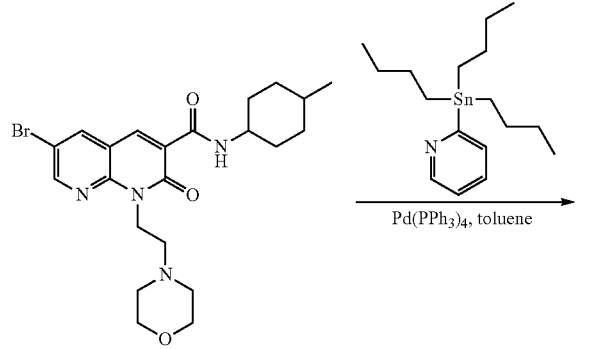

-continued

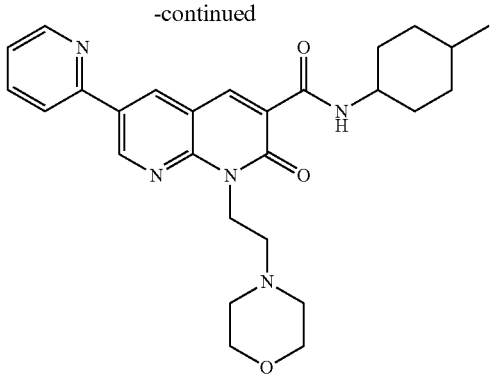

To a mixture of 6-bromo-N-(4-methylcyclohexyl)-1-(2-morpholinoethyl)-2-oxo-1,8-naphthyridine-3-carboxamide (55 mg, 115.21 μmol, 1 eq) and tributyl(2-pyridyl)stannane (50.90 mg, 138.25 μmol, 1.2 eq) in toluene (1 mL) was added Pd(PPh$_3$)$_4$ (13.31 mg, 11.52 μmol, 0.1 eq), and then the mixture was stirred at 120° C. for 12 h under N$_2$. LCMS showed complete consumption of the starting material and formation of a new peak with desired mass.

The mixture was concentrated, and the residue was purified by prep-HPLC (neutral condition) to produce N-(4-methylcyclohexyl)-1-(2-morpholinoethyl)-2-oxo-6-(pyridin-2-yl)-1,2-dihydro-1,8-naphthyridine-3-carboxamide (9 mg, 18.73 μmol) as a white solid.
$^1$H NMR (400 MHz, CDCl$_3$) δ=10.10-9.53 (m, 1H), 9.33 (d, J=2.4 Hz, 1H), 8.98 (s, 1H), 8.76 (d, J=4.8 Hz, 1H), 8.70-8.65 (m, 1H), 7.88-7.79 (m, 2H), 7.34 (ddd, J=1.4, 5.0, 6.8 Hz, 1H), 4.88-4.77 (m, 2H), 4.34-3.87 (m, 1H), 3.70 (br s, 4H), 2.77 (q, J=7.3 Hz, 2H), 2.65 (br s, 4H), 2.13-1.62 (m, 5H), 1.42-1.09 (m, 4H), 1.02-0.91 (m, 3H). LCMS for product (ESI+): m/z 476.3 [M+H]$^+$, Rt: 3.203 min.
LCMS Method The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Example 63—Synthesis of N-(4-methylcyclohexyl)-1-(2-morpholinoethyl)-2-oxo-6-(pyrimidin-2-yl)-1,2-dihydro-1,8-naphthyridine-3-carboxamide (Compound 63)

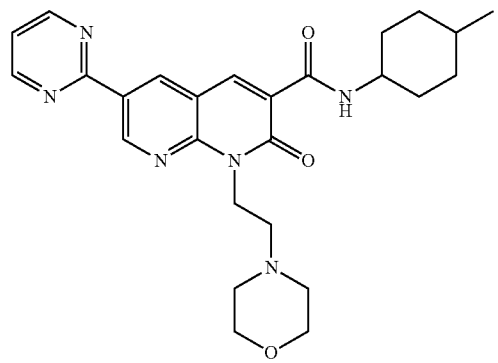

Preparation of N-(4-methylcyclohexyl)-1-(2-morpholinoethyl)-2-oxo-6-(pyrimidin-2-yl)-1,2-dihydro-1,8-naphthyridine-3-carboxamide

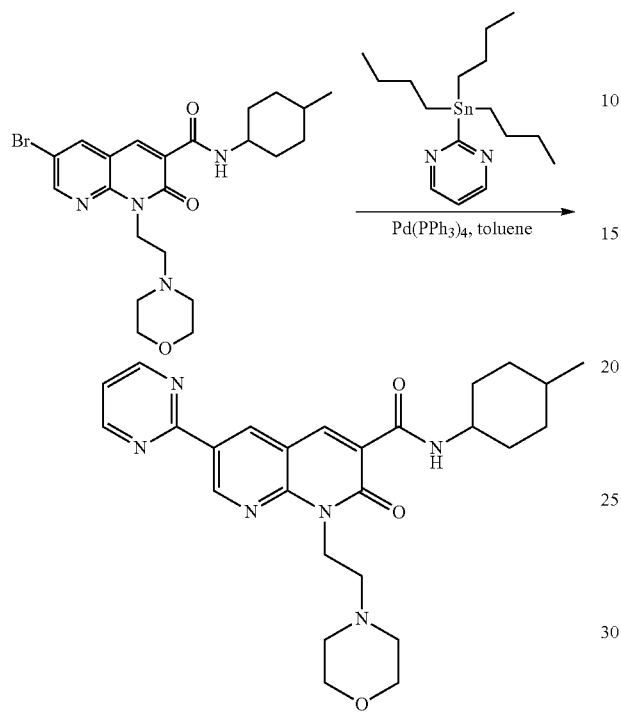

To a mixture of 6-bromo-N-(4-methylcyclohexyl)-1-(2-morpholinoethyl)-2-oxo-1,8-naphthyridine-3-carboxamide (40 mg, 83.79 μmol, 1 eq) and tributyl(pyrimidin-2-yl)stannane (37.11 mg, 100.55 μmol, 1.2 eq) in toluene (1 mL) was added Pd(PPh$_3$)$_4$ (9.68 mg, 8.38 μmol, 0.1 eq), and then the mixture was stirred at 120° C. for 2 h under N$_2$. LCMS showed complete consumption of the starting material and formation of a new peak with desired mass.

The mixture was concentrated, and the residue was purified by prep-HPLC (neutral condition) to produce N-(4-methylcyclohexyl)-1-(2-morpholinoethyl)-2-oxo-6-(pyrimidin-2-yl)-1,2-dihydro-1,8-naphthyridine-3-carboxamide (4.3 mg, 8.74 μmol) as a white solid.

$^1$H NMR (400 MHz, CDCl$_3$) δ=9.99 (br d, J=6.9 Hz, 1H), 9.74 (d, J=2.3 Hz, 1H), 9.59 (br d, J=7.9 Hz, 1H), 9.12-9.08 (m, 1H), 9.00 (s, 1H), 8.86 (d, J=4.8 Hz, 2H), 7.32-7.28 (m, 1H), 4.91-4.79 (m, 2H), 4.34-3.88 (m, 1H), 3.68 (br s, 4H), 2.81-2.74 (m, 2H), 2.64 (br s, 4H), 2.13-1.64 (m, 5H), 1.53-1.07 (m, 4H), 1.01-0.92 (m, 3H). LCMS for product (ESI+): m/z 477.3 [M+H]$^+$, Rt: 3.173 min.

LCMS Method

The gradient was 5-95% B in 0.7 min, 95-95% B in 0.45 min, 95-5% B in 0.01 min, and then held at 0% B for 0.44 min (1.5 mL/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Example 64—Synthesis of 6-bromo-N-(1-(4-fluorophenyl)ethyl)-2-oxo-1-(pyrimidin-2-ylmethyl)-1,2-dihydro-1,8-naphthyridine-3-carboxamide (Compound 64)

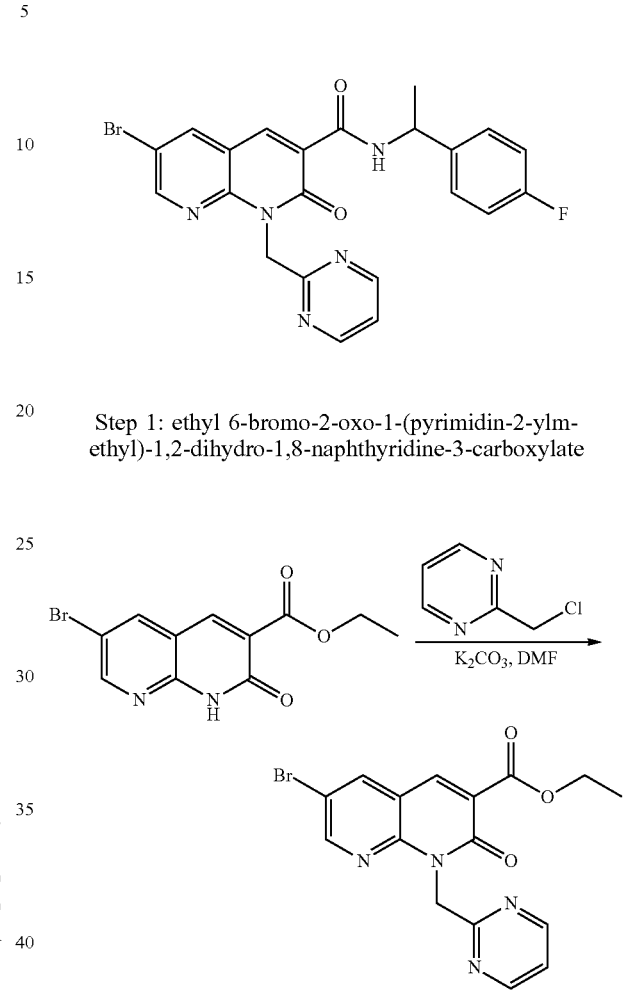

Step 1: ethyl 6-bromo-2-oxo-1-(pyrimidin-2-ylmethyl)-1,2-dihydro-1,8-naphthyridine-3-carboxylate To a solution of ethyl 6-bromo-2-oxo-1H-1,8-naphthyridine-3-carboxylate (250 mg, 841.46 μmol, 1 eq), 2-(chloromethyl)pyrimidine (216.35 mg, 1.68 mmol, 2 eq) in DMF (3 mL) was added K$_2$CO$_3$ (313.99 mg, 2.27 mmol, 2.7 eq) at 20° C., the mixture was stirred at 80° C. for 3 h. LCMS showed complete consumption of the starting material and formation of a new peak with desired mass. The reaction mixture was poured into water (30 mL), extracted with ethyl acetate (3×30 mL).

The organic phase was washed with brine (30 mL), dried over Na$_2$SO$_4$ and concentrated. The residue was purified by silica gel chromatography (column height: 250 mm, diameter: 100 mm, 100-200 mesh silica gel, Petroleum ether/Ethyl acetate=0:1) to produce ethyl 6-bromo-2-oxo-1-(pyrimidin-2-ylmethyl)-1,2-dihydro-1,8-naphthyridine-3-carboxylate (160 mg, 411.10 mol) as a yellow solid.

$^1$H NMR (400 MHz, CDCl$_3$) δ=8.59 (d, J=5.1 Hz, 2H), 8.57 (d, J=2.2 Hz, 1H), 8.39 (s, 1H), 8.13 (d, J=2.4 Hz, 1H), 7.13 (t, J=4.9 Hz, 1H), 5.98 (s, 2H), 4.43 (q, J=7.2 Hz, 2H), 1.41 (t, J=7.2 Hz, 3H). LCMS for product (ESI+): m/z 388.9, 390.9 [M+H]$^+$, Rt: 1.758 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 2: 6-bromo-2-oxo-1-(pyrimidin-2-ylmethyl)-1,2-dihydro-1,8-naphthyridine-3-carboxylic acid

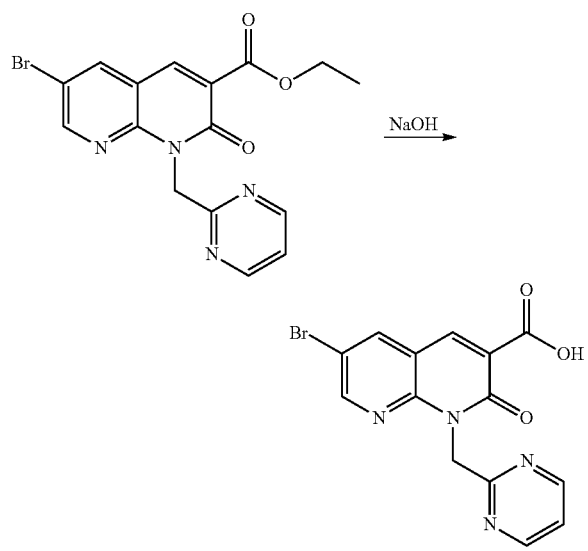

A solution of ethyl 6-bromo-2-oxo-1-(pyrimidin-2-ylmethyl)-1,8-naphthyridine-3-carboxylate (155 mg, 398.25 µmol, 1 eq) in DMSO (3 mL) was added NaOH (2 M, 398.25 µL, 2 eq) at 20° C. The mixture was stirred at 20° C. for 0.5 h. LCMS showed complete consumption of the starting material and formation of a new peak with desired mass. The pH of the reaction mixture was adjusted to 4 by dropwise addition hydrochloric acid (0.5 N) dropwise. The aqueous phase was extracted with ethyl acetate (3×30 mL).

The combined organic phase was washed with brine (30 mL), dried over anhydrous $Na_2SO_4$, filtered and concentrated in vacuum to yield 6-bromo-2-oxo-1-(pyrimidin-2-ylmethyl)-1,2-dihydro-1,8-naphthyridine-3-carboxylic acid (160 mg) as a yellow solid (used without further purification).

$^1$H NMR (400 MHz, DMSO-$d_6$) δ=14.25-12.63 (m, 1H), 8.87 (s, 1H), 8.81 (s, 2H), 8.69 (d, J=5.0 Hz, 2H), 7.39 (t, J=4.9 Hz, 1H), 5.85 (s, 2H). LCMS for product (ESI+): m/z 361.0, 363.0 [M+H]$^+$, Rt: 0.858 min.

LCMS Method

The column used for chromatography was Xbridge Shield RP18 2.1*50 mm, (5 µm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 2.20 min 0.5% B in 0.01 min, 5-95% B (0.01-1.00 min), 95%-100% B (1.00 min-1.80 min), 100-5% B (1.80-1.81 min) with a hold at 5% B for 0.39 min. The flow rate was 1.0 mL/min(0.01-2.20 min).

Step 3: Preparation of 6-bromo-N-(1-(4-fluorophenyl)ethyl)-2-oxo-1-(pyrimidin-2-ylmethyl)-1,2-dihydro-1,8-naphthyridine-3-carboxamide

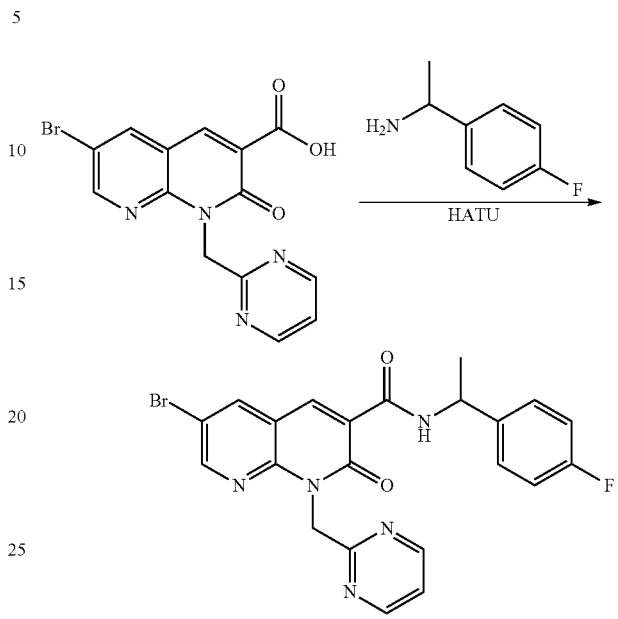

To a solution of 6-bromo-2-oxo-1-(pyrimidin-2-ylmethyl)-1,8-naphthyridine-3-carboxylic acid (100 mg, 276.89 µmol, 1 eq) in DMF (1 mL) was added HATU (210.57 mg, 553.79 µmol, 2 eq), DIEA (107.36 mg, 830.68 µmol, 144.69 µL, 3 eq) at 20° C., the mixture was stirred at 20° C. for 0.5 h. Added 1-(4-fluorophenyl)ethanamine (42.39 mg, 304.58 µmol, 39.99 µL, 1.1 eq) at 20° C., the mixture was stirred at 20° C. for 0.5 h. LCMS showed complete consumption of the starting material and formation of a new peak with desired mass. To the mixture was added water (30 mL), the aqueous phase was extracted with ethyl acetate (3×30 mL).

The combined organic phase was washed with brine (30 mL), dried over anhydrous $Na_2SO_4$, filtered and concentrated in vacuum. The residue was purified using HPLC (neutral condition) to produce 6-bromo-N-(1-(4-fluorophenyl)ethyl)-2-oxo-1-(pyrimidin-2-ylmethyl)-1,2-dihydro-1,8-naphthyridine-3-carboxamide (130 mg) as a yellow solid.

$^1$H NMR (400 MHz, CDCl$_3$) δ=9.94 (br d, J=7.3 Hz, 1H), 8.87 (s, 1H), 8.67-8.55 (m, 3H), 8.20 (d, J=2.2 Hz, 1H), 7.35 (dd, J=5.4, 8.7 Hz, 2H), 7.16 (t, J=4.9 Hz, 1H), 7.00 (t, J=8.7 Hz, 2H), 6.00 (s, 2H), 5.28 (t, J=7.2 Hz, 1H), 1.55 (d, J=7.1 Hz, 3H). LCMS for product (ESI+): m/z 482.1, 484.1 [M+H]$^+$, Rt: 2.597 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 65—Synthesis of 6-(4-fluorophenyl)-N-(1-(4-fluorophenyl)ethyl)-2-oxo-1-(pyrimidin-2-ylmethyl)-1,2-dihydro-1,8-naphthyridine-3-carboxamide (Compound 65)

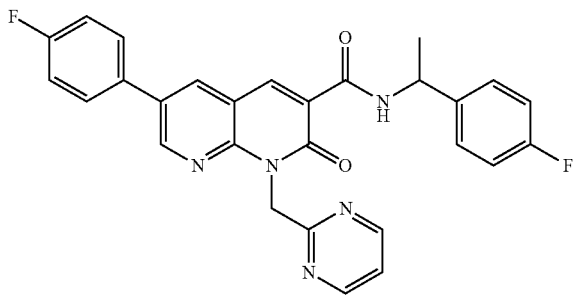 [SMILES: CC(NC(=O)c1cc2cc(-c3ccc(F)cc3)cnc2n(Cc2ncccn2)c1=O)c1ccc(F)cc1]

Preparation of 6-(4-fluorophenyl)-N-(1-(4-fluorophenyl)ethyl)-2-oxo-1-(pyrimidin-2-ylmethyl)-1,2-dihydro-1,8-naphthyridine-3-carboxamide

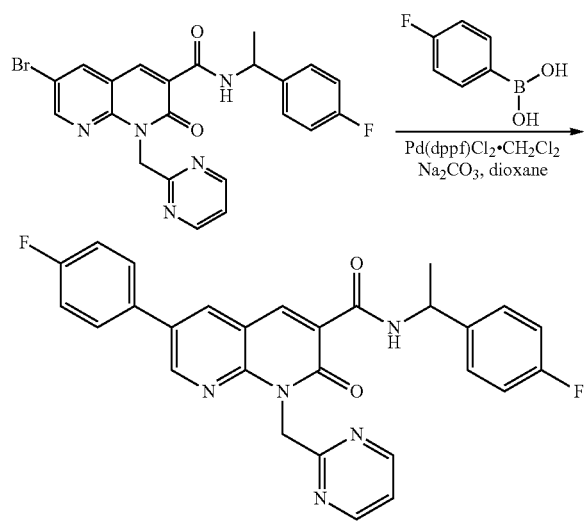

To a solution of 6-bromo-N-[1-(4-fluorophenyl)ethyl]-2-oxo-1-(pyrimidin-2-ylmethyl)-1,8-naphthyridine-3-carboxamide (60 mg, 124.40 µmol, 1 eq), (4-fluorophenyl)boronic acid (34.81 mg, 248.81 µmol, 2 eq) in H$_2$O (0.5 mL), dioxane (2 mL) was added Na$_2$CO$_3$ (26.37 mg, 248.81 µmol, 2 eq) at 20° C. Added Pd(dppf)Cl$_2$·CH$_2$Cl$_2$ (10.16 mg, 12.44 µmol, 0.1 eq) under N$_2$, the mixture was stirred at 100° C. for 1 h. LCMS showed complete consumption of the starting material and formation of a new peak with desired mass.

The mixture was filtered and the filtrate was purified by prep-HPLC (column: Waters Xbridge BEH C18 100*25 mm*5 µm; mobile phase: [water (10 mM NH$_4$HCO$_3$)-ACN]; B %: 40%-70%, 8 min) to produce 6-(4-fluorophenyl)-N-(1-(4-fluorophenyl)ethyl)-2-oxo-1-(pyrimidin-2-ylmethyl)-1,2-dihydro-1,8-naphthyridine-3-carboxamide (38.8 mg, 77.91 µmol) as a light yellow solid.

$^1$H NMR (400 MHz, CDCl$_3$) δ=10.04 (br d, J=7.7 Hz, 1H), 9.02 (s, 1H), 8.79 (d, J=2.2 Hz, 1H), 8.65 (d, J=4.9 Hz, 2H), 8.21 (d, J=2.0 Hz, 1H), 7.56 (br dd, J=5.2, 8.3 Hz, 2H), 7.38 (br dd, J=5.6, 7.8 Hz, 2H), 7.25-7.14 (m, 3H), 7.02 (br t, J=8.7 Hz, 2H), 6.10 (br d, J=2.4 Hz, 2H), 5.31 (br t, J=6.9 Hz, 1H), 1.58 (br d, J=7.3 Hz, 3H). LCMS for product (ESI+): m/z 498.2, [M+H]$^+$, Rt: 2.789 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 66—Synthesis of 6-(4-isopropoxyphenyl)-1-(4-fluorobenzyl)-2-oxo-N-(spiro[3.3]heptan-2-yl)-1,2-dihydro-1,8-naphthyridine-3-carboxamide— (Compound 66)

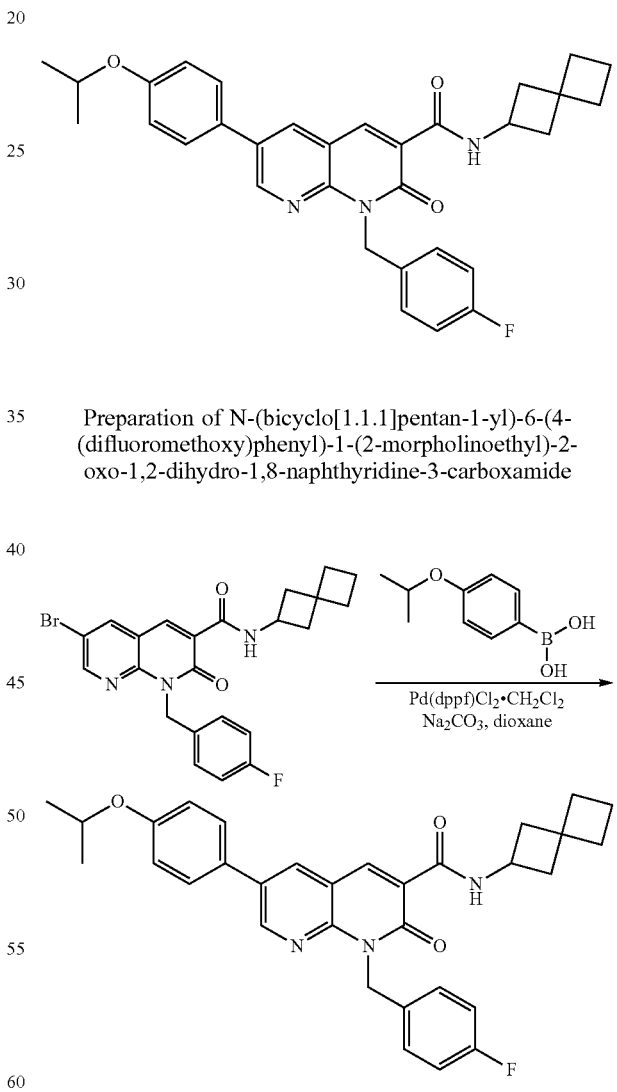

Preparation of N-(bicyclo[1.1.1]pentan-1-yl)-6-(4-(difluoromethoxy)phenyl)-1-(2-morpholinoethyl)-2-oxo-1,2-dihydro-1,8-naphthyridine-3-carboxamide To a solution of 6-bromo-1-[(4-fluorophenyl)methyl]-2-oxo-N-spiro[3.3]heptan-2-yl-1,8-naphthyridine-3-carboxamide (80 mg, 170.09 µmol, 1 eq), (4-isopropoxyphenyl) boronic acid (61.24 mg, 340.18 µmol, 2 eq) in dioxane (2 mL) and H$_2$O (0.5 mL) was added Na$_2$CO$_3$ (36.06 mg, 340.18 µmol, 2 eq) at 20° C. Added Pd(dppf)Cl$_2$·CH$_2$Cl$_2$ (13.89 mg, 17.01 μmol, 0.1 eq) under N₂, the mixture was stirred at 100° C. for 1 h. LCMS showed complete consumption of the starting material and formation of a new peak with desired mass.

The mixture was evaporated under reduced pressure and the residue was dissolved in DMF and filtered. The filtrate was purified by prep-HPLC (column: Waters Xbridge BEH C18 100*25 mm*5 μm; mobile phase: [water (10 mM NH₄HCO₃)-ACN]; B %: 40%-70%, 8 min) to produce 6-(4-isopropoxyphenyl)-1-(4-fluorobenzyl)-2-oxo-N-(spiro [3.3]heptan-2-yl)-1,2-dihydro-1,8-naphthyridine-3-carboxamide (31.9 mg, 60.69 μmol) as a light yellow solid.

¹H NMR (400 MHz, CDCl₃) δ=9.82 (br d, J=7.3 Hz, 1H), 8.93 (s, 1H), 8.92 (d, J=2.2 Hz, 1H), 8.17 (d, J=2.2 Hz, 1H), 7.60-7.37 (m, 4H), 7.08-6.89 (m, 4H), 5.81 (s, 2H), 4.63 (td, J=6.0, 12.1 Hz, 1H), 4.52-4.36 (m, 1H), 2.65-2.42 (m, 2H), 2.09 (t, J=7.2 Hz, 2H), 2.05-1.95 (m, 4H), 1.90-1.83 (m, 2H), 1.39 (d, J=6.2 Hz, 6H). LCMS for product (ESI+): m/z 526.3 [M+H]⁺, Rt: 3.476 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 67—Synthesis of 6-(4-cyclopropoxyphenyl)-1-(4-fluorobenzyl)-2-oxo-N-(spiro[3.3]heptan-2-yl)-1,2-dihydro-1,8-naphthyridine-3-carboxamide (Compound 67)

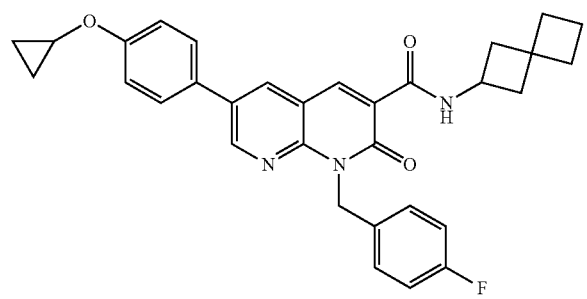 [SMILES: O=C(NC1CC2(CCC2)C1)c1cc2cc(-c3ccc(OC4CC4)cc3)cnc2n(Cc2ccc(F)cc2)c1=O]

Preparation of 6-(4-cyclopropoxyphenyl)-1-(4-fluorobenzyl)-2-oxo-N-(spiro[3.3]heptan-2-yl)-1,2-dihydro-1,8-naphthyridine-3-carboxamide

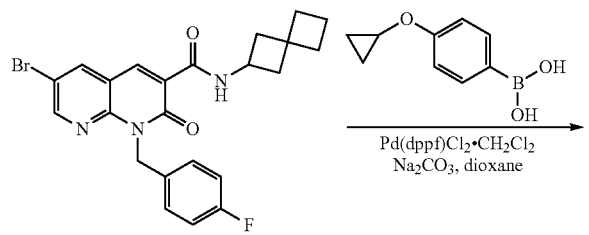

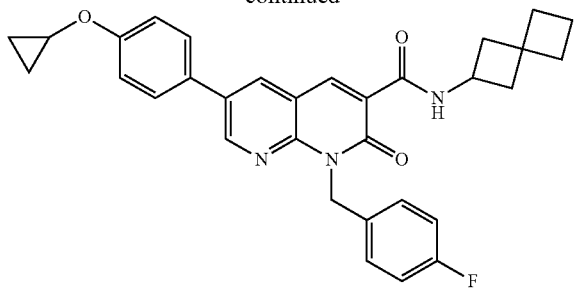

To a solution of 6-bromo-1-[(4-fluorophenyl)methyl]-2-oxo-N-spiro[3.3]heptan-2-yl-1,8-naphthyridine-3-carboxamide (80 mg, 170.09 μmol, 1 eq), [4-(cyclopropoxy)phenyl]boronic acid (60.55 mg, 340.18 μmol, 2 eq) in dioxane (2 mL) and H₂O (0.5 mL) was added Na₂CO₃ (36.06 mg, 340.18 μmol, 2 eq) at 20° C. Added Pd(dppf)Cl₂·CH₂Cl₂ (13.89 mg, 17.01 μmol, 0.1 eq) under N₂, the mixture was stirred at 100° C. for 1 h. LCMS showed complete consumption of the starting material and formation of a new peak with desired mass.

The mixture was concentrated under reduced pressure and the residue was dissolved in DMF and filtered. The filtrate was purified by prep-HPLC (column: Waters Xbridge BEH C18 100*25 mm*5 μm; mobile phase: [water (10 mM NH₄HCO₃)-ACN]; B %: 40%-70%, 8 min) to produce the desired product (41.6 mg, 77.07 μmol) was obtained as a light yellow solid.

¹H NMR (400 MHz, CDCl₃) δ=9.82 (br d, J=7.5 Hz, 1H), 8.94 (s, 1H), 8.92 (d, J=2.0 Hz, 1H), 8.18 (d, J=2.0 Hz, 1H), 7.55 (d, J=8.4 Hz, 2H), 7.49 (dd, J=5.5, 8.4 Hz, 2H), 7.20 (d, J=8.6 Hz, 2H), 6.99 (t, J=8.7 Hz, 2H), 5.81 (s, 2H), 4.57-4.37 (m, 1H), 3.90-3.74 (m, 1H), 2.60-2.42 (m, 2H), 2.10 (t, J=7.3 Hz, 2H), 2.06-1.95 (m, 4H), 1.90-1.82 (m, 2H), 0.92-0.78 (m, 4H). LCMS for product (ESI+): m/z 524.2 [M+H]⁺, Rt: 3.438 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 68—Synthesis of 1-(4-fluorobenzyl)-6-(4-(methylsulfonyl)phenyl)-2-oxo-N-(spiro[3.3]heptan-2-yl)-1,2-dihydro-1,8-naphthyridine-3-carboxamide (Compound 68)

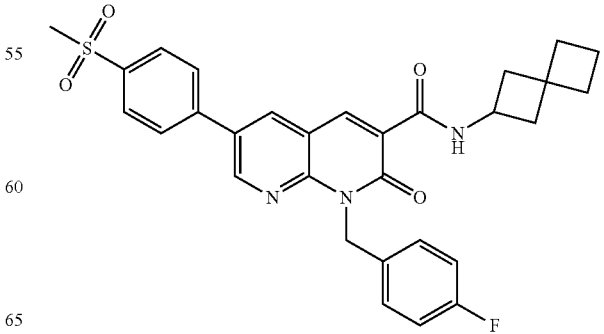

Preparation of 1-(4-fluorobenzyl)-6-(4-(methylsulfonyl)phenyl)-2-oxo-N-(spiro[3.3]heptan-2-yl)-1,2-dihydro-1,8-naphthyridine-3-carboxamide Example 69—Synthesis of 6-(5-cyanopyridin-2-yl)-1-(4-fluorobenzyl)-2-oxo-N-(spiro[3.3]heptan-2-yl)-1,2-dihydro-1,8-naphthyridine-3-carboxamide (Compound 69)

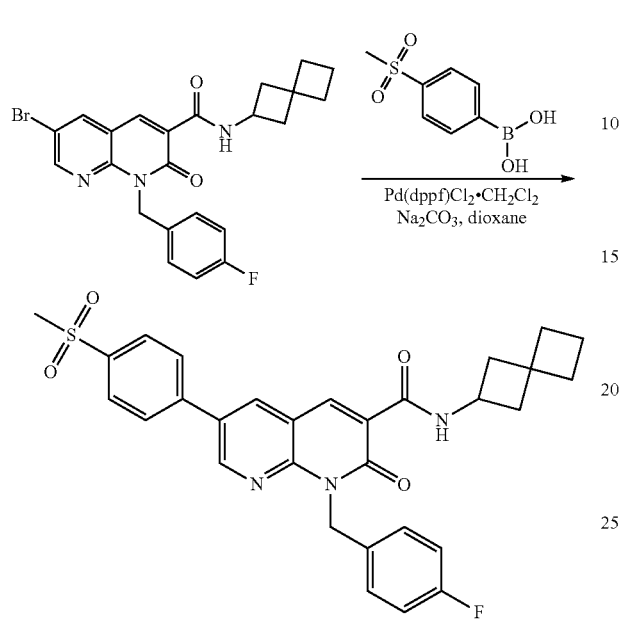

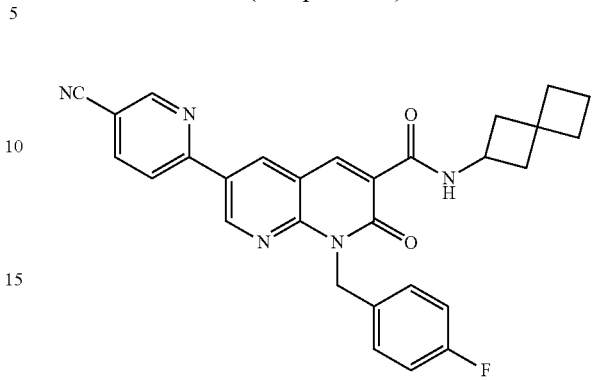

Step 1: Preparation of 1-(4-fluorobenzyl)-2-oxo-N-(spiro[3.3]heptan-2-yl)-6-(4,4,5,5-tetramethyl-1,3,2-dioxaborolan-2-yl)-1,2-dihydro-1,8-naphthyridine-3-carboxamide

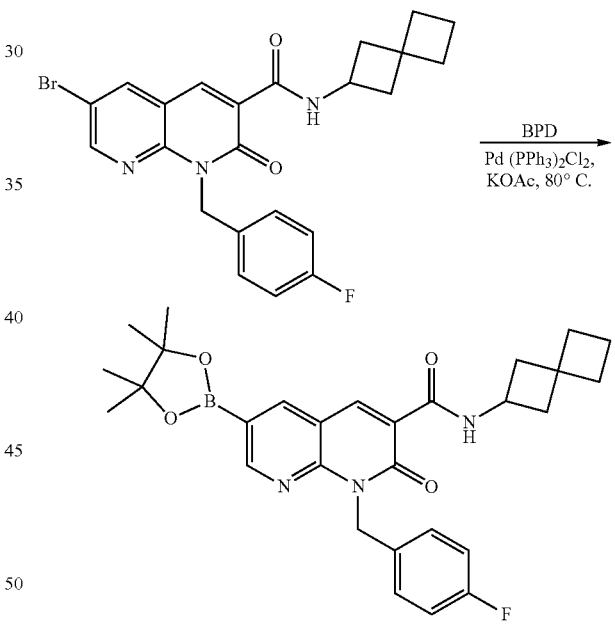

To a solution of 6-bromo-1-[(4-fluorophenyl)methyl]-2-oxo-N-spiro[3.3]heptan-2-yl-1,8-naphthyridine-3-carboxamide (80 mg, 170.09 μmol, 1 eq), (4-methylsulfonylphenyl)boronic acid (68.04 mg, 340.18 μmol, 2 eq) in dioxane (2 mL) and H$_2$O (0.5 mL) was added Na$_2$CO$_3$ (36.06 mg, 340.18 μmol, 2 eq) at 20° C. Added Pd(dppf)Cl$_2$·CH$_2$Cl$_2$ (13.89 mg, 17.01 μmol, 0.1 eq) under N$_2$, the mixture was stirred at 100° C. for 1 h. LCMS showed complete consumption of the starting material and formation of a new peak with desired mass.

The mixture was concentrated under reduced pressure and the residue was dissolved in DMF and filtered. The filtrate was purified by prep-HPLC (column: Waters Xbridge BEH C18 100*25 mm*5 μm; mobile phase: [water (10 mM NH$_4$HCO$_3$)-ACN]; B %: 40%-70%, 8 min) to yield 1-(4-fluorobenzyl)-6-(4-(methylsulfonyl)phenyl)-2-oxo-N-(spiro[3.3]heptan-2-yl)-1,2-dihydro-1,8-naphthyridine-3-carboxamide (54.4 mg) as a white solid.

$^1$H NMR (400 MHz, CDCl$_3$) δ=9.75 (br d, J=7.9 Hz, 1H), 8.98 (d, J=2.2 Hz, 1H), 8.96 (s, 1H), 8.28 (d, J=2.2 Hz, 1H), 8.11 (d, J=8.2 Hz, 2H), 7.83 (d, J=8.2 Hz, 2H), 7.51 (dd, J=5.3, 8.6 Hz, 2H), 7.07-6.91 (m, 2H), 5.82 (s, 2H), 4.55-4.38 (m, 1H), 3.13 (s, 3H), 2.61-2.46 (m, 2H), 2.10 (t, J=7.2 Hz, 2H), 2.06-1.95 (m, 4H), 1.92-1.80 (m, 2H). LCMS for product (ESI+): m/z 546.2 [M+H]$^+$, Rt: 3.050 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

To a solution of 6-bromo-1-[(4-fluorophenyl)methyl]-2-oxo-N-spiro[3.3]heptan-2-yl-1,8-naphthyridine-3-carboxamide (50 mg, 106.31 μmol, 1 eq) in dioxane (1.2 mL) was added 4,4,5,5-tetramethyl-2-(4,4,5,5-tetramethyl-1,3,2-dioxaborolan-2-yl)-1,3,2-dioxaborolane (215.96 mg, 850.46 μmol, 8 eq), potassium; acetate (31.30 mg, 318.92 μmol, 3 eq) at 20° C. Added Pd(PPh$_3$)$_2$Cl$_2$ (7.46 mg, 10.63 μmol, 0.1 eq) at 20° C., the mixture was stirred at 100° C. for 1 h. One additional vial was set up as described above, all two reaction mixtures were combined for work-up. LCMS showed complete consumption of the starting material and formation of a new peak with desired mass.

The mixture was concentrated under reduced pressure and the residue was triturated with petroleum ether to give 1-(4-fluorobenzyl)-2-oxo-N-(spiro[3.3]heptan-2-yl)-6-(4,4,5,5-tetramethyl-1,3,2-dioxaborolan-2-yl)-1,2-dihydro-1,8-naphthyridine-3-carboxamide (130 mg) as a yellow solid (used without further purification).

Step 2: Preparation of 6-(5-cyanopyridin-2-yl)-1-(4-fluorobenzyl)-2-oxo-N-(spiro[3.3]heptan-2-yl)-1,2-dihydro-1,8-naphthyridine-3-carboxamide

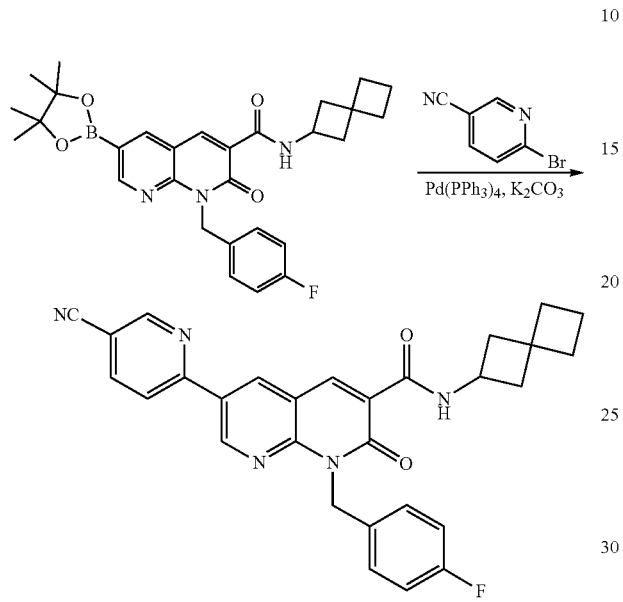

To a solution of 1-[(4-fluorophenyl)methyl]-2-oxo-N-spiro[3.3]heptan-2-yl-6-(4,4,5,5-tetramethyl-1,3,2-dioxaborolan-2-yl)-1,8-naphthyridine-3-carboxamide (50 mg, 96.64 μmol, 1 eq) in dioxane (2 mL) and $H_2O$ (0.5 mL) was added 6-bromopyridine-3-carbonitrile (26.70 mg, 145.92 μmol, 1.51 eq), $K_2CO_3$ (26.71 mg, 193.27 μmol, 2 eq) at 20° C. Added Pd(PPh$_3$)$_4$ (11.17 mg, 9.66 μmol, 0.1 eq) under N2, the mixture was stirred at 80° C. for 1 h. LCMS showed complete consumption of the starting material and formation of a new peak with desired mass.

The mixture was concentrated under reduced pressure and the residue was dissolved in DMF and filtered. The filtrate was purified by prep-HPLC (column: Waters Xbridge BEH C18 100*25 mm*5 μm; mobile phase: [water (10 mM $NH_4HCO_3$)-ACN]; B %: 40%-70%, 8 min) to produce 6-(5-cyanopyridin-2-yl)-1-(4-fluorobenzyl)-2-oxo-N-(spiro[3.3]heptan-2-yl)-1,2-dihydro-1,8-naphthyridine-3-carboxamide (18 mg, 35.74 μmol) as a white solid.

$^1$H NMR (400 MHz, CDCl$_3$) δ=9.71 (br d, J=7.5 Hz, 1H), 9.41 (d, J=2.3 Hz, 1H), 9.04-8.95 (m, 2H), 8.75 (d, J=2.3 Hz, 1H), 8.11 (dd, J=2.1, 8.3 Hz, 1H), 7.94 (d, J=8.3 Hz, 1H), 7.51 (dd, J=5.4, 8.6 Hz, 2H), 7.06-6.95 (m, 2H), 5.82 (s, 2H), 4.55-4.38 (m, 1H), 2.60-2.48 (m, 2H), 2.13-2.06 (m, 2H), 2.04-1.96 (m, 4H), 1.90-1.82 (m, 2H). LCMS for product (ESI+): m/z 494.1 [M+H]$^+$, Rt: 3.178 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 70—Synthesis of 6-bromo-1-(4-fluorobenzyl)-2-oxo-N-(pyridin-2-yl)-1,2-dihydro-1,8-naphthyridine-3-carboxamide (Compound 70)

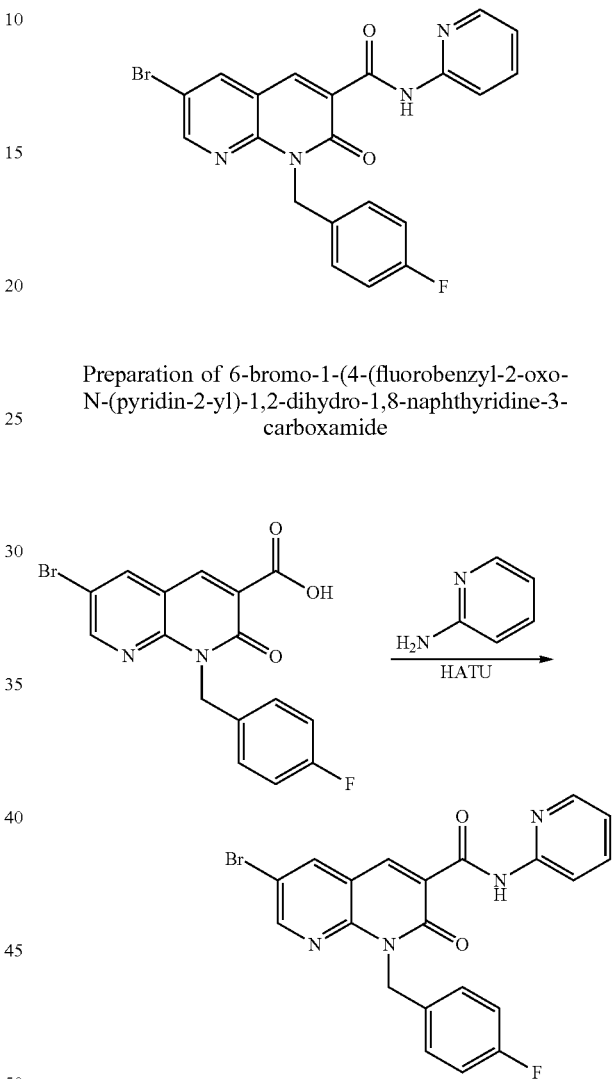

Preparation of 6-bromo-1-(4-(fluorobenzyl-2-oxo-N-(pyridin-2-yl)-1,2-dihydro-1,8-naphthyridine-3-carboxamide To a solution of 6-bromo-1-[(4-fluorophenyl)methyl]-2-oxo-1,8-naphthyridine-3-carboxylic acid (50 mg, 132.57 μmol, 1 eq) in DMF (1 mL) was added HATU (100.81 mg, 265.14 μmol, 2 eq), DIEA (51.40 mg, 397.70 μmol, 69.27 μL, 3 eq) at 20° C., the mixture was stirred at 20° C. for 0.5 h. Added pyridin-2-amine (13.72 mg, 145.83 μmol, 1.1 eq) at 20° C., the mixture was stirred at 20° C. for 0.5 h. LCMS showed complete consumption of the starting material and formation of a new peak with desired mass.

The mixture was filtered and the filtrate was purified by prep-HPLC (column: Waters Xbridge BEH C18 100*25 mm*5 μm; mobile phase: [water (10 mM $NH_4HCO_3$)-ACN]; B %: 40%-70%, 8 bmin) to produce 6-bromo-1-(4-fluorobenzyl)-2-oxo-N-(pyridin-2-yl)-1,2-dihydro-1,8-naphthyridine-3-carboxamide (15.2 mg, 32.29 μmol) as a white solid.

¹H NMR (400 MHz, CDCl₃) δ=12.30 (br s, 1H), 8.90 (s, 1H), 8.80 (d, J=2.2 Hz, 1H), 8.42 (dd, J=1.0, 4.7 Hz, 1H), 8.36 (d, J=8.4 Hz, 1H), 8.24 (d, J=2.4 Hz, 1H), 7.80-7.71 (m, 1H), 7.60 (dd, J=5.4, 8.3 Hz, 2H), 7.13-7.07 (m, 1H), 6.97 (t, J=8.6 Hz, 2H), 5.78 (s, 2H). LCMS for product (ESI+): m/z 453.0, 455.0 [M+H]+, Rt: 2.856 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 71—Synthesis of 6-bromo-1-(4-fluorobenzyl)-2-oxo-N-(p-tolyl)-1,2-dihydro-1,8-naphthyridine-3-carboxamide (Compound 71)

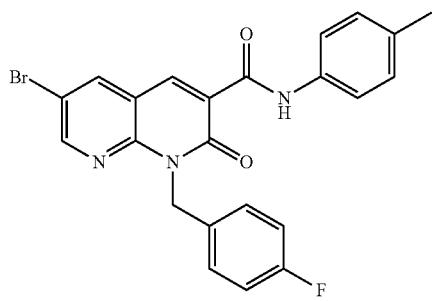

Preparation of 6-bromo-1-(4-fluorobenzyl)-2-oxo-N-(p-tolyl)-1,2-dihydro-1,8-naphthyridine-3-carboxamide

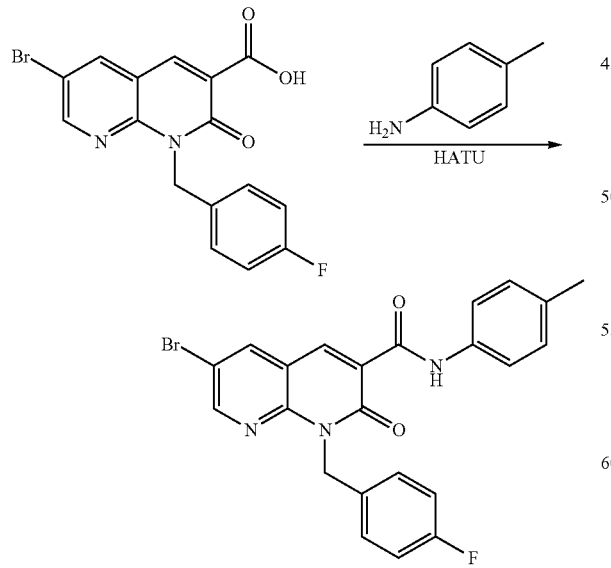

To a solution of 6-bromo-1-[(4-fluorophenyl)methyl]-2-oxo-1,8-naphthyridine-3-carboxylic acid (80 mg, 212.11 μmol, 1 eq) in DMF (2 mL) was added HATU (161.30 mg, 424.22 μmol, 2 eq), DIEA (82.24 mg, 636.33 μmol, 110.84 μL, 3 eq) at 20° C., the mixture was stirred at 20° C. for 0.5 h. Added 4-methylaniline (25.00 mg, 233.32 μmol, 25.69 μL, 1.1 eq) at 20° C., the mixture was stirred at 20° C. for 0.5 h. LCMS showed complete consumption of the starting material and formation of a new peak with desired mass.

The mixture was filtered and the filtrate was purified by prep-HPLC (column: Waters Xbridge BEH C18 100*25 mm*5 μm; mobile phase: [water (10 mM NH₄HCO₃)-ACN]; B %: 40%-70%, 8 bmin) to yield 6-bromo-1-(4-fluorobenzyl)-2-oxo-N-(p-tolyl)-1,2-dihydro-1,8-naphthyridine-3-carboxamide (14 mg, 29.90 μmol) as a yellow solid.

¹H NMR (400 MHz, CDCl₃) δ=11.74 (s, 1H), 8.92 (s, 1H), 8.78 (d, J=2.4 Hz, 1H), 8.24 (d, J=2.3 Hz, 1H), 7.67 (d, J=8.4 Hz, 2H), 7.51 (dd, J=5.5, 8.6 Hz, 2H), 7.19 (d, J=8.1 Hz, 2H), 6.99 (t, J=8.7 Hz, 2H), 5.79 (s, 2H), 2.36 (s, 3H). LCMS for product (ESI+): m/z 465.9, 467.9 [M+H]+, Rt: 3.231 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 72—Synthesis of 6-bromo-4-methyl-N-(4-methylcyclohexyl)-1-(2-morpholinoethyl)-2-oxo-1,2-dihydro-1,8-naphthyridine-3-carboxamide (Compound 72)

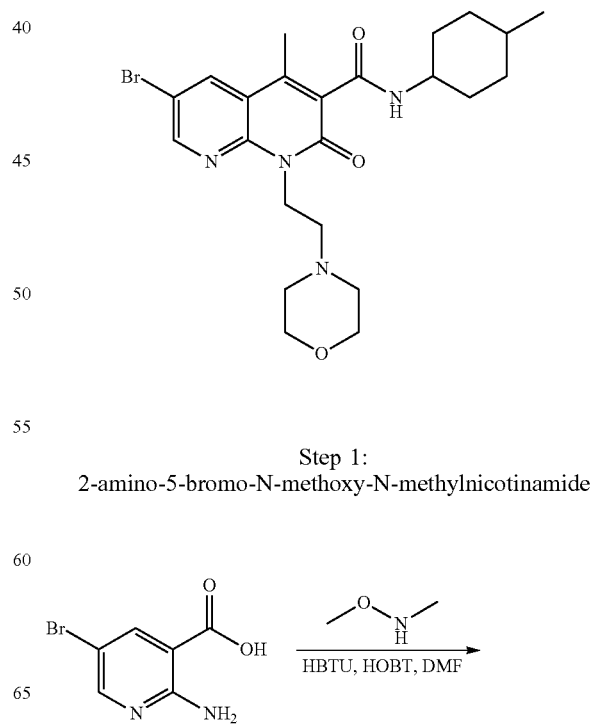

Step 1: 2-amino-5-bromo-N-methoxy-N-methylnicotinamide

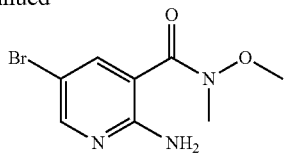

To a solution of 2-amino-5-bromo-pyridine-3-carboxylic acid (10 g, 46.08 mmol, 1 eq) in DMF (100 mL) was added HBTU (24.46 g, 64.51 mmol, 1.4 eq) and HOBT (8.72 g, 64.51 mmol, 1.4 eq) at 0° C. A solution of N-methoxymethanamine; hydrochloride (4.94 g, 50.69 mmol, 1.1 eq) and DIEA (11.91 g, 92.16 mmol, 16 mL, 2 eq) in DMF (20 mL) was added into the mixture at 0° C. The mixture was stirred at 25° C. for 5 h. LCMS showed complete consumption of the starting material and formation of a new peak. The reaction mixture was poured into water (200 mL), extracted with ethyl acetate (3×300 mL), separated, the organic layer was washed with brine (200 mL), dried over $Na_2SO_4$ and concentrated.

The residue was purified by silica gel column chromatography (Petroleum ether/Ethyl acetate=50:1 to 1:1) to produce 2-amino-5-bromo-N-methoxy-N-methylnicotinamide (11 g, 42.29 mmol) as a yellow solid.

$^1$H NMR (400 MHz, $CDCl_3$) δ=8.16 (d, J=2.4 Hz, 1H), 7.90 (d, J=2.4 Hz, 1H), 5.66 (br s, 2H), 3.57 (s, 3H), 2.80 (s, 3H). LCMS for product (ESI+): m/z 260.0, 262.0 $[M+H]^+$, Rt: 0.758 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 2:
1-(2-amino-5-bromopyridin-3-yl)ethan-1-one

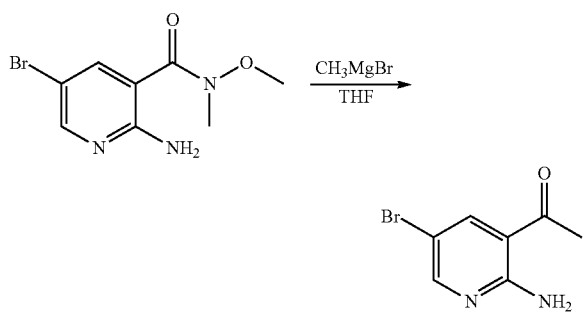

To a solution of 2-amino-5-bromo-N-methoxy-N-methylpyridine-3-carboxamide (10 g, 38.45 mmol, 1 eq) in THF (150 mL) was added bromo(methyl)magnesium (3 M, 51.3 mL, 4 eq) at 0° C. The mixture was stirred at 25° C. for 2 h. LCMS showed complete consumption of the starting material and formation of a new peak. The mixture was poured into saturated $NH_4Cl$ (500 mL), extracted with ethyl acetate (3×300 mL), separated, the organic layer was washed with brine (300 mL), dried over $Na_2SO_4$ and concentrated.

The residue was purified by silica gel column chromatography (Petroleum ether/Ethyl acetate=100:1 to 1:1) to produce 1-(2-amino-5-bromopyridin-3-yl)ethan-1-one (5 g, 23.25 mmol) as a yellow solid $^1$H NMR (400 MHz, $CDCl_3$) δ=8.26 (d, J=2.5 Hz, 1H), 8.07 (d, J=2.4 Hz, 1H), 2.57 (s, 3H). LCMS for product (ESI+): m/z 215.0, 217.0 $[M+H]^+$, Rt: 0.957 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 3: ethyl 3-((3-acetyl-5-bromopyridin-2-yl)amino)-3-oxopropanoate

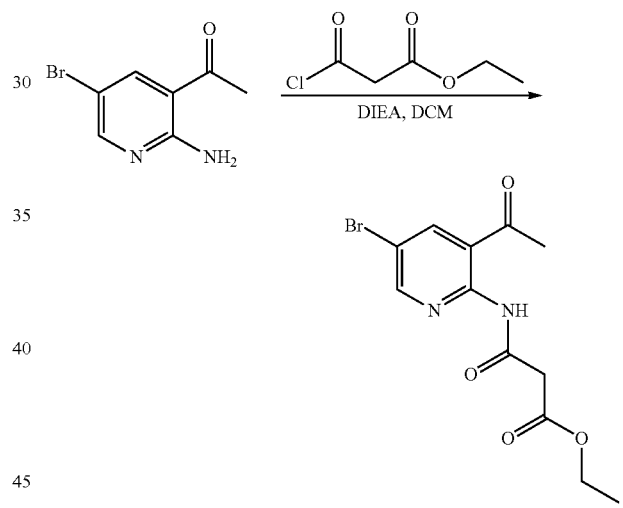

To a mixture of 1-(2-amino-5-bromo-3-pyridyl) ethanone (3.5 g, 16.28 mmol, 1 eq) in DCM (35 mL) was added DIEA (5.26 g, 40.69 mmol, 7.1 mL, 2.5 eq) at 0° C. A solution of ethyl 3-chloro-3-oxo-propanoate (6.13 g, 40.69 mmol, 5.11 mL, 2.5 eq) in DCM (35 mL) was added into the mixture at 0° C. The mixture was stirred at 25° C. for 12 h. LCMS showed formation of a new peak.

The mixture was concentrated to yield ethyl 3-((3-acetyl-5-bromopyridin-2-yl)amino)-3-oxopropanoate (5.3 g, 16.10 mmol) as a red oil (used without further purification).

LCMS for product (ESI+): m/z 329.0, 330.9 $[M+H]^+$, Rt: 0.929 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 4: ethyl 6-bromo-4-methyl-2-oxo-1,2-dihydro-1,8-naphthyridine-3-carboxylate

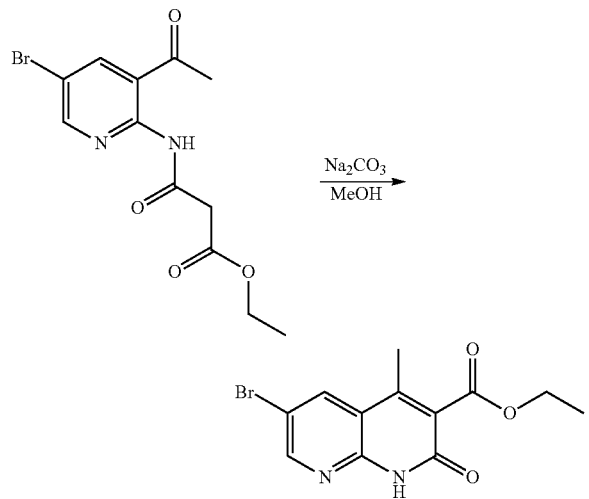

To a solution of ethyl 3-[(3-acetyl-5-bromo-2-pyridyl)amino]-3-oxo-propanoate (5 g, 15.19 mmol, 1 eq) in MeOH (50 mL) was added Na$_2$CO$_3$ (1.26 g, 15.19 mmol, 1 eq). The mixture was stirred at 25° C. for 2 h. LCMS showed complete consumption of the starting material and formation of a new peak.

The mixture was poured into saturated NH$_4$Cl (100 mL). The mixture was filtered, and solid was washed with water and air-dried to produce ethyl 6-bromo-4-methyl-2-oxo-1,2-dihydro-1,8-naphthyridine-3-carboxylate (2.7 g, 8.68 mmol) as a gray solid.

$^1$H NMR (400 MHz, DMSO-d$_6$) δ=8.67 (d, J=2.3 Hz, 1H), 8.45 (d, J=2.3 Hz, 1H), 4.31 (q, J=7.1 Hz, 2H), 2.38 (s, 3H), 1.28 (t, J=7.1 Hz, 3H). LCMS for product (ESI+): m/z 311.0, 313.0 [M+H]$^+$, Rt: 1.158 min.

LCMS Method

The gradient was 5-95% B in 0.7 min, 95-95% B in 0.45 min, 95-5% B in 0.01 min, and then held at 0% B for 0.44 min (1.5 mL/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 5: 6-bromo-4-methyl-2-oxo-1,2-dihydro-1,8-naphthyridine-3-carboxylic acid

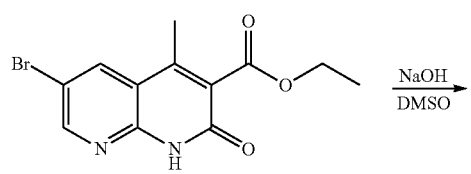

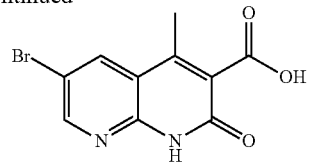

To a solution of ethyl 6-bromo-4-methyl-2-oxo-1H-1,8-naphthyridine-3-carboxylate (2 g, 6.43 mmol, 1 eq) in DMSO (20 mL) was added NaOH (2 M, 10 mL, 3.11 eq) at 25° C. The mixture was stirred at 80° C. for 24 h. LCMS showed complete consumption of the starting material and formation of a new peak.

The mixture was poured into HCl (200 mL, 2M), the mixture was filtered, and the solid was air-dried to produce 6-bromo-4-methyl-2-oxo-1,2-dihydro-1,8-naphthyridine-3-carboxylic acid (1.4 g, 4.95 mmol) as a white solid.

$^1$H NMR (400 MHz, DMSO-d$_6$) δ=12.57 (br s, 1H), 8.67 (d, J=2.3 Hz, 1H), 8.46 (d, J=2.3 Hz, 1H), 2.44 (s, 3H). LCMS for product (ESI+): m/z 282.9, 284.9 [M+H]$^+$, Rt: 0.791 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Step 6: 6-bromo-4-methyl-N-(4-methylcyclohexyl)-2-oxo-1,2-dihydro-1,8-naphthyridine-3-carboxamide

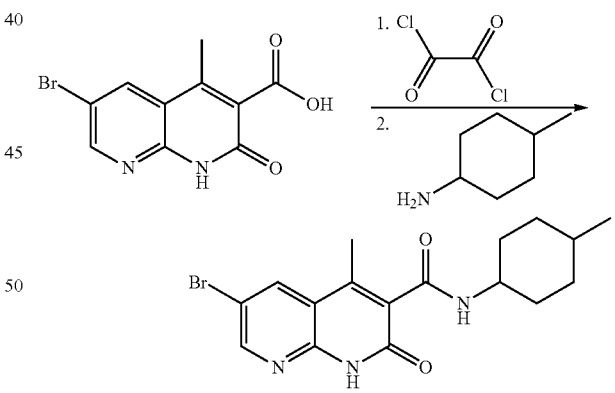

To a solution of 6-bromo-4-methyl-2-oxo-1H-1,8-naphthyridine-3-carboxylic acid (1.2 g, 4.24 mmol, 1 eq) in DCM (15 mL) was added oxalyl chloride (1.08 g, 8.48 mmol, 742.17 μL, 2 eq) and DMF (309.84 mg, 4.24 mmol, 326.14 μL, 1 eq). The mixture was stirred at 0° C. for 1 h. A solution of 4-methylcyclohexanamine (1.5 g, 13.25 mmol, 1.75 mL, 3.13 eq) and TEA (5.15 g, 50.87 mmol, 7.1 mL, 12 eq) in DCM (10 mL) was added into the mixture at 0° C., the mixture was stirred at 0° C. for 3 h. TLC showed starting material was consumed and a new spot was formed.

The mixture was concentrated and the residue was triturated in HCl (30 mL, 0.5 M) for 1 h, then triturated in petroleum ether (15 mL), then the mixture was filtered and the solid was air-dried to produce 6-bromo-4-methyl-N-(4-methylcyclohexyl)-2-oxo-1,2-dihydro-1,8-naphthyridine-3-carboxamide (1.4 g, 3.70 mmol) as a gray solid (used without further purification).

$^1$H NMR (400 MHz, DMSO-d$_6$) δ=12.34 (br s, 1H), 8.62 (s, 1H), 8.41 (s, 1H), 8.30-8.14 (m, 1H), 4.13-3.54 (m, 1H), 2.34 (d, J=2.3 Hz, 3H), 1.93-1.79 (m, 1H), 1.72-1.62 (m, 2H), 1.55 (br dd, J=3.1, 10.1 Hz, 1H), 1.51-1.41 (m, 2H), 1.35-1.28 (m, 1H), 1.25-1.16 (m, 1H), 1.07-0.94 (m, 1H), 0.87 (br dd, J=2.2, 6.1 Hz, 3H).

Step 7: Preparation of 6-bromo-4-methyl-N-(4-methylcyclohexyl)-1-(2-morpholinoethyl)-2-oxo-1,2-dihydro-1,8-naphthyridine-3-carboxamide

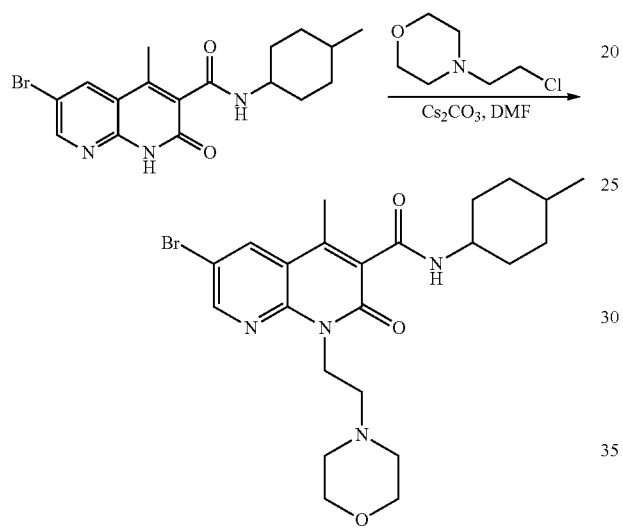

To a solution of 6-bromo-4-methyl-N-(4-methylcyclohexyl)-2-oxo-1H-1,8-naphthyridine-3-carboxamide (400 mg, 1.06 mmol, 1 eq) in DMF (5 mL) was added Cs$_2$CO$_3$ (2.07 g, 6.34 mmol, 6 eq) at 20° C. The mixture was stirred at 50° C. for 1 h. 4-(2-chloroethyl)morpholine (316.43 mg, 2.11 mmol, 2 eq) was added to the mixture at 50° C., the mixture was stirred at 50° C. for 11 h. LCMS showed complete consumption of the starting material and formation of a new peak.

The mixture was poured into NH$_4$Cl (200 mL), extracted with ethyl acetate (3×50 mL), separated, the organic layer was washed with brine (30 mL), dried over Na$_2$SO$_4$ and concentrated to produce 6-bromo-4-methyl-N-(4-methylcyclohexyl)-1-(2-morpholinoethyl)-2-oxo-1,2-dihydro-1,8-naphthyridine-3-carboxamide (300 mg, 610.48 µmol) as a brown oil (used without further purification).

$^1$H NMR (400 MHz, CDCl$_3$) δ=8.63 (d, J=1.8 Hz, 1H), 8.23 (dd, J=2.2, 4.7 Hz, 1H), 7.42-6.81 (m, 1H), 4.86-4.47 (m, 2H), 4.35-3.83 (m, 1H), 3.78-3.52 (m, 4H), 2.95-2.29 (m, 9H), 2.21-2.08 (m, 1H), 1.94-1.64 (m, 5H), 1.34-1.21 (m, 2H), 1.19-1.06 (m, 1H), 0.94 (dd, J=6.5, 10.8 Hz, 3H). LCMS for product (ESI+): m/z 491.1, 493.1 [M+H]$^+$, Rt: 0.935 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Example 73—Synthesis of 6-(4-methoxyphenyl)-4-methyl-N-(4-methylcyclohexyl)-1-(2-morpholinoethyl)-2-oxo-1,2-dihydro-1,8-naphthyridine-3-carboxamide (Compound 73)

Preparation of 6-(4-methoxyphenyl)-4-methyl-N-(4-methylcyclohexyl)-1-(2-morpholinoethyl)-2-oxo-1,2-dihydro-1,8-naphthyridine-3-carboxamide

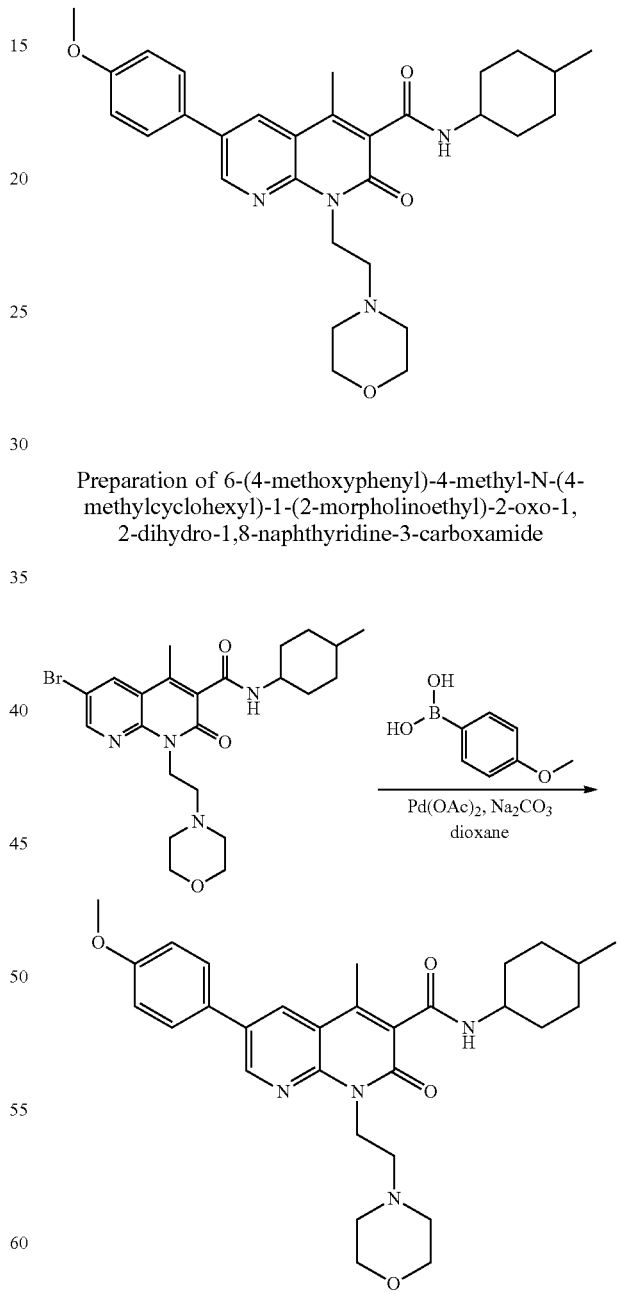

To a solution of (4-methoxyphenyl)boronic acid (56.24 mg, 370.08 µmol, 2 eq) in dioxane (0.8 mL) and water (0.2 mL) was added Pd(OAc)$_2$ (4.15 mg, 18.50 µmol, 0.1 eq), Na$_2$CO$_3$ (30.72 mg, 370.08 µmol, 2 eq) and 6-bromo-4- methyl-N-(4-methylcyclohexyl)-1-(2-morpholinoethyl)-2-oxo-1,8-naphthyridine-3-carboxamide (90.93 mg, 185.04 µmol, 1 eq) at 25° C. The mixture was stirred at 100° C. for 4 h. LCMS showed complete consumption of the starting material and formation of a new peak.

The mixture was poured into NH$_4$Cl (10 mL), extracted with ethyl acetate (3×5 mL), separated, the organic layer was washed with brine (5 mL), dried over Na$_2$SO$_4$ and concentrated. The residue was purified by prep-HPLC (column: Waters Xbridge BEH C18 100*30 mm*10 µm; mobile phase: [water (10 mM NH$_4$HCO$_3$)-ACN]; B %: 37%-60%, 10 min) to produce 6-(4-methoxyphenyl)-4-methyl-N-(4-methylcyclohexyl)-1-(2-morpholinoethyl)-2-oxo-1,2-dihydro-1,8-naphthyridine-3-carboxamide (40.5 mg, 77.31 µmol) as a white solid.

$^1$H NMR (400 MHz, CDCl$_3$) δ=8.79 (br s, 1H), 8.25-8.13 (m, 1H), 7.62-7.40 (m, 3H), 7.04 (br d, J=8.4 Hz, 2H), 4.71 (q, J=7.0 Hz, 2H), 4.35-3.81 (m, 4H), 3.69 (br s, 4H), 2.84-2.48 (m, 9H), 2.14 (br d, J=9.9 Hz, 1H), 1.92-1.81 (m, 1H), 1.80-1.75 (m, 1H), 1.70-1.46 (m, 3H), 1.27 (br t, J=12.0 Hz, 2H), 1.19-1.01 (m, 1H), 0.93 (br dd, J=6.5, 12.0 Hz, 3H). LCMS for product (ESI+): m/z 519.3 [M+H]$^+$, Rt: 3.065 min.

LCMS Method

The gradient was 5-95% B in 1.0 min, 95-100% B in 0.8 min, 100-5% B in 0.01 min, and then held at 5% B for 0.24 min (1.0 m/min flow rate). Mobile phase A was 10 mM NH$_4$HCO$_3$ in water, mobile phase B was CH$_3$CN. The column used for the chromatography was Xbridge Shield RP18 2.1*50 mm, 5 µm column. Detection methods are diode array (DAD) and positive electrospray ionization (MS).

Example 74—Synthesis of 6-(4-methoxyphenyl)-4-methyl-1-(2-morpholinoethyl)-2-oxo-N-(spiro[3.3]heptan-2-yl)-1,2-dihydro-1,8-naphthyridine-3-carboxamide (Compound 74)

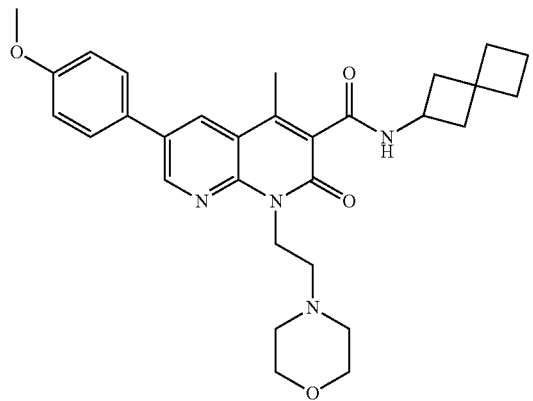 [SMILES: COc1ccc(-c2cnc3c(c2)c(C)c(C(=O)NC2CC4(CCC4)C2)c(=O)n3CCN2CCOCC2)cc1]

Step 1: Preparation of ethyl 6-bromo-4-methyl-1-(2-morpholinoethyl)-2-oxo-1,2-dihydro-1,8-naphthyridine-3-carboxylate

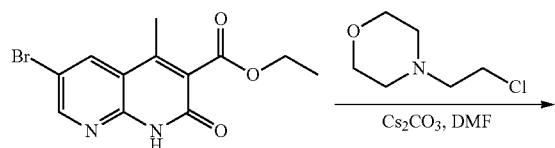

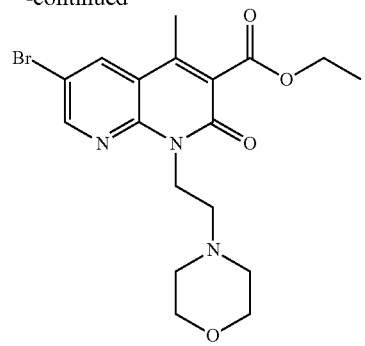

To a solution of ethyl 6-bromo-4-methyl-2-oxo-1H-1,8-naphthyridine-3-carboxylate (600 mg, 1.93 mmol, 1 eq) in DMF (6 mL) was added Cs$_2$CO$_3$ (3.14 g, 9.64 mmol, 5 eq) at 25° C. The mixture was stirred at 50° C. for 1 h. 4-(2-chloroethyl)morpholine (577.06 mg, 3.86 mmol, 2 eq) was added into the mixture at 50° C., the mixture was stirred at 50° C. for 11 h. LCMS showed complete consumption of the starting material and formation of a new peak.

The mixture was poured into NH$_4$Cl (100 mL), extracted with ethyl acetate (3×50 mL), separated, the organic layer was washed with brine (30 mL), dried over Na$_2$SO$_4$ (50 g) and concentrated. The residue was purified by prep-TLC (SiO$_2$, ethyl acetate) to produce ethyl 6-bromo-4-methyl-1-(2-morpholinoethyl)-2-oxo-1,2-dihydro-1,8-naphthyridine-3-carboxylate (550 mg, 1.30 mmol) as a colorless oil.

$^1$H NMR (400 MHz, CDCl$_3$) δ=8.63 (d, J=2.3 Hz, 1H), 8.14 (d, J=2.3 Hz, 1H), 4.67-4.57 (m, 2H), 4.45 (q, J=7.1 Hz, 2H), 3.75-3.58 (m, 4H), 2.74-2.64 (m, 2H), 2.59 (br s, 4H), 2.43 (s, 3H), 1.41 (t, J=7.1 Hz, 3H). LCMS for product (ESI+): m/z 424.1, 426.1 [M+H]$^+$, Rt: 1.988 min.

LCMS Method

The column used for chromatography was Xbridge Shield RP18 2.1*50 mm, (5 µm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 2: Preparation of ethyl 6-(4-methoxyphenyl)-4-methyl-1-(2-morpholinoethyl)-2-oxo-1,2-dihydro-1,8-naphthyridine-3-carboxylate

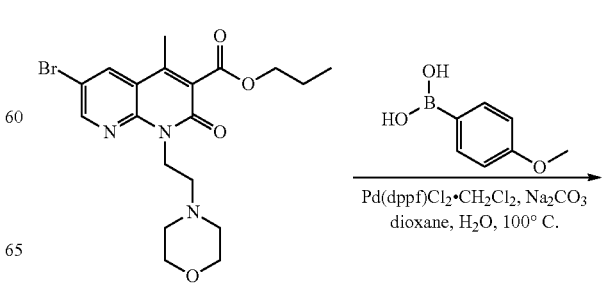

327
-continued

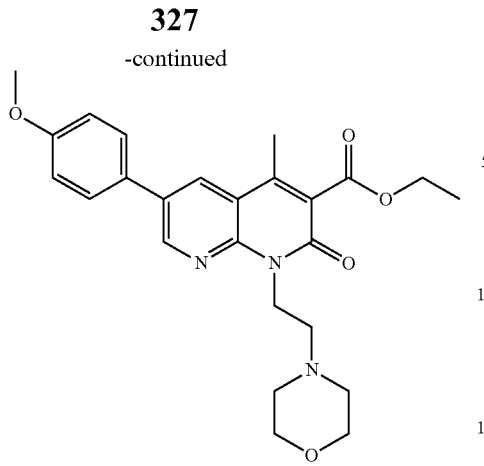

To a solution of ethyl 6-bromo-4-methyl-1-(2-morpholinoethyl)-2-oxo-1,8-naphthyridine-3-carboxylate (550 mg, 1.30 mmol, 1 eq) in dioxane (5 mL) and water (1 mL) was added (4-methoxyphenyl)boronic acid (393.96 mg, 2.59 mmol, 2 eq), $Na_2CO_3$ (274.79 mg, 2.59 mmol, 2 eq) and $Pd(dppf)Cl_2 \cdot CH_2Cl_2$ (105.86 mg, 129.63 µmol, 0.1 eq) under $N_2$. The mixture was stirred at 100° C. for 12 h. LCMS showed complete consumption of the starting material and formation of a new peak.

The mixture was poured into $NH_4Cl$ (100 mL), extracted with ethyl acetate (3×50 mL), separated, the organic layer was washed with brine (30 mL), dried over $Na_2SO_4$ (30 g) and concentrated to produce ethyl 6-(4-methoxyphenyl)-4-methyl-1-(2-morpholinoethyl)-2-oxo-1,2-dihydro-1,8-naphthyridine-3-carboxylate (550 mg, 1.22 mmol) as a brown oil.

LCMS for product (ESI+): m/z 452.2 [M+H]$^+$, Rt: 1.233 min.

LCMS Method

The column used for chromatography was Xbridge Shield RP18 2.1*50 mm, (5 µm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 3: Preparation of 6-(4-methoxyphenyl)-4-methyl-1-(2-morpholinoethyl)-2-oxo-1,2-dihydro-1,8-naphthyridine-3-carboxylic acid

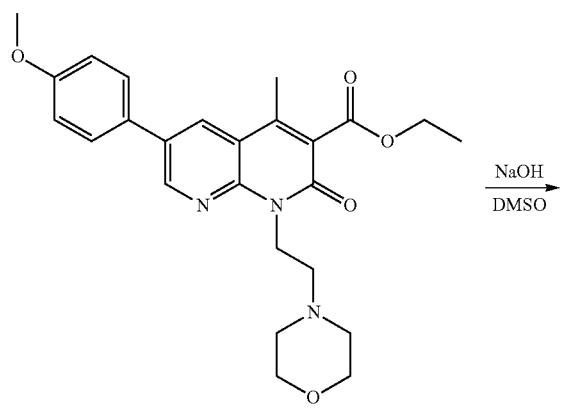

328
-continued

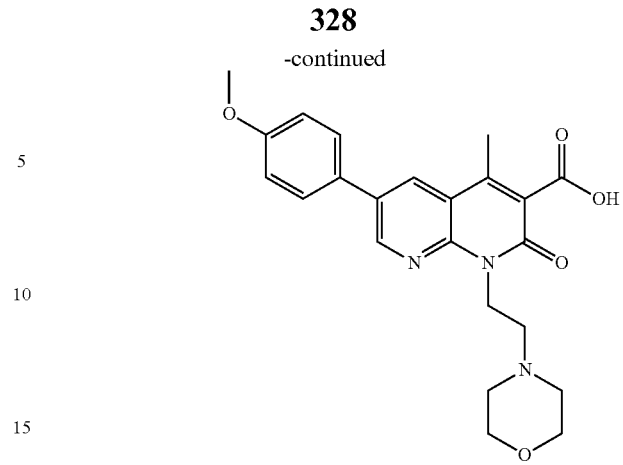

To a solution of ethyl 6-(4-methoxyphenyl)-4-methyl-1-(2-morpholinoethyl)-2-oxo-1,8-naphthyridine-3-carboxylate (500 mg, 1.11 mmol, 1 eq) in DMSO (3.5 mL) was added NaOH (2 M, 1.4 mL, 2.53 eq) at 25° C. The mixture was stirred at 25° C. for 2 h. LCMS showed complete consumption of the starting material and formation of a new peak.

The mixture was poured into HCl (2 mL, 2 N), washed with ethyl acetate (3×5 mL), separated, and the aqueous layer was lyophilized to yield 6-(4-methoxyphenyl)-4-methyl-1-(2-morpholinoethyl)-2-oxo-1,2-dihydro-1,8-naphthyridine-3-carboxylic acid (250 mg, 590.37 µmol) as an orange solid.

$^1$H NMR (400 MHz, DMSO-d$_6$) δ=8.89 (d, J=1.8 Hz, 1H), 8.34 (d, J=1.8 Hz, 1H), 7.79 (br d, J=8.6 Hz, 2H), 7.08 (br d, J=8.6 Hz, 2H), 4.54 (br t, J=7.0 Hz, 2H), 3.82 (s, 3H), 3.54 (br s, 4H), 2.54 (s, 3H), 2.46 (br s, 6H). LCMS for product (ESI+): m/z 424.1 [M+H]$^+$, Rt: 1.374 min.

LCMS Method

The column used for chromatography was Xbridge Shield RP18 2.1*50 mm, (5 µm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 4: Preparation of 6-(4-methoxyphenyl)-4-methyl-1-(2-morpholinoethyl)-2-oxo-N-(spiro[3.3]heptan-2-yl)-1,2-dihydro-1,8-naphthyridine-3-carboxamide

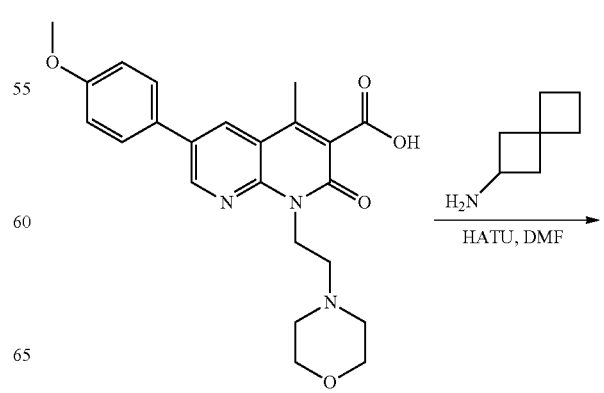

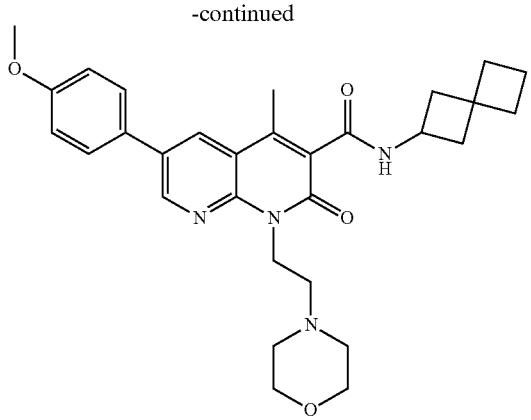

To a solution of 6-(4-methoxyphenyl)-4-methyl-1-(2-morpholinoethyl)-2-oxo-1,8-naphthyridine-3-carboxylic acid (70 mg, 165.30 μmol, 1 eq) in DMF (1 mL) was added HATU (94.28 mg, 247.96 μmol, 1.5 eq), DIEA (42.73 mg, 330.61 μmol, 57 μL, 2 eq) and spiro[3.3]heptan-2-amine (26.85 mg, 181.84 μmol, 1.1 eq, HCl). The mixture was stirred at 25° C. for 1 h. LCMS showed complete consumption of the starting material and formation of a new peak.

The mixture was filtered, and the filtrate was purified by prep-HPLC (column: Welch Xtimate C18 150*30 mm*5 μm; mobile phase: [water (10 mM NH$_4$HCO$_3$)-ACN]; B %: 35%-65%, 3 min) to produce 6-(4-methoxyphenyl)-4-methyl-1-(2-morpholinoethyl)-2-oxo-N-(spiro[3.3]heptan-2-yl)-1,2-dihydro-1,8-naphthyridine-3-carboxamide (20.0 mg, 47.18 μmol) as a light yellow solid.

$^1$H NMR (400 MHz, CDCl$_3$) δ=8.80 (d, J=2.0 Hz, 1H), 8.22 (d, J=2.1 Hz, 1H), 7.66-7.50 (m, 3H), 7.05 (d, J=8.6 Hz, 2H), 4.72 (br t, J=7.0 Hz, 2H), 4.52-4.32 (m, 1H), 3.89 (s, 3H), 3.70 (br t, J=4.3 Hz, 4H), 2.88-2.69 (m, 5H), 2.63 (br s, 4H), 2.58-2.48 (m, 2H), 2.09 (br t, J=7.3 Hz, 2H), 2.02-1.92 (m, 4H), 1.90-1.79 (m, 2H). LCMS for product (ESI+): m/z 517.3 [M+H]$^+$, Rt: 1.007 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Example 75—Synthesis of N-(1-(4-fluorophenyl)ethyl)-6-(4-methoxyphenyl)-4-methyl-1-(2-morpholinoethyl)-2-oxo-1,2-dihydro-1,8-naphthyridine-3-carboxamide (Compound 75)

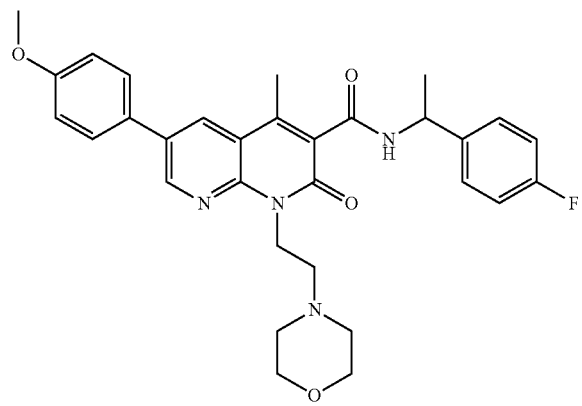 [SMILES: COc1ccc(-c2cnc3c(c2)c(C)c(C(=O)NC(C)c2ccc(F)cc2)c(=O)n3CCN2CCOCC2)cc1]

Preparation of N-(1-(4-fluorophenyl)ethyl)-6-(4-methoxyphenyl)-4-methyl-1-(2-morpholinoethyl)-2-oxo-1,2-dihydro-1,8-naphthyridine-3-carboxamide

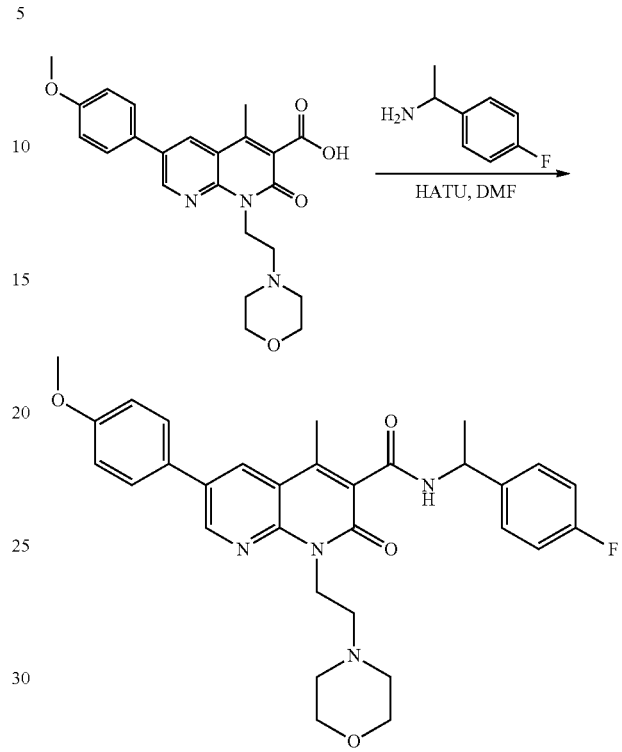

To a solution of 6-(4-methoxyphenyl)-4-methyl-1-(2-morpholinoethyl)-2-oxo-1,8-naphthyridine-3-carboxylic acid (70 mg, 165.30 μmol, 1 eq) in DMF (1 mL) was added HATU (94.28 mg, 247.96 μmol, 1.5 eq), DIEA (42.73 mg, 330.61 μmol, 57 μL, 2 eq) and 1-(4-fluorophenyl)ethanamine (25.31 mg, 181.84 μmol, 23.87 μL, 1.1 eq). The mixture was stirred at 25° C. for 1 h. LCMS showed complete consumption of the starting material and formation of a new peak.

The mixture was filtered and the filtrate was purified by prep-HPLC (column: Welch Xtimate C18 150*30 mm*5 μm; mobile phase: [water (10 mM NH$_4$HCO$_3$)-ACN]; B %: 35%-65%, 3 min) to produce N-(1-(4-fluorophenyl)ethyl)-6-(4-methoxyphenyl)-4-methyl-1-(2-morpholinoethyl)-2-oxo-1,2-dihydro-1,8-naphthyridine-3-carboxamide (24.4 mg, 44.76 μmol) as a light yellow solid.

$^1$H NMR (400 MHz, CDCl$_3$) δ=8.81 (br s, 1H), 8.23 (br s, 1H), 8.07 (br d, J=7.0 Hz, 1H), 7.55 (br d, J=8.3 Hz, 2H), 7.49-7.37 (m, 2H), 7.05 (br d, J=5.0 Hz, 4H), 5.30 (br t, J=6.9 Hz, 1H), 4.74 (br t, J=6.6 Hz, 2H), 3.89 (s, 3H), 3.69 (br s, 4H), 2.74 (br s, 5H), 2.63 (br s, 4H), 1.61 (br d, J=6.8 Hz, 3H). LCMS for product (ESI+): m/z 545.3 [M+H]$^+$, Rt: 1.000 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Example 76—Synthesis of 6-bromo-1-(4-fluorobenzyl)-4-methyl-2-oxo-N-(spiro[3.3]heptan-2-yl)-1,2-dihydro-1,8-naphthyridine-3-carboxamide (Compound 76)

Step 1: Preparation of ethyl 6-bromo-1-(4-fluorobenzyl)-4-methyl-2-oxo-1,2-dihydro-1,8-naphthyridine-3-carboxylate

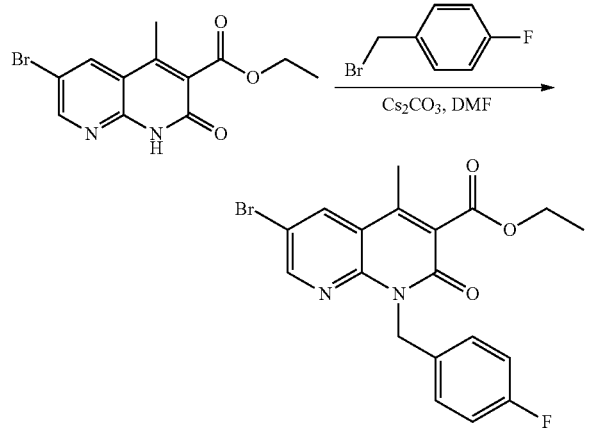

To a mixture of ethyl 6-bromo-4-methyl-2-oxo-1H-1,8-naphthyridine-3-carboxylate (90 mg, 289.27 μmol, 1 eq) in DMF (1 mL) as added Cs$_2$CO$_3$ (282.75 mg, 867.80 μmol, 3 eq) at 20° C. for 1 h, and then 1-(bromomethyl)-4-fluorobenzene (65.61 mg, 347.12 μmol, 42.89 μL, 1.2 eq) was added dropwise at 50° C. The mixture was stirred at 50° C. for 1 h. LCMS showed complete consumption of the starting material and formation of a new peak. The reaction mixture was poured into water (10 mL). The aqueous phase was extracted with ethyl acetate (3×5 mL).

The combined organic phase was dried with anhydrous Na$_2$SO$_4$, filtered and concentrated to produce ethyl 6-bromo-1-(4-fluorobenzyl)-4-methyl-2-oxo-1,2-dihydro-1,8-naphthyridine-3-carboxylate (110 mg, 262.38 μmol) as a red oil (used without further purification).

$^1$H NMR (400 MHz, CDCl$_3$) δ=8.67 (d, J=2.0 Hz, 1H), 8.14 (d, J=2.0 Hz, 1H), 7.51 (dd, J=5.5, 8.5 Hz, 2H), 6.94 (t, J=8.8 Hz, 2H), 5.64 (s, 2H), 4.47 (q, J=7.2 Hz, 2H), 2.43 (s, 3H), 1.42 (t, J=7.0 Hz, 3H).

Step 2: Preparation of 6-bromo-1-(4-fluorobenzyl)-4-methyl-2-oxo-1,2-dihydro-1,8-naphthyridine-3-carboxylic acid

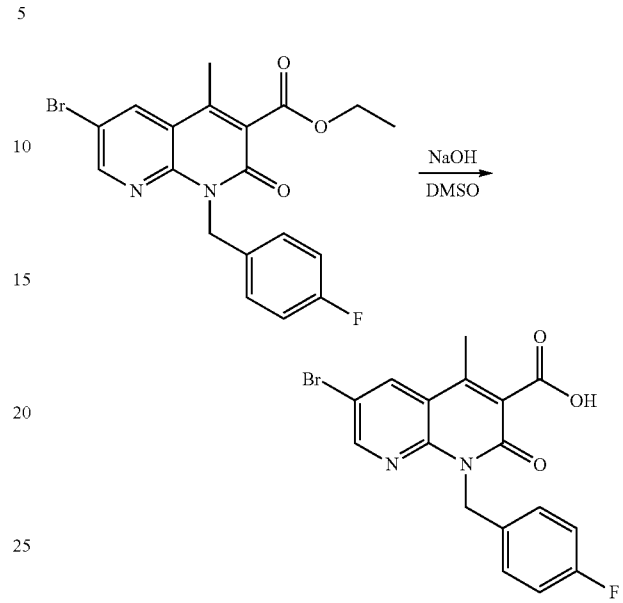

To a mixture of ethyl 6-bromo-1-[(4-fluorophenyl)methyl]-4-methyl-2-oxo-1,8-naphthyridine-3-carboxylate (110 mg, 262.38 μmol, 1 eq) in DMSO (1 mL) was added NaOH (2 M, 0.26 mL, 2 eq) at 20° C. The mixture was stirred at 20° C. for 12 h. LCMS showed complete consumption of the starting material and formation of a new peak. The reaction mixture was poured into water (20 mL). The aqueous phase was extracted with ethyl acetate (3×10 mL).

The combined organic phase was dried with anhydrous Na$_2$SO$_4$, filtered and concentrated. The residue was purified by prep-TLC (petroleum ether/ethyl acetate, 3:1) to produce 6-bromo-1-(4-fluorobenzyl)-4-methyl-2-oxo-1,2-dihydro-1,8-naphthyridine-3-carboxylic acid (21 mg, 53.68 μmol) as a white solid.

$^1$H NMR (400 MHz, CDCl$_3$) δ=8.83 (d, J=2.0 Hz, 1H), 8.51 (d, J=2.0 Hz, 1H), 7.52 (dd, J=5.5, 8.5 Hz, 2H), 6.98 (t, J=8.5 Hz, 2H), 5.78 (s, 2H), 3.08 (s, 3H).

Step 3: Preparation of 6-bromo-1-(4-fluorobenzyl)-4-methyl-2-oxo-N-(spiro[3.3]heptan-2-yl)-1,2-dihydro-1,8-naphthyridine-3-carboxamide

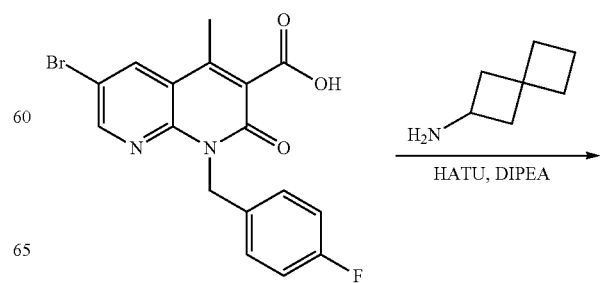

-continued

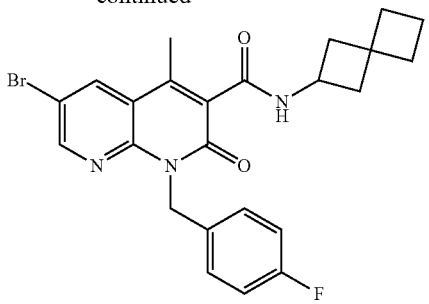

To a mixture of 6-bromo-1-[(4-fluorophenyl)methyl]-4-methyl-2-oxo-1,8-naphthyridine-3-carboxylic acid (21 mg, 53.68 µmol, 1 eq) and spiro[3.3]heptan-2-amine (8.72 mg, 59.05 µmol, 1.1 eq, HCl) in DMF (0.5 mL) was added HATU (40.82 mg, 107.36 µmol, 2 eq) and DIPEA (20.81 mg, 161.05 µmol, 28.05 µL, 3 eq) at 20° C. The mixture was stirred at 20° C. for 2 h. LCMS showed complete consumption of the starting material and formation of a new peak.

The mixture was filtered and the filtrate was purified by prep-HPLC (column: Waters Xbridge BEH C18 100*30 mm*10 µm; mobile phase: [water (10 mM $NH_4HCO_3$)-ACN]; B %: 45%-70%, 10 min) to produce 6-bromo-1-(4-fluorobenzyl)-4-methyl-2-oxo-N-(spiro[3.3]heptan-2-yl)-1,2-dihydro-1,8-naphthyridine-3-carboxamide (7.3 mg, 15.03 µmol) as a white solid.

$^1$H NMR (400 MHz, DMSO-$d_6$) δ=8.75 (d, J=2.0 Hz, 1H), 8.57 (d, J=7.5 Hz, 1H), 8.51 (d, J=2.0 Hz, 1H), 7.33 (dd, J=5.8, 8.8 Hz, 2H), 7.10 (t, J=8.8 Hz, 2H), 5.52 (s, 2H), 4.20-4.11 (m, 1H), 2.36-2.31 (m, 5H), 2.02 (t, J=7.3 Hz, 2H), 1.93-1.85 (m, 4H), 1.82-1.75 (m, 2H). LCMS for product (ESI-): m/z 484.2, 486.1 [M+H]$^+$, Rt: 3.323 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 77—Synthesis of 6-bromo-1-(4-cyanobenzyl)-4-methyl-2-oxo-N-(spiro[3.3]heptan-2-yl)-1,2-dihydro-1,8-naphthyridine-3-carboxamide (Compound 77)

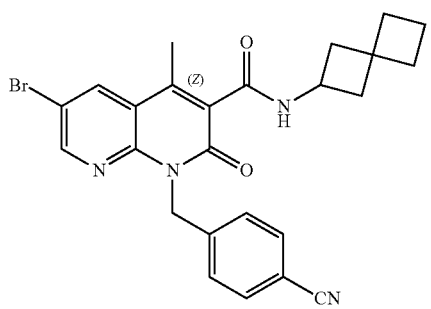 [SMILES: Cc1c(C(=O)NC2CC3(CCC3)C2)c(=O)n(Cc2ccc(C#N)cc2)c2ncc(Br)cc12]

Preparation of 6-bromo-1-(4-cyanobenzyl)-4-methyl-2-oxo-N-(spiro[3.3]heptan-2-yl)-1,2-dihydro-1,8-naphthyridine-3-carboxamide

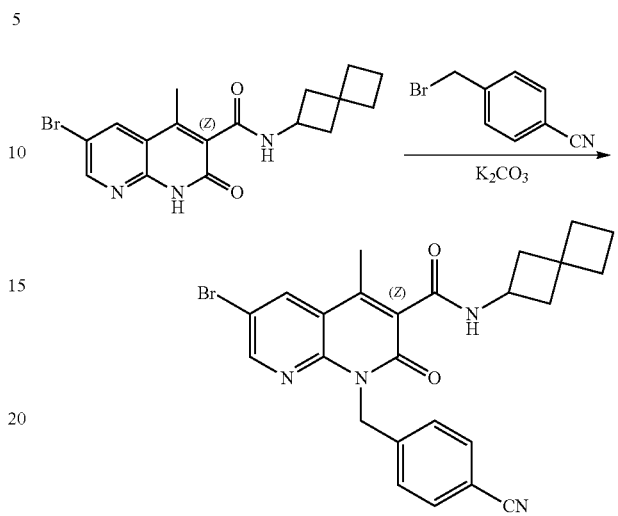

To a mixture of 6-bromo-4-methyl-2-oxo-N-spiro[3.3]heptan-2-yl-1H-1,8-naphthyridine-3-carboxamide (50 mg, 132.89 µmol, 1 eq) and 4-(bromomethyl)benzonitrile (31.26 mg, 159.47 mol, 1.2 eq) in DMF (1 mL) was added $K_2CO_3$ (55.10 mg, 398.67 µmol, 3 eq) in one portion at 20° C. The mixture was stirred at 20° C. for 2 h. LC-MS showed Reactant 1 was consumed completely and one main peak with desired m/z. LCMS showed complete consumption of the starting material and formation of a new peak. The mixture was filtered and the residue was purified by prep-HPLC (column: Waters Xbridge BEH C18 100*25 mm*5 µm; mobile phase: [water (10 mM $NH_4HCO_3$)-ACN]; B %: 45%-75%, 8 min) to produce 6-bromo-1-(4-cyanobenzyl)-4-methyl-2-oxo-N-(spiro[3.3]heptan-2-yl)-1,2-dihydro-1,8-naphthyridine-3-carboxamide (15.8 mg, 31.74 µmol) as a white solid.

$^1$H NMR (400 MHz, CDCl$_3$) δ=8.63 (d, J=2.0 Hz, 1H), 8.27 (d, J=2.5 Hz, 1H), 7.61-7.54 (m, 2H), 7.53-7.47 (m, 2H), 7.34 (br d, J=6.5 Hz, 1H), 5.73 (s, 2H), 4.42 (sxt, J=7.9 Hz, 1H), 2.68 (s, 3H), 2.59-2.49 (m, 2H), 2.09 (t, J=7.3 Hz, 2H), 2.01-1.92 (m, 4H), 1.90-1.82 (m, 2H). LCMS for product (ESI+): m/z 491.1, 493.1 [M+H]$^+$, Rt: 2.716 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 78—Synthesis of 6-bromo-1-(3-cyanobenzyl)-4-methyl-2-oxo-N-(spiro[3.3]heptan-2-yl)-1,2-dihydro-1,8-naphthyridine-3-carboxamide (Compound 78)

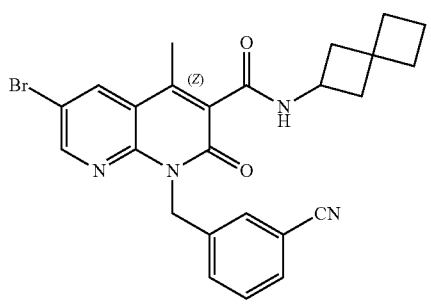 [SMILES: Cc1c(C(=O)NC2CC3(CCC3)C2)c(=O)n(Cc2cccc(C#N)c2)c2ncc(Br)cc12]

Preparation of 6-bromo-1-(3-cyanobenzyl)-4-methyl-2-oxo-N-(spiro[3.3]heptan-2-yl)-1,2-dihydro-1,8-naphthyridine-3-carboxamide

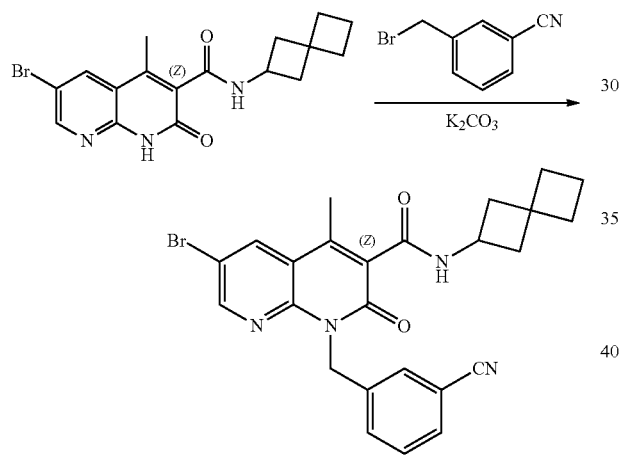

To a mixture of 6-bromo-4-methyl-2-oxo-N-spiro[3.3]heptan-2-yl-1H-1,8-naphthyridine-3-carboxamide (50 mg, 132.89 μmol, 1 eq) and 3-(bromomethyl)benzonitrile (31.26 mg, 159.47 μmol, 1.2 eq) in DMF (1 mL) was added $K_2CO_3$ (55.10 mg, 398.67 μmol, 3 eq) at 20° C. The mixture was stirred at 20° C. for 2 h. LCMS showed complete consumption of the starting material and formation of a new peak.

The mixture was filtered and the filtrate was purified by prep-HPLC (column: Waters Xbridge BEH C18 100*25 mm*5 μm; mobile phase: [water (10 mM $NH_4HCO_3$)-ACN]; B %: 45%-75%, 8 min) to produce 6-bromo-1-(3-cyanobenzyl)-4-methyl-2-oxo-N-(spiro[3.3]heptan-2-yl)-1,2-dihydro-1,8-naphthyridine-3-carboxamide (8.6 mg, 17.36 μmol) as a white solid.

$^1$H NMR (400 MHz, $CDCl_3$) δ=8.66 (d, J=2.0 Hz, 1H), 8.27 (d, J=2.0 Hz, 1H), 7.78-7.65 (m, 2H), 7.53 (d, J=8.0 Hz, 1H), 7.44-7.37 (m, 1H), 7.34 (br d, J=7.0 Hz, 1H), 5.70 (s, 2H), 4.43 (sxt, J=7.9 Hz, 1H), 2.59-2.50 (m, 2H), 2.09 (t, J=7.5 Hz, 2H), 2.01-1.93 (m, 4H), 1.90-1.81 (m, 2H). LCMS for product (ESI+): m/z 491.1, 493.1 [M+H]$^+$, Rt: 2.730 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 79—Synthesis of 6-bromo-1-(4-fluorobenzyl)-4-methyl-N-(4-methylcyclohexyl)-2-oxo-1,2-dihydro-1,8-naphthyridine-3-carboxamide (Compound 79)

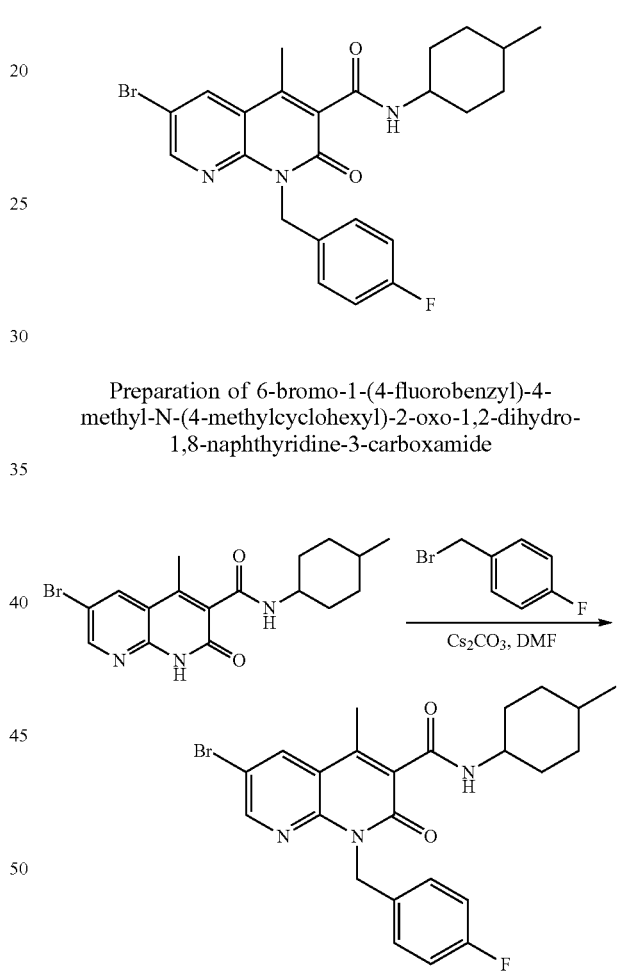

Preparation of 6-bromo-1-(4-fluorobenzyl)-4-methyl-N-(4-methylcyclohexyl)-2-oxo-1,2-dihydro-1,8-naphthyridine-3-carboxamide To a solution of 6-bromo-4-methyl-N-(4-methylcyclohexyl)-2-oxo-1H-1,8-naphthyridine-3-carboxamide (400 mg, 1.06 mmol, 1 eq) in DMF (4 mL) was added $Cs_2CO_3$ (2.07 g, 6.34 mmol, 6 eq). The mixture was stirred at 50° C. for 1 h, 1-(bromomethyl)-4-fluoro-benzene (199.89 mg, 1.06 mmol, 130.65 μL, 1 eq) was added into the mixture at 50° C., the mixture was stirred at 50° C. for 0.5 h. LCMS showed complete consumption of the starting material and formation of a new peak. The mixture was poured into $NH_4Cl$ (50 mL), extracted with ethyl acetate (3×30 mL), the organic layer was washed with brine (30 mL), dried over $Na_2SO_4$ (30 g) and concentrated.

The residue was purified by prep-HPLC (NH₄CO₃ column: Waters Xbridge BEH C18 100*30 mm*10 μm; mobile phase: [water (10 mM NH₄HCO₃)-ACN]; B %: 50%-75%, 10 min) to produce the desired product 6-bromo-1-[(4-fluorophenyl)methyl]-4-methyl-N-(4-methylcyclohexyl)-2-oxo-1,8-naphthyridine-3-carboxamide (28.5 mg, 58.60 μmol) as a white solid and 6-bromo-1-[(4-fluorophenyl)methyl]-4-methyl-N-(4-methylcyclohexyl)-2-oxo-1,8-naphthyridine-3-carboxamide (300 mg, 616.81 μmol) as a brown solid.

¹H NMR (400 MHz, DMSO-d₆) δ=8.75 (dd, J=1.2, 2.2 Hz, 1H), 8.58-8.44 (m, 1H), 8.32-8.15 (m, 1H), 7.42-7.28 (m, 2H), 7.18-7.05 (m, 2H), 5.53 (d, J=3.6 Hz, 2H), 4.08-3.57 (m, 1H), 2.38 (d, J=1.3 Hz, 3H), 1.96-1.81 (m, 1H), 1.74-1.61 (m, 2H), 1.60-1.34 (m, 3H), 1.33-1.19 (m, 2H), 1.15-0.95 (m, 1H), 0.87 (dd, J=1.9, 6.4 Hz, 3H). LCMS for product (ESI+): m/z 486.1, 488.1 [M+H]⁺, Rt: 1.235 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Example 80—Synthesis of 1-(4-fluorobenzyl)-6-(4-methoxyphenyl)-4-methyl-N-(4-methylcyclohexyl)-2-oxo-1,2-dihydro-1,8-naphthyridine-3-carboxamide (Compound 80)

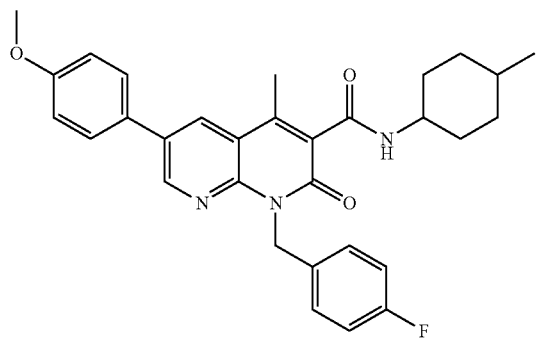

Preparation of 1-(4-fluorobenzyl)-6-(4-methoxyphenyl)-4-methyl-N-(4-methylcyclohexyl)-2-oxo-1,2-dihydro-1,8-naphthyridine-3-carboxamide

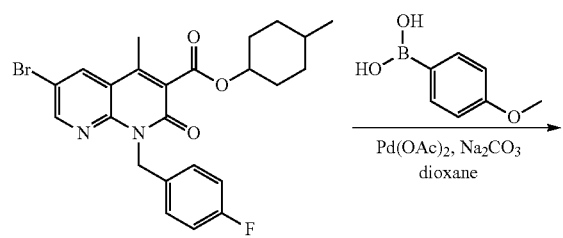

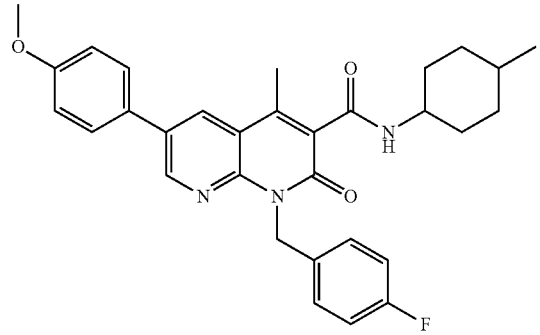 [SMILES: COc1ccc(-c2cnc3c(c2)c(C)c(C(=O)NC2CCC(C)CC2)c(=O)n3Cc2ccc(F)cc2)cc1]

To a solution of (4-methoxyphenyl)boronic acid (56.24 mg, 370.08 μmol, 2 eq) in dioxane (0.8 mL) and water (0.2 mL) was added Pd(OAc)₂ (4.15 mg, 18.50 μmol, 0.1 eq) and Na₂CO₃ (19.61 mg, 185.04 μmol, 1 eq) and 6-bromo-1-[(4-fluorophenyl)methyl]-4-methyl-N-(4-methylcyclohexyl)-2-oxo-1,8-naphthyridine-3-carboxamide (90 mg, 185.04 μmol, 1 eq) at 25° C. The mixture was stirred at 100° C. for 4 h. LCMS showed complete consumption of the starting material and formation of a new peak.

The mixture was poured into NH₄Cl (10 mL), extracted with ethyl acetate (3×5 mL), the organic layer was washed with brine (3 mL), dried over Na₂SO₄ (5 g) and concentrated. The residue was purified by prep-HPLC (Waters Xbridge BEH C18 100*30 mm*10 μm; mobile phase: [water (10 mM NH₄HCO₃)-ACN]; B %: 47%-70%, 10 min) to produce 1-(4-fluorobenzyl)-6-(4-methoxyphenyl)-4-methyl-N-(4-methylcyclohexyl)-2-oxo-1,2-dihydro-1,8-naphthyridine-3-carboxamide (32 mg, 62.31 μmol) as a white solid.

¹H NMR (400 MHz, CDCl₃) δ=8.82 (br s, 1H), 8.21 (br s, 1H), 7.57-7.41 (m, 4.5H), 7.04-6.9 (m, 4.5H), 5.74 (br d, J=6.8 Hz, 2H), 4.35-3.75 (m, 4H), 2.72 (br d, J=5.5 Hz, 3H), 2.14 (br d, J=10.4 Hz, 1H), 1.92-1.64 (m, 4H), 1.55-1.19 (m, 3H), 1.18-1.03 (m, 1H), 0.93 (br dd, J=6.4, 13.4 Hz, 3H). LCMS for product (ESI+): m/z 514.3 [M+H]⁺, Rt: 3.500 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% trifluoroacetic acid in water, mobile phase B was 0.018% trifluoroacetic acid in acetonitrile. The column used for the chromatography is a Chromolith Flash RP-18e 25-2 mm column. Detection methods are diode array (DAD) and evaporative light scattering (ELSD) detection as well as positive electrospray ionization (MS).

Example 81—Synthesis of 6-bromo-1-(4-fluorobenzyl)-2-oxo-N-(spiro[3.3]heptan-2-yl)-1,2-dihydro-1,8-naphthyridine-3-carboxamide (Compound 81)

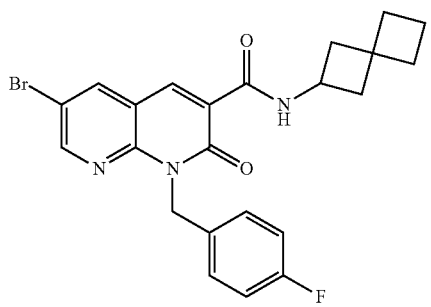

Step 1: Preparation of ethyl 6-bromo-1-(4-fluorobenzyl)-2-oxo-1,2-dihydro-1,8-naphthyridine-3-carboxylate

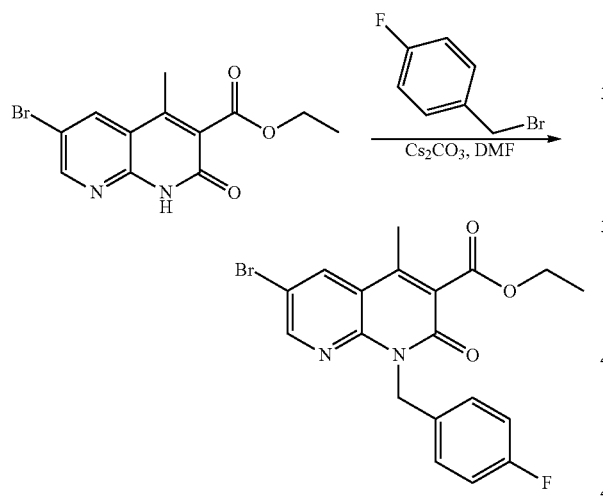

To a solution of ethyl 6-bromo-2-oxo-1H-1,8-naphthyridine-3-carboxylate (300 mg, 1.01 mmol, 1 eq) in DMF (2 mL) was added $Cs_2CO_3$ (921.19 mg, 2.83 mmol, 2.8 eq). The mixture was stirred at 20° C. for 1 h, then added 1-(bromomethyl)-4-fluoro-benzene (381.73 mg, 2.02 mmol, 249.50 μL, 2 eq). The mixture was stirred at 50° C. for 3 h. LCMS showed complete consumption of the starting material and formation of a new peak. The reaction mixture was poured into water (10 mL), extracted with ethyl acetate (3×10 mL).

The organic phase was washed with brine (10 mL), dried over $Na_2SO_4$ and concentrated to yield ethyl 6-bromo-1-(4-fluorobenzyl)-2-oxo-1,2-dihydro-1,8-naphthyridine-3-carboxylate (300 mg) as a yellow solid (used without further purification).

$^1$H NMR (400 MHz, $CDCl_3$) δ=8.72 (d, J=2.2 Hz, 1H), 8.26 (s, 1H), 8.09 (d, J=2.4 Hz, 1H), 7.54 (dd, J=5.6, 8.7 Hz, 2H), 6.95 (t, J=8.7 Hz, 2H), 5.68 (s, 2H), 4.52-4.36 (m, 2H), 1.42 (t, J=7.2 Hz, 3H). LCMS for product (ESI+): m/z 405.1, 406.9 [M+H]$^+$, Rt: 2.492 min.

LCMS Method

The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Step 2: Preparation of 6-bromo-1-(4-fluorobenzyl)-2-oxo-1,2-dihydro-1,8-naphthyridine-3-carboxylic acid

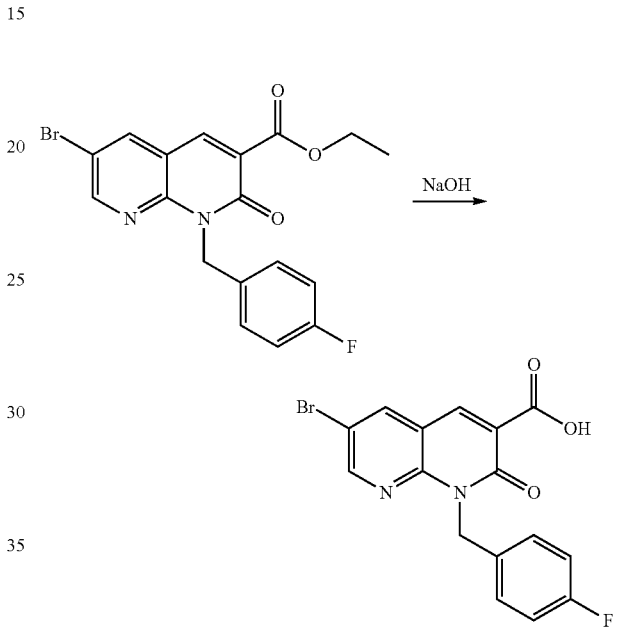

To a solution of ethyl 6-bromo-1-[(4-fluorophenyl)methyl]-2-oxo-1,8-naphthyridine-3-carboxylate (270 mg, 666.31 μmol, 1 eq) in DMSO (2 mL) was added NaOH (2 M, 666.31 μL, 2 eq) at 20° C., the mixture was stirred at 20° C. for 0.5 h. LCMS showed complete consumption of the starting material and formation of a new peak. The mixture was poured into water (10 mL) and extracted with ethyl acetate (3×10 mL).

The combined organic phase was washed with brine (10 mL), dried with anhydrous $Na_2SO_4$, filtered and concentrated in vacuum to produce 6-bromo-1-(4-fluorobenzyl)-2-oxo-1,2-dihydro-1,8-naphthyridine-3-carboxylic acid (240 mg) as a yellow solid (used without further purification).

$^1$H NMR (400 MHz, DMSO-$d_6$) δ=14.03-13.68 (m, 1H), 8.93 (d, J=2.4 Hz, 1H), 8.84-8.79 (m, 2H), 7.45-7.33 (m, 2H), 7.15-7.08 (m, 2H), 5.64 (s, 2H). LCMS for product (ESI+): m/z 377.0, 379.0 [M+H]$^+$, Rt: 1.390 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Step 3: Preparation of 6-bromo-1-(4-fluorobenzyl)-2-oxo-N-(spiro[3.3]heptan-2-yl)-1,2-dihydro-1,8-naphthyridine-3-carboxamide

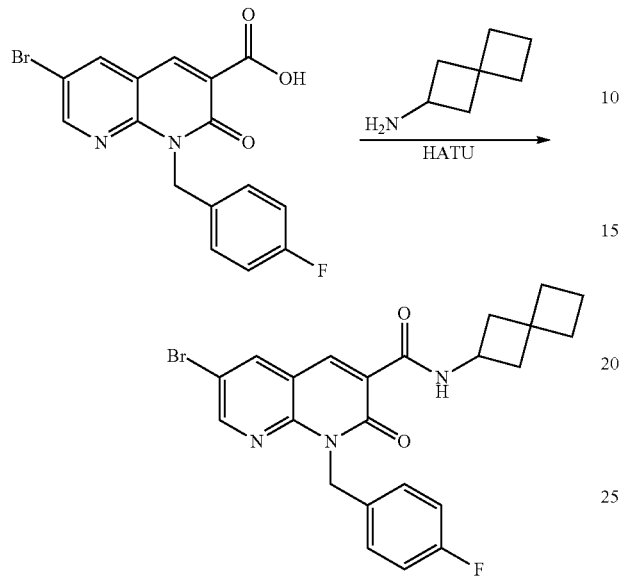

To a solution of 6-bromo-1-[(4-fluorophenyl)methyl]-2-oxo-1,8-naphthyridine-3-carboxylic acid (80 mg, 212.11 μmol, 1 eq) in DMF (1 mL) was added HATU (161.30 mg, 424.22 μmol, 2 eq), DIEA (82.24 mg, 636.33 μmol, 110.84 μL, 3 eq) at 20° C., the mixture was stirred at 20° C. for 0.5 h. Added spiro[3.3]heptan-2-amine (31.32 mg, 212.11 μmol, 1 eq, HCl) at 20° C., the mixture was stirred at 20° C. for 0.5 h. LCMS showed complete consumption of the starting material and formation of a new peak.

The mixture was filtered and the filtrate was purified by prep-HPLC (column: Waters X bridge BEH C18 100*25 mm*5 μm; mobile phase: [water (10 mM $NH_4HCO_3$)-ACN]; B %: 50%-80%, 8 min) to produce 6-bromo-1-(4-fluorobenzyl)-2-oxo-N-(spiro[3.3]heptan-2-yl)-1,2-dihydro-1,8-naphthyridine-3-carboxamide (10.9 mg) as a light yellow solid.

$^1$H NMR (400 MHz, $CDCl_3$) δ=9.72 (br d, J=7.1 Hz, 1H), 8.80 (s, 1H), 8.73 (d, J=2.4 Hz, 1H), 8.20 (d, J=2.2 Hz, 1H), 7.45 (dd, J=5.5, 8.4 Hz, 2H), 6.98 (t, J=8.6 Hz, 2H), 5.73 (s, 2H), 4.51-4.37 (m, 1H), 2.57-2.46 (m, 2H), 2.09 (t, J=7.3 Hz, 2H), 2.04-1.94 (m, 4H), 1.90-1.81 (m, 2H). LCMS for product (ESI+): m/z 469.9, 471.9 [M+H]$^+$, Rt: 3.235 min. LCMS Method The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 82—Synthesis of N-(bicyclo[1.1.1]pentan-1-yl)-6-bromo-1-(4-fluorobenzyl)-2-oxo-1,2-dihydro-1,8-naphthyridine-3-carboxamide (Compound 82)

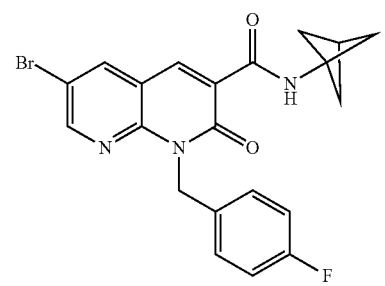 [SMILES: O=C(NC12CC(C1)C2)c1cc2cc(Br)cnc2n(Cc2ccc(F)cc2)c1=O]

Preparation of N-(bicyclo[1.1.1]pentan-1-yl)-6-bromo-1-(4-fluorobenzyl)-2-oxo-1,2-dihydro-1,8-naphthyridine-3-carboxamide

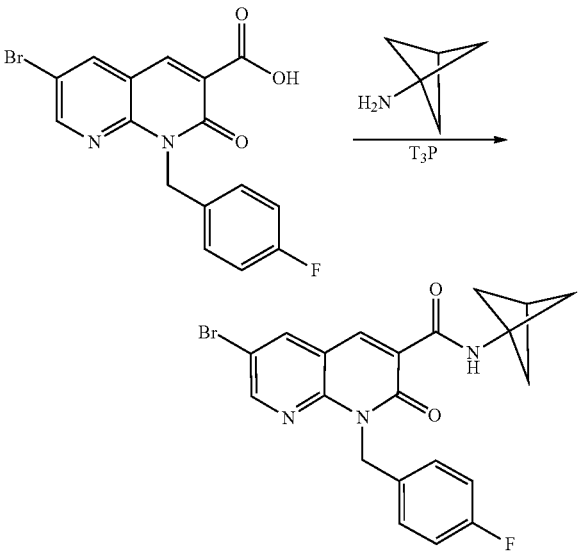

To a solution of 6-bromo-1-[(4-fluorophenyl)methyl]-2-oxo-1,8-naphthyridine-3-carboxylic acid (40 mg, 106.05 μmol, 1 eq) in DMF (1 mL) was added bicyclo[1.1.1]pentan-3-amine (15.22 mg, 127.27 μmol, 1.2 eq, HCl), DIEA (82.24 mg, 636.33 μmol, 110.83 μL, 6 eq) and T3P (134.98 mg, 212.11 μmol, 126.15 μL, 50% purity, 2 eq).

The mixture was stirred at 20° C. for 1 h. LCMS showed complete consumption of the starting material and formation of a new peak. The resulting solid was collected by filtration, triturated 1 methanol (1 mL) and filtered to produce N-(bicyclo[1.1.1]pentan-1-yl)-6-bromo-1-(4-fluorobenzyl)-2-oxo-1,2-dihydro-1,8-naphthyridine-3-carboxamide (14.6 mg, 33.01 μmol) as a white solid.

$^1$H NMR (400 MHz, DMSO-$d_6$) δ=9.81 (s, 1H), 8.89-8.82 (m, 3H), 7.33 (dd, J=5.7, 8.6 Hz, 2H), 7.10 (t, J=8.9 Hz, 2H), 5.63 (s, 2H), 2.55-2.53 (m, 1H), 2.11 (s, 6H). LCMS for product (ESI+): m/z 442.1, 444.1 [M+H]$^+$, Rt: 3.510 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Example 83—Synthesis of N-(bicyclo[1.1.1]pentan-1-yl)-6-cyclopropyl-1-(4-fluorobenzyl)-2-oxo-1,2-dihydro-1,8-naphthyridine-3-carboxamide (Compound 83)

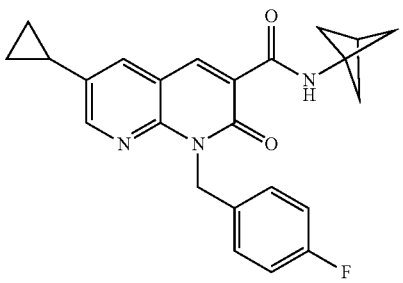 [SMILES: O=C(NC12CC(C1)C2)c1cc2cc(C3CC3)cnc2n(Cc2ccc(F)cc2)c1=O]

Preparation of N-(bicyclo[1.1.1]pentan-1-yl)-6-cyclopropyl-1-(4-fluorobenzyl)-2-oxo-1,2-dihydro-1,8-naphthyridine-3-carboxamide

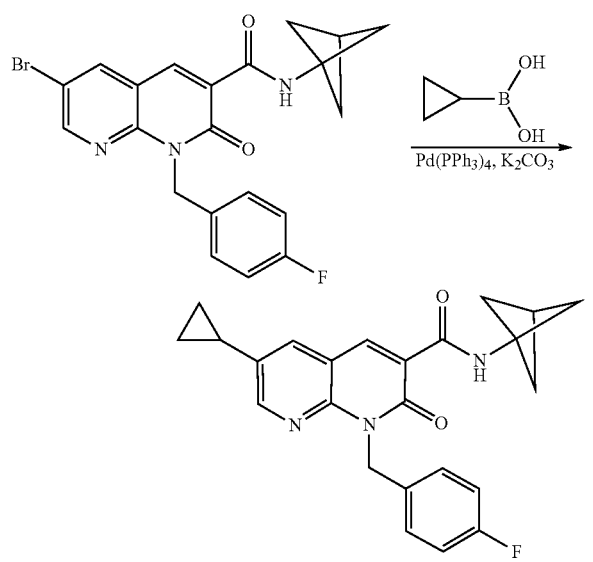

A mixture of N-(3-bicyclo[1.1.1]pentanyl)-6-bromo-1-[(4-fluorophenyl)methyl]-2-oxo-1,8-naphthyridine-3-carboxamide (50 mg, 113.05 μmol, 1 eq), cyclopropylboronic acid (11.65 mg, 135.66 μmol, 1.2 eq), K$_2$CO$_3$ (46.87 mg, 339.15 μmol, 3 eq), Pd(PPh$_3$)$_4$ (13.06 mg, 11.31 μmol, 0.1 eq) in dioxane (0.4 mL) and water (0.1 mL) was degassed and purged with N$_2$ for 3 times, and then the mixture was stirred at 100° C. for 2 h under N$_2$. LCMS showed complete consumption of the starting material and formation of a new peak.

The mixture was concentrated and the residue was purified by prep-HPLC (column: Phenomenex Luna 80*30 mm*3 μm; mobile phase: [water (10 mM NH$_4$HCO$_3$)-ACN]; B %: 50%-80%, 7 min) to produce N-(bicyclo[1.1.1]pentan-1-yl)-6-cyclopropyl-1-(4-fluorobenzyl)-2-oxo-1,2-dihydro-1,8-naphthyridine-3-carboxamide (7.5 mg, 18.59 μmol) as a yellow solid.

$^1$H NMR (400 MHz, MeOD-d$_4$) δ=8.78 (s, 1H), 8.63 (d, J=2.4 Hz, 1H), 7.95 (d, J=2.4 Hz, 1H), 7.44 (dd, J=5.5, 8.6 Hz, 2H), 6.98 (t, J=8.8 Hz, 2H), 5.76 (s, 2H), 2.50 (s, 1H), 2.20 (s, 6H), 2.13-2.02 (m, 1H), 1.15-1.05 (m, 2H), 0.88-0.79 (m, 2H). LCMS for product (ESI+): m/z 404.2 [M+H]$^+$, Rt: 3.603 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 m/min (0.01-4.30 min).

Example 84—Synthesis of N-(bicyclo[1.1.1]pentan-1-yl)-1-(4-fluorobenzyl)-6-isopropyl-2-oxo-1,2-dihydro-1,8-naphthyridine-3-carboxamide (Compound 84)

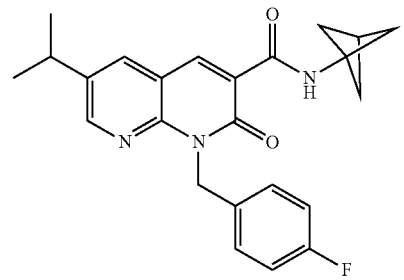 [SMILES: CC(C)c1cnc2c(c1)cc(C(=O)NC13CC(C1)C3)c(=O)n2Cc1ccc(F)cc1]

Preparation of N-(bicyclo[1.1.1]pentan-1-yl)-1-(4-fluorobenzyl)-6-isopropyl-2-oxo-1,2-dihydro-1,8-naphthyridine-3-carboxamide

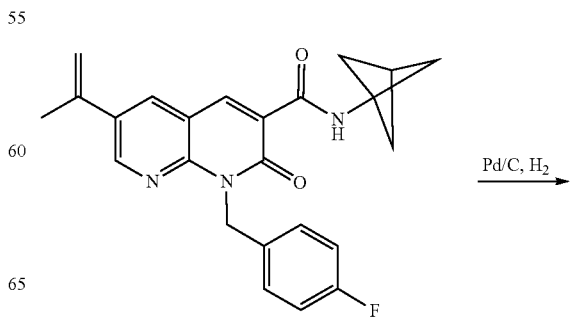

-continued

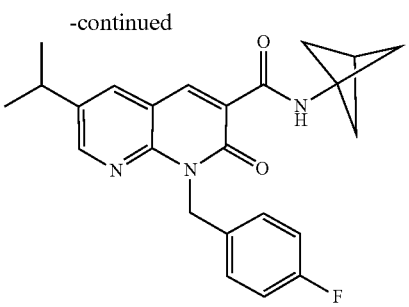

To a solution of N-(3-bicyclo[1.1.1]pentanyl)-1-[(4-fluorophenyl)methyl]-6-isopropenyl-2-oxo-1,8-naphthyridine-3-carboxamide (70 mg, 173.50 μmol, 1 eq) in ethyl acetate (5 mL) was added Pd/C (6.44 mg, 5.46 μmol, 10% purity, 3.15e-2 eq). The mixture was stirred under $H_2$ (15 Psi) at 25° C. for 3 h. LCMS showed complete consumption of the starting material and formation of a new peak.

The mixture was filtered, and the filtrate was concentrated under reduced pressure. The residue was purified by prep-HPLC (column: Waters Xbridge BEH C18 100*25 mm*5 μm; mobile phase: [water (10 mM $NH_4HCO_3$)-ACN]; B %: 40%-70%, 10 min) to produce N-(bicyclo[1.1.1]pentan-1-yl)-1-(4-fluorobenzyl)-6-isopropyl-2-oxo-1,2-dihydro-1,8-naphthyridine-3-carboxamide (25.4 mg, 62.64 μmol) as a white solid.

$^1$H NMR (400 MHz, MeOD-$d_4$) δ=8.83 (s, 1H), 8.69 (d, J=2.4 Hz, 1H), 8.20 (d, J=2.4 Hz, 1H), 7.54-7.39 (m, 2H), 6.98 (t, J=8.8 Hz, 2H), 5.77 (s, 2H), 3.11 (td, J=6.9, 13.9 Hz, 1H), 2.50 (s, 1H), 2.20 (s, 6H), 1.35 (d, J=7.0 Hz, 6H). LCMS for product (ESI+): m/z 406.3 [M+H]$^+$, Rt: 3.659 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Example 85—Synthesis of (R)—N-(1-(4-cyanophenyl)ethyl)-1-(4-fluorobenzyl)-6-isopropyl-2-oxo-1,2-dihydro-1,8-naphthyridine-3-carboxamide (Compound 85)

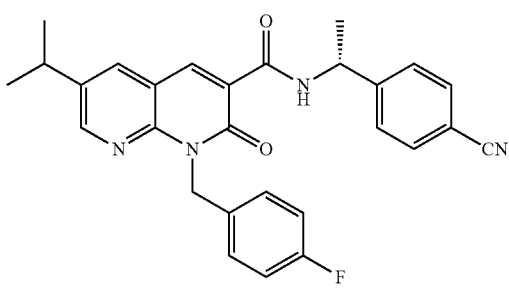 [SMILES: CC(C)c1cnc2c(c1)cc(C(=O)N[C@H](C)c1ccc(C#N)cc1)c(=O)n2Cc1ccc(F)cc1]

Step 1: Preparation of ethyl 1-(4-fluorobenzyl)-2-oxo-6-(prop-1-en-2-yl)-1,2-dihydro-1,8-naphthyridine-3-carboxylate

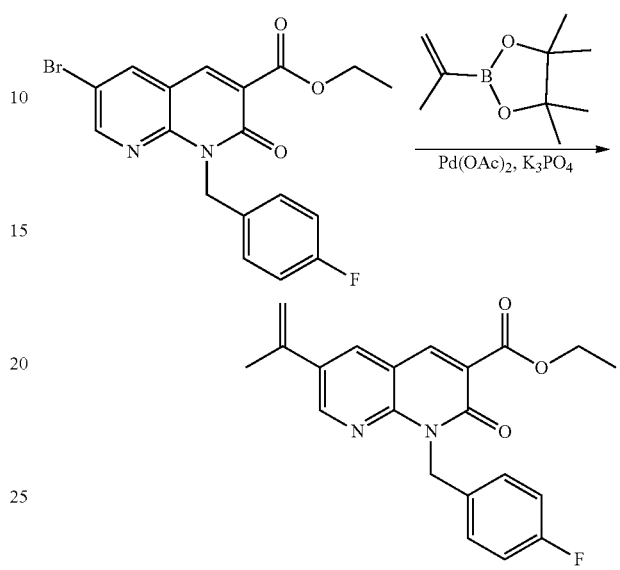

A mixture of 2-isopropenyl-4,4,5,5-tetramethyl-1,3,2-dioxaborolane (311.02 mg, 1.85 mmol, 1.5 eq), ethyl 6-bromo-1-[(4-fluorophenyl)methyl]-2-oxo-1,8-naphthyridine-3-carboxylate (500 mg, 1.23 mmol, 1 eq) tricyclohexylphosphane (34.60 mg, 123.39 μmol, 40.00 μL, 0.1 eq), $K_3PO_4$ (916.72 mg, 4.32 mmol, 3.5 eq) and Pd(OAc)$_2$ (27.70 mg, 123.39 μmol, 0.1 eq) in water (0.5 mL) and toluene (5 mL) was degassed and purged with $N_2$ for 3 times, and then the mixture was stirred at 100° C. for 2 h under $N_2$. LCMS showed complete consumption of the starting material and formation of a new peak.

The mixture was poured into water (100 mL), extracted with ethyl acetate (3×50 mL), the organic layer was washed with brine (30 mL), dried over $Na_2SO_4$ and concentrated. The residue was purified by silica gel column chromatography (Petroleum ether/Ethyl acetate, 50:1 to 1:1) to produce ethyl 1-(4-fluorobenzyl)-2-oxo-6-(prop-1-en-2-yl)-1,2-dihydro-1,8-naphthyridine-3-carboxylate (400 mg, 1.09 mmol) as a yellow solid.

$^1$H NMR (400 MHz, CDCl$_3$) δ=8.85 (d, J=2.3 Hz, 1H), 8.38 (s, 1H), 7.97 (d, J=2.3 Hz, 1H), 7.57 (dd, J=5.6, 8.5 Hz, 2H), 6.94 (t, J=8.7 Hz, 2H), 5.73 (s, 2H), 5.49 (s, 1H), 5.24 (s, 1H), 4.43 (q, J=7.2 Hz, 2H), 2.22 (s, 3H), 1.42 (t, J=7.2 Hz, 3H). LCMS for product (ESI+): m/z 367.2 [M+H]$^+$, Rt: 1.159 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% CF$_3$CO$_2$H in water, mobile phase B was 0.018% CF$_3$CO$_2$H in CH$_3$CN. The column used for the chromatography is a Chromolith Flash RP-18e 25-2 mm column. Detection methods are diode array (DAD) and evaporative light scattering (ELSD) detection as well as positive electrospray ionization (MS).

Step 2: Preparation of 1-(4-fluorobenzyl)-6-isopropyl-2-oxo-1,2-dihydro-1,8-naphthyridine-3-carboxylic acid

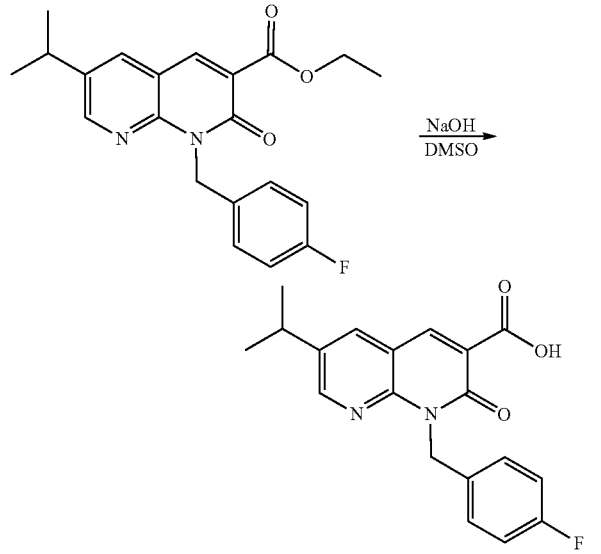

Step 3: Preparation of (R)—N-(1-(4-cyanophenyl)ethyl)-1-(4-fluorobenzyl)-6-isopropyl-2-oxo-1,2-dihydro-1,8-naphthyridine-3-carboxamide

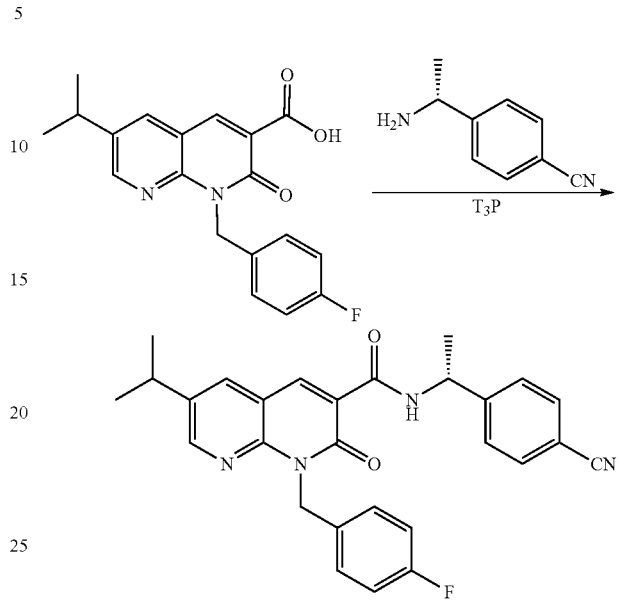

To a solution of ethyl 1-[(4-fluorophenyl)methyl]-6-isopropyl-2-oxo-1,8-naphthyridine-3-carboxylate (200 mg, 542.89 µmol, 1 eq) in DMSO (6 mL) was added NaOH (2 M, 0.8 mL, 3 eq). The mixture was stirred at 25° C. for 2 h. LCMS showed complete consumption of the starting material and formation of a new peak.

The mixture was acidified to pH 5 by dropwise addition of 2 N hydrochloric acid dropwise at 0° C., the mixture was filtered, and the resulting solid was purified by prep-HPLC (column: Phenomenex Gemini-NX C18 75*30 mm*3 µm; mobile phase: [water (10 mM $NH_4HCO_3$)-ACN]; B %: 1%-40%, 12 min) to produce 1-(4-fluorobenzyl)-6-isopropyl-2-oxo-1,2-dihydro-1,8-naphthyridine-3-carboxylic acid (100 mg, 293.82 µmol) as a white solid.

$^1$H NMR (400 MHz, $CDCl_3$) δ=14.33 (s, 1H), 8.90 (s, 1H), 8.75 (d, J=2.3 Hz, 1H), 7.96 (d, J=2.3 Hz, 1H), 7.57 (dd, J=5.5, 8.6 Hz, 2H), 6.99 (t, J=8.7 Hz, 2H), 5.82 (s, 2H), 3.12 (td, J=6.9, 13.9 Hz, 1H), 1.37 (d, J=7.0 Hz, 6H). LCMS for product (ESI+): m/z 341.1 [M+H]$^+$, Rt: 1.046 min.
LCMS Method The gradient was 5-95% B in 1.0 min, 95-100% B in 0.8 min, 100-5% B in 0.01 min, and then held at 5% B for 0.24 min (1.0 m/min flow rate). Mobile phase A was 10 mM $NH_4HCO_3$ in water, mobile phase B was $CH_3CN$. The column used for the chromatography was Xbridge Shield RP18 2.1*50 mm, 5 µm column. Detection methods are diode array (DAD) and positive electrospray ionization (MS).

To a solution of 1-[(4-fluorophenyl)methyl]-6-isopropyl-2-oxo-1,8-naphthyridine-3-carboxylic acid (50 mg, 146.91 µmol, 1 eq) in DMF (0.5 mL) was added DIEA (56.96 mg, 440.73 µmol, 76.76 µL, 3 eq) and 4-[(1R)-1-aminoethyl]benzonitrile (32.20 mg, 176.29 µmol, 1.2 eq, HCl) at 0° C. T3P (186.97 mg, 293.82 µmol, 174.74 µL, 50% purity, 2 eq) was added into the mixture at 0° C. The mixture was stirred at 25° C. for 2 h. LCMS showed complete consumption of the starting material and formation of a new peak.

The mixture was filtered and the filtrate was purified by prep-HPLC (column: Waters Xbridge Prep OBD C18 150*40 mm*10 µm; mobile phase: [water (10 mM $NH_4HCO_3$)-ACN]; B %: 55%-85%, 8 min) to produce (R)—N-(1-(4-cyanophenyl)ethyl)-1-(4-fluorobenzyl)-6-isopropyl-2-oxo-1,2-dihydro-1,8-naphthyridine-3-carboxamide (26.0 mg, 55.49 µmol) as a white solid.

$^1$H NMR (400 MHz, $CDCl_3$) δ=10.25 (br d, J=7.1 Hz, 1H), 8.84 (s, 1H), 8.64 (d, J=2.3 Hz, 1H), 7.88 (d, J=2.3 Hz, 1H), 7.64 (d, J=8.3 Hz, 2H), 7.55-7.44 (m, 4H), 6.99 (t, J=8.7 Hz, 2H), 5.87-5.71 (m, 2H), 5.32 (t, J=7.1 Hz, 1H), 3.08 (td, J=6.9, 13.9 Hz, 1H), 1.62 (d, J=7.0 Hz, 3H), 1.35 (d, J=6.9 Hz, 6H). LCMS for product (ESI+): m/z 469.3 [M+H]$^+$, Rt: 3.447 min.
LCMS Method The column used for chromatography was Xbridge Shield RP18 2.1*50 mm, (5 µm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Example 86—Synthesis of N-(1-(4-cyanophenyl)cyclopropyl)-1-(4-fluorobenzyl)-6-isopropyl-2-oxo-1,2-dihydro-1,8-naphthyridine-3-carboxamide (Compound 86)

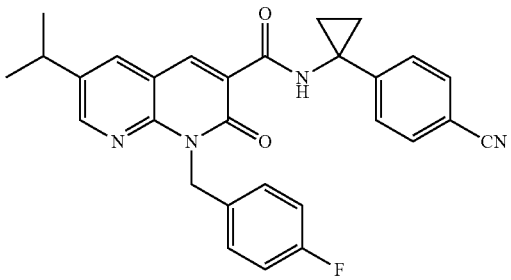 [SMILES: CC(C)c1cnc2c(c1)cc(C(=O)NC1(c3ccc(C#N)cc3)CC1)c(=O)n2Cc1ccc(F)cc1]

Preparation of N-(1-(4-cyanophenyl)cyclopropyl)-1-(4-fluorobenzyl)-6-isopropyl-2-oxo-1,2-dihydro-1,8-naphthyridine-3-carboxamide

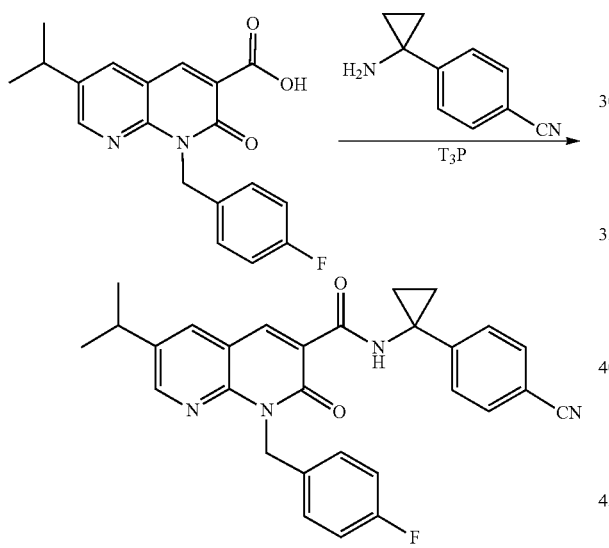

To a solution of 1-[(4-fluorophenyl)methyl]-6-isopropyl-2-oxo-1,8-naphthyridine-3-carboxylic acid (50 mg, 146.91 μmol, 1 eq) in DMF (0.5 mL) was added DIEA (56.96 mg, 440.73 μmol, 76.76 μL, 3 eq) and 4-(1-aminocyclopropyl)benzonitrile (34.32 mg, 176.29 μmol, 1.2 eq, HCl) at 0° C. T3P (186.97 mg, 293.82 μmol, 174.74 μL, 50% purity, 2 eq) was added into the mixture at 0° C. The mixture was stirred at 25° C. for 2 h. LCMS showed complete consumption of the starting material and formation of a new peak.

The mixture was filtered and the filtrate was purified by prep-HPLC (column: Waters Xbridge Prep OBD C18 150*40 mm*10 μm; mobile phase: [water (10 mM NH$_4$HCO$_3$)-ACN]; B %: 50%-70%, 8 min) to produce N-(1-(4-cyanophenyl)cyclopropyl)-1-(4-fluorobenzyl)-6-isopropyl-2-oxo-1,2-dihydro-1,8-naphthyridine-3-carboxamide (33.0 mg, 68.67 μmol) as a white solid.

$^1$H NMR (400 MHz, CDCl$_3$) δ=10.40 (s, 1H), 8.87 (s, 1H), 8.66 (d, J=2.3 Hz, 1H), 7.90 (d, J=2.3 Hz, 1H), 7.57 (d, J=8.5 Hz, 2H), 7.49 (dd, J=5.5, 8.6 Hz, 2H), 7.35 (d, J=8.5 Hz, 2H), 6.99 (t, J=8.7 Hz, 2H), 5.79 (s, 2H), 3.09 (td, J=6.9, 13.9 Hz, 1H), 1.53-1.47 (m, 2H), 1.46-1.40 (m, 2H), 1.36 (d, J=7.0 Hz, 6H). LCMS for product (ESI+): m/z 481.3 [M+H]$^+$, Rt: 3.458 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Example 87—Synthesis of (R)-6-bromo-1-(4-fluorobenzyl)-N-(1-(4-fluorophenyl)ethyl)-2-oxo-1,2-dihydro-1,8-naphthyridine-3-carboxamide (Compound 87)

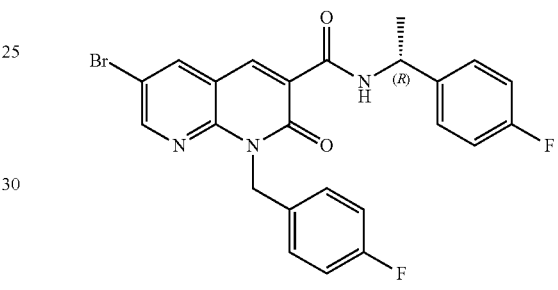

Preparation of (R)-6-bromo-1-(4-fluorobenzyl)-N-(1-(4-fluorophenyl)ethyl)-2-oxo-1,2-dihydro-1,8-naphthyridine-3-carboxamide

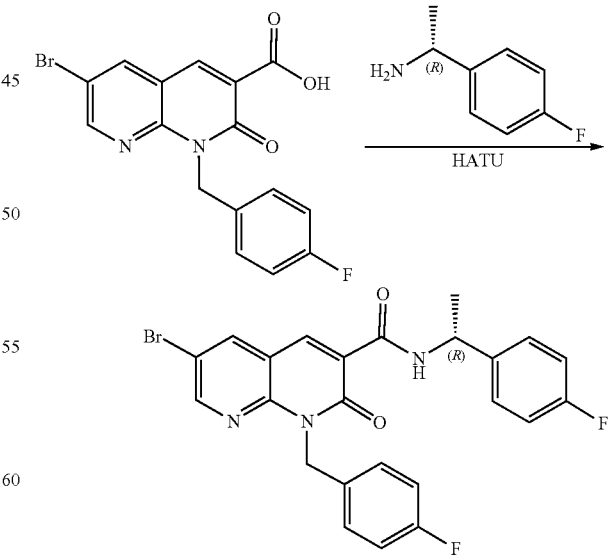

To a solution of 6-bromo-1-[(4-fluorophenyl)methyl]-2-oxo-1,8-naphthyridine-3-carboxylic acid (80 mg, 212.11 umol, 1 eq) in DMF (1 mL) was added HATU (161.30 mg, 424.22 µmol, 2 eq), DIEA (82.24 mg, 636.33 µmol, 110.84 µL, 3 eq) at 20° C., the mixture was stirred at 20° C. for 0.5 h. Added (1R)-1-(4-fluorophenyl)ethanamine (29.52 mg, 212.11 µmol, 1 eq) at 20° C., the mixture was stirred at 20° C. for 0.5 h. LCMS showed complete consumption of the starting material and formation of a new peak.

The mixture was filtered and the filtrate was purified by prep-HPLC (column: Waters X bridge BEH C18 100*25 mm*5 µm; mobile phase: [water (10 mM NH$_4$HCO$_3$)-ACN]; B %: 50%-80%, 8 min) to produce (R)-6-bromo-1-(4-fluorobenzyl)-N-(1-(4-fluorophenyl)ethyl)-2-oxo-1,2-dihydro-1,8-naphthyridine-3-carboxamide (18.7 mg, 37.53 µmol) as a light yellow solid.

$^1$H NMR (400 MHz, CDCl$_3$) δ=10.02 (br d, J=7.1 Hz, 1H), 8.80 (s, 1H), 8.74 (d, J=2.2 Hz, 1H), 8.18 (d, J=2.2 Hz, 1H), 7.51-7.42 (m, 2H), 7.42-7.35 (m, 2H), 7.10-6.93 (m, 4H), 5.73 (d, J=2.9 Hz, 2H), 5.37-5.23 (m, 1H), 1.61 (d, J=6.8 Hz, 3H). LCMS for product (ESI+): m/z 497.9, 499.9 [M+H]$^+$, Rt: 3.094 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 88—Synthesis of (R)-1-(4-fluorobenzyl)-N-(1-(4-fluorophenyl)ethyl)-2-oxo-6-(prop-1-en-2-yl)-1,2-dihydro-1,8-naphthyridine-3-carboxamide (Compound 88)

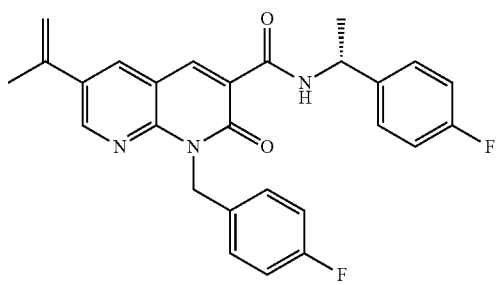

Preparation of (R)-1-(4-fluorobenzyl)-N-(1-(4-fluorophenyl)ethyl)-2-oxo-6-(prop-1-en-2-yl)-1,2-dihydro-1,8-naphthyridine-3-carboxamide

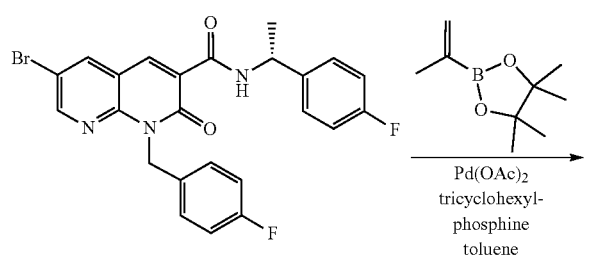

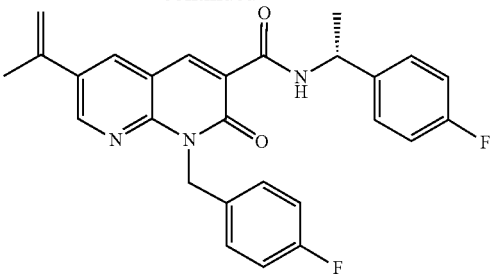

To a solution of 2-isopropenyl-4,4,5,5-tetramethyl-1,3,2-dioxaborolane (35.41 mg, 210.71 µmol, 1.5 eq), 6-bromo-N-[(1R)-1-(4-fluorophenyl)ethyl]-1-[(4-fluorophenyl)methyl]-2-oxo-1,8-naphthyridine-3-carboxamide (70 mg, 140.47 µmol, 1 eq) in toluene (2 mL) and water (0.2 mL) was added K$_3$PO$_4$ (104.36 mg, 491.65 µmol, 3.5 eq), tricyclohexylphosphane (3.94 mg, 14.05 µmol, 4.55 µL, 0.1 eq) at 20° C. Pd(OAc)$_2$ (3.15 mg, 14.05 µmol, 0.1 eq) was added into the mixture under N$_2$, the mixture was stirred at 110° C. for 1 h. The mixture was stirred at 25° C. for 2 h. LCMS showed complete consumption of the starting material and formation of a new peak.

The mixture was concentrated and the residue was purified by prep-HPLC (column: Waters Xbridge BEH C18 100*25 mm*5 µm; mobile phase: [water (10 mM NH$_4$HCO$_3$)-ACN]; B %: 65%-90%, 10 min) to produce (R)-1-(4-fluorobenzyl)-N-(1-(4-fluorophenyl)ethyl)-2-oxo-6-(prop-1-en-2-yl)-1,2-dihydro-1,8-naphthyridine-3-carboxamide (14.1 mg, 29.58 µmol) as a white solid.

$^1$H NMR (400 MHz, CDCl$_3$) δ=10.10 (br d, J=7.8 Hz, 1H), 8.89 (s, 1H), 8.87 (d, J=2.5 Hz, 1H), 8.05 (d, J=2.5 Hz, 1H), 7.53-7.44 (m, 2H), 7.43-7.36 (m, 2H), 7.08-6.94 (m, 4H), 5.78 (d, J=4.5 Hz, 2H), 5.50 (s, 1H), 5.31 (t, J=7.1 Hz, 1H), 5.26 (s, 1H), 2.23 (s, 3H), 1.61 (d, J=7.0 Hz, 3H). LCMS for product (ESI+): m/z 460.2 [M+H]+, Rt: 3.130 min.

LCMS Method

The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization.

Example 89—Synthesis of (R)-1-(4-fluorobenzyl)-N-(1-(4-fluorophenyl)ethyl)-6-isopropyl-2-oxo-1,2-dihydro-1,8-naphthyridine-3-carboxamide (Compound 89)

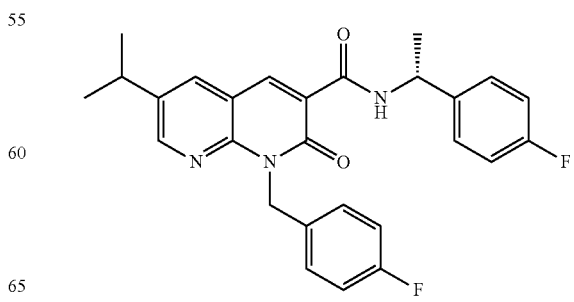

353
Preparation of (R)-1-(4-fluorobenzyl)-N-(1-(4-fluorophenyl)ethyl)-6-isopropyl-2-oxo-1,2-dihydro-1,8-naphthyridine-3-carboxamide

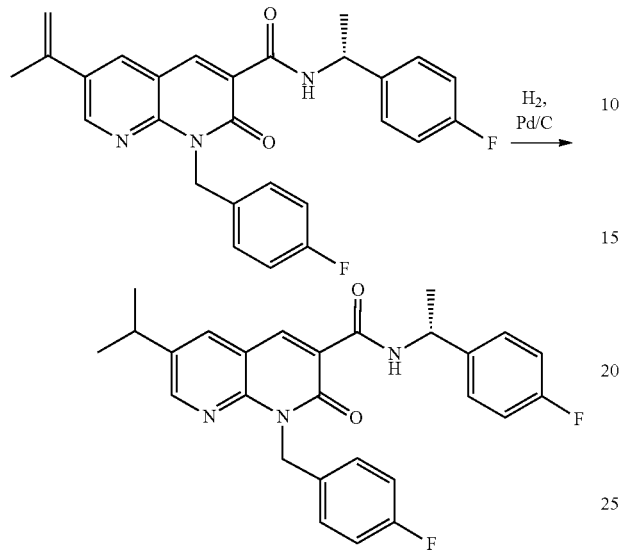

To a mixture of N-[(1R)-1-(4-fluorophenyl)ethyl]-1-[(4-fluorophenyl)methyl]-6-isopropenyl-2-oxo-1,8-naphthyridine-3-carboxamide (50 mg, 108.82 μmol, 1 eq), Pd/C (13.06 mg, 108.82 μmol, 10% purity, 1 eq) in EtOH (5 mL) was stirred at 20° C. for 1 h under $H_2$ (15 psi). The mixture was stirred at 25° C. for 2 h. LCMS showed complete consumption of the starting material and formation of a new peak.

The product was filtered. The filtrate was purified by prep-HPLC (column: Waters Xbridge BEH C18 100*25 mm*5 μm; mobile phase: [water (10 mM $NH_4HCO_3$)-ACN]; B %: 65%-90%, 10 min) to produce (R)-1-(4-fluorobenzyl)-N-(1-(4-fluorophenyl)ethyl)-6-isopropyl-2-oxo-1,2-dihydro-1,8-naphthyridine-3-carboxamide (7 mg, 14.26 μmol) as a white solid.

$^1$H NMR (400 MHz, $CDCl_3$) δ=10.15 (br d, J=7.4 Hz, 1H), 8.86 (s, 1H), 8.62 (d, J=2.3 Hz, 1H), 7.88 (d, J=2.1 Hz, 1H), 7.47 (dd, J=5.5, 8.4 Hz, 2H), 7.39 (dd, J=5.4, 8.4 Hz, 2H), 7.10-6.92 (m, 4H), 5.89-5.70 (m, 2H), 5.31 (quin, J=7.1 Hz, 1H), 3.07 (td, J=6.9, 13.8 Hz, 1H), 1.61 (s, 3H), 1.35 (d, J=7.0 Hz, 6H). LCMS for product (ESI+): m/z 462.2 [M+H]+, Rt: 3.146 min.

LCMS Method

The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization.

354
Example 90—Synthesis of (S)-6-bromo-1-(4-fluorobenzyl)-N-(1-(4-fluorophenyl)ethyl)-2-oxo-1,2-dihydro-1,8-naphthyridine-3-carboxamide (Compound 90)

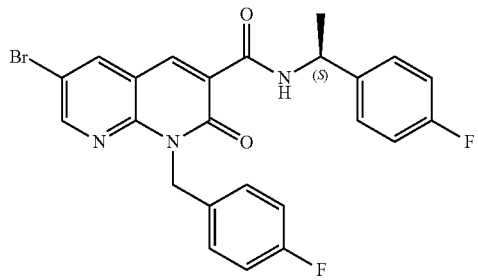

Preparation of (S)-6-bromo-1-(4-fluorobenzyl)-N-(1-(4-fluorophenyl)ethyl)-2-oxo-1,2-dihydro-1,8-naphthyridine-3-carboxamide

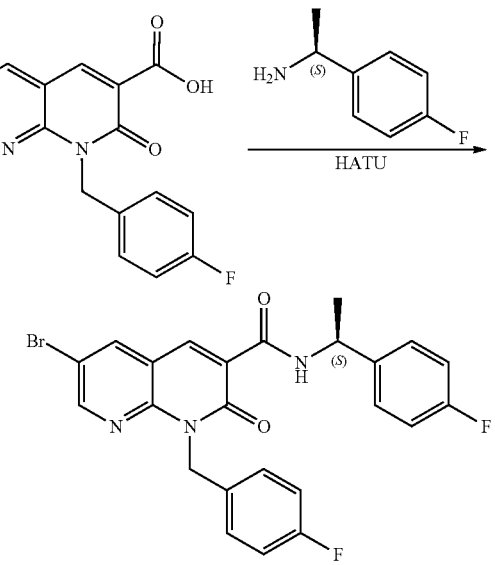

To a solution of 6-bromo-1-[(4-fluorophenyl)methyl]-2-oxo-1,8-naphthyridine-3-carboxylic acid in DMF (1 mL) was added HATU (161.30 mg, 424.22 μmol, 2 eq), DIEA (82.24 mg, 636.33 μmol, 110.84 μL, 3 eq) at 20° C., the mixture was stirred at 20° C. for 0.5 h. Added (1S)-1-(4-fluorophenyl)ethanamine (29.52 mg, 212.11 μmol, 1 eq) at 20° C., the mixture was stirred at 20° C. for 0.5 h. LCMS showed complete consumption of the starting material and formation of a new peak with desired mass. The mixture was filtered and the filtrate was purified by prep-HPLC (column: Waters X bridge BEH C18 100*25 mm*5 μm; mobile phase: [water (10 mM $NH_4HCO_3$)-ACN]; B %: 50%-80%, 8 min) to produce (S)-6-bromo-1-(4-fluorobenzyl)-N-(1-(4-fluorophenyl)ethyl)-2-oxo-1,2-dihydro-1,8-naphthyridine-3-carboxamide (21.4 mg, 42.94 μmol) was obtained as a light yellow solid.

$^1$H NMR (400 MHz, $CDCl_3$) δ=10.13-9.95 (m, 1H), 8.80 (s, 1H), 8.74 (d, J=2.4 Hz, 1H), 8.18 (d, J=2.4 Hz, 1H), 7.46

(dd, J=5.5, 8.6 Hz, 2H), 7.41-7.35 (m, 2H), 7.12-6.93 (m, 4H), 5.73 (d, J=2.6 Hz, 2H), 5.37-5.24 (m, 1H), 1.61 (d, J=6.8 Hz, 3H). LCMS for product (ESI+): m/z 497.9, 499.9 [M+H]+, Rt: 3.092 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 91—Synthesis of (R)-6-bromo-N-(1-(4-cyanophenyl)ethyl)-1-(4-fluorobenzyl)-2-oxo-1,2-dihydro-1,8-naphthyridine-3-carboxamide (Compound 91)

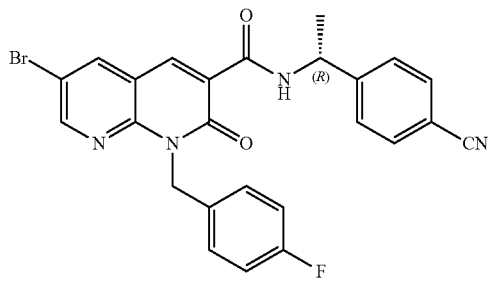

Preparation of (R)-6-bromo-N-(1-(4-cyanophenyl) ethyl)-1-(4-fluorobenzyl)-2-oxo-1,2-dihydro-1,8-naphthyridine-3-carboxamide

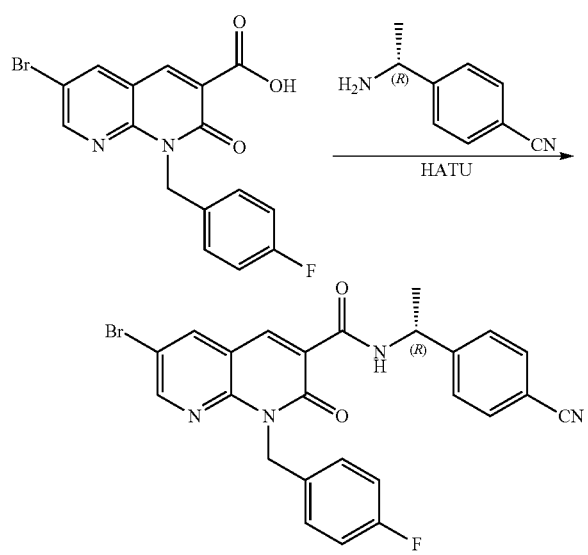

A mixture of 6-bromo-1-[(4-fluorophenyl)methyl]-2-oxo-1,8-naphthyridine-3-carboxylic acid (90 mg, 238.62 μmol, 1 eq), HATU (181.46 mg, 477.25 μmol, 2 eq) and DIEA (92.52 mg, 715.87 μmol, 124.69 μL, 3 eq) in DMF (1 mL) was stirred at 25° C. for 0.5 h, to the mixture was added 4-[(1R)-1-aminoethyl]benzonitrile (34.88 mg, 238.62 μmol, 1 eq), the mixture was stirred at 25° C. for 0.5 h. LCMS showed complete consumption of the starting material and formation of a new peak with desired mass.

The mixture was filtered, and the filtrate was purified by prep-HPLC (HCl condition) to produce (R)-6-bromo-N-(1-(4-cyanophenyl)ethyl)-1-(4-fluorobenzyl)-2-oxo-1,2-dihydro-1,8-naphthyridine-3-carboxamide (14 mg, 27.70 μmol) as a white solid.

$^1$H NMR (400 MHz, DMSO-d6) δ=9.90-9.88 (m, 1H), 8.88-8.82 (m, 3H), 7.82-7.80 (d, J=8.4 Hz, 2H), 7.60-7.58 (d, J=8.4 Hz, 2H), 7.35-7.31 (m, 2H), 7.13-7.09 (m, 2H), 5.69-5.61 (m, 2H), 5.22-5.14 (m, 1H), 1.51-1.50 (d, J=6.8 Hz, 3H). LCMS for product (ESI+): m/z 504.9, 506.9 [M+H]+, Rt: 2.972 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH4HCO3, mobile phase B was Acetonitrile. The column used for chromatography was a Xbridge Shield RP18 2.1*50 mm column (5 um particles). Detection methods are diode array (DAD) as well as positive electrospray ionization.

Example 92—Synthesis of 6-bromo-N-(1-(4-cyanophenyl)cyclopropyl)-1-(4-fluorobenzyl)-2-oxo-1,2-dihydro-1,8-naphthyridine-3-carboxamide (Compound 92)

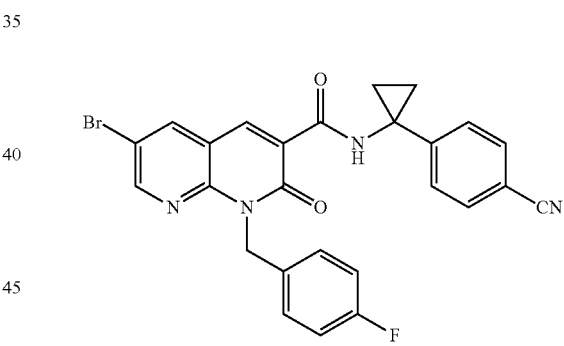

Preparation of 6-bromo-N-(1-(4-cyanophenyl)cyclopropyl)-1-(4-fluorobenzyl)-2-oxo-1,2-dihydro-1,8-naphthyridine-3-carboxamide

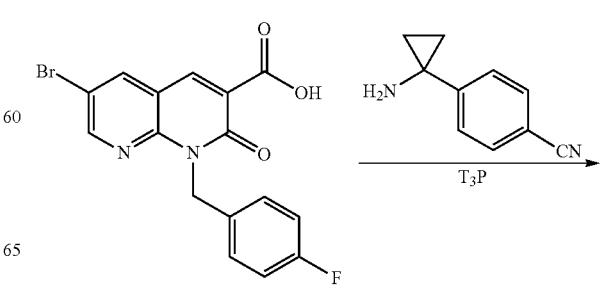

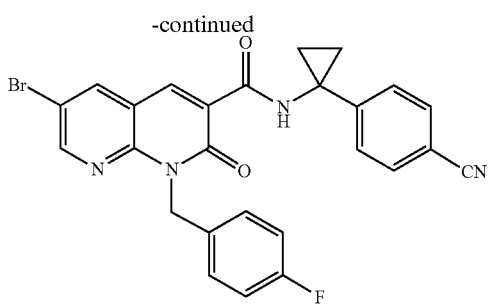

To a mixture of 6-bromo-1-[(4-fluorophenyl)methyl]-2-oxo-1,8-naphthyridine-3-carboxylic acid (50 mg, 132.57 μmol, 1 eq) in DMF (1 mL) was added DIEA (102.80 mg, 795.41 μmol, 138.55 μL, 6 eq), 4-(1-aminocyclopropyl)benzonitrile (51.61 mg, 265.14 μmol, 2 eq, HCl) and T3P (168.72 mg, 265.14 μmol, 157.68 μL, 50% purity, 2 eq), the mixture was stirred at 25° C. for 1 h. LCMS showed complete consumption of the starting material and formation of a new peak with desired mass.

The mixture was poured into water (10 mL) and the solid was collected by filtration and air-dried. The mixture was purified by prep-HPLC (neutral condition) to produce 6-bromo-N-(1-(4-cyanophenyl)cyclopropyl)-1-(4-fluorobenzyl)-2-oxo-1,2-dihydro-1,8-naphthyridine-3-carboxamide (24 mg, 45.42 μmol) was obtained as a white solid.

$^1$H NMR (400 MHz, DMSO-d$_6$) δ=9.99 (s, 1H), 8.88 (s, 1H), 8.82 (br s, 2H), 7.73 (br d, J=8.1 Hz, 2H), 7.39-7.34 (m, 4H), 7.11 (br t, J=8.8 Hz, 2H), 5.65 (s, 2H), 1.41 (br d, J=7.6 Hz, 4H). LCMS for product (ESI+): m/z 517.1, 519.1 [M+H]$^+$, Rt: 3.403 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 μm particles). Detection methods are diode array (DAD) and evaporative light scattering (ELSD) detection as well as positive electrospray ionization.

Example 93—Synthesis of 6-cyclopropyl-1-(4-fluorobenzyl)-2-oxo-N-(spiro[3.3]heptan-2-yl)-1,2-dihydro-1,8-naphthyridine-3-carboxamide (Compound 93)

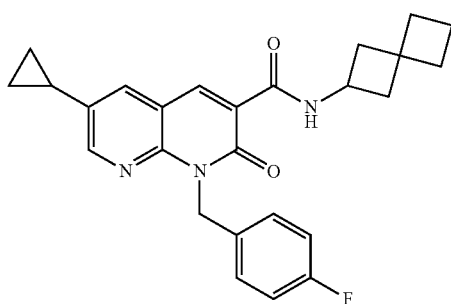

Preparation of 6-cyclopropyl-1-(4-fluorobenzyl)-2-oxo-N-(spiro[3.3]heptan-2-yl)-1,2-dihydro-1,8-naphthyridine-3-carboxamide

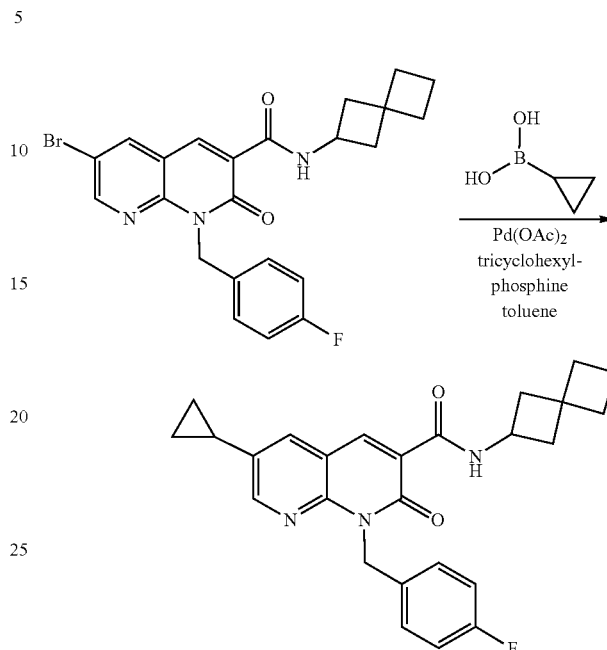

To a solution of 6-bromo-1-[(4-fluorophenyl)methyl]-2-oxo-N-spiro[3.3]heptan-2-yl-1,8-naphthyridine-3-carboxamide (100 mg, 212.62 μmol, 1 eq), cyclopropylboronic acid (23.74 mg, 276.40 μmol, 1.3 eq) in toluene (2 mL), H$_2$O (0.15 mL) was added K$_3$PO$_4$ (157.96 mg, 744.15 μmol, 3.5 eq) and tricyclohexylphosphane (5.96 mg, 21.26 μmol, 6.89 μL, 0.1 eq) at 20° C. Added Pd(OAc)$_2$ (4.77 mg, 21.26 μmol, 0.1 eq) under N$_2$, the mixture was stirred at 100° C. for 1 h. LCMS showed complete consumption of the starting material and formation of a new peak with desired mass.

The mixture was concentrated and the residue was purified by prep-HPLC (column: Waters Xbridge BEH C18 100*25 mm*5 μm; mobile phase: [water (10 mM NH$_4$HCO$_3$)-ACN]; B %: 50%-80%, 10 min) to produce 6-cyclopropyl-1-(4-fluorobenzyl)-2-oxo-N-(spiro[3.3]heptan-2-yl)-1,2-dihydro-1,8-naphthyridine-3-carboxamide (25.6 mg, 59.09 μmol) as a white solid. $^1$H NMR (400 MHz, CDCl$_3$) δ=9.82 (br d, J=7.4 Hz, 1H), 8.82 (s, 1H), 8.54 (d, J=2.3 Hz, 1H), 7.68 (d, J=2.4 Hz, 1H), 7.45 (dd, J=5.4, 8.6 Hz, 2H), 7.03-6.86 (m, 2H), 5.76 (s, 2H), 4.45 (sxt, J=8.0 Hz, 1H), 2.51 (ddd, J=2.9, 7.6, 9.2 Hz, 2H), 2.09 (t, J=7.2 Hz, 2H), 2.04-1.94 (m, 5H), 1.90-1.80 (m, 2H), 1.14-1.05 (m, 2H), 0.83-0.75 (m, 2H). LCMS for product (ESI+): m/z 432.2 [M+H]+, Rt: 3.211 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 94—Synthesis of (R)-6-cyclopropyl-1-(4-fluorobenzyl)-N-(1-(4-fluorophenyl)ethyl)-2-oxo-1,2-dihydro-1,8-naphthyridine-3-carboxamide (Compound 94)

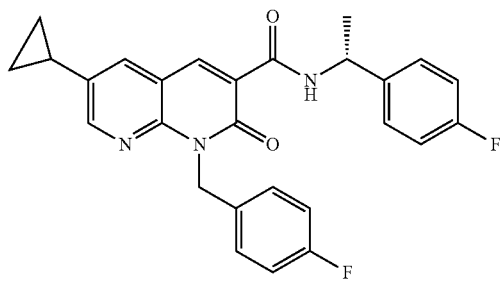 [SMILES: C[C@@H](NC(=O)c1cc2cc(C3CC3)cnc2n(Cc2ccc(F)cc2)c1=O)c1ccc(F)cc1]

Step 1: Preparation of ethyl 6-cyclopropyl-1-(4-fluorobenzyl)-2-oxo-1,2-dihydro-1,8-naphthyridine-3-carboxylate

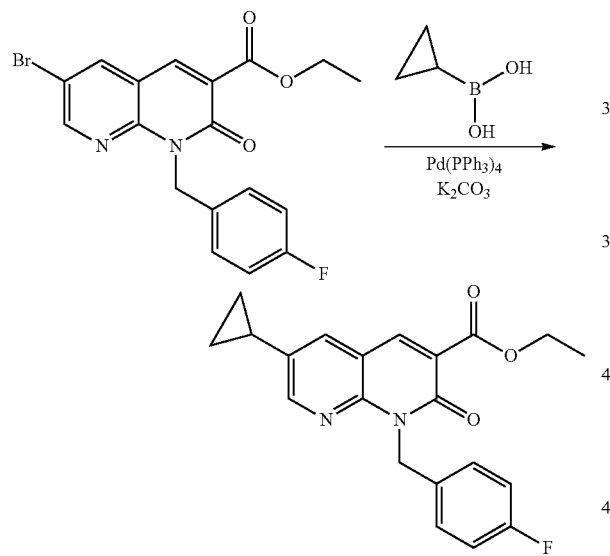

To a mixture of ethyl 6-bromo-1-[(4-fluorophenyl)methyl]-2-oxo-1,8-naphthyridine-3-carboxylate (200 mg, 493.56 μmol, 1 eq), K$_2$CO$_3$ (204.64 mg, 1.48 mmol, 3 eq) and cyclopropylboronic acid (63.59 mg, 740.34 μmol, 1.5 eq) in dioxane (2 mL) and H$_2$O (0.2 mL) was added Pd(PPh$_3$)$_4$ (57.03 mg, 49.36 μmol, 0.1 eq) under N$_2$. The mixture was stirred at 100° C. for 1 h. LCMS showed complete consumption of the starting material and formation of a new peak with desired mass. The reaction mixture was poured into water (20 mL) and extracted with ethyl acetate (3×5 mL).

The combined organic phase was dried with anhydrous Na$_2$SO$_4$, filtered and concentrated in vacuum to produce ethyl 6-cyclopropyl-1-(4-fluorobenzyl)-2-oxo-1,2-dihydro-1,8-naphthyridine-3-carboxylate (170 mg, 463.99 μmol) as a yellow solid (used without further purification).

$^1$H NMR (400 MHz, CDCl$_3$) δ=8.85 (s, 1H), 8.67 (d, J=2.3 Hz, 1H), 7.74 (d, J=2.3 Hz, 1H), 7.55 (br d, J=3.4 Hz, 2H), 7.01-6.96 (m, 2H), 5.81 (s, 2H), 3.72 (s, 2H), 1.30-1.24 (m, 1H), 1.21-1.11 (m, 2H), 0.87-0.79 (m, 2H). LCMS for product (ESI+): m/z 367.2, 339.2 [M+H]$^+$, Rt: 1.128/1.249 min.

LCMS Method

The column used for chromatography was a HALO AQ-C18 2.1*30 mm, (2.7 m particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 mL/min.

Step 2: Preparation of 6-cyclopropyl-1-(4-fluorobenzyl)-2-oxo-1,2-dihydro-1,8-naphthyridine-3-carboxylic acid

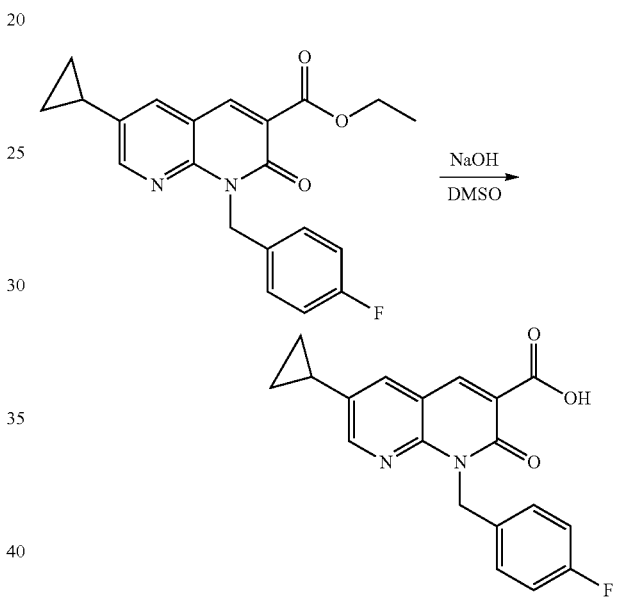

To a mixture of ethyl 6-cyclopropyl-1-[(4-fluorophenyl)methyl]-2-oxo-1,8-naphthyridine-3-carboxylate (170 mg, 463.99 μmol, 1 eq) in DMSO (2 mL) was added NaOH (2 M, 2.32 mL, 10 eq). The mixture was stirred at 50° C. for 2 h. LCMS showed complete consumption of the starting material and formation of a new peak with desired mass. The reaction mixture was poured into water (20 mL) and extracted with ethyl acetate (3×5 mL).

The combined organic phase was dried with anhydrous Na$_2$SO$_4$, filtered and concentrated in vacuum to produce 6-cyclopropyl-1-(4-fluorobenzyl)-2-oxo-1,2-dihydro-1,8-naphthyridine-3-carboxylic acid (150 mg, 443.35 μmol) that was used without further purification.

LCMS for product (ESI+): m/z 339.2 [M+H]$^+$, Rt: 1.188 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 3: Preparation of (R)-6-cyclopropyl-1-(4-fluorobenzyl)-N-(1-(4-fluorophenyl)ethyl)-2-oxo-1,2-dihydro-1,8-naphthyridine-3-carboxamide

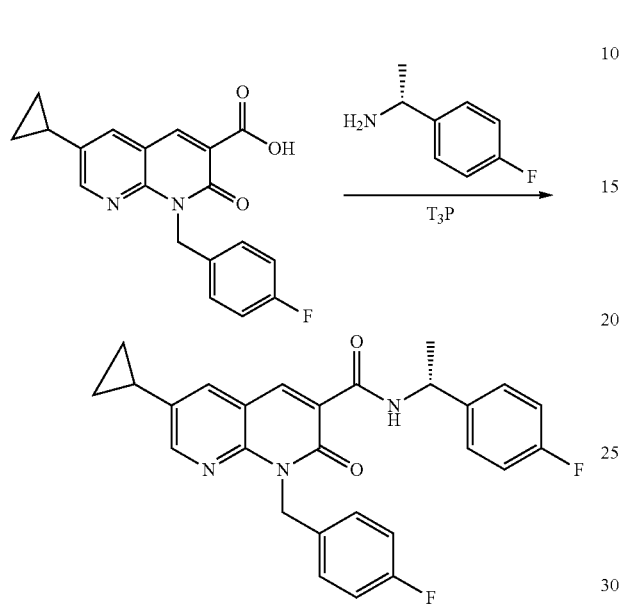

To a mixture of 6-cyclopropyl-1-[(4-fluorophenyl)methyl]-2-oxo-1,8-naphthyridine-3-carboxylic acid (35 mg, 103.45 µmol, 1 eq), DIEA (80.22 mg, 620.69 µmol, 108.11 µL, 6 eq) and (1R)-1-(4-fluorophenyl)ethanamine (17.28 mg, 124.14 µmol, 1.2 eq) in DMF (1 mL) was added T3P (131.66 mg, 206.90 µmol, 123.05 µL, 50% purity, 2 eq). The mixture was stirred at 20° C. for 1 h. LCMS showed complete consumption of the starting material and formation of a new peak with desired mass.

The mixture was filtered and the filtrate was purified by prep-HPLC (column: Phenomenex Gemini-NX 150*30 mm*5 µm; mobile phase: [water (10 mM NH$_4$HCO$_3$)-ACN]; B %: 40%-70%, 8 min) to produce (R)-6-cyclopropyl-1-(4-fluorobenzyl)-N-(1-(4-fluorophenyl)ethyl)-2-oxo-1,2-dihydro-1,8-naphthyridine-3-carboxamide (26.5 mg, 57.67 µmol) as a white solid.

$^1$H NMR (400 MHz, CDCl$_3$) δ=10.14 (br d, J=7.5 Hz, 1H), 8.82 (s, 1H), 8.54 (d, J=2.3 Hz, 1H), 7.67 (d, J=2.3 Hz, 1H), 7.50-7.33 (m, 4H), 7.10-6.90 (m, 4H), 5.82-5.71 (m, 2H), 5.30 (quin, J=7.1 Hz, 1H), 2.06-1.96 (m, 1H), 1.60 (d, J=7.0 Hz, 3H), 1.14-1.06 (m, 2H), 0.82-0.75 (m, 2H). LCMS for product (ESI+): m/z 460.2 [M+H]$^+$, Rt: 3.521 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH$_4$HCO$_3$, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 95—Synthesis of (R)—N-(1-(4-cyanophenyl)ethyl)-6-cyclopropyl-1-(4-fluorobenzyl)-2-oxo-1,2-dihydro-1,8-naphthyridine-3-carboxamide (Compound 95)

Preparation of (R)—N-(1-(4-cyanophenyl)ethyl)-6-cyclopropyl-1-(4-fluorobenzyl)-2-oxo-1,2-dihydro-1,8-naphthyridine-3-carboxamide

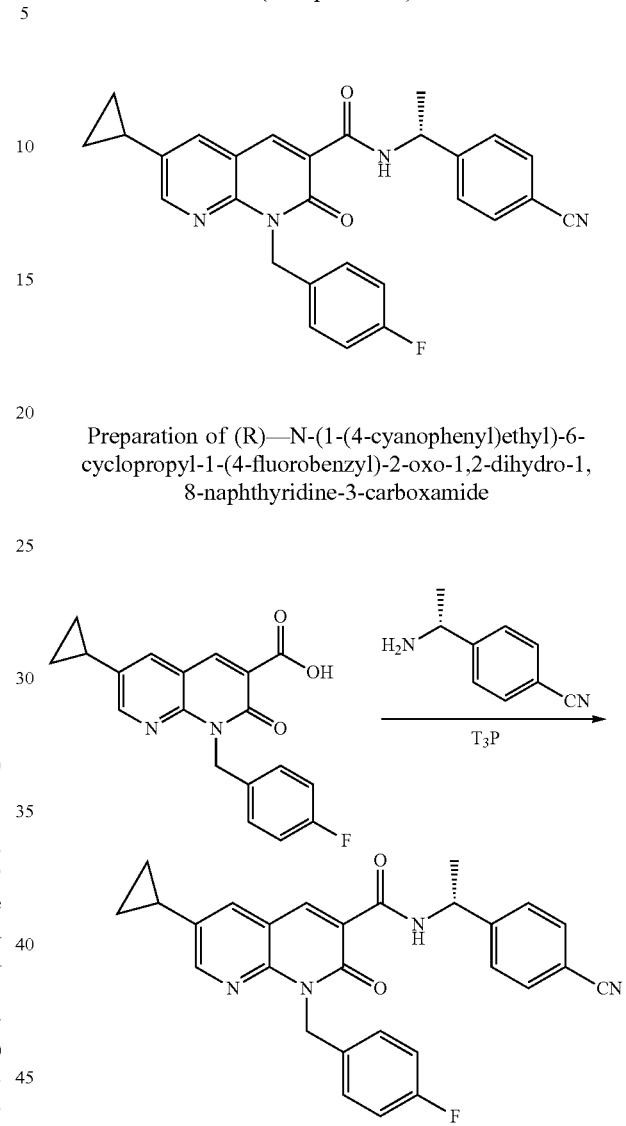

To a mixture of 6-cyclopropyl-1-[(4-fluorophenyl)methyl]-2-oxo-1,8-naphthyridine-3-carboxylic acid (35 mg, 103.45 µmol, 1 eq), DIEA (80.22 mg, 620.69 µmol, 108.11 µL, 6 eq) and 4-[(1R)-1-aminoethyl]benzonitrile (22.67 mg, 124.14 µmol, 1.2 eq, HCl) in DMF (1 mL) was added T3P (131.66 mg, 206.90 µmol, 123.05 µL, 50% purity, 2 eq). The mixture was stirred at 20° C. for 1 h. LCMS showed complete consumption of the starting material and formation of a new peak with desired mass.

The mixture was filtered and the filtrate was purified by prep-HPLC (column: Phenomenex Gemini-NX 150*30 mm*5 µm; mobile phase: [water (10 mM NH$_4$HCO$_3$)-ACN]; B %: 45%-75%, 8 min) to produce (R)—N-(1-(4-cyanophenyl)ethyl)-6-cyclopropyl-1-(4-fluorobenzyl)-2-oxo-1,2-dihydro-1,8-naphthyridine-3-carboxamide (20.2 mg, 43.30 µmol) as a white solid.

$^1$H NMR (400 MHz, CDCl$_3$) δ=10.25 (br d, J=7.3 Hz, 1H), 8.80 (s, 1H), 8.56 (d, J=2.3 Hz, 1H), 7.70-7.59 (m, 3H), 7.54-7.41 (m, 4H), 6.98 (t, J=8.7 Hz, 2H), 5.85-5.72 (m,

2H), 5.31 (quin, J=7.1 Hz, 1H), 2.07-1.96 (m, 1H), 1.62 (d, J=7.0 Hz, 3H), 1.15-1.06 (m, 2H), 0.83-0.75 (m, 2H). LCMS for product (ESI−): m/z 467.2 [M+H]+, Rt: 3.420 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH₄HCO₃, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 96—Synthesis of 6-bromo-2-oxo-1-(pyridin-3-ylmethyl)-N-(spiro[3.3]heptan-2-yl)-1,2-dihydro-1,8-naphthyridine-3-carboxamide (Compound 96)

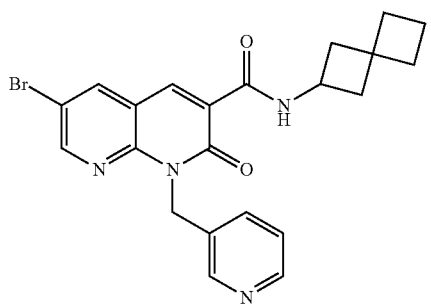 [SMILES: O=C(NC1CC2(CCC2)C1)c1cc2cc(Br)cnc2n(Cc2cccnc2)c1=O]

Step 1: Preparation of ethyl 6-bromo-2-oxo-1-(pyridin-3-ylmethyl)-1,2-dihydro-1,8-naphthyridine-3-carboxylate

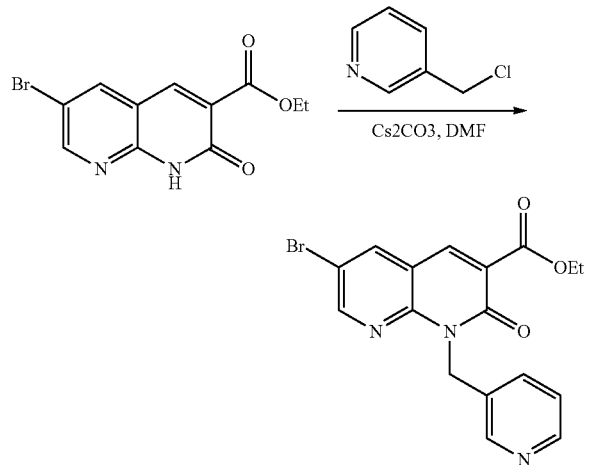

Ethyl 6-bromo-2-oxo-1H-1,8-naphthyridine-3-carboxylate (0.5 g, 1.68 mmol, 1 eq) and 3-(chloromethyl) pyridine (414 mg, 2.52 mmol, 1.5 eq, HCl) were dissolved in DMF (20 mL). Cs₂CO₃ (1.64 g, 5.05 mmol, 3.0 eq) was added into the reaction solution. The solution was stirred at 50° C. for 2 h. LCMS showed complete consumption of the starting material and formation of a new peak with desired mass. Water (50 mL) and ethyl acetate (50 mL) were added and the mixture was stirred for 5 min.

The two phases were separated, and the aqueous phase was extracted with ethyl acetate (3×20 mL). The combined organic phase was washed with brine (50 mL), dried over anhydrous Na₂SO₄, filtered and concentrated to produce ethyl 6-bromo-2-oxo-1-(pyridin-3-ylmethyl)-1,2-dihydro-1,8-naphthyridine-3-carboxylate (0.4 g, 1.03 mmol) as a yellow solid.

¹H NMR (400 MHz, CHLOROFORM-d) δ=8.74 (s, 1H), 8.72 (s, 1H), 8.40 (d, J=2.4 Hz, 1H), 8.20 (s, 1H), 8.02 (s, 1H), 7.80 (d, J=7.6 Hz, 1H), 7.11-7.13 (m, 1H), 5.64 (s, 2H), 4.35 (q, J=6.8 Hz, 2H), 1.34 (t, J=7.1 Hz, 3H).

Step 2: Preparation of 6-bromo-2-oxo-1-(pyridin-3-ylmethyl)-1,2-dihydro-1,8-naphthyridine-3-carboxylic acid

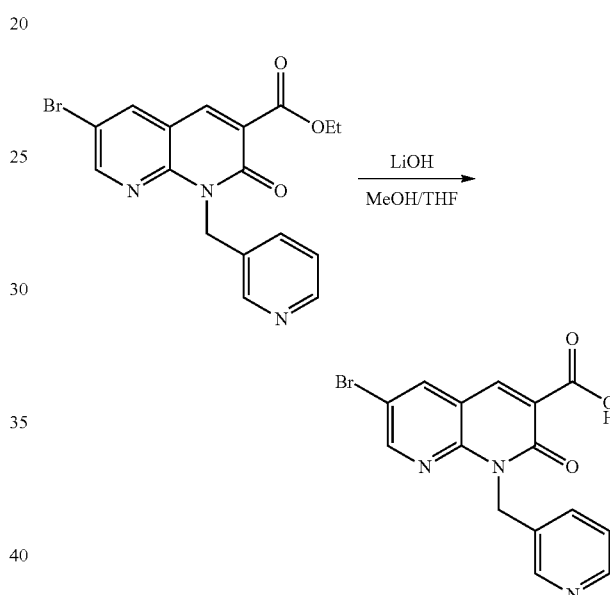

Ethyl 6-bromo-2-oxo-1-(3-pyridylmethyl)-1,8-naphthyridine-3-carboxylate (400 mg, 1.03 mmol, 1 eq) was dissolved in THF (5 mL), MeOH (5 mL) and H₂O (5 mL). LiOH·H₂O (173 mg, 4.12 mmol, 4.0 eq) was added into the reaction solution, the solution was stirred at 30° C. for 2 h. LCMS showed complete consumption of the starting material and formation of a new peak with desired mass. The pH of the reaction mixture was adjusted to 5-6 by dropwise addition of 6 N HCl.

The solvent was removed under reduced pressure to produce 6-bromo-2-oxo-1-(pyridin-3-ylmethyl)-1,2-dihydro-1,8-naphthyridine-3-carboxylic acid (300 mg, 832.96 µmol) as a red oil (used in next step without purification).

LCMS (ESI+): m/z 359.9, 361.9 (M+H)+, Rt: 0.934 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% CF₃CO₂H in water, mobile phase B was 0.018% CF₃CO₂H in CH₃CN. The column used for the chromatography is a Chromolith Flash RP-18e 25-2 mm column. Detection methods are diode array (DAD) and evaporative light scattering (ELSD) detection as well as positive electrospray ionization (MS).

Step 3: Preparation of 6-bromo-2-oxo-1-(pyridin-3-ylmethyl)-N-(spiro[3.3]heptan-2-yl)-1,2-dihydro-1,8-naphthyridine-3-carboxamide

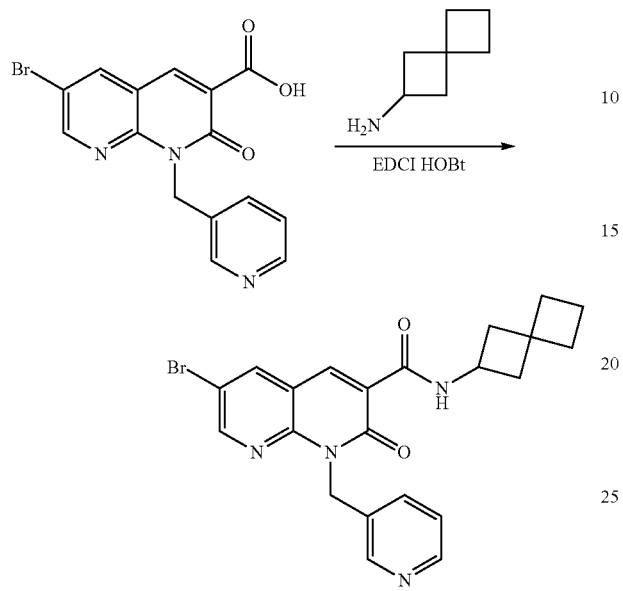

6-bromo-2-oxo-1-(3-pyridylmethyl)-1,8-naphthyridine-3-carboxylic acid (80 mg, 222 μmol, 1.0 eq), spiro[3.3]heptan-2-amine (32.8 mg, 222 μmol, 1.0 eq, HCl), EDCI (85.2 mg, 444 μmol, 2.0 eq), HOBt (60.0 mg, 444 μmol, 2.0 eq) were dissolved in DMF (10 mL). The solution was stirred at 30° C. for 15 min. Then TEA (112.38 mg, 1.11 mmol, 154.58 μL, 5.0 eq) was added into the reaction solution. The solution was stirred at 30° C. for 12 h. LCMS showed complete consumption of the starting material and formation of a new peak with desired mass.

The solvent was removed under reduced pressure and the residue was purified by prep-HPLC (Column: Waters Xbridge BEH C18 100*25 mm*5 μm; mobile phase: [water (10 mM NH$_4$HCO$_3$)—CH$_3$CN]; B %: 40%-70%, 8 min) to produce the desired product (17.5 mg, 38.6 μmol) as a white solid.

The mixture was concentrated and the residue was purified by prep-HPLC (column: Phenomenex Luna 80*30 mm*3 μm; mobile phase: [water (10 mM NH$_4$HCO$_3$)-ACN]; B %: 50%-80%, 7 min) to produce N-(bicyclo[1.1.1]pentan-1-yl)-6-cyclopropyl-1-(4-fluorobenzyl)-2-oxo-1,2-dihydro-1,8-naphthyridine-3-carboxamide (7.5 mg, 18.59 μmol) as a yellow solid.

$^1$H NMR (400 MHz, METHANOL-d$_4$) δ=8.83-8.81 (m, 2H), 8.69 (s, 1H), 8.56 (d, J=2.4 Hz, 1H), 8.41 (dd, J=1.5, 4.9 Hz, 1H), 7.91 (dd, J=1.7, 8.1 Hz, 1H), 7.36 (dd, J=4.9, 7.8 Hz, 1H), 5.83 (s, 2H), 4.34 (t, J=7.8 Hz, 1H), 2.54-2.47 (m, 2H), 2.14-2.09 (m, 2H), 2.04-1.97 (m, 4H), 1.91-1.89 (m, 2H). LCMS (ESI+): m/z 453.1, 455.1 (M+H)$^+$, Rt: 2.235 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 97—Synthesis of 6-(4-fluorophenyl)-2-oxo-1-(pyridin-3-ylmethyl)-N-(spiro[3.3]heptan-2-yl)-1,2-dihydro-1,8-naphthyridine-3-carboxamide (Compound 97)

Preparation of 6-(4-fluorophenyl)-2-oxo-1-(pyridin-3-ylmethyl)-N-(spiro[3.3]heptan-2-yl)-1,2-dihydro-1,8-naphthyridine-3-carboxamide

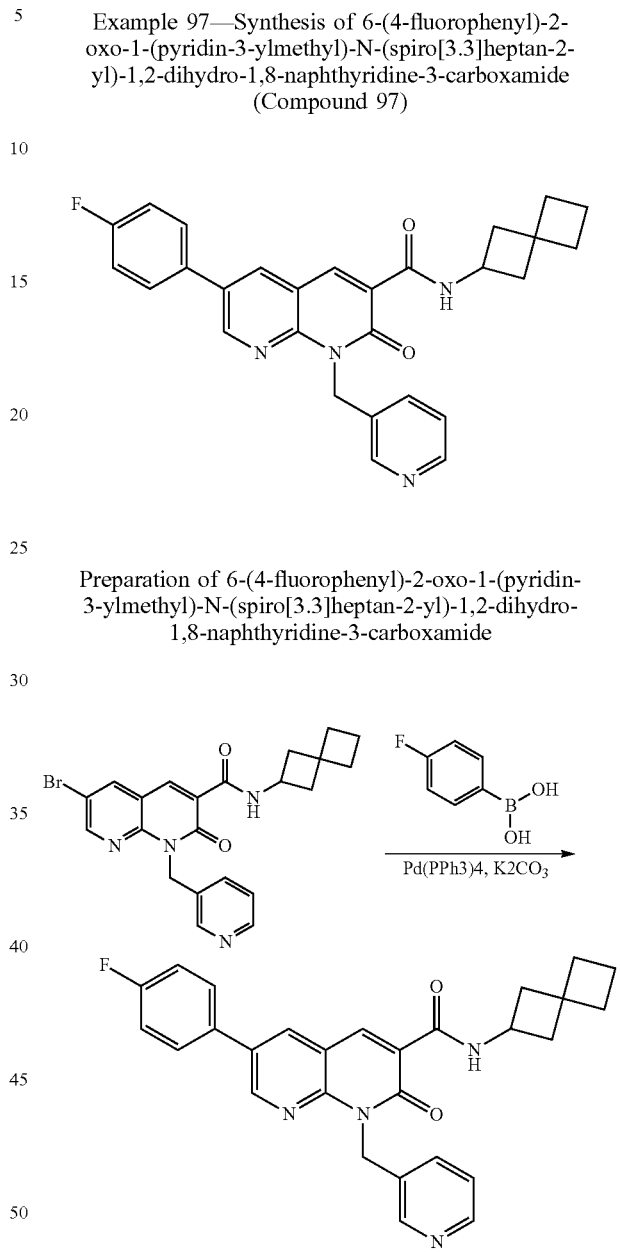

4-fluorophenyl)boronic acid (9.26 mg, 66.2 μmol, 1.5 eq), 6-bromo-2-oxo-1-(3-pyridylmethyl)-N-spiro[3.3]heptan-2-yl-1,8-naphthyridine-3-carboxamide (20 mg, 44.1 μmol, 1.0 eq), Pd(PPh$_3$)$_4$ (5.10 mg, 4.41 μmol, 0.1 eq) and K$_2$CO$_3$ (12.2 mg, 88.2 μmol, 2.0 eq) were dissolved in dioxane (2 mL) and H$_2$O (0.5 mL). The suspension was stirred at 80° C. for 2 h. LCMS showed complete consumption of the starting material and formation of a new peak with desired mass.

The solvent was removed under reduced pressure and the residue was purified by prep-HPLC. (Column: Welch Xtimate C18 150*25 mm*5 μm; mobile phase: [water (0.04% HCl)—CH$_3$CN]; B %: 30%-60%, 10 min) to produce 6-(4-fluorophenyl)-2-oxo-1-(pyridin-3-ylmethyl)-N-(spiro[3.3]

heptan-2-yl)-1,2-dihydro-1,8-naphthyridine-3-carboxamide (20 mg, 39.6 μmol, HCl) as a white solid (used in next step without purification).

(400 MHz, METHANOL-d₄) δ=9.06-9.00 (m, 2H), 8.97 (s, 1H), 8.74-8.65 (m, 2H), 8.61 (d, J=2.4 Hz, 1H), 7.95 (dd, J=5.6, 8.1 Hz, 1H), 7.78 (dd, J=5.1, 8.6 Hz, 2H), 7.27 (t, J=8.8 Hz, 2H), 6.02 (s, 2H), 4.36 (t, J=8.1 Hz, 1H), 2.52 (ddd, J=2.7, 7.5, 9.4 Hz, 2H), 2.13 (t, J=7.3 Hz, 2H), 2.05-1.96 (m, 4H), 1.92-1.83 (m, 2H). LCMS (ESI+): m/z 469.2 (M+H)⁺, Rt: 2.445 min.

LCMS Method

The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile. The column used for chromatography was a Kinetex C18 50*2.1 mm column (5 um particles). Detection methods are diode array (DAD) and evaporative light scattering (ELSD) detection as well as positive electrospray ionization.

Example 98—Synthesis of 6-bromo-N-(1-(4-fluorophenyl)ethyl)-2-oxo-1-(pyridin-3-ylmethyl)-1,2-dihydro-1,8-naphthyridine-3-carboxamide (Compound 98)

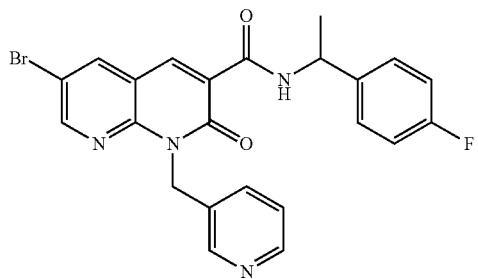 [SMILES: CC(NC(=O)c1cc2cc(Br)cnc2n(Cc2cccnc2)c1=O)c1ccc(F)cc1]

Preparation of 6-bromo-N-(1-(4-fluorophenyl)ethyl)-2-oxo-1-(pyridin-3-ylmethyl)-1,2-dihydro-1,8-naphthyridine-3-carboxamide

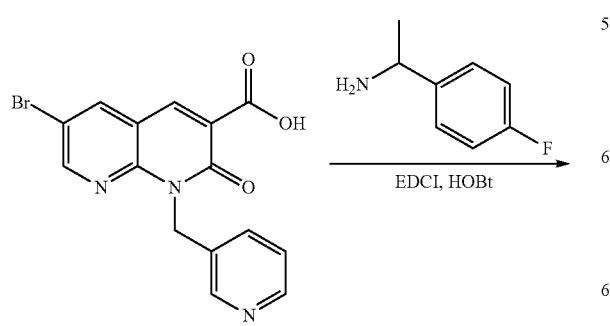

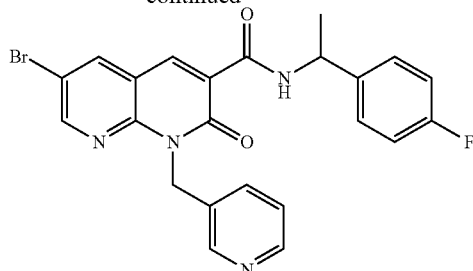

6-bromo-2-oxo-1-(3-pyridylmethyl)-1,8-naphthyridine-3-carboxylic acid (50.00 mg, 138.83 μmol, 1.0 eq) 1-(4-fluorophenyl)ethanamine (19.32 mg, 138.83 μmol, 18.23 μL, 1 eq), EDCI (53.23 mg, 277.66 μmol, 2.0 eq), HOBt (37.52 mg, 277.66 μmol, 2.0 eq) were dissolved in DMF (2 mL). The solution was stirred at 30° C. for 15 min, then TEA (70.24 mg, 694.15 μmol, 96.62 μL, 5.0 eq) was added into the reaction solution. The solution was stirred at 30° C. for 12 h. LCMS showed complete consumption of the starting material and formation of a new peak with desired mass.

The mixture was purified by prep-HPLC (column: Phenomenex Luna C18 200*40 mm*10 μm; mobile phase: [water (10 mM NH₄HCO₃)-ACN]; B %: 40%-70%, 10 min) to produce 6-bromo-N-(1-(4-fluorophenyl)ethyl)-2-oxo-1-(pyridin-3-ylmethyl)-1,2-dihydro-1,8-naphthyridine-3-carboxamide (7.5 mg, 15.43 μmol) as a white solid.

¹H NMR (400 MHz, CDCl3) δ=9.97-9.98 (d, 1H), 8.81 (s, 2H), 8.74-8.75 (d, 1H), 8.50-8.51 (d, 1H), 8.18-8.19 (d, 1H), 7.79-7.81 (d, 1H), 7.36-7.40 (m, 2H), 7.24-7.27 (m, 1H), 7.02-7.06 (t, 2H), 5.77 (d, 2H), 5.27-5.31 (m, 1H), 1.57-1.62 (d, 3H). LCMS (ESI+): m/z 481.1, 483.1 [M+H]⁺, Rt: 2.176 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH₄HCO₃, mobile phase B was Acetonitrile. The column used for chromatography was a Xbridge Shield RP18 2.1*50 mm column (5 um particles). Detection methods are diode array (DAD) and evaporative light scattering (ELSD) detection as well as positive electrospray ionization.

Example 99—Synthesis of 6-bromo-1-((5-fluoropyridin-2-yl)methyl)-2-oxo-N-(spiro[3.3]heptan-2-yl)-1,2-dihydro-1,8-naphthyridine-3-carboxamide (Compound 99)

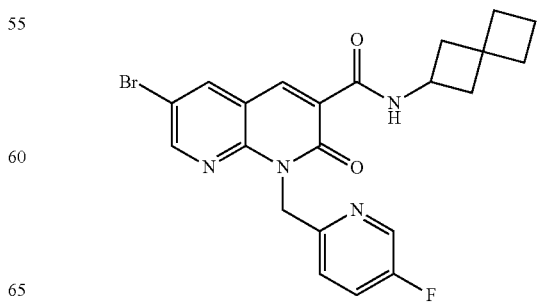

Step 1: Preparation of ethyl 6-bromo-1-((5-fluoro-pyridin-2-yl)methyl)-2-oxo-1,2-dihydro-1,8-naphthyridine-3-carboxylate

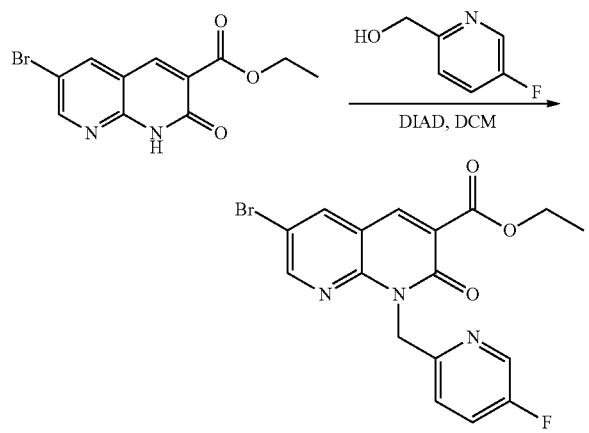

To a solution of ethyl 6-bromo-2-oxo-1H-1,8-naphthyridine-3-carboxylate (150 mg, 504.87 μmol, 1 eq) in DCM (3 mL) was added (5-fluoro-2-pyridyl)methanol (77.01 mg, 605.85 μmol, 1.2 eq) and PPh$_3$ (198.63 mg, 757.31 μmol, 1.5 eq) and DIAD (153.13 mg, 757.31 μmol, 147.24 μL, 1.5 eq) at 0° C. The mixture was stirred at 25° C. for 2 h. LCMS showed complete consumption of the starting material and formation of a new peak with desired mass.

The mixture was concentrated, and the residue was purified by prep-TLC (Petroleum ether/Ethyl acetate, 2:1) to produce ethyl 6-bromo-1-((5-fluoropyridin-2-yl)methyl)-2-oxo-1,2-dihydro-1,8-naphthyridine-3-carboxylate (200 mg, 492.36 μmol) as a yellow solid.

LCMS for product (ESI+): m/z 406.0, 408.0 [M+H]$^+$, Rt: 1.209 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Step 2: Preparation of 6-bromo-1-((5-fluoropyridin-2-yl)methyl)-2-oxo-1,2-dihydro-1,8-naphthyridine-3-carboxylic acid

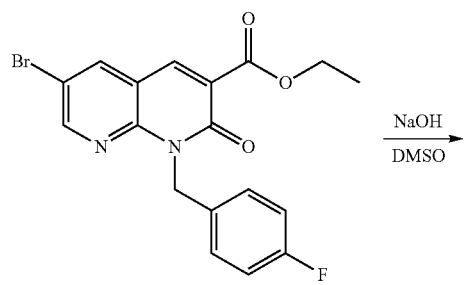

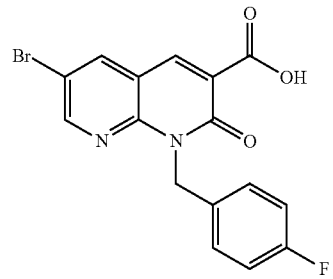

To a solution of ethyl 6-bromo-1-[(5-fluoro-2-pyridyl)methyl]-2-oxo-1,8-naphthyridine-3-carboxylate (200 mg, 492.36 μmol, 1 eq) in DMSO (2 mL) was added NaOH (2 M, 0.8 mL, 32.50 eq). The mixture was stirred at 25° C. for 2 h. LCMS showed complete consumption of the starting material and formation of a new peak with desired mass. The pH of the reaction mixture was adjusted to 5 dropwise addition of 2 N hydrochloric acid at 0° C.

The mixture was filtered, and the resulting solid was collected by filtration and air-dried to produce 6-bromo-1-((5-fluoropyridin-2-yl)methyl)-2-oxo-1,2-dihydro-1,8-naphthyridine-3-carboxylic acid (70 mg, 185.11 μmol) as a pink solid.

$^1$H NMR (400 MHz, DMSO-d$_6$) δ=13.77 (br d, J=2.1 Hz, 1H), 8.88 (s, 1H), 8.85-8.79 (m, 2H), 8.38 (d, J=2.8 Hz, 1H), 7.76-7.52 (m, 2H), 5.78 (s, 2H). LCMS for product (ESI+): m/z 377.9, 379.9 [M+H]$^+$, Rt: 0.864 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Step 3: Preparation of 6-bromo-1-((5-fluoropyridin-2-yl)methyl)-2-oxo-N-(spiro[3.3]heptan-2-yl)-1,2-dihydro-1,8-naphthyridine-3-carboxamide

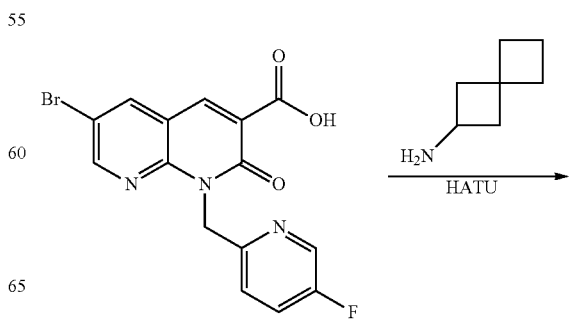

-continued

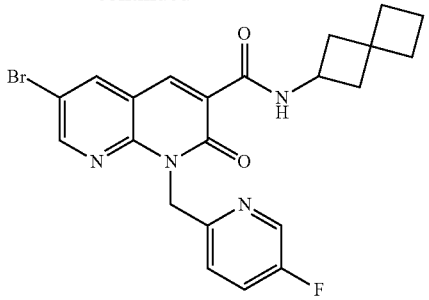 [SMILES: O=C(NC1CC2(CCC2)C1)c1cc2cc(Br)cnc2n(Cc2ccc(F)cn2)c1=O]

To a solution of 6-bromo-1-[(5-fluoro-2-pyridyl)methyl]-2-oxo-1,8-naphthyridine-3-carboxylic acid (50 mg, 132.22 μmol, 1 eq) in DMF (0.5 mL) was added HATU (80.44 mg, 211.55 μmol, 1.6 eq) and DIEA (51.27 mg, 396.67 μmol, 69.09 μL, 3 eq). The mixture was stirred at 25° C. for 0.5 h, a solution of spiro[3.3]heptan-2-amine (21.47 mg, 145.44 μmol, 1.1 eq, HCl) and DIEA (25.63 mg, 198.33 μmol, 34.55 μL, 1.5 eq) in DMF (0.5 mL) was added into the mixture at 50° C. The mixture was stirred at 50° C. for 1.5 h. HATU (50.27 mg, 132.22 μmol, 1 eq) was added into the mixture at 50° C., the mixture was stirred at 50° C. for 1 h. LCMS showed complete consumption of the starting material and formation of a new peak with desired mass.

The resulting solid was collected by filtration and washed with water (10 mL) to produce 6-bromo-1-((5-fluoropyridin-2-yl)methyl)-2-oxo-N-(spiro[3.3]heptan-2-yl)-1,2-dihydro-1,8-naphthyridine-3-carboxamide (6 mg, 12.46 μmol) as a yellow solid.

$^1$H NMR (400 MHz, DMSO-$d_6$) δ=9.56 (br d, J=7.4 Hz, 1H), 8.91 (s, 1H), 8.83 (d, J=2.3 Hz, 1H), 8.78 (d, J=2.3 Hz, 1H), 8.37 (d, J=2.6 Hz, 1H), 7.66 (dt, J=2.9, 8.8 Hz, 1H), 7.38 (dd, J=4.2, 8.6 Hz, 1H), 5.77 (s, 2H), 4.35-4.19 (m, 1H), 2.41-2.37 (m, 2H), 2.03 (br t, J=7.3 Hz, 2H), 1.97-1.86 (m, 4H), 1.79 (q, J=7.6 Hz, 2H). LCMS for product (ESI+): m/z 471.1, 473.1 [M+H]+, Rt: 2.910 min.

LCMS Method

The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% $CF_3CO_2H$ in water, mobile phase B was 0.018% $CF_3CO_2H$ in $CH_3CN$. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 100—Synthesis of (R)—N-(1-(4-fluorophenyl)ethyl)-1-((5-fluoropyridin-2-yl)methyl)-6-isopropyl-2-oxo-1,2-dihydro-1,8-naphthyridine-3-carboxamide (Compound 100)

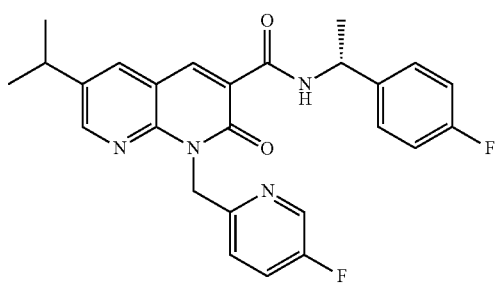

Step 1: Preparation of ethyl 1-((5-fluoropyridin-2-yl)methyl)-2-oxo-6-(prop-1-en-2-yl)-1,2-dihydro-1,8-naphthyridine-3-carboxylate

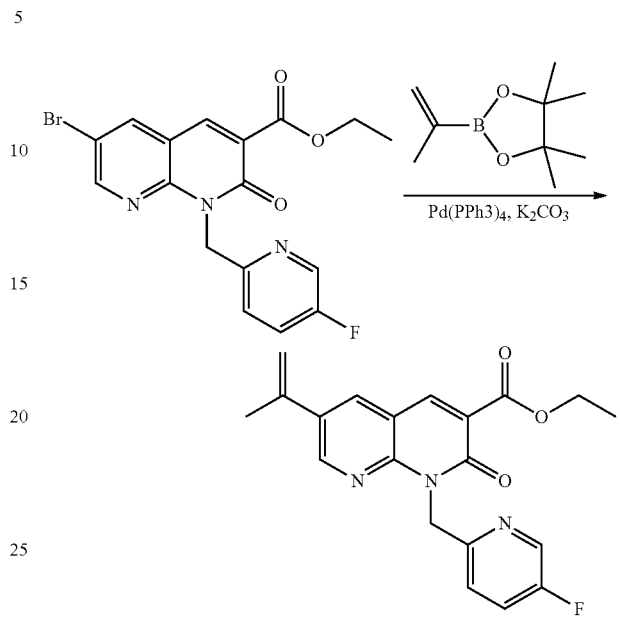

A mixture of 2-isopropenyl-4,4,5,5-tetramethyl-1,3,2-dioxaborolane (337.91 mg, 2.01 mmol, 5 eq), ethyl 6-bromo-1-[(5-fluoro-2-pyridyl)methyl]-2-oxo-1,8-naphthyridine-3-carboxylate (163.37 mg, 402.18 μmol, 1 eq), $K_2CO_3$ (166.75 mg, 1.21 mmol, 3 eq) and Pd(PPh$_3$)$_4$ (46.47 mg, 40.22 μmol, 0.1 eq) in water (0.2 mL) and dioxane (2 mL) was stirred at 100° C. for 2 h. LCMS showed complete consumption of the starting material and formation of a new peak with desired mass.

The mixture was poured into water (50 mL), extracted with ethyl acetate (3×30 mL), the organic layer was washed with brine (10 mL), dried over $Na_2SO_4$ and concentrated to produce ethyl 1-((5-fluoropyridin-2-yl)methyl)-2-oxo-6-(prop-1-en-2-yl)-1,2-dihydro-1,8-naphthyridine-3-carboxylate (140 mg, 381.08 μmol) as a white solid.

LCMS for product (ESI+): m/z 368.2 [M+H]+, Rt: 0.743 min.

LCMS Method

The gradient was 5-95% B in 0.7 min, 95-95% B in 0.45 min, 95-5% B in 0.01 min, and then held at 0% B for 0.44 min (1.5 m/min flow rate). Mobile phase A was 0.0375% $CF_3CO_2H$ in water, mobile phase B was 0.018% $CF_3CO_2H$ in $CH_3CN$. The column used for the chromatography is a Chromolith Flash RP-18e 25-2 mm column. Detection methods are diode array (DAD) and evaporative light scattering (ELSD) detection as well as positive electrospray ionization (MS).

Step 2: Preparation of 1-((5-fluoropyridin-2-yl)methyl)-2-oxo-6-(prop-1-en-2-yl)-1,2-dihydro-1,8-naphthyridine-3-carboxylic acid

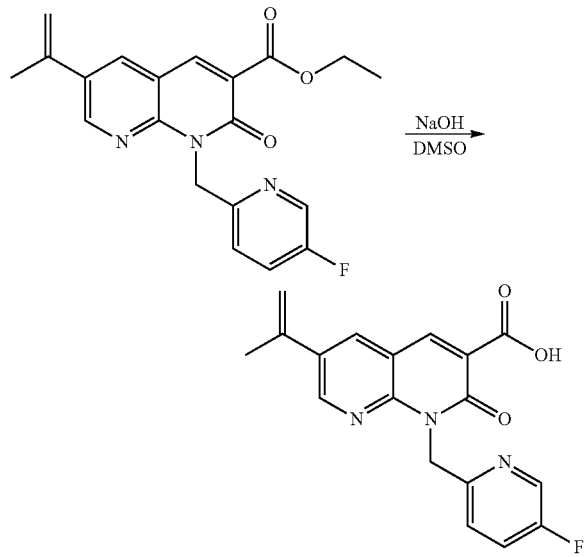

Step 3: Preparation of (R)—N-(1-(4-fluorophenyl)ethyl)-1-((5-fluoropyridin-2-yl)methyl)-2-oxo-6-(prop-1-en-2-yl)-1,2-dihydro-1,8-naphthyridine-3-carboxamide

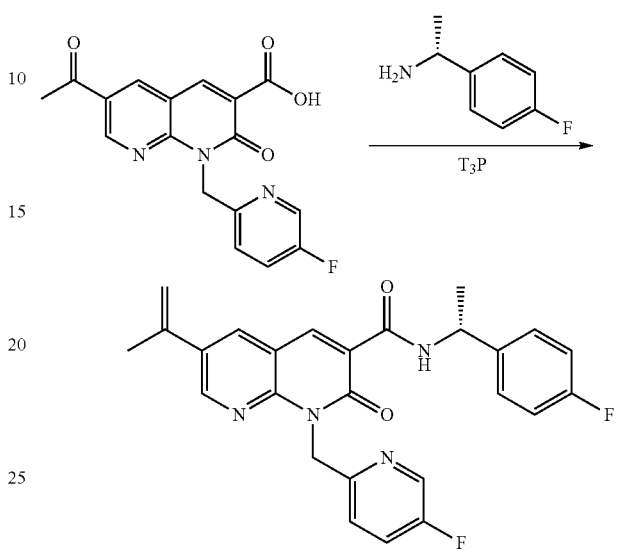

To a solution of ethyl 1-[(5-fluoro-2-pyridyl) methyl]-6-isopropenyl-2-oxo-1,8-naphthyridine-3-carboxylate (120 mg, 326.64 μmol, 1 eq) in DMSO (2.5 mL) was added NaOH (2 M, 1.6 mL, 10 eq). The mixture was stirred at 25° C. for 2 h. LCMS showed complete consumption of the starting material and formation of a new peak with desired mass. The mixture was poured into water (50 mL), extracted with ethyl acetate (3×50 mL), separated, the aqueous layer was acidified to pH 2 by dropwise addition of 2 N hydrochloric acid at 0° C.

The mixture was filtered, the resulting solid was air-dried to produce 1-((5-fluoropyridin-2-yl)methyl)-2-oxo-6-(prop-1-en-2-yl)-1,2-dihydro-1,8-naphthyridine-3-carboxylic acid as a white solid. $^1$H NMR (400 MHz, CDCl$_3$) δ=14.09 (br s, 1H), 8.98 (s, 1H), 8.90 (d, J=2.4 Hz, 1H), 8.31 (d, J=2.4 Hz, 1H), 8.15 (d, J=2.3 Hz, 1H), 7.44-7.31 (m, 2H), 5.99 (s, 2H), 5.53 (s, 1H), 5.31 (s, 1H), 2.24 (s, 3H). LCMS for product (ESI+): m/z 340.3 [M+H]$^+$, Rt: 0.983 min.

LCMS Method

The gradient was 5-95% B in 1.0 min, 95-100% B in 0.8 min, 100-5% B in 0.01 min, and then held at 5% B for 0.24 min (1.0 m/min flow rate). Mobile phase A was 10 mM NH$_4$HCO$_3$ in water, mobile phase B was CH$_3$CN. The column used for the chromatography was Xbridge Shield RP18 2.1*50 mm, 5 μm column. Detection methods are diode array (DAD) and positive electrospray ionization (MS).

To a solution of 1-[(5-fluoro-2-pyridyl)methyl]-6-isopropenyl-2-oxo-1,8-naphthyridine-3-carboxylic acid (60 mg, 176.82 μmol, 1 eq) in DMF (0.5 mL) was added DIEA (68.56 mg, 530.47 μmol, 92.40 μL, 3 eq) and (1R)-1-(4-fluorophenyl)ethanamine (37.27 mg, 212.19 μmol, 1.2 eq, HCl) at 0° C. T3P (225.05 mg, 353.65 μmol, 210.33 μL, 50% purity, 2 eq) was added into the mixture at 0° C. The mixture was stirred at 25° C. for 2 h. LCMS showed complete consumption of the starting material and formation of a new peak with desired mass.

The mixture was poured into water (30 mL), extracted with ethyl acetate (3×10 mL), the organic layer was washed with brine (10 mL), dried over Na$_2$SO$_4$ and concentrated to produce (R)—N-(1-(4-fluorophenyl)ethyl)-1-((5-fluoropyridin-2-yl)methyl)-2-oxo-6-(prop-1-en-2-yl)-1,2-dihydro-1,8-naphthyridine-3-carboxamide (52 mg, 112.93 μmol) as a yellow solid.

LCMS for product (ESI+): m/z 461.3 [M+H]$^+$, Rt: 0.841 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 4: Preparation of (R)—N-(1-(4-fluorophenyl)ethyl)-1-((5-fluoropyridin-2-yl)methyl)-6-isopropyl-2-oxo-1,2-dihydro-1,8-naphthyridine-3-carboxamide

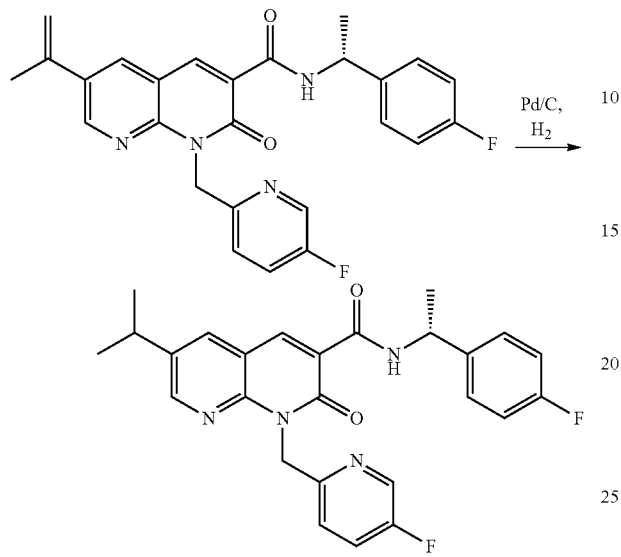

To a solution of Pd/C (6.44 mg, 5.46 μmol, 10% purity, 0.2 eq) in EtOAc (1 mL) was added N-[(1R)-1-(4-fluorophenyl) ethyl]-1-[(5-fluoro-2-pyridyl)methyl]-6-isopropenyl-2-oxo-1,8-naphthyridine-3-carboxamide (50 mg, 108.58 μmol, 1 eq). The mixture was stirred at 25° C. under H₂ (15 Psi) for 1 h. LCMS showed complete consumption of the starting material and formation of a new peak with desired mass. The mixture was filtered, and the filtrate was concentrated and the residue was purified by prep-HPLC (column: Waters Xbridge BEH C18 100*25 mm*5 μm; mobile phase: [water (10 mM NH₄HCO₃)-ACN]; B %: 40%-70%, 10 min) to produce (R)—N-(1-(4-fluorophenyl)ethyl)-1-((5-fluoropyridin-2-yl)methyl)-6-isopropyl-2-oxo-1,2-dihydro-1,8-naphthyridine-3-carboxamide (41.0 mg, 88.47 μmol) as a white solid.

¹H NMR (400 MHz, CDCl₃) δ=10.07 (br d, J=7.5 Hz, 1H), 8.92 (s, 1H), 8.56 (d, J=2.6 Hz, 1H), 8.37 (d, J=2.6 Hz, 1H), 7.90 (d, J=2.2 Hz, 1H), 7.37 (dd, J=5.3, 8.8 Hz, 2H), 7.35-7.29 (m, 1H), 7.20 (dd, J=4.4, 8.3 Hz, 1H), 7.06-6.98 (m, 2H), 5.93 (d, J=3.5 Hz, 2H), 5.31 (t, J=7.2 Hz, 1H), 3.06 (td, J=7.1, 13.8 Hz, 1H), 1.58 (d, J=7.0 Hz, 3H), 1.34 (d, J=7.0 Hz, 6H). LCMS for product (ESI+): m/z 463.2 [M+H]⁺, Rt: 3.324 min.

LCMS Method

The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Example 101—Synthesis of (R)—N-(1-(4-cyanophenyl)ethyl)-1-(4-fluorobenzyl)-6-(oxetan-3-yl)-2-oxo-1,2-dihydro-1,8-naphthyridine-3-carboxamide (Compound 101)

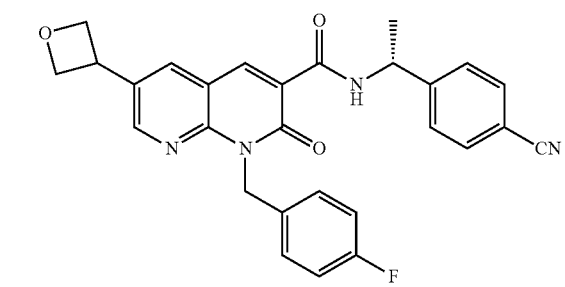 [SMILES: C[C@@H](NC(=O)c1cc2cc(C3COC3)cnc2n(Cc2ccc(F)cc2)c1=O)c1ccc(C#N)cc1]

Step 1: Preparation of ethyl 1-(4-fluorobenzyl)-6-(oxetan-3-yl)-2-oxo-1,2-dihydro-1,8-naphthyridine-3-carboxylate

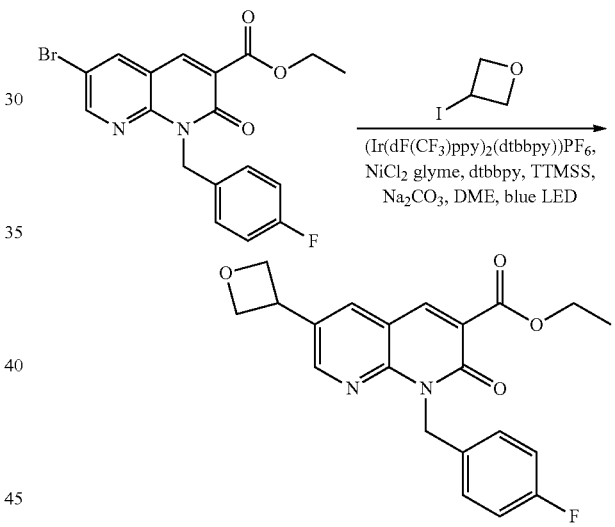

To a 8 mL tube equipped was added thyl 6-bromo-1-[(4-fluorophenyl)methyl]-2-oxo-1,8-naphthyridine-3-carboxylate (50 mg, 123.39 μmol, 1 eq) and 3-iodooxetane (34.05 mg, 185.09 μmol, 1.5 eq), the tube was moved into glove box, photocatalyst 4-tert-butyl-2-(4-tert-butyl-2-pyridyl) pyridine (165.59 ug, 6.17e-1 μmol, 0.005 eq), dichloronickel; 1,2-dimethoxyethane (135.56 ug, 6.17e-1 μmol, 0.005 eq), TTMSS (30.68 mg, 123.39 μmol, 38.07 μL, 1 eq) and Na₂CO₃ (26.16 mg, 246.78 μmol, 2 eq) were added. The tube was sealed in glove box before DME (0.5 mL) was added bis[3,5-difluoro-2-[5-(trifluoromethyl)-2-pyridyl] phenyl]iridium(1+); 4-tert-butyl-2-(4-tert-butyl-2-pyridyl) pyridine; hexafluorophosphate (1.38 mg, 1.23 μmol, 0.01 eq) was added as a stock solution in DME (0.5 mL). The reaction mixture was moved out from glove box and irradiated with a 34 W blue LED lamp at 25° C. for 6 h. Four additional vials were set up as described above and all five reaction mixture were combined. LCMS showed complete consumption of the starting material and formation of a new peak with desired mass. The mixture was poured into water (20 mL). The aqueous layer was extracted with EtOAc (2×20 mL).

The combined organic phase was washed with brine, dried over Na$_2$SO$_4$ and concentrated. The residue was purified by column chromatography (SiO$_2$, Petroleum ether/Ethyl acetate, 10:1 to 1:1) to produce ethyl 1-(4-fluorobenzyl)-6-(oxetan-3-yl)-2-oxo-1,2-dihydro-1,8-naphthyridine-3-carboxylate (110 mg, 287.67 μmol) as a yellow oil.

LCMS for product (ESI+): m/z 383.0 [M+H]+, Rt: 2.012 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 4.30 min 0.5% B in 0.01 min, 5-95% B (0.01-3.00 min), with a hold at 95% B for 0.50 min. 95-5% B (3.50-3.51 min), 5% B in 3.51 min, with a hold at 5% B for 0.79 min. The flow rate was 1.0 mL/min.

Step 2: Preparation of 1-(4-fluorobenzyl)-6-(oxetan-3-yl)-2-oxo-1,2-dihydro-1,8-naphthyridine-3-carboxylic acid

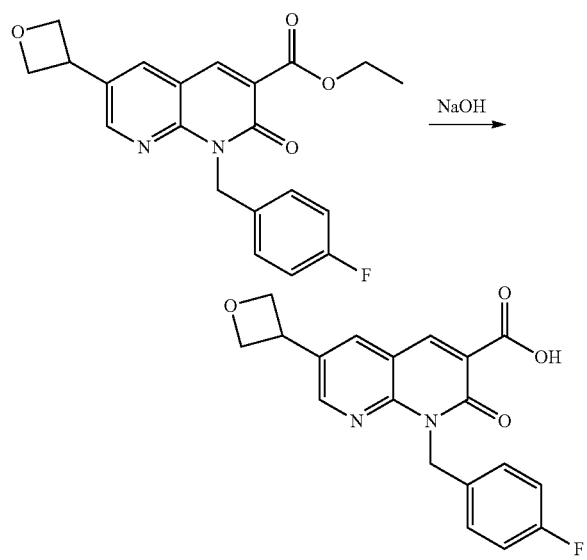

To a solution of ethyl 1-[(4-fluorophenyl)methyl]-6-(oxetan-3-yl)-2-oxo-1,8-naphthyridine-3-carboxylate (108 mg, 282.44 μmol, 1 eq) in MeOH (1 mL) was added NaOH (2 M, 564.88 μL, 4 eq). The mixture was stirred at 25° C. for 2 h. LCMS showed complete consumption of the starting material and formation of a new peak with desired mass. The mixture was pH of the reaction mixture was adjusted to 6 by dropwise addition of 2 N hydrochloric.

The resulting solid was collected by filtration to produce 1-(4-fluorobenzyl)-6-(oxetan-3-yl)-2-oxo-1,2-dihydro-1,8-naphthyridine-3-carboxylic acid (60 mg, 169.33 μmol) as a brown solid.

$^1$H NMR (400 MHz, DMSO-d$_6$) δ=8.66 (s, 1H), 8.52 (s, 1H), 8.42 (s, 1H), 7.35 (br dd, J=6.0, 7.9 Hz, 2H), 7.07 (br t, J=8.7 Hz, 2H), 5.63 (s, 2H), 4.97 (dd, J=6.0, 8.4 Hz, 2H), 4.69 (t, J=6.4 Hz, 2H), 4.40 (quin, J=7.7 Hz, 1H). LCMS for product (ESI+): m/z 355.2 [M+H]+, Rt: 1.031 min.

LCMS Method

The column used for chromatography was a HALO AQ-C18 2.1*30 mm, (2.7 μm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 2.20 min 0.5% B in 0.01 min, 5-95% B (0.01-1.00 min), 95-100% B (1.00-1.80 min), 5% B in 1.81 min, with a hold at 5% B for 0.40 min. The flow rate was 1.0 m/min.

Step 3: Preparation of (R)—N-(1-(4-cyanophenyl)ethyl)-1-(4-fluorobenzyl)-6-(oxetan-3-yl)-2-oxo-1,2-dihydro-1,8-naphthyridine-3-carboxamide

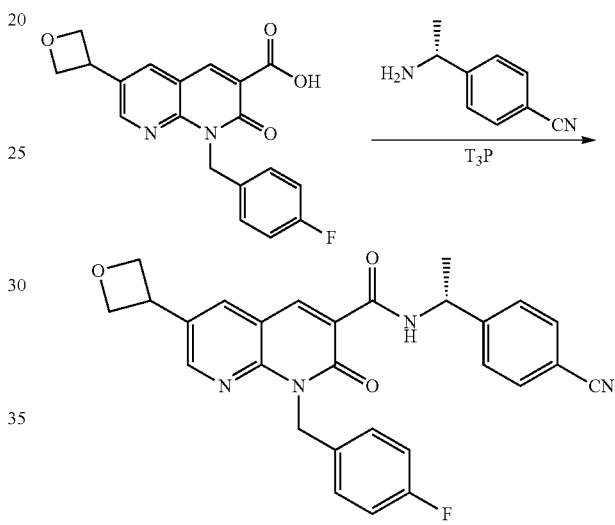

To a solution of 1-[(4-fluorophenyl)methyl]-6-(oxetan-3-yl)-2-oxo-1,8-naphthyridine-3-carboxylic acid (18 mg, 50.80 μmol, 1 eq) and 4-[(1R)-1-aminoethyl]benzonitrile (11.13 mg, 60.96 μmol, 1.2 eq, HCl) in DMF (0.5 mL) was added DIEA (39.39 mg, 304.80 μmol, 53.09 μL, 6 eq) and T3P (129.31 mg, 203.20 μmol, 120.85 μL, 50% purity, 4 eq) at 0° C. The mixture was stirred at 25° C. for 2 h. LCMS showed complete consumption of the starting material and formation of a new peak with desired mass.

The mixture was filtered and the filtrate was purified by prep-HPLC (neutral condition) to produce (R)—N-(1-(4-cyanophenyl)ethyl)-1-(4-fluorobenzyl)-6-(oxetan-3-yl)-2-oxo-1,2-dihydro-1,8-naphthyridine-3-carboxamide (7.2 mg, 14.92 μmol) was obtained as a white solid.

$^1$H NMR (400 MHz, DMSO-d$_6$) δ=9.98 (br d, J=7.3 Hz, 1H), 8.91 (s, 1H), 8.76 (d, J=2.1 Hz, 1H), 8.67 (d, J=2.1 Hz, 1H), 7.82 (d, J=8.1 Hz, 2H), 7.60 (d, J=8.3 Hz, 2H), 7.34 (dd, J=5.7, 8.3 Hz, 2H), 7.11 (t, J=8.8 Hz, 2H), 5.78-5.65 (m, 2H), 5.22 (quin, J=7.0 Hz, 1H), 4.97 (dd, J=6.1, 8.3 Hz, 2H), 4.70 (t, J=5.9 Hz, 2H), 4.42 (quin, J=7.5 Hz, 1H), 1.52 (d, J=7.0 Hz, 3H). LCMS for product (ESI+): m/z 483.3 [M+H]+, Rt: 3.131 min.

LCMS Method

The gradient was 5-95% B in 1.0 min, 95-100% B in 0.8 min, 100-5% B in 0.01 min, and then held at 5% B for 0.24 min (1.0 mL/min flow rate). Mobile phase A was 10 mM NH$_4$HCO$_3$ in water, mobile phase B was CH$_3$CN. The column used for the chromatography was Xbridge Shield RP18 2.1*50 mm, 5 μm column. Detection methods are diode array (DAD) and positive electrospray ionization (MS).

Example 102—Synthesis of 1-(4-fluorobenzyl)-6-(oxetan-3-yl)-2-oxo-N-(spiro[3.3]heptan-2-yl)-1,2-dihydro-1,8-naphthyridine-3-carboxamide (Compound 102)

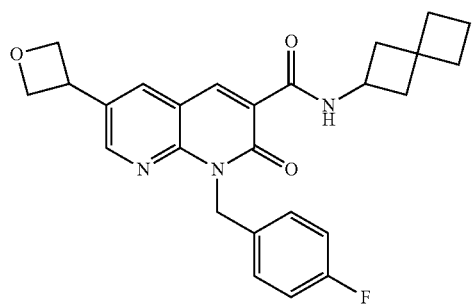 [SMILES: O=C(NC1CC2(CCC2)C1)c1cc2cc(C3COC3)cnc2n(Cc2ccc(F)cc2)c1=O]

Preparation of 1-(4-fluorobenzyl)-6-(oxetan-3-yl)-2-oxo-N-(spiro[3.3]heptan-2-yl)-1,2-dihydro-1,8-naphthyridine-3-carboxamide

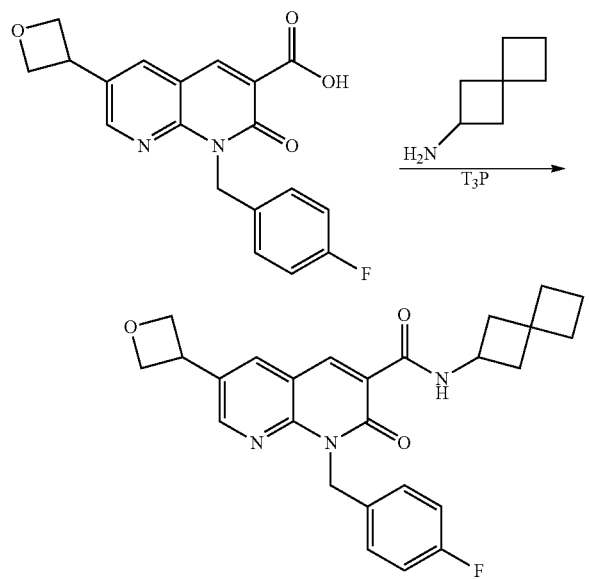

To a solution of 1-[(4-fluorophenyl)methyl]-6-(oxetan-3-yl)-2-oxo-1,8-naphthyridine-3-carboxylic acid (18 mg, 50.80 μmol, 1 eq) and spiro[3.3]heptan-2-amine (9.00 mg, 60.96 μmol, 1.2 eq, HCl) in DMF (0.5 mL) was added DIEA (39.39 mg, 304.80 μmol, 53.09 μL, 6 eq) and T3P (129.31 mg, 203.20 μmol, 120.85 μL, 50% purity, 4 eq) at 0° C. The mixture was stirred at 25° C. for 2 h. LCMS showed complete consumption of the starting material and formation of a new peak with desired mass.

The mixture was filtered, and the filtrate was purified by prep-HPLC (neutral condition) to produce 1-(4-fluorobenzyl)-6-(oxetan-3-yl)-2-oxo-N-(spiro[3.3]heptan-2-yl)-1,2-dihydro-1,8-naphthyridine-3-carboxamide (7.5 mg, 16.01 μmol) as a white solid.

$^1$H NMR (400 MHz, DMSO-$d_6$) δ=9.67 (br d, J=7.6 Hz, 1H), 8.92 (s, 1H), 8.75 (d, J=2.0 Hz, 1H), 8.68 (d, J=2.0 Hz, 1H), 7.32 (dd, J=5.8, 8.3 Hz, 2H), 7.10 (t, J=8.8 Hz, 2H), 5.68 (s, 2H), 4.97 (dd, J=6.1, 8.2 Hz, 2H), 4.71 (t, J=6.4 Hz, 2H), 4.42 (quin, J=7.6 Hz, 1H), 4.33-4.23 (m, 1H), 2.42-2.38 (m, 2H), 2.05 (br t, J=7.3 Hz, 2H), 1.97-1.90 (m, 4H), 1.84-1.75 (m, 2H). LCMS for product (ESI+): m/z 448.3 [M+H]+, Rt: 3.364 min.

LCMS Method

The gradient was 5-95% B in 1.0 min, 95-100% B in 0.8 min, 100-5% B in 0.01 min, and then held at 5% B for 0.24 min (1.0 m/min flow rate). Mobile phase A was 10 mM NH$_4$HCO$_3$ in water, mobile phase B was CH$_3$CN. The column used for the chromatography was Xbridge Shield RP18 2.1*50 mm, 5 μm column. Detection methods are diode array (DAD) and positive electrospray ionization (MS).

Example 103—Synthesis of (R)-1-(4-fluorobenzyl)-N-(1-(4-fluorophenyl)ethyl)-6-(oxetan-3-yl)-2-oxo-1,2-dihydro-1,8-naphthyridine-3-carboxamide (Compound 103)

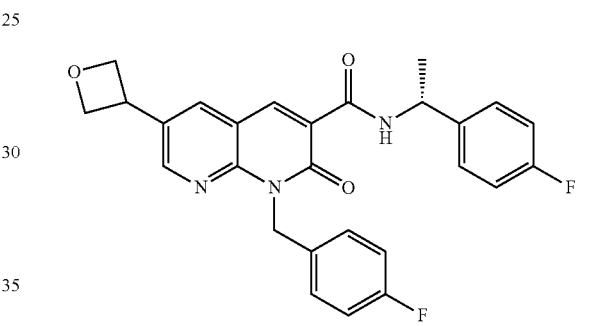

Preparation of (R)-1-(4-fluorobenzyl)-N-(1-(4-fluorophenyl)ethyl)-6-(oxetan-3-yl)-2-oxo-1,2-dihydro-1,8-naphthyridine-3-carboxamide

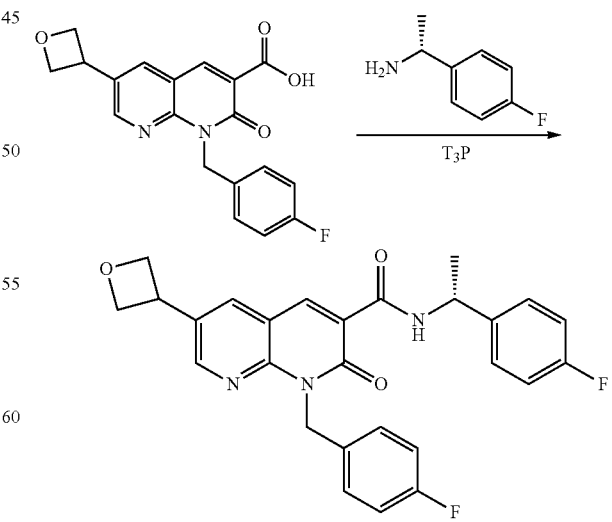

To a solution of 1-[(4-fluorophenyl)methyl]-6-(oxetan-3-yl)-2-oxo-1,8-naphthyridine-3-carboxylic acid (18 mg, 50.80 µmol, 1 eq) and (1R)-1-(4-fluorophenyl)ethanamine (8.48 mg, 60.96 µmol, 1.2 eq) in DMF (0.5 mL) was added DIEA (39.39 mg, 304.80 µmol, 53.09 µL, 6 eq) and T3P (129.31 mg, 203.20 µmol, 120.85 µL, 50% purity, 4 eq) at 0° C. The mixture was stirred at 25° C. for 2 h. LCMS showed complete consumption of the starting material and formation of a new peak with desired mass.

The mixture was filtered, and the filtrate was purified by prep-HPLC (neutral condition) to produce (R)-1-(4-fluorobenzyl)-N-(1-(4-fluorophenyl)ethyl)-6-(oxetan-3-yl)-2-oxo-1,2-dihydro-1,8-naphthyridine-3-carboxamide (10 mg, 21.03 µmol) was obtained as a white solid.

$^1$H NMR (400 MHz, DMSO-$d_6$) δ=9.92 (br d, J=7.8 Hz, 1H), 8.94 (s, 1H), 8.75 (d, J=1.9 Hz, 1H), 8.68 (d, J=2.0 Hz, 1H), 7.44 (dd, J=5.8, 8.3 Hz, 2H), 7.33 (dd, J=5.7, 8.2 Hz, 2H), 7.17 (t, J=8.8 Hz, 2H), 7.10 (t, J=8.8 Hz, 2H), 5.69 (br d, J=4.3 Hz, 2H), 5.17 (quin, J=6.9 Hz, 1H), 4.97 (dd, J=6.2, 8.2 Hz, 2H), 4.71 (t, J=6.3 Hz, 2H), 4.42 (quin, J=7.5 Hz, 1H), 1.50 (d, J=6.9 Hz, 3H). LCMS for product (ESI+): m/z 476.3 [M+H]$^+$, Rt: 3.243 min.

LCMS Method

The gradient was 5-95% B in 1.0 min, 95-100% B in 0.8 min, 100-5% B in 0.01 min, and then held at 5% B for 0.24 min (1.0 mL/min flow rate). Mobile phase A was 10 mM NH$_4$HCO$_3$ in water, mobile phase B was CH$_3$CN. The column used for the chromatography was Xbridge Shield RP18 2.1*50 mm, 5 µm column. Detection methods are diode array (DAD) and positive electrospray ionization (MS)

Example 104—Synthesis of (R)-6-bromo-1-(4-cyanobenzyl)-N-(1-(4-fluorophenyl)ethyl)-2-oxo-1,2-dihydro-1,8-naphthyridine-3-carboxamide (Compound 104)

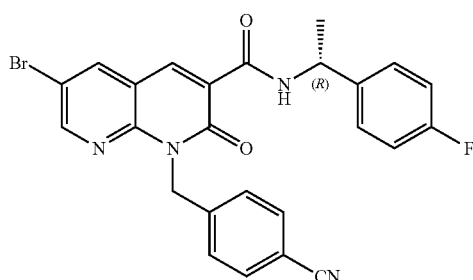

Step 1: Preparation of (R)-6-bromo-N-(1-(4-fluorophenyl)ethyl)-2-oxo-1,2-dihydro-1,8-naphthyridine-3-carboxamide

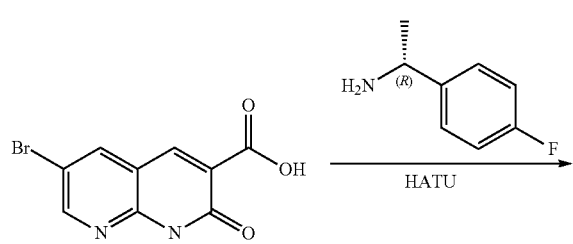

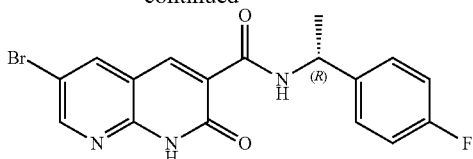

To a solution of 6-bromo-2-oxo-1H-1,8-naphthyridine-3-carboxylic acid (500 mg, 1.86 mmol, 1 eq) in DMF (4 mL) was added HATU (847.93 mg, 2.23 mmol, 1.2 eq) and DIEA (720.55 mg, 5.58 mmol, 1 mL, 3 eq) at 25° C. The mixture was stirred at 25° C. for 0.5 h, a solution of (1R)-1-(4-fluorophenyl)ethanamine (310.36 mg, 2.23 mmol, 1.2 eq) in DMF (1 mL) was added into the mixture at 25° C., the mixture was stirred at 25° C. for 2 h. LCMS showed starting material was consumed, desired product was detected. LCMS showed complete consumption of the starting material and formation of a new peak with desired mass. The mixture was filtered, and the resulting solid was dried was and triturated with in acetate (10 mL).

The solid was collected by filtration and purified by prep-HPLC (column: Waters Xbridge BEH C18 100*30 mm*10 µm; mobile phase: [water (10 mM NH$_4$HCO$_3$)-ACN]; B %: 35%-65%, 8 min) (R)-6-bromo-N-(1-(4-fluorophenyl)ethyl)-2-oxo-1,2-dihydro-1,8-naphthyridine-3-carboxamide (250 mg, 640.69 µmol) as a brown solid.

$^1$H NMR (400 MHz, DMSO-$d_6$) δ=13.13-12.92 (m, 1H), 10.00 (br d, J=7.4 Hz, 1H), 8.84-8.76 (m, 2H), 8.71 (d, J=2.1 Hz, 1H), 7.43 (dd, J=5.7, 8.3 Hz, 2H), 7.17 (br t, J=8.8 Hz, 2H), 5.16 (br t, J=7.0 Hz, 1H), 1.49 (d, J=6.9 Hz, 3H). LCMS for product (ESI+): m/z 390.0

LCMS Method

The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min(0.01-4.30 min).

Step 2: Preparation (R)-6-bromo-1-(4-cyanobenzyl)-N-(1-(4-fluorophenyl)ethyl)-2-oxo-1,2-dihydro-1,8-naphthyridine-3-carboxamide

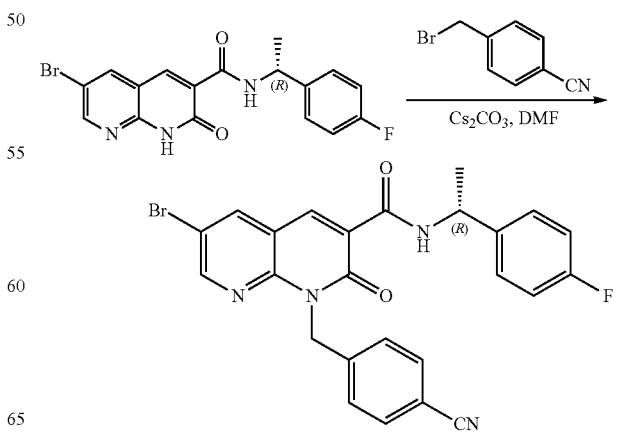

To a solution of 6-bromo-N-[(1R)-1-(4-fluorophenyl)ethyl]-2-oxo-1H-1,8-naphthyridine-3-carboxamide (130 mg, 333.16 µmol, 1 eq) in DMF (1.5 mL) was added K₂CO₃ (138.14 mg, 999.47 µmol, 3 eq) at 50° C. The mixture was stirred at 50° C. for 1 h, 4-(bromomethyl)benzonitrile (130.63 mg, 666.31 µmol, 2 eq) was added, the mixture was stirred at 50° C. for 2 h. LCMS showed complete consumption of the starting material and formation of a new peak with the desired mass.

The resulting solid was collected by filtration and triturated in methanol/dichloromethane (1:1, 5 mL) to produce (R)-6-bromo-1-(4-cyanobenzyl)-N-(1-(4-fluorophenyl)ethyl)-2-oxo-1,2-dihydro-1,8-naphthyridine-3-carboxamide (24.4 mg, 47.71 µmol) as a white solid.

$^1$H NMR (400 MHz, DMSO-d$_6$) δ=9.77 (d, J=7.5 Hz, 1H), 8.91 (s, 1H), 8.87-8.79 (m, 2H), 7.75 (d, J=8.3 Hz, 2H), 7.48-7.38 (m, 4H), 7.17 (t, J=8.9 Hz, 2H), 5.73 (br d, J=3.2 Hz, 2H), 5.17 (t, J=7.3 Hz, 1H), 1.48 (d, J=6.8 Hz, 3H). LCMS for product (ESI+): m/z 505.0, 507.1 [M+H]+, Rt: 2.915 min.

LCMS Method

The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF₃CO₂H in water, mobile phase B was 0.018% CF₃CO₂H in CH₃CN. The column used for the chromatography was a 2.0×50 mm phenomenex Luna-C18 column (5 µm particles). Detection methods are diode array (DAD) and evaporative light scattering (ELSD) detection as well as positive electrospray ionization (MS).

Example 105—Synthesis of N-(4-fluorobenzyl)-6-(4-methoxyphenyl)-1-(2-morpholinoethyl)-2-oxo-1,2-dihydro-1,8-naphthyridine-3-carboxamide (Compound 105)

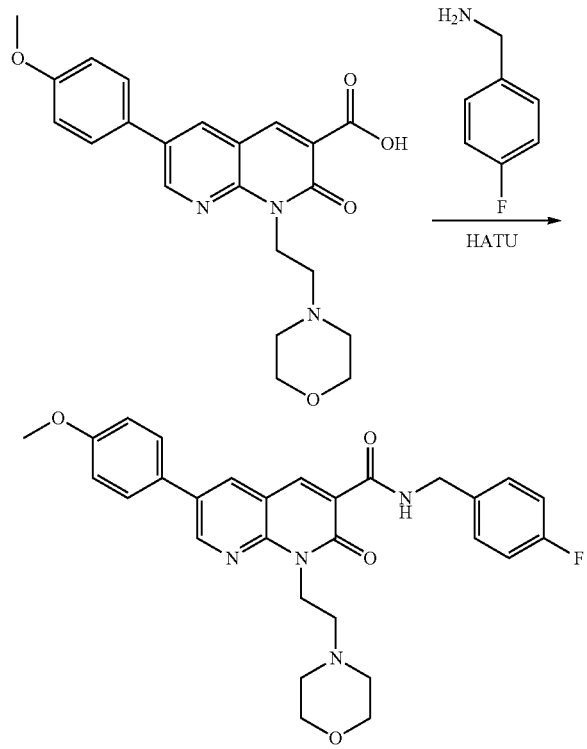

Compound 105

To a solution of 6-(4-methoxyphenyl)-1-(2-morpholinoethyl)-2-oxo-1,8-naphthyridine-3-carboxylic acid (70 mg, 170.97 µmol, 1 eq) in DMF (1 mL) was added HATU (130.01 mg, 341.94 µmol, 2 eq), DIEA (66.29 mg, 512.90 µmol, 89.34 µL, 3 eq) at 20° C. (4-fluorophenyl)methanamine (25.67 mg, 205.16 µmol, 23.34 µL, 1.2 eq) was added into the mixture at 20° C., the mixture was stirred at 20° C. for 1 h. LCMS showed complete consumption of the starting material and formation of a new peak with the desired mass. The mixture was filtered and the filtrate was purified by prep-HPLC (column: Waters Xbridge BEH C18 100*25 mm*5 um; mobile phase: [water (10 mM NH₄HCO₃)-ACN]; B %: 50%-85%, 8 min) to afford the desired product (30 mg, 56.51 µmol) as a light yellow solid.

$^1$H NMR (400 MHz, CDCl₃) 10.18 (br t, J=5.6 Hz, 1H), 8.97 (s, 1H), 8.91 (d, J=2.3 Hz, 1H), 8.18 (d, J=2.3 Hz, 1H), 7.57 (d, J=8.7 Hz, 2H), 7.37 (dd, J=5.5, 8.3 Hz, 2H), 7.10-6.99 (m, 4H), 4.79 (t, J=7.1 Hz, 2H), 4.67 (d, J=5.7 Hz, 2H), 3.89 (s, 3H), 3.72-3.66 (m, 4H), 2.75 (br t, J=7.2 Hz, 2H), 2.63 (br s, 4H).

LCMS for product (ESI+): m/z 517.1 [M+H]⁺, Rt: 2.177 min.

LC/MS (The gradient was 5% B in 0.40 min and 5-95% B at 0.4-3.0 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) as well as positive electrospray ionization. MS range was 100-1000.

Additional Compounds prepared by following or adapting the procedures described herein include:

6-(4-fluorophenyl)-2-oxo-1-(pyridin-2-ylmethyl)-N-(spiro[3.3]heptan-2-yl)-1,2-dihydro-1,8-naphthyridine-3-carboxamide (Compound 106)

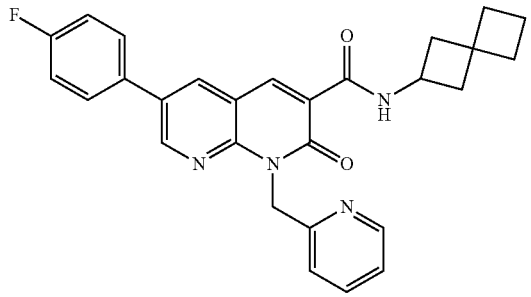 [SMILES: O=C(NC1CC2(CCC2)C1)c1cc2cc(-c3ccc(F)cc3)cnc2n(Cc2ccccn2)c1=O]

6-bromo-N-(1-(4-fluorophenyl)ethyl)-2-oxo-1-(pyridin-3-ylmethyl)-1,2-dihydro-1,8-naphthyridine-3-carboxamide (Compound 107)

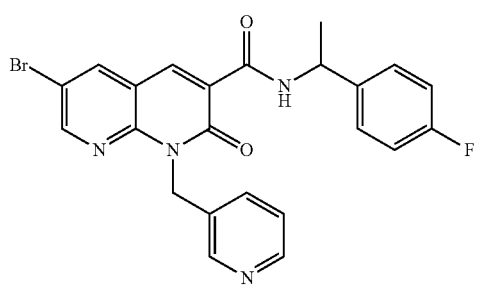 [SMILES: CC(NC(=O)c1cc2cc(Br)cnc2n(Cc2cccnc2)c1=O)c1ccc(F)cc1]

385

(R)—N-(1-(4-cyanophenyl)ethyl)-1-((5-fluoropyridin-2-yl)methyl)-6-isopropyl-2-oxo-1,2-dihydro-1,8-naphthyridine-3-carboxamide (Compound 108)

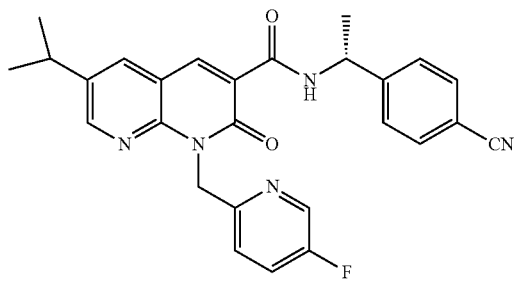 [SMILES: CC(C)c1cnc2c(c1)cc(C(=O)N[C@H](C)c1ccc(C#N)cc1)c(=O)n2Cc1ccc(F)cn1]

6-(4-fluorophenyl)-4-hydroxy-N-((1s,4s)-4-methylcyclohexyl)-1-(2-morpholinoethyl)-2-oxo-1,2-dihydro-1,8-naphthyridine-3-carboxamide (Compound 109)

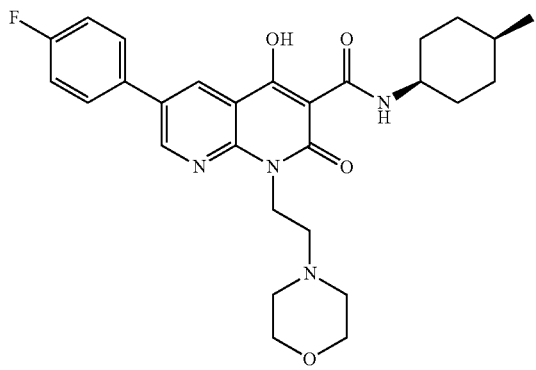 [SMILES: C[C@H]1CC[C@@H](NC(=O)c2c(O)c3cc(-c4ccc(F)cc4)cnc3n(CCN3CCOCC3)c2=O)CC1]

Example 110—Synthesis of 6-(4-fluorophenyl)-4-hydroxy-N-(3-methylbicyclo[1.1.1]pentan-1-yl)-1-(2-morpholinoethyl)-2-oxo-1,2-dihydro-1,8-naphthyridine-3-carboxamide (Compound 110)

386

Preparation of 6-(4-fluorophenyl)-4-hydroxy-N-(3-methylbicyclo[1.1.1]pentan-1-yl)-1-(2-morpholinoethyl)-2-oxo-1,2-dihydro-1,8-naphthyridine-3-carboxamide

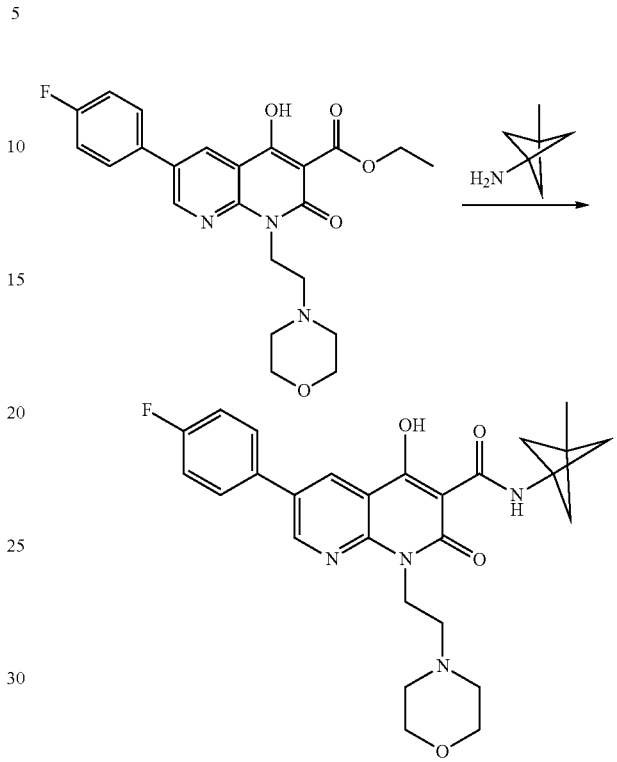

To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (54.09 mg, 418.49 μmol, 72.89 μL, 4 eq) and 3-methylbicyclo[1.1.1]pentan-1-amine (16.78 mg, 125.55 μmol, 1.2 eq, HCl). The mixture was stirred at 120° C. for 5 h. The mixture was concentrated to give crude product, which was triturated with methanol (2 mL). Then the mixture was filtered, the filter cake was dried to give the desired compound (39.5 mg, 80.20 μmol, 76.65% yield, 100% purity).

$^1$H NMR (400 MHz, CDCl$_3$) δ=1.29 (s, 3H), 2.08 (s, 6H), 2.51-2.80 (m, 6H), 3.71 (br s, 4H), 4.48-4.79 (m, 2H), 7.21 (br t, J=8.63 Hz, 2H), 7.58-7.67 (m, 2H), 8.60 (d, J=2.50 Hz, 1H), 8.88 (d, J=2.50 Hz, 1H), 10.46 (br d, J=4.50 Hz, 1H). LCMS for product (ESI+): m/z 493.1 (M+H)$^+$, Rt:2.530 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 111—Synthesis of N-(3,3-dimethylcyclobutyl)-6-(4-fluorophenyl)-4-hydroxy-1-(2-morpholinoethyl)-2-oxo-1,2-dihydro-1,8-naphthyridine-3-carboxamide (Compound 111)

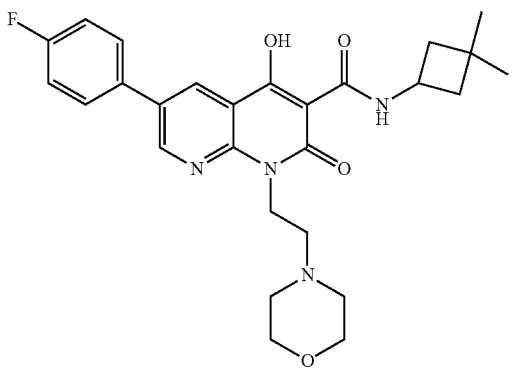 [SMILES: CC1(C)CC(NC(=O)c2c(O)c3cc(-c4ccc(F)cc4)cnc3n(CCN3CCOCC3)c2=O)C1]

Preparation of N-(3,3-dimethylcyclobutyl)-6-(4-fluorophenyl)-4-hydroxy-1-(2-morpholinoethyl)-2-oxo-1,2-dihydro-1,8-naphthyridine-3-carboxamide

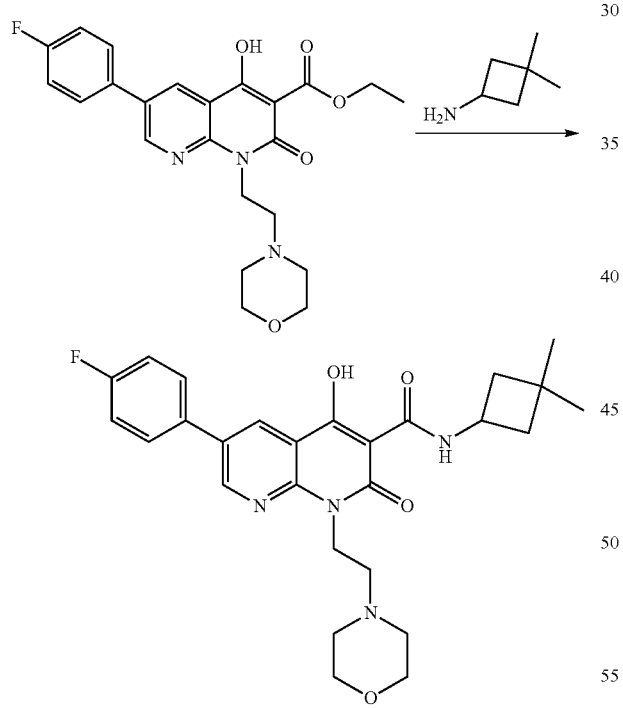

To a solution of 6-(4-fluorophenyl)-4-hydroxy-1-(2-morpholinoethyl)-2-oxo-1,8-naphthyridine-3-carboxylate (50 mg, 102.05 µmol, 1 eq, HCl) in toluene (1 mL) was added DIEA (52.76 mg, 408.21 µmol, 71.10 µL, 4 eq) and 3,3-dimethylcyclobutanamine (16.61 mg, 122.46 µmol, 1.2 eq, HCl). The mixture was stirred at 120° C. for 5 h. The mixture was concentrated to give crude product, which was triturated with methanol (2 mL). Then the mixture was filtered, the filter cake was dried to give the desired compound (31.3 mg, 63.29 mol, 62.02% yield, 100% purity).

$^1$H NMR (400 MHz, CDCl$_3$) δ=1.18 (s, 3H), 1.22 (s, 3H), 1.84-1.94 (m, 2H), 2.27-2.35 (m, 2H), 2.45-2.69 (m, 4H), 2.72 (br t, J=7.00 Hz, 2H), 3.71 (br s, 4H), 4.43-4.58 (m, 1H), 4.63-4.88 (m, 2H), 7.21 (t, J=8.57 Hz, 2H), 7.62 (dd, J=8.69, 5.19 Hz, 2H), 8.60 (d, J=2.50 Hz, 1H), 8.89 (d, J=2.38 Hz, 1H), 10.33 (br d, J=6.00 Hz, 1H). LCMS for product (ESI+): m/z 495.2 (M+H)$^+$, Rt:2.528 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 µm particles). Detection methods are diode array (DAD) as well as positive electrospray ionization.

Example 112—Synthesis of 6-(4-fluorophenyl)-4-hydroxy-1-(2-morpholinoethyl)-2-oxo-N-(spiro[2.3]hexan-5-yl)-1,2-dihydro-1,8-naphthyridine-3-carboxamide (Compound 112)

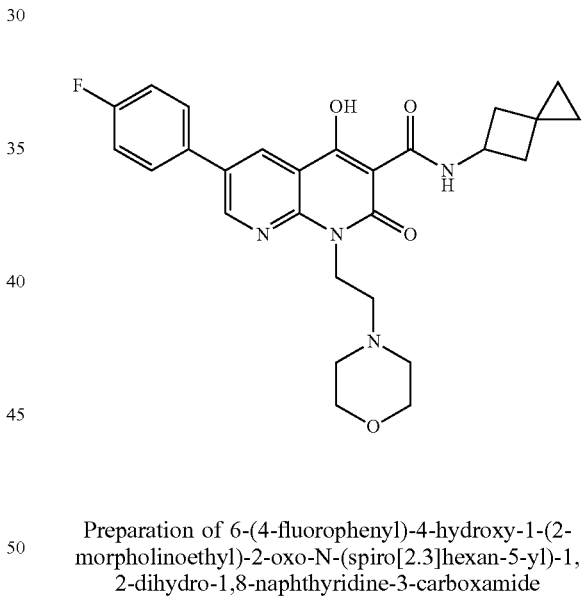

Preparation of 6-(4-fluorophenyl)-4-hydroxy-1-(2-morpholinoethyl)-2-oxo-N-(spiro[2.3]hexan-5-yl)-1,2-dihydro-1,8-naphthyridine-3-carboxamide

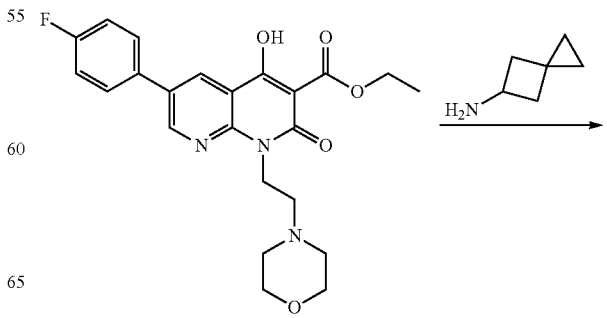

389
-continued

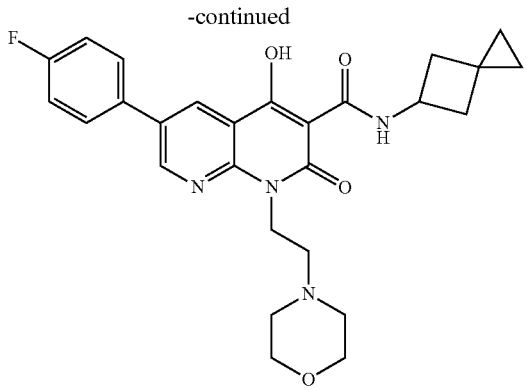

To a solution of 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (54.09 mg, 418.49 μmol, 72.89 uL, 4 eq) and spiro[2.3]hexan-5-amine (16.78 mg, 125.55 μmol, 1.2 eq, HCl). The mixture was stirred at 120° C. for 5 h. The mixture was concentrated to give the crude product, which was triturated with methanol (2 mL). Then the mixture was filtered, the filter cake was dried to give the desired compound (36.5 mg, 74.11 μmol, 70.83% yield, 100% purity).

$^1$H NMR (400 MHz, CDCl$_3$) δ=0.43-0.59 (m, 4H), 2.36-2.48 (m, 4H), 2.54-2.78 (m, 6H), 3.72 (br s, 4H), 4.57-4.93 (m, 3H), 7.19-7.24 (m, 2H), 7.58-7.68 (m, 2H), 8.60 (d, J=2.50 Hz, 1H), 8.89 (d, J=2.50 Hz, 1H), 10.34-10.56 (m, 1H). LCMS for product (ESI+): m/z 493.1 (M+H)$^+$, Rt:2.480 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 113—Synthesis of 6-(4-fluorophenyl)-4-hydroxy-N-((1s,3s)-3-methylcyclobutyl)-1-(2-morpholinoethyl)-2-oxo-1,2-dihydro-1,8-naphthyridine-3-carboxamide (Compound 113)

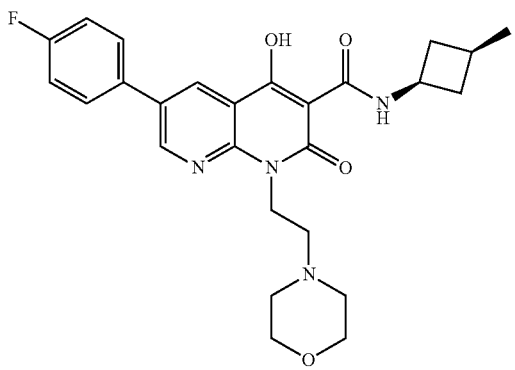

390
Preparation of 6-(4-fluorophenyl)-4-hydroxy-N-((1s,3s)-3-methylcyclobutyl)-1-(2-morpholinoethyl)-2-oxo-1,2-dihydro-1,8-naphthyridine-3-carboxamide

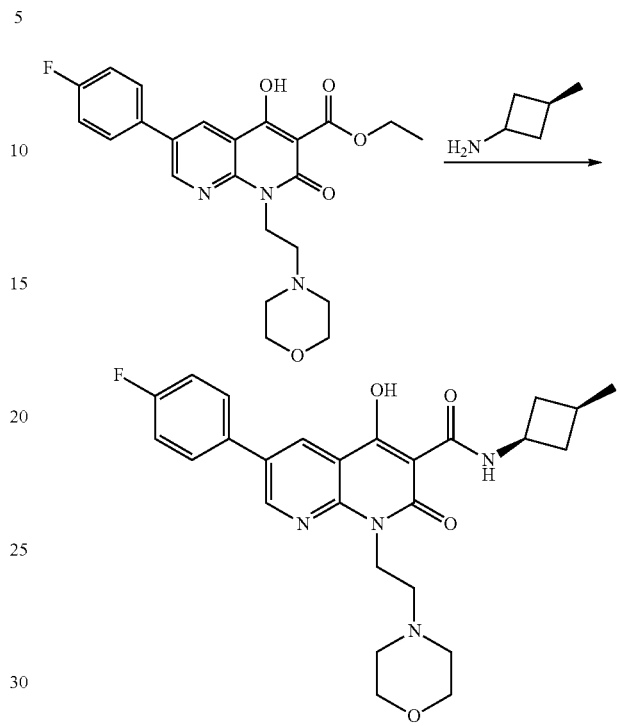

To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (54.09 mg, 418.49 μmol, 72.89 μL, 4 eq) and 3-methylcyclobutanamine (15.27 mg, 125.55 mol, 1.2 eq, HCl). The mixture was stirred at 120° C. for 5 h. The mixture was concentrated to give crude product, which was triturated with methanol (2 mL). Then the mixture was filtered, the filter cake was dried to give the desired compound (31.1 mg, 64.27 μmol, 61.43% yield, 99.3% purity) as a yellow solid.

$^1$H NMR (400 MHz, CDCl$_3$) δ=1.13 (d, J=6.63 Hz, 3H), 1.61-1.76 (m, 2H), 2.06-2.23 (m, 1H), 2.41-2.81 (m, 8H), 3.71 (br s, 4H), 4.20-4.46 (m, 1H), 4.69 (br t, J=6.44 Hz, 2H), 7.21 (t, J=8.63 Hz, 2H), 7.58-7.68 (m, 2H), 8.60 (d, J=2.38 Hz, 1H), 8.88 (d, J=2.50 Hz, 1H), 10.13-10.43 (m, 1H). LCMS for product (ESI+): m/z 481.1 (M+H)$^+$, Rt:2.448 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 114—Synthesis of 6-(4-fluorophenyl)-4-hydroxy-N-((1r,3r)-3-methylcyclobutyl)-1-(2-morpholinoethyl)-2-oxo-1,2-dihydro-1,8-naphthyridine-3-carboxamide (Compound 114)

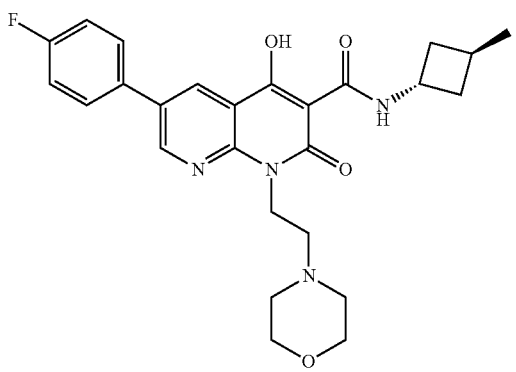 [SMILES: C[C@H]1C[C@H](NC(=O)c2c(O)c3cc(-c4ccc(F)cc4)cnc3n(CCN3CCOCC3)c2=O)C1]

Preparation of 6-(4-fluorophenyl)-4-hydroxy-N-((1r,3r)-3-methylcyclobutyl)-1-(2-morpholinoethyl)-2-oxo-1,2-dihydro-1,8-naphthyridine-3-carboxamide

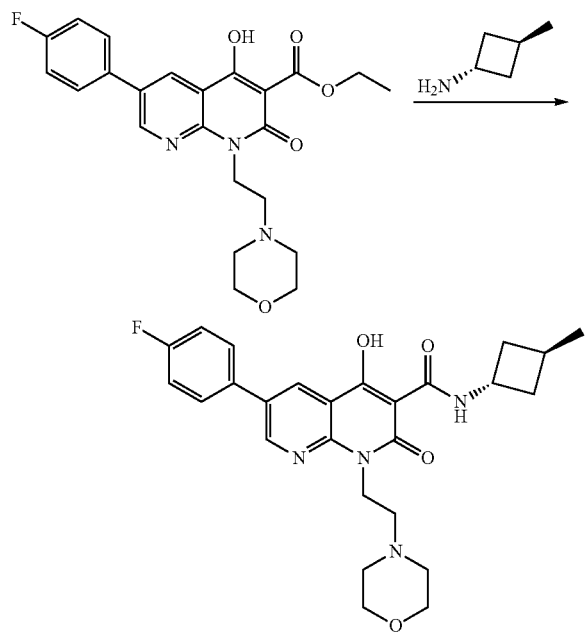

To a solution of ethyl 6-(4-fluorophenyl)-4-hydroxy-1-(2-morpholinoethyl)-2-oxo-1,8-naphthyridine-3-carboxylate (50 mg, 104.62 µmol, 1 eq, HCl) in toluene (1 mL) was added DIEA (54.09 mg, 418.49 µmol, 72.89 uL, 4 eq) and 3-methylcyclobutanamine (15.27 mg, 125.55 mol, 1.2 eq, HCl). The mixture was stirred at 120° C. for 5 h. The mixture was concentrated to give crude product, which was triturated with methanol (2 mL). Then the mixture was filtered, the filter cake was dried to give the desired compound (27.9 mg, 58.06 µmol, 55.50% yield, 100% purity).

$^1$H NMR (400 MHz, CDCl$_3$) δ=1.22 (d, J=7.00 Hz, 3H), 2.08-2.18 (m, 2H), 2.23-2.34 (m, 2H), 2.40-2.54 (m, 1H), 2.58-2.81 (m, 6H), 3.71 (br s, 4H), 4.67 (dq, J=14.66, 7.29 Hz, 3H), 7.17-7.23 (m, 2H), 7.59-7.65 (m, 2H), 8.60 (d, J=2.50 Hz, 1H), 8.89 (d, J=2.50 Hz, 1H), 10.40 (br d, J=6.88 Hz, 1H). LCMS for product (ESI+): m/z 481.1 (M+H)$^+$, Rt:2.448 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 115—Synthesis of N-(bicyclo[2.1.1]hexan-1-yl)-6-(4-fluorophenyl)-4-hydroxy-1-(2-morpholinoethyl)-2-oxo-1,2-dihydro-1,8-naphthyridine-3-carboxamide (Compound 115)

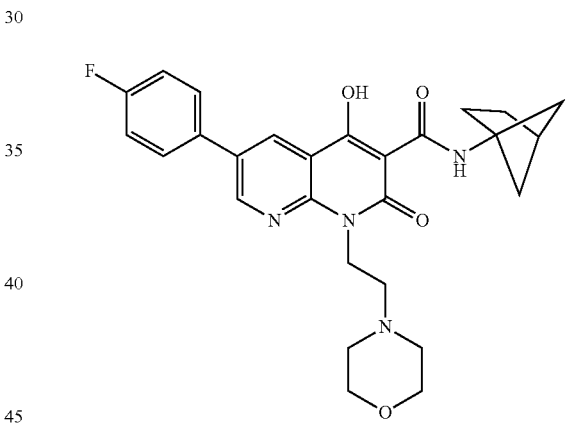

Preparation of N-(bicyclo[2.1.1]hexan-1-yl)-6-(4-fluorophenyl)-4-hydroxy-1-(2-morpholinoethyl)-2-oxo-1,2-dihydro-1,8-naphthyridine-3-carboxamide

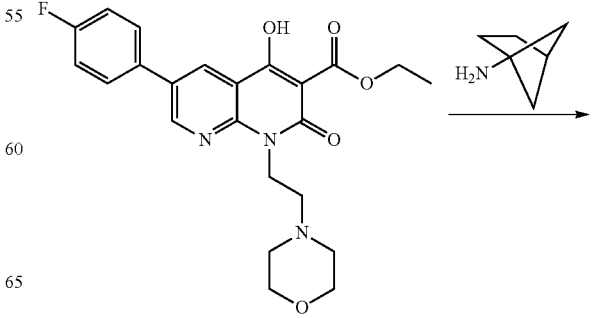

-continued

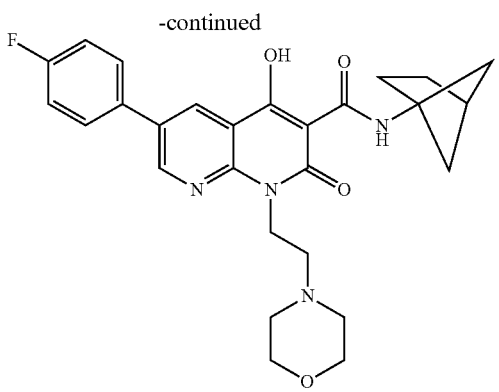

To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (54.09 mg, 418.49 μmol, 72.89 uL, 4 eq) and bicyclo[2.1.1]hexan-1-amine (16.78 mg, 125.55 μmol, 1.2 eq, HCl). The mixture was stirred at 120° C. for 3 h. The mixture was concentrated to give crude product, which was triturated with methanol (2 mL). Then the mixture was filtered, the filter cake was dried to give the desired compound (30.5 mg, 61.92 mol, 59.19% yield, 100% purity).

$^1$H NMR (400 MHz, CDCl$_3$) δ=1.58-1.62 (m, 2H), 1.72-1.81 (m, 2H), 1.91-2.01 (m, 4H), 2.46 (br s, 1H), 2.53-2.95 (m, 6H), 3.72 (br s, 4H), 4.70 (br d, J=1.88 Hz, 2H), 7.21 (t, J=8.57 Hz, 2H), 7.63 (dd, J=8.63, 5.13 Hz, 2H), 8.61 (d, J=2.38 Hz, 1H), 8.88 (d, J=2.38 Hz, 1H), 10.41-10.66 (m, 1H). LCMS for product (ESI+): m/z 493.2 (M+H)$^+$, Rt:2.526 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 116—Synthesis of N-(bicyclo[2.2.2]octan-1-yl)-6-(4-fluorophenyl)-4-hydroxy-1-(2-morpholinoethyl)-2-oxo-1,2-dihydro-1,8-naphthyridine-3-carboxamide (Compound 116)

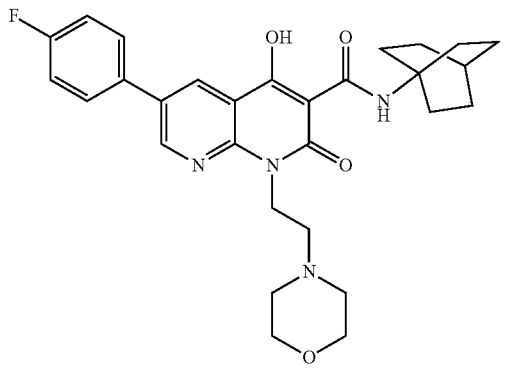 [SMILES: O=C(NC12CCC(CC1)CC2)c1c(O)c2cc(-c3ccc(F)cc3)cnc2n(CCN2CCOCC2)c1=O]

Preparation of N-(bicyclo[2.2.2]octan-1-yl)-6-(4-fluorophenyl)-4-hydroxy-1-(2-morpholinoethyl)-2-oxo-1,2-dihydro-1,8-naphthyridine-3-carboxamide

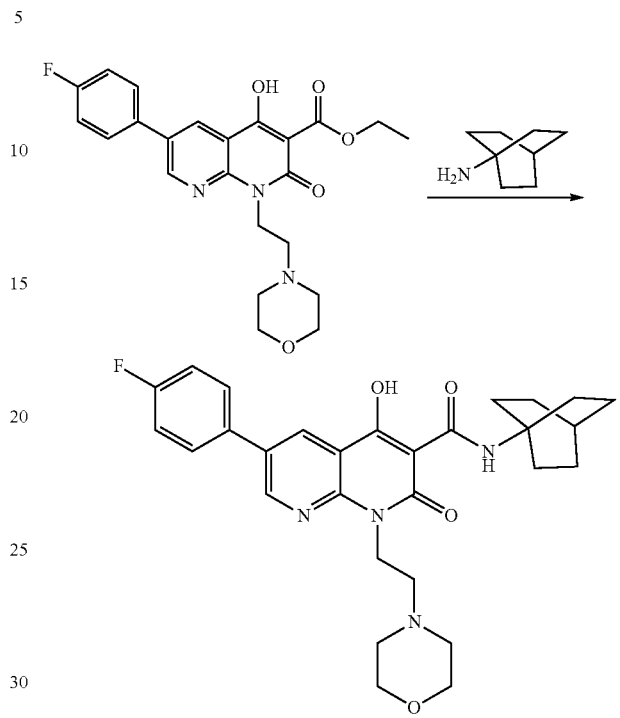

To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (54.09 mg, 418.49 μmol, 72.89 uL, 4 eq) and bicyclo[2.2.2]octan-1-amine (20.30 mg, 125.55 μmol, 1.2 eq, HCl). The mixture was stirred at 120° C. for 5 h. The mixture was concentrated to give crude product, which was triturated with methanol (2 mL). Then the mixture was filtered, the filter cake was dried to give the desired compound (21.4 mg, 39.34 mol, 37.60% yield, 95.7% purity).

$^1$H NMR (400 MHz, CDCl$_3$) δ=1.62-1.66 (m, 1H), 1.69-1.78 (m, 6H), 1.96-2.08 (m, 6H), 2.57-2.81 (m, 6H), 3.70 (br s, 4H), 4.55-4.76 (m, 2H), 7.19-7.23 (m, 2H), 7.59-7.65 (m, 2H), 8.59 (d, J=2.50 Hz, 1H), 8.87 (d, J=2.50 Hz, 1H), 10.15 (br s, 1H). LCMS for product (ESI+): m/z 521.2 (M+H)$^+$, Rt:2.646 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 117—Synthesis of 6-(4-fluorophenyl)-4-hydroxy-N-(1-hydroxy-2-methylpropan-2-yl)-1-(2-morpholinoethyl)-2-oxo-1,2-dihydro-1,8-naphthyridine-3-carboxamide (Compound 117)

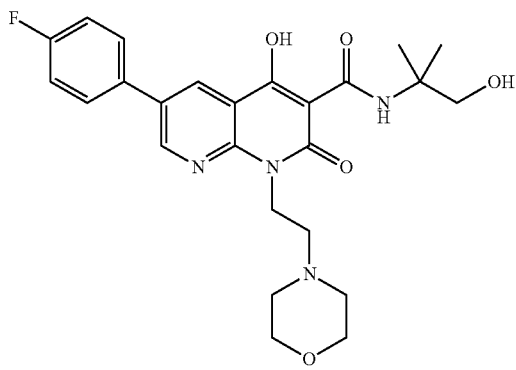 [SMILES: CC(C)(CO)NC(=O)c1c(O)c2cc(-c3ccc(F)cc3)cnc2n(CCN2CCOCC2)c1=O]

Preparation of 6-(4-fluorophenyl)-4-hydroxy-N-(1-hydroxy-2-methylpropan-2-yl)-1-(2-morpholinoethyl)-2-oxo-1,2-dihydro-1,8-naphthyridine-3-carboxamide

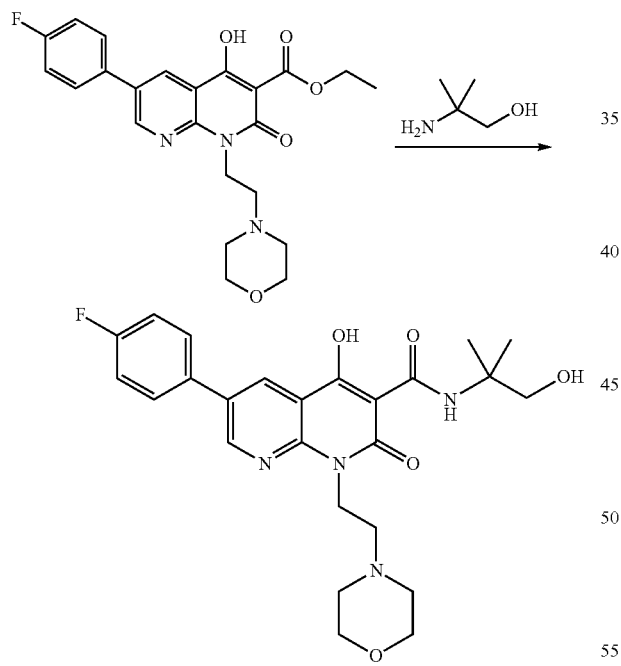

To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (40.56 mg, 313.86 μmol, 54.67 uL, 3 eq) and 2-amino-2-methyl-propan-1-ol (11.19 mg, 125.54 μmol, 11.98 μL, 1.2 eq). The mixture was stirred at 120° C. for 10 h. The mixture was concentrated to give crude product, which was triturated with methanol (2 mL). Then the mixture was filtered, the filter cake was dried to give the desired compound (26.3 mg, 51.13 mol, 48.87% yield, 94.2% purity).

$^1$H NMR (400 MHz, CDCl$_3$) δ=1.47-1.48 (s, 6H), 2.53-2.82 (m, 6H), 3.62-3.87 (m, 7H), 4.68 (br d, J=6.50 Hz, 2H), 7.19-7.25 (m, 2H), 7.59-7.65 (m, 2H), 8.59 (d, J=2.38 Hz, 1H), 8.89 (d, J=2.50 Hz, 1H), 10.59 (br s, 1H). LCMS for product (ESI+): m/z 485.1 (M+H)$^+$, Rt:2.241 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 118—Synthesis of N-(tert-butyl)-6-(4-fluorophenyl)-4-hydroxy-1-(2-morpholinoethyl)-2-oxo-1,2-dihydro-1,8-naphthyridine-3-carboxamide (Compound 118)

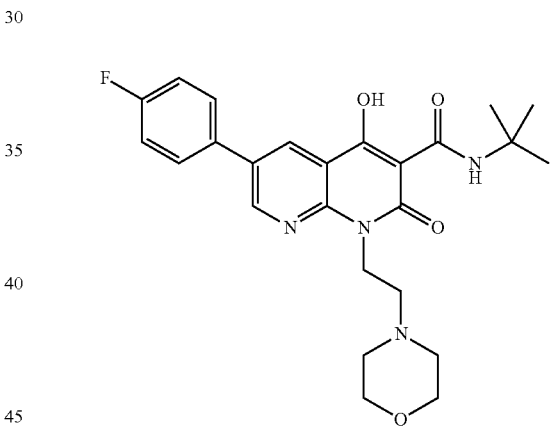

Preparation of N-(tert-butyl)-6-(4-fluorophenyl)-4-hydroxy-1-(2-morpholinoethyl)-2-oxo-1,2-dihydro-1,8-naphthyridine-3-carboxamide

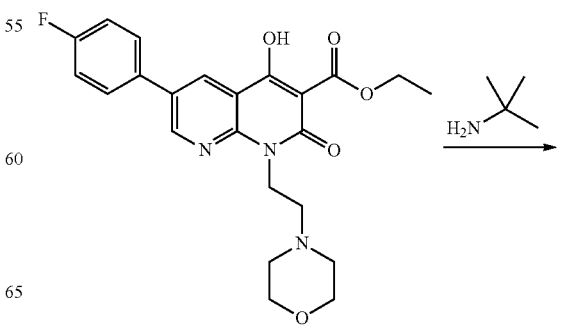

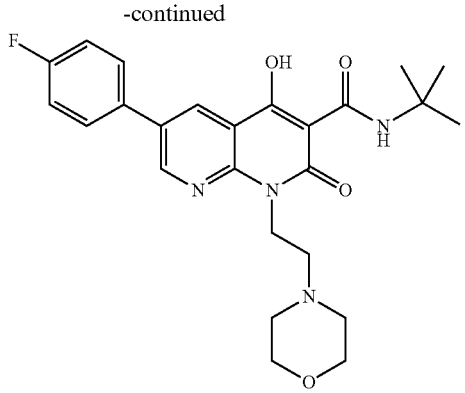

To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (40.56 mg, 313.86 μmol, 54.67 uL, 3 eq) and 2-methylpropan-2-amine (9.18 mg, 125.54 mol, 13.19 uL, 1.2 eq). The mixture was stirred at 120° C. for 10 h. The mixture was concentrated to give crude product, which was triturated with methanol (2 mL). Then the mixture was filtered, the filter cake was dried to give the desired compound (28.2 mg, 58.99 mol, 56.38% yield, 98% purity).

$^1$H NMR (400 MHz, CDCl$_3$) δ=1.52 (s, 9H), 2.56-2.78 (m, 6H), 3.71 (br s, 4H), 4.68 (br t, J=6.13 Hz, 2H), 7.19-7.24 (m, 2H), 7.60-7.65 (m, 2H), 8.60 (d, J=2.50 Hz, 1H), 8.87 (d, J=2.50 Hz, 1H), 10.23-10.40 (m, 1H). LCMS for product (ESI+): m/z 469.1 (M+H)$^+$, Rt:2.448 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 μm particles). Detection methods are diode array (DAD) as well as positive electrospray ionization.

Example 119—Synthesis of methyl 2-(6-(4-fluorophenyl)-4-hydroxy-1-(2-morpholinoethyl)-2-oxo-1,2-dihydro-1,8-naphthyridine-3-carboxamido)-2-methylpropanoate (Compound 119)

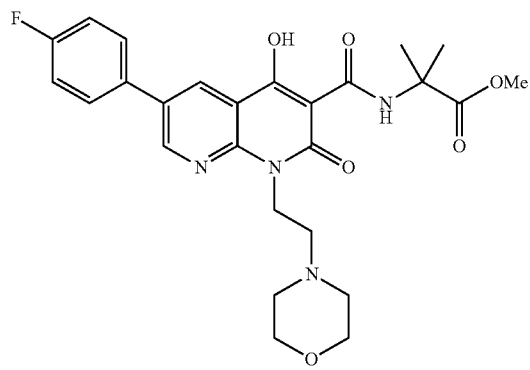 [SMILES: COC(=O)C(C)(C)NC(=O)c1c(O)c2cc(-c3ccc(F)cc3)cnc2n(CCN2CCOCC2)c1=O]

Preparation of methyl 2-(6-(4-fluorophenyl)-4-hydroxy-1-(2-morpholinoethyl)-2-oxo-1,2-dihydro-1,8-naphthyridine-3-carboxamido)-2-methylpropanoate

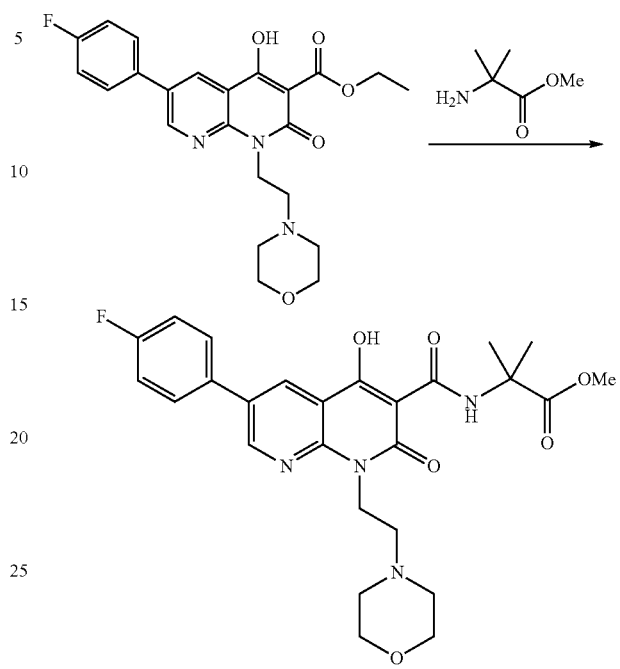

To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (40.56 mg, 313.86 μmol, 54.67 uL, 3 eq) and methyl 2-amino-2-methyl-propanoate (19.28 mg, 125.54 μmol, 11.98 μL, 1.2 eq, HCl). The mixture was stirred at 120° C. for 5 h. The mixture was concentrated to give crude product, which was triturated with methanol (2 mL). Then the mixture was filtered, the filter cake was dried to give the desired compound (35 mg, 68.29 μmol, 65.27% yield).

$^1$H NMR (400 MHz, CDCl$_3$) δ=1.68 (s, 6H) 2.49-2.76 (m, 6H) 3.71 (br s, 4H) 3.79 (s, 3H) 4.53-4.86 (m, 2H) 7.19-7.23 (m, 2H) 7.62 (dd, J=8.63, 5.25 Hz, 2H) 8.59 (d, J=2.50 Hz, 1H) 8.89 (d, J=2.38 Hz, 1H) 10.64 (br s, 1H).

Example 120—Synthesis of 2-(6-(4-fluorophenyl)-4-hydroxy-1-(2-morpholinoethyl)-2-oxo-1,2-dihydro-1,8-naphthyridine-3-carboxamido)-2-methylpropanoic acid (Compound 120)

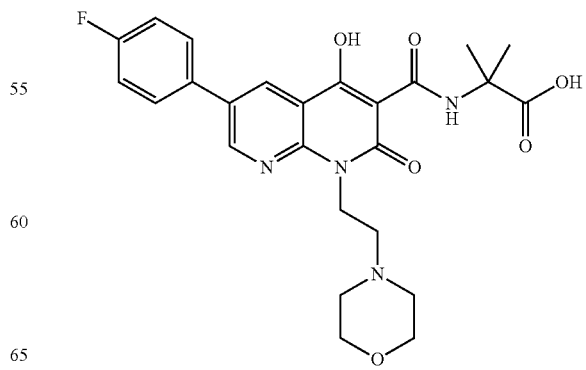

399

Preparation of 2-(6-(4-fluorophenyl)-4-hydroxy-1-(2-morpholinoethyl)-2-oxo-1,2-dihydro-1-S-naphthyridine-3-carboxamido)-2-methylpropanoic acid

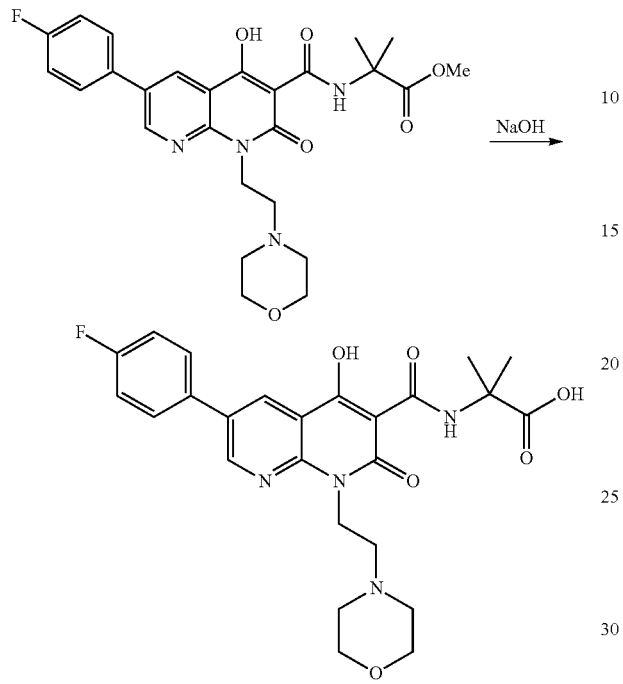

To a solution of methyl 2-(6-(4-fluorophenyl)-4-hydroxy-1-(2-morpholinoethyl)-2-oxo-1,2-dihydro-1,8-naphthyridine-3-carboxamido)-2-methylpropanoate (30 mg, 58.53 μmol, 1 eq) in DMSO (0.3 mL) was added NaOH (2 M, 0.1 mL, 3.42 eq). The mixture was stirred at 20° C. for 1 h. The mixture was filtered, the filtrate was purified by prep-HPLC (column: Phenomenex Luna 80*30 mm*3 um; mobile phase: [water (0.04% HCl)-ACN]; B %: 10%-50%, 8 min) to give the desired compound (8.1 mg, 15.55 μmol, 26.57% yield, 95.7% purity, HCl).

$^1$H NMR (400 MHz, CDCl$_3$) δ=1.58 (s, 6H), 3.08-3.23 (m, 2H), 3.41-3.54 (m, 2H), 3.59-3.75 (m, 4H), 3.90-4.09 (m, 2H), 4.78 (br s, 2H), 7.37 (t, J=8.82 Hz, 2H), 7.84-7.93 (m, 2H), 8.64 (d, J=2.13 Hz, 1H), 9.13 (d, J=2.50 Hz, 1H), 9.59-10.00 (m, 1H), 10.58 (s, 1H), 12.70-13.20 (m, 1H). LCMS for product (ESI+): m/z 499.1 (M+H)$^+$, Rt:2.196 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

400

Example 121—Synthesis of 6-(4-fluorophenyl)-4-hydroxy-N-(1-(hydroxymethyl)cyclohexyl)-1-(2-morpholinoethyl)-2-oxo-1,2-dihydro-1,8-naphthyridine-3-carboxamide (Compound 121)

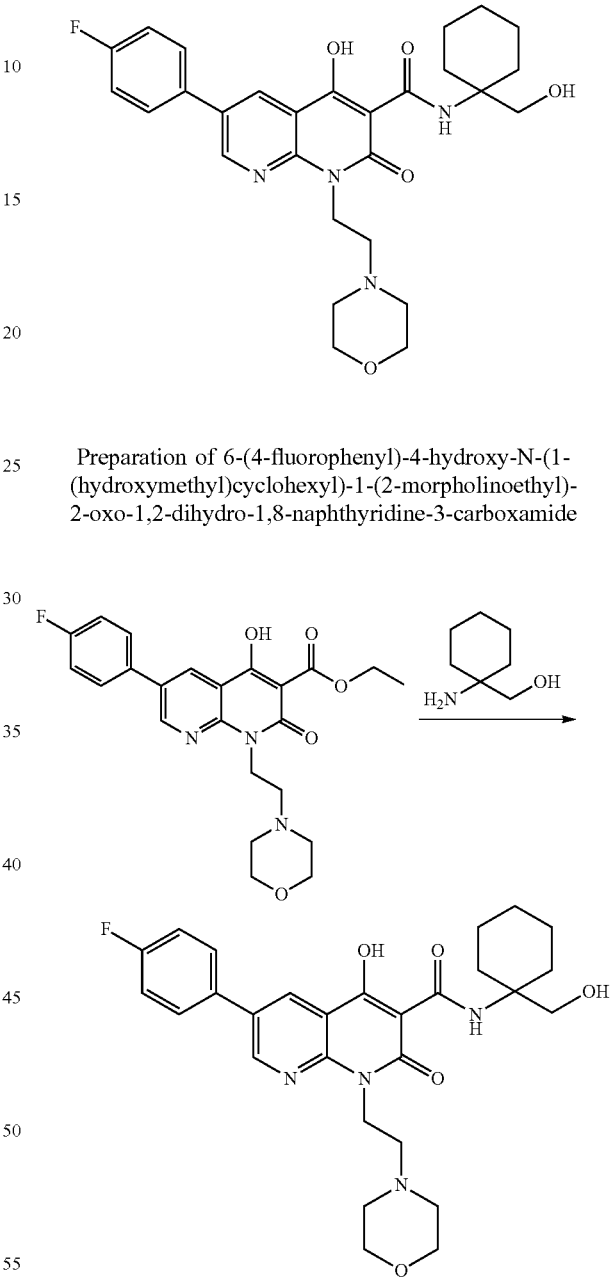

Preparation of 6-(4-fluorophenyl)-4-hydroxy-N-(1-(hydroxymethyl)cyclohexyl)-1-(2-morpholinoethyl)-2-oxo-1,2-dihydro-1,8-naphthyridine-3-carboxamide To a solution of ethyl 6-(4-fluorophenyl)-4-hydroxy-1-(2-morpholinoethyl)-2-oxo-1,8-naphthyridine-3-carboxylate (50 mg, 104.62 μmol, 1 eq, HCl) in toluene (1 mL) was added DIEA (40.56 mg, 313.86 μmol, 54.67 uL, 3 eq) and (1-aminocyclohexyl)methanol (20.80 mg, 125.54 μmol, 11.98 μL, 1.2 eq, HCl). The mixture was stirred at 120° C. for 10 h. The mixture was concentrated to give crude product, which was triturated with methanol (2 mL). Then the mixture was filtered, the filter cake was dried to give product, the product was diluted with MeOH (0.5 mL) then added HCl (31.79 mg, 313.86 µmol, 31.16 µL, 36% purity, 3 eq), the mixture was blow-dried and lyophilized to give the desired compound (17.6 mg, 32.83 µmol, 31.38% yield, 97.3% purity, HCl).

$^1$H NMR (400 MHz, CDCl$_3$) δ=1.22-1.54 (m, 3H), 1.55-1.75 (m, 5H), 2.17 (br d, J=12.47 Hz, 2H), 2.96-3.08 (m, 2H), 3.43 (br s, 2H), 3.72-3.92 (m, 4H), 3.98-4.08 (m, 2H), 4.25-4.47 (m, 2H), 5.05 (br t, J=6.17 Hz, 2H), 7.22 (t, J=8.50 Hz, 2H), 7.62 (dd, J=8.56, 5.26 Hz, 2H), 8.64 (s, 1H), 8.87 (d, J=1.96 Hz, 1H), 10.28 (br s, 1H), 12.94-13.38 (m, 1H). LCMS for product (ESI+): m/z 525.2 (M+H)$^+$, Rt:2.356 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 122—Synthesis of N-(bicyclo[1.1.1]pentan-1-yl)-6-(5-fluoropyridin-2-yl)-4-hydroxy-1-(2-morpholinoethyl)-2-oxo-1,2-dihydro-1,8-naphthyridine-3-carboxamide (Compound 122)

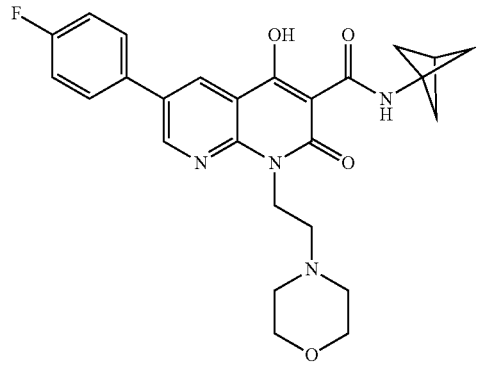 [SMILES: O=C(NC12CC(C1)C2)c1c(O)c2cc(-c3ccc(F)cc3)cnc2n(CCN2CCOCC2)c1=O]

Preparation of N-(bicyclo[1.1.1]pentan-1-yl)-6-(5-fluoropyridin-2-yl)-4-hydroxy-1-(2-morpholinoethyl)-2-oxo-1,2-dihydro-1,8-naphthyridine-3-carboxamide

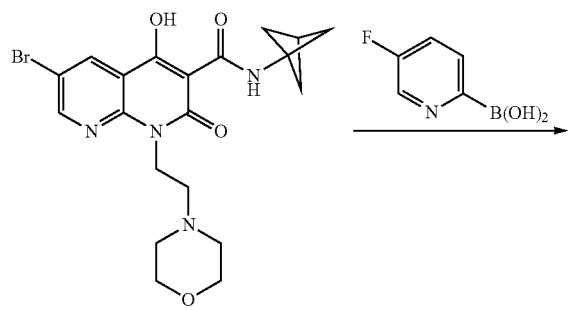

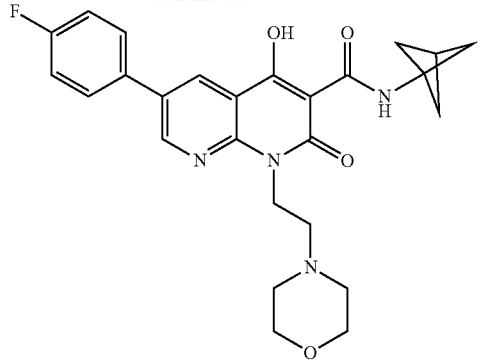

To a mixture of N-(bicyclo[1.1.1]pentan-1-yl)-6-bromo-4-hydroxy-1-(2-morpholinoethyl)-2-oxo-1,2-dihydro-1,8-naphthyridine-3-carboxamide (50 mg, 107.92 µmol, 1 eq) and (5-fluoro-2-pyridyl)boronic acid (18.25 mg, 129.50 µmol, 1.2 eq) in dioxane (1 mL) and H$_2$O (0.2 mL) was added K$_2$CO$_3$ (44.75 mg, 323.75 µmol, 3 eq) and Pd(dppf)Cl$_2$ (7.90 mg, 10.79 mol, 0.1 eq). The mixture was stirred at 100° C. for 2 h under N$_2$. The mixture was concentrated and purified by prep-HPLC (HCl condition) to give the desired compound (12 mg, 23.52 µmol, 21.80% yield, 94% purity).

$^1$H NMR (400 MHz, CDCl$_3$) δ=2.24 (s, 6H), 2.55 (s, 1H), 3.04 (br s, 2H), 3.29-3.50 (m, 2H), 3.63-3.82 (m, 2H), 3.94-4.09 (m, 2H), 4.27-4.47 (m, 2H), 5.05 (br s, 2H), 7.47-7.66 (m, 1H), 7.84 (br s, 1H), 8.60 (br s, 1H), 8.98 (s, 1H), 9.33 (br s, 1H), 10.21 (br s, 1H), 13.24-13.70 (m, 1H). LCMS for product (ESI+): m/z 480.1 (M+H)$^+$, Rt:2.331 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 µm particles). Detection methods are diode array (DAD) as well as positive electrospray ionization.

Example 123—Synthesis of N-(bicyclo[1.1.1]pentan-1-yl)-4-hydroxy-1-(2-morpholinoethyl)-2-oxo-6-(pyridin-3-yl)-1,2-dihydro-1,8-naphthyridine-3-carboxamide (Compound 123)

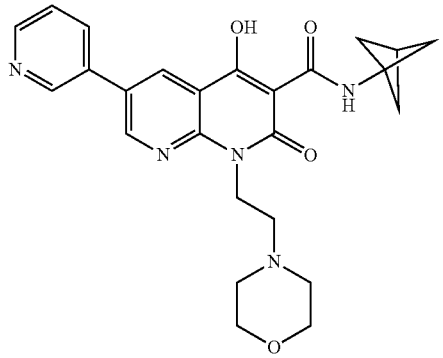 [SMILES: O=C(NC12CC(C1)C2)c1c(O)c2cc(-c3cccnc3)cnc2n(CCN2CCOCC2)c1=O]

403

Preparation of N-(bicyclo[1.1.1]pentan-1-yl)-4-hydroxy-1-(2-morpholinoethyl)-2-oxo-6-(pyridin-3-yl)-1,2-dihydro-1,8-naphthyridine-3-carboxamide

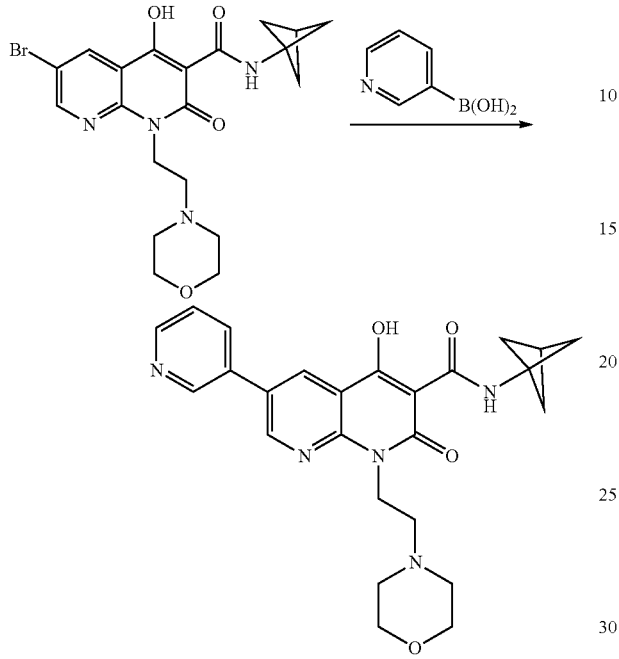

To a mixture of N-(bicyclo[1.1.1]pentan-1-yl)-6-bromo-4-hydroxy-1-(2-morpholinoethyl)-2-oxo-1,2-dihydro-1,8-naphthyridine-3-carboxamide (50 mg, 107.92 μmol, 1 eq) and 3-pyridylboronic acid (15.92 mg, 129.50 μmol, 1.2 eq) in dioxane (0.5 mL) and H₂O (0.1 mL) was added K₂CO₃ (44.75 mg, 323.75 μmol, 3 eq) and Pd(dppf)Cl₂ (7.90 mg, 10.79 μmol, 0.1 eq). The mixture was stirred at 100° C. for 12 h under N₂. The mixture was filtered and the filtrate was purified by prep-HPLC (HCl condition) to give the desired compound (20 mg, 43.34 μmol, 40.16% yield, 100% purity).

$^1$H NMR (400 MHz, CDCl$_3$) δ=2.18 (s, 6H), 2.56 (s, 1H), 3.12-3.23 (m, 2H), 3.50 (br s, 2H), 3.65-3.78 (m, 4H), 4.00 (br d, J=12.76 Hz, 2H), 4.80 (br t, J=6.13 Hz, 2H), 7.80 (dd, J=8.00, 5.25 Hz, 1H), 8.59 (br d, J=8.00 Hz, 1H), 8.78 (dd, J=5.07, 1.19 Hz, 1H), 8.85 (d, J=2.50 Hz, 1H), 9.25 (dd, J=7.38, 2.00 Hz, 2H), 10.45 (br s, 1H), 10.51-10.68 (m, 1H). LCMS for product (ESI+): m/z 462.2 (M+H)⁺, Rt:1.904 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 m particles). Detection methods are diode array (DAD) as well as positive electrospray ionization.

404

Example 124—Synthesis of N-(bicyclo[1.1.1]pentan-1-yl)-4-hydroxy-1-(2-morpholinoethyl)-2-oxo-6-(pyridin-4-yl)-1,2-dihydro-1,8-naphthyridine-3-carboxamide (Compound 124)

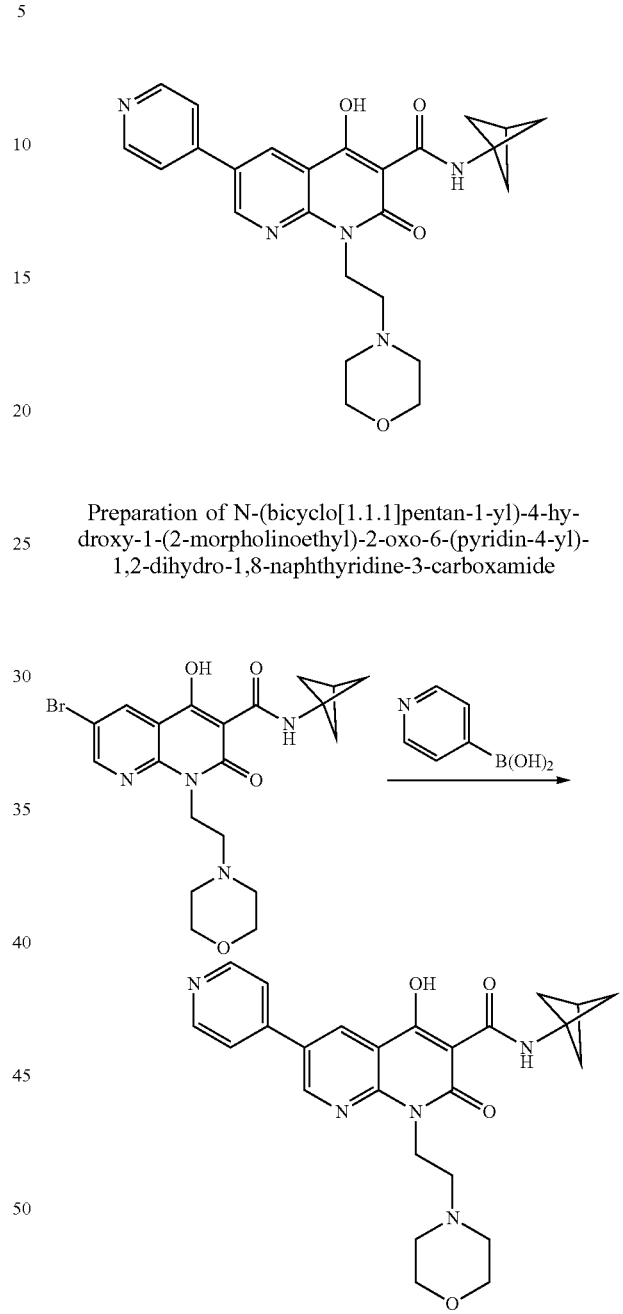

Preparation of N-(bicyclo[1.1.1]pentan-1-yl)-4-hydroxy-1-(2-morpholinoethyl)-2-oxo-6-(pyridin-4-yl)-1,2-dihydro-1,8-naphthyridine-3-carboxamide To a mixture of N-(bicyclo[1.1.1]pentan-1-yl)-6-bromo-4-hydroxy-1-(2-morpholinoethyl)-2-oxo-1,2-dihydro-1,8-naphthyridine-3-carboxamide (50 mg, 107.92 μmol, 1 eq) and 4-pyridylboronic acid (15.92 mg, 129.50 μmol, 1.2 eq) in dioxane (0.5 mL) and H₂O (0.1 mL) was added K₂CO₃ (44.75 mg, 323.75 μmol, 3 eq) and Pd(dppf)Cl₂ (7.90 mg, 10.79 μmol, 0.1 eq). The mixture was stirred at 100° C. for 2 h under N₂. The mixture was filtered and the filtrate was purified by prep-HPLC (HCl condition) to give the desired compound (30 mg, 65.00 mol, 60.24% yield, 100% purity).

$^1$H NMR (400 MHz, CDCl$_3$) δ=2.19 (s, 6H), 2.56 (s, 1H), 3.17 (br s, 2H), 3.45-3.54 (m, 2H), 3.67 (br d, J=11.38 Hz,

2H), 3.72-3.83 (m, 2H), 3.99 (br d, J=11.51 Hz, 2H), 4.81 (br t, J=6.07 Hz, 2H), 8.35 (br d, J=5.75 Hz, 2H), 8.91 (br d, J=6.25 Hz, 2H), 8.96 (d, J=2.38 Hz, 1H), 9.38 (d, J=2.50 Hz, 1H), 10.41 (br s, 1H), 10.89 (br d, J=8.88 Hz, 1H). LCMS for product (ESI+): m/z 462.1 (M+H)$^+$, Rt:1.810 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 125—Synthesis of N-(bicyclo[1.1.1]pentan-1-yl)-6-(cyclopent-1-en-1-yl)-4-hydroxy-1-(2-morpholinoethyl)-2-oxo-1,2-dihydro-1,8-naphthyridine-3-carboxamide (Compound 125)

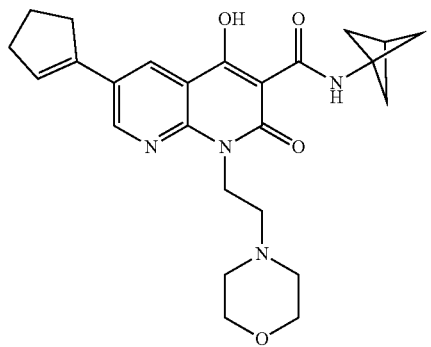 [SMILES: O=C(NC12CC(C1)C2)c1c(O)c2cc(C3=CCCC3)cnc2n(CCN2CCOCC2)c1=O]

Preparation of N-(bicyclo[1.1.1]pentan-1-yl)-6-(cyclopent-1-en-1-yl)-4-hydroxy-1-(2-morpholinoethyl)-2-oxo-1,2-dihydro-1,8-naphthyridine-3-carboxamide

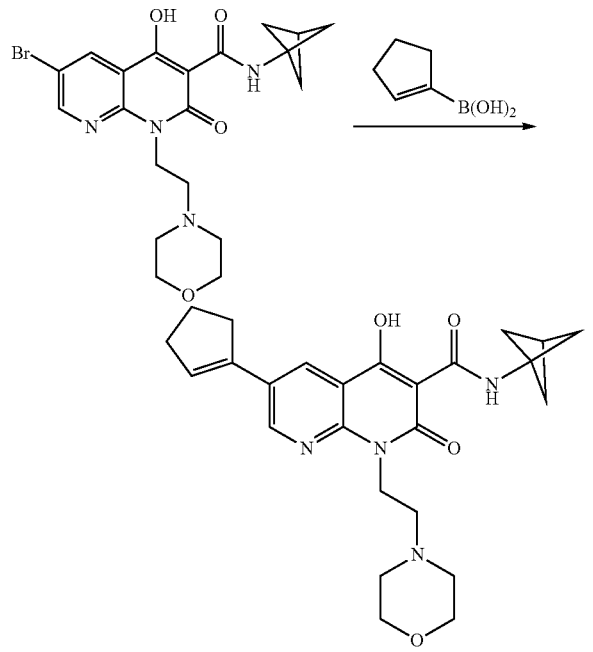

To a mixture of N-(bicyclo[1.1.1]pentan-1-yl)-6-bromo-4-hydroxy-1-(2-morpholinoethyl)-2-oxo-1,2-dihydro-1,8-naphthyridine-3-carboxamide (100 mg, 215.83 μmol, 1 eq) and cyclopenten-1-ylboronic acid (84.56 mg, 755.41 μmol, 3.5 eq) in dioxane (1 mL) and H$_2$O (0.2 mL) was added K$_2$CO$_3$ (89.49 mg, 647.49 μmol, 3 eq) and Pd(dppf)Cl$_2$ (15.79 mg, 21.58 μmol, 0.1 eq). The mixture was stirred at 50° C. for 2 h under N2. The mixture was filtered, the filtrate was concentrated. The residue was purified by prep-HPLC (HCl condition) to give the desired compound (55 mg, 116.95 μmol, 54.19% yield, 95.8% purity).

$^1$H NMR (400 MHz, CDCl$_3$) δ=2.04-2.14 (m, 2H), 2.23 (s, 6H), 2.54 (s, 1H), 2.61 (br t, J=6.23 Hz, 2H), 2.74-2.83 (m, 2H), 2.97-3.10 (m, 2H), 3.32-3.43 (m, 2H), 3.62-3.76 (m, 2H), 4.01 (br dd, J=12.35, 1.71 Hz, 2H), 4.34-4.46 (m, 2H), 5.02 (br s, 2H), 6.38 (br s, 1H), 8.40 (s, 1H), 8.80 (br s, 1H), 10.25 (s, 1H), 13.34-13.74 (m, 1H). LCMS for product (ESI+): m/z 451.2 (M+H)$^+$, Rt:2.506 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 μm particles). Detection methods are diode array (DAD) as well as positive electrospray ionization.

Example 126—Synthesis of N-(bicyclo[1.1.1]pentan-1-yl)-6-cyclopentyl-4-hydroxy-1-(2-morpholinoethyl)-2-oxo-1,2-dihydro-1,8-naphthyridine-3-carboxamide (Compound 126)

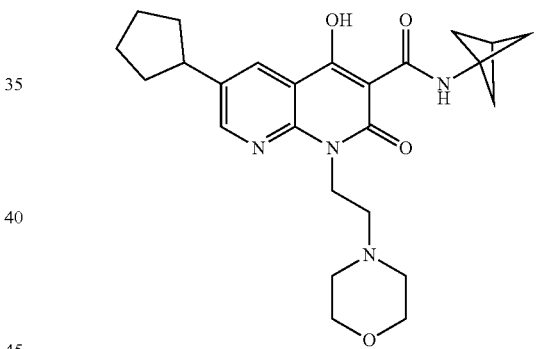

Preparation of N-(bicyclo[1.1.1]pentan-1-yl)-6-cyclopentyl-4-hydroxy-1-(2-morpholinoethyl)-2-oxo-1,2-dihydro-1,8-naphthyridine-3-carboxamide

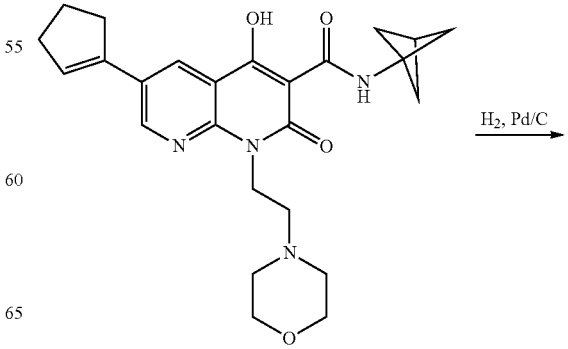

-continued

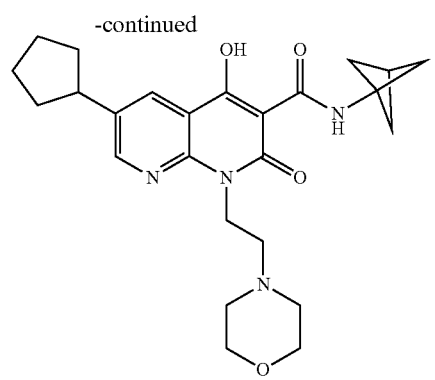

To a mixture of Pd/C (1 mg, 110.98 µmol, 10% purity, 1 eq) in THF (5 mL) was added N-(bicyclo[1.1.1]pentan-1-yl)-6-(cyclopent-1-en-1-yl)-4-hydroxy-1-(2-morpholinoethyl)-2-oxo-1,2-dihydro-1,8-naphthyridine-3-carboxamide (50 mg, 110.98 µmol, 1 eq). The mixture was stirred at 0° C. for 2 h under $H_2$ (15 psi). The reaction was filtered, the filtrate was concentrated. The residue was purified by prep-HPLC (neutral condition) to give the desired compound (16 mg, 34.68 µmol, 31.25% yield, 98.1% purity).

$^1$H NMR (400 MHz, CDCl$_3$) δ=1.59-1.70 (m, 2H), 1.72-1.83 (m, 2H), 1.85-1.97 (m, 2H), 2.13-2.20 (m, 2H), 2.23 (s, 6H), 2.54 (s, 1H), 2.98-3.19 (m, 3H), 3.34-3.44 (m, 2H), 3.68 (br d, J=11.98 Hz, 2H), 4.01 (dd, J=12.72, 2.69 Hz, 2H), 4.37 (br t, J=11.80 Hz, 2H), 5.02 (t, J=6.85 Hz, 2H), 8.36 (d, J=2.32 Hz, 1H), 8.58 (d, J=2.32 Hz, 1H), 10.23 (s, 1H), 13.35-13.55 (m, 1H). LCMS for product (ESI+): m/z 453.1 (M+H)$^+$, Rt:2.518 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 µm particles). Detection methods are diode array (DAD) as well as positive electrospray ionization.

Example 127—Synthesis of N-(bicyclo[1.1.1]pentan-1-yl)-6-cyclobutyl-4-hydroxy-1-(2-morpholinoethyl)-2-oxo-1,2-dihydro-1,8-naphthyridine-3-carboxamide (Compound 127)

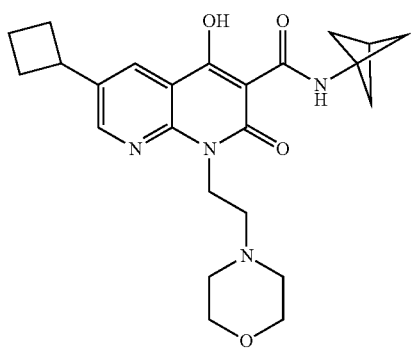 [SMILES: O=C(NC12CC(C1)C2)c1c(O)c2cc(C3CCC3)cnc2n(CCN2CCOCC2)c1=O]

Step 1. Preparation of ethyl 6-cyclobutyl-4-hydroxy-1-(2-morpholinoethyl)-2-oxo-1,2-dihydro-1,8-naphthyridine-3-carboxylate

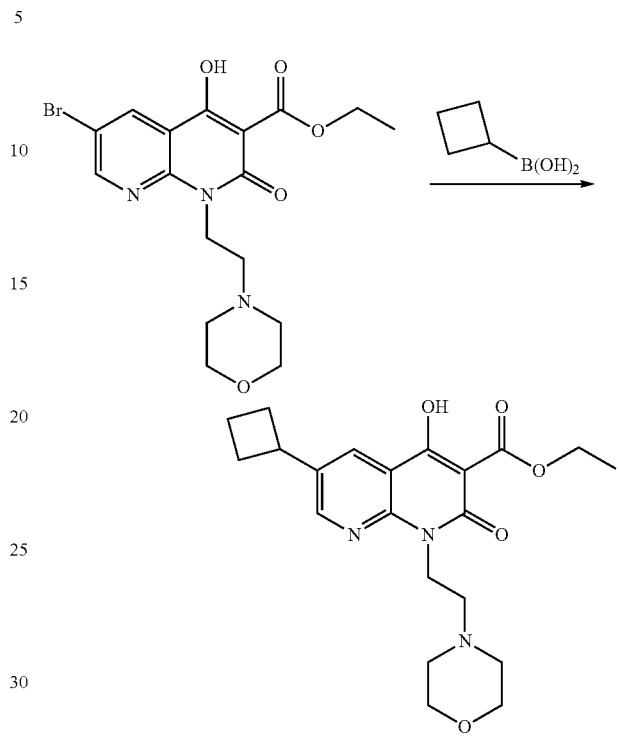

To a solution of ethyl 6-bromo-4-hydroxy-1-(2-morpholinoethyl)-2-oxo-1,2-dihydro-1,8-naphthyridine-3-carboxylate (100 mg, 234.60 µmol, 1 eq) and cyclobutylboronic acid (234.42 mg, 2.35 mmol, 10 eq) in Tol. (2 mL) and $H_2O$ (0.5 mL) was added $Cs_2CO_3$ (152.87 mg, 469.20 µmol, 2 eq) and DTBPF PdCl$_2$ (15.29 mg, 23.46 µmol, 0.1 eq). The mixture was stirred at 80° C. for 12 h under $N_2$. One additional vial was set up as described above and all two reaction mixtures were combined. The mixture was filtered, the filtrate was concentrated. The residue was purified by prep-HPLC (neutral condition) to give the desired compound (3 mg, 7.47 µmol, 3.19% yield).

LCMS for product (ESI+): m/z 402.2 (M+H)$^+$, Rt:1.816 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 µm particles). Detection methods are diode array (DAD) as well as positive electrospray ionization.

Step 2. Preparation of N-(bicyclo[1.1.1]pentan-1-yl)-6-cyclobutyl-4-hydroxy-1-(2-morpholinoethyl)-2-oxo-1,2-dihydro-1,8-naphthyridine-3-carboxamide

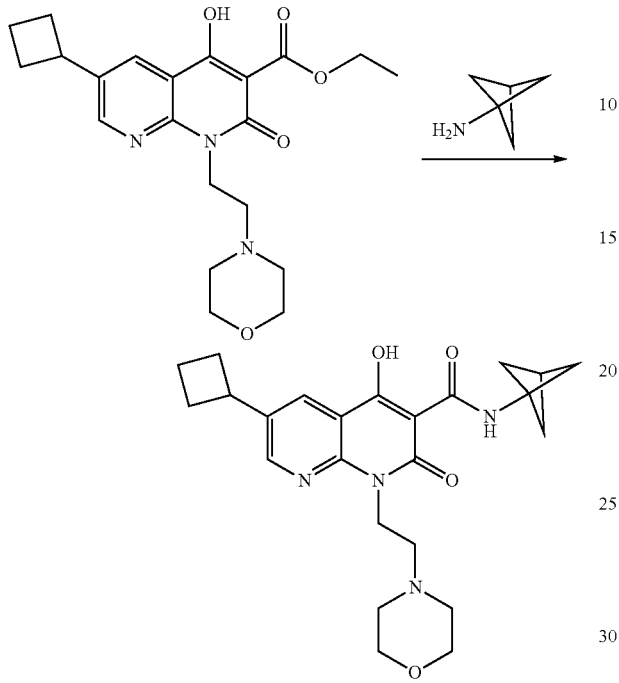

To a solution of ethyl 6-cyclobutyl-4-hydroxy-1-(2-morpholinoethyl)-2-oxo-1,2-dihydro-1,8-naphthyridine-3-carboxylate (3 mg, 7.47 μmol, 1 eq) and bicyclo[1.1.1]pentan-1-amine (983.06 μg, 8.22 μmol, 1.1 eq, HCl) in Tol. (1 mL) was added DIEA (965.81 ug, 7.47 μmol, 1.30 μL, 1 eq). The mixture was stirred at 120° C. for 2 h. The mixture was concentrated. The residue was purified by prep-HPLC (HCl condition) to give the desired compound (1.5 mg, 3.04 μmol, 40.74% yield, 89% purity).

$^1$H NMR (400 MHz, CDCl$_3$) δ=1.91-2.00 (m, 1H), 2.03-2.21 (m, 3H), 2.23 (s, 6H), 2.40-2.49 (m, 2H), 2.54 (s, 1H), 2.97-3.09 (m, 2H), 3.37 (br s, 2H), 3.60-3.72 (m, 3H), 4.01 (br d, J=10.76 Hz, 2H), 4.38 (br t, J=12.23 Hz, 2H), 5.00 (br t, J=6.66 Hz, 2H), 8.33 (d, J=1.83 Hz, 1H), 8.53 (d, J=2.08 Hz, 1H), 10.26 (s, 1H), 13.48 (br d, J=2.20 Hz, 1H). LCMS for product (ESI+): m/z 439.1 (M+H)$^+$, Rt:2.449 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 μm particles). Detection methods are diode array (DAD) as well as positive electrospray ionization.

Example 128—Synthesis of N-(bicyclo[1.1.1]pentan-1-yl)-6-(4-fluorophenyl)-4-hydroxy-2-oxo-1-(2-(piperidin-1-yl)ethyl)-1,2-dihydro-1,8-naphthyridine-3-carboxamide (Compound 128)

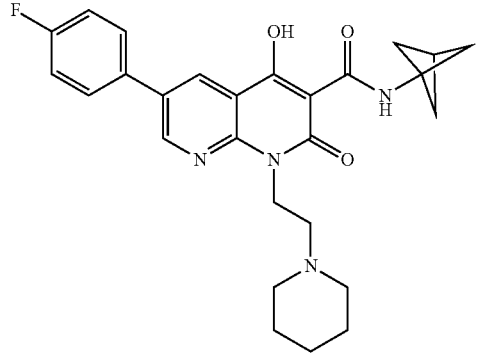 [SMILES: O=C(NC12CC(C1)C2)c1c(O)c2cc(-c3ccc(F)cc3)cnc2n(CCN2CCCCC2)c1=O]

Step 1. Preparation of ethyl 6-bromo-4-hydroxy-2-oxo-1-(2-(piperidin-1-yl)ethyl)-1,2-dihydro-1,8-naphthyridine-3-carboxylate

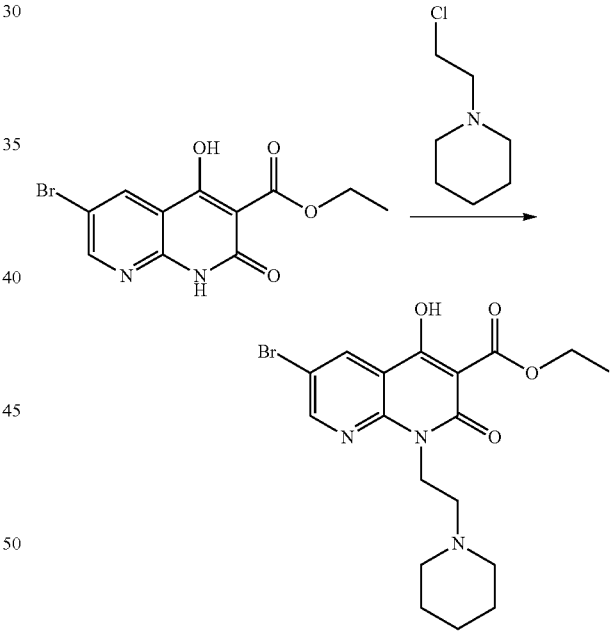

To a solution of ethyl 6-bromo-4-hydroxy-2-oxo-1,2-dihydro-1,8-naphthyridine-3-carboxylate (200 mg, 638.77 μmol, 1 eq) in DMF (3 mL) was added Cs$_2$CO$_3$ (1.66 g, 5.11 mmol, 8 eq), 1-(2-chloroethyl)piperidine (141.12 mg, 766.52 μmol, 1.2 eq, HCl) at 20° C. The mixture was stirred at 50° C. for 3 h. The mixture was filtered, the filtrate was concentrated to give crude product, which was triturated with ethyl acetate (3 mL). Then filtered, the filter cake was washed with ethyl acetate (2 mL) and dried to give the desired compound (180 mg, 424.24 μmol, 66.42% yield).

$^1$H NMR (400 MHz, CDCl$_3$) 5=1.19 (t, J=7.07 Hz, 3H), 1.37 (br d, J=5.25 Hz, 2H), 1.44-1.51 (m, 4H), 2.26-2.47 (m,

6H), 4.03 (q, J=7.00 Hz, 2H), 4.17-4.34 (m, 2H), 8.20 (d, J=2.50 Hz, 1H), 8.45 (d, J=2.63 Hz, 1H).

Step 2. Preparation of ethyl 6-(4-fluorophenyl)-4-hydroxy-2-oxo-1-(2-(piperidin-1-yl)ethyl)-1,2-dihydro-1,8-naphthyridine-3-carboxylate

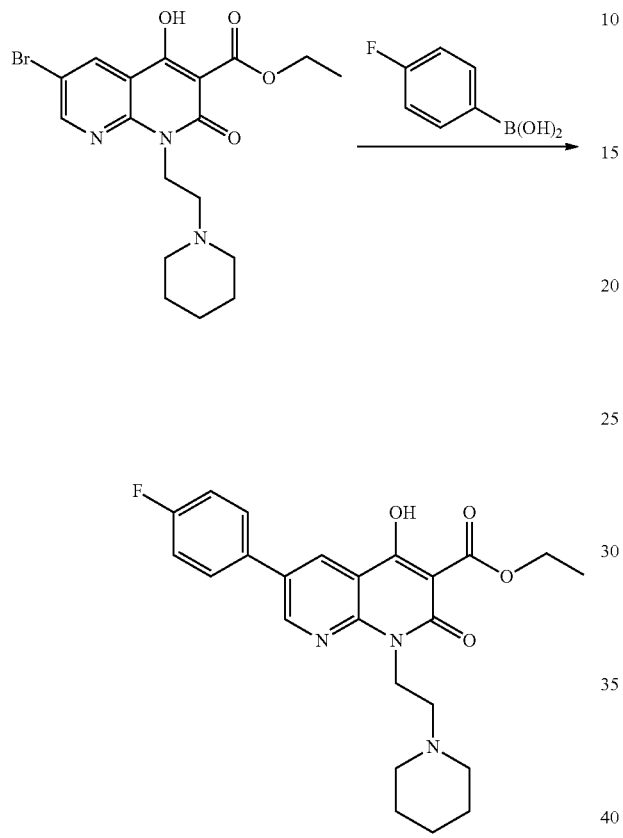

To a solution of ethyl 6-bromo-4-hydroxy-2-oxo-1-(2-(piperidin-1-yl)ethyl)-1,2-dihydro-1,8-naphthyridine-3-carboxylate (180 mg, 424.24 μmol, 1 eq) in dioxane (2 mL) and water (0.2 mL) was added (4-fluorophenyl)boronic acid (71.23 mg, 509.09 μmol, 1.2 eq), $K_2CO_3$ (175.90 mg, 1.27 mmol, 3 eq) and $Pd(dppf)Cl_2$ (31.04 mg, 42.42 μmol, 0.1 eq) under N2. The mixture was stirred at 100° C. for 2 h. The mixture was concentrated to give crude product, which was purified by prep-HPLC (column: Phenomenex Luna 80*30 mm*3 μm; mobile phase: [water (0.04% HCl)-ACN]; B %: 20%-45%, 8 min) to give the desired compound (40 mg, 91.02 μmol, 21.45% yield).

$^1$H NMR (400 MHz, CDCl$_3$) δ=1.50 (t, J=7.13 Hz, 3H), 1.78-1.97 (m, 3H), 2.25-2.52 (m, 2H), 2.72-2.99 (m, 2H), 3.35 (br s, 2H), 3.75 (br d, J=11.76 Hz, 2H), 4.56 (q, J=7.13 Hz, 2H), 5.02 (br dd, J=7.82, 6.32 Hz, 2H), 7.18-7.25 (m, 2H), 7.55-7.65 (m, 2H), 8.58 (d, J=2.25 Hz, 1H), 8.92 (d, J=2.38 Hz, 1H), 12.45-12.72 (m, 1H), 14.44 (s, 1H).

Step 3. Preparation of N-(bicyclo[1.1.1]pentan-1-yl)-6-(4-fluorophenyl)-4-hydroxy-2-oxo-1-(2-(piperidin-1-yl)ethyl)-1,2-dihydro-1,8-naphthyridine-3-carboxamide

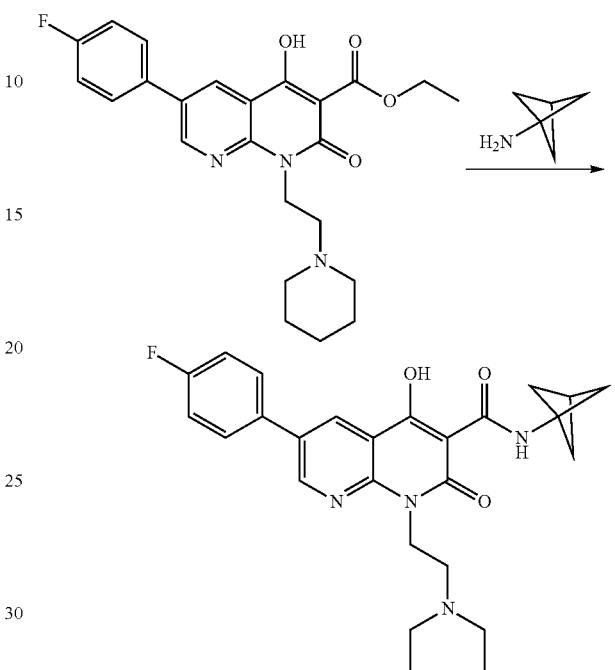

To a solution of ethyl 6-(4-fluorophenyl)-4-hydroxy-2-oxo-1-(2-(piperidin-1-yl)ethyl)-1,2-dihydro-1,8-naphthyridine-3-carboxylate (40 mg, 84.04 μmol, 1 eq, HCl) in toluene (1 mL) was added DIEA (43.45 mg, 336.18 μmol, 58.55 μL, 4 eq) and bicyclo[1.1.1]pentan-1-amine (10.05 mg, 84.04 μmol, 1 eq, HCl). The mixture was stirred at 120° C. for 5 h. The mixture was concentrated to give crude product, which was triturated with methanol (2 mL). Then the mixture was filtered, the filter cake was dried to give the desired compound (29.5 mg, 61.90 μmol, 73.66% yield, 100% purity).

$^1$H NMR (400 MHz, CDCl$_3$) δ=1.54-1.66 (m, 6H), 2.23 (s, 6H), 2.30-2.98 (m, 7H), 4.50-4.92 (m, 2H), 7.21 (br t, J=8.50 Hz, 2H), 7.63 (dd, J=8.51, 5.25 Hz, 2H), 8.59 (d, J=2.25 Hz, 1H), 8.89 (d, J=2.25 Hz, 1H), 10.23-10.73 (m, 1H). LCMS for product (ESI+): m/z 477.1 (M+H)$^+$, Rt:2.539 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 μm particles). Detection methods are diode array (DAD) as well as positive electrospray ionization.

Example 129—Synthesis of N-(bicyclo[1.1.1]pentan-1-yl)-6-(4-fluorophenyl)-4-hydroxy-2-oxo-1-(pyridin-4-ylmethyl)-1,2-dihydro-1,8-naphthyridine-3-carboxamide (Compound 129)

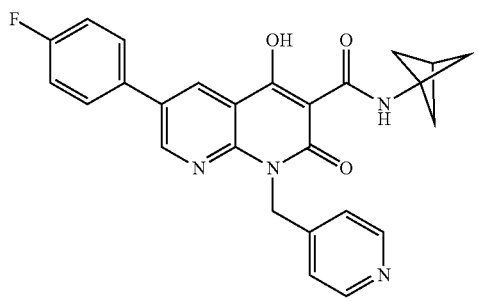 [SMILES: O=C(NC12CC(C1)C2)c1c(O)c2cc(-c3ccc(F)cc3)cnc2n(Cc2ccncc2)c1=O]

Step 1. Preparation of ethyl 6-bromo-4-hydroxy-2-oxo-1-(pyridin-4-ylmethyl)-1,2-dihydro-1,8-naphthyridine-3-carboxylate

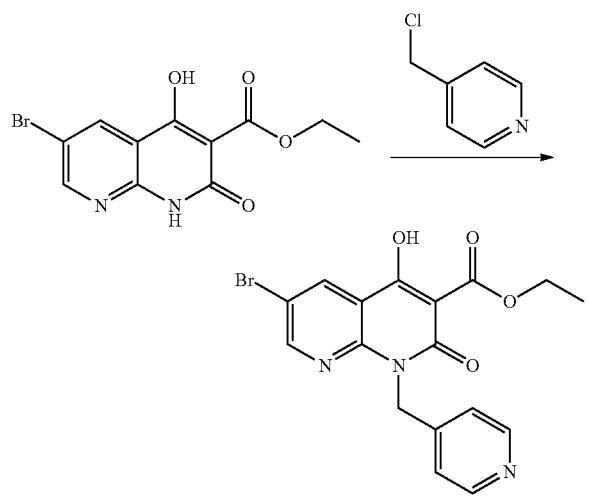

To a solution of ethyl 6-bromo-4-hydroxy-2-oxo-1,2-dihydro-1,8-naphthyridine-3-carboxylate (200 mg, 638.77 μmol, 1 eq) in DMF (3 mL) was added $Cs_2CO_3$ (1.66 g, 5.11 mmol, 8 eq) and 4-(chloromethyl)pyridine (125.73 mg, 766.52 μmol, 1.2 eq, HCl) at 20° C., the mixture was stirred at 50° C. for 3 h. The mixture was filtered, the filtrate was concentrated to give crude product which was triturated with ethyl acetate (3 mL). Then the mixture was filtered, and the filter cake was washed with ethyl acetate (2 mL) and dried to give the desired compound (180 mg, 445.31 μmol, 69.71% yield).

$^1$H NMR (400 MHz, $CDCl_3$) δ=1.19 (t, J=7.13 Hz, 3H), 4.04 (q, J=7.13 Hz, 2H), 5.38 (s, 2H), 7.09 (d, J=6.00 Hz, 2H), 8.26 (d, J=2.63 Hz, 1H), 8.36-8.44 (m, 3H).

Step 2. Preparation of ethyl 6-(4-fluorophenyl)-4-hydroxy-2-oxo-1-(pyridin-4-ylmethyl)-1,2-dihydro-1,8-naphthyridine-3-carboxylate

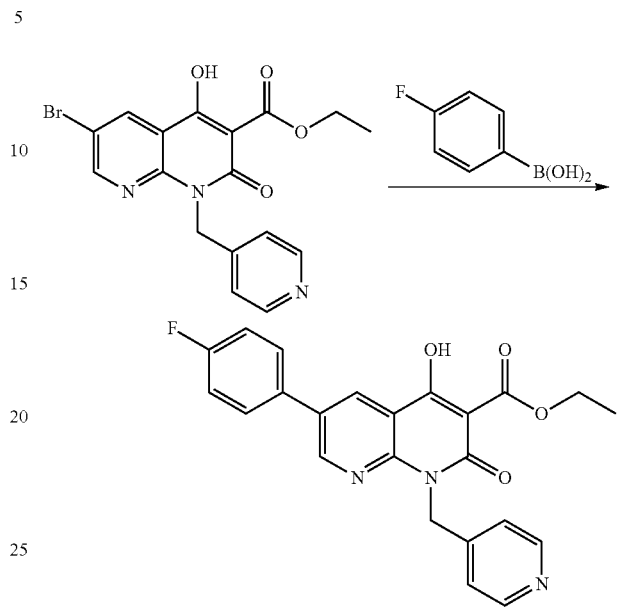

To a solution of ethyl 6-bromo-4-hydroxy-2-oxo-1-(pyridin-4-ylmethyl)-1,2-dihydro-1,8-naphthyridine-3-carboxylate (180 mg, 445.31 μmol, 1 eq) in dioxane (2 mL) and water (0.2 mL) was added (4-fluorophenyl)boronic acid (74.77 mg, 534.37 μmol, 1.2 eq), $K_2CO_3$ (184.64 mg, 1.34 mmol, 3 eq) and Pd(dppf)$Cl_2$ (32.58 mg, 44.53 μmol, 0.1 eq) under $N_2$. The mixture was stirred at 100° C. for 2 h. The mixture was concentrated to give crude product, which was purified by prep-HPLC (column: Phenomenex Luna 80*30 mm*3 μm; mobile phase: [water (0.04% HCl)-ACN]; B %: 20%-45%, 8 min) to give the desired compound (40 mg, 95.37 μmol, 21.42% yield).

$^1$H NMR (400 MHz, $CDCl_3$) δ=1.48-1.52 (m, 3H), 4.56 (q, J=7.34 Hz, 2H), 5.90 (br s, 2H), 7.19-7.26 (m, 3H), 7.60 (br s, 2H), 7.81-8.09 (m, 2H), 8.64 (s, 2H), 8.85 (br d, J=1.13 Hz, 1H), 14.60 (s, 1H).

Step 3. Preparation of N-(bicyclo[1.1.1]pentan-1-yl)-6-(4-fluorophenyl)-4-hydroxy-2-oxo-1-(pyridin-4-ylmethyl)-1,2-dihydro-1,8-naphthyridine-3-carboxamide

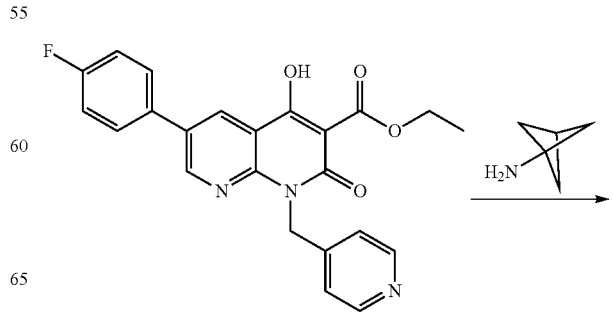

-continued

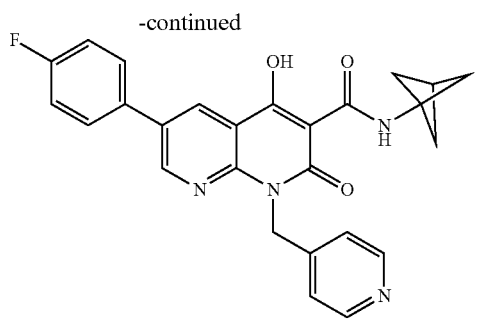

To a solution of ethyl 6-(4-fluorophenyl)-4-hydroxy-2-oxo-1-(pyridin-4-ylmethyl)-1,2-dihydro-1,8-naphthyridine-3-carboxylate (31 mg, 68.00 µmol, 1 eq, HCl) in toluene (0.5 mL) was added DIEA (35.15 mg, 272.01 µmol, 47.38 uL, 4 eq) and bicyclo[1.1.1]pentan-1-amine (9.76 mg, 81.60 µmol, 1.2 eq, HCl). The mixture was stirred at 120° C. for 5 h. The mixture was concentrated to give crude product, which was triturated with methanol (2 mL). Then the mixture was filtered, the filter cake was dried to give the desired compound (16.4 mg, 35.93 mol, 52.83% yield, 100% purity).

$^1$H NMR (400 MHz, CDCl$_3$) δ=2.16-2.25 (m, 6H), 2.54 (s, 1H), 5.76 (s, 2H), 7.18-7.23 (m, 2H), 7.33 (br d, J=4.88 Hz, 2H), 7.62 (dd, J=8.50, 5.25 Hz, 2H), 8.55 (br d, J=4.75 Hz, 2H), 8.65 (d, J=2.25 Hz, 1H), 8.85 (d, J=2.13 Hz, 1H), 10.34 (s, 1H). LCMS for product (ESI+): m/z 457.1 (M+H)$^+$, Rt:2.572 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 130—Synthesis of N-(bicyclo[1.1.1]pentan-1-yl)-6-(4-fluorophenyl)-4-hydroxy-2-oxo-1-(pyridin-3-ylmethyl)-1,2-dihydro-1,8-naphthyridine-3-carboxamide (Compound 130)

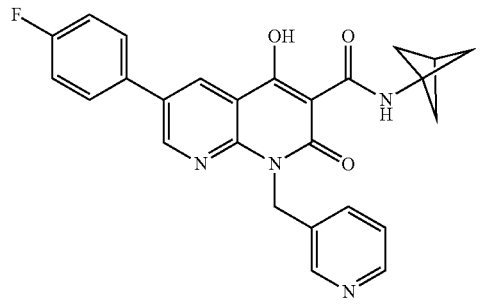 [SMILES: O=C(NC12CC(C1)C2)c1c(O)c2cc(-c3ccc(F)cc3)cnc2n(Cc2cccnc2)c1=O]

Step 1. Preparation of ethyl 6-bromo-4-hydroxy-2-oxo-1-(pyridin-3-ylmethyl)-1,2-dihydro-1,8-naphthyridine-3-carboxylate

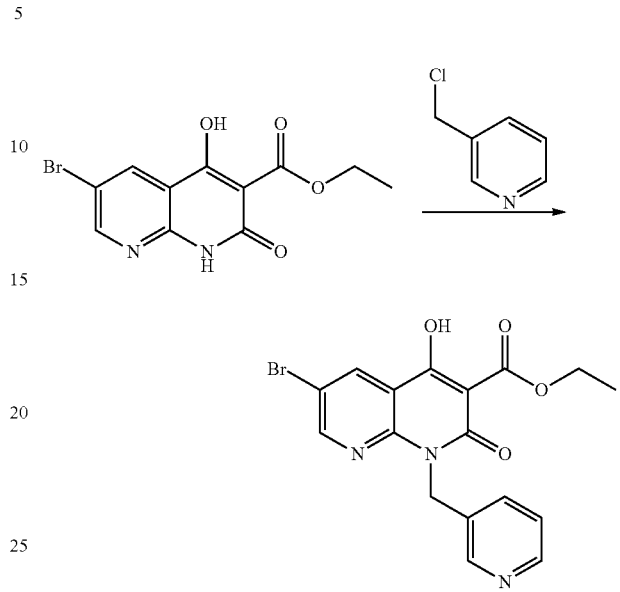

To a solution of ethyl 6-bromo-4-hydroxy-2-oxo-1,2-dihydro-1,8-naphthyridine-3-carboxylate (200 mg, 638.77 µmol, 1 eq) in DMF (3 mL) was added Cs$_2$CO$_3$ (1.66 g, 5.11 mmol, 8 eq) and 4-(chloromethyl)pyridine (125.73 mg, 766.52 µmol, 1.2 eq, HCl) at 20° C., the mixture was stirred at 50° C. for 3 h. The mixture was filtered, the filtrate was concentrated to give crude product which was triturated with ethyl acetate (3 mL). Then the mixture was filtered, and the filter cake was washed with ethyl acetate (2 mL) and dried to give the desired compound (180 mg, 445.31 µmol, 69.71% yield).

$^1$H NMR (400 MHz, CDCl$_3$) δ=1.19 (t, J=7.13 Hz, 3H), 4.05 (q, J=7.21 Hz, 2H), 5.39 (s, 2H), 7.26 (dd, J=7.69, 4.82 Hz, 1H), 7.57 (br d, J=7.88 Hz, 1H), 8.25 (d, J=2.38 Hz, 1H), 8.38 (br d, J=4.50 Hz, 1H), 8.44 (d, J=2.38 Hz, 1H), 8.49 (s, 1H).

Step 2. Preparation of ethyl 6-(4-fluorophenyl)-4-hydroxy-2-oxo-1-(pyridin-3-ylmethyl)-1,2-dihydro-1,8-naphthyridine-3-carboxylate

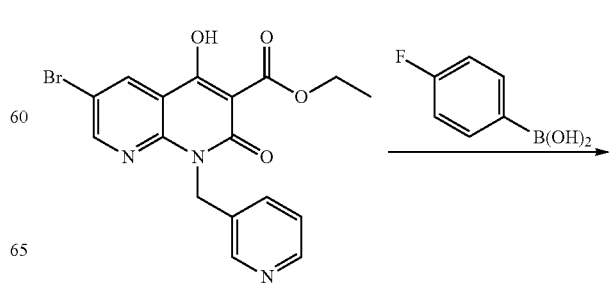

-continued

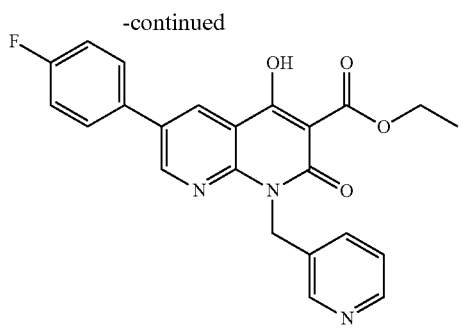

To a solution of ethyl 6-bromo-4-hydroxy-2-oxo-1-(pyridin-3-ylmethyl)-1,2-dihydro-1,8-naphthyridine-3-carboxylate (180 mg, 445.31 μmol, 1 eq) in dioxane (2 mL) and water (0.2 mL) was added (4-fluorophenyl)boronic acid (74.77 mg, 534.37 μmol, 1.2 eq), K$_2$CO$_3$ (184.64 mg, 1.34 mmol, 3 eq) and Pd(dppf)Cl$_2$ (32.58 mg, 44.53 μmol, 0.1 eq) under N$_2$. The mixture was stirred at 100° C. for 2 h. The mixture was filtered, and the filter cake was washed with dioxane and dried to give the desired compound (40 mg, 95.37 μmol, 21.42% yield).

$^1$H NMR (400 MHz, CDCl$_3$) δ=1.22 (t, J=7.13 Hz, 3H), 4.09 (q, J=7.13 Hz, 2H), 5.52 (s, 2H), 7.24-7.34 (m, 3H), 7.67 (dt, J=7.85, 1.89 Hz, 1H), 7.71-7.77 (m, 2H), 8.37 (dd, J=4.75, 1.63 Hz, 1H), 8.46 (d, J=2.50 Hz, 1H), 8.60 (d, J=1.75 Hz, 1H), 8.65 (d, J=2.63 Hz, 1H).

Step 3. Preparation of N-(bicyclo[1.1.1]pentan-1-yl)-6-(4-fluorophenyl)-4-hydroxy-2-oxo-1-(pyridin-3-ylmethyl)-1,2-dihydro-1,8-naphthyridine-3-carboxamide

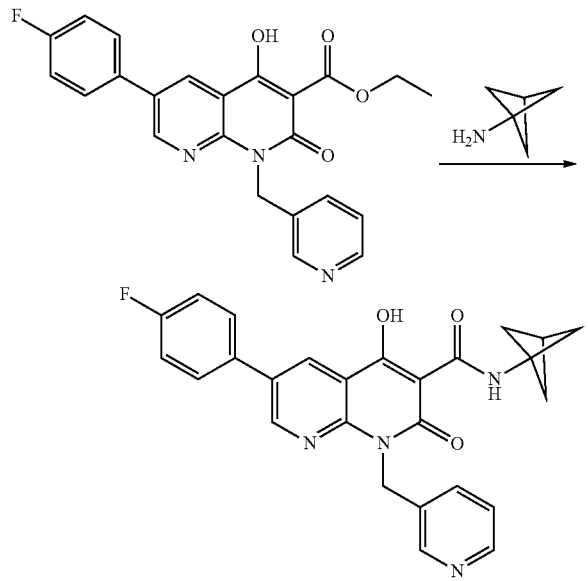

To a solution of ethyl 6-(4-fluorophenyl)-4-hydroxy-2-oxo-1-(pyridin-4-ylmethyl)-1,2-dihydro-1,8-naphthyridine-3-carboxylate (31 mg, 73.91 μmol, 1 eq) in toluene (0.5 mL) was added DIEA (38.21 mg, 295.66 μmol, 51.50 μL, 4 eq) and bicyclo[1.1.1]pentan-1-amine (10.61 mg, 88.70 μmol, 1.2 eq, HCl). The mixture was stirred at 120° C. for 5 h. The mixture was concentrated to give crude product, which was triturated with methanol (2 mL). Then the mixture was filtered, the filter cake dried to give the desired compound (6.1 mg, 13.07 μmol, 17.68% yield, 97.8% purity).

$^1$H NMR (400 MHz, CDCl$_3$) δ=2.23 (s, 6H), 2.54 (s, 1H), 5.74 (s, 2H), 7.14-7.26 (m, 3H), 7.62 (dd, J=8.63, 5.25 Hz, 2H), 7.79 (br d, J=8.00 Hz, 1H), 8.50 (dd, J=4.82, 1.19 Hz, 1H), 8.61 (d, J=2.38 Hz, 1H), 8.80 (d, J=1.38 Hz, 1H), 8.90 (d, J=2.38 Hz, 1H), 10.35-10.54 (m, 1H). LCMS for product (ESI+): m/z 457.1 (M+H)$^+$, Rt: 2.638 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 131—Synthesis of N-(bicyclo[1.1.1]pentan-1-yl)-6-(4-fluorophenyl)-1-((5-fluoropyridin-2-yl)methyl)-4-hydroxy-2-oxo-1,2-dihydro-1,8-naphthyridine-3-carboxamide (Compound 131)

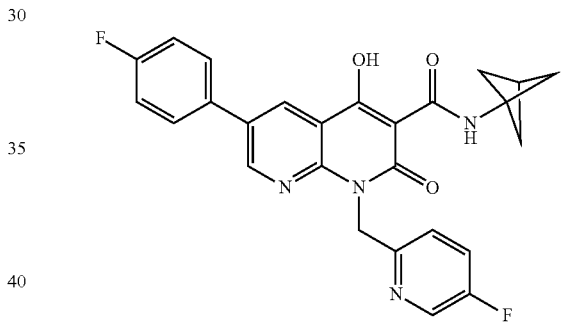

Step 1. Preparation of 2-(chloromethyl)-5-fluoropyridine

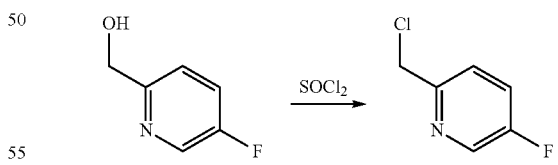

To a solution of the alcohol (300 mg, 2360.04 μmol, 1 eq) in CHCl$_3$ (3 mL) was added a solution of SOCl$_2$ (421.17 mg, 3.54 mmol, 85.60 μL, 1.5 eq) in CHCl$_3$ (1.5 mL) at 20° C. The mixture was stirred at 20° C. for 2 h. The mixture was concentrated to give crude product, which was triturated with ethyl acetate (2 mL). And the mixture was filtered, the filter cake was dried to give the desired compound (300 mg, 2.06 mmol, 87.33% yield).

$^1$H NMR (400 MHz, CDCl$_3$) δ=7.65 (dd, J=8.63, 4.50 Hz, 1H) 7.79 (td, J=8.69, 2.88 Hz, 1H) 8.57 (d, J=3.00 Hz, 1H).

Step 2. Preparation of ethyl 6-bromo-1-((5-fluoro-pyridin-2-yl)methyl)-4-hydroxy-2-oxo-1,2-dihydro-1,8-naphthyridine-3-carboxylate

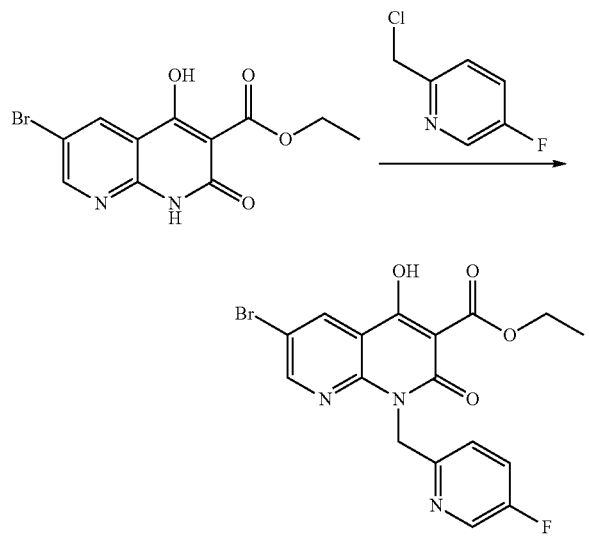

To a solution of ethyl 6-bromo-4-hydroxy-2-oxo-1,2-dihydro-1,8-naphthyridine-3-carboxylate (200 mg, 638.67 µmol, 1 eq) in DMF (2 mL) was added Cs$_2$CO$_3$ (1.67 g, 5.11 mmol, 8 eq), 2-(chloromethyl)-5-fluoro-pyridine (162.78 mg, 0.89 mmol, 1.4 eq, HCl) at 20° C., the mixture was stirred at 50° C. for 11 h. The mixture was filtered, the filtrate was concentrated to give crude product, which was triturated with ethyl acetate (5 mL). Then the mixture was filtered and the filter cake was dried to give the desired compound (100 mg, 157.90 µmol, 25.22% yield).

$^1$H NMR (400 MHz, CDCl$_3$) δ=1.19 (t, J=7.04 Hz, 3H), 4.05 (q, J=7.04 Hz, 2H), 5.46 (s, 2H), 6.95 (dd, J=8.66, 4.40 Hz, 1H), 7.56 (td, J=8.80, 2.93 Hz, 1H), 8.27 (d, J=2.64 Hz, 1H), 8.34-8.38 (m, 1H), 8.44 (d, J=2.93 Hz, 1H).

Step 3. Preparation of ethyl 6-(4-fluorophenyl)-1-((5-fluoropyridin-2-yl)methyl)-4-hydroxy-2-oxo-1,2-dihydro-1,8-naphthyridine-3-carboxylate

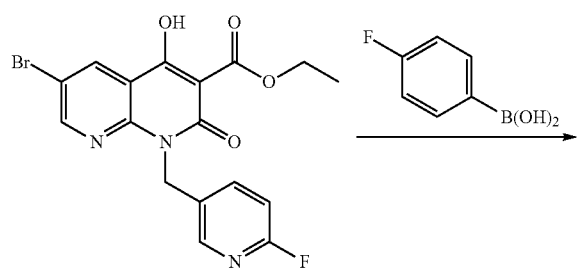

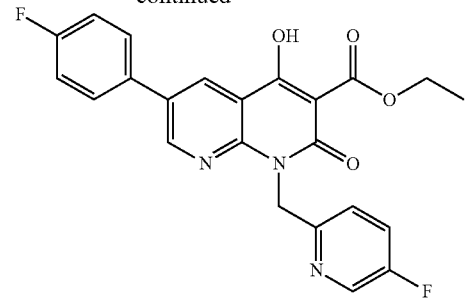

To a solution of ethyl 6-bromo-1-((5-fluoropyridin-2-yl)methyl)-4-hydroxy-2-oxo-1,2-dihydro-1,8-naphthyridine-3-carboxylate (100 mg, 157.90 µmol, 1 eq) in dioxane (1 mL) and water (0.1 mL) was added (4-fluorophenyl)boronic acid (39.77 mg, 284.22 µmol, 1.2 eq), K$_2$CO$_3$ (98.21 mg, 710 µmol, 3 eq) and Pd(dppf)Cl$_2$ (17.33 mg, 23.63 µmol, 0.1 eq) under N$_2$. The mixture was stirred at 100° C. for 2 h. The mixture was filtered, the filtrate was purified by prep-HPLC (column: Phenomenex Luna 80*30 mm*3 µm; mobile phase: [water (0.04% HCl)-ACN]; B %: 25%-40%, 8 min) to give the desired compound (30 mg, 68.59 µmol, 28.96% yield).

$^1$H NMR (400 MHz, CDCl$_3$) δ=1.21 (d, J=7.00 Hz, 3H), 4.05 (q, J=7.05 Hz, 2H), 5.53 (s, 2H), 6.94 (dd, J=8.82, 4.44 Hz, 1H), 7.29-7.33 (m, 2H), 7.52-7.58 (m, 1H), 7.67-7.73 (m, 2H), 8.42 (d, J=2.63 Hz, 1H), 8.45 (d, J=2.88 Hz, 1H), 8.59 (d, J=2.50 Hz, 1H).

Step 4. Preparation of N-(bicyclo[1.1.1]pentan-1-yl)-6-(4-fluorophenyl)-1-((5-fluoropyridin-2-yl)methyl)-4-hydroxy-2-oxo-1,2-dihydro-1,8-naphthyridine-3-carboxamide

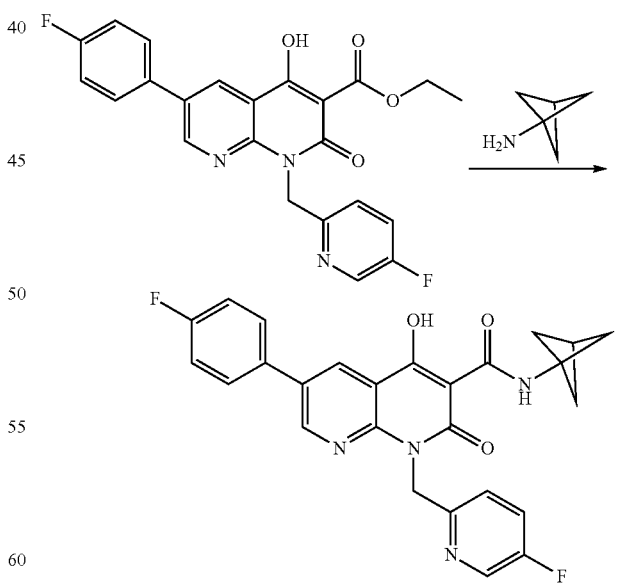

To a solution of ethyl 6-(4-fluorophenyl)-1-((5-fluoropyridin-2-yl)methyl)-4-hydroxy-2-oxo-1,2-dihydro-1,8-naphthyridine-3-carboxylate (30 mg, 63.31 µmol, 1 eq, HCl) in toluene (1 mL) was added DIEA (32.73 mg, 253.24 µmol, 44.11 uL, 4 eq) and bicyclo[1.1.1]pentan-1-amine (11.36 mg, 94.97 μmol, 1.5 eq, HCl). The mixture was stirred at 120° C. for 5 h. The mixture was concentrated to give crude product, which was purified by prep-HPLC (column: Waters Xbridge BEH C18 100*25 mm*5 μm; mobile phase: [water (10 mM NH₄HCO₃)-ACN]; B %: 50%-85%, 10 min) to give the desired compound (4.7 mg, 9.91 μmol, 15.65% yield, 100% purity).

¹H NMR (400 MHz, CDCl₃) δ=2.21 (s, 6H), 2.52 (s, 1H), 5.86 (s, 2H), 7.15-7.25 (m, 3H), 7.30-7.37 (m, 1H), 7.58-7.63 (m, 2H), 8.39 (d, J=2.75 Hz, 1H), 8.64 (d, J=2.38 Hz, 1H), 8.84 (d, J=2.50 Hz, 1H), 10.42 (s, 1H). LCMS for product (ESI+): m/z 475.1 (M+H)⁺, Rt:3.332 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 μm particles). Detection methods are diode array (DAD) as well as positive electrospray ionization.

Example 132—Synthesis of N-(bicyclo[1.1.1]pentan-1-yl)-6-(4-fluorophenyl)-4-hydroxy-1-(2-(4-methylpiperazin-1-yl)ethyl)-2-oxo-1,2-dihydro-1,8-naphthyridine-3-carboxamide (Compound 132)

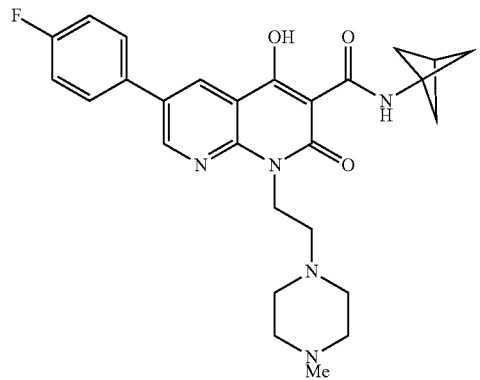 [SMILES: CN1CCN(CCn2c(=O)c(C(=O)NC34CC(C3)C4)c(O)c3cc(-c4ccc(F)cc4)cnc32)CC1]

Step 1. Preparation of ethyl 6-bromo-4-hydroxy-2-oxo-1-(2-(4-methylpiperazin-1-yl)ethyl)-1,2-dihydro-1,8-naphthyridine-3-carboxylate

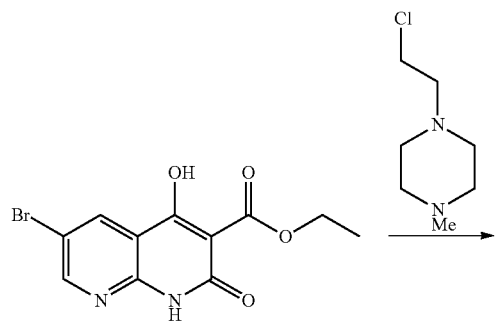

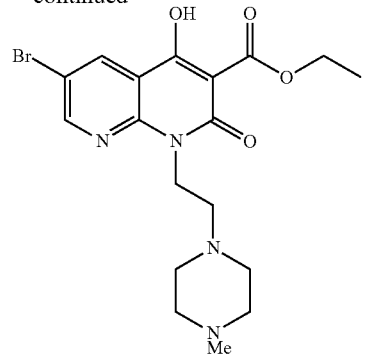

To a solution of ethyl 6-bromo-4-hydroxy-2-oxo-1,2-dihydro-1,8-naphthyridine-3-carboxylate (200 mg, 638.77 μmol, 1 eq) in NMP (3 mL) was added NaH (76.64 mg, 1.92 mmol, 2.55e-1 μL, 60% purity, 3 eq). The mixture was stirred at 20° C. for 1 h. 1-(2-chloroethyl)-4-methyl-piperazine (190.79 mg, 958.15 μmol, 1.5 eq, HCl) and DIEA (82.56 mg, 638.77 μmol, 111.26 μL, 1 eq) was added into the mixture at 20° C., the mixture was stirred at 100° C. for 24 h. The mixture was filtered, the filtrate was purified by prep-HPLC (column: Phenomenex Luna 80*30 mm*3 μm; mobile phase: [water (0.04% HCl)-ACN]; B %: 1%-30%, 8 min) to give the desired compound (80 mg, 182.11 μmol, 28.51% yield).

¹H NMR (400 MHz, CDCl₃) δ=1.47 (t, J=7.00 Hz, 3H), 2.89 (br s, 3H), 3.44-3.68 (m, 4H), 3.91-4.19 (m, 6H), 4.52 (q, J=7.05 Hz, 2H), 4.85 (br t, J=5.19 Hz, 2H), 8.47-8.73 (m, 2H), 13.53-13.77 (m, 1H), 14.39 (s, 1H).

Step 2. Preparation of ethyl 6-(4-fluorophenyl)-4-hydroxy-2-oxo-1-(2-(4-methylpiperazin-1-yl)ethyl)-1,2-dihydro-1,8-naphthyridine-3-carboxylate

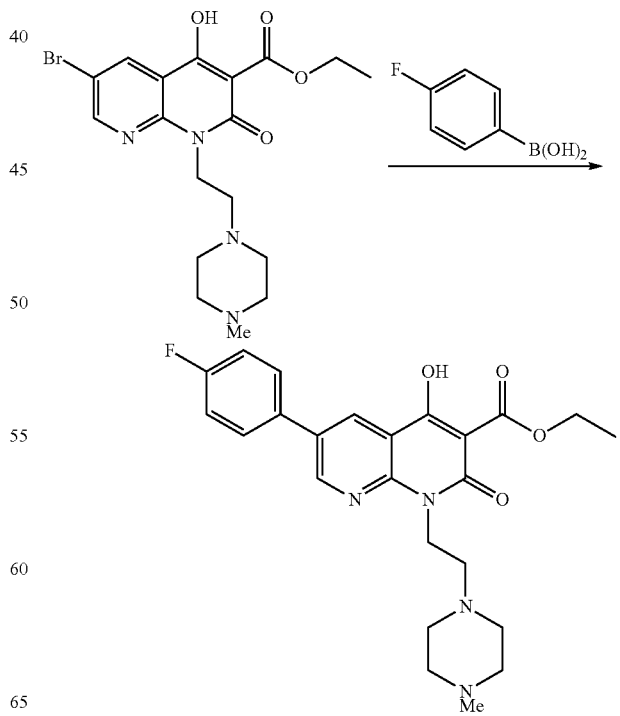

To a solution of ethyl 6-bromo-4-hydroxy-2-oxo-1-(2-(4-methylpiperazin-1-yl)ethyl)-1,2-dihydro-1,8-naphthyridine-3-carboxylate (80 mg, 182.11 µmol, 1 eq) in dioxane (1 mL) and water (0.1 mL) was added (4-fluorophenyl)boronic acid (30.58 mg, 218.53 µmol, 1.2 eq), K$_2$CO$_3$ (75.51 mg, 546.32 µmol, 3 eq) and Pd(dppf)Cl$_2$ (13.32 mg, 18.21 µmol, 0.1 eq) under N$_2$. The mixture was stirred at 100° C. for 2 h. The mixture was poured into water (10 mL), the mixture was filtered, the filtrate was acidified by adding 12 N hydrochloric acid dropwise to pH=2 at 0° C. The mixture was filtered, the filter cake was washed with water and dried to give the desired compound (35 mg, 71.29 µmol, 39.15% yield, HCl).

LCMS for product (ESI+): m/z 455.2 (M+H)$^+$, Rt:1.434 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Step 3. Preparation of N-(bicyclo[1.1.1]pentan-1-yl)-6-(4-fluorophenyl)-4-hydroxy-1-(2-(4-methylpiperazin-1-yl)ethyl)-2-oxo-1,2-dihydro-1,8-naphthyridine-3-carboxamide

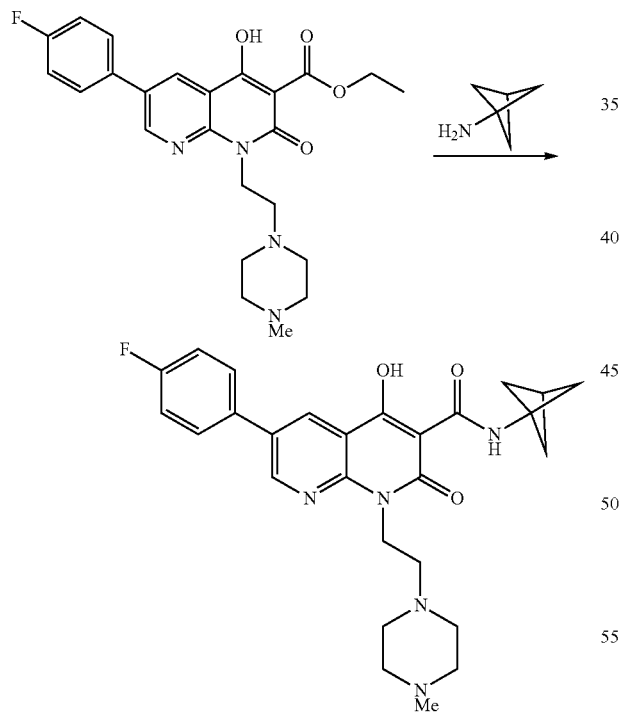

To a solution of ethyl 6-(4-fluorophenyl)-4-hydroxy-2-oxo-1-(2-(4-methylpiperazin-1-yl)ethyl)-1,2-dihydro-1,8-naphthyridine-3-carboxylate (35 mg, 71.29 µmol, 1 eq, HCl) in toluene (0.5 mL) was added DIEA (27.64 mg, 213.87 µmol, 37.25 uL, 3 eq) and bicyclo[1.1.1]pentan-1-amine (10.23 mg, 85.55 µmol, 2.40 µL, 1.2 eq, HCl). The mixture was stirred at 120° C. for 5 h. The mixture was concentrated to give crude product, which was triturated with methanol (2 mL). Then the mixture was filtered, the filter cake was dissolved into DCM (2 mL) and added HCl (43.32 mg, 427.74 µmol, 42.47 µL, 36% purity, 6 eq). The mixture was concentrated and lyophilized to give the desired compound (16.5 mg, 31.25 µmol, 43.83% yield, 100% purity, HCl).

$^1$H NMR (400 MHz, CDCl$_3$) δ=2.24 (s, 6H) 2.55 (s, 1H) 2.86-2.95 (m, 3H) 3.43-3.61 (m, 4H) 3.91-4.10 (m, 4H) 4.34 (br d, J=19.76 Hz, 2H) 4.98 (br t, J=6.25 Hz, 2H) 7.20-7.24 (m, 2H) 7.59-7.65 (m, 2H) 8.64 (d, J=2.38 Hz, 1H) 8.84 (d, J=2.38 Hz, 1H) 10.15 (s, 1H) 13.93-14.02 (m, 1H). LCMS for product (ESI+): m/z 492.2 (M+H)$^+$, Rt:2.423 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 µm particles). Detection methods are diode array (DAD) as well as positive electrospray ionization.

Example 133—Synthesis of N-(bicyclo[1.1.1]pentan-1-yl)-6-(4-fluorophenyl)-4-hydroxy-2-oxo-1-(2-(4-fluoropiperidin-1-yl)ethyl)-1,2-dihydro-1,8-naphthyridine-3-carboxamide (Compound 133)

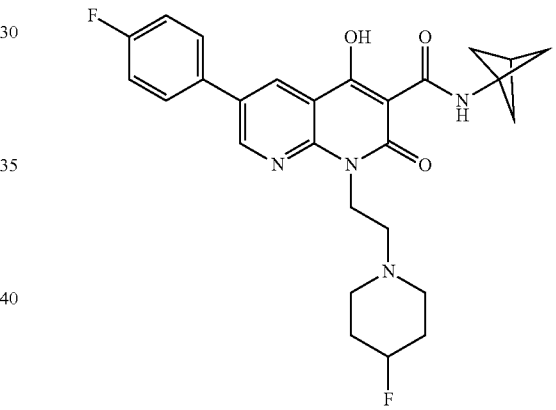

Step 1. Preparation of 2-(4-fluoropiperidin-1-yl)ethan-1-ol

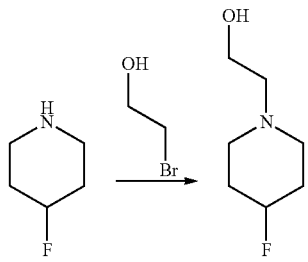

To a solution of 4-fluropiperidine (1 g, 9.70 mmol, 1 eq) in ACN (10 mL) was added 2-bromoethanol (2.42 g, 19.39 mmol, 1.38 mL, 2 eq) and K$_2$CO$_3$ (6.70 g, 48.48 mmol, 5 eq). The mixture was stirred at 20° C. for 2 h. The mixture was poured into water (100 mL), extracted with ethyl acetate (3×50 mL), the organic layer was washed with brine (30 mL), dried over Na₂SO₄ and concentrated to give 2-(4-fluoropiperidin-1-yl)ethan-1-ol (500 mg, 3.40 mmol, 35.04% yield).

¹H NMR (400 MHz, CDCl₃) δ=1.80-2.02 (m, 4H), 2.39-2.52 (m, 2H), 2.52-2.59 (m, 2H), 2.61-2.70 (m, 2H), 3.61 (t, J=5.44 Hz, 2H), 4.58-4.85 (m, 1H).

Step 2. Preparation of 1-(2-chloroethyl)-4-fluoropiperidine

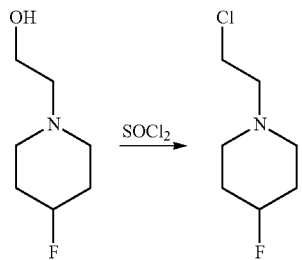

To a solution of 2-(4-fluoropiperidin-1-yl)ethan-1-ol (150 mg, 1.02 mmol, 1 eq) in DCE (2 mL) was added SOCl₂ (363.72 mg, 3.06 mmol, 221.78 μL, 3 eq). The mixture was stirred at 85° C. for 12 h. The mixture was concentrated to give crude product, which was triturated with ethyl acetate (10 mL). The mixture was filtered, the filter cake was dried to give the desired compound (130 mg, 784.85 μmol, 77.02% yield).

Step 3. Preparation of ethyl 6-bromo-4-hydroxy-2-oxo-1-(2-(4-fluoropiperidin-1-yl)ethyl)-1,2-dihydro-1,8-naphthyridine-3-carboxylate

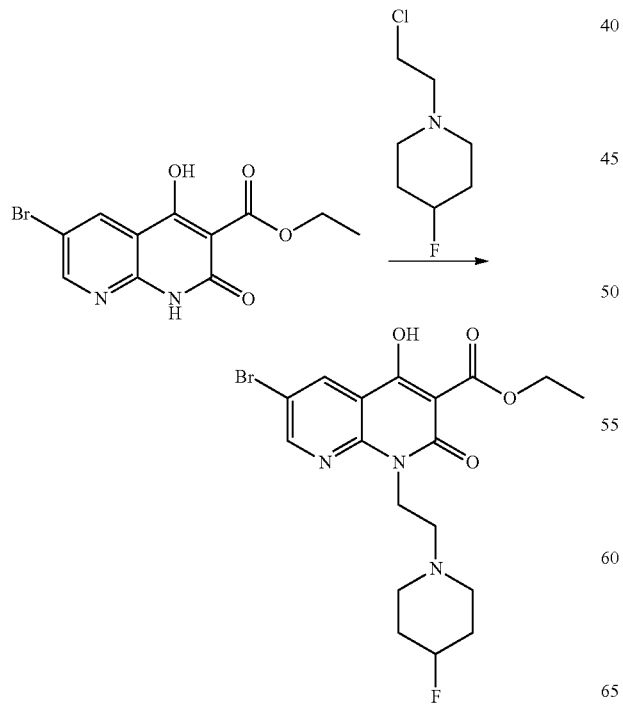

To a solution of ethyl 6-bromo-4-hydroxy-2-oxo-1,2-dihydro-1,8-naphthyridine-3-carboxylate (200 mg, 638.77 μmol, 1 eq) in DMF (2 mL) was added Cs₂CO₃ (1.66 g, 5.11 mmol, 8 eq), 1-(2-chloroethyl)-4-fluoro-piperidine (322.73 mg, 1.60 mmol, 2.5 eq, HCl) at 20° C., the mixture was stirred at 50° C. for 11 h. The mixture was filtered and the filtrate was concentrated to give crude product, which was triturated with ethyl acetate (5 mL). Then the mixture was filtered, the filter cake was dried to give the desired compound (120 mg, 271.32 μmol, 42.48% yield).

LCMS for product (ESI+): m/z 442.2, 444.2 (M+H)⁺, Rt:0.722 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 m particles). Detection methods are diode array (DAD) as well as positive electrospray ionization.

Step 4. Preparation of ethyl 6-(4-fluorophenyl)-4-hydroxy-2-oxo-1-(2-(4-fluoropiperidin-1-yl)ethyl)-1,2-dihydro-1,8-naphthyridine-3-carboxylate

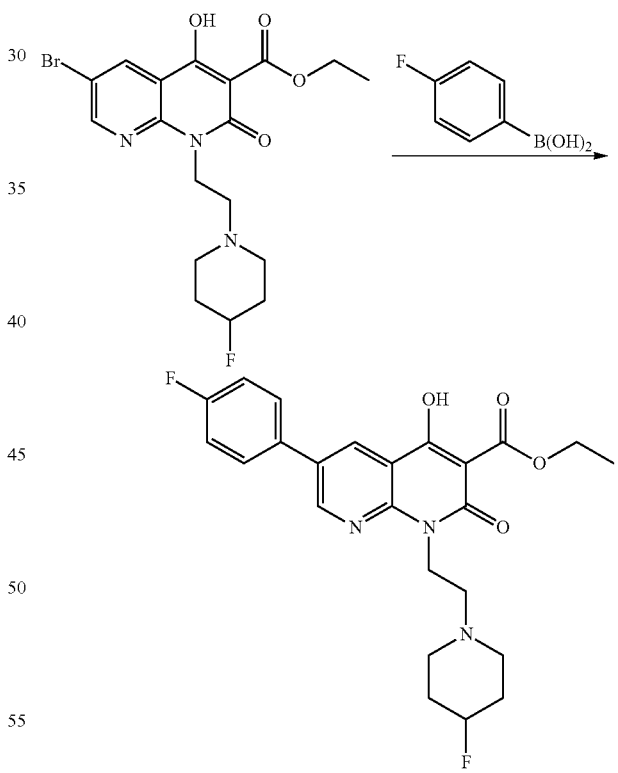

To a solution of ethyl 6-bromo-4-hydroxy-2-oxo-1-(2-(4-fluoropiperidin-1-yl)ethyl)-1,2-dihydro-1,8-naphthyridine-3-carboxylate (120 mg, 271.32 μmol, 1 eq) in dioxane (2 mL) and water (0.2 mL) was added (4-fluorophenyl)boronic acid (45.56 mg, 325.59 μmol, 1.2 eq), K₂CO₃ (112.50 mg, 813.97 μmol, 3 eq) and Pd(dppf)Cl₂ (19.85 mg, 27.13 μmol, 0.1 eq) under N₂. The mixture was stirred at 100° C. for 2 h. The mixture was filtered, the filtrate was purified by prep-HPLC (column: Phenomenex Luna 80*30 mm*3 μm;

mobile phase: [water (0.04% HCl)-ACN]; B %: 10%-40%, 8 min) to give the desired compound (80 mg, 174.88 µmol, 64.45% yield) as a yellow solid.

¹H NMR (400 MHz, CDCl₃) δ=1.50 (t, J=7.07 Hz, 3H), 2.13-2.24 (m, 2H), 2.54-2.87 (m, 2H), 3.04-3.28 (m, 2H), 3.40 (br d, J=1.25 Hz, 2H), 3.73 (br d, J=10.01 Hz, 2H), 4.55 (q, J=7.09 Hz, 2H), 4.87-5.11 (m, 3H), 7.20-7.24 (m, 2H), 7.59 (dd, J=8.63, 5.13 Hz, 2H), 8.59 (d, J=2.13 Hz, 1H), 8.89 (d, J=2.13 Hz, 1H), 12.44-12.75 (m, 1H), 14.45 (s, 1H).

Step 5. Preparation of N-(bicyclo[1.1.1]pentan-1-yl)-6-(4-fluorophenyl)-4-hydroxy-2-oxo-1-(2-(4-fluoropiperidin-1-yl)ethyl)-1,2-dihydro-1,8-naphthyridine-3-carboxamide

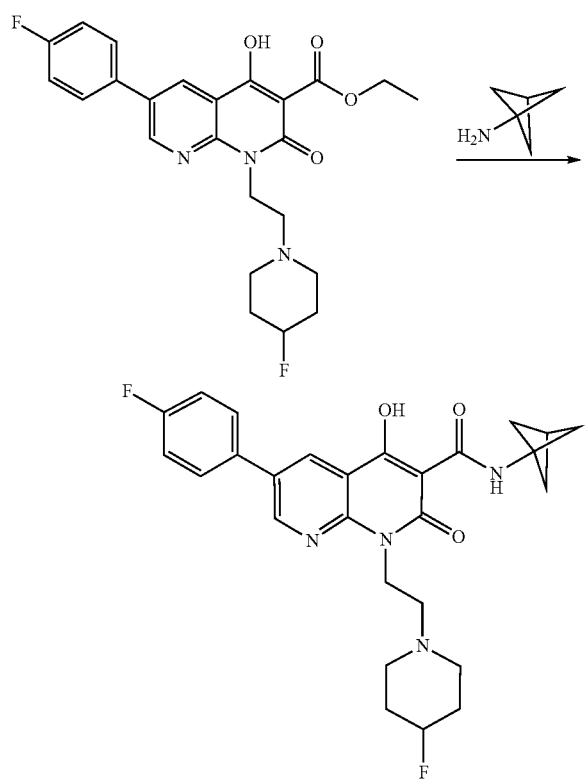

To a solution of ethyl 6-(4-fluorophenyl)-4-hydroxy-2-oxo-1-(2-(4-fluoropiperidin-1-yl)ethyl)-1,2-dihydro-1,8-naphthyridine-3-carboxylate (40 mg, 80.98 µmol, 1 eq, HCl) in toluene (1 mL) was added DIEA (41.87 mg, 323.93 µmol, 56.42 µL, 4 eq) and spiro[2.3]hexan-5-amine (12.99 mg, 97.18 µmol, 1.2 eq, HCl). The mixture was stirred at 120° C. for 5 h. The mixture was concentrated to give crude product, which was triturated with methanol (2 mL). Then the mixture was filtered, the filter cake was dried to give product, the product was dissolved in MeOH (0.5 mL) then added HCl (9.02 mg, 89.08 µmol, 8.85 uL, 36% purity, 1.1 eq), the mixture was blow-dried and lyophilized to give the desired compound (20.2 mg, 38.81 µmol, 47.92% yield, 97.7% purity, HCl).

¹H NMR (400 MHz, CDCl₃) δ=0.45-0.52 (m, 2H), 0.53-0.61 (m, 2H), 2.15-2.26 (m, 2H), 2.37-2.53 (m, 4H), 2.61-2.90 (m, 2H), 3.14-3.32 (m, 2H), 3.39 (br s, 2H), 3.60-3.77 (m, 2H), 4.63-4.78 (m, 1H), 4.92-5.14 (m, 3H), 7.20-7.24 (m, 2H), 7.62 (dd, J=8.63, 5.25 Hz, 2H), 8.62 (d, J=2.13 Hz, 1H), 8.89 (d, J=2.25 Hz, 1H), 10.22 (br d, J=7.25 Hz, 1H), 12.82-13.26 (m, 1H). LCMS for product (ESI+): m/z 509.1 (M+H)⁺, Rt:2.530 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 µm particles). Detection methods are diode array (DAD) as well as positive electrospray ionization.

Example 134—Synthesis of 1-(4-fluorobenzyl)-4-hydroxy-2-oxo-N-(spiro[3.3]heptan-2-yl)-1,2-dihydro-1,8-naphthyridine-3-carboxamide (Compound 134)

Preparation of 1-(4-fluorobenzyl)-4-hydroxy-2-oxo-N-(spiro[3.3]heptan-2-yl)-1,2-dihydro-1,8-naphthyridine-3-carboxamide

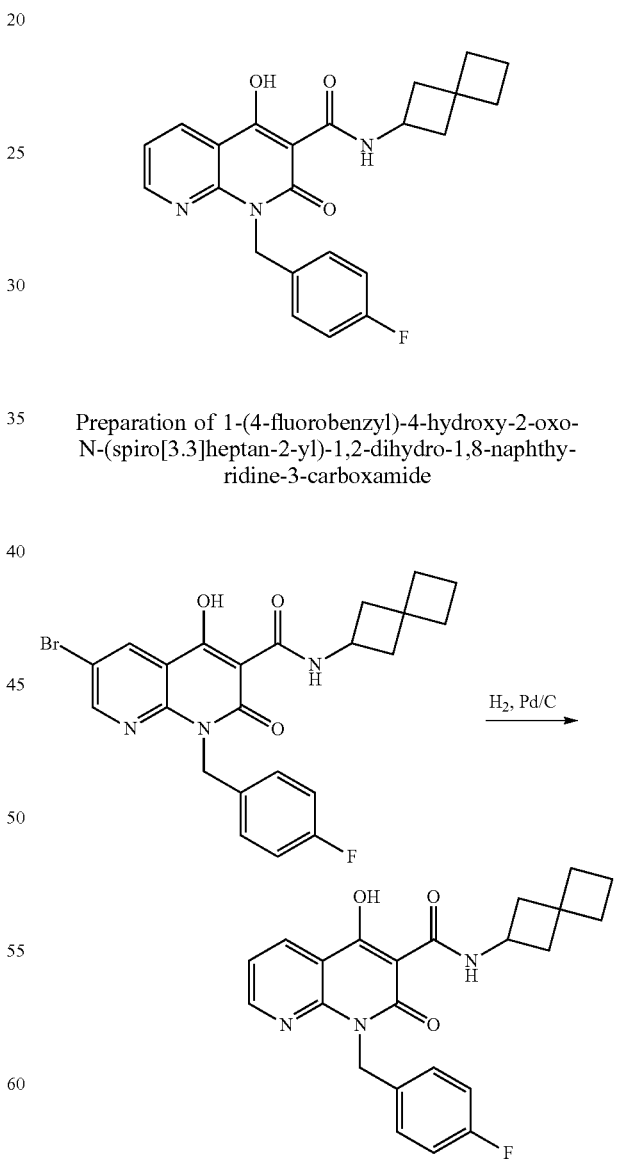

To a mixture of Pd/C (0.01 mg, 19.13 µmol, 10% purity, 1 eq) in THF (1 mL) was added 6-bromo-1-(4-fluorobenzyl)-4-hydroxy-2-oxo-N-(spiro[3.3]heptan-2-yl)-1,2-dihydro-1,8-naphthyridine-3-carboxamide (10 mg, 19.13 μmol, 1 eq, HCl). The mixture was stirred at 0° C. for 1 h under H₂ (15 psi). The reaction was filtered, the filtrate was purified by prep-HPLC (neutral condition) to give the desired compound (1 mg, 2.45 μmol, 12.83% yield, 100% purity).

¹H NMR (400 MHz, CDCl₃) δ=1.80-1.91 (m, 2H), 1.94-2.13 (m, 6H), 2.44-2.55 (m, 2H), 4.38 (sxt, J=8.00 Hz, 1H), 5.68 (s, 2H), 6.91-7.02 (m, 2H), 7.25 (d, J=4.77 Hz, 1H), 7.42 (dd, J=8.50, 5.56 Hz, 2H), 8.48 (dd, J=7.82, 1.83 Hz, 1H), 8.70 (dd, J=4.71, 1.90 Hz, 1H), 10.25 (br d, J=7.46 Hz, 1H). LCMS for product (ESI+): m/z 408.1 (M+H)⁺, Rt:3.530 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 μm particles). Detection methods are diode array (DAD) as well as positive electrospray ionization.

Example 135—Synthesis of 4-hydroxy-2-oxo-1-(2-morpholinoethyl)-N-(spiro[3.3]heptan-2-yl)-1,2-dihydro-1,8-naphthyridine-3-carboxamide (Compound 135)

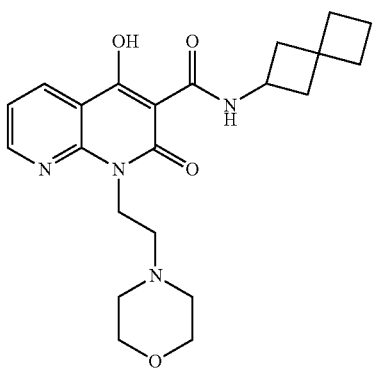 [SMILES: O=C(NC1CC2(CCC2)C1)c1c(O)c2cccnc2n(CCN2CCOCC2)c1=O]

Preparation of 4-hydroxy-2-oxo-1-(2-morpholinoethyl)-N-(spiro[3.3]heptan-2-yl)-1,2-dihydro-1,8-naphthyridine-3-carboxamide

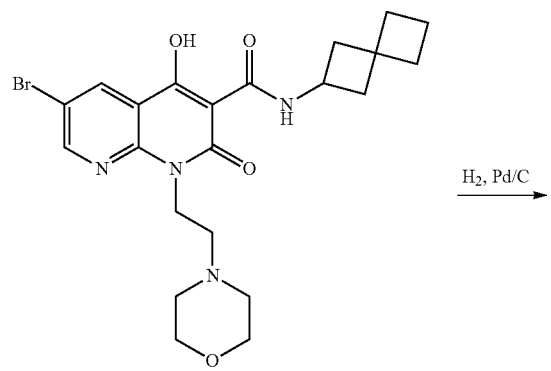

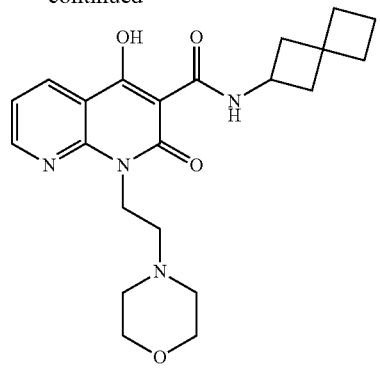

To a mixture of Pd/C (0.01 mg, 7.58 μmol, 10% purity, 1 eq) in THF (1 mL) was added 6-bromo-4-hydroxy-2-oxo-1-(2-morpholinoethyl)-N-(spiro[3.3]heptan-2-yl)-1,2-dihydro-1,8-naphthyridine-3-carboxamide (4 mg, 7.58 μmol, 1 eq, HCl) and TEA (76.68 μg, 7.58e-1 μmol, 1.05e-1 μL, 0.1 eq). The mixture was stirred at 0° C. for 1 h under H₂ (15 psi). The reaction was filtered, the filtrate was purified by prep-HPLC (neutral condition) to give the desired compound (1 mg, 2.29 μmol, 30.20% yield, 94.4% purity).

¹H NMR (400 MHz, CDCl₃) δ=1.82-1.90 (m, 2H), 1.96-2.11 (m, 6H), 2.37-2.85 (m, 8H), 3.70 (br s, 4H), 4.33-4.47 (m, 1H), 4.54-4.79 (m, 2H), 7.22-7.26 (m, 1H), 8.46 (dd, J=7.82, 1.69 Hz, 1H), 8.69 (dd, J=4.63, 1.88 Hz, 1H), 10.20-10.37 (m, 1H). LCMS for product (ESI+): m/z 413.2 (M+H)⁺, Rt:3.580 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 m particles). Detection methods are diode array (DAD) as well as positive electrospray ionization.

Example 136—Synthesis of N-(bicyclo[1.1.1]pentan-1-yl)-4-hydroxy-1-(2-morpholinoethyl)-2-oxo-1,2-dihydro-1,8-naphthyridine-3-carboxamide (Compound 136)

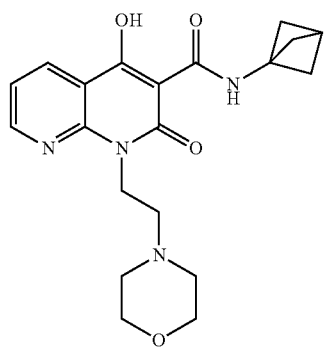

Step 1. Preparation of methyl 2-[(3-ethoxy-3-oxo-propanoyl)amino]pyridine-3-carboxylate

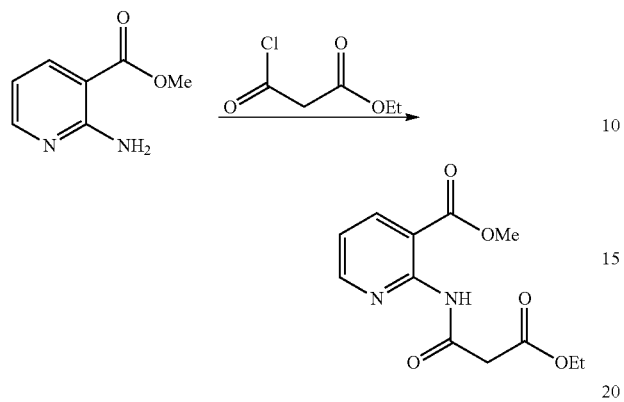

To a solution of methyl 2-aminopyridine-3-carboxylate (2 g, 13.14 mmol, 1 eq) in THF (80 mL) was added Py (1.56 g, 19.72 mmol, 1.59 mL, 1.5 eq) and ethyl 3-chloro-3-oxo-propanoate (2.37 g, 15.77 mmol, 1.98 mL, 1.2 eq) at 0° C. The mixture was stirred at 20° C. for 1 hr. The reaction mixture was quenched by addition water 80 mL at 25° C., and extracted with ethyl acetate 80 mL (80 mL*3). The combined organic layers were washed with brine 50 mL (50 mL *2), dried over Na$_2$SO$_4$, filtered and concentrated under reduced pressure to give methyl 2-[(3-ethoxy-3-oxo-propanoyl)amino]pyridine-3-carboxylate (4.1 g, 9.69 mmol, 73.69% yield, 62.9% purity).

LCMS for product (ESI+): m/z 267.0 [M+H]$^+$, Rt: 0.690 min.

Step 2. Preparation of ethyl 4-hydroxy-2-oxo-1H-1,8-naphthyridine-3-carboxylate

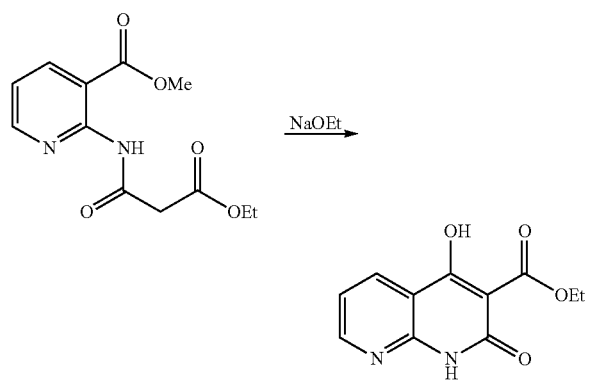

To a solution of methyl 2-[(3-ethoxy-3-oxo-propanoyl)amino]pyridine-3-carboxylate (4.1 g, 9.69 mmol, 62.9% purity, 1 eq) in EtOH (100 mL) was added NaOEt (2.64 g, 38.74 mmol, 4 eq). The mixture was stirred at 90° C. for 1 hr. The mixture was acidified to PH=4 by dropwise addition of 1 M HCl, the resulting (precipitated) solid was collected by filtration to give ethyl 4-hydroxy-2-oxo-1H-1,8-naphthyridine-3-carboxylate (2.2 g, 9.39 mmol, 96.98% yield).

$^1$H NMR (400 MHz, DMSO-d$_6$) δ=13.36-12.82 (m, 1H), 11.93 (br s, 1H), 8.61 (br d, J=3.3 Hz, 1H), 8.32 (br d, J=7.0 Hz, 1H), 7.28 (dd, J=4.7, 7.8 Hz, 1H), 4.33 (q, J=7.1 Hz, 2H), 1.30 (t, J=7.0 Hz, 3H).

Step 3. Preparation of ethyl 4-hydroxy-1-(2-morpholinoethyl)-2-oxo-1,8-naphthyridine-3-carboxylate

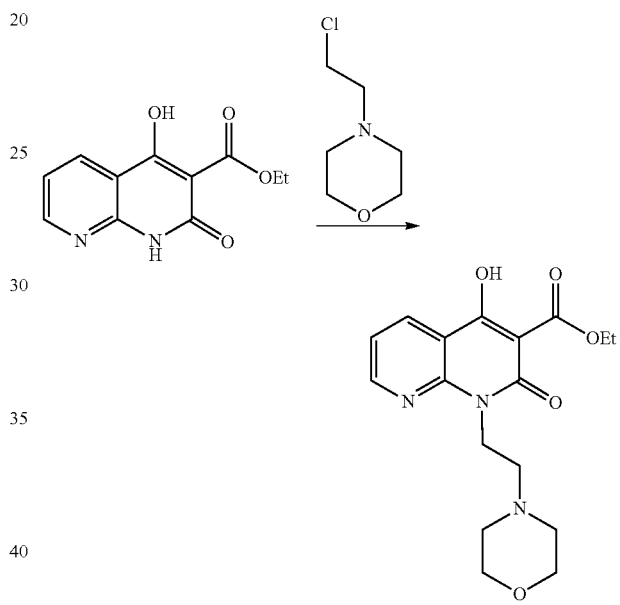

To a solution of ethyl 4-hydroxy-2-oxo-1H-1,8-naphthyridine-3-carboxylate (500 mg, 2.13 mmol, 1 eq) in DMF (10 mL) was added Cs$_2$CO$_3$ (5.56 g, 17.08 mmol, 8 eq) at 20° C. for 1 h, Then added 4-(2-chloroethyl)morpholine (638.83 mg, 4.27 mmol, 2 eq). The mixture was heated to 140° C. and stirred for 16 h. The reaction mixture was filtered and concentrated under reduced pressure to give a residue. The residue was triturated with Petroleum ether: Ethyl acetate (10 ml/10 ml) at 20° C. for 0.5 h. The resulting (precipitated) solid was collected by filtration to give ethyl 4-hydroxy-1-(2-morpholinoethyl)-2-oxo-1,8-naphthyridine-3-carboxylate (650 mg, 1.87 mmol, 87.65% yield).

$^1$H NMR (400 MHz, DMSO-d$_6$) δ=8.36 (dd, J=1.8, 4.6 Hz, 1H), 8.16 (dd, J=1.7, 7.5 Hz, 1H), 6.99 (dd, J=4.7, 7.5 Hz, 1H), 4.38-4.26 (m, 2H), 4.03 (q, J=7.1 Hz, 2H), 3.56 (br t, J=4.5 Hz, 4H), 3.33 (br s, 2H), 2.45 (br d, J=5.3 Hz, 4H), 1.19 (t, J=7.1 Hz, 3H).

433

Step 4. Preparation of N-(bicyclo[1.1.1]pentan-1-yl)-4-hydroxy-1-(2-morpholinoethyl)-2-oxo-1,2-dihydro-1,8-naphthyridine-3-carboxamide

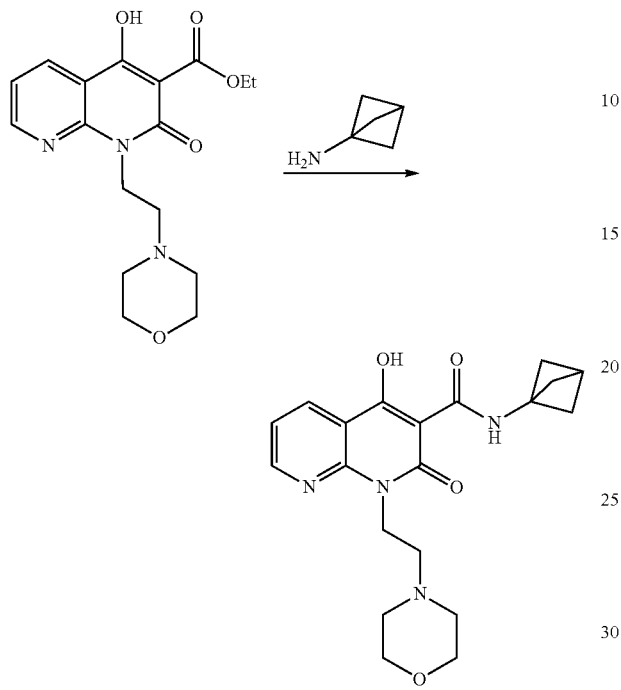

To a solution of bicyclo[1.1.1]pentan-1-amine (62.33 mg, 521.15 µmol, 1.2 eq, HCl) and ethyl 4-hydroxy-1-(2-morpholinoethyl)-2-oxo-1,8-naphthyridine-3-carboxylate (150.86 mg, 434.29 µmol, 1 eq) in toluene (4 mL) was added DIEA (140.32 mg, 1.09 mmol, 189.11 µL, 2.5 eq). The mixture was heated to 120° C. and stirred for 1.5 hr. The reaction mixture was directly concentrated. The residue was purified by prep-HPLC (FA condition; column: Phenomenex Synergi C18 150*25 mm*10 µm; mobile phase: [water (0.225% FA)-ACN]; B %: 17%-37%, 9 min) and lyophilized to give N-(1-bicyclo[1.1.1]pentanyl)-4-hydroxy-1-(2-morpholinoethyl)-2-oxo-1,8-naphthyridine-3-carboxamide (45 mg, 113.57 µmol, 26.15% yield, 97.02% purity).

$^1$H NMR (400 MHz, Methanol-d4) δ=8.74 (dd, J=1.8, 4.6 Hz, 1H), 8.50 (dd, J=1.8, 7.9 Hz, 1H), 7.37 (dd, J=4.7, 7.9 Hz, 1H), 4.71 (t, J=6.8 Hz, 2H), 3.74-3.65 (m, 4H), 2.86 (t, J=6.8 Hz, 2H), 2.77 (br s, 4H), 2.51 (s, 1H), 2.21 (s, 6H). LCMS for product (ESI+): m/z 385.1 [M+H]$^+$, Rt: 0.798 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 µm particles). Detection methods are diode array (DAD) as well as positive electrospray ionization.

434

Example 137—Synthesis of 4-hydroxy-N-((1s,4s)-4-methylcyclohexyl)-1-(2-morpholinoethyl)-2-oxo-1,2-dihydro-1,8-naphthyridine-3-carboxamide (Compound 137)

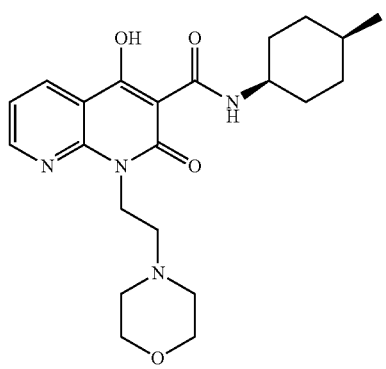 [SMILES: C[C@H]1CC[C@@H](NC(=O)c2c(O)c3cccnc3n(CCN3CCOCC3)c2=O)CC1]

Preparation of 4-hydroxy-N-((1s,4S)-4-methylcyclohexyl)-1-(2-morpholinoethyl)-2-oxo-1,2-dihydro-1,8-naphthyridine-3-carboxamide

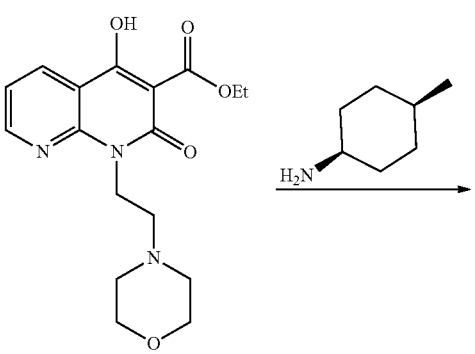

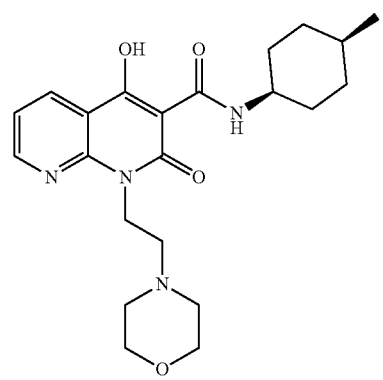

To a mixture of ethyl 4-hydroxy-1-(2-morpholinoethyl)-2-oxo-1,8-naphthyridine-3-carboxylate (80 mg, 230.31 µmol, 1 eq) in toluene (2 mL) was added DIPEA (74.42 mg, 575.78 µmol, 100.29 µL, 2.5 eq) and 4-methylcyclohexanamine (34.47 mg, 230.31 µmol, 1 eq, HCl) in one portion at 20° C. under N$_2$. The mixture was then heated to 120° C. and stirred for 2 hours. The reaction mixture was concentrated to obtain a residue. The residue was purified by prep-HPLC (FA condition, column: Phenomenex Synergi C18 150*25 mm*10 um; mobile phase: [water (0.225% FA)-ACN]; B %:

15%-45%, 10 min) and lyophilized to obtain desired product 4-hydroxy-N-((1s,4S)-4-methylcyclohexyl)-1-(2-morpholinoethyl)-2-oxo-1,2-dihydro-1,8-naphthyridine-3-carboxamide (28 mg, 67.55 µmol, 29.33% yield).

$^1$H NMR (400 MHz, DMSO-d6) δ=10.56 (br d, J=6.3 Hz, 1H), 8.82 (dd, J=1.5, 4.5 Hz, 1H), 8.46 (br d, J=6.8 Hz, 1H), 7.44-7.42 (m, 1H), 4.56 (br t, J=6.9 Hz, 2H), 4.21-3.99 (m, 1H), 3.52 (t, J=4.4 Hz, 4H), 2.58 (br t, J=6.9 Hz, 2H), 2.48 (br s, 4H), 1.81-1.71 (m, 2H), 1.68-1.58 (m, 4H), 1.57-1.48 (m, 1H), 1.24-1.10 (m, 2H), 0.94 (d, J=6.5 Hz, 3H). LCMS for product (ESI+): m/z 415.2 [M+H]$^+$, Rt: 0.777 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 m particles). Detection methods are diode array (DAD) as well as positive electrospray ionization.

Example 138—Synthesis of 4-hydroxy-N-[1-(hydroxymethyl)cyclohexyl]-1-(2-morpholinoethyl)-2-oxo-1,8-naphthyridine-3-carboxamide (Compound 138)

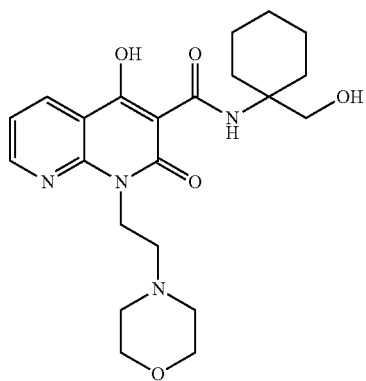 [SMILES: O=C(NC1(CO)CCCCC1)c1c(O)c2cccnc2n(CCN2CCOCC2)c1=O]

Preparation of 4-hydroxy-N-[1-(hydroxymethyl)cyclohexyl]-1-(2-morpholinoethyl)-2-oxo-1,8-naphthyridine-3-carboxamide

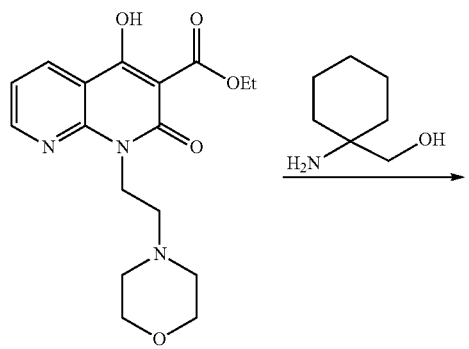

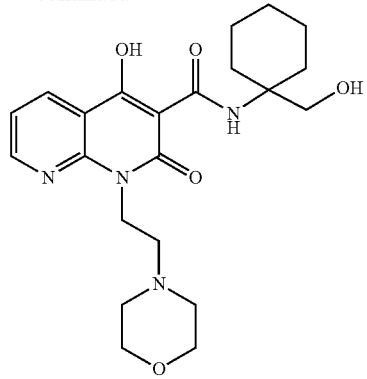

To a mixture of ethyl 4-hydroxy-1-(2-morpholinoethyl)-2-oxo-1,8-naphthyridine-3-carboxylate (80 mg, 230.31 µmol, 1 eq) in toluene (2 mL) was added (1-aminocyclohexyl)methanol hydrochloride (30.52 mg, 184.24 µmol, 0.8 eq) and DIPEA (89.30 mg, 690.92 µmol, 120.35 µL, 3 eq) in one portion at 20° C. The mixture was heated to 120° C. and stirred at 120° C. for 2 h. The reaction mixture was concentrated to obtain a residue. The residue was purified by prep-HPLC (FA condition, column: Phenomenex Synergi C18 150*25 mm*10 µm; mobile phase: [water (0.225% FA)-ACN]; B %: 9%-39%, 10 min). Compound 4-hydroxy-N-[1-(hydroxymethyl)cyclohexyl]-1-(2-morpholinoethyl)-2-oxo-1,8-naphthyridine-3-carboxamide (40 mg, 92.92 µmol, 40.34% yield).

$^1$H NMR (400 MHz, DMSO-d$_6$) δ=10.30 (br d, J=1.0 Hz, 1H), 8.80 (br s, 1H), 8.45 (br d, J=7.9 Hz, 1H), 8.14 (s, 0.74H, HCOOH), 7.44-7.41 (m, 1H), 4.99-4.68 (m, 1H), 4.54 (br t, J=6.4 Hz, 2H), 3.63 (s, 2H), 3.54-3.50 (m, 4H), 2.56 (br t, J=6.9 Hz, 2H), 2.48 (br s, 4H), 2.13 (br d, J=6.0 Hz, 2H), 1.57 (br d, J=4.0 Hz, 3H), 1.44-1.42 (m, 4H), 1.27 (br d, J=2.1 Hz, 1H). LCMS for product (ESI+): m/z 431.1 [M+H]$^+$, Rt: 0.720 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 m particles). Detection methods are diode array (DAD) as well as positive electrospray ionization.

Example 139—Synthesis of N-(1-bicyclo[1.1.1]pentanyl)-1-[(4-fluorophenyl)methyl]-4-hydroxy-2-oxo-1,8-naphthyridine-3-carboxamide (Compound 139)

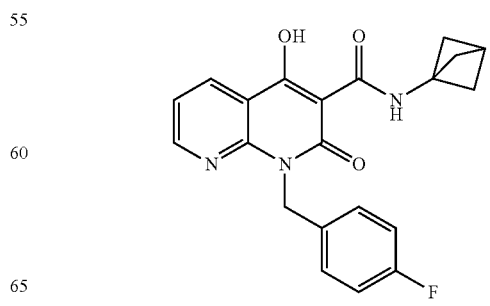

Step 1. Preparation of ethyl 1-[(4-fluorophenyl)methyl]-4-hydroxy-2-oxo-1,8-naphthyridine-3-carboxylate

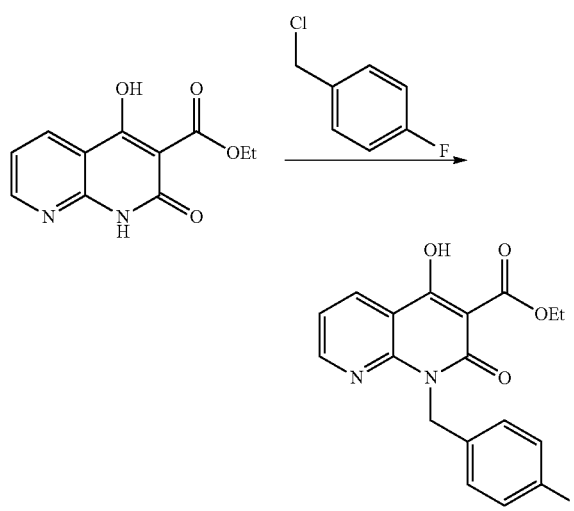

To a solution of ethyl 4-hydroxy-2-oxo-1H-1,8-naphthyridine-3-carboxylate (500 mg, 2.13 mmol, 1 eq) in DMF (10 mL) was added Cs$_2$CO$_3$ (5.56 g, 17.08 mmol, 8 eq) at 20° C. for 1 h, (bromomethyl)-4-fluoro-benzene (807.08 mg, 4.27 mmol, 527.50 µL, 2 eq) was added to the mixture. The mixture was stirred at 90° C. for 16 h. Then Cs$_2$CO$_3$ (1.39 g, 4.27 mmol, 2 eq) and 1-(bromomethyl)-4-fluoro-benzene (403.54 mg, 2.13 mmol, 263.06 µL, 1 eq) was added, the mixture was stirred at 90° C. for other 16 h. The reaction mixture was filtered and concentrated under reduced pressure to give a residue. The crude product was triturated with Petroleum ether: Ethyl acetate (10 ml/10 ml) at 20° C. for 0.5 h. The cake was purified by reverser-phase HPLC (0.05% FA condition; water/ACN=45%/55%) and lyophilized to give ethyl 1-[(4-fluorophenyl) methyl]-4-hydroxy-2-oxo-1,8-naphthyridine-3-carboxylate (170 mg, 496.61 µmol, 23.26% yield).

$^1$H NMR (400 MHz, DMSO-d$_6$) δ=8.70 (dd, J=1.6, 4.6 Hz, 1H), 8.43 (dd, J=1.7, 7.9 Hz, 1H), 7.38-7.35 (m, 1H), 7.34-7.29 (m, 2H), 7.09 (t, J=8.8 Hz, 2H), 5.51 (s, 2H), 4.31 (q, J=7.1 Hz, 2H), 1.29 (t, J=7.1 Hz, 3H).

Step 2. Preparation of 4-hydroxy-N-(1-bicyclo[1.1.1]pentanyl)-1-[(4-fluorophenyl)methyl]-4-hydroxy-2-oxo-1,8-naphthyridine-3-carboxamide

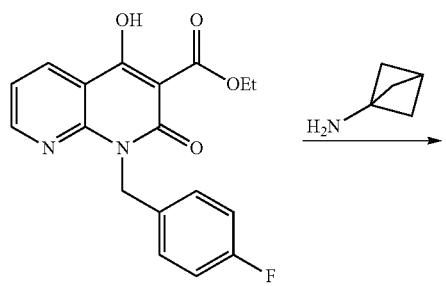

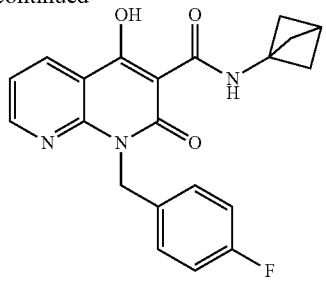

To the solution of ethyl 1-[(4-fluorophenyl)methyl]-4-hydroxy-2-oxo-1,8-naphthyridine-3-carboxylate (60 mg, 175.27 µmol, 1 eq) and bicyclo[1.1.1]pentan-1-amine (25.15 mg, 210.33 µmol, 1.2 eq, HCl) in toluene (3 mL) was added DIEA (56.63 mg, 438.19 µmol, 76.32 µL, 2.5 eq), the mixture was stirred at 120° C. for 1.5 h. The reaction mixture was directly concentrated. The residue was purified by prep-HPLC (FA condition; column: Phenomenex Synergi C18 150*25 mm*10 um; mobile phase: [water (0.225% FA)-ACN]; B %: 78%-100%, 10 min) and lyophilized to give N-(1-bicyclo[1.1.1]pentanyl)-1-[(4-fluorophenyl)methyl]-4-hydroxy-2-oxo-1,8-naphthyridine-3-carboxamide (28 mg, 73.80 µmol, 42.11% yield, 100% purity).

$^1$H NMR (400 MHz, DMSO-d6) δ=10.51 (br s, 1H), 8.80 (dd, J=1.8, 4.6 Hz, 1H), 8.49 (dd, J=1.8, 7.9 Hz, 1H), 7.45 (dd, J=4.7, 7.9 Hz, 1H), 7.35-7.26 (m, 2H), 7.14-7.02 (m, 2H), 5.58 (s, 2H), 2.53 (br s, 1H), 2.15 (s, 6H). LCMS for product (ESI+): m/z 380.0 [M+H]$^+$, Rt: 1.134 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 µm particles). Detection methods are diode array (DAD) as well as positive electrospray ionization.

Example 140—Synthesis of 1-[(4-fluorophenyl)methyl]-4-hydroxy-N-(2-hydroxy-1,1-dimethyl-ethyl)-2-oxo-1,8-naphthyridine-3-carboxamide (Compound 140)

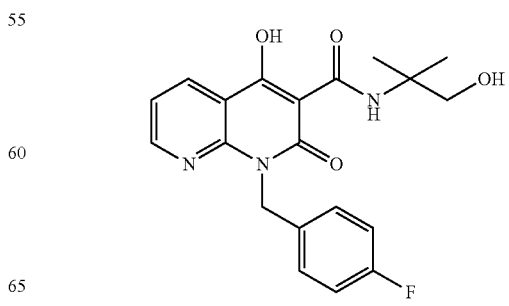

439

Preparation of 1-[(4-fluorophenyl)methyl]-4-hydroxy-N-(2-hydroxy-1,1-dimethyl-ethyl)-2-oxo-1,8-naphthyridine-3-carboxamide

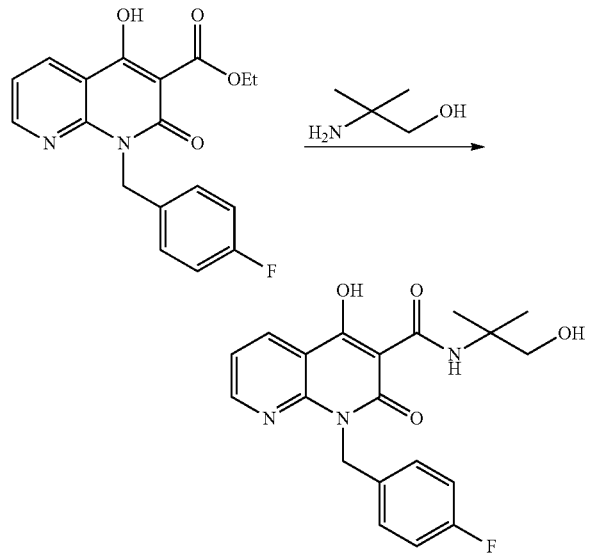

To a solution of ethyl 1-[(4-fluorophenyl)methyl]-4-hydroxy-2-oxo-1,8-naphthyridine-3-carboxylate (40 mg, 116.85 μmol, 1 eq) and 2-amino-2-methyl-propan-1-ol (17.61 mg, 197.56 μmol, 18.85 μL, 1.69 eq) in toluene (2 mL) was added DIEA (37.75 mg, 292.12 μmol, 50.88 μL, 2.5 eq), the mixture was stirred at 120° C. for 1.5 h. The reaction mixture was directly concentrated. The residue was purified by prep-HPLC (FA condition; column: Phenomenex Synergi C18 150*25 mm*10 μm; mobile phase: [water (0.225% FA)-ACN]; B %: 57%-77%, 10 min) and lyophilized to give 1-[(4-fluorophenyl)methyl]-4-hydroxy-N-(2-hydroxy-1,1-dimethyl-ethyl)-2-oxo-1,8-naphthyridine-3-carboxamide (29 mg, 72.65 μmol, 62.17% yield, 96.54% purity).

$^1$H NMR (400 MHz, DMSO-$d_6$) δ=10.36 (s, 1H), 8.77 (dd, J=1.7, 4.5 Hz, 1H), 8.48 (dd, J=1.8, 7.9 Hz, 1H), 7.44 (dd, J=4.6, 7.9 Hz, 1H), 7.29 (br dd, J=5.7, 8.4 Hz, 2H), 7.15-7.04 (m, 2H), 5.59 (s, 2H), 5.16 (t, J=5.3 Hz, 1H), 3.47 (d, J=5.4 Hz, 2H), 1.36 (s, 6H). LCMS for product (ESI+): m/z 386.0 [M+H]$^+$, Rt: 0.989 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

440

Example 141—Synthesis of 1-[(4-fluorophenyl)methyl]-4-hydroxy-N-(3-methyl-1-bicyclo[1.1.1]pentanyl)-2-oxo-1,8-naphthyridine-3-carboxamide (Compound 141)

Preparation of 1-[(4-fluorophenyl)methyl]-4-hydroxy-N-(3-methyl-1-bicyclo[1.1.1]pentanyl)-2-oxo-1,8-naphthyridine-3-carboxamide

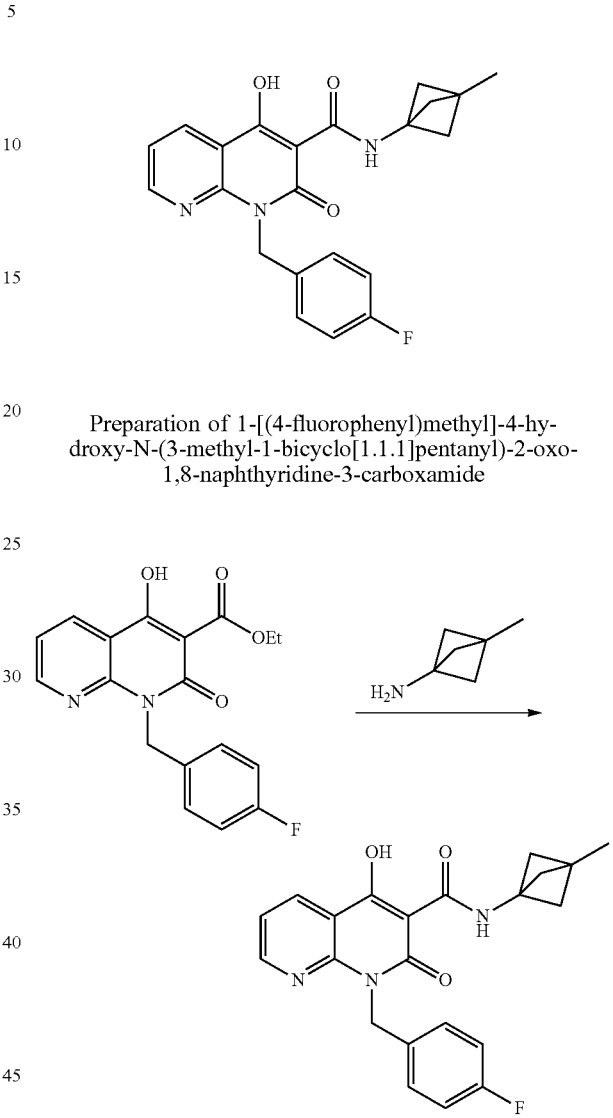

To a solution of ethyl 1-[(4-fluorophenyl)methyl]-4-hydroxy-2-oxo-1,8-naphthyridine-3-carboxylate (50 mg, 146.06 μmol, 1 eq) and 3-methylbicyclo[1.1.1]pentan-1-amine (23.42 mg, 175.27 μmol, 1.2 eq, HCl) in toluene (2 mL) was added DIEA (47.19 mg, 365.15 μmol, 63.60 μL, 2.5 eq). The mixture was stirred at 120° C. for 1.5 hr. The reaction mixture was directly concentrated. The residue was purified by prep-HPLC (FA condition; column: Phenomenex Synergi C18 150*25 mm*10 μm; mobile phase: [water (0.225% FA)-ACN]; B %: 85%-100%, 10 min) and lyophilized to give 1-[(4-fluorophenyl)methyl]-4-hydroxy-N-(3-methyl-1-bicyclo[1.1.1]pentanyl)-2-oxo-1,8-naphthyridine-3-carboxamide (28 mg, 69.26 μmol, 47.42% yield, 97.31% purity).

$^1$H NMR (400 MHz, DMSO-$d_6$) δ=10.48 (br s, 1H), 8.78 (br d, J=3.0 Hz, 1H), 8.48 (dd, J=1.6, 7.9 Hz, 1H), 7.44 (dd, J=4.7, 7.8 Hz, 1H), 7.31 (dd, J=5.6, 8.6 Hz, 2H), 7.08 (t, J=8.9 Hz, 2H), 5.58 (s, 2H), 2.02 (s, 6H), 1.24 (s, 3H). LCMS for product (ESI+): m/z 386.0 [M+H]$^+$, Rt: 0.989 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 μm particles). Detection methods are diode array (DAD) as well as positive electrospray ionization.

Example 142—Synthesis of 1-[(4-fluorophenyl) methyl]-4-hydroxy-2-oxo-N-spiro[2.3]hexan-5-yl-1,8-naphthyridine-3-carboxamide (Compound 142)

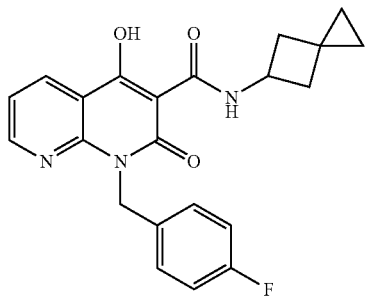 [SMILES: O=C(NC1CC2(CC2)C1)c1c(O)c2cccnc2n(Cc2ccc(F)cc2)c1=O]

Preparation of 1-[(4-fluorophenyl) methyl]-4-hydroxy-2-oxo-N-spiro[2.3]hexan-5-yl-1,8-naphthyridine-3-carboxamide

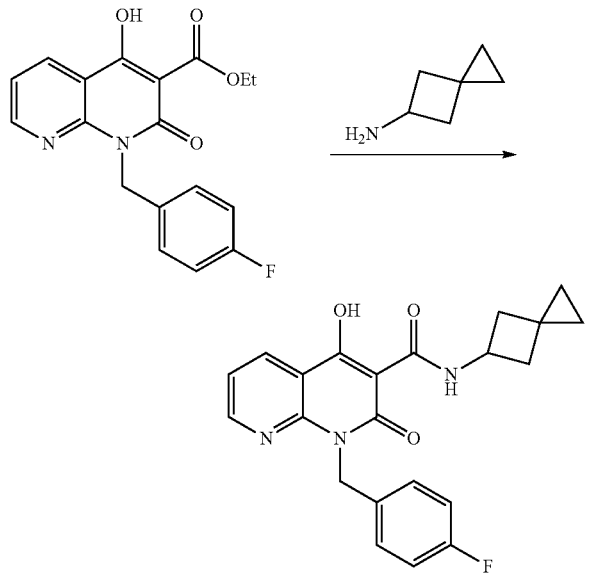

To a solution of ethyl 1-[(4-fluorophenyl)methyl]-4-hydroxy-2-oxo-1,8-naphthyridine-3-carboxylate (50 mg, 146.06 μmol, 1 eq) and spiro[2.3]hexan-5-amine (23.42 mg, 175.27 μmol, 1.2 eq, HCl) in toluene (2 mL) was added DIEA (47.19 mg, 365.15 μmol, 63.60 μL, 2.5 eq). The reaction mixture was stirred at 120° C. for 1.5 hr. The reaction mixture was directly concentrated. Then added DMF 2 ml into the residue and the precipitated collected by filtration, the resulting (precipitated) solid was triturated with EtOH at 20° C. for 30 min and collected by filtration. 1-[(4-fluorophenyl) methyl]-4-hydroxy-2-oxo-N-spiro[2.3]hexan-5-yl-1,8-naphthyridine-3-carboxamide (23 mg, 58.46 μmol, 40.03% yield, 100% purity).

¹H NMR (400 MHz, DMSO-d₆) δ=10.42 (br dd, J=1.7, 3.9 Hz, 1H), 8.79 (dd, J=1.8, 4.6 Hz, 1H), 8.49 (dd, J=1.7, 7.8 Hz, 1H), 7.45 (dd, J=4.6, 7.9 Hz, 1H), 7.32 (dd, J=5.6, 8.6 Hz, 2H), 7.10 (t, J=8.8 Hz, 2H), 5.61 (s, 2H), 4.64-4.48 (m, 1H), 2.43-2.27 (m, 4H), 0.54-0.48 (m, 2H), 0.47-0.40 (m, 2H). LCMS for product (ESI+): m/z 394.0 [M+H]⁺, Rt: 1.146 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H₂O+10 mM NH₄HCO₃, mobile phase B was Acetonitrile. The column used for chromatography was a Xbridge Shield RP18 2.1*50 mm column (5 μm particles). Detection methods are diode array (DAD) as well as positive electrospray ionization.

Example 143—Synthesis of 1-(4-fluorobenzyl)-4-hydroxy-N-((1s,4s)-4-methylcyclohexyl)-2-oxo-1,2-dihydro-1,8-naphthyridine-3-carboxamide (Compound 143)

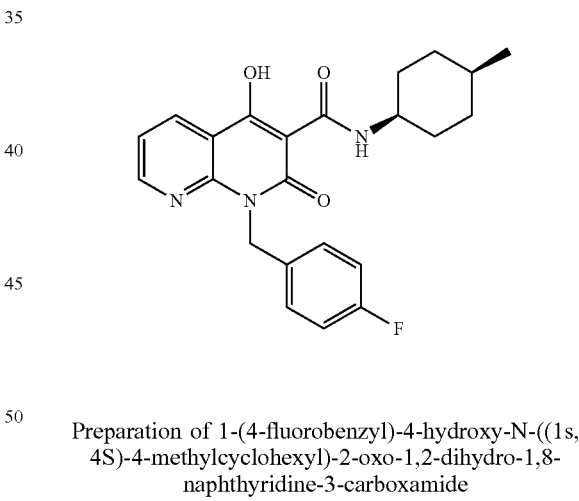

Preparation of 1-(4-fluorobenzyl)-4-hydroxy-N-((1s,4S)-4-methylcyclohexyl)-2-oxo-1,2-dihydro-1,8-naphthyridine-3-carboxamide

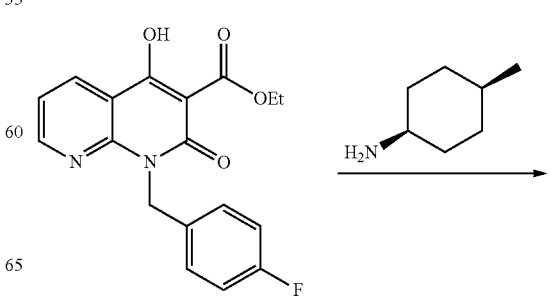

443
-continued

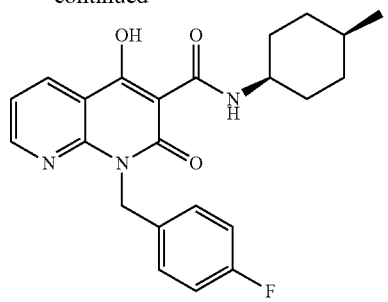

To the suspension of ethyl 1-[(4-fluorophenyl)methyl]-4-hydroxy-2-oxo-1,8-naphthyridine-3-carboxylate (50 mg, 146.06 μmol, 1 eq) and 4-methylcyclohexanamine (21.86 mg, 146.06 μmol, 1 eq, HCl) toluene (2 mL) was added DIEA (47.19 mg, 365.15 μmol, 63.60 μL, 2.5 eq). The mixture was stirred at 120° C. for 1.5 h. The reaction mixture was directly concentrated. The residue was purified by prep-HPLC (FA condition; column: Unisil 3-100 C18 Ultra 150*50 mm*3 μm; mobile phase: [water (0.225% FA)-ACN]; B %: 70%-100%, 10 min) and lyophilized to give 1-[(4-fluorophenyl)methyl]-4-hydroxy-N-((1s,4S)-4-methylcyclohexyl)-2-oxo-1,8-naphthyridine-3-carboxamide (24 mg, 55.62 μmol, 38.08% yield, 94.89% purity).

$^1$H NMR (400 MHz, DMSO-$d_6$) δ=10.45 (br d, J=6.4 Hz, 1H), 8.78 (dd, J=1.6, 4.6 Hz, 1H), 8.49 (dd, J=1.6, 7.9 Hz, 1H), 7.44 (dd, J=4.6, 7.9 Hz, 1H), 7.30 (dd, J=5.7, 8.4 Hz, 2H), 7.10 (t, J=8.9 Hz, 2H), 5.61 (s, 2H), 4.18-4.05 (m, 1H), 1.82-1.69 (m, 2H), 1.68-1.45 (m, 5H), 1.22-1.08 (m, 2H), 0.92 (d, J=6.5 Hz, 3H). LCMS for product (ESI+): m/z 410.1 [M+H]$^+$, Rt: 1.201 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 144—Synthesis of 1-(4-fluorobenzyl)-4-hydroxy-N-((1r,4r)-4-methylcyclohexyl)-2-oxo-1,2-dihydro-1,8-naphthyridine-3-carboxamide (Compound 144)

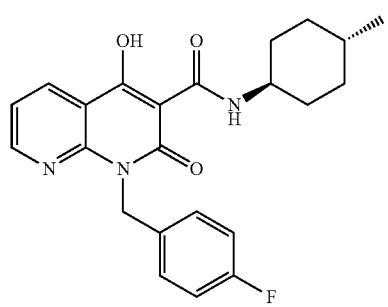 [SMILES: C[C@H]1CC[C@H](NC(=O)c2c(O)c3cccnc3n(Cc3ccc(F)cc3)c2=O)CC1]

444
Preparation of 1-(4-fluorobenzyl)-4-hydroxy-N-((1R,4R)-4-methylcyclohexyl)-2-oxo-1,2-dihydro-1,8-naphthyridine-3-carboxamide

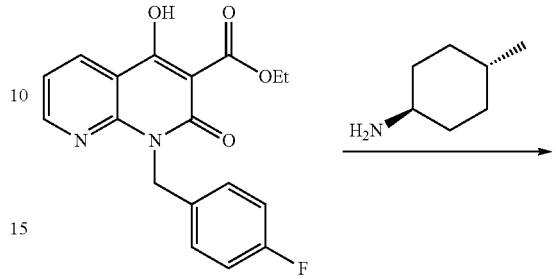

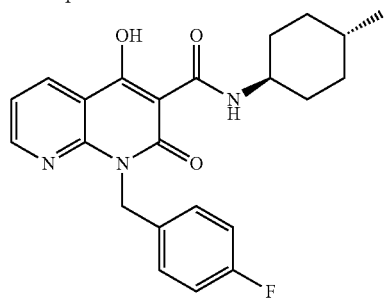

To a solution of ethyl 1-[(4-fluorophenyl)methyl]-4-hydroxy-2-oxo-1,8-naphthyridine-3-carboxylate (45 mg, 131.46 μmol, 1 eq) and 4-methylcyclohexanamine; hydrochloride (19.67 mg, 131.46 μmol, 1 eq) in toluene (3 mL) was added DIEA (42.47 mg, 328.64 μmol, 57.24 μL, 2.5 eq). The mixture was stirred at 120° C. for 1.5 hr. The reaction mixture was directly concentrated. The residue was purified by prep-HPLC (FA condition; column: Phenomenex Synergi C18 150*25 mm*10 μm; mobile phase: [water (0.225% FA)-ACN]; B %: 85%-100%, 10 min) and lyophilized to give 1-[(4-fluorophenyl)methyl]-4-hydroxy-N-((1R,4R)-4-methylcyclohexyl)-2-oxo-1,8-naphthyridine-3-carboxamide (25 mg, 61.06 μmol, 46.45% yield, 100% purity).

$^1$H NMR (400 MHz, DMSO-$d_6$) δ=10.07 (br d, J=6.6 Hz, 1H), 8.78 (dd, J=1.8, 4.7 Hz, 1H), 8.48 (dd, J=1.9, 7.9 Hz, 1H), 7.44 (dd, J=4.6, 7.9 Hz, 1H), 7.34-7.27 (m, 2H), 7.09 (br dd, J=4.6, 9.0 Hz, 2H), 5.59 (s, 2H), 3.82-3.68 (m, 1H), 1.99-1.87 (m, 2H), 1.70 (br d, J=11.1 Hz, 2H), 1.45-1.27 (m, 3H), 1.11-0.96 (m, 2H), 0.88 (d, J=6.5 Hz, 3H). LCMS for product (ESI+): m/z 410.1 [M+H]$^+$, Rt: 1.217 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 μm particles). Detection methods are diode array (DAD) as well as positive electrospray ionization.

Example 145—Synthesis of 1-[(4-fluorophenyl)methyl]-4-hydroxy-N-[1-(hydroxymethyl)cyclohexyl]-2-oxo-1,8-naphthyridine-3-carboxamide (Compound 145)

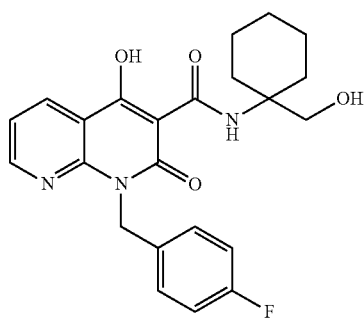 [SMILES: O=C(NC1(CO)CCCCC1)c1c(O)c2cccnc2n(Cc2ccc(F)cc2)c1=O]

Preparation of 1-[(4-fluorophenyl)methyl]-4-hydroxy-N-[1-(hydroxymethyl)cyclohexyl]-2-oxo-1,8-naphthyridine-3-carboxamide

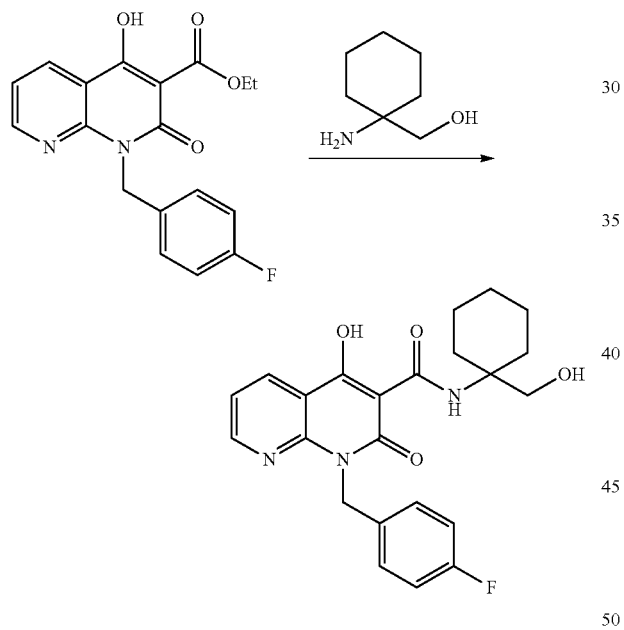

To a solution of ethyl 1-[(4-fluorophenyl)methyl]-4-hydroxy-2-oxo-1,8-naphthyridine-3-carboxylate (40 mg, 116.85 μmol, 1 eq) and (1-aminocyclohexyl)methanol (21.29 mg, 128.53 μmol, 1.1 eq, HCl) in toluene (1.5 mL) was added DIEA (37.75 mg, 292.12 μmol, 50.88 μL, 2.5 eq). The mixture was stirred at 120° C. for 1.5 hr. The reaction mixture was directly concentrated. The residue was first purified by prep-HPLC (FA condition; column: Phenomenex Synergi C18 150*25 mm*10 μm; mobile phase: [water (0.225% FA)-ACN]; B %: 68%-88%, 10 min) and lyophilized. Then the crude product was second purified by prep-HPLC (FA condition; column: Phenomenex Synergi C18 150*25 mm*10 μm; mobile phase: [water (0.225% FA)-ACN]; B %: 74%-94%, 8 min) and lyophilized to give 1-[(4-fluorophenyl)methyl]-4-hydroxy-N-[1-(hydroxymethyl)cyclohexyl]-2-oxo-1,8-naphthyridine-3-carboxamide (8.6 mg, 20.11 μmol, 17.21% yield, 99.48% purity).

$^1$H NMR (400 MHz, DMSO-$d_6$) δ=10.43-10.13 (m, 1H), 8.85-8.65 (m, 1H), 8.47 (br d, J=5.7 Hz, 1H), 7.46-7.37 (m, 1H), 7.29 (br d, J=4.9 Hz, 2H), 7.09 (br s, 2H), 5.59 (br s, 2H), 4.99-4.65 (m, 1H), 3.61 (s, 2H), 2.10 (br s, 2H), 1.53 (br s, 3H), 1.41 (br s, 6H), 1.23 (br s, 2H). LCMS for product (ESI+): m/z 426.0 [M+H]$^+$, Rt: 1.066 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 m particles). Detection methods are diode array (DAD) as well as positive electrospray ionization.

Example 146—Synthesis of N-(bicyclo[1.1.1]pentan-1-yl)-8-hydroxy-5-(2-morpholinoethyl)-6-oxo-5,6-dihydropyrido[2,3-b]pyrazine-7-carboxamide (Compound 146)

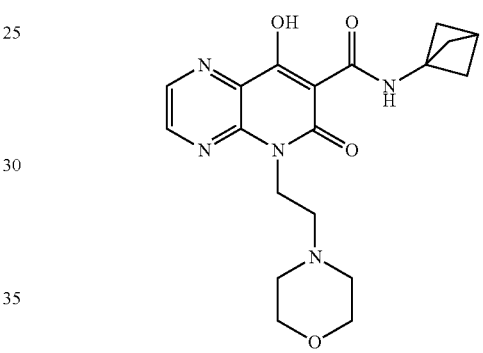

Step 1. Preparation of methyl 3-[(3-ethoxy-3-oxopropanoyl)amino]pyrazine-2-carboxylate

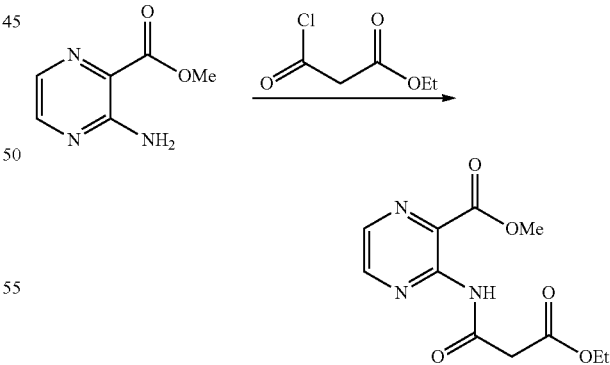

To a mixture of methyl 3-aminopyrazine-2-carboxylate (2 g, 13.06 mmol, 1 eq) in DCM (30 mL) was added ethyl 3-chloro-3-oxopropanoate (7.68 g, 50.94 mmol, 6.39 mL, 3.9 eq) in DCM (5 mL) in dropwise at 0° C. under N$_2$. The mixture was stirred at 0° C. for 5 min, then DIEA (5.07 g, 39.18 mmol, 6.81 mL, 3.0 eq) was added in dropwise, after addition, the mixture was warmed to 20° C. and stirred for 16 h. The reaction mixture was concentrated to obtain a residue. The crude product methyl 3-[(3-ethoxy-3-oxo-propanoyl)amino]pyrazine-2-carboxylate (5 g, crude) was used into the next step without further purification.

LCMS for product (ESI+): m/z 268.1 [M+H]⁺, Rt: 0.701 min.

Step 2. Preparation of ethyl 8-hydroxy-6-oxo-5H-pyrido[2,3-b]pyrazine-7-carboxylate

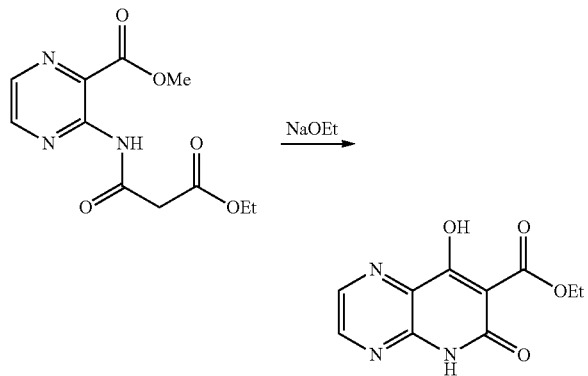

To a mixture of methyl 3-[(3-ethoxy-3-oxo-propanoyl)amino]pyrazine-2-carboxylate (3.49 g, 13.07 mmol, 1 eq) in EtOH (35 mL) was added EtONa (3.56 g, 52.28 mmol, 4 eq) in one portion at 20° C. under N₂. The mixture was heated to 80° C. for 2 h. The reaction mixture was cooled to 20° C., then added water 5 mL to dissolve the solid, and the reaction mixture got a clear solution, then 1M HCl solution about 10 mL was added, then the solid was appeared. The precipitated solid was stirred at 20° C. for 0.5 h, then filtered and washed with water 20 mL, the filter cake was dried by reduced pressure to obtain the desired product. Compound ethyl 8-hydroxy-6-oxo-5H-pyrido[2,3-b]pyrazine-7-carboxylate (2.5 g, 10.63 mmol, 81.33% yield) was obtained as a brown solid.

1H NMR (400 MHz, DMSO-d6) δ=12.31 (br s, 2H), 8.68 (br s, 1H), 8.57 (br s, 1H), 4.27 (q, J=6.9 Hz, 2H), 1.28 (br t, J=7.0 Hz, 3H). LCMS for product (ESI+): m/z 236.1 [M+H]⁺, Rt: 0.426 min.

Step 3. Preparation of ethyl 8-hydroxy-5-(2-morpholinoethyl)-6-oxo-pyrido[2,3-b]pyrazine-7-carboxylate

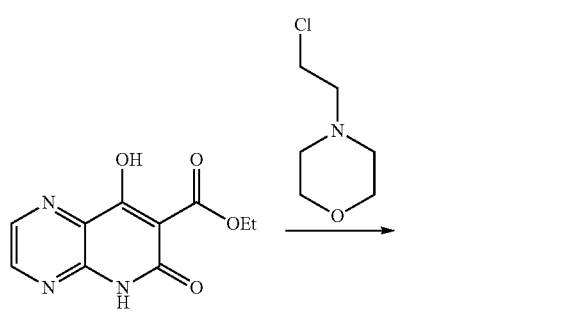

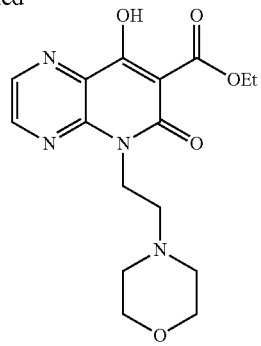

To a mixture of ethyl 8-hydroxy-6-oxo-5H-pyrido[2,3-b]pyrazine-7-carboxylate (200 mg, 850.36 μmol, 1 eq) in DMF (4 mL) was added Cs₂CO₃ (2.22 g, 6.80 mmol, 8 eq) in one portion at 20° C. under N₂. The mixture was stirred at 20° C. for 30 min, then 4-(2-chloroethyl)morpholine (127.23 mg, 850.36 μmol, 1 eq) was added, the mixture was heated to 140° C. for 12 h. The reaction mixture was cooled to 20° C., then filtered and washed with DMF 5 mL, then concentrated to obtain a residue. 5 mL EA was added into the residue, and then stirred at 20° C. for 30 min, the solid was formed, then EA was removed by reduced pressure to obtain desired product. Compound ethyl 8-hydroxy-5-(2-morpholinoethyl)-6-oxo-pyrido[2,3-b]pyrazine-7-carboxylate (130 mg, 373.18 μmol, 43.89% yield) was obtained.

¹H NMR (400 MHz, DMSO-d6) δ=8.62-8.55 (m, 1H), 8.45 (br s, 1H), 4.37 (br t, J=6.9 Hz, 2H) 4.16 (q, J=7.2 Hz, 2H), 3.67-3.47 (m, 4H), 2.65-2.53 (m, 6H), 1.24 (br t, J=7.1 Hz, 3H). LCMS for product (ESI+): m/z 349.1 [M+H]⁺, Rt: 0.633 min.

Step 4. Preparation of N-(bicyclo[1.1.1]pentan-1-yl)-8-hydroxy-5-(2-morpholinoethyl)-6-oxo-5,6-dihydropyrido[2,3-b]pyrazine-7-carboxamide

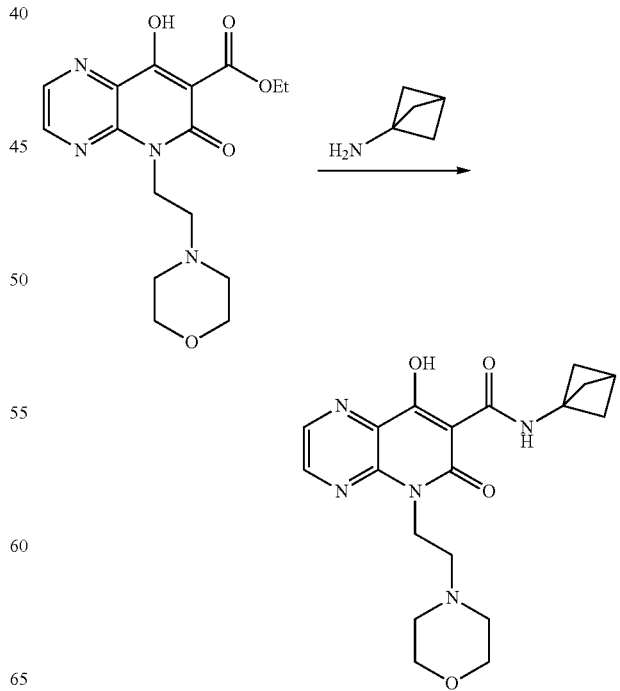

To a mixture of ethyl 8-hydroxy-5-(2-morpholinoethyl)-6-oxo-pyrido[2,3-b]pyrazine-7-carboxylate (130 mg, 373.18 μmol, 1 eq) in toluene (3 mL) was added bicyclo[1.1.1]pentan-1-amine (31.02 mg, 373.18 μmol, 1 eq) and DIEA (120.58 mg, 932.96 μmol, 162.51 μL, 2.5 eq) in one portion at 20° C. under N2. The mixture was then heated to 120° C. and stirred for 3 h. The reaction mixture was concentrated to obtain a residue. The residue was purified by prep-HPLC (FA condition, column: Phenomenex Synergi C18 150*25 mm*10 um; mobile phase: [water (0.225% FA)-ACN]; B %: 4%-34%, 10 min) and lyophilized to obtain desired product. Compound N-(1-bicyclo[1.1.1]pentanyl)-8-hydroxy-5-(2-morpholinoethyl)-6-oxo-pyrido[2,3-b]pyrazine-7-carboxamide (25.4 mg, 65.90 μmol, 17.66% yield) was obtained. 1H NMR (EW28564-42-P1, 400 MHz, CHLOROFORM-d) δ=10.36 (br s, 1H), 8.66 (s, 2H), 4.64 (t, J=7.0 Hz, 2H), 3.71 (br t, J=4.3 Hz, 4H), 2.74 (br t, J=6.9 Hz, 2H), 2.66 (br s, 4H), 2.54 (s, 1H), 2.23 (s, 6H). LCMS for product (ESI+): m/z 386.1 [M+H]+, Rt: 0. 0.667 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H2O+10 mM NH4HCO3, mobile phase B was Acetonitrile. The column used for chromatography was a Xbridge Shield RP18 2.1*50 mm column (5 μm particles). Detection methods are diode array (DAD) as well as positive electrospray ionization.

Example 147—Synthesis of N-(bicyclo[1.1.1]pentan-1-yl)-5-(4-fluorobenzyl)-8-hydroxy-6-oxo-5,6-dihydropyrido[2,3-b]pyrazine-7-carboxamide (Compound 147)

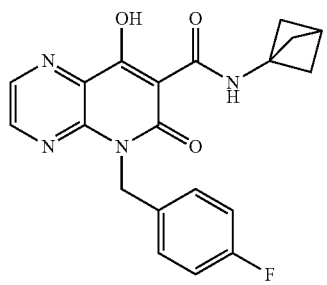 [SMILES: O=C(NC12CC(C1)C2)c1c(O)c2nccnc2n(Cc2ccc(F)cc2)c1=O]

Step 1. Preparation of ethyl 5-[(4-fluorophenyl)methyl]-8-hydroxy-6-oxo-pyrido[2,3-b]pyrazine-7-carboxylate

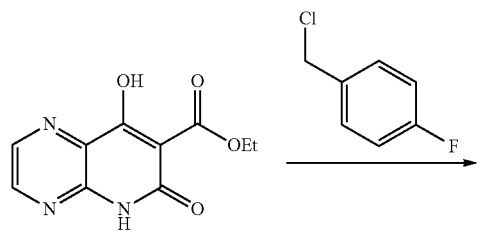

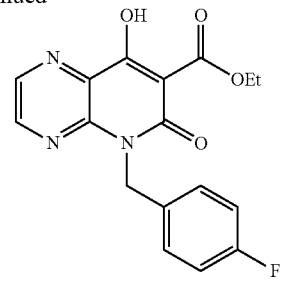

To a mixture of ethyl 8-hydroxy-6-oxo-5H-pyrido[2,3-b]pyrazine-7-carboxylate (500 mg, 2.13 mmol, 1 eq) in DMF (10 mL) was added Cs2CO3 (4.16 g, 12.76 mmol, 6 eq) in one portion at 20° C. under N2. The mixture was heated to 50° C. and stirred at 50° C. for 15 min, then 1-(chloromethyl)-4-fluoro-benzene (368.82 mg, 2.55 mmol, 304.81 μL, 1.2 eq) was added, the mixture was stirred at 50° C. for 16 h. The reaction mixture was cooled to 20° C., then the reaction mixture was filtered and washed with DMF 10 mL, the filter cake was dissolved in water 5 mL, and added 1M HCl solution 10 mL to adjust pH to 3, the solid was appeared, then filtered and washed with water 10 mL, the filter cake was dried by reduced pressure to obtain desired product. Compound ethyl 5-[(4-fluorophenyl)methyl]-8-hydroxy-6-oxo-pyrido[2,3-b]pyrazine-7-carboxylate (480 mg, 1.40 mmol, 65.77% yield) was obtained as a gray solid.

$^1$H NMR (400 MHz, DMSO-d6) δ=12.74-12.31 (m, 1H), 8.79 (d, J=2.3 Hz, 1H), 8.65 (d, J=2.3 Hz, 1H), 7.41-7.27 (m, 2H), 7.11 (t, J=4.5, 9.0 Hz, 2H), 5.47 (s, 2H), 4.35-4.23 (m, 2H), 1.28 (t, J=7.1 Hz, 3H). LCMS for product (ESI+): m/z 344.1 [M+H]+, Rt: 0.993 min.

Step 2. Preparation of N-(bicyclo[1.1.1]pentan-1-yl)-5-(4-fluorobenzyl)-8-hydroxy-6-oxo-5,6-dihydropyrido[2,3-b]pyrazine-7-carboxamide

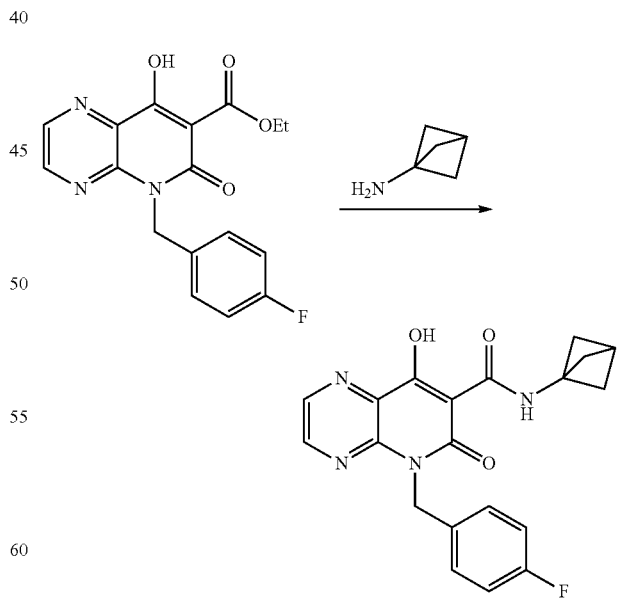

To a solution of ethyl 5-[(4-fluorophenyl)methyl]-8-hydroxy-6-oxo-pyrido[2,3-b]pyrazine-7-carboxylate (200 mg, 582.57 μmol, 1 eq) and bicyclo[1.1.1]pentan-1-amine (83.60 mg, 699.08 μmol, 1.2 eq, HCl) in toluene (5 mL) was added DIEA (188.23 mg, 1.46 mmol, 253.68 μL, 2.5 eq). The mixture was stirred at 120° C. for 2 h. The reaction mixture was directly concentrated. The residue was purified by prep-HPLC (column: Unisil 3-100 C18 Ultra 150*50 mm*3 μm; mobile phase: [FA condition; water (0.225% FA)-ACN]; B %: 58%-88%, 10 min) and lyophilized to give N-(bicyclo[1.1.1]pentan-1-yl)-5-(4-fluorobenzyl)-8-hydroxy-6-oxo-5,6-dihydropyrido[2,3-b]pyrazine-7-carboxamide (28 mg, 69.26 μmol, 47.42% yield, 97.31% purity).

$^1$H NMR (400 MHz, DMSO-$d_6$) δ=10.48 (br s, 1H), 8.78 (br d, J=3.0 Hz, 1H), 8.48 (dd, J=1.6, 7.9 Hz, 1H), 7.44 (dd, J=4.7, 7.8 Hz, 1H), 7.31 (dd, J=5.6, 8.6 Hz, 2H), 7.08 (t, J=8.9 Hz, 2H), 5.58 (s, 2H), 2.02 (s, 6H), 1.24 (s, 3H). LCMS for product (ESI+): m/z 381.0 [M+H]$^+$, Rt: 1.031 min.

LCMS Method

The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was $H_2O$+10 mM $NH_4HCO_3$, mobile phase B was Acetonitrile. The column used for chromatography was a Xbridge Shield RP18 2.1*50 mm column (5 m particles). Detection methods are diode array (DAD) as well as positive electrospray ionization.

Example 148—Synthesis of 4-hydroxy-6-(4-methoxyphenyl)-N-((1R,4R)-4-methylcyclohexyl)-1-(2-morpholinoethyl)-2-oxo-1,2-dihydro-1,8-naphthyridine-3-carboxamide (Compound 148)

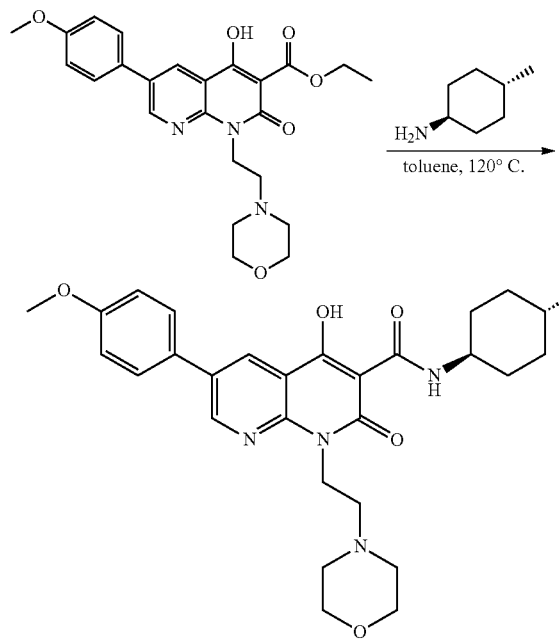

To a solution of ethyl 4-hydroxy-6-(4-methoxyphenyl)-1-(2-morpholinoethyl)-2-oxo-1,2-dihydro-1,8-naphthyridine-3-carboxylate (50 mg, 110.26 μmol, 1 eq), trans-4-methylcyclohexanamine (19.80 mg, 132.31 μmol, 1.2 eq, HCl) in toluene (1 mL) was added DIEA (19.95 mg, 154.36 μmol, 26.89 uL, 1.4 eq) at 20° C., the mixture was stirred at 120° C. for 2 h. The mixture was concentrated, and the residue was triturated in MeOH (5 mL) and filtered, and the filter cake was washed with MeOH (2 mL) and dried. The solid was dissolved in DCM (0.5 mL) then acidified to pH 2 by dropwise addition of 12 M hydrochloric acid. The mixture was concentrated and lyophilized to give 4-hydroxy-6-(4-methoxyphenyl)-N-((1R,4R)-4-methylcyclohexyl)-1-(2-morpholinoethyl)-2-oxo-1,2-dihydro-1,8-naphthyridine-3-carboxamide (33.0 mg, 62.94 μmol).

$^1$H NMR (400 MHz, CDCl$_3$) δ=13.74-13.52 (m, 1H), 9.98-9.80 (m, 1H), 8.89 (d, J=2.4 Hz, 1H), 8.61 (d, J=2.4 Hz, 1H), 7.64-7.55 (m, 2H), 7.05 (d, J=8.8 Hz, 2H), 5.04 (br t, J=6.9 Hz, 2H), 4.40 (br t, J=12.2 Hz, 2H), 4.09-3.96 (m, 2H), 3.93-3.83 (m, 4H), 3.75-3.64 (m, 2H), 3.46-3.35 (m, 2H), 3.14-3.00 (m, 2H), 2.14-2.04 (m, 2H), 1.83-1.73 (m, 2H), 1.44-1.32 (m, 3H), 1.17-1.06 (m, 2H), 0.94 (d, J=6.5 Hz, 3H). LCMS for product (ESI-): m/z 521.2 [M+H]$^+$, Rt: 2.582 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 μm particles). Detection methods are diode array (DAD) and evaporative light scattering (ELSD) detection as well as positive electrospray ionization. MS range was 100-1000.

Example 149—Synthesis of 4-hydroxy-6-(4-methoxyphenyl)-N-((1s,4S)-4-methylcyclohexyl)-1-(2-morpholinoethyl)-2-oxo-1,2-dihydro-1,8-naphthyridine-3-carboxamide (Compound 149)

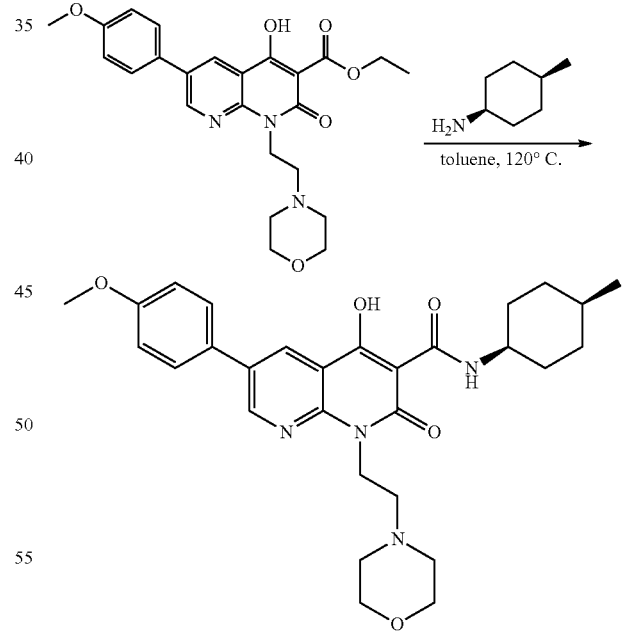

To a solution of ethyl 4-hydroxy-6-(4-methoxyphenyl)-1-(2-morpholinoethyl)-2-oxo-1,2-dihydro-1,8-naphthyridine-3-carboxylate (100 mg, 220.51 μmol, 1 eq) in toluene (1 mL) was added DIEA (34.20 mg, 264.62 μmol, 46.09 uL, 1.2 eq) and 4-methylcyclohexanamine (39.60 mg, 264.62 μmol, 1.2 eq, HCl). The mixture was stirred at 110° C. for 2 h. The mixture was concentrated, and the residue was purified by prep-HPLC (column: Waters Xbridge BEH C18

100*25 mm*5 um; mobile phase: [water (10 mM NH$_4$HCO$_3$)-ACN]; B %: 75%-95%, 10 min) to give 4-hydroxy-6-(4-methoxyphenyl)-N-((1s,4S)-4-methylcyclohexyl)-1-(2-morpholinoethyl)-2-oxo-1,2-dihydro-1,8-naphthyridine-3-carboxamide (40.2 mg, 77.22 μmol).

$^1$H NMR (400 MHz, CDCl3) δ=13.69-13.47 (m, 1H), 10.26 (br d, J=7.7 Hz, 1H), 8.89 (s, 1H), 8.62 (s, 1H), 7.59 (d, J=8.4 Hz, 2H), 7.05 (d, J=8.4 Hz, 2H), 5.06 (br s, 2H), 4.57-4.30 (m, 2H), 4.29-4.19 (m, 1H), 4.03 (br d, J=11.2 Hz, 2H), 3.89 (s, 3H), 3.80-3.53 (m, 2H), 3.42 (br s, 2H), 3.21-2.98 (m, 2H), 1.93-1.80 (m, 2H), 1.76-1.60 (m, 5H), 1.35-1.27 (m, 2H), 1.01 (d, J=6.4 Hz, 3H). LCMS for product (ESI+): m/z 521.2 [M+H]$^+$, Rt: 2.589 min.

LC/MS (The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF3CO2H in water, mobile phase B was 0.018% CF3CO2H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 150—Synthesis of (R)—N-(1-(4-fluorophenyl)ethyl)-4-hydroxy-6-(4-methoxyphenyl)-1-(2-morpholinoethyl)-2-oxo-1,2-dihydro-1,8-naphthyridine-3-carboxamide (Compound 150)

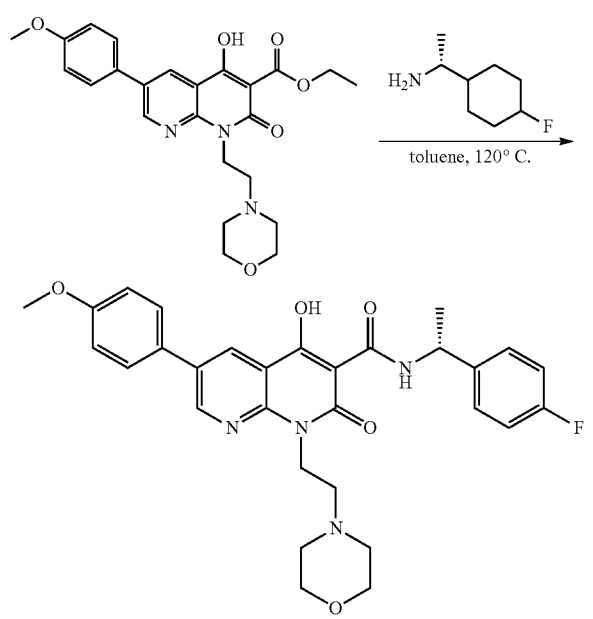

To a solution of ethyl 4-hydroxy-6-(4-methoxyphenyl)-1-(2-morpholinoethyl)-2-oxo-1,2-dihydro-1,8-naphthyridine-3-carboxylate (50 mg, 110.26 μmol, 1 eq), (1R)-1-(4-fluorophenyl)ethanamine (18.41 mg, 132.31 μmol, 1.2 eq) in toluene (5 mL) was added DIEA (1.42 mg, 11.03 μmol, 1.92 μL, 0.1 eq) at 20° C., the mixture was stirred at 120° C. for 2 h. The mixture was concentrated, and the residue was triturated in MeOH (5 mL) and dried. The solid was dissolved in DCM (0.5 mL) then acidified to pH 2 by dropwise addition of 12 M hydrochloric acid. The mixture was concentrated and lyophilized to give (R)—N-(1-(4-fluorophenyl)ethyl)-4-hydroxy-6-(4-methoxyphenyl)-1-(2-morpholinoethyl)-2-oxo-1,2-dihydro-1,8-naphthyridine-3-carboxamide (34.8 mg, 63.67 μm).

$^1$H NMR (400 MHz, CDCl$_3$) δ=13.73-13.53 (m, 1H), 10.37 (br d, J=7.8 Hz, 1H), 8.90 (d, J=2.4 Hz, 1H), 8.60 (d, J=2.4 Hz, 1H), 7.58 (d, J=8.6 Hz, 2H), 7.38 (dd, J=5.4, 8.5 Hz, 2H), 7.11-7.02 (m, 4H), 5.25 (quin, J=7.3 Hz, 1H), 5.05 (br t, J=6.9 Hz, 2H), 4.40 (br t, J=12.1 Hz, 2H), 4.08-3.98 (m, 2H), 3.89 (s, 3H), 3.77-3.66 (m, 2H), 3.40 (br s, 2H), 3.13-3.00 (m, 2H), 1.63 (d, J=7.0 Hz, 3H). LCMS for product (ESI-): m/z 547.2 [M+H]$^+$, Rt: 2.455 min. LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 μm particles). Detection methods are diode array (DAD) and evaporative light scattering (ELSD) detection as well as positive electrospray ionization. MS range was 100-1000.

Example 151—Synthesis of (R)—N-(1-(4-fluorophenyl)ethyl)-4-hydroxy-6-(4-methoxyphenyl)-1-(2-morpholinoethyl)-2-oxo-1,2-dihydro-1,8-naphthyridine-3-carboxamide (Compound 151)

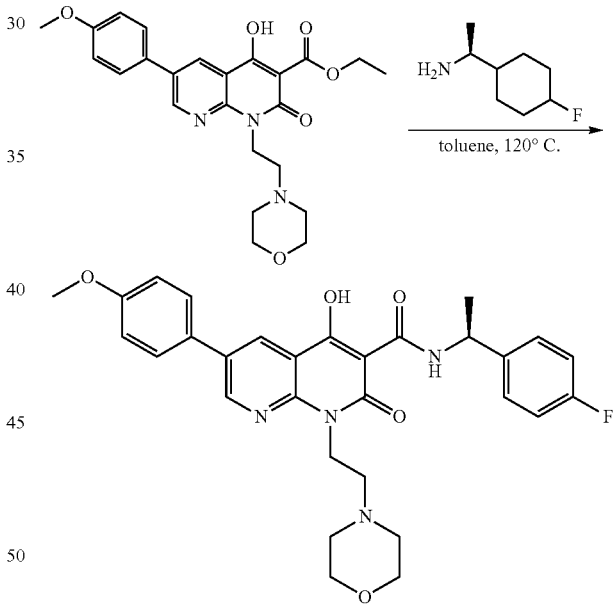

To a solution of ethyl 4-hydroxy-6-(4-methoxyphenyl)-1-(2-morpholinoethyl)-2-oxo-1,2-dihydro-1,8-naphthyridine-3-carboxylate (50 mg, 110.26 μmol, 1 eq), (1S)-1-(4-fluorophenyl)ethanamine (18.41 mg, 132.31 μmol, 1.2 eq) in toluene (5 mL) was added DIEA (1.42 mg, 11.03 μmol, 1.92 μL, 0.1 eq) at 20° C., the mixture was stirred at 120° C. for 2 h. The mixture was concentrated, and the residue was triturated in MeOH (5 mL) then filtered and dried. The solid was dissolved in DCM (0.5 mL) then acidified to pH 2 by dropwise addition of 12 M hydrochloric acid. The mixture was concentrated and lyophilized to give (S)—N-(1-(4-fluorophenyl)ethyl)-4-hydroxy-6-(4-methoxyphenyl)-1-(2-morpholinoethyl)-2-oxo-1,2-dihydro-1,8-naphthyridine-3-carboxamide (34.5 mg, 63.12 μmol).

¹H NMR (400 MHz, CDCl₃) δ=13.69-13.51 (m, 1H), 10.37 (br d, J=7.5 Hz, 1H), 8.90 (d, J=2.1 Hz, 1H), 8.60 (d, J=2.1 Hz, 1H), 7.58 (d, J=8.6 Hz, 2H), 7.38 (dd, J=5.4, 8.5 Hz, 2H), 7.13-7.00 (m, 4H), 5.25 (quin, J=7.1 Hz, 1H), 5.05 (br t, J=6.8 Hz, 2H), 4.40 (br t, J=12.2 Hz, 2H), 4.02 (br d, J=11.9 Hz, 2H), 3.89 (s, 3H), 3.72 (br d, J=10.8 Hz, 2H), 3.40 (br d, J=1.1 Hz, 2H), 3.07 (br d, J=10.0 Hz, 2H), 1.63 (d, J=7.0 Hz, 3H). LCMS for product (ESI-): m/z 547.2 [M+H]⁺, Rt: 2.464 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 m particles). Detection methods are diode array (DAD) and evaporative light scattering (ELSD) detection as well as positive electrospray ionization. MS range was 100-1000.

Example 152—Synthesis of N-cyclohexyl-4-hydroxy-6-(4-methoxyphenyl)-1-(2-morpholinoethyl)-2-oxo-1,2-dihydro-1,8-naphthyridine-3-carboxamide (Compound 152)

¹H NMR (400 MHz, CDCl₃) δ=13.75-13.41 (m, 1H), 10.20-9.72 (m, 1H), 9.02-8.77 (m, 1H), 8.70-8.54 (m, 1H), 7.59 (br d, J=8.2 Hz, 2H), 7.11-6.87 (m, 2H), 5.12-4.94 (m, 2H), 4.47-4.35 (m, 2H), 4.13-3.93 (m, 3H), 3.91-3.85 (m, 3H), 3.76-3.65 (m, 2H), 3.44-3.33 (m, 2H), 3.17-3.00 (m, 2H), 2.06-1.96 (m, 2H), 1.85-1.76 (m, 2H), 1.71-1.63 (m, 1H), 1.52-1.38 (m, 4H), 1.36-1.27 (m, 1H). LCMS for product (ESI-): m/z 507.2 [M+H]⁺, Rt: 2.479 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 μm particles). Detection methods are diode array (DAD) and evaporative light scattering (ELSD) detection as well as positive electrospray ionization. MS range was 100-1000.

Example 153—Synthesis of N-cyclohexyl-6-(4-fluorophenyl)-4-hydroxy-1-(2-morpholinoethyl)-2-oxo-1,2-dihydro-1,8-naphthyridine-3-carboxamide (Compound 153)

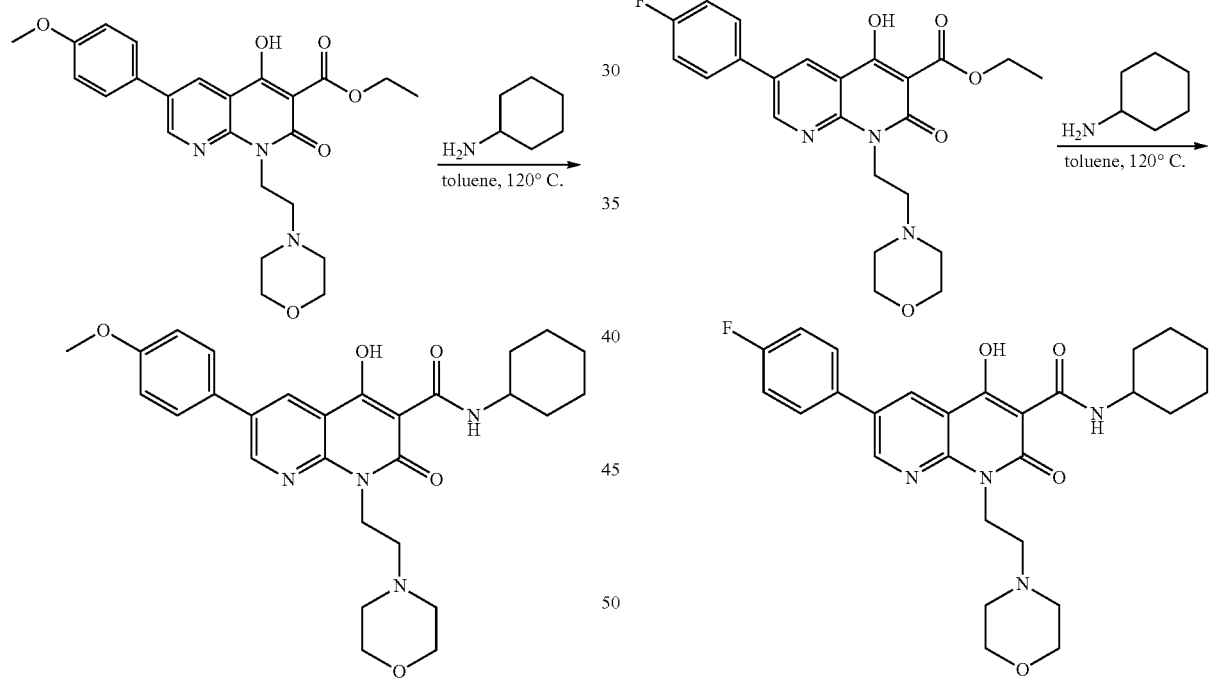

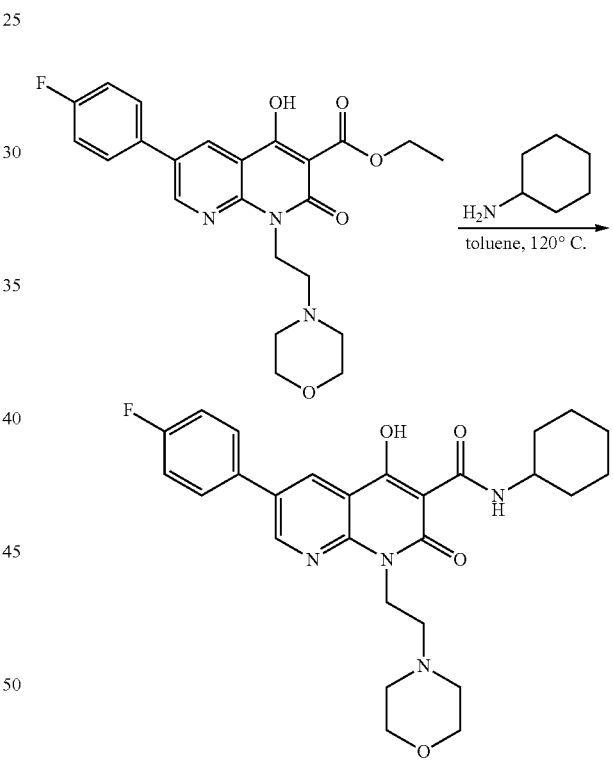

To a solution of ethyl 4-hydroxy-6-(4-methoxyphenyl)-1-(2-morpholinoethyl)-2-oxo-1,2-dihydro-1,8-naphthyridine-3-carboxylate (50 mg, 110.26 μmol, 1 eq), cyclohexanamine (12.03 mg, 121.28 μmol, 13.88 μL, 1.1 eq) in toluene (1 mL) was added DIEA (1.42 mg, 11.03 μmol, 1.92 μL, 0.1 eq) at 20° C., the mixture was stirred at 120° C. for 1 h. The mixture was concentrated, and the residue was triturated in MeOH (5 mL) and dried. The solid was dissolved in DCM (0.5 mL) then acidified to pH 2 by dropwise addition of 12 M hydrochloric acid. The mixture was concentrated and lyophilized to give N-cyclohexyl-4-hydroxy-6-(4-methoxyphenyl)-1-(2-morpholinoethyl)-2-oxo-1,2-dihydro-1,8-naphthyridine-3-carboxamide (30 mg, 59.22 μmol).

To a solution of ethyl 6-(4-fluorophenyl)-4-hydroxy-1-(2-morpholinoethyl)-2-oxo-1,2-dihydro-1,8-naphthyridine-3-carboxylate (60 mg, 135.92 μmol, 1 eq), cyclohexanamine (14.83 mg, 149.51 μmol, 17.11 μL, 1.1 eq) in toluene (1 mL) was added DIEA (1.76 mg, 13.59 μmol, 2.37 μL, 0.1 eq) at 20° C., the mixture was stirred at 120° C. for 1 h. The mixture was concentrated, and the residue was triturated in MeOH (5 mL) and dried. The solid was dissolved in DCM (0.5 mL) then acidified to pH 2 by dropwise addition of 12 M hydrochloric acid. The mixture was concentrated and lyophilized to give N-cyclohexyl-6-(4-fluorophenyl)-4-hydroxy-1-(2-morpholinoethyl)-2-oxo-1,2-dihydro-1,8-naphthyridine-3-carboxamide (57 mg, 107.34 μmol, HCl).

$^1$H NMR (400 MHz, CDCl$_3$) δ=13.81-13.21 (m, 1H), 10.16-9.57 (m, 1H), 8.88 (d, J=2.4 Hz, 1H), 8.63 (d, J=2.4 Hz, 1H), 7.74-7.57 (m, 2H), 7.22 (t, J=8.6 Hz, 2H), 5.05 (br t, J=6.8 Hz, 2H), 4.49-4.32 (m, 2H), 4.06-3.88 (m, 3H), 3.80-3.63 (m, 2H), 3.40 (br s, 2H), 3.18-2.94 (m, 2H), 2.02 (br d, J=9.8 Hz, 2H), 1.80 (br dd, J=4.5, 9.3 Hz, 2H), 1.70-1.64 (m, 1H), 1.50-1.40 (m, 4H), 1.34-1.26 (m, 1H). LCMS for product (ESI−): m/z 495.1 [M+H]$^+$, Rt: 2.513 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 μm particles). Detection methods are diode array (DAD) and evaporative light scattering (ELSD) detection as well as positive electrospray ionization. MS range was 100-1000.

Example 154—Synthesis of 6-bromo-4-hydroxy-N-((1R,4R)-4-methylcyclohexyl)-1-(2-morpholinoethyl)-2-oxo-1,2-dihydro-1,8-naphthyridine-3-carboxamide (Compound 154)

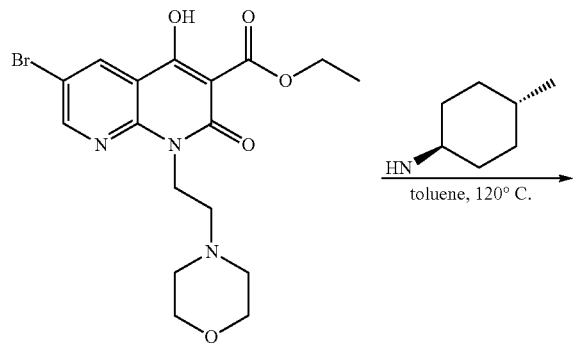

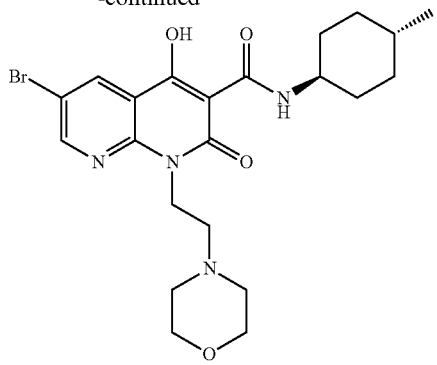

To a solution of ethyl 6-bromo-4-hydroxy-1-(2-morpholinoethyl)-2-oxo-1,2-dihydro-1,8-naphthyridine-3-carboxylate (300 mg, 703.79 μmol, 1 eq) in toluene (3 mL) was added DIEA (181.92 mg, 1.41 mmol, 245.17 μL, 2 eq) and 4-methylcyclohexanamine (126.40 mg, 844.55 mol, 1.2 eq, HCl). The mixture was stirred at 110° C. for 2 h. The mixture was concentrated to give 6-bromo-4-hydroxy-N-((1R,4R)-4-methylcyclohexyl)-1-(2-morpholinoethyl)-2-oxo-1,2-dihydro-1,8-naphthyridine-3-carboxamide (300 mg, 608.03 μmol) was used without further purification.

LCMS for product (ESI+): m/z 493.2, 495.2 [M+H]$^+$, Rt: 1.656 min.

LC/MS (The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF$_3$CO$_2$H in water, mobile phase B was 0.018% CF$_3$CO$_2$H in CH$_3$CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 155—Synthesis of 6-(4-(difluoromethoxy)phenyl)-4-hydroxy-N-((1R,4R)-4-methylcyclohexyl)-1-(2-morpholinoethyl)-2-oxo-1,2-dihydro-1,8-naphthyridine-3-carboxamide (Compound 155)

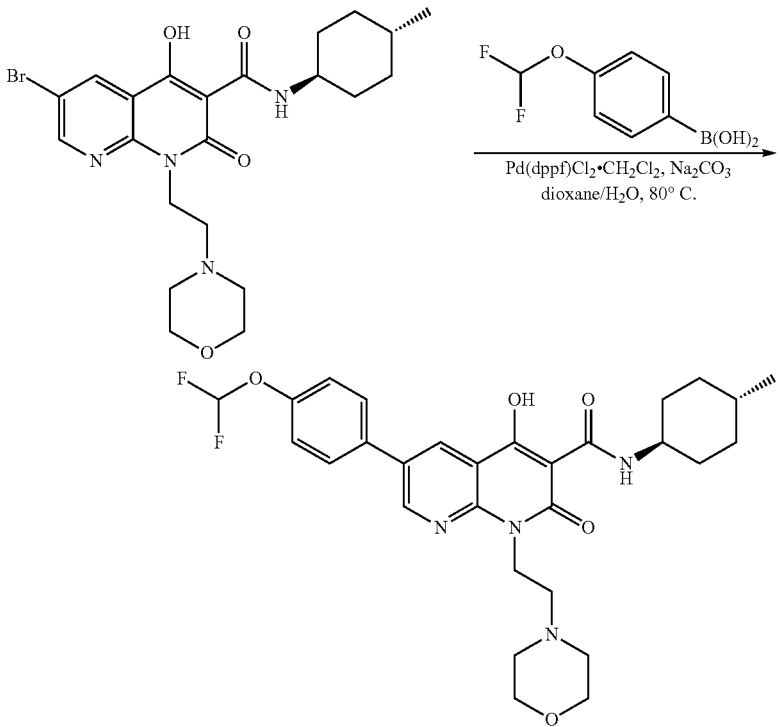

To a mixture of 6-bromo-4-hydroxy-N-((1R,4R)-4-methylcyclohexyl)-1-(2-morpholinoethyl)-2-oxo-1,2-dihydro-1,8-naphthyridine-3-carboxamide (100 mg, 202.68 μmol, 1 eq), [4-(difluoromethoxy) phenyl]boronic acid (26.66 mg, 141.87 μmol, 0.7 eq), Na₂CO₃ (32.22 mg, 304.02 μmol, 1.5 eq) in dioxane (2 mL) and water (0.2 mL) was added Pd(dppf)Cl₂·CH₂Cl₂ (16.55 mg, 20.27 μmol, 0.1 eq) under N₂. The mixture was stirred at 80° C. for 2 h. The mixture was concentrated, and the residue was purified by prep-HPLC (column: Welch Xtimate C18 150*25 mm*5 μm; mobile phase: [water (0.04% HCl)-ACN]; B %: 20%-50%, 8 min) to give 6-(4-(difluoromethoxy)phenyl)-4-hydroxy-N-((1R,4R)-4-methylcyclohexyl)-1-(2-morpholinoethyl)-2-oxo-1,2-dihydro-1,8-naphthyridine-3-carboxamide (33.5 mg, 57.12 μmol).

¹H NMR (400 MHz, CDCl₃) δ=13.84-13.11 (m, 1H), 10.00-9.70 (m, 1H), 9.05-8.77 (m, 1H), 8.65 (br s, 1H), 7.76-7.53 (m, 2H), 7.28 (br d, J=2.5 Hz, 2H), 6.79-6.38 (m, 1H), 5.22-4.66 (m, 2H), 4.61-4.27 (m, 2H), 4.25-3.64 (m, 5H), 3.61-3.27 (m, 2H), 3.23-2.84 (m, 2H), 2.17-2.00 (m, 2H), 1.81 (br d, J=12.8 Hz, 2H), 1.43-1.32 (m, 3H), 1.17-1.07 (m, 2H), 0.94 (d, J=6.3 Hz, 3H). LCMS for product (ESI+): m/z 557.1 [M+H]⁺, Rt: 2.668 min.

LC/MS (The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% CF₃CO₂H in water, mobile phase B was 0.018% CF₃CO₂H in CH₃CN. The column used for the chromatography was a 2.0×50 mm phenomenex Luna-C18 column (5 μm particles). Detection methods are diode array (DAD) and evaporative light scattering (ELSD) detection as well as positive electrospray ionization (MS).

Example 156—Synthesis of ethyl 4-hydroxy-1-(2-morpholinoethyl)-2-oxo-6-(4,4,5,5-tetramethyl-1,3,2-dioxaborolan-2-yl)-1,2-dihydroquinoline-3-carboxylate (Compound 156)

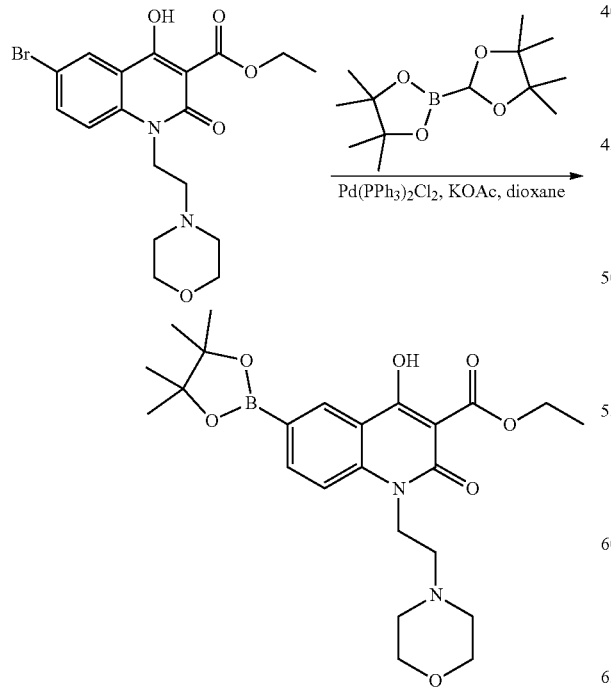

To a solution of ethyl 6-bromo-4-hydroxy-1-(2-morpholinoethyl)-2-oxo-1,2-dihydroquinoline-3-carboxylate (500 mg, 1.18 mmol, 1 eq), BPD (2.99 g, 11.76 mmol, 10 eq), potassium acetate (346.16 mg, 3.53 mmol, 3 eq) in dioxane (10 mL) was added Pd(PPh₃)₂Cl₂ (82.52 mg, 117.57 μmol, 0.1 eq) at 20° C., the mixture was stirred at 90° C. for 2 h. The mixture was concentrated, and the residue was dissolved in DMF and filtered, the filtrate was purified by prep-HPLC (NH₄HCO₃ condition) to give ethyl 4-hydroxy-1-(2-morpholinoethyl)-2-oxo-6-(4,4,5,5-tetramethyl-1,3,2-dioxaborolan-2-yl)-1,2-dihydroquinoline-3-carboxylate (350 mg, 741.00 μmol).

LCMS for product (ESI−): m/z 473.2 [M+H]⁺, Rt: 1.411 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.30 min 0.5% B in 0.01 min, 5-95% B (0.01-3.00 min), and hold at 95% B within 0.5 min, 95-5% B (3.50-3.51 min), with a hold at 5% B for 0.79 min. The flow rate was 1.0 mL/min (0.01-4.30 min).

Example 157—Synthesis of ethyl 6-(4-(difluoromethoxy)phenyl)-4-hydroxy-1-(2-morpholinoethyl)-2-oxo-1,2-dihydroquinoline-3-carboxylate (Compound 157)

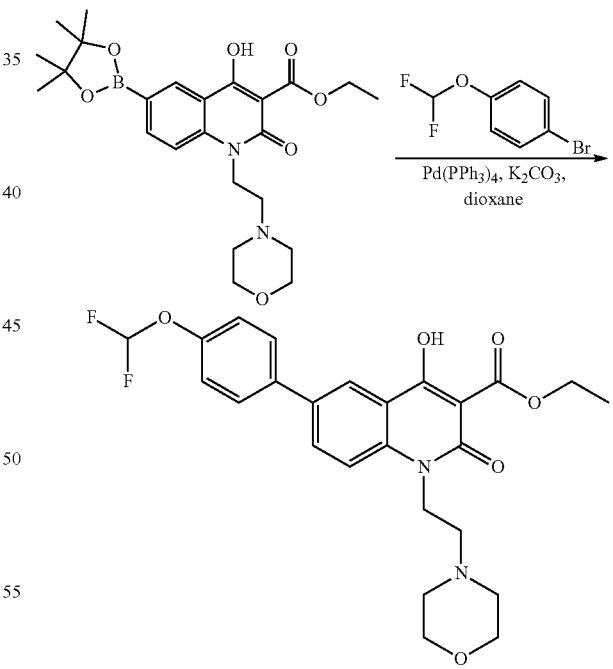

To a solution of ethyl 4-hydroxy-1-(2-morpholinoethyl)-2-oxo-6-(4,4,5,5-tetramethyl-1,3,2-dioxaborolan-2-yl)-1,2-dihydroquinoline-3-carboxylate (300 mg, 635.14 μmol, 1 eq), 1-bromo-4-(difluoromethoxy)benzene (141.65 mg, 635.14 μmol, 86.90 uL, 1.0 eq), K₂CO₃ (175.56 mg, 1.27 mmol, 2 eq) in dioxane (4 mL) and H₂O (1 mL) was added Pd(PPh₃)₄ (73.39 mg, 63.51 mol, 0.1 eq) under N₂ at 20° C., the mixture was stirred at 100° C. for 2 h. The mixture was concentrated, and the residue was dissolved in DMF and purified by prep-HPLC (column: Waters Xbridge Prep OBD C18 150*40 mm*10 um; mobile phase: [water (10 mM NH₄HCO₃)-ACN]; B %: 20%-50%, 8 min) to give ethyl 6-(4-(difluoromethoxy)phenyl)-4-hydroxy-1-(2-morpholinoethyl)-2-oxo-1,2-dihydroquinoline-3-carboxylate (70 mg, 143.30 μmol).

$^1$H NMR (400 MHz, CDCl₃) δ=8.38 (d, J=2.2 Hz, 1H), 7.89 (dd, J=2.3, 8.9 Hz, 1H), 7.69-7.62 (m, 2H), 7.46 (d, J=8.9 Hz, 1H), 7.25 (d, J=8.7 Hz, 2H), 6.79-6.33 (m, 1H), 4.54 (q, J=7.2 Hz, 2H), 4.48-4.38 (m, 2H), 3.82-3.68 (m, 4H), 2.72-2.60 (m, 6H), 1.50 (t, J=7.1 Hz, 3H). LCMS for product (ESI-): m/z 489.2 [M+H]⁺, Rt: 1.569 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 μm particles). Detection methods are diode array (DAD) and evaporative light scattering (ELSD) detection as well as positive electrospray ionization. MS range was 100-1000.

Example 158—Synthesis of 6-(4-(difluoromethoxy)phenyl)-4-hydroxy-N-((1s,4S)-4-methylcyclohexyl)-1-(2-morpholinoethyl)-2-oxo-1,2-dihydroquinoline-3-carboxamide (Compound 158)

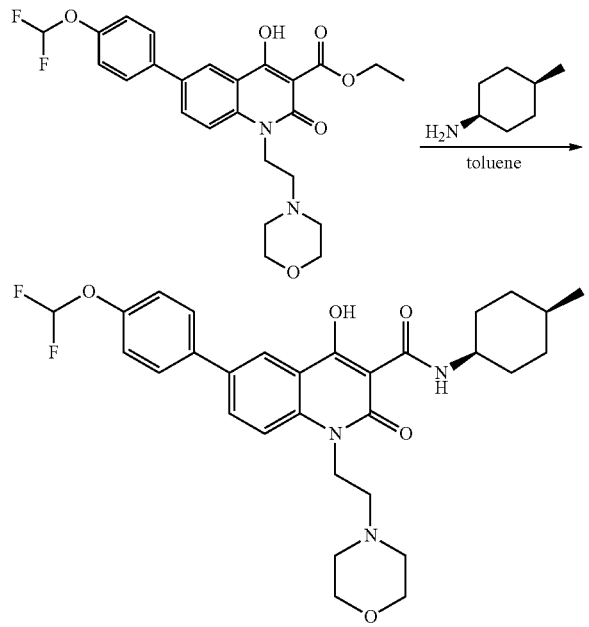

To a solution of ethyl 6-(4-(difluoromethoxy)phenyl)-4-hydroxy-1-(2-morpholinoethyl)-2-oxo-1,2-dihydroquinoline-3-carboxylate (58 mg, 118.74 μmol, 1 eq), cis-4-methylcyclohexanamine (23.10 mg, 154.36 μmol, 1.3 eq, HCl) in toluene (2 mL) was added DIEA (23.02 mg, 178.10 μmol, 31.02 μL, 1.5 eq) at 20° C., the mixture was stirred at 120° C. for 1 h. The mixture was concentrated, and the residue was triturated in MeOH (5 mL), the mixture was filtered, and the filter cake was washed with MeOH and dried to give 6-(4-(difluoromethoxy)phenyl)-4-hydroxy-N-((1s,4S)-4-methylcyclohexyl)-1-(2-morpholinoethyl)-2-oxo-1,2-dihydroquinoline-3-carboxamide (27 mg, 47.96 μmol).

$^1$H NMR (400 MHz, CDCl₃) δ=14.07-13.68 (m, 1H), 10.25 (br d, J=7.9 Hz, 1H), 8.42 (s, 1H), 8.25 (br d, J=8.8 Hz, 1H), 8.09-8.02 (m, 1H), 7.67 (d, J=8.5 Hz, 2H), 7.24 (br d, J=8.3 Hz, 2H), 6.79-6.24 (m, 1H), 4.98 (br d, J=5.5 Hz, 2H), 4.38-4.21 (m, 3H), 4.08 (br d, J=11.6 Hz, 2H), 3.59 (br d, J=11.3 Hz, 2H), 3.36-3.22 (m, 2H), 3.17-3.03 (m, 2H), 1.84 (br dd, J=4.6, 8.8 Hz, 2H), 1.76-1.61 (m, 5H), 1.29 (br d, J=12.3 Hz, 2H), 1.01 (d, J=6.5 Hz, 3H). LCMS for product (ESI-): m/z 556.2 [M+H]⁺, Rt: 2.653 min.

LC/MS (The column used for chromatography was a Chromolith RP-18e 25-2 mm. Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 4.3 min 0.5% B in 0.01 min, 5-95% B (0.01-3.00 min), 95-95% B (3.00-3.50 min), 5% B at 3.51 min with a hold at 5% B for 0.79 min. The flow rate was 0.8 mL/min.

Example 159—Synthesis of 6-(4-fluorophenyl)-4-hydroxy-N-((1s,4S)-4-methylcyclohexyl)-1-(2-morpholinoethyl)-2-oxo-1,2-dihydroquinoline-3-carboxamide (Compound 159)

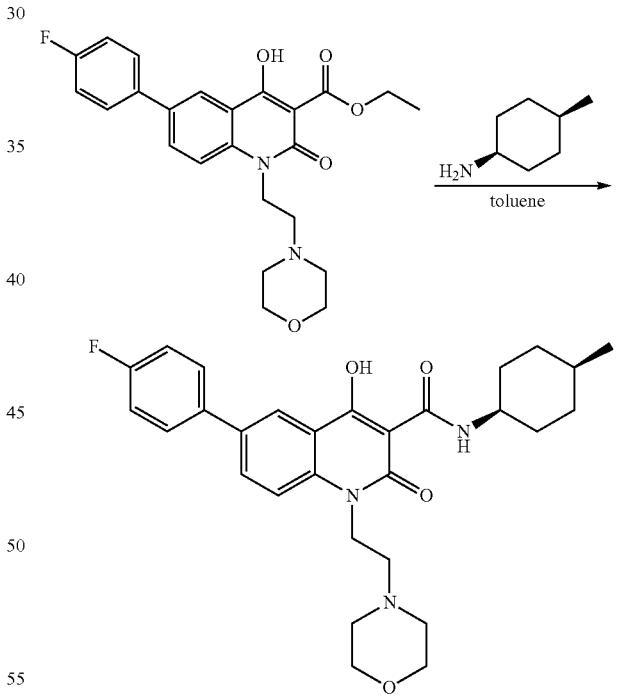

To a solution of ethyl 6-(4-fluorophenyl)-4-hydroxy-1-(2-morpholinoethyl)-2-oxo-1,2-dihydroquinoline-3-carboxylate (100 mg, 227.03 μmol, 1 eq), cis-4-methylcyclohexanamine (40.77 mg, 272.44 μmol, 1.2 eq, HCl) in toluene (1 mL) was added DIEA (41.08 mg, 317.85 μmol, 55.36 μL, 1.4 eq) at 20° C., the mixture was stirred at 120° C. for 2 h. The mixture was concentrated and the reside was dissolved in DMF and purified by prep-HPLC (column: Welch Xtimate C18 150*25 mm*5 μm; mobile phase: [water (0.04% HCl)-ACN]; B %: 20%-50%, 8 min) to give 6-(4-fluorophenyl)-4-hydroxy-N-((1s,4S)-4-methylcyclohexyl)-1-(2-morpholinoethyl)-2-oxo-1,2-dihydroquinoline-3-carboxamide (31.6 mg, 61.57 µmol).

¹H NMR (400 MHz, CDCl₃) δ=14.00-13.56 (m, 1H), 10.38-10.14 (m, 1H), 8.40 (d, J=2.0 Hz, 1H), 8.23 (br d, J=8.4 Hz, 1H), 8.04 (br d, J=7.1 Hz, 1H), 7.63 (dd, J=5.3, 8.6 Hz, 2H), 7.17 (t, J=8.6 Hz, 2H), 4.97 (br d, J=5.0 Hz, 2H), 4.41-4.18 (m, 3H), 4.16-4.01 (m, 2H), 3.60 (br d, J=11.0 Hz, 2H), 3.26 (br s, 2H), 3.18-3.01 (m, 2H), 1.89-1.79 (m, 2H), 1.76-1.61 (m, 5H), 1.36-1.25 (m, 2H), 1.00 (d, J=6.5 Hz, 3H). LCMS for product (ESI-): m/z 508.2 [M+H]⁺, Rt: 2.613 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 µm particles). Detection methods are diode array (DAD) and evaporative light scattering (ELSD) detection as well as positive electrospray ionization. MS range was 100-1000.

Example 160—Synthesis of ethyl 4-hydroxy-6-(4-methoxyphenyl)-1-(2-morpholinoethyl)-2-oxo-1,2-dihydroquinoline-3-carboxylate (Compound 160)

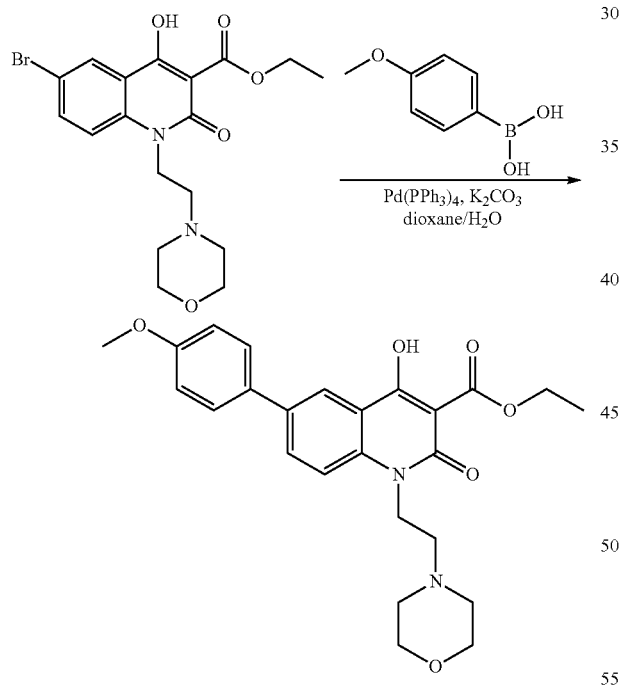

To a solution of ethyl 6-bromo-4-hydroxy-1-(2-morpholinoethyl)-2-oxo-1,2-dihydroquinoline-3-carboxylate (600 mg, 1.41 mmol, 1 eq), (4-methoxyphenyl)boronic acid (257.26 mg, 1.69 mmol, 1.2 eq), K₂CO₃ (584.98 mg, 4.23 mmol, 3 eq) in dioxane (10 mL) and H₂O (1 mL) was added Pd(PPh₃)₄ (163.03 mg, 141.09 µmol, 0.1 eq) at 20° C., the mixture was stirred at 100° C. for 2 h. The mixture was evaporated, and the residue was dissolved in DMF and purified by prep-HPLC (column: Phenomenex luna C18 80*40 mm*3 µm; mobile phase: [water (0.04% HCl)-ACN]; B %: 20%-50%, 7 min) to give ethyl 4-hydroxy-6-(4-methoxyphenyl)-1-(2-morpholinoethyl)-2-oxo-1,2-dihydroquinoline-3-carboxylate (200 mg, 441.99 µmol).

LCMS for product (ESI-): m/z 453.2 [M+H]⁺, Rt: 1.521 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.5 min 0.5% B in 0.01 min, 5-95% B (0.01-3.00 min), 95% B (3.00-3.50 min), 95-5% B (3.50-4.00 min) and hold at 5% B for 0.5 min. The flow rate was 1.0 m/min.

Example 161—Synthesis of 4-hydroxy-6-(4-methoxyphenyl)-N-((1s,4S)-4-methylcyclohexyl)-1-(2-morpholinoethyl)-2-oxo-1,2-dihydroquinoline-3-carboxamide (Compound 161)

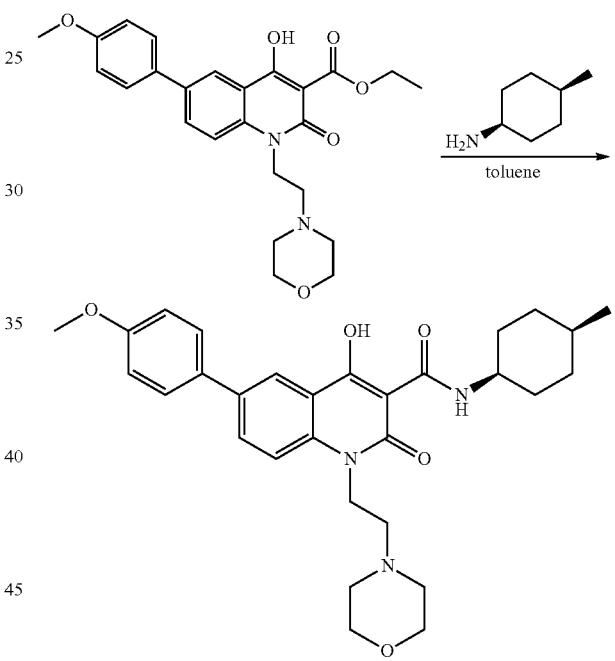

To a solution of ethyl 4-hydroxy-6-(4-methoxyphenyl)-1-(2-morpholinoethyl)-2-oxo-1,2-dihydroquinoline-3-carboxylate (80 mg, 176.80 µmol, 1.08 eq), cis-4-methylcyclohexanamine (29.38 mg, 196.34 µmol, 1.2 eq, HCl) in toluene (1 mL) was added DIEA (52.86 mg, 409.03 mol, 71.24 uL, 2.5 eq) at 20° C., the mixture was stirred at 120° C. for 1 h. The mixture was evaporated the residue was triturated in MeOH (5 mL) and filtered, and the filter cake was washed with MeOH and dried to give 4-hydroxy-6-(4-methoxyphenyl)-N-((1s,4S)-4-methylcyclohexyl)-1-(2-morpholinoethyl)-2-oxo-1,2-dihydroquinoline-3-carboxamide (32.4 mg, 61.67 µmol).

¹H NMR (400 MHz, CDCl₃) δ=13.99-13.73 (m, 1H), 10.28 (br d, J=7.1 Hz, 1H), 8.41 (s, 1H), 8.18 (br d, J=6.6 Hz, 1H), 8.06 (br d, J=7.0 Hz, 1H), 7.61 (br d, J=8.5 Hz, 2H), 7.02 (br d, J=8.4 Hz, 2H), 5.05-4.86 (m, 2H), 4.41-4.19 (m, 3H), 4.07 (br d, J=13.5 Hz, 2H), 3.88 (s, 3H), 3.67-3.53 (m, 2H), 3.34-3.20 (m, 2H), 3.17-3.03 (m, 2H), 1.84 (br dd,

J=5.1, 8.9 Hz, 2H), 1.76-1.64 (m, 5H), 1.33-1.25 (m, 2H), 1.00 (d, J=6.4 Hz, 3H). LCMS for product (ESI-): m/z 520.2 [M+H]⁺, Rt: 2.597 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000.

Example 162—Synthesis of ethyl 6-bromo-1-(2,2-diethoxyethyl)-4-hydroxy-2-oxo-1,2-dihydro-1,8-naphthyridine-3-carboxylate (Compound 162)

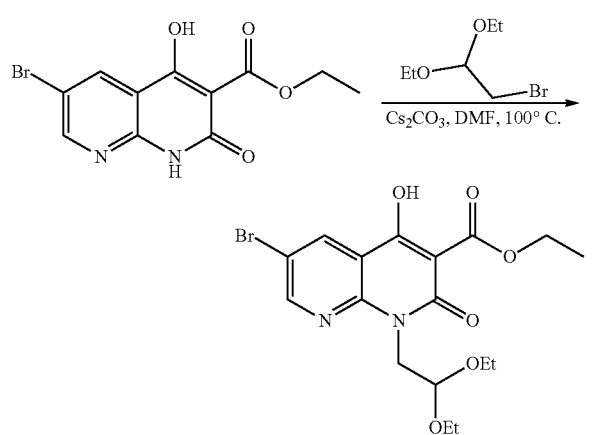

To a solution of ethyl 6-bromo-4-hydroxy-2-oxo-1,2-dihydro-1,8-naphthyridine-3-carboxylate (300 mg, 958.15 μmol, 1 eq) in DMF (20 mL) was added 2-bromo-1,1-diethoxy-ethane (377.64 mg, 1.92 mmol, 288.28 μL, 2 eq), Cs₂CO₃ (3.12 g, 9.58 mmol, 10 eq) at 20° C. The mixture was stirred at 100° C. for 12 h. Two additional vials were set up as described above. All three reaction mixtures were combined for purification. The mixture was filtered, and the filtrate was purified by prep-HPLC (column: Waters X bridge BEH C18 100*25 mm*5 μm; mobile phase: [water (10 mM NH₄HCO₃)-ACN]; B %: 50%-80%, 8 min) to give ethyl 6-bromo-1-(2,2-diethoxyethyl)-4-hydroxy-2-oxo-1,2-dihydro-1,8-naphthyridine-3-carboxylate (570 mg, 1.33 mmol).

¹H NMR (400 MHz, CDCl₃) δ=8.71 (br s, 1H), 8.52 (br s, 1H), 5.04 (br t, J=5.4 Hz, 1H), 4.65 (br d, J=5.5 Hz, 2H), 4.53 (q, J=6.9 Hz, 2H), 3.81-3.69 (m, 2H), 3.56-3.45 (m, 2H), 1.48 (br t, J=7.1 Hz, 3H), 1.08 (br t, J=6.9 Hz, 6H).

LCMS for product (ESI+): m/z 430.0 [M+H]⁺, Rt: 1.502 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.5 min 5% B in 0.01 min, 5-95% B (0.01-3.00 min), 95% B (3.00-3.50 min), 95-5% B (3.50-4.00 min) and hold at 5% B for 0.5 min. The flow rate was 1.0 m/min.

Example 163—Synthesis of ethyl 1-(2,2-diethoxyethyl)-6-(4-fluorophenyl)-4-hydroxy-2-oxo-1,2-dihydro-1,8-naphthyridine-3-carboxylate (Compound 163)

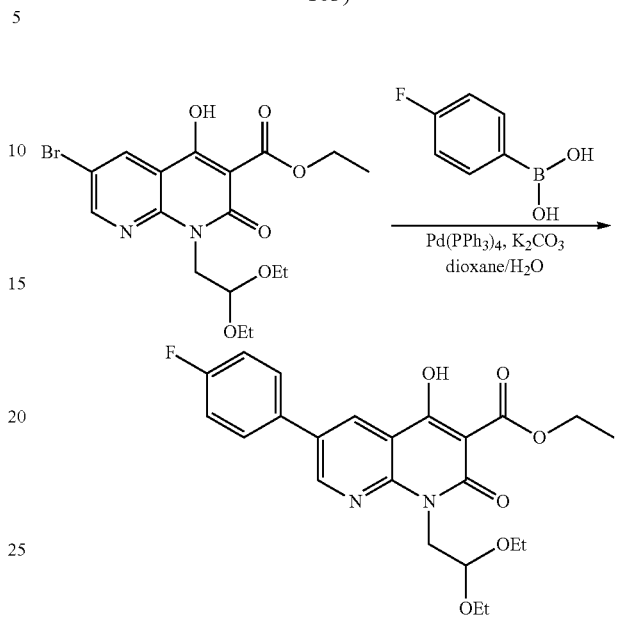

To a solution of ethyl 6-bromo-1-(2,2-diethoxyethyl)-4-hydroxy-2-oxo-1,2-dihydro-1,8-naphthyridine-3-carboxylate (550 mg, 1.28 mmol, 1 eq), (4-fluorophenyl)boronic acid (215.13 mg, 1.54 mmol, 1.2 eq) in dioxane (10 mL) and H₂O (1 mL) was added K₂CO₃ (531.24 mg, 3.84 mmol, 3 eq), Pd(PPh₃)₄ (148.06 mg, 128.13 μmol, 0.1 eq) under N₂ at 20° C. The mixture was stirred at 100° C. for 2 h. The mixture was concentrated and the residue was dissolved in DMF, and purified by prep-HPLC (column: Phenomenex Gemini-NX 80*40 mm*3 um; mobile phase: [water (10 mM NH₄HCO₃)-ACN]; B %: 15%-35%, 8 min) to give ethyl 1-(2,2-diethoxyethyl)-6-(4-fluorophenyl)-4-hydroxy-2-oxo-1,2-dihydro-1,8-naphthyridine-3-carboxylate (300 mg, 674.99 mol).

¹H NMR (400 MHz, CDCl₃) δ=14.54-14.01 (m, 1H), 8.91 (d, J=2.5 Hz, 1H), 8.55 (d, J=2.4 Hz, 1H), 7.77-7.51 (m, 2H), 7.21 (t, J=8.6 Hz, 2H), 5.11 (t, J=5.8 Hz, 1H), 4.74 (d, J=5.8 Hz, 2H), 4.55 (q, J=7.1 Hz, 2H), 3.79 (qd, J=7.1, 9.4 Hz, 2H), 3.52 (qd, J=7.0, 9.4 Hz, 2H), 1.50 (t, J=7.1 Hz, 3H), 1.09 (t, J=7.1 Hz, 6H). LCMS for product (ESI+): m/z 445.2[M+H]⁺, Rt: 1.640 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.5 min 0.5% B in 0.01 min, 5-95% B (0.01-3.00 min), 95% B (3.00-3.50 min), 95-5% B (3.50-4.00 min) and hold at 5% for 0.5 min. The flow rate was 1.0 mL/min.

Example 164—Synthesis of N-(bicyclo[1.1.1]pentan-1-yl)-1-(2,2-diethoxyethyl)-6-(4-fluorophenyl)-4-hydroxy-2-oxo-1,2-dihydro-1,8-naphthyridine-3-carboxamide (Compound 164)

Example 164A—Synthesis of N-(bicyclo[1.1.1]pentan-1-yl)-6-(4-fluorophenyl)-4-hydroxy-2-oxo-1-(2-oxoethyl)-1,2-dihydro-1,8-naphthyridine-3-carboxamide (Compound 164A)

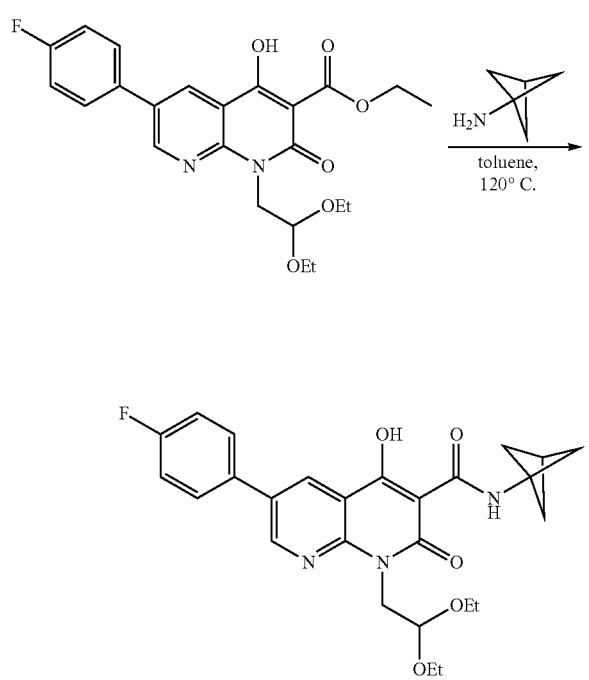

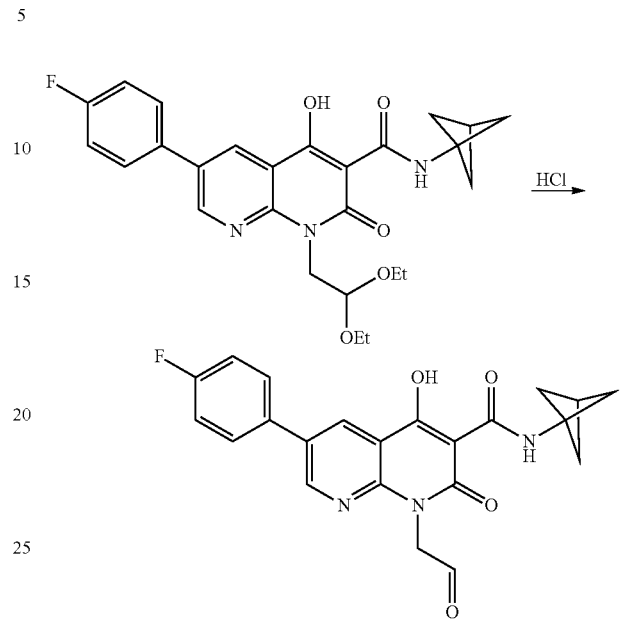

To a solution of ethyl 1-(2,2-diethoxyethyl)-6-(4-fluorophenyl)-4-hydroxy-2-oxo-1,2-dihydro-1,8-naphthyridine-3-carboxylate (257 mg, 578.24 μmol, 1 eq) in toluene (5 mL) was added bicyclo[1.1.1]pentan-1-amine (89.90 mg, 751.71 μmol, 1.3 eq, HCl), DIEA (112.10 mg, 867.36 μmol, 151.08 μL, 1.5 eq) at 20° C., the mixture was stirred at 120° C. for 1 h. The mixture was concentrated to give N-(bicyclo[1.1.1]pentan-1-yl)-1-(2,2-diethoxyethyl)-6-(4-fluorophenyl)-4-hydroxy-2-oxo-1,2-dihydro-1,8-naphthyridine-3-carboxamide (250 mg, crude).

LCMS for product (ESI+): m/z 482.2 [M+H]$^+$, Rt: 1.203 min.

LC/MS (The column used for chromatography was a Chromolith RP-18e 25-2 mm, (3 μm particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.00 min 0.5% B in 0.01 min, 5-95% B (0.01-1.00 min), 95-100% B (1.00-1.80 min), 5% B in 1.81 min with a hold at 5% B for 0.19 min. The flow rate was 1.0 m/min (0.00-1.80 min) and 1.2 mL/min (1.81-2.00 min).

To a solution of N-(bicyclo[1.1.1]pentan-1-yl)-1-(2,2-diethoxyethyl)-6-(4-fluorophenyl)-4-hydroxy-2-oxo-1,2-dihydro-1,8-naphthyridine-3-carboxamide (220 mg, 456.89 μmol, 1 eq) in THF (10 mL) was added HCl (2 M, 4.57 mL, 20 eq) at 20° C., the mixture was stirred at 50° C. for 3 h. The mixture was concentrated to give N-(bicyclo[1.1.1]pentan-1-yl)-6-(4-fluorophenyl)-4-hydroxy-2-oxo-1-(2-oxoethyl)-1,2-dihydro-1,8-naphthyridine-3-carboxamide (250 mg, crude).

$^1$H NMR (400 MHz, DMSO-d$_6$) δ=10.38 (br s, 1H), 9.71 (s, 1H), 9.07 (d, J=2.4 Hz, 1H), 8.63 (d, J=2.4 Hz, 1H), 7.89 (dd, J=5.4, 8.8 Hz, 2H), 7.36 (t, J=8.8 Hz, 2H), 5.31 (s, 2H), 2.54 (s, 1H), 2.16 (s, 6H).

Example 165—Synthesis of 1-(2-(6-oxa-3-azabicyclo[3.1.1]heptan-3-yl)ethyl)-N-(bicyclo[1.1.1]pentan-1-yl)-6-(4-fluorophenyl)-4-hydroxy-2-oxo-1,2-dihydro-1,8-naphthyridine-3-carboxamide (Compound 165)

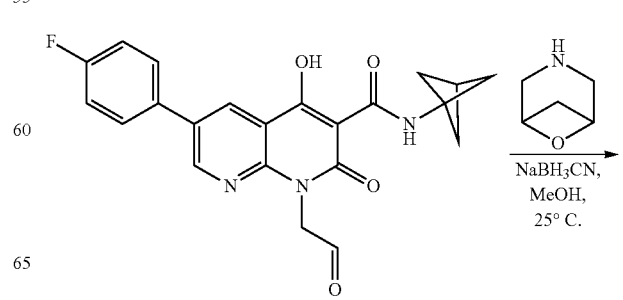

469

-continued

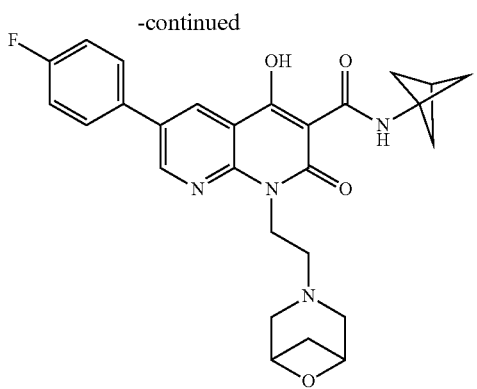

470

-continued

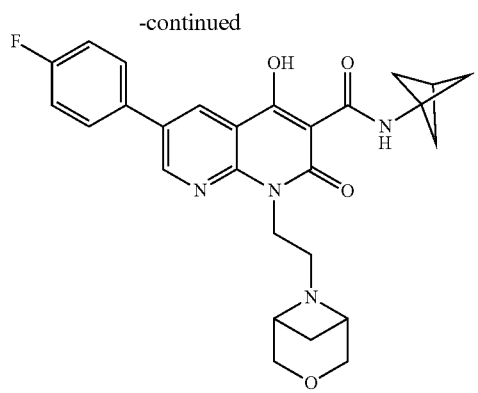

To a solution of N-(bicyclo[1.1.1]pentan-1-yl)-6-(4-fluorophenyl)-4-hydroxy-2-oxo-1-(2-oxoethyl)-1,2-dihydro-1,8-naphthyridine-3-carboxamide (30 mg, 73.64 μmol, 1 eq), 6-oxa-3-azabicyclo[3.1.1]heptane (10.98 mg, 81.00 μmol, 1.1 eq, HCl) in MeOH (5 mL) was added NaOAc (18.12 mg, 220.92 μmol, 3 eq) to adjust the PH to 7. Then NaBH$_3$CN (13.88 mg, 220.92 mol, 3 eq) was added at 20° C., the mixture was stirred at 20° C. for 2 h. The mixture was concentrated and the residue was dissolved in DMF and purified by prep-HPLC (column: Welch Xtimate C18 100*25 mm*3 μm; mobile phase: [water (0.05% HCl)-ACN]; B %: 20%-50%, 8 min) to give 1-(2-(6-oxa-3-azabicyclo[3.1.1]heptan-3-yl)ethyl)-N-(bicyclo[1.1.1]pentan-1-yl)-6-(4-fluorophenyl)-4-hydroxy-2-oxo-1,2-dihydro-1,8-naphthyridine-3-carboxamide (11 mg, 21.91 mol).

$^1$H NMR (400 MHz, CDCl$_3$) δ=13.54-13.35 (m, 1H), 10.27 (s, 1H), 8.90 (br s, 1H), 8.62 (s, 1H), 7.62 (br dd, J=5.3, 8.1 Hz, 2H), 7.22 (br t, J=8.4 Hz, 2H), 5.11 (br s, 2H), 4.69 (br d, J=5.9 Hz, 2H), 4.19-4.02 (m, 2H), 3.55 (br s, 4H), 3.43-3.33 (m, 1H), 3.05 (br d, J=10.1 Hz, 1H), 2.55 (s, 1H), 2.24 (s, 6H). LCMS for product (ESI+): m/z 491.1 [M+H]$^+$, Rt: 2.447 min.

LC/MS (The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% Trifluoroacetic Acid in water, mobile phase B was 0.018% Trifluoroacetic Acid in acetonitrile. The column used for chromatography was a Kinetex C18 50*2.1 mm column (5 um particles). Detection methods are diode array (DAD) and evaporative light scattering (ELSD) detection as well as positive electrospray ionization. MS range was 100-1000.

Example 166—Synthesis of 1-(2-(3-oxa-6-azabicyclo[3.1.1]heptan-6-yl)ethyl)-N-(bicyclo[1.1.1]pentan-1-yl)-6-(4-fluorophenyl)-4-hydroxy-2-oxo-1,2-dihydro-1,8-naphthyridine-3-carboxamide (Compound 166)

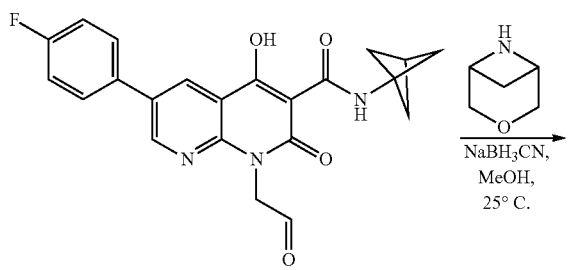

To a solution of N-(bicyclo[1.1.1]pentan-1-yl)-6-(4-fluorophenyl)-4-hydroxy-2-oxo-1-(2-oxoethyl)-1,2-dihydro-1,8-naphthyridine-3-carboxamide (30 mg, 73.64 μmol, 1 eq), 3-oxa-6-azabicyclo[3.1.1]heptane (11.98 mg, 88.37 μmol, 1.2 eq, HCl) in MeOH (2 mL) was added NaOAc (18.12 mg, 220.92 μmol, 3 eq) to adjust the PH to 7. NaBH$_3$CN (13.88 mg, 220.92 μmol, 3 eq) was added, the mixture was stirred at 20° C. for 3 h. The mixture was concentrated and the residue was dissolved in DMF and purified by prep-HPLC (column: Waters Xbridge BEH C18 100*25 mm*5 μm; mobile phase: [water (10 mM NH$_4$HCO$_3$)-ACN]; B %: 60%-90%, 10 min) to give 1-(2-(3-oxa-6-azabicyclo[3.1.1]heptan-6-yl)ethyl)-N-(bicyclo[1.1.1]pentan-1-yl)-6-(4-fluorophenyl)-4-hydroxy-2-oxo-1,2-dihydro-1,8-naphthyridine-3-carboxamide (6.7 mg, 13.52 μmol).

$^1$H NMR (400 MHz, CDCl$_3$) δ=10.52 (s, 1H), 8.89 (d, J=2.4 Hz, 1H), 8.60 (d, J=2.5 Hz, 1H), 7.66-7.59 (m, 2H), 7.21 (t, J=8.6 Hz, 2H), 4.64-4.51 (m, 2H), 4.34 (d, J=10.9 Hz, 2H), 3.74 (d, J=10.8 Hz, 2H), 3.61 (d, J=6.0 Hz, 2H), 3.03-2.96 (m, 2H), 2.66 (q, J=6.5 Hz, 1H), 2.54 (s, 1H), 2.23 (s, 6H), 1.87 (d, J=8.4 Hz, 1H). LCMS for product (ESI+): m/z 491.2[M+H]$^+$, Rt: 2.267 min.

LC/MS (The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 μm particles). Detection methods are diode array (DAD) and evaporative light scattering (ELSD) detection as well as positive electrospray ionization. MS range was 100-1000.

Example 167—Synthesis of 6-bromo-2H-pyrido[2,3-d][1,3]oxazine-2,4(1H)-dione (Compound 167)

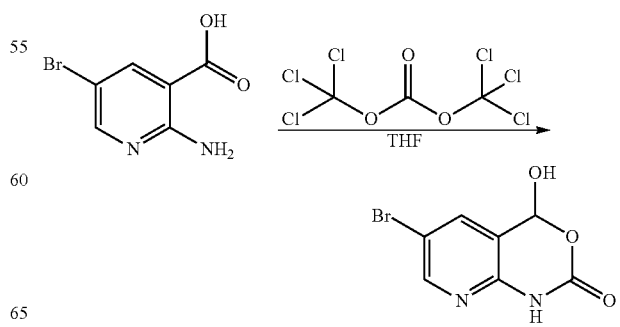

To a solution of 2-amino-5-bromonicotinic acid (1.2 g, 5.53 mmol, 1 eq) in THF (25 mL) was added a solution of bis(trichloromethyl) carbonate (3.61 g, 12.16 mmol, 2.2 eq) in THF (15 mL) at 25° C., the mixture was stirred at 60° C. for 12 h. One additional vial was set up as described above. The mixtures were combined and filtered, and the filtrate was concentrated to give 6-bromo-2H-pyrido[2,3-d][1,3]oxazine-2,4(1H)-dione (5 g, crude).

LCMS for product (ESI+): m/z 242.7, 240.7 [M−H]⁻, Rt: 0.807 min.

LC/MS (The column used for chromatography was Xbridge Shield RP18 2.1*50 mm, (5 m particles). Detection methods are diode array (DAD). MS mode was negative electrospray ionization. MS range was 100-1000. Mobile phase A was 10 mM Ammonium bicarbonate in water, and mobile phase B was HPLC grade acetonitrile. The gradient was 5-95% B in 2.05 min 0.5% B in 0.01 min, 5-95% B (0.01-1.00 min), 95-100% B (1.00-1.80 min), 5% B in 1.81 min with a hold at 5% B for 0.24 min. The flow rate was 1.0 m/min.

Example 168—Synthesis of benzyl 6-bromo-4-hydroxy-2-oxo-1,2-dihydro-1,8-naphthyridine-3-carboxylate (Compound 168)

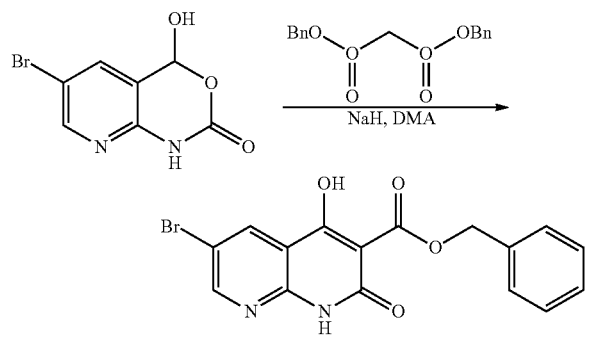

To a solution of NaH (790.00 mg, 19.75 mmol, 60% purity, 2 eq) in DMA (10 mL) was added dibenzyl propanedioate (5.62 g, 19.75 mmol, 2 eq) and then a solution of 6-bromo-1H-pyrido[2,3-d][1,3]oxazine-2,4-dione (2.4 g, 9.88 mmol, 1 eq) in DMA (10 mL) was added at 20° C., the mixture was stirred at 90° C. for 3 h. The mixture was poured into water and acidified by adding 2 N hydrochloric acid dropwise to pH 3. Then filtered, and the filter cake was dried to give benzyl 6-bromo-4-hydroxy-2-oxo-1,2-dihydro-1,8-naphthyridine-3-carboxylate (3 g, crude).

$^1$H NMR (400 MHz, DMSO-$d_6$) δ=12.15-11.96 (m, 1H), 8.68 (d, J=2.1 Hz, 1H), 8.55 (d, J=2.1 Hz, 1H), 7.48 (br d, J=7.3 Hz, 2H), 7.41-7.29 (m, 3H), 5.32 (s, 2H). LCMS for product (ESI+): m/z 375.0, 377.0 [M+H]⁺, Rt: 0.836 min.

LC/MS (The column used for chromatography was a Luna-C18 2.0*30 mm, (3 μm particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.00 min 0.5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min).

Example 169—Synthesis of benzyl 6-bromo-4-hydroxy-1-(2-morpholinoethyl)-2-oxo-1,2-dihydro-1,8-naphthyridine-3-carboxylate (Compound 169)

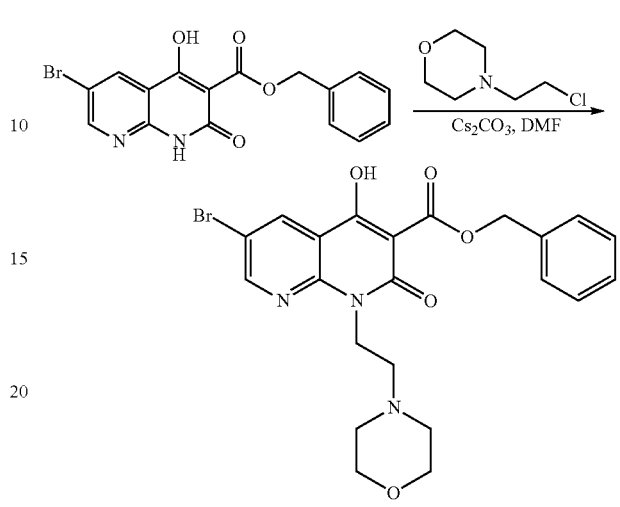

To a solution of benzyl 6-bromo-4-hydroxy-2-oxo-1,2-dihydro-1,8-naphthyridine-3-carboxylate (1.3 g, 3.47 mmol, 1 eq) in DMF (15 mL) was added 4-(2-chloroethyl)morpholine (709.25 mg, 3.81 mmol, 1.1 eq, HCl), Cs₂CO₃ (9.03 g, 27.72 mmol, 8 eq) at 20° C., the mixture was stirred at 50° C. for 12 h. The mixture was filtered and the filtrate was purified by prep-HPLC (column: Phenomenex Gemini-NX 80*40 mm*33 μm; mobile phase: [water (10 mM NH₄HCO₃)-ACN]; B %: 10%-30%, 8 min) to give benzyl 6-bromo-4-hydroxy-1-(2-morpholinoethyl)-2-oxo-1,2-dihydro-1,8-naphthyridine-3-carboxylate (1.6 g, 3.28 mmol).

LCMS for product (ESI+): m/z 488.0, 490.0 [M+H]⁺, Rt: 0.989 min.

LC/MS (The column used for chromatography was Xbridge Shield RP18 2.1*50 mm, (5 μm particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 2.05 min 0.5% B in 0.01 min, 5-95% B (0.01-1.00 min), 95-100% B (1.00-1.80 min), 5% B in 1.81 min with a hold at 5% B for 0.24 min. The flow rate was 1.0 mL/min.

Example 170—Synthesis of benzyl 6-(4-fluorophenyl)-4-hydroxy-1-(2-morpholinoethyl)-2-oxo-1,2-dihydro-1,8-naphthyridine-3-carboxylate (Compound 170)

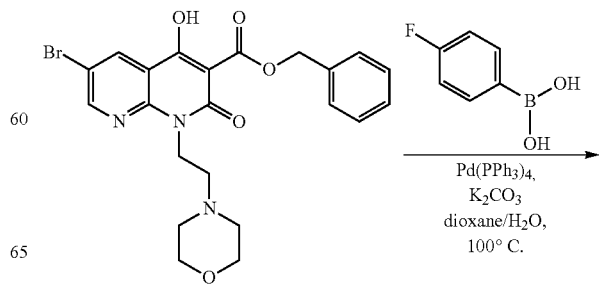

473

-continued

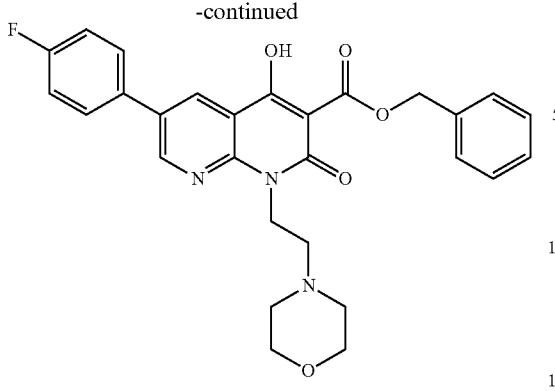

474

-continued

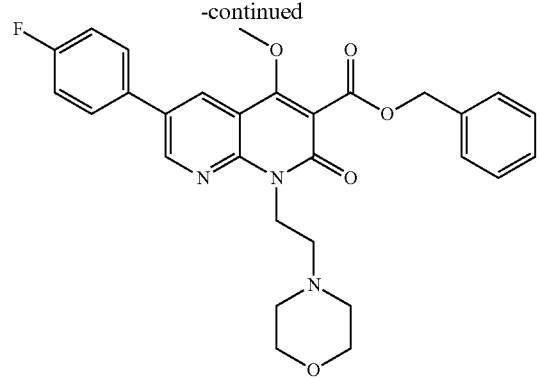

To a solution of benzyl 6-bromo-4-hydroxy-1-(2-morpholinoethyl)-2-oxo-1,2-dihydro-1,8-naphthyridine-3-carboxylate (800 mg, 1.64 mmol, 1 eq), (4-fluorophenyl) boronic acid (229.22 mg, 1.64 mmol, 1 eq) in dioxane (8 mL) and H₂O (0.8 mL) was added K₂CO₃ (452.84 mg, 3.28 mmol, 2 eq), Pd(PPh₃)₄ (189.31 mg, 163.82 μmol, 0.1 eq) under N₂ at 20° C. The mixture was stirred at 100° C. for 1 h. The mixture was concentrated and dissolved in DMF then purified by prep-HPLC (column: Kromasil C18 (250*50 mm*10 um); mobile phase: [water (10 mM NH₄HCO₃)-ACN]; B %: 20%-40%, 10 min) to give benzyl 6-(4-fluorophenyl)-4-hydroxy-1-(2-morpholinoethyl)-2-oxo-1,2-dihydro-1,8-naphthyridine-3-carboxylate (350 mg, 695.11 μmol).

¹H NMR (400 MHz, DMSO-d₆) δ=8.84 (d, J=2.1 Hz, 1H), 8.49 (d, J=2.3 Hz, 1H), 7.78 (dd, J=5.6, 8.4 Hz, 2H), 7.48 (br d, J=7.4 Hz, 2H), 7.38-7.26 (m, 5H), 5.16 (s, 2H), 4.61-4.53 (m, 2H), 3.73 (br s, 4H), 3.17-3.06 (m, 6H). LCMS for product (ESI+): m/z 504.1 [M+H]⁺, Rt: 1.437 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.5 min 0.5% B in 0.01 min, 5-95% B (0.01-3.00 min), 95% B (3.00-3.50 min), 95-5% B (3.50-4.00 min) and hold at 5% B for 0.5 min. The flow rate was 1.0 m/min.

Example 171—Synthesis of benzyl 6-(4-fluorophenyl)-4-methoxy-1-(2-morpholinoethyl)-2-oxo-1,2-dihydro-1,8-naphthyridine-3-carboxylate (Compound 171)

To a solution of benzyl 6-(4-fluorophenyl)-4-hydroxy-1-(2-morpholinoethyl)-2-oxo-1,2-dihydro-1,8-naphthyridine-3-carboxylate (100 mg, 198.60 μmol, 1 eq), dimethyl sulfate (27.55 mg, 218.46 μmol, 20.72 μL, 1.1 eq) in acetone (8 mL) was added K₂CO₃ (54.90 mg, 397.20 mol, 2 eq) at 20° C. The mixture was stirred at 55° C. for 12 h. One additional vial was set up as described above. The combined mixture was poured into water (40 mL). The aqueous phase was extracted with ethyl acetate (3×40 mL), the combined organic phase was washed with brine (30 mL), dried with anhydrous Na₂SO₄, filtered, and concentrated to give crude product, which was purified by silica gel chromatography (column height: mesh silica gel, Petroleum ether: Ethyl acetate=1:2) to give benzyl 6-(4-fluorophenyl)-4-methoxy-1-(2-morpholinoethyl)-2-oxo-1,2-dihydro-1,8-naphthyridine-3-carboxylate (80 mg, 154.58 μmol).

¹H NMR (400 MHz, CDCl₃) δ=8.79 (d, J=2.4 Hz, 1H), 8.36 (d, J=2.5 Hz, 1H), 7.60-7.55 (m, 2H), 7.50 (dd, J=1.6, 7.9 Hz, 2H), 7.42-7.34 (m, 3H), 7.22-7.15 (m, 2H), 5.45 (s, 2H), 4.79-4.61 (m, 2H), 3.94 (s, 3H), 3.83-3.66 (m, 4H), 2.91-2.58 (m, 6H). LCMS for product (ESI+): m/z 518.2 [M+H]+, Rt: 1.359 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 2.05 min 0.5% B in 0.01 min, 5-95% B (0.01-1.00 min), 95-100% B (1.00-1.80 min), 5% B in 1.81 min with a hold at 5% B for 0.24 min. The flow rate was 1.0 mL/min.

Example 172—Synthesis of 6-(4-fluorophenyl)-4-methoxy-1-(2-morpholinoethyl)-2-oxo-1,2-dihydro-1,8-naphthyridine-3-carboxylic acid (Compound 172)

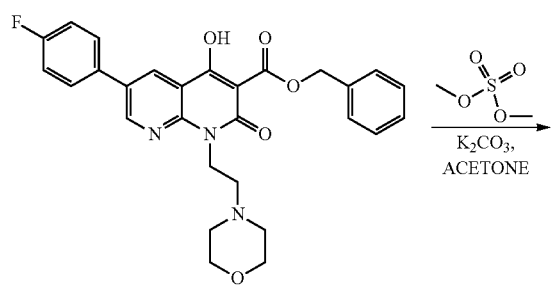

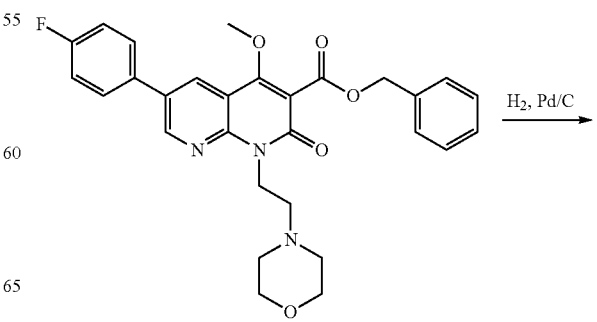

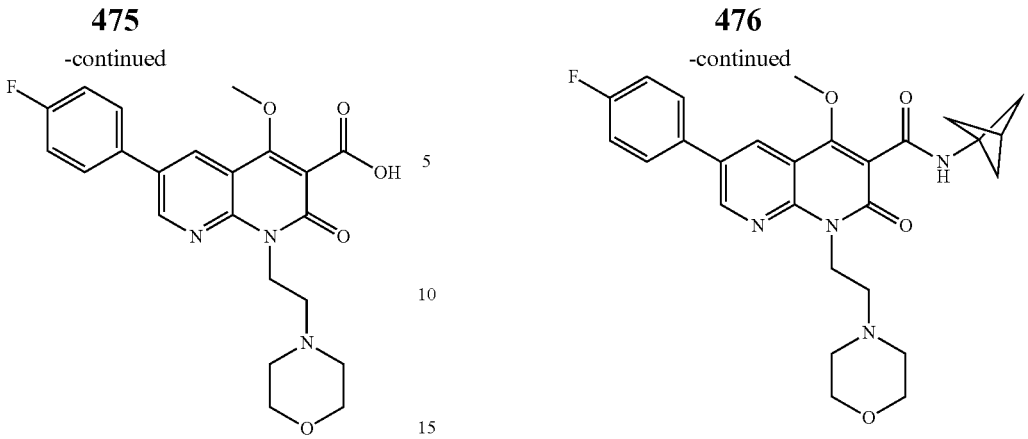

To a mixture of Pd/C (10 mg, 135.25 μmol, 10% purity, 1 eq) in THF (5 mL) was added benzyl 6-(4-fluorophenyl)-4-methoxy-1-(2-morpholinoethyl)-2-oxo-1,2-dihydro-1,8-naphthyridine-3-carboxylate (70 mg, 135.25 μmol, 1 eq) at 20° C., the mixture was stirred at 20° C. for 2 h under H$_2$ (15 psi). The mixture was filtered, and the filtrate was concentrated to give 6-(4-fluorophenyl)-4-methoxy-1-(2-morpholinoethyl)-2-oxo-1,2-dihydro-1,8-naphthyridine-3-carboxylic acid (45 mg, crude).

$^1$H NMR (400 MHz, DMSO-d$_6$) δ=8.89 (d, J=2.3 Hz, 1H), 8.36 (d, J=2.3 Hz, 1H), 7.83 (dd, J=5.5, 8.5 Hz, 2H), 7.34 (br t, J=8.8 Hz, 2H), 4.48 (br t, J=7.3 Hz, 2H), 4.15 (s, 3H), 3.57-3.52 (m, 4H), 2.57-2.51 (m, 6H). LCMS for product (ESI+): m/z 428.2 [M+H]$^+$, Rt: 0.677 min.

LC/MS (The column used for chromatography was a Chromolith RP-18e 25-2 mm, (3 μm particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.00 min 0.5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min)

Example 173—Synthesis of N-(bicyclo[1.1.1]pentan-1-yl)-6-(4-fluorophenyl)-4-methoxy-1-(2-morpholinoethyl)-2-oxo-1,2-dihydro-1,8-naphthyridine-3-carboxamide (Compound 173)

To a solution of 6-(4-fluorophenyl)-4-methoxy-1-(2-morpholinoethyl)-2-oxo-1,2-dihydro-1,8-naphthyridine-3-carboxylic acid (38 mg, 88.90 μmol, 1 eq) in DMF (0.3 mL) was added HATU (67.61 mg, 177.81 μmol, 2 eq) and DIEA (45.96 mg, 355.62 μmol, 61.94 μL, 4 eq). The mixture was stirred at 25° C. for 0.5 h, bicyclo[1.1.1]pentan-1-amine (13.82 mg, 115.58 mol, 1.3 eq, HCl) was added into the mixture, the mixture was stirred at 25° C. for 1 h. The mixture was filtered, and the filtrate was purified by prep-HPLC (column: Phenomenex Gemini-NX C18 75*30 mm*3 μm; mobile phase: [water (10 mM NH$_4$HCO$_3$)-ACN]; B %: 30%-60%, 8 min) to give N-(bicyclo[1.1.1]pentan-1-yl)-6-(4-fluorophenyl)-4-methoxy-1-(2-morpholinoethyl)-2-oxo-1,2-dihydro-1,8-naphthyridine-3-carboxamide (12.1 mg, 24.57 μmol).

$^1$H NMR (400 MHz, MeOD) δ=8.90 (d, J=2.4 Hz, 1H), 8.52 (d, J=2.4 Hz, 1H), 7.76-7.70 (m, 2H), 7.25 (t, J=8.8 Hz, 2H), 4.68 (t, J=7.0 Hz, 2H), 4.24 (s, 3H), 3.68-3.63 (m, 4H), 2.73 (t, J=7.0 Hz, 2H), 2.63 (br d, J=3.9 Hz, 4H), 2.49 (s, 1H), 2.20 (s, 6H).

LCMS for product (ESI+): m/z 493.2 [M+H]$^+$, Rt: 2.911 min.

LC/MS (The column used for chromatography was a Chromolith RP-18e 25-2 mm, (3 m particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.00 min 0.5% B in 0.01 min, 5-95% B (0.01-1.00 min), 95-100% B (1.00-1.80 min), 5% B in 1.81 min with a hold at 5% B for 0.19 min. The flow rate was 1.0 m/min (0.00-1.80 min) and 1.2 mL/min (1.81-2.00 min)

Example 174—Synthesis of benzyl 4-hydroxy-6-(4-methoxyphenyl)-1-(2-morpholinoethyl)-2-oxo-1,2-dihydro-1,8-naphthyridine-3-carboxylate (Compound 174)

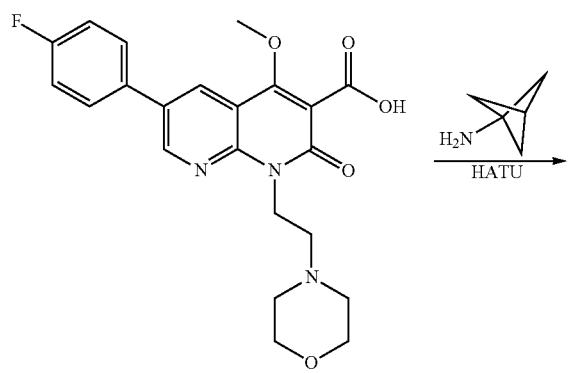
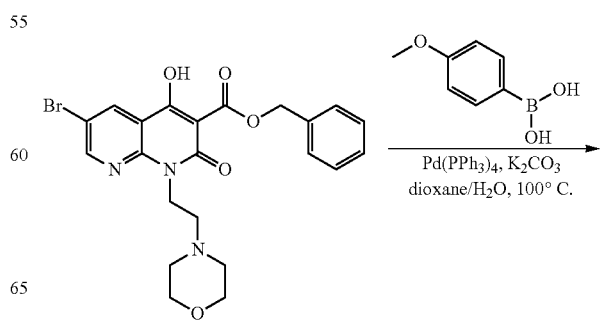

477
-continued

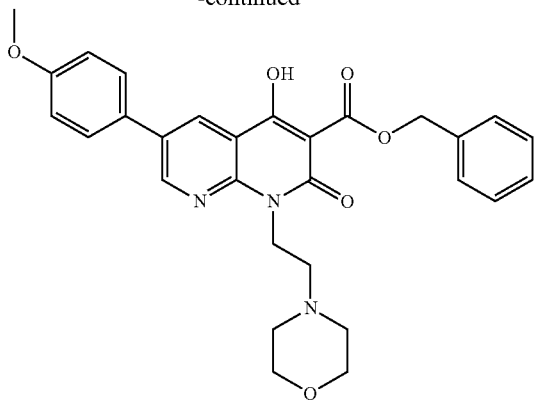

To a solution of benzyl 6-bromo-4-hydroxy-1-(2-morpholinoethyl)-2-oxo-1,2-dihydro-1,8-naphthyridine-3-carboxylate (760 mg, 1.56 mmol, 1 eq), (4-methoxyphenyl) boronic acid (236.49 mg, 1.56 mmol, 1 eq) in dioxane (4 mL) and H$_2$O (0.4 mL) was added K$_2$CO$_3$ (430.20 mg, 3.11 mmol, 2 eq), Pd(PPh$_3$)$_4$ (179.84 mg, 155.63 μmol, 0.1 eq) under N$_2$ at 20° C. The mixture was stirred at 100° C. for 1 h. The mixture was concentrated and dissolved in DMF then purified by prep-HPLC (column: Kromasil C18 (250*50 mm*10 um); mobile phase: [water (10 mM NH$_4$HCO$_3$)-ACN]; B %: 20%-40%, 10 min) to give benzyl 4-hydroxy-6-(4-methoxyphenyl)-1-(2-morpholinoethyl)-2-oxo-1,2-dihydro-1,8-naphthyridine-3-carboxylate (300 mg, 581.90 μmol).

$^1$H NMR (400 MHz, DMSO-d$_6$) δ=8.83 (d, J=2.1 Hz, 1H), 8.48 (d, J=2.1 Hz, 1H), 7.68 (d, J=8.5 Hz, 2H), 7.49 (d, J=7.6 Hz, 2H), 7.40-7.29 (m, 3H), 7.06 (d, J=8.5 Hz, 2H), 5.19 (s, 2H), 4.56 (br t, J=6.1 Hz, 2H), 3.81 (s, 3H), 3.71 (br s, 4H), 3.12-3.02 (m, 6H). LCMS for product (ESI+): m/z 516.1 [M+H]$^+$, Rt: 1.397 min.

LC/MS (The column used for chromatography was Xbridge Shield RP18 2.1*50 mm, (5 um particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 4.5 min 0.5% B in 0.01 min, 5-95% B (0.01-3.00 min), 95% B (3.00-3.50 min), 95-5% B (3.50-4.00 min) and hold at 5% B for 0.5 min. The flow rate was 1.0 m/min.

Example 175—Synthesis of benzyl 4-methoxy-6-(4-methoxyphenyl)-1-(2-morpholinoethyl)-2-oxo-1,2-dihydro-1,8-naphthyridine-3-carboxylate (Compound 175)

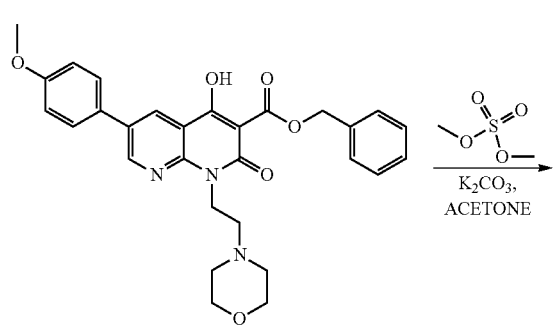

478
-continued

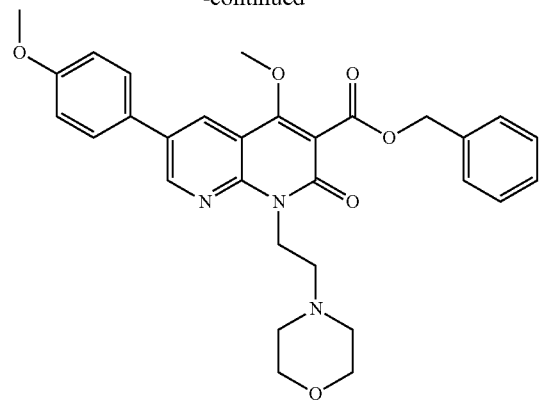

To a solution of benzyl 4-hydroxy-6-(4-methoxyphenyl)-1-(2-morpholinoethyl)-2-oxo-1,2-dihydro-1,8-naphthyridine-3-carboxylate (100 mg, 193.97 μmol, 1 eq), dimethyl sulfate (26.91 mg, 213.36 μmol, 20.23 μL, 1.1 eq) in acetone (3 mL) was added K$_2$CO$_3$ (53.62 mg, 387.93 μmol, 2 eq) at 20° C. The mixture was stirred at 55° C. for 12 h. One additional vial was set up as described above. The mixture was poured into water (40 mL). The aqueous phase was extracted with ethyl acetate (3×40 mL), the combined organic phase was washed with brine (30 mL), dried with anhydrous Na$_2$SO$_4$, filtered, and concentrated to give crude product, which was purified by silica gel chromatography (column height: mesh silica gel, Petroleum ether: Ethyl acetate=1:2) to give benzyl 4-methoxy-6-(4-methoxyphenyl)-1-(2-morpholinoethyl)-2-oxo-1,2-dihydro-1,8-naphthyridine-3-carboxylate (70 mg, 132.18 μmol) as colorless oil.

$^1$H NMR (400 MHz, CDCl$_3$) δ=8.80 (d, J=2.4 Hz, 1H), 8.37-8.33 (m, 1H), 7.56-7.46 (m, 4H), 7.43-7.33 (m, 3H), 7.06-6.99 (m, 2H), 5.44 (s, 2H), 4.81-4.61 (m, 2H), 3.93 (s, 3H), 3.88 (s, 3H), 3.85-3.62 (m, 4H), 3.10-2.40 (m, 6H) LCMS for product (ESI+): m/z 530.3 [M+H]$^+$, Rt: 1.343 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 2.05 min 0.5% B in 0.01 min, 5-95% B (0.01-1.00 min), 95-100% B (1.00-1.80 min), 5% B in 1.81 min with a hold at 5% B for 0.24 min. The flow rate was 1.0 mL/min.

Example 176—Synthesis of 4-methoxy-6-(4-methoxyphenyl)-1-(2-morpholinoethyl)-2-oxo-1,2-dihydro-1,8-naphthyridine-3-carboxylic acid (Compound 176)

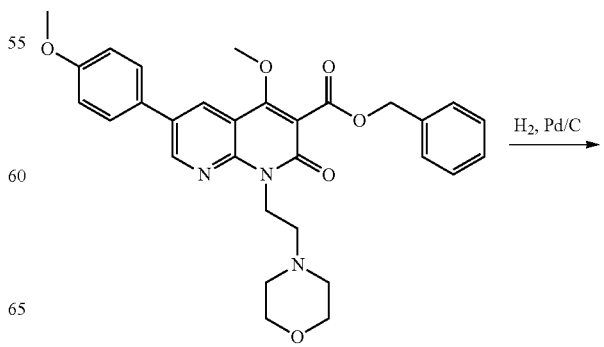

-continued

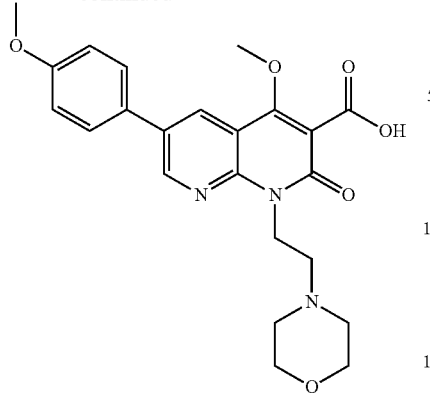

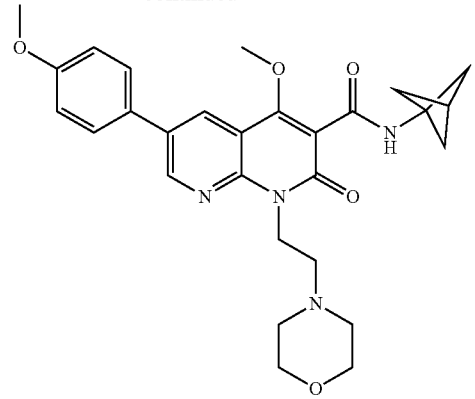

To a mixture of Pd/C (10 mg, 113.30 μmol, 10% purity, 1 eq) in THF (5 mL) was added benzyl 4-methoxy-6-(4-methoxyphenyl)-1-(2-morpholinoethyl)-2-oxo-1,2-dihydro-1,8-naphthyridine-3-carboxylate (60 mg, 113.30 μmol, 1 eq) at 20° C., the mixture was stirred at 20° C. for 2 h under $H_2$ (15 psi). The mixture was filtered, and filtrate was concentrated to give 4-methoxy-6-(4-methoxyphenyl)-1-(2-morpholinoethyl)-2-oxo-1,2-dihydro-1,8-naphthyridine-3-carboxylic acid (25 mg, 56.89 μmol).

$^1$H NMR (400 MHz, DMSO-$d_6$) δ=8.99 (d, J=2.4 Hz, 1H), 8.43 (d, J=2.4 Hz, 1H), 7.75 (d, J=8.8 Hz, 2H), 7.08 (d, J=8.8 Hz, 2H), 4.51 (br t, J=7.0 Hz, 2H), 4.13 (s, 3H), 3.85-3.80 (m, 3H), 3.55 (br d, J=4.3 Hz, 4H), 2.61-2.51 (m, 6H). LCMS for product (ESI+): m/z 440.2 [M+H]$^+$, Rt: 0.133 min, 0.682 min.

LC/MS (The column used for chromatography was a Chromolith RP-18e 25-2 mm, (3 um particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.00 min 0.5% B in 0.01 min, 5-95% B (0.01-1.00 min), 95-100% B (1.00-1.80 min), 5% B in 1.81 min with a hold at 5% B for 0.19 min. The flow rate was 1.0 m/min (0.00-1.80 min) and 1.2 mL/min (1.81-2.00 min)

Example 177—Synthesis of N-(bicyclo[1.1.1]pentan-1-yl)-4-methoxy-6-(4-methoxyphenyl)-1-(2-morpholinoethyl)-2-oxo-1,2-dihydro-1,8-naphthyridine-3-carboxamide (Compound 177)

To a solution of 4-methoxy-6-(4-methoxyphenyl)-1-(2-morpholinoethyl)-2-oxo-1,2-dihydro-1,8-naphthyridine-3-carboxylic acid (20 mg, 45.51 μmol, 1 eq) in DMF (0.3 mL) was added HATU (34.61 mg, 91.02 μmol, 2 eq) and DIEA (23.53 mg, 182.04 μmol, 31.71 μL, 4 eq). The mixture was stirred at 25° C. for 0.5 h, bicyclo[1.1.1]pentan-1-amine (7.08 mg, 59.16 μmol, 1.3 eq, HCl) was added into the mixture, the mixture was stirred at 25° C. for 1 h. The mixture was filtered, and the filtrate was purified by prep-HPLC (column: Phenomenex Gemini-NX C18 75*30 mm*3 um; mobile phase: [water (10 mM NH$_4$HCO$_3$)-ACN]; B %: 25%-55%, 8 min) to give N-(bicyclo[1.1.1]pentan-1-yl)-4-methoxy-6-(4-methoxyphenyl)-1-(2-morpholinoethyl)-2-oxo-1,2-dihydro-1,8-naphthyridine-3-carboxamide (6.4 mg, 12.47 μmol).

$^1$H NMR (400 MHz, MeOD) δ=8.90 (d, J=2.4 Hz, 1H), 8.50 (d, J=2.4 Hz, 1H), 7.65 (d, J=8.8 Hz, 2H), 7.08 (d, J=8.8 Hz, 2H), 4.69 (br t, J=7.2 Hz, 2H), 4.25 (s, 3H), 3.86 (s, 3H), 3.67 (br t, J=4.7 Hz, 4H), 2.74 (br t, J=7.0 Hz, 2H), 2.64 (br s, 4H), 2.50 (s, 1H), 2.21 (s, 6H).

LCMS for product (ESI+): m/z 505.2 [M+H]$^+$, Rt: 2.861 min.

LC/MS (The column used for chromatography was a Chromolith RP-18e 25-2 mm, (3 μm particles). Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.00 min 0.5% B in 0.01 min, 5-95% B (0.01-1.00 min), 95-100% B (1.00-1.80 min), 5% B in 1.81 min with a hold at 5% B for 0.19 min. The flow rate was 1.0 mL/min (0.00-1.80 min) and 1.2 mL/min (1.81-2.00 min)

Example 178—Synthesis of ethyl 4-isopropoxy-6-(4-methoxyphenyl)-1-(2-morpholinoethyl)-2-oxo-1,2-dihydro-1,8-naphthyridine-3-carboxylate (Compound 178)

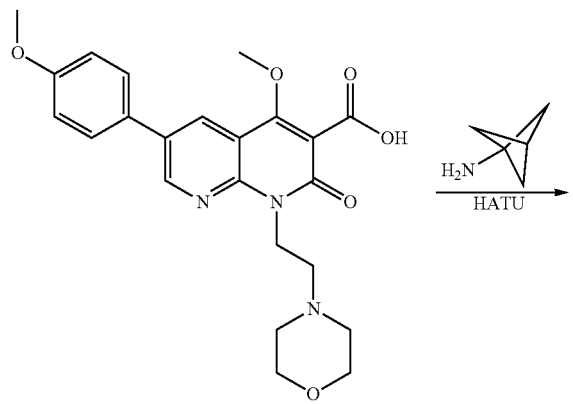

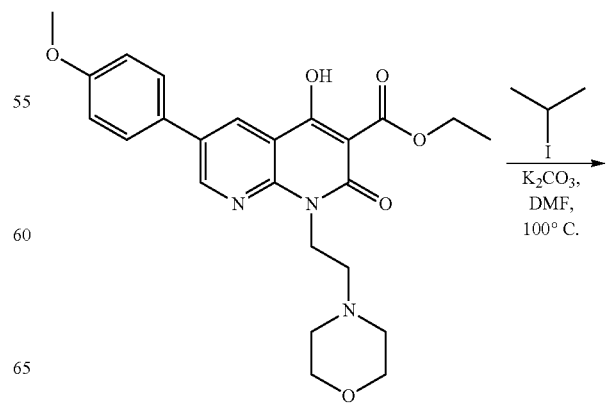

481

-continued

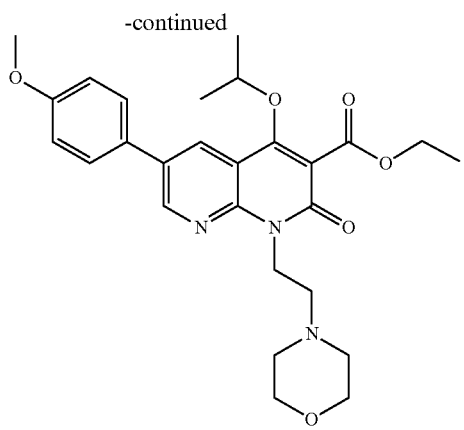

482

-continued

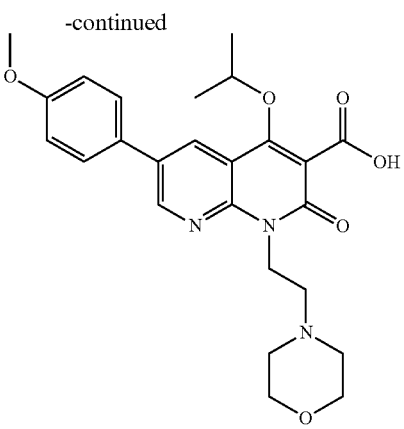

To a solution of ethyl 4-hydroxy-6-(4-methoxyphenyl)-1-(2-morpholinoethyl)-2-oxo-1,2-dihydro-1,8-naphthyridine-3-carboxylate (50 mg, 110.26 µmol, 1 eq) in DMF (1 mL) was added K$_2$CO$_3$ (30.48 mg, 220.51 µmol, 2 eq) at 20° C., the mixture was stirred at 20° C. for 0.5 h. 2-iodopropane (37.49 mg, 220.51 µmol, 22.05 µL, 2 eq) was added to the mixture at 20° C., the mixture was stirred at 100° C. for 12 h. The mixture was poured into water (10 mL), then extracted with ethyl acetate (3×10 mL). The combined organic phase was washed with brine (10 mL), dried with anhydrous Na$_2$SO$_4$, filtered, and concentrated to give ethyl 4-isopropoxy-6-(4-methoxyphenyl)-1-(2-morpholinoethyl)-2-oxo-1,2-dihydro-1,8-naphthyridine-3-carboxylate (40 mg, crude).

$^1$H NMR (400 MHz, CDCl$_3$) δ=8.80 (d, J=2.5 Hz, 1H), 8.35 (d, J=2.4 Hz, 1H), 7.57-7.53 (m, 2H), 7.07-7.04 (m, 2H), 4.84-4.76 (m, 1H), 4.70-4.64 (m, 2H), 4.46 (q, J=7.2 Hz, 2H), 3.89 (s, 3H), 3.73-3.68 (m, 4H), 2.77-2.71 (m, 2H), 2.64 (br d, J=4.1 Hz, 4H), 1.46-1.40 (m, 9H). LCMS for product (ESI+): m/z 496.2 [M+H]$^+$, Rt: 1.351 min.

LC/MS (The column used for chromatography was Xbridge Shield RP18 2.1*50 mm, (5 m particles). Detection methods are diode array (DAD). MS mode was positive electrospray ionization. MS range was 100-1000. Mobile phase A was 10 mM Ammonium bicarbonate in water, and mobile phase B was HPLC grade acetonitrile. The gradient was 5-95% B in 2.05 min 0.5% B in 0.01 min, 5-95% B (0.01-1.00 min), 95-100% B (1.00-1.80 min), 5% B in 1.81 min with a hold at 5% B for 0.24 min. The flow rate was 1.0 mL/min.

Example 179—Synthesis of 4-isopropoxy-6-(4-methoxyphenyl)-1-(2-morpholinoethyl)-2-oxo-1,2-dihydro-1,8-naphthyridine-3-carboxylic acid (Compound 179)

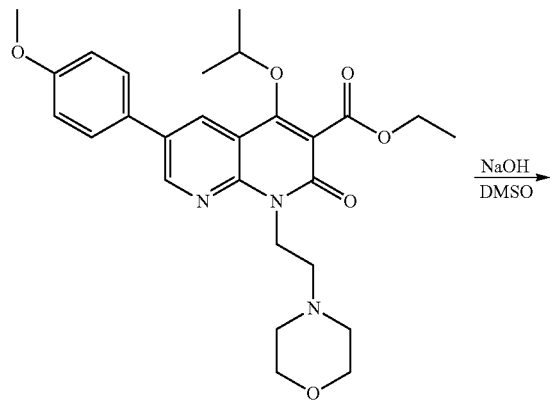

To a solution of ethyl 4-isopropoxy-6-(4-methoxyphenyl)-1-(2-morpholinoethyl)-2-oxo-1,2-dihydro-1,8-naphthyridine-3-carboxylate (37 mg, 74.66 µmol, 1 eq) in DMSO (1 mL) was added NaOH (2 M, 74.66 µL, 2 eq) at 20° C., the mixture was stirred at 20° C. for 2 h. The mixture was filtered and the filtrate was purified by prep-HPLC column: (Welch Xtimate C18 100*25 mm*3 µm; mobile phase: [water (0.05% HCl)-ACN]; B %: 5%-30%, 8 min) to give 4-isopropoxy-6-(4-methoxyphenyl)-1-(2-morpholinoethyl)-2-oxo-1,2-dihydro-1,8-naphthyridine-3-carboxylic acid (8 mg, 17.11 µmol).

$^1$H NMR (400 MHz, DMSO-d$_6$) δ=8.99 (d, J=2.3 Hz, 1H), 8.43 (d, J=2.3 Hz, 1H), 7.74 (d, J=8.6 Hz, 2H), 7.11 (d, J=8.8 Hz, 2H), 4.88 (quin, J=6.0 Hz, 1H), 4.74 (br t, J=5.8 Hz, 2H), 3.83 (s, 3H), 3.50 (br d, J=4.6 Hz, 4H), 2.53-2.50 (m, 6H), 1.39 (d, J=6.0 Hz, 6H). LCMS for product (ESI+): m/z 468.4 [M+H]$^+$, Rt: 1.711 min.

LC/MS (The column used for chromatography was a HALO AQ-C18 2.1*30 mm, (2.7 µm particles). Detection methods are diode array (DAD). MS mode was positive electrospray ionization. MS range was 100-1000. Mobile phase A was 0.037% TFA in water, and mobile phase B was 0.018% TFA in HPLC grade acetonitrile. The gradient was 5-95% B in 4.30 min 0.5% B in 0.01 min, 5-95% B (0.01-3.00 min), with a hold at 95% B for 0.50 min. 95-5% B (3.50-3.51 min), 5% B in 3.51 min, with a hold at 5% B for 0.79 min. The flow rate was 1.0 mL/min.

Example 180—Synthesis of N-(bicyclo[1.1.1]pentan-1-yl)-4-isopropoxy-6-(4-methoxyphenyl)-1-(2-morpholinoethyl)-2-oxo-1,2-dihydro-1,8-naphthyridine-3-carboxamide (Compound 180)

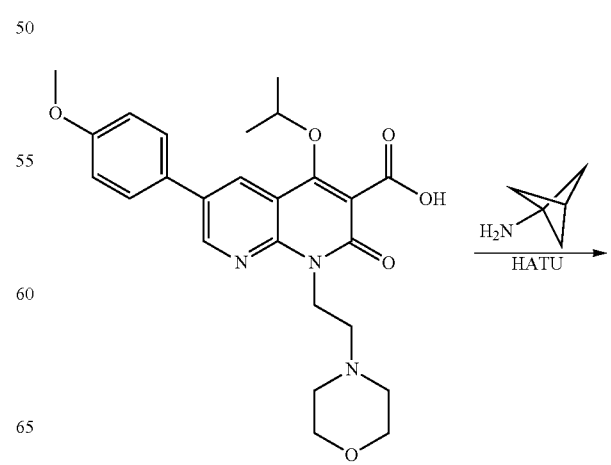

-continued

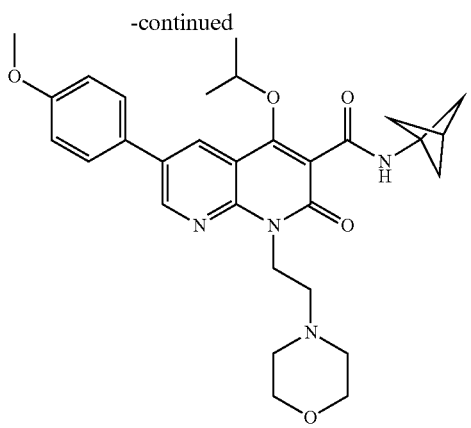

To a solution of 4-isopropoxy-6-(4-methoxyphenyl)-1-(2-morpholinoethyl)-2-oxo-1,2-dihydro-1,8-naphthyridine-3-carboxylic acid (5 mg, 10.69 µmol, 1 eq) in DMF (1 mL) was added HATU (8.13 mg, 21.39 µmol, 2 eq), DIEA (5.53 mg, 42.78 µmol, 7.45 µL, 4 eq) at 20° C., the mixture was stirred at 20° C. for 0.5 h. Bicyclo[1.1.1]pentan-1-amine (2.56 mg, 21.39 µmol, 2 eq, HCl) to the mixture at 20° C., the mixture was stirred at 20° C. for 1 h. The mixture was filtered and the filtrate was purified by prep-HPLC (column: Waters Xbridge BEH C18 100*25 mm*5 um; mobile phase: [water (10 mM NH$_4$HCO$_3$)-ACN]; B %: 35%-65%, 10 min) to give N-(bicyclo[1.1.1]pentan-1-yl)-4-isopropoxy-6-(4-methoxyphenyl)-1-(2-morpholinoethyl)-2-oxo-1,2-dihydro-1,8-naphthyridine-3-carboxamide (1.2 mg, 2.23 µmol).

$^1$H NMR (400 MHz, CDCl$_3$) δ=8.82 (d, J=2.5 Hz, 1H), 8.46-8.41 (m, 1H), 8.05-8.00 (m, 1H), 7.58-7.52 (m, 2H), 7.06 (d, J=8.8 Hz, 2H), 4.97-4.91 (m, 1H), 4.72-4.67 (m, 2H), 3.89 (s, 3H), 3.73-3.68 (m, 4H), 2.73 (t, J=7.2 Hz, 2H), 2.66-2.60 (m, 4H), 2.51 (s, 1H), 2.22 (s, 6H), 1.40 (d, J=6.0 Hz, 6H). LCMS for product (ESI+): m/z 533.3 [M+H]$^+$, Rt: 3.071 min.

LC/MS (The gradient was 5% B in 0.40 min and 5-95% B at 0.40-3.40 min, hold on 95% B for 0.45 min, and then 95-5% B in 0.01 min, the flow rate was 0.8 ml/min. Mobile phase A was H$_2$O+10 mM NH$_4$HCO$_3$, mobile phase B was Acetonitrile. The column used for chromatography was a Xbridge Shield RP18 2.1*50 mm column (5 µm particles). Detection methods are diode array (DAD) and evaporative light scattering (ELSD) detection as well as positive electrospray ionization. MS range was 100-1000.

Pharmaceutical Compositions

Example A-1: Parenteral Pharmaceutical Composition

To prepare a parenteral pharmaceutical composition suitable for administration by injection (subcutaneous, intravenous), 1-1000 mg of a water-soluble salt of a compound described herein, or a pharmaceutically acceptable salt, solvate or stereoisomer thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection.

Example A-2: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 1-1000 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 1-1000 mg of a compound described herein, or a pharmaceutically acceptable salt thereof, is placed into Size 4 capsule, or size 1 capsule (hypromellose or hard gelatin) and the capsule is closed.

BIOLOGICAL EXAMPLES

Example B-1: CB$_1$ and CB2 Receptor Binding Assays

The compounds were evaluated in CB$_1$R and CB$_2$R binding assays using membranes from HEK-293 cells transfected with cDNAs encoding the human recombinant CB$_1$R (B$_{max}$=2.5 pmol/mg protein) and human recombinant CB$_2$R (B$_{max}$=4.7 µmol/mg protein) (Perkin-Elmer). These membranes were incubated with [$^3$H]-(−)-cis-3-[2-hydroxy-4-(1,1-dimethylheptyl)phenyl]-trans-4-(3-hydroxypropyl)cyclohexanol ([$^3$H]CP-55,940) (0.14 nM/K$_d$=0.18 nM and 0.084 nM/K$_d$=0.31 nM for CB$_1$R and CB$_2$R, respectively) as high-affinity ligand and displaced with 100 nM (R)-(+)-[2,3-dihydro-5-methyl-3-(4-morpholinylmethyl)pyrrolo[1,2,3-de]-1,4-benzoxazin-6-yl]-1-naphthalenylmethanone (WIN-55,212-2) as heterologous competitor for nonspecific binding (K$_i$=9.2 and 2.1 nM, respectively, for CB$_1$R and CB$_2$R). Compounds were tested following the procedure described by the cell membrane manufacturer. CB$_1$R binding protocol involves the use of the same solution buffer used for both incubation and washing reaction (Tris-HCl, 50 mM; EDTA, 2.5 mM; MgCl$_2$, 2.5 mM; BSA, 0.5 mg/mL at pH 7.4), 0.4 nM for [$^3$H]CP-55,940, test compounds (concentrations from 0.001 to 10 µM), and finally 8 µg/sample membrane in a total volume of 200 µL. CB$_2$R binding assays were carried out with two different buffers: incubation buffer (Tris-HCl, 50 mM; MgCl$_2$, 5 mM; CaCl$_2$ 1 mM; BSA, 0.2% at pH 7.4) and washing buffer (Tris-HCl, 50 mM; NaCl 500 mM; BSA, 0.1% at pH 7.4). The assay mixture contained incubation buffer, 0.4 nM [$^3$H]CP-55,940, test substances (concentrations from 0.001 to 10 µM), and 4 µg/sample membrane in a total assay volume of 200 µL. Assays were performed in duplicate and incubated for 120 min at 37° C. After the incubation, the assay mixture is filtered through 96 GF/C filter plates (Perkin Elmer #6005174) using Perkin Elmer Filtermate Harvester, and then washed four times with ice-cold washing buffer. The filters are dried for 1 hour at 50° C. and [$^3$H] trapped on filter counted for radioactivity in Perkin Elmer Microscint 20 cocktail (#6013329) using Perkin Elmer MicroBeta2 Reader. The results are expressed as a percent inhibition of the control radioligand specific binding calculated using the following equation: % Inhibition=(1−(Assay well−Average_LC)/(Average_HC−Average_LC))×100%. Data are analyzed and IC50 is calculated using GraphPad Prism 5 and the model "log(inhibitor) vs. response—Variable slope". The binding affinity of the compounds is determined by using the Cheng and Prusoff equation Ki=IC50/(1+[radioligand]/Kd).

Example B-2: CB2 Receptor cAMP Assay cAMP Hunter CHO-K-1 cell lines expressing human $CB_2$ receptor (Eurofins) were expanded from freezer stocks according to standard procedures. Cells were seeded in a total volume of 20 μL into white walled, 384-well microplates and incubated at 37° C. for the appropriate time prior to testing. cAMP modulation in agonist, inverse agonist or antagonist format was determined using the DiscoverX HitHunter cAMP XS+ assay (Eurofins). For agonist determination, cells were incubated with sample in the presence of EC80 forskolin to induce response. Media was aspirated from cells and replaced with 15 μL 2:1 HBSS/10 mM Hepes: cAMP XS+Ab reagent. Intermediate dilution of sample stocks was performed to generate 4× sample in assay buffer containing 4×EC80 forskolin. 5 μL of 4× sample was added to cells and incubated at 37° C. or room temperature for 30 or 60 minutes. Final assay vehicle concentration was 1%. For inverse agonist determination, cells were preincubated with sample in the presence of EC20 forskolin. Media was aspirated from cells and replaced with 15 μL 2:1 HBSS/10 mM Hepes: cAMP XS+Ab reagent. Intermediate dilution of sample stocks was performed to generate 4× sample in assay buffer containing 4×EC20 forskolin. 5 μL of 4× sample was added to cells and incubated at 37° C. or room temperature for 30 or 60 minutes. Final assay vehicle concentration was 1%. For antagonist determination, cells were pre-incubated with sample followed by agonist challenge at the EC80 concentration. Media was aspirated from cells and replaced with 10 μL 1:1 HBSS/Hepes: cAMP XS+Ab reagent. 5 μL of 4× compound was added to the cells and incubated at 37° C. or room temperature for 30 minutes. 5 μL of 4×EC80 agonist was added to cells and incubated at 37° C. or room temperature for 30 or 60 minutes. EC80 forksolin was included. After appropriate compound incubation, assay signal was generated through incubation with 20 μL cAMP XS+ED/CL lysis cocktail for one hour followed by incubation with 20 μL cAMP XS+EA reagent for three hours at room temperature. Microplates were read following signal generation with a PerkinElmer Envision instrument for chemiluminescent signal detection. Compound activity was analyzed using CBIS data analysis suite (ChemInnovation, CA). For agonist mode assay, percentage activity is calculated using the following formula: % Activity=100%×(1−(mean RLU of test sample−mean RLU of MAX control)/(mean RLU of vehicle control−mean RLU of MAX control)). For inverse agonist mode assay, percentage activity is calculated using the following formula: % Inverse Agonist Activity=100%×((mean RLU of test sample−mean RLU of EC20 forskolin)/(mean RLU of forskolin positive control−mean RLU of EC20 control)). For antagonist mode assay, percentage inhibition is calculated using the following formula: % Inhibition=100%×(mean RLU of test sample−mean RLU of EC80 control)/(mean RLU of forskolin positive control−mean RLU of EC80 control). Data are analyzed and $IC_{50}$ is calculated using GraphPad Prism 5 and the model "log(inhibitor) vs. response—Variable slope".

Illustrative binding affinities for representative compounds are described in Table 1. The potencies are divided into three criteria: + means that $IC_{50}$ is greater than 1000 nM; ++ means $IC_{50}$ is between 100 nM and 999 nM; +++ means $IC_{50}$ is below 100 nM. In some embodiments, compounds with $IC_{50}$ designated "+" may have $IC_{50}$s between 1 μM to 30 μM.

TABLE 1

| Compound | CB2 $IC_{50}$ (nM) | CB1 $IC_{50}$ (nM) | cAMP $IC_{50}$ (nM)/ Max Stimulation % |
|---|---|---|---|
| 1 | ++ | + | |
| 2 | ++ | + | |
| 3 | ++ | + | |
| 4 | ++ | | |
| 5 | 6.5 | 3872 | 70 (75%) |
| 6 | 6.1 | >10000 | >1000 |
| 7 | + | + | >1000 |
| 8 | 20 | >10000 | 40 (32%) |
| 9 | +++ | + | 71 (7%) |
| 10 | 7 | >10000 | 7 (82%) |
| 11 | ++ | + | 81 (60%) |
| 12 | + | + | |
| 13 | 17 | >10000 | 62 (67%) |
| 14 | +++ | | |
| 15 | 8.8 | >10000 | 21 (75%) |
| 16 | 22.6 | >10000 | 7 (30%) |
| 17 | ++ | + | |
| 18 | + | + | |
| 19 | 20 | >10000 | 43 (81%) |
| 20 | 4.7 | >10000 | 7 (93%) |
| 21 | ++ | + | |
| 22 | ++ | + | |
| 23 | +++ | ++ | |
| 24 | + | + | |
| 25 | + | + | |
| 26 | 2.2 | >10000 | |
| 27 | 2 | >10000 | |
| 28 | 0.7 | >10000 | |
| 29 | 1.2 | >10000 | 5 (107%) |
| 30 | 1.2 | >10000 | 17 (89%) |
| 31 | +++ | + | 127 (78%) |
| 32 | 0.8 | 39 | |
| 33 | 4 | >10000 | 6 (100, 79%) |
| 34 | 1 | 184 | |
| 35 | 7.5 | 358 | |
| 36 | 5 | >10000 | 13 (89%) |
| 37 | 0.6 | 112 | |
| 38 | +++ | ++ | |
| 39 | 1.2 | >10000 | |
| 40 | 7 | >10000 | 10 (74%) |
| 41 | ++ | + | |
| 42 | 23 | >10000 | 14 (73%) |
| 43 | ++ | | |
| 44 | 7.2 | 6083 | >1000 |
| 45 | +++ | + | 15 (70%) |
| 46 | 6 | 8608 | 14 (77%) |
| 47 | 24.9 | >10000 | 0.5 (48%) |
| 48 | 4.5 | >10000 | 0.2 (66%) |
| 49 | ++ | | |
| 50 | 4.3 | 2781 | 0.6 (80%) |
| 51 | 2.1 | >10000 | 2 (108%) |
| 52 | 10 | 962 | 1 (77%) |
| 53 | +++ | + | 2 (85%) |
| 54 | +++ | + | |
| 55 | 0.6 | 2944 | 11 (84%) |
| 56 | +++ | + | |
| 57 | +++ | + | 8 (63%) |
| 58 | 5.58 | >10000 | 20 (77%) |
| 59 | 130 | >10000 | 119 (75%) |
| 61 | +++ | + | 13 (83%) |
| 62 | +++ | + | 13 (33%) |
| 63 | +++ | + | >1000 |
| 64 | + | + | |
| 65 | ++ | + | |
| 66 | + | + | |

TABLE 1-continued

| Compound | CB2 IC$_{50}$ (nM) | CB1 IC$_{50}$ (nM) | cAMP IC$_{50}$ (nM)/ Max Stimulation % |
|---|---|---|---|
| 67 | + | + | |
| 68 | ++ | + | |
| 69 | +++ | + | 21 (79%) |
| 70 | +++ | + | |
| 71 | + | + | |
| 72 | +++ | + | |
| 73 | ++ | + | |
| 74 | + | + | |
| 75 | + | + | |
| 76 | +++ | + | |
| 77 | ++ | + | |
| 78 | ++ | + | |
| 80 | ++ | + | |
| 81 | 5 | >10000 | |
| 82 | +++ | + | 1 (86%) |
| 83 | +++ | + | 5 (93%) |
| 84 | 3.7 | 413 | |
| 85 | 7.9 | 605 | 0.5 (93%) |
| 86 | +++ | + | |
| 87 | 5 | 4583 | |
| 88 | 6.7 | >10000 | |
| 89 | +++ | + | 7 (92%) |
| 90 | 11 | 348 | |
| 91 | 7 | >10000 | |
| 92 | +++ | | 3.6 (108%) |
| 93 | 3.6 | >10000 | |
| 94 | 4.1 | 3264 | 0.8 (55%) |
| 95 | 3.2 | 895 | 2 (60%) |
| 96 | +++ | + | |
| 97 | +++ | + | |
| 99 | 12 | >10000 | 53 (89%) |
| 100 | 4 | 2882 | 2 (82%) |
| 101 | 7.6 | 2107 | 21 (71%) |
| 102 | 2.3 | 1609 | 3 (79%) |
| 103 | 3 | 2905 | 9 (91%) |
| 104 | +++ | + | |
| 105 | 14 | >10000 | 28 (116%) |
| 106 | +++ | + | |
| 108 | ++ | + | |
| 109 | +++ | + | |
| 110 | ++ | ++ | |
| 111 | +++ | ++ | |
| 112 | +++ | + | |
| 113 | + | + | |
| 114 | ++ | + | |
| 115 | 29 | 552 | |
| 116 | 31 | 1481 | |
| 117 | ++ | + | |
| 118 | ++ | + | |
| 119 | ++ | + | |
| 120 | + | + | |
| 121 | 9 | 2315 | |
| 122 | ++ | + | |
| 123 | + | + | |
| 124 | + | + | |
| 125 | ++ | + | |
| 126 | + | + | |
| 127 | + | + | |
| 128 | ++ | + | |
| 129 | + | + | |
| 130 | + | + | |
| 131 | + | + | |
| 132 | ++ | + | |
| 133 | ++ | + | |
| 134 | ++ | + | |
| 135 | +++ | + | |
| 136 | + | + | |
| 137 | 15 | >10000 | |
| 138 | ++ | + | |
| 139 | + | + | |
| 140 | ++ | + | |
| 141 | ++ | + | |
| 142 | ++ | + | |
| 143 | 34 | 3357 | |
| 144 | 1498 | >10000 | |
| 145 | +++ | + | |
| 146 | + | + | |
| 147 | + | + | |
| 148 | + | + | |
| 149 | +++ | + | |
| 150 | ++ | + | |
| 151 | + | + | |
| 152 | ++ | + | |
| 153 | +++ | + | |
| 155 | + | + | |
| 158 | +++ | + | |
| 159 | +++ | ++ | |
| 161 | +++ | + | |
| 165 | + | | |
| 166 | + | | |
| 173 | + | | |
| 177 | + | | |
| 180 | + | | |

Blank means not tested

Example B-3: In Vitro Mixed Lymphocyte Reaction Assay

Dendritic cells (DC) were generated by culturing monocytes isolated from freshly isolated human PBMCs using a monocyte purification kit (Miltenyi Biotec) in vitro for 7 days with 500 U/mL interleukin-4 (IL-4) and 250 U/mL GM-CSF (R&D Systems). CD$^{4+}$ T cells ($1 \times 10^5$) and allogeneic DCs ($1 \times 10^4$) were co-cultured with or without CB$_2$R antagonists and/or anti-PD-(L)-1 antibody added at the initiation of the assay. After 5 days, IFNγ secretion in culture supernatants was analyzed by ELISA (BD Biosciences).

Example B-4: In Vitro T Cell Exhaustion Assay

Freshly isolated human PBMCs from healthy donors were cultured for 3 days with or without CB$_2$R antagonists and/or anti-PD-(L)-1 antibodies at the initiation of the assay together with serial dilutions of staphylococcal enterotoxin B (SEB; Toxin Technology). IL-2 levels in culture supernatants were measured by ELISA analysis (BD Biosciences).

Example B-5: In Vivo B16F10 Tumor Growth Inhibition Study

C57BL/6 inbred female mice, aged at 8-9 week, were purchased from Charles River. On the day of inoculation (Day 0), B16F10 cells were harvested, washed and counted. Cells were re-suspended as single cell solution in PBS at a concentration of $5 \times 10^6$ cells/mL at the final step. Immediately, five hundred thousand ($5 \times 10^5$) of B16F10 cells suspended in 0.1 mL PBS were injected in the right flank of C57BL/6 mice subcutaneously using 27G needles. When palpable, tumors were measured by a caliper and tumor volumes (mm$^3$) were calculated by length×width×height× 0.5236. Mice with the tumor size approximate to 100 mm$^3$ were randomly assigned into one of four groups (n=10). Each group received vehicle (BID), CB$_2$R antagonists at 1 mg/kg (QD) and/or mouse anti-PD-1 (RMP1-14) at 5 mg/kg (Q2D), intraperitoneally. Tumor size and body weight were determined every 2-3 days. Percent tumor growth inhibition (TGI) was defined as the difference between the Median Tumor Volume (MTV) of a test group and control group, using the formula: % TGI=((MTVcontrol−MTVtreated/MTVcontrol))×100.

Example B-6: Combination with Anti-PD-1/Anti-PD-L1 Agents

CB$_2$ receptor antagonists can be used in combination with other therapies that further enhance the antitumor immune response. When PD-1 and PD-L1 join together, they form a biochemical shield protecting tumor cells from being destroyed by the immune system. In some embodiments, CB$_2$ receptor antagonists are combined with anti-PD-1/anti-PD-L1 agents to treat cancer. Combination therapy is advantageous when efficacy is greater than either agent alone or when the dose required for either drug is reduced thereby improving the side effect profile.

Example B-7: In Vivo PK

Compounds described herein are tested in vivo and PK parameters are determined. as follows. Test compound is administered to six male SD rats, IV (n=3) at a dose level of 1 mg/kg and (PO) at dose level of 5 mg/kg PO (n=3). The dosing solution for IV administration is prepared by dissolving the compound in DMSO/PEG400/Water=10:30:60 as a 0.5 mg/mL solution (2 mL/kg dose volume). The dosing suspension for oral administration is formulated in 0.5% Methylcellulose as a 1 mg/mL suspension for the 5 mg/kg oral dose level (5 mL/kg dose volume).

Blood samples are collected from rats via jugular vein cannulation into EDTA-K2 tubes. For the IV administration experiment, blood samples are collected pre-dose, at 5 min, 15 min, 30 min, 1 h, 2 h, 4 h, 8 h, and 24 h post-dose administration. For PO administration, blood samples are collected pre-dose, at 15 min, 30 min, 1 h, 2 h, 4 h, 8 h, and 24 h post-dose administration.

For the IV administration experiment, blood concentrations of the compound are determined using LC-MS/MS with a lower limit of quantitation of 10 ng/mL. For the PO administration experiment, plasma concentrations of the compound are determined using LC-MS/MS with a lower limit of quantitation of 1 ng/mL. The pharmacokinetic parameters are determined by non-compartmental analysis using WinNonlin.

Certain compounds described herein have higher bioavailability and improved PK compared to previously described compounds and demonstrate an improvement when R$^1$ is OH vs H, and/or when R$^4$ is a bridged cycloalkyl.

The examples and embodiments described herein are for illustrative purposes only and various modifications or changes suggested to persons skilled in the art are to be included within the spirit and purview of this application and scope of the appended claims.

What is claimed is:

1. A method for treating bladder cancer, colon cancer, brain cancer, breast cancer, endometrial cancer, heart cancer, kidney cancer, lung cancer, liver cancer, uterine cancer, blood and lymphatic cancer, ovarian cancer, pancreatic cancer, prostate cancer, thyroid cancer, or skin cancer in a mammal in need thereof, the method comprising administering to the mammal a compound selected from:

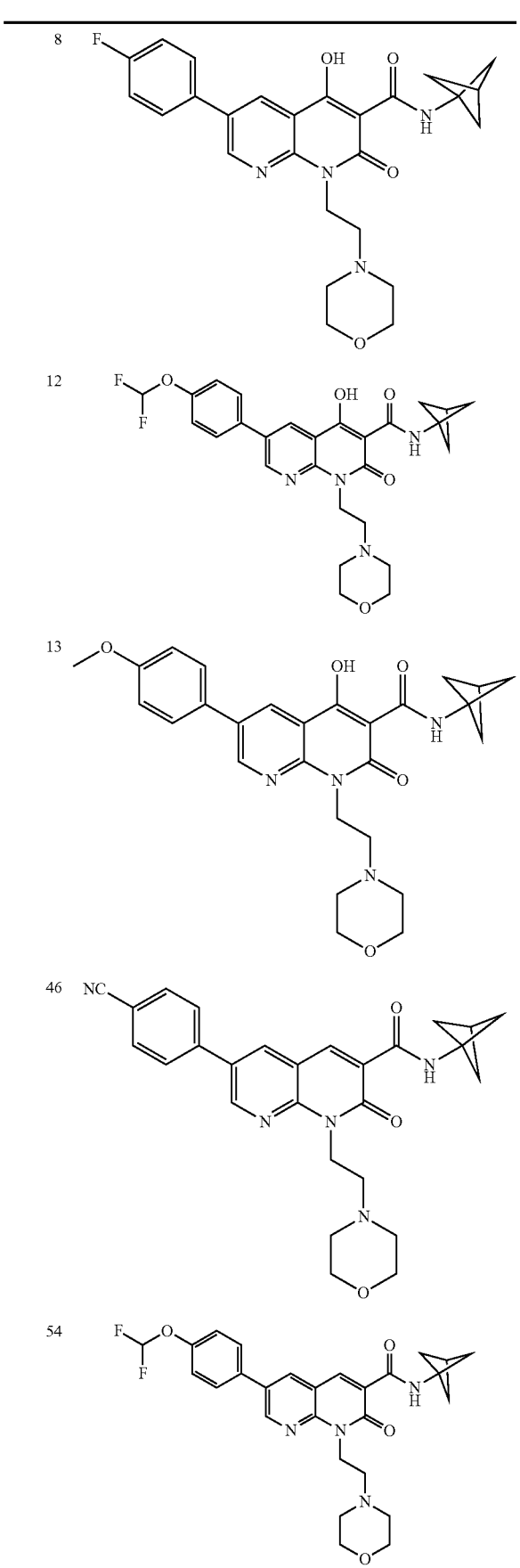

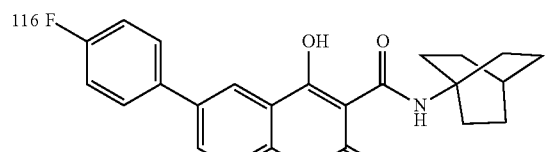
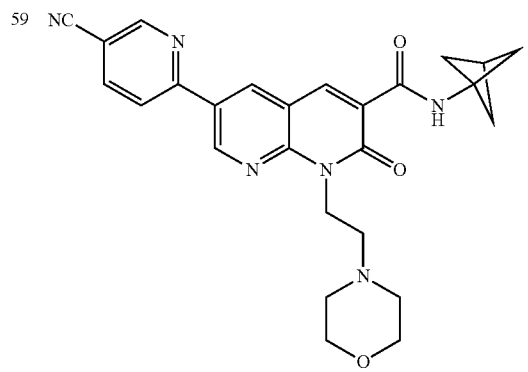
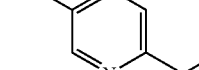
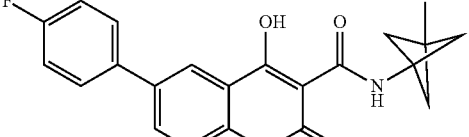

| 125 | 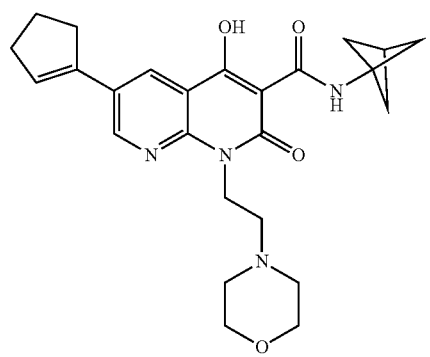 [SMILES: O=C(NC12CC(C1)C2)c1c(O)c2cc(C3=CCCC3)cnc2n(CCN2CCOCC2)c1=O] |
| 126 | 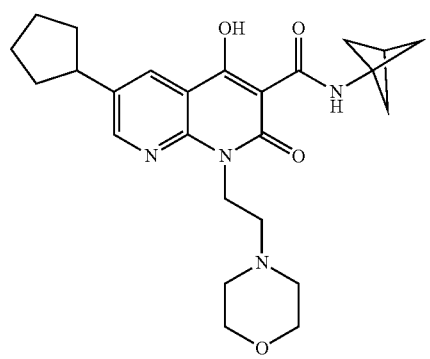 [SMILES: O=C(NC12CC(C1)C2)c1c(O)c2cc(C3CCCC3)cnc2n(CCN2CCOCC2)c1=O] |
| 127 | 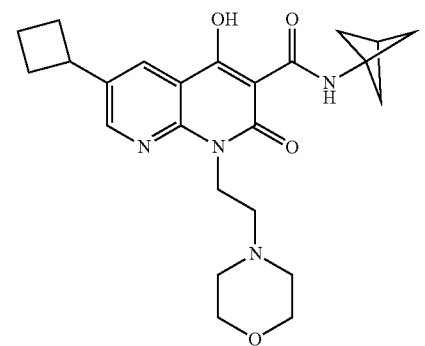 [SMILES: O=C(NC12CC(C1)C2)c1c(O)c2cc(C3CCC3)cnc2n(CCN2CCOCC2)c1=O] |
| 128 | 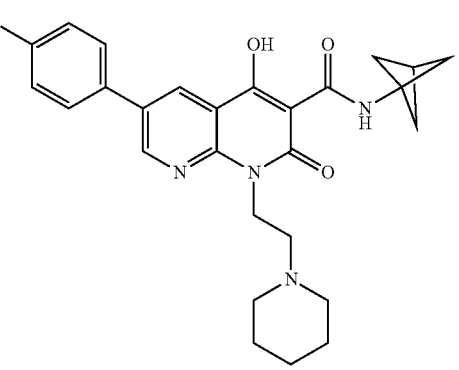 |
| 129 | 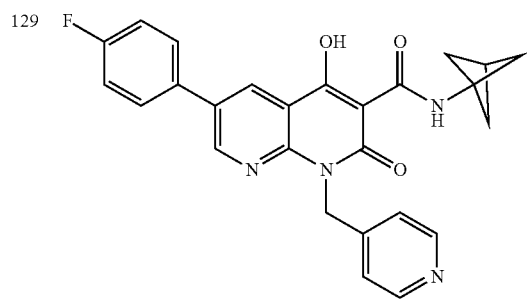 |
| 130 | 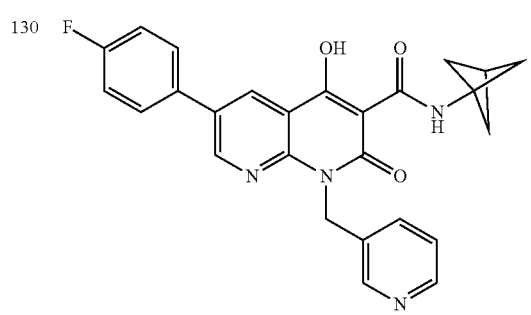 |
| 131 | 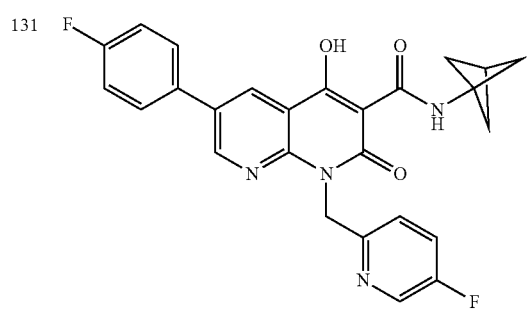 |
| 132 | 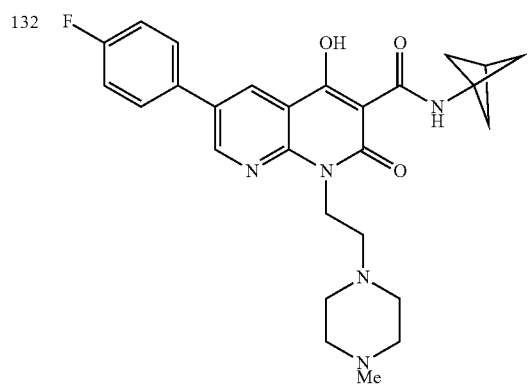 |

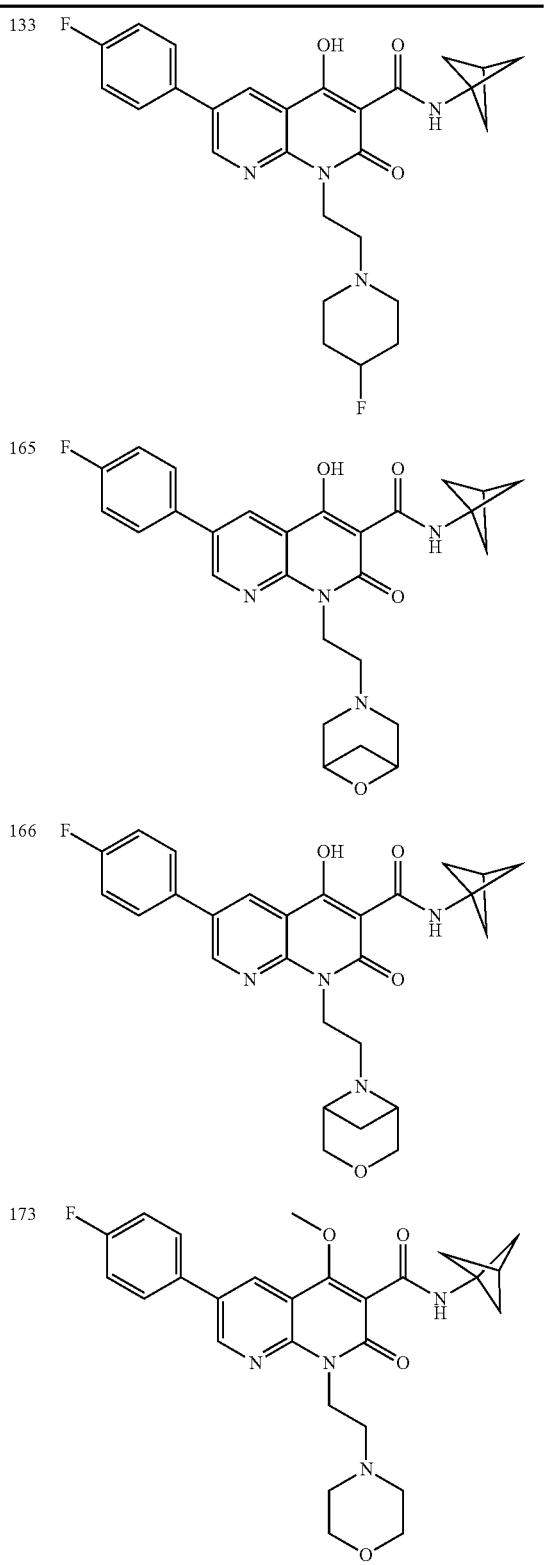

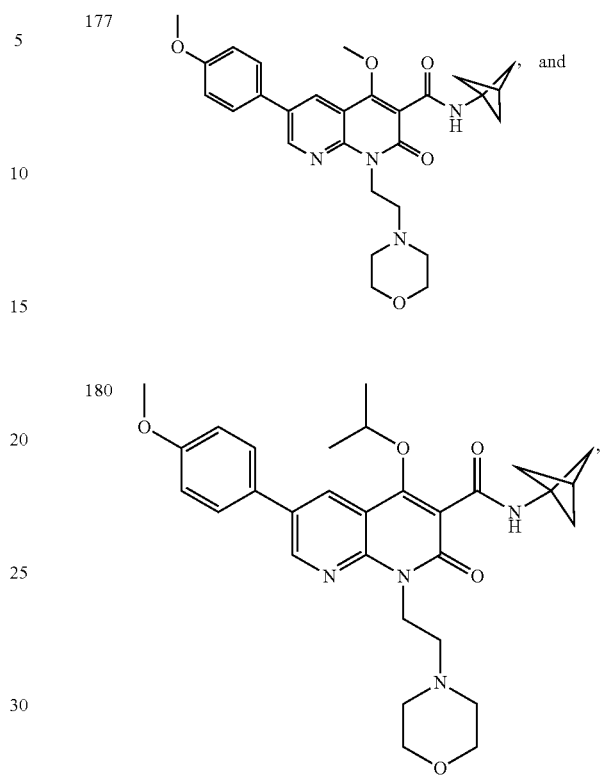

or a pharmaceutically acceptable salt or stereoisomer thereof.

2. The method of claim 1, wherein the cancer is a solid tumor.

3. The method of claim 1, wherein the cancer is prostate cancer, breast cancer, colon cancer, or lung cancer.

4. The method of claim 2, wherein the cancer is a sarcoma, carcinoma, or lymphoma.

5. The method of claim 1, further comprising administering at least one additional therapy to the mammal in need thereof.

6. The method of claim 1, further comprising administering at least one immune checkpoint inhibitor to the mammal in need thereof.

7. The method of claim 6, wherein the immune checkpoint inhibitor is an anti-PD-1 agent or an anti-PD-L1 agent.

8. The method of claim 7, wherein the anti-PD-1 agent or anti-PD-L1 agent is nivolumab, pembrolizumab, cemiplimab, labrolizumab, avelumab, durvalumab or atezolizumab.

9. The method of claim 1, wherein the mammal is a human.

* * * * *